US008420759B2

(12) United States Patent
Feher et al.

(10) Patent No.: US 8,420,759 B2
(45) Date of Patent: Apr. 16, 2013

(54) POLYMERS OF ISOPRENE FROM RENEWABLE RESOURCES

(75) Inventors: Frank J. Feher, Copley, OH (US); Gregory M. Whited, Belmont, CA (US); Gopal K. Chotani, Cupertino, CA (US); Fernando Valle, Burlingame, CA (US); Carol Fioresi, Redwood City, CA (US); Karl J. Sanford, Cupertino, CA (US); Joseph C. McAuliffe, Sunnyvale, CA (US); Marguerite Cervin, Redwood City, CA (US); Aaron S. Puhala, Kent, OH (US); Andrei Miasnikov, Mountain View, CA (US); Ilana S. Aldor, Palo Alto, CA (US)

(73) Assignees: The Goodyear Tire & Rubber Company, Akron, OH (US); Danisco US, Inc., Palo Alto, CA (US)

( * ) Notice: Subject to any disclaimer, the term of this patent is extended or adjusted under 35 U.S.C. 154(b) by 0 days.

(21) Appl. No.: 12/459,399

(22) Filed: Jun. 30, 2009

(65) Prior Publication Data

US 2011/0237769 A1    Sep. 29, 2011

Related U.S. Application Data

(60) Provisional application No. 61/133,521, filed on Jun. 30, 2008.

(51) Int. Cl.
| | | |
|---|---|---|
| C08F 36/08 | (2006.01) | |
| G01N 33/44 | (2006.01) | |
| C07C 11/18 | (2006.01) | |
| C12P 5/02 | (2006.01) | |

(52) U.S. Cl.
USPC ......... 526/340.2; 526/75; 526/337; 526/340; 525/321; 585/18; 435/167; 436/85; 436/173

(58) Field of Classification Search ............ 526/75, 526/337, 340, 340.2; 436/85, 173; 530/450, 530/350; 528/930; 435/167; 525/321; 585/18; 73/64.54
See application file for complete search history.

(56) References Cited

U.S. PATENT DOCUMENTS

| | | | |
|---|---|---|---|
| 3,146,278 A | 8/1964 | Habeshaw et al. ............ 585/315 |
| 3,149,182 A | 9/1964 | Porter et al. .................. 525/271 |
| 3,231,635 A | 1/1966 | Holden et al. ................ 525/271 |
| 3,437,711 A | 8/1969 | Yanagita et at .............. 585/608 |
| 3,574,780 A | 4/1971 | Watanabe et al. ............ 585/327 |
| 3,621,072 A | 11/1971 | Watanabe et al. ............ 585/622 |
| 3,662,016 A | 5/1972 | Furuoya et al. .............. 585/608 |
| 3,931,136 A | 1/1976 | Mori et al. ................... 526/142 |
| 3,972,955 A | 8/1976 | Halcour et al. .............. 585/327 |
| 4,000,209 A | 12/1976 | Downs et al. ................ 585/608 |
| 4,014,952 A | 3/1977 | Adema et al. ................ 585/608 |
| 4,067,923 A | 1/1978 | Belyaev et al. .............. 585/607 |
| 4,385,151 A * | 5/1983 | Furukawa et al. ............ 524/420 |
| 4,430,487 A | 2/1984 | Sandstrom .................... 526/83 |
| 4,511,751 A | 4/1985 | Ninagawa et al. ............ 585/608 |
| 4,894,425 A | 1/1990 | Hellermann et al. ......... 526/181 |
| 5,061,765 A | 10/1991 | Hsu et al. ..................... 526/141 |
| 5,082,906 A | 1/1992 | Hsu et al. ..................... 526/93 |
| 5,137,998 A | 8/1992 | Hsu et al. ..................... 526/174 |
| 5,177,290 A | 1/1993 | Ryu et al. ..................... 585/327 |
| 5,242,984 A | 9/1993 | Dillman et al. ............... 525/314 |
| 5,356,997 A | 10/1994 | Massie, II et al. ............ 525/237 |
| 5,677,402 A | 10/1997 | Halasa et al. ................. 526/17 |
| 5,919,867 A | 7/1999 | Yasuda et al. ................ 525/299 |
| 5,919,876 A | 7/1999 | Castner ........................ 526/141 |
| 6,066,705 A | 5/2000 | Calderon et al. |
| 6,204,358 B1 * | 3/2001 | Tanaka et al. ................ 526/336 |
| 6,313,216 B1 | 11/2001 | Christian et al. ............. 524/575 |
| 6,562,895 B2 | 5/2003 | Blok et al. ................... 524/534 |
| 6,576,728 B1 | 6/2003 | Jasiunas et al. .............. 526/174 |
| 6,627,721 B1 | 9/2003 | Rodewald et al. ............ 526/338 |
| 6,780,948 B2 | 8/2004 | Rachita et al. ............... 526/164 |
| 6,936,669 B2 | 8/2005 | Halasa et al. ................. 526/260 |
| 7,091,150 B2 | 8/2006 | Halasa et al. ................. 502/134 |
| 7,199,201 B2 | 4/2007 | Halasa et al. ................. 526/335 |
| 7,351,768 B2 | 4/2008 | Rachita et al. ............... 525/105 |
| 2009/0203102 A1 | 8/2009 | Cervin et al. ................. 435/167 |
| 2010/0003716 A1 * | 1/2010 | Cervin et al. ................. 435/40.5 |
| 2010/0086978 A1 | 4/2010 | Beck et al. ................... 435/131 |
| 2010/0113846 A1 | 5/2010 | McAuliffe et al. ........... 585/315 |
| 2010/0167370 A1 | 7/2010 | Chotani et al. ............... 435/167 |
| 2010/0184178 A1 | 7/2010 | Beck et al. ................... 435/167 |

OTHER PUBLICATIONS

Hawley's Condensed Chemical Dictionary, 14th ed., 2002, entry for "rubber, natural".*
H.-W. Yeh, W.-M. Wang, Proc. Nat. Sci. Counc. ROC(B) 2001, 25, 137-47.
J. Bricout, J. Koziet, J. Agric. Food Chem. 1987, 35, 758-70.
J. E. Spangenberg, Isotopes Environ. Health Stud. 2006, 42, 231-8.
B. L. Zhang, S. Buddrus, MI Trierweiler, G. J. Martin, J. Agric. Food Chem. 1998, 46, 1374-80.
D. Weber, H. Kexel, H.-L. Schmidt, J. Agric. Food Chem. 1997, 45, 2042-6.
W. R. Abraham, C. Hess, O. Pelz, *Appl. Environ. Microbiol.* 1998, 64, 4202-9.
U.S. Appl. No. 61/097,163 Sep. 15, 2008 Chotani et al.
U.S. Appl. 61/013,574 Dec. 13, 2007 Cervin et al.

* cited by examiner

*Primary Examiner* — Fred M Teskin
(74) *Attorney, Agent, or Firm* — Aric W. Ledford; Alvin T. Rockhill

(57) ABSTRACT

It has been found that certain cells in culture can convert more than about 0.002 percent of the carbon available in the cell culture medium into isoprene. These cells have a heterologous nucleic acid that (i) encodes an isoprene synthase polypeptide and (ii) is operably linked to a promoter. The isoprene produced in such a cultured medium can then be recovered and polymerized into synthetic rubbers and other useful polymeric materials. The synthetic isoprene containing polymers of this invention offer the benefit of being verifiable as to being derived from non-petrochemical based resources. They can also be analytically distinguished from rubbers that come from natural sources. The present invention more specifically discloses a polyisoprene polymer which is comprised of repeat units that are derived from isoprene monomer, wherein the polyisoprene polymer has $\delta^{13}C$ value of greater than −22‰.

20 Claims, 171 Drawing Sheets

Figure 1

1-
atgtgtgcgacctcttctcaatttactcagattaccgagcataattcccgtcgttccgcaaact
atcagccaaacctgtggaatttcgaattcctgcaatccctggagaacgacctgaaagtggaaaa
gctggaggagaaagcgaccaaactggaggaagaagttcgctgcatgatcaaccgtgtagacacc
cagccgctgtccctgctggagctgatcgacgatgtgcagcgcctggtctgacctacaaatttg
aaaaagacatcattaaagccctggaaaacatcgtactgctggacgaaaacaaaaagaacaaatc
tgacctgcacgcaaccgctctgtctttccgtctgctgcgtcagcacggtttcgaggtttctcag
gatgttttgagcgtttcaaggataaagaaggtggtttcagcggtgaactgaaaggtgacgtcc
aaggcctgctgagcctgtatgaagcgtcttacctgggtttcgagggtgagaacctgctggagga
ggcgcgtacctttccatcacccacctgaagaacaacctgaagaaggcattaataccaaggtt
gcagaacaagtgagccacgccctggaactgccatatcaccagcgtctgcaccgtctggaggcac
gttggttcctggataaatacgaaccgaaagaaccgcatcaccagctgctgctggagctggcgaa
gctggatttaacatggtacagaccctgcaccagaaagagctgcaagatctgtcccgctggtgg
accgagatgggcctggctagcaaactggattttgtacgcgaccgcctgatggaagtttatttct
gggcactgggtatggcgccagacccgcagtttggtgaatgtcgcaaagctgttactaaaatgtt
tggtctggtgacgatcatcgatgacgtgtatgacgtttatggcactctggacgaactgcaactg
ttcaccgatgctgtagagcgctgggacgttaacgctattaacaccctgccggactatatgaaac
tgtgtttcctggcactgtacaacaccgttaacgacacgtcctattctattctgaaagagaaagg
tcataacaacctgtcctatctgacgaaaagctggcgtgaactgtgcaaagcctttctgcaagag
gcgaaatggtccaacaacaaaattatcccggctttctccaagtacctggaaaacgccagcgttt
cctcctccggtgtagcgctgctggcgccgtcttacttttccgtatgccagcagcaggaagacat
ctccgaccacgcgctgcgttccctgaccgacttccatggtctggtgcgttctagctgcgttatc
ttccgcctgtgcaacgatctggccacctctgcggcggagctggaacgtggcgagactaccaatt
ctatcattagctacatgcacgaaaacgatggtaccagcgaggaacaggcccgcgaagaactgcg
taaactgatcgacgccgaatggaaaaagatgaatcgtgaacgcgttagcgactccaccctgctg
cctaaagcgttcatggaaatcgcagttaacatggcacgtgtttcccactgcacctaccagtatg
gcgatggtctgggtcgcccagactacgcgactgaaaaccgcatcaaactgctgctgattgaccc
tttcccgattaaccagctgatgtatgtc
taactgcag
(SEQ ID NO:1)

Figure 3A

1-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccATGtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaagacatcattaaagccctggaaaacatcgtac
tgctggacgaaaacaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggatttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgacccttttcccgattaaccagctgatgtatgtcTAActgca
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg

Figure 3B agggtggcgggcaggacgcccgccataaactgccaggcatcaaattaagcagaaggccatcctg
acggatggccttttttgcgtttctacaaactcttttttgtttattttttctaaatacattcaaatat
gtatccgctcatgagacaataaccctgataaatgcttcaataatattgaaaaaggaagagtatg
agtattcaacatttccgtgtcgcccttattccctttttttgcggcatttttgccttcctgtttttg
ctcacccagaaacgctggtgaaagtaaaagatgctgaagatcagttgggtgcacgagtgggtta
catcgaactggatctcaacagcggtaagatccttgagagttttcgccccgaagaacgttttcca
atgatgagcacttttaaagttctgctatgtggcgcggtattatcccgtgttgacgccgggcaag
agcaactcggtcgccgcatacactattctcagaatgacttggttgagtactcaccagtcacaga
aaagcatcttacggatggcatgacagtaagagaattatgcagtgctgccataaccatgagtgat
aacactgcggccaacttacttctgacaacgatcggaggaccgaaggagctaaccgcttttttgc
acaacatggggggatcatgtaactcgccttgatcgttgggaaccggagctgaatgaagccatacc
aaacgacgagcgtgacaccacgatgcctgtagcaatggcaacaacgttgcgcaaactattaact
ggcgaactacttactctagcttcccggcaacaattaatagactggatggaggcggataaagttg
caggaccacttctgcgctcggcccttccggctggctggtttattgctgataaatctggagccgg
tgagcgtgggtctcgcggtatcattgcagcactggggccagatggtaagccctcccgtatcgta
gttatctacacgacggggagtcaggcaactatggatgaacgaaatagacagatcgctgagatag
gtgcctcactgattaagcattggtaactgtcagaccaagtttactcatatatactttagattga
tttaaaacttcatttttaatttaaaaggatctaggtgaagatcctttttgataatctcatgacc
aaaatcccttaacgtgagttttcgttccactgagcgtcagacccgtagaaaagatcaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccgt
aagcggcagggtcggaacaggagagcgcacgagggagcttccaggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaaccttttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct

Figure 3C

Gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
(SEQ ID NO:2)

Figure 5A 1-
ttctcatgtttgacagcttatcatcgataagctttaatgcggtagtttatcacagttaaattgc
taacgcagtcaggcaccgtgtatgaaatctaacaatgcgctcatcgtcatcctcggcaccgtca
ccctggatgctgtaggcataggcttggttatgccggtactgccgggcctcttgcgggatatccg
gatatagttcctcctttcagcaaaaaacccctcaagacccgtttagaggccccaaggggttatg
ctagttattgctcagcggtggcagcagccaactcagcttcctttcgggctttgttagcagccgg
atccctgcagttagacatacatcagctggttaatcgggaaaggggtcaatcagcagcagtttgat
gcggttttcagtcgcgtagtctgggcgacccagaccatcgccatactggtaggtgcagtgggaa
acacgtgccatgttaactgcgatttccatgaacgctttaggcagcagggtggagtcgctaacgc
gttcacgattcatctttttccattcggcgtcgatcagtttacgcagttcttcgcgggcctgttc
ctcgctggtaccatcgttttcgtgcatgtagctaatgatagaattggtagtctcgccacgttcc
agctccgccgcagaggtggccagatcgttgcacaggcggaagataacgcagctagaacgcacca
gaccatggaagtcggtcagggaacgcagcgcgtggtcggagatgtcttcctgctgctggcatac
ggaaaagtaagacggcgccagcagcgctacaccggaggaggaaacgctggcgttttccaggtac
ttggagaaagccgggataattttgttgttggaccatttcgcctcttgcagaaaggctttgcaca
gttcacgccagcttttcgtcagataggacaggttgttatgacctttctctttcagaatagaata
ggacgtgtcgttaacggtgttgtacagtgccaggaaacacagtttcatatagtccggcagggtg
ttaatagcgttaacgtccagcgctctacagcatcggtgaacagttgcagttcgtccagagtgc
cataaacgtcatacacgtcatcgatgatcgtcaccagaccaaacatttttagtaacagctttgcg
acattcaccaaactgcgggtctggcgccatacccagtgcccagaaataaacttccatcaggcgg
tcgcgtacaaaatccagtttgctagccaggcccatctcggtccaccagcgggacagatcttgca
gctctttctggtgcagggtctgtaccatgttaaaatccagcttcgccagctccagcagcagctg
gtgatgcggttctttcggttcgtatttatccaggaaccaacgtgcctccagacggtgcagacgc
tggtgatatggcagttccagggcgtggctcacttgttctgcaaccttggtattaatgccttctt
tcaggttgttcttcaggtgggtgatggaaaaggtacgcgcctcctccagcaggttctcaccctc
gaaacccaggtaagacgcttcatacaggctcagcaggccttggacgtcacctttcagttcaccg
ctgaaaccaccttctttatccttgaaacgctcaaaaacatcctgagaaacctcgaaaccgtgct
gacgcagcagacggaaagacagagcggttgcgtgcaggtcagatttgttcttttttgttttcgtc
cagcagtacgatgttttccagggctttaatgatgtctttttcaaatttgtaggtcagacccagg
cgctgcacatcgtcgatcagctccagcagggacagcggctgggtgtctacacggttgatcatgc
agcgaacttcttcctccagtttggtcgctttctcctccagcttttccactttcaggtcgttctc
cagggattgcaggaattcgaaattccacaggtttggctgatagtttgcggaacgacgggaatta
tgctcggtaatctgagtaaattgagaagaggtcgcacacatatgacgaccttcgatatggccgc
tgctgtgatgatgatgatgatgatgatgatgatggcccatggtatatctccttcttaaagttaa
acaaaattatttctagaggggaattgttatccgctcacaattcccctatagtgagtcgtattaa
tttcgcgggatcgagatctcgatcctctacgccggacgcatcgtggccggcatcaccggcgcca
caggtgcggttgctggcgcctatatcgccgacatcaccgatggggaagatcgggctcgccactt
cgggctcatgagcgcttgtttcggcgtgggtatggtggcaggccccgtggccgggggactgttg
ggcgccatctccttgcatgcaccattccttgcggcggcggtgctcaacggcctcaacctactac
tgggctgcttcctaatgcaggagtcgcataagggagagcgtcgagatcccggacaccatcgaat
ggcgcaaaacctttcgcggtatggcatgatagcgcccggaagagagtcaattcagggtggtgaa
tgtgaaaccagtaacgttatacgatgtcgcagagtatgccggtgtctcttatcagaccgtttcc
cgcgtggtgaaccaggccagccacgtttctgcgaaaacgcgggaaaaagtggaagcggcgatgg
cggagctgaattacattcccaaccgcgtggcacaacaactggcgggcaaacagtcgttgctgat
tggcgttgccacctccagtctggccctgcacgcgccgtcgcaaattgtcgcggcgattaaatct

Figure 5B cgcgccgatcaactgggtgccagcgtggtggtgtcgatggtagaacgaagcggcgtcgaagcct
gtaaagcggcggtgcacaatcttctcgcgcaacgcgtcagtgggctgatcattaactatccgct
ggatgaccaggatgccattgctgtggaagctgcctgcactaatgttccggcgttatttcttgat
gtctctgaccagacacccatcaacagtattattttctcccatgaagacggtacgcgactgggcg
tggagcatctggtcgcattgggtcaccagcaaatcgcgctgttagcgggcccattaagttctgt
ctcggcgcgtctgcgtctggctggctggcataaatatctcactcgcaatcaaattcagccgata
gcggaacgggaaggcgactggagtgccatgtccggttttcaacaaaccatgcaaatgctgaatg
agggcatcgttcccactgcgatgctggttgccaacgatcagatggcgctgggcgcaatgcgcgc
cattaccgagtccgggctgcgcgttggtgcggatatctcggtagtgggatacgacgataccgaa
gacagctcatgttatatcccgccgttaaccaccatcaaacaggattttcgcctgctggggcaaa
ccagcgtggaccgcttgctgcaactctctcagggccaggcggtgaagggcaatcagctgttgcc
cgtctcactggtgaaagaaaaaccaccctggcgcccaatacgcaaaccgcctctcccgcgcg
ttggccgattcattaatgcagctggcacgacaggtttccgactggaaagcgggcagtgagcgc
aacgcaattaatgtaagttagctcactcattaggcaccgggatctcgaccgatgcccttgagag
ccttcaacccagtcagctccttccggtgggcgcggggcatgactatcgtcgccgcacttatgac
tgtcttctttatcatgcaactcgtaggacaggtgccggcagcgctctgggtcatttcggcgag
gaccgctttcgctggagcgcgacgatgatcggcctgtcgcttgcggtattcggaatcttgcacg
ccctcgctcaagccttcgtcactggtcccgccaccaaacgtttcggcgagaagcaggccattat
cgccggcatggcggccgacgcgctgggctacgtcttgctggcgttcgcgacgcgaggctggatg
gccttccccattatgattcttctcgcttccggcggcatcgggatgcccgcgttgcaggccatgc
tgtccaggcaggtagatgacgaccatcagggacagcttcaaggatcgctcgcggctcttaccag
cctaacttcgatcactggaccgctgatcgtcacggcgatttatgccgcctcggcgagcacatgg
aacggggttggcatggattgtaggcgccgccctataccttgtctgcctcccgcgttgcgtcgcg
gtgcatggagccgggccacctcgacctgaatgaagccggcggcacctcgctaacggattcacc
actccaagaattggagccaatcaattcttgcggagaactgtgaatgcgcaaaccaacccttggc
agaacatatccatcgcgtccgccatctccagcagccgcacgcggcgcatctcgggcagcgttgg
gtcctggccacgggtgcgcatgatcgtgctcctgtcgttgaggacccggctaggctggcggggt
tgccttactggttagcagaatgaatcaccgatacgcgagcgaacgtgaagcgactgctgctgca
aaacgtctgcgacctgagcaacaacatgaatggtcttcggtttccgtgtttcgtaaagtctgga
aacgcggaagtcagcgccctgcaccattatgttccggatctgcatcgcaggatgctgctggcta
ccctgtggaacacctacatctgtattaacgaagcgctggcattgaccctgagtgattttctct
ggtcccgccgcatccataccgccagttgtttaccctcacaacgttccagtaaccgggcatgttc
atcatcagtaacccgtatcgtgagcatcctctctcgtttcatcggtatcattaccccatgaac
agaaatccccttacacggaggcatcagtgaccaaacaggaaaaaccgcccttaacatggccc
gctttatcagaagccagacattaacgcttctggagaaactcaacgagctggacgcggatgaaca
ggcagacatctgtgaatcgcttcacgaccacgctgatgagctttaccgcagctgcctcgcgcgt
ttcggtgatgacggtgaaaacctctgacacatgcagctcccggagacggtcacagcttgtctgt
aagcggatgccgggagcagacaagcccgtcagggcgcgtcagcgggtgttggcgggtgtcgggg
cgcagccatgacccagtcacgtagcgatagcggagtgtatactggcttaactatgcggcatcag
agcagattgtactgagagtgcaccatatgcggtgtgaaataccgcacagatgcgtaaggaga
aaataccgcatcaggcgctcttccgcttcctcgctcactgactcgctgcgctcggtcgttcggc
tgcggcgagcggtatcagctcactcaaaggcggtaatacggttatccacagaatcagggataa
cgcaggaaagaacatgtgagcaaaaggccagcaaaaggccaggaaccgtaaaaaggccgcgttg
ctggcgttttccataggctccgcccccctgacgagcatcacaaaaatcgacgctcaagtcaga

Figure 5C ggtggcgaaacccgacaggactataaagataccaggcgtttccccctggaagctccctcgtgcg
ctctcctgttccgaccctgccgcttaccggatacctgtccgcctttctcccttcgggaagcgtg
gcgctttctcatagctcacgctgtaggtatctcagttcggtgtaggtcgttcgctccaagctgg
gctgtgtgcacgaaccccccgttcagcccgaccgctgcgccttatccggtaactatcgtcttga
gtccaacccggtaagacacgacttatcgccactggcagcagccactggtaacaggattagcaga
gcgaggtatgtaggcggtgctacagagttcttgaagtggtggcctaactacggctacactagaa
ggacagtatttggtatctgcgctctgctgaagccagttaccttcggaaaaagagttggtagctc
ttgatccggcaaacaaaccaccgctggtagcggtggttttttttgtttgcaagcagcagattacg
cgcagaaaaaaggatctcaagaagatcctttgatcttttctacggggtctgacgctcagtgga
acgaaaactcacgttaagggattttggtcatgagattatcaaaaaggatcttcacctagatcct
tttaaattaaaaatgaagttttaaatcaatctaaagtatatatgagtaaacttggtctgacagt
taccaatgcttaatcagtgaggcacctatctcagcgatctgtctatttcgttcatccatagttg
cctgactccccgtcgtgtagataactacgatacgggagggcttaccatctggccccagtgctgc
aatgataccgcgagacccacgctcaccggctccagatttatcagcaataaaccagccagccgga
agggccgagcgcagaagtggtcctgcaactttatccgcctccatccagtctattaattgttgcc
gggaagctagagtaagtagttcgccagttaatagtttgcgcaacgttgttgccattgctgcagg
catcgtggtgtcacgctcgtcgtttggtatggcttcattcagctccggttcccaacgatcaagg
cgagttacatgatcccccatgttgtgcaaaaaagcggttagctccttcggtcctccgatcgttg
tcagaagtaagttggccgcagtgttatcactcatggttatggcagcactgcataattctcttac
tgtcatgccatccgtaagatgcttttctgtgactggtgagtactcaaccaagtcattctgagaa
tagtgtatgcggcgaccgagttgctcttgcccggcgtcaacacgggataataccgcgccacata
gcagaactttaaaagtgctcatcattggaaaacgttcttcggggcgaaaactctcaaggatctt
accgctgttgagatccagttcgatgtaaccactcgtgcacccaactgatcttcagcatctttt
actttcaccagcgtttctgggtgagcaaaaacaggaaggcaaaatgccgcaaaaaagggaataa
gggcgacacggaaatgttgaatactcatactcttccttttcaatattattgaagcatttatca
gggttattgtctcatgagcggatacatatttgaatgtatttagaaaaataaacaaataggggtt
ccgcgcacatttccccgaaaagtgccacctgacgtctaagaaaccattattatcatgacattaa
cctataaaaataggcgtatcacgaggccctttcgtcttcaagaa
(SEQ ID NO:5)

Figure 7A

1-
cccgtcttactgtcgggaattcgcgttggccgattcattaatgcagctggcacgacaggtttcc
cgactggaaagcgggcagtgagcgcaacgcaattaatgtgagttagctcactcattaggcaccc
caggctttacactttatgcttccggctcgtatgttgtgtggaattgtgagcggataacaatttc
acacaggaaacagctatgaccatgattacgccaagcttgtatcgattaaataaggaggaataaa
ccatgtgtgcgacctcttctcaatttactcagattaccgagcataattcccgtcgttccgcaaa
ctatcagccaaacctgtggaatttcgaattcctgcaatccctggagaacgacctgaaagtggaa
aagctggaggagaaagcgaccaaactggaggaagaagttcgctgcatgatcaaccgtgtagaca
cccagccgctgtccctgctggagctgatcgacgatgtgcagcgcctgggtctgacctacaaatt
tgaaaaagacatcattaaagccctggaaaacatcgtactgctggacgaaaacaaaaagaacaaa
tctgacctgcacgcaaccgctctgtctttccgtctgctgcgtcagcacggtttcgaggtttctc
aggatgttttgagcgtttcaaggataaagaaggtggtttcagcggtgaactgaaaggtgacgt
ccaaggcctgctgagcctgtatgaagcgtcttacctgggtttcgagggtgagaacctgctggag
gaggcgcgtaccttttccatcacccacctgaagaacaacctgaaagaaggcattaataccaagg
ttgcagaacaagtgagccacgccctggaactgccatatcaccagcgtctgcaccgtctggaggc
acgttggttcctggataaatacgaaccgaaagaaccgcatcaccagctgctgctggagctggcg
aagctggattttaacatggtacagaccctgcaccagaaagagctgcaagatctgtcccgctggt
ggaccgagatgggcctggctagcaaactggatttgtacgcgaccgcctgatggaagtttattt
ctgggcactgggtatggcgccagaccgcagtttggtgaatgtcgcaaagctgttactaaaatg
tttggtctggtgacgatcatcgatgacgtgtatgacgtttatggcactctggacgaactgcaac
tgttcaccgatgctgtagagcgctgggacgttaacgctattaacaccctgccggactatatgaa
actgtgtttcctggcactgtacaacaccgttaacgacacgtcctattctattctgaaagagaaa
ggtcataacaacctgtcctatctgacgaaaagctggcgtgaactgtgcaaagcctttctgcaag
aggcgaaatggtccaacaacaaaattatcccggctttctccaagtacctggaaaacgccagcgt
ttcctcctccggtgtagcgctgctggcgccgtcttacttttccgtatgccagcagcaggaagac
atctccgaccacgcgctgcgttccctgaccgacttccatggtctggtgcgttctagctgcgtta
tcttccgcctgtgcaacgatctggccacctctgcggcggagctggaacgtggcgagactaccaa
ttctatcattagctacatgcacgaaaacgatggtaccagcgaggaacaggcccgcgaagaactg
cgtaaactgatcgacgccgaatggaaaaagatgaatcgtgaacgcgttagcgactccaccctgc
tgcctaaagcgttcatggaaatcgcagttaacatggcacgtgtttcccactgcacctaccagta
tggcgatggtctgggtcgcccagactacgcgactgaaaaccgcatcaaactgctgctgattgac
cctttcccgattaaccagctgatgtatgtctaactgcaggtcgactctagaggatccccgggta
ccgagctcgaattcactggccgtcgttttacaacgtcgtgactgggaaaaccctggcgttaccc
aacttaatcgccttgcagcacatcccctttcgccagctggcgtaatagcgaagaggcccgcac
cgatcgcccttcccaacagttgcgcagcctgaatggcgaatggcgcctgatgcggtattttctc
cttacgcatctgtgcggtatttcacaccgcatatggtgcactctcagtacaatctgctctgatg
ccgcatagttaagccagccccgacacccgccaacacccgctgacgagcttagtaaagccctcgc
tagattttaatgcggatgttgcgattacttcgccaactattgcgataacaagaaaaagccagcc
tttcatgatatatctcccaatttgtgtagggcttattatgcacgcttaaaaataataaaagcag
acttgacctgatagtttggctgtgagcaattatgtgcttagtgcatctaacgcttgagttaagc
cgcgccgcgaagcggcgtcggcttgaacgaattgttagacattatttgccgactaccttggtga
tctcgcctttcacgtagtggacaaattcttccaactgatctgcgcgcgaggccaagcgatcttc
ttcttgtccaagataagcctgtctagcttcaagtatgacgggctgatactgggccggcaggcgc
tccattgcccagtcggcagcgacatccttcggcgcgattttgccggttactgcgctgtaccaaa
tgcgggacaacgtaagcactacatttcgctcatcgccagcccagtcgggcggcgagttccatag

Figure 7B

```
cgttaaggtttcatttagcgcctcaaatagatcctgttcaggaaccggatcaaagagttcctcc
gccgctggacctaccaaggcaacgctatgttctcttgcttttgtcagcaagatagccagatcaa
tgtcgatcgtggctggctcgaagatacctgcaagaatgtcattgcgctgccattctccaaattg
cagttcgcgcttagctggataacgccacggaatgatgtcgtcgtgcacaacaatggtgacttct
acagcgcggagaatctcgctctctccaggggaagccgaagtttccaaaaggtcgttgatcaaag
ctcgccgcgttgtttcatcaagccttacggtcaccgtaaccagcaaatcaatatcactgtgtgg
cttcaggccgccatccactgcggagccgtacaaatgtacggccagcaacgtcggttcgagatgg
cgctcgatgacgccaactacctctgatagttgagtcgatacttcggcgatcaccgcttccctca
tgatgtttaactttgttttagggcgactgccctgctgcgtaacatcgttgctgctccataacat
caaacatcgacccacggcgtaacgcgcttgctgcttggatgcccgaggcatagactgtacccca
aaaaaacagtcataacaagccatgaaaaccgccactgcgccgttaccaccgctgcgttcggtca
aggttctggaccagttgcgtgagcgcatacgctacttgcattacagcttacgaaccgaacaggc
ttatgtccactgggttcgtgccttcatccgtttccacggtgtgcgtcacccggcaaccttgggc
agcagcgaagtcgaggcatttctgtcctggctggcgaacgagcgcaaggtttcggtctccacgc
atcgtcaggcattggcggccttgctgttcttctacggcaaggtgctgtgcacggatctgccctg
gcttcaggagatcggaagacctcggccgtcgcggcgcttgccggtggtgctgaccccggatgaa
gtggttcgcatcctcggttttctggaaggcgagcatcgtttgttcgcccagcttctgtatggaa
cgggcatgcggatcagtgagggtttgcaactgcgggtcaaggatctggatttcgatcacggcac
gatcatcgtgcgggagggcaagggctccaaggatcgggccttgatgttacccgagagcttggca
cccagcctgcgcgagcaggggaattaattcccacgggttttgctgcccgcaaacgggctgttct
ggtgttgctagtttgttatcagaatcgcagatccggcttcagccggtttgccggctgaaagcgc
tatttcttccagaattgccatgattttttccccacgggaggcgtcactggctcccgtgttgtcg
gcagctttgattcgataagcagcatcgcctgtttcaggctgtctatgtgtgactgttgagctgt
aacaagttgtctcaggtgttcaatttcatgttctagttgctttgttttactggtttcacctgtt
ctattaggtgttacatgctgttcatctgttacattgtcgatctgttcatggtgaacagctttga
atgcaccaaaaactcgtaaaagctctgatgtatctatctttttacaccgttttcatctgtgca
tatggacagttttcccttgatatgtaacggtgaacagttgttctacttttgtttgttagtctt
gatgcttcactgatagatacaagagccataagaacctcagatccttccgtatttagccagtatg
ttctctagtgtggttcgttgttttgcgtgagccatgagaacgaaccattgagatcatacttac
tttgcatgtcactcaaaaattttgcctcaaaactggtgagctgaattttgcagttaaagcatc
gtgtagtgttttcttagtccgttatgtaggtaggaatctgatgtaatggttgttggtattttg
tcaccattcattttatctggttgttctcaagttcggttacgagatccatttgtctatctagtt
caacttggaaaatcaacgtatcagtcgggcggcctcgcttatcaaccaccaatttcatattgct
gtaagtgtttaaatctttacttattggtttcaaaacccattggttaagccttttaaactcatgg
tagttattttcaagcattaacatgaacttaaattcatcaaggctaatctctatatttgccttgt
gagttttcttttgtgttagttcttttaataaccactcataaatcctcatagagtatttgttttc
aaaagacttaacatgttccagattatattttatgaatttttttaactggaaaagataaggcaat
atctcttcactaaaaactaattctaattttcgcttgagaacttggcatagtttgtccactgga
aaatctcaaagcctttaaccaaggattcctgatttccacagttctcgtcatcagctctctggt
tgctttagctaatacaccataagcattttccctactgatgttcatcatctgagcgtattggtta
taagtgaacgataccgtccgttctttccttgtagggttttcaatcgtggggttgagtagtgcca
cacagcataaaattagcttggtttcatgctccgttaagtcatagcgactaatcgctagttcatt
tgctttgaaaacaactaattcagacatacatctcaattggtctaggtgattttaatcactatac
caattgagatgggctagtcaatgataattactagtccttttcctttgagttgtgggtatctgta
```

Figure 7C

Aattctgctagacctttgctggaaaacttgtaaattctgctagaccctctgtaaattccgctag
acctttgtgtgtttttttgtttatattcaagtggttataatttatagaataaagaaagaataa
aaaaagataaaaagaatagatcccagccctgtgtataactcactactttagtcagttccgcagt
attacaaaaggatgtcgcaaacgctgtttgctcctctacaaaacagaccttaaaaccctaaagg
cttaagtagcaccctcgcaagctcgggcaaatcgctgaatattccttttgtctccgaccatcag
gcacctgagtcgctgtcttttttcgtgacattcagttcgctgcgctcacggctctggcagtgaat
ggggtaaatggcactacaggcgccttttatggattcatgcaaggaaactacccataatacaag
aaaagcccgtcacgggcttctcagggcgttttatggcgggtctgctatgtggtgctatctgact
ttttgctgttcagcagttcctgccctctgattttccagtctgaccacttcggattatcccgtga
caggtcattcagactggctaatgcacccagtaaggcagcggtatcatcaacaggctta
(SEQ ID NO:7)

Figure 12A 1-
gaattgctccatttctcttctgctatcaaaataacagactcgtgatttccaaacgagctttcaa
aaaagcctctgcccttgcaaatcggatgcctgtctataaaattcccgatattggttaaacagc
ggcgcaatggcggccgcatctgatgtctttgcttggcgaatgttcatcttatttcttcctccct
ctcaataatttttcattctatcccttttctgtaaagtttattttcagaatactttatcatc
atgctttgaaaaaatatcacgataatatccattgttctcacggaagcacacgcaggtcatttga
acgaattttcgacaggaatttgccgggactcaggagcatttaacctaaaaaagcatgacatt
tcagcataatgaacatttactcatgtctatttcgttcttttctgtatgaaaatagttatttcg
agtctctacggaaatagcgagagatgatatacctaaatagagataaaatcatctcaaaaaatg
ggtctactaaaatattattccatctattacaataaattcacagaatagtcttttaagtaagtct
actctgaattttttaaaaggagagggtaaagagtgtgtgcgacctcttctcaatttactcaga
ttaccgagcataattcccgtcgttccgcaaactatcagccaaacctgtggaatttcgaattcct
gcaatccctggagaacgacctgaaagtggaaaagctggaggagaaagcgaccaaactggaggaa
gaagttcgctgcatgatcaaccgtgtagacacccagccgctgtccctgctggagctgatcgacg
atgtgcagcgcctgggtctgacctacaaatttgaaaaagacatcattaaagccctggaaacat
cgtactgctggacgaaaacaaaaagaacaaatctgacctgcacgcaaccgctctgtctttccgt
ctgctgcgtcagcacggtttcgaggtttctcaggatgttttgagcgtttcaaggataaagaag
gtggtttcagcggtgaactgaaaggtgacgtccaaggcctgctgagcctgtatgaagcgtctta
cctgggtttcgagggtgagaacctgctggaggaggcgcgtaccttttccatcacccacctgaag
aacaacctgaaagaaggcattaataccaaggttgcagaacaagtgagccacgccctggaactgc
catatcaccagcgtctgcaccgtctggaggcacgttggttcctggataaatacgaaccgaaaga
accgcatcaccagctgctgctggagctggcgaagctggattttaacatggtacagaccctgcac
cagaaagagctgcaagatctgtcccgctggtggaccgagatgggcctggctagcaaactggatt
ttgtacgcgaccgcctgatggaagtttattctgggcactgggtatggcgccagacccgcagtt
tggtgaatgtcgcaaagctgttactaaaatgtttggtctggtgacgatcatcgatgacgtgtat
gacgtttatggcactctggacgaactgcaactgttcaccgatgctgtagagcgctgggacgtta
acgctattaacaccctgccggactatatgaaactgtgtttcctggcactgtacaacaccgttaa
cgacacgtcctattctattctgaaagagaaaggtcataacaacctgtcctatctgacgaaaagc
tggcgtgaactgtgcaaagcctttctgcaagaggcgaaatggtccaacaacaaaattatcccgg
ctttctccaagtacctggaaaacgccagcgtttcctcctccggtgtagcgctgctggcgccgtc
ttacttttccgtatgccagcagcaggaagacatctccgaccacgcgctgcgttccctgaccgac
ttccatggtctggtgcgttctagctgcgttatcttccgcctgtgcaacgatctggccacctctg
cggcggagctggaacgtggcgagactaccaattctatcattagctacatgcacgaaaacgatgg
taccagcgaggaacaggcccgcgaagaactgcgtaaactgatcgacgccgaatggaaaagatg
aatcgtgaacgcgttagcgactccaccctgctgcctaaagcgttcatggaaatcgcagttaaca
tggcacgtgtttcccactgcacctaccagtatggcgatggtctgggtcgcccagactacgcgac
tgaaaaccgcatcaaactgctgctgattgaccctttcccgattaaccagctgatgtatgtctaa
aaaaaaccggccttggccccgccggttttttattattttcttcctccgcatgttcaatccgct
ccataatcgacggatggctccctctgaaattttaacgagaaacggcgggttgacccggctcag
tcccgtaacggccaagtcctgaaacgtctcaatcgccgcttcccggtttccggtcagctcaatg
ccgtaacggtcggcggcgttttcctgataccgggagacggcattcgtaatcggatcctctagag
tcgacctgcaggcatgcaagctttgcctcgcgcgtttcggtgatgacggtgaaaacctctgaca
catgcagctcccggagacggtcacagcttgtctgtaagcggatgccgggagcagacaagcccgt
cagggcgcgtcagcgggtgttggcgggtgtcggggcgcagccatgacccagtcacgtagcgata

Figure 12B gcggagtgtatactggcttaactatgcggcatcagagcagattgtactgagagtgcaccatatg
cggtgtgaaataccgcacagatgcgtaaggagaaaataccgcatcaggcgctcttccgcttcct
cgctcactgactcgctgcgctcggtcgttcggctgcggcgagcggtatcagctcactcaaaggc
ggtaatacggttatccacagaatcaggggataacgcaggaaagaacatgtgagcaaaaggccag
caaaaggccaggaaccgtaaaaaggccgcgttgctggcgtttttccataggctccgcccccctg
acgagcatcacaaaaatcgacgctcaagtcagaggtggcgaaacccgacaggactataaagata
ccaggcgtttccccctggaagctccctcgtgcgctctcctgttccgaccctgccgcttaccgga
tacctgtccgcctttctcccttcgggaagcgtggcgctttctcaatgctcacgctgtaggtatc
tcagttcggtgtaggtcgttcgctccaagctgggctgtgtgcacgaaccccccgttcagcccga
ccgctgcgccttatccggtaactatcgtcttgagtccaacccggtaagacacgacttatcgcca
ctggcagcagccactggtaacaggattagcagagcgaggtatgtaggcggtgctacagagttct
tgaagtggtggcctaactacggctacactagaaggacagtatttggtatctgcgctctgctgaa
gccagttaccttcggaaaaagagttggtagctcttgatccggcaaacaaaccaccgctggtagc
ggtggtttttttgtttgcaagcagcagattacgcgcagaaaaaaaggatctcaagaagatcctt
tgatcttttctacggggtctgacgctcagtggaacgaaaactcacgttaagggattttggtcat
gagattatcaaaaggatcgaagtcggttcagaaaagaaggatatggatctggagctgtaata
·taaaaaccttcttcaactaacggggcaggttagtgacattagaaaaccgactgtaaaaagtaca
gtcggcattatctcatattataaaagccagtcattaggcctatctgacaattcctgaatagagt
tcataaacaatcctgcatgataaccatcacaaacagaatgatgtacctgtaaagatagcggtaa
atatattgaattacctttattaatgaattttcctgctgtaataatgggtagaaggtaattacta
ttattattgatatttaagttaaacccagtaaatgaagtccatggaataatagaaagagaaaaag
cattttcaggtataggtgttttgggaaacaatttaaaagaaccattatatttctctacatcaga
aaggtataaatcataaaactctttgaagtcattctttacaggagtccaaataccagagaatgtt
ttagatacaccatcaaaaattgtataaagtggctctaacttatcccaataacctaactctccgt
cgctattgtaaccagttctaaaagctgtatttgagtttatcacccttgtcactaagaaaataaa
tgcagggtaaaatttatatccttcttgttttatgtttcggtataaaacactaatatcaatttct
gtggttatactaaaagtcgtttgttggttcaaataatgattaaatatctctttctcttccaat
tgtctaaatcaattttattaaagttcatttgatatgcctcctaaatttttatctaaagtgaatt
taggaggcttacttgtctgctttcttcattagaatcaatcctttttaaagtcaatattactgt
aacataaatatatattttaaaaatatcccactttatccaattttcgtttgttgaactaatgggt
gctttagttgaagaataaagaccacattaaaaaatgtggtcttttgtgtttttttaaaggattt
gagcgtacgcgaaaaatccttttctttctttcttatcttgataataagggtaactattgccggt
tgtccattcatggctgaactctgcttcctctgttgacatgacacacatcatctcaatatccgaa
tagggcccatcagtctgacgaccaagagagccataaacaccaatagccttaacatcatccccat
atttatccaatattcgttccttaatttcatgaacaatcttcattctttcttctctagtcattat
tattggtccattcactattctcattccttttcagataattttagatttgcttttctaaataag
aatatttggagagcaccgttcttattcagctattaataactcgtcttcctaagcatccttcaat
ccttttaataacaattatagcatctaatcttcaacaaactggcccgtttgttgaactactcttt
aataaaataattttccgttcccaattccacattgcaataatagaaaatccatcttcatcggct
.ttttcgtcatcatctgtatgaatcaaatcgccttcttctgtgtcatcaaggtttaattttttat
gtatttcttttaacaaaccaccataggagattaaccttttacggtgtaaaccttcctccaaatc
agacaaacgtttcaaattcttttcttcatcatcggtcataaaatccgtatcctttacaggatat
tttgcagtttcgtcaattgccgattgtatatccgatttatatttattttcggtcgaatcattt
gaacttttacatttggatcatagtctaatttcattgccttttccaaaattgaatccattgttt

Figure 12C

```
ttgattcacgtagttttctgttattctaaaataagttggttccacacataccattacatgcatg
tgctgattataagaattatctttattatttattgtcacatccgttgcacgcataaaaccaacaa
gattttattaattttttttatattgcatcattcggcgaaatccttgagccatatctgtcaaact
cttatttaattcttcgccatcataaacattttaactgttaatgtgagaaacaaccaacgaact
gttggcttttgtttaataacttcagcaacaaccttttgtgactgaatgccatgtttcattgctc
tcctccagttgcacattggacaaagcctggatttgcaaaaccacactcgataccactttctttc
gcctgtttcacgattttgtttatactctaatatttcagcacaatctttactctttcagccttt
ttaaattcaagaatatgcagaagttcaaagtaatcaacattagcgattttcttttctctccatg
gtctcacttttccacttttttgtcttgtccactaaaacccttgattttcatctgaataaatgct
actattaggacacataatattaaaagaaaccccatctatttagttatttgtttagtcacttat
aactttaacagatggggttttctgtgcaaccaatttaagggttttcaatactttaaaacaca
tacataccaacacttcaacgcacctttcagcaactaaaataaaaatgacgttatttctatatgt
atcaagataagaaagaacaagttcaaaaccatcaaaaaaagacacctttcaggtgctttttt
attttataaactcattccctgatctcgacttcgttctttttttacctctcggttatgagttagt
tcaaattcgttcttttttaggttctaaatcgtgttttttcttggaattgtgctgttttatcctta
ccttgtctacaaacccttaaaaacgttttaaaggcttttaagccgtctgtacgttccttaag
```

(SEQ ID NO:57)

Figure 13

```
ATGTGTGCAACCTCCTCCCAGTTTACTCAGATTACCGAGCATAATTCTCGACGATCTGCTAACT
ACCAGCCGAACCTTTGGAACTTTGAGTTTCTCCAGTCTCTCGAAAATGACCTGAAGGTGGAAAA
GCTCGAGGAGAAGGCGACCAAACTCGAGGAGGAGGTGCGATGTATGATCAACAGAGTTGACACC
CAACCCCTGTCTTTGCTGGAGCTGATCGACGATGTGCAGCGGTTGGGTTTGACTTATAAATTCG
AGAAGGACATTATCAAGGCACTGGAGAACATTGTGCTCCTCGACGAGAACAAGAAGAACAAGTC
TGATCTTCACGCTACCGCTCTCTCTTTCCGACTTCTTCGACAACACGGCTTCGAGGTGTCGCAG
GACGTCTTCGAGAGATTTAAGGACAAGGAGGGAGGATTTAGCGGCGAGCTGAAGGGAGACGTTC
AGGGTCTTCTCTCCTTGTACGAGGCGTCCTACCTGGGATTCGAGGGAGAGAACCTCCTGGAGGA
AGCTCGTACATTTTCCATCACTCACCTTAAGAATAACCTTAAGGAGGGAATTAACACCAAGGTG
GCCGAGCAGGTTTCTCACGCCCTGGAGCTCCCCTACCACCAACGGCTCCATAGACTGGAGGCTC
GTTGGTTCCTGGACAAATATGAGCCAAAGGAGCCTCATCATCAGTTGCTGTTGGAGTTGGCCAA
GCTGGACTTCAATATGGTTCAGACGCTGCACCAAAAGGAGTTGCAGGACCTGTCTCGATGGTGG
ACCGAGATGGGATTGGCCTCGAAGCTGGATTTTGTCCGTGACCGACTTATGGAGGTCTATTTTT
GGGCCCTTGGAATGGCGCCTGACCCCCAGTTCGGAGAGTGCCGGAAGGCGGTGACGAAGATGTT
CGGTCTTGTGACTATCATCGACGACGTCTACGATGTCTACGGCACACTCGACGAGTTGCAGCTG
TTCACTGACGCCGTCGAGCGATGGGATGTGAACGCCATTAATACTCTCCCTGACTATATGAAGC
TGTGCTTCCTGGCTCTGTACAACACTGTCAACGATACCTCGTACTCTATCCTCAAGGAGAAGGG
ACACAACAATCTCTCCTACTTGACCAAATCCTGGCGAGAACTGTGCAAGGCTTTTCTGCAGGAG
GCTAAATGGTCCAATAACAAGATCATTCCTGCTTTTTCTAAATACCTGGAAAATGCCTCGGTGT
CGAGCTCTGGCGTCGCCCTTCTGGCCCCTTCCTACTTCTCCGTCTGCCAGCAGCAGGAGGATAT
TTCCGATCATGCTCTTAGATCGCTGACCGATTTTCACGGCCTCGTGCGATCTTCCTGCGTGATT
TTTCGGTTGTGTAATGACCTTGCGACCTCTGCTGCTGAGCTGGAACGAGGCGAGACTACAAATT
CCATTATTTCTTACATGCACGAAAACGATGGAACATCTGAAGAACAGGCTAGAGAGGAACTGCG
AAAGTTGATCGACGCCGAGTGGAAGAAGATGAACAGAGAGCGGGTGTCCGACTCTACCCTGCTT
CCCAAGGCCTTCATGGAGATCGCCGTGAACATGGCTCGAGTTTCCCATTGTACTTACCAGTACG
GTGACGGCCTGGGTCGTCCGGACTACGCTACAGAGAACCGAATCAAGCTGCTGCTCATCGACCC
CTTCCCTATCAACCAATTGATGTACGTGTAA
```
(SEQ ID NO:8)

Figure 15A

```
   1 TCGACCGGTG AGAAGAACAG CATCGGGACA AGGGAAGGAA GAACAAAGAC AAAGAAAACA
  61 AAAGAAAGCA ATTGAAAACA AAACAAAACA ATTTTCATTC CTTCTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCCAACC TCCCATTTCC TCCTTACGGC CCGATAGCGA
 301 TCGTCTTTCC CTCGCTATCA CTCGCTACCG GCCCCTCCTC TGCACCGTAA CCTCCTACGT
 361 ATTTACCATA TCATAAAGTT TTTTCCGACG CTTATCGCTG ACCCCTGTC GCCCTCCTAT
 421 TGGCTTCCGG ATTATCTTCT TGTCCATAAG GTGATCCATG CTTCCTGAAG ATTCCCGAAA
 481 TGTGTCCACT TTGGCGGGGA ATCATTCCAT CCACTTCTTT CTCTCTCGCT TTCCTCATTC
 541 GGCGCTCCCC TTCCGCGTCT CATTGGTCTT CCGCTCCGTT TTTGCTTTGC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG CCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC CTTCGTGTTT ACCAAAGTTG GAACACTTTT GCTAATCCTG ATAGACCCAA
 901 CCTTAAGAAG AGAAATGATA CACCTGCAAG TGGATATCAA GTTGAAAAAG TCGTAATTTT
 961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGAG GCACAAACTC CTATAGATAA
1381 TTTGAATCAA CATTACATCC CCTTTTAGC TTTAATGAAT ACAACATTAA ATTTTAGTAC
1441 TTCTGCCTGG TGCCAAAAAC ACTCTGCTGA TAAATCCTGT GACCTAGGTT TATCCATGCC
1501 TTCTAAATTG TCCATAAAAG ATAATGGTAA CAAGGTCGCA TTGGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAATTCCAG GTTGCAATGA TCAAACAGCC GAGGGTTACT GTCCTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCCATCT ACCATCTCGG GGTTAGAGTG
2401 GAAAGAAAGT CTTGTTCTTT TATTTCCTTT TTTCCATCTT CAAGGCTTTT CTTTTCTTCC
2461 TCCTCCTCGT TCATCTTGAG GTTTGACGTG TCTGTTTAGA ATTTTGAGCT GTTGCAGCAT
2521 CTTATTTTTT GTTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTGAGCT ATAGTTAAGT GTAAGGGCCC TACTGCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGACTTGC TCGGCACCTT ACGAGAAATC AAAGTCTTTG GGTTCCGGGG GGAGTATGGT
2881 CGCAGGCCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCGA TAACGAACGA GACCTTAACC TGCTAAATAG CTGGATCAGC
3121 CATTTTGGCT GATCATTAGC TTCTTAGAGG GACTATTGGC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

Figure 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCGGTA
3721 GTCTAATATC TAGCAAAAAT CTTTTGGGTG AAAAGGCTTG CAATTTCACG ACACCGAACT
3781 ATTTGTCATT TTTTAATAAG GAAGTTTTCC ATAAATTCCT GTAATTCTCG GTTGATCTAA
3841 TTGAAAAGAG TAGTTTTGCA TCACGATGAG GAGGGCTTTT GTAGAAAGAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATTGGATT ATGTCAGGAA AAGAACGACA ATTTTGCATC
4561 CAAATTGTCT AAATTTTAGA GTTGCTTGAA AACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAAGA GACCGCCTCG
5041 TTTCTTTTTC TTCGTCGAAA AAGGCAATAA AAATTTTTAT CACGTTTCTT TTTCTTGAAA
5101 TTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC AGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTTCTTT TTTTTCTGTA
5941 CAGACGCGAG CTTCCCAGTA AATGTGCCAT CTCGTAGGCA GAAAACGGTT CCCCCGTAGG
6001 GTCTCTCTCT TGGCCTCCTT TCTAGGTCGG GCTGATTGCT CTTGAAGCTC TCTAGGGGGG
6061 CTCACACCAT AGGCAGATAA CGTTCCCCAC CGGCTCGCCT CGTAAGCGCA CAAGGACTGC
6121 TCCCAAAGAT CCTAGGCGGG ATTTTGCCGA TTTCGGCCTA AAGGAACCGG AACACGTAGA
6181 AAGCCAGTGC GCAGAAACGG TGCTGACCGC GGATGAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

Figure 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```

(SEQ ID NO:11)

Figure 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTGACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GGCTTCGAGG TGTCGCAGGA CGTCTTCGAG AGATTTAAGG
 421 ACAAGGAGGG AGGATTTAGC GGCGAGCTGA AGGGAGACGT TCAGGGTCTT CTCTCCTTGT
 481 ACGAGGCGTC CTACCTGGGA TTCGAGGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCAG
1141 AACTGTGCAA GGCTTTTCTG CAGGAGGCTA AATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTCCGA TCATGCTCTT AGATCGCTGA
1321 CCGATTTTCA CGGCCTCGTG CGATCTTCCT GCGTGATTTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
```

(SEQ ID NO:12)

Figure 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 GTCGTTGTAT GAGGCCTCGT TCCTGGCTCT TGAGGGCGAG AATATTCTGG ATGAGGCTCG
 541 GGTTTTCGCT ATTTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAG CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGGCAG TGGGTGTGGC CTTTGAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA ACAAATCTAC
1201 TCCTACATTT GATGACTACT TCGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
```

(SEQ ID NO:13)

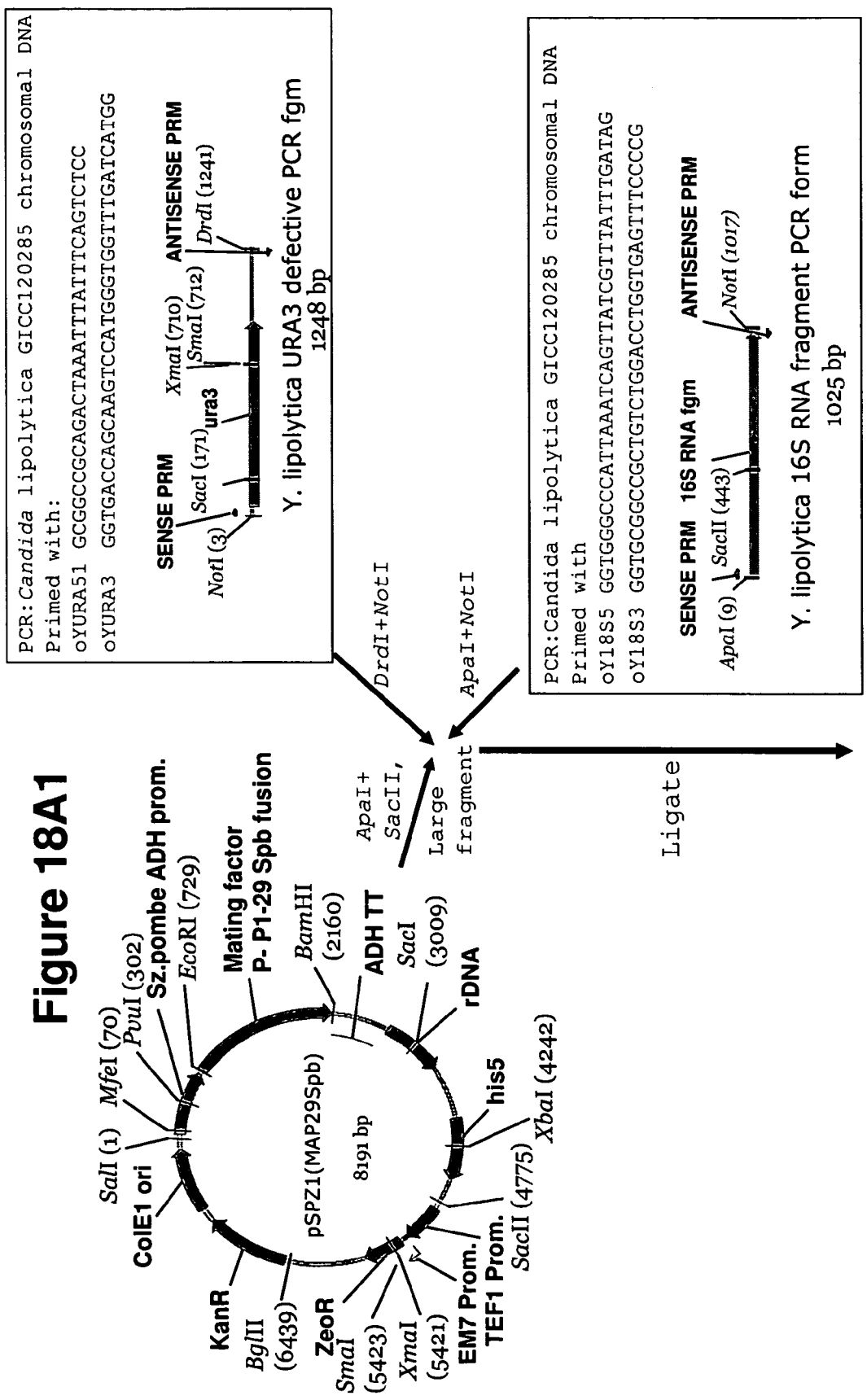

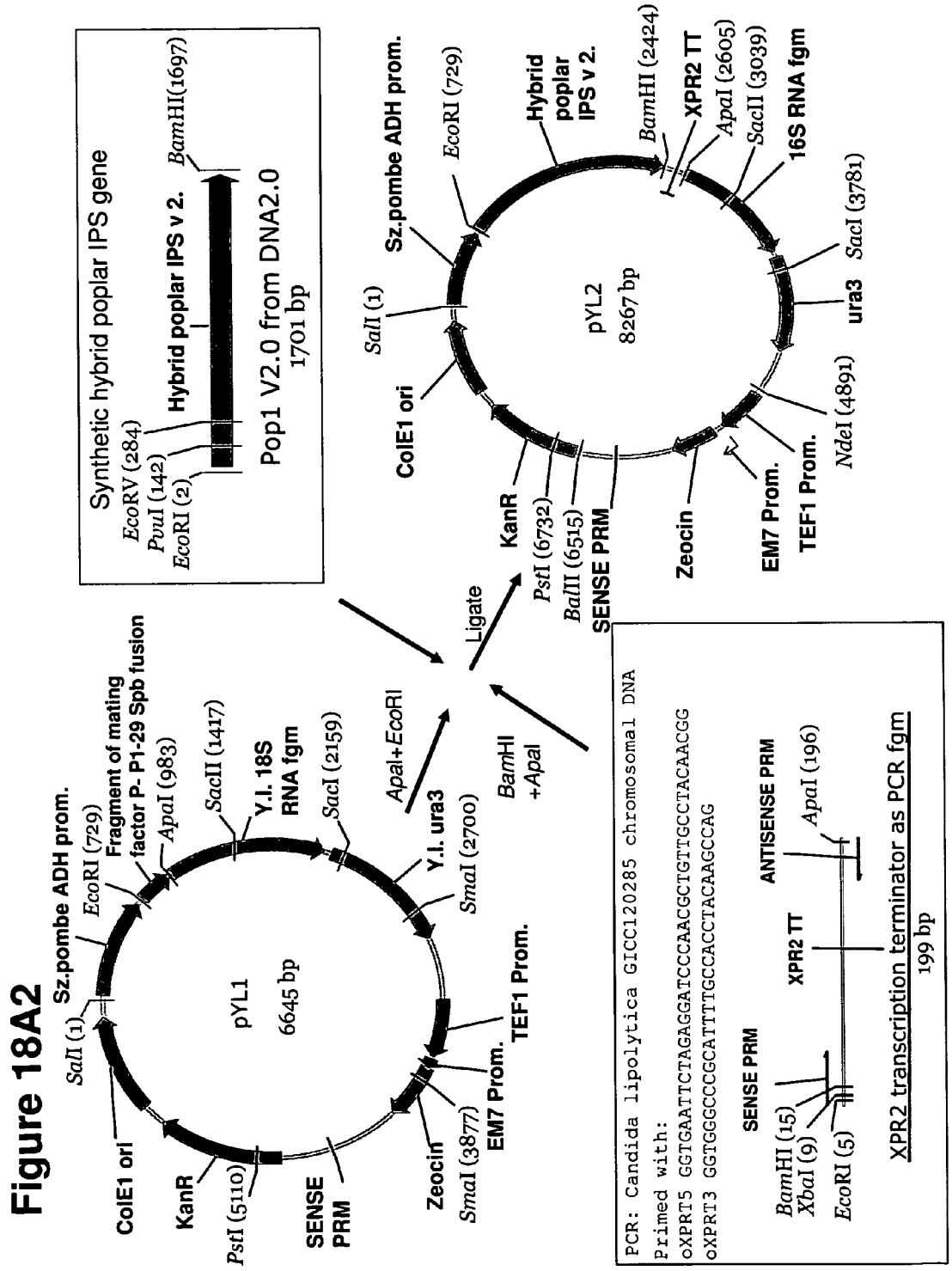
Figure 18A2

Y. lipolytica CLIB122:: pYLA(KZ1)

Figure 22A 1-
gctggtaccatatgggaattcgaagctttctagaacaaaaactcatctcagaagaggatctgaa
tagcgccgtcgaccatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtgggtctcccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg
agggtggcgggcaggacgcccgccataaactgccaggcatcaaattaagcagaaggccatcctg
acggatggccttttttgcgtttctacaaactcttttgtttattttctaaatacattcaaatat
gtatccgcttaaccggaattgccagctggggcgccctctggtaaggttgggaagccctgcaaag
taaactggatggctttctcgccgccaaggatctgatggcgcaggggatcaagctctgatcaaga
gacaggatgaggatcgtttcgcatgattgaacaagatggattgcacgcaggttctccggccgct
tgggtggagaggctattcggctatgactgggcacaacagacaatcggctgctctgatgccgccg
tgttccggctgtcagcgcaggggcgcccggttctttttgtcaagaccgacctgtccggtgccct
gaatgaactgcaagacgaggcagcgcggctatcgtggctggccacgacgggcgttccttgcgca
gctgtgctcgacgttgtcactgaagcgggaagggactggctgctattgggcgaagtgccggggc
aggatctcctgtcatctcaccttgctcctgccgagaaagtatccatcatggctgatgcaatgcg
gcggctgcatacgcttgatccggctacctgcccattcgaccaccaagcgaaacatcgcatcgag
cgagcacgtactcggatggaagccggtcttgtcgatcaggatgatctggacgaagagcatcagg
ggctcgcgccagccgaactgttcgccaggctcaaggcgagcatgcccgacggcgaggatctcgt
cgtgacccatggcgatgcctgcttgccgaatatcatggtggaaaatggccgcttttctggattc
atcgactgtggccggctgggtgtggcggaccgctatcaggacatagcgttggctacccgtgata
ttgctgaagagcttggcggcgaatgggctgaccgcttcctcgtgctttacggtatcgccgctcc
cgattcgcagcgcatcgccttctatcgccttcttgacgagttcttctgacatgaccaaaatccc
ttaacgtgagttttcgttccactgagcgtcagaccccgtagaaaagatcaaaggatcttcttga
gatccttttttttctgcgcgtaatctgctgcttgcaaacaaaaaaaccaccgctaccagcggtgg
tttgtttgccggatcaagagctaccaactctttttccgaaggtaactggcttcagcagagcgca
gataccaaatactgtccttctagtgtagccgtagttaggccaccacttcaagaactctgtagca
ccgcctacatacctcgctctgctaatcctgttaccagtggctgctgccagtggcgataagtcgt
gtcttaccgggttggactcaagacgatagttaccggataaggcgcagcggtcgggctgaacggg
gggttcgtgcacacagcccagcttggagcgaacgacctacaccgaactgagatacctacagcgt
gagctatgagaaagcgccacgcttcccgaagggagaaaggcggacaggtatccggtaagcggca
gggtcggaacaggagagcgcacgagggagcttccaggggaaacgcctggtatctttatagtcc
tgtcgggtttcgccacctctgacttgagcgtcgatttttgtgatgctcgtcaggggggcggagc
ctatggaaaaacgccagcaacgcggcctttttacggttcctggccttttgctggccttttgctc
acatgttctttcctgcgttatcccctgattctgtggataaccgtattaccgcctttgagtgagc
tgataccgctcgccgcagccgaacgaccgagcgcagcgagtcagtgagcgaggaagcggaagag
cgcctgatgcggtatttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgcctgacgggcttgtctgc
tcccggcatccgcttacagacaagctgtgaccgtctccgggagctgcatgtgtcagaggttttc
accgtcatcaccgaaacgcgcgaggcagcagatcaattcgcgcgcgaaggcgaagcggcatgca
tttacgttgacaccatcgaatggtgcaaaacctttcgcggtatggcatgatagcgcccggaaga

Figure 22B gagtcaattcagggtggtgaatgtgaaaccagtaacgttatacgatgtcgcagagtatgccggt
gtctcttatcagaccgtttcccgcgtggtgaaccaggccagccacgtttctgcgaaaacgcggg
aaaaagtggaagcggcgatggcggagctgaattacattcccaaccgcgtggcacaacaactggc
gggcaaacagtcgttgctgattggcgttgccacctccagtctggccctgcacgcgccgtcgcaa
attgtcgcggcgattaaatctcgcgccgatcaactgggtgccagcgtggtggtgtcgatggtag
aacgaagcggcgtcgaagcctgtaaagcggcggtgcacaatcttctcgcgcaacgcgtcagtgg
gctgatcattaactatccgctggatgaccaggatgccattgctgtggaagctgcctgcactaat
gttccggcgttatttcttgatgtctctgaccagacacccatcaacagtattatttctcccatg
aagacggtacgcgactgggcgtggagcatctggtcgcattgggtcaccagcaaatcgcgctgtt
agcgggcccattaagttctgtctcggcgcgtctgcgtctggctggctggcataaatatctcact
cgcaatcaaattcagccgatagcggaacgggaaggcgactggagtgccatgtccggttttcaac
aaaccatgcaaatgctgaatgagggcatcgttcccactgcgatgctggttgccaacgatcagat
ggcgctgggcgcaatgcgcgccattaccgagtccgggctgcgcgttggtgcggatatctcggta
gtgggatacgacgataccgaagacagctcatgttatatcccgccgtcaaccaccatcaaacagg
attttcgcctgctggggcaaaccagcgtggaccgcttgctgcaactctctcagggccaggcggt
gaagggcaatcagctgttgcccgtctcactggtgaaaagaaaaaccacctggcgcccaatacg
caaaccgcctctccccgcgcgttggccgattcattaatgcagctggcacgacaggtttcccgac
tggaaagcgggcagtgagcgcaacgcaattaatgtgagttagcgcgaattgatctggtttgaca
gcttatcatcgactgcacggtgcaccaatgcttctggcgtcaggcagccatcggaagctgtggt
atggctgtgcaggtcgtaaatcactgcataattcgtgtcgctcaaggcgcactcccgttctgga
taatgttttttgcgccgacatcataacggttctggcaaatattctgaaatgagctgttgacaat
taatcatccggctcgtataatgtgtggaattgtgagcggataacaatttcacacaggaaacagc
gccgctgagaaaagcgaagcggcactgctctttaacaatttatcagacaatctgtgtgggcac
tcgaccggaattatcgattaactttattattaaaaattaaagaggtatatattaatgtatcgat
taaataaggaggaataaaccatgtgtgcgacctcttctcaatttactcagattaccgagcataa
ttcccgtcgttccgcaaactatcagccaaacctgtggaatttcgaattcctgcaatccctggag
aacgacctgaaagtggaaaagctggaggagaaagcgaccaaactggaggaagaagttcgctgca
tgatcaaccgtgtagacacccagccgctgtccctgctggagctgatcgacgatgtgcagcgcct
gggtctgacctacaaatttgaaaagacatcattaaagccctggaaaacatcgtactgctggac
gaaaacaaaagaacaaatctgacctgcacgcaaccgctctgtctttccgtctgctgcgtcagc
acggtttcgaggtttctcaggatgttttgagcgtttcaaggataaagaaggtggtttcagcgg
tgaactgaaaggtgacgtccaaggcctgctgagcctgtatgaagcgtcttacctgggtttcgag
ggtgagaacctgctggaggaggcgcgtacctttccatcacccacctgaagaacaacctgaaag
aaggcattaataccaaggttgcagaacaagtgagccacgccctggaactgccatatcaccagcg
tctgcaccgtctggaggcacgttggttcctggataaatacgaaccgaaagaaccgcatcaccag
ctgctgctggagctggcgaagctggattttaacatggtacagaccctgcaccagaaagagctgc
aagatctgtcccgctggtggaccgagatgggcctggctagcaaactggattttgtacgcgaccg
cctgatggaagtttatttctgggcactgggtatggcgccagaccgcagtttggtgaatgtcgc
aaagctgttactaaaatgtttggtctggtgacgatcatcgatgacgtgtatgacgtttatggca
ctctggacgaactgcaactgttcaccgatgctgtagagcgctgggacgttaacgctattaacac
cctgccggactatatgaaactgtgtttcctggcactgtacaacaccgttaacgacacgtcctat
tctattctgaaagagaaaggtcataacaacctgtcctatctgacgaaaagctggcgtgaactgt
gcaaagcctttctgcaagaggcgaaatggtccaacaacaaaattatcccggctttctccaagta
cctggaaaacgccagcgtttcctcctccggtgtagcgctgctggcgccgtcttacttttccgta

Figure 22C

```
tgccagcagcaggaagacatctccgaccacgcgctgcgttccctgaccgacttccatggtctgg
tgcgttctagctgcgttatcttccgcctgtgcaacgatctggccacctctgcggcggagctgga
acgtggcgagactaccaattctatcattagctacatgcacgaaaacgatggtaccagcgaggaa
caggcccgcgaagaactgcgtaaactgatcgacgccgaatggaaaaagatgaatcgtgaacgcg
ttagcgactccaccctgctgcctaaagcgttcatggaaatcgcagttaacatggcacgtgtttc
ccactgcacctaccagtatggcgatggtctgggtcgcccagactacgcgactgaaaaccgcatc
aaactgctgctgattgaccctttcccgattaaccagctgatgtatgtctaactgcatcgccctt
aggaggtaaaaaaaatgactgccgacaacaatagtatgccccatggtgcagtatctagttacg
ccaaattagtgcaaaaccaaacacctgaagacattttggaagagtttcctgaaattattccatt
acaacaaagacctaatacccgatctagtgagacgtcaaatgacgaaagcggagaaacatgtttt
tctggtcatgatgaggagcaaattaagttaatgaatgaaaattgtattgttttggattgggacg
ataatgctattggtgccggtaccaagaaagtttgtcatttaatggaaaatattgaaaagggttt
actacatcgtgcattctccgtctttattttcaatgaacaaggtgaattacttttacaacaaaga
gccactgaaaaaataactttccctgatctttggactaacacatgctgctctcatccactatgta
ttgatgacgaattaggtttgaagggtaagctagacgataagattaagggcgctattactgcggc
ggtgagaaaactagatcatgaattaggtattccagaagatgaaactaagacaaggggtaagttt
cacttttaaacagaatccattacatggcaccaagcaatgaaccatggggtgaacatgaaattg
attacatcctattttataagatcaacgctaaagaaaacttgactgtcaacccaaacgtcaatga
agttagagacttcaaatggggtttcaccaaatgatttgaaaactatgtttgctgacccaagttac
aagtttacgccttggtttaagattatttgcgagaattacttattcaactggtgggagcaattag
atgacctttctgaagtggaaaatgacaggcaaattcatagaatgctataacaacgcgtcctgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgacctttt
gctgcgggtctggcgattggtgggtacaaaccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg
```

Figure 22D cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgca
(SEQ ID NO:20)

Figure 25A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatggatccgagctcggatccactagtaacggccgcc
agtgtgctggaattcgcccttaggaggtaaaaaaacatgtcattaccgttcttaacttctgcac
cgggaaaggttattattttggtgaacactctgctgtgtacaacaagcctgccgtcgctgctag
tgtgtctgcgttgagaacctacctgctaataagcgagtcatctgcaccagatactattgaattg
gacttcccggacattagctttaatcataagtggtccatcaatgatttcaatgccatcaccgagg
atcaagtaaactcccaaaaattggccaaggctcaacaagccaccgatggcttgtctcaggaact
cgttagtcttttggatccgttgttagctcaactatccgaatccttccactaccatgcagcgttt
tgtttcctgtatatgtttgtttgcctatgccccatgccaagaatattaagttttctttaaagt
ctactttacccatcggtgctgggttgggctcaagcgcctctatttctgtatcactggccttagc
tatggcctacttggggggggttaataggatctaatgacttggaaaagctgtcagaaaacgataag
catatagtgaatcaatgggccttcataggtgaaaagtgtattcacggtaccccttcaggaatag
ataacgctgtggccacttatggtaatgccctgctatttgaaaaagactcacataatggaacaat
aaacacaaacaattttaagttcttagatgatttcccagccattccaatgatcctaacctatact
agaattccaaggtctacaaaagatcttgttgctcgcgttcgtgtgttggtcaccgagaaatttc
ctgaagttatgaagccaattctagatgccatgggtgaatgtgccctacaaggcttagagatcat
gactaagttaagtaaatgtaaaggcaccgatgacgaggctgtagaaactaataatgaactgtat
gaacaactattggaattgataagaataaatcatggactgcttgtctcaatcggtgtttctcatc
ctggattagaacttattaaaaatctgagcgatgatttgagaattggctccacaaaacttaccgg
tgctggtggcggcggttgctctttgactttgttacgaagagacattactcaagagcaaattgac
agcttcaaaaagaaattgcaagatgatttagttacgagacatttgaaacagacttgggtggga
ctggctgctgtttgttaagcgcaaaaaatttgaataaagatcttaaaatcaaatccctagtatt
ccaattatttgaaaataaaactaccacaaagcaacaaattgacgatctattattgccaggaaac
acgaatttaccatggacttcataagctaatttgcgataggcctgcacccttaaggaggaaaaaa
acatgtcagagttgagagccttcagtgccccagggaaagcgttactagctggtggatatttagt
tttagatacaaaatatgaagcatttgtagtcggattatcggcaagaatgcatgctgtagcccat
ccttacggttcattgcaagggtctgataagtttgaagtgcgtgtgaaaagtaaacaatttaaag
atggggagtggctgtaccatataagtcctaaaagtggcttcattcctgtttcgataggcggatc
taagaacccttttcattgaaaaagttatcgctaacgtatttagctactttaaacctaacatggac
gactactgcaatagaaacttgttcgttattgatattttctctgatgatgcctaccattctcagg
aggatagcgttaccgaacatcgtggcaacagaagattgagttttcattcgcacagaattgaaga
agttcccaaaacagggctgggctcctcggcaggtttagtcacagttttaactacagctttggcc
tccttttttgtatcggacctggaaaataatgtagacaaatatagagaagttattcataatttag
cacaagttgctcattgtcaagctcagggtaaaattggaagcgggtttgatgtagcggcggcagc
atatggatctatcagatatagaagattcccacccgcattaatctctaatttgccagatattgga
agtgctacttacggcagtaaactggcgcatttggttgatgaagaagactggaatattacgatta
aaagtaaccatttaccttcgggattaactttatggatgggcgatattaagaatggttcagaaac
agtaaaactggtccagaaggtaaaaaattggtatgattcgcatatgccagaaagcttgaaaata

Figure 25B

```
tatacagaactcgatcatgcaaattctagatttatggatggactatctaaactagatcgcttac
acgagactcatgacgattacagcgatcagatatttgagtctcttgagaggaatgactgtacctg
tcaaaagtatcctgaaatcacagaagttagagatgcagttgccacaattagacgttcctttaga
aaaataactaaagaatctggtgccgatatcgaacctcccgtacaaactagcttattggatgatt
gccagaccttaaaaggagttcttacttgcttaatacctggtgctggtggttatgacgccattgc
agtgattactaagcaagatgttgatcttagggctcaaaccgctaatgacaaaagattttctaag
gttcaatggctggatgtaactcaggctgactgggtgttaggaaagaaaaagatccggaaactt
atcttgataaataacttaaggtagctgcatgcagaattcgcccttaaggaggaaaaaaaaatga
ccgtttacacagcatccgttaccgcacccgtcaacatcgcaacccttaagtattgggggaaaag
ggacacgaagttgaatctgcccaccaattcgtccatatcagtgactttatcgcaagatgacctc
agaacgttgacctctgcggctactgcacctgagtttaacgcgacactttgtggttaaatggag
aaccacacagcatcgacaatgaaagaactcaaaattgtctgcgcgacctacgccaattaagaaa
ggaaatggaatcgaaggacgcctcattgcccacattatctcaatggaaactccacattgtctcc
gaaaataacttttcctacagcagctggtttagcttcctccgctgctggctttgctgcattggtct
ctgcaattgctaagttataccaattaccacagtcaacttcagaaatatctagaatagcaagaaa
ggggtctggttcagcttgtagatcgttgtttggcggatacgtggcctgggaaatgggaaaagct
gaagatggtcatgattccatggcagtacaaatcgcagacagctctgactggcctcagatgaaag
cttgtgtcctagttgtcagcgatattaaaaaggatgtgagttccactcagggtatgcaattgac
cgtggcaacctccgaactatttaaagaaagaattgaacatgtcgtaccaaagagatttgaagtc
atgcgtaaagccattgttgaaaaagatttcgccacctttgcaaaggaaacaatgatggattcca
actctttccatgccacatgtttggactcttccctccaatattctacatgaatgacacttccaa
gcgtatcatcagttggtgccacaccattaatcagttttacggagaaacaatcgttgcatacacg
tttgatgcaggtccaaatgctgtgttgtactacttagctgaaaatgagtcgaaactctttgcat
ttatctataaattgtttggctctgttcctggatgggacaagaaatttactactgagcagcttga
ggctttcaaccatcaatttgaatcatctaactttactgcacgtgaattggatcttgagttgcaa
aaggatgttgccagagtgattttaactcaagtcggttcaggcccacaagaaacaaacgaatctt
tgattgacgcaaagactggtctaccaaaggaataagatcaattcgctgcatcgcccttaggagg
taaaaaaaatgactgccgacaacaatagtatgcccatggtgcagtatctagttacgccaaat
tagtgcaaaaccaaacacctgaagacattttggaagagtttcctgaaattattccattacaaca
aagacctaatacccgatctagtgagacgtcaaatgacgaaagcggagaaacatgttttctggt
catgatgaggagcaaattaagttaatgaatgaaaattgtattgttttggattgggacgataatg
ctattggtgccggtaccaagaaagtttgtcatttaatggaaaatattgaaaagggtttactaca
tcgtgcattctccgtctttattttcaatgaacaaggtgaattacttttacaacaaagagccact
gaaaaaataactttccctgatctttggactaacacatgctgctctcatccactatgtattgatg
acgaattaggtttgaagggtaagctagacgataagattaagggcgctattactgcggcggtgag
aaaactagatcatgaattaggtattccagaagatgaaactaagacaaggggtaagtttcacttt
ttaaacagaatccattacatggcaccaagcaatgaaccatggggtgaacatgaaattgattaca
tcctattttataagatcaacgctaaagaaacttgactgtcaacccaaacgtcaatgaagttag
agacttcaaatgggtttcaccaaatgatttgaaaactatgtttgctgacccaagttacaagttt
acgccttggtttaagattatttgcgagaattacttattcaactggtgggagcaattagatgacc
tttctgaagtggaaaatgacaggcaaattcatagaatgctataacaacgcgtcctgcattcgcc
cttaggaggtaaaaaaacatgtgtgcgacctcttctcaatttactcagattaccgagcataatt
cccgtcgttccgcaaactatcagccaaacctgtggaatttcgaattcctgcaatccctggagaa
cgacctgaaagtggaaaagctggaggagaaagcgaccaaactggaggaagaagttcgctgcatg
```

Figure 25C atcaaccgtgtagacacccagccgctgtccctgctggagctgatcgacgatgtgcagcgcctgg
gtctgacctacaaatttgaaaaagacatcattaaagccctggaaaacatcgtactgctggacga
aaacaaaaagaacaaatctgacctgcacgcaaccgctctgtctttccgtctgctgcgtcagcac
ggtttcgaggtttctcaggatgttttgagcgtttcaaggataaagaaggtggtttcagcggtg
aactgaaaggtgacgtccaaggcctgctgagcctgtatgaagcgtcttacctgggtttcgaggg
tgagaacctgctggaggaggcgcgtaccttttccatcacccacctgaagaacaacctgaaagaa
ggcattaataccaaggttgcagaacaagtgagccacgccctggaactgccatatcaccagcgtc
tgcaccgtctggaggcacgttggttcctggataaatacgaaccgaaagaaccgcatcaccagct
gctgctggagctggcgaagctggattttaacatggtacagaccctgcaccagaaagagctgcaa
gatctgtcccgctggtggaccgagatgggcctggctagcaaactggattttgtacgcgaccgcc
tgatggaagtttatttctgggcactgggtatggcgccagacccgcagtttggtgaatgtcgcaa
agctgttactaaaatgtttggtctggtgacgatcatcgatgacgtgtatgacgtttatggcact
ctggacgaactgcaactgttcaccgatgctgtagagcgctgggacgttaacgctattaacaccc
tgccggactatatgaaactgtgtttcctggcactgtacaacaccgttaacgacacgtcctattc
tattctgaaagagaaaggtcataacaacctgtcctatctgacgaaaagctggcgtgaactgtgc
aaagcctttctgcaagaggcgaaatggtccaacaacaaaattatcccggctttctccaagtacc
tggaaaacgccagcgtttcctcctccggtgtagcgctgctggcgccgtcttacttttccgtatg
ccagcagcaggaagacatctccgaccacgcgctgcgttccctgaccgacttccatggtctggtg
cgttctagctgcgttatcttccgcctgtgcaacgatctggccacctctgcggcggagctggaac
gtggcgagactaccaattctatcattagctacatgcacgaaaacgatggtaccagcgaggaaca
ggcccgcgaagaactgcgtaaactgatcgacgccgaatggaaaaagatgaatcgtgaacgcgtt
agcgactccaccctgctgcctaaagcgttcatggaaatcgcagttaacatggcacgtgtttccc
actgcacctaccagtatggcgatggtctgggtcgcccagactacgcgactgaaaaccgcatcaa
actgctgctgattgacccttttcccgattaaccagctgatgtatgtctaactgcagctggtacca
tatgggaattcgaagctttctagaacaaaaactcatctcagaagaggatctgaatagcgccgtc
gaccatcatcatcatcattgagtttaaacggtctccagcttggctgttttggcggatgaga
gaagattttcagcctgatacagattaaatcagaacgcagaagcggtctgataaaacagaatttg
cctggcggcagtagcgcggtggtcccacctgaccccatgccgaactcagaagtgaaacgccgta
gcgccgatggtagtgtggggtctccccatgcgagagtagggaactgccaggcatcaaataaaac
gaaaggctcagtcgaaagactgggcctttcgtttatctgttgtttgtcggtgaacgctctcct
gagtaggacaaatccgccgggagcggatttgaacgttgcgaagcaacggcccggagggtggcgg
gcaggacgcccgccataaactgccaggcatcaaattaagcagaaggccatcctgacggatggcc
ttttgcgtttctacaaactcttttgtttattttctaaatacattcaaatatgtatccgctt
aaccggaattgccagctggggcgccctctggtaaggttgggaagccctgcaaagtaaactggat
ggctttctcgccgccaaggatctgatggcgcaggggatcaagctctgatcaagagacaggatga
ggatcgtttcgcatgattgaacaagatggattgcacgcaggttctccggccgcttgggtggaga
ggctattcggctatgactgggcacaacagacaatcggctgctctgatgccgccgtgttccggct
gtcagcgcaggggcgcccggttcttttgtcaagaccgacctgtccggtgccctgaatgaactg
caagacgaggcagcgcggctatcgtggctggccacgacgggcgttccttgcgcagctgtgctcg
acgttgtcactgaagcgggaagggactggctgctattgggcgaagtgccggggcaggatctcct
gtcatctcaccttgctcctgccgagaaagtatccatcatggctgatgcaatgcggcggctgcat
acgcttgatccggctacctgcccattcgaccaccaagcgaaacatcgcatcgagcgagcacgta
ctcggatggaagccggtcttgtcgatcaggatgatctggacgaagagcatcagggctcgcgcc
agccgaactgttcgccaggctcaaggcgagcatgcccgacggcgaggatctcgtcgtgacccat

Figure 25D

```
ggcgatgcctgcttgccgaatatcatggtggaaaatggccgcttttctggattcatcgactgtg
gccggctgggtgtggcggaccgctatcaggacatagcgttggctaccgtgatattgctgaaga
gcttggcggcgaatgggctgaccgcttcctcgtgctttacggtatcgccgctcccgattcgcag
cgcatcgccttctatcgccttcttgacgagttcttctgacgcatgaccaaaatcccttaacgtg
agttttcgttccactgagcgtcagaccccgtagaaaagatcaaaggatcttcttgagatcctt
ttttctgcgcgtaatctgctgcttgcaaacaaaaaaccaccgctaccagcggtggtttgtttg
ccggatcaagagctaccaactcttttccgaaggtaactggcttcagcagagcgcagataccaa
atactgtccttctagtgtagccgtagttaggccaccacttcaagaactctgtagcaccgcctac
atacctcgctctgctaatcctgttaccagtggctgctgccagtggcgataagtcgtgtcttacc
gggttggactcaagacgatagttaccggataaggcgcagcggtcgggctgaacgggggttcgt
gcacacagcccagcttggagcgaacgacctacaccgaactgagatacctacagcgtgagctatg
agaaagcgccacgcttcccgaagggagaaaggcggacaggtatccggtaagcggcagggtcgga
acaggagagcgcacgagggagcttccaggggggaaacgcctggtatctttatagtcctgtcgggt
ttcgccacctctgacttgagcgtcgattttgtgatgctcgtcaggggggcggagcctatggaa
aaacgccagcaacgcggcctttttacggttcctggccttttgctggccttttgctcacatgttc
tttcctgcgttatccctgattctgtggataaccgtattaccgcctttgagtgagctgataccg
ctcgccgcagccaacgaccgagcgcagcgagtcagtgagcgaggaagcggaagagcgcctgat
gcggtattttctccttacgcatctgtgcggtatttcacaccgcatatggtgcactctcagtaca
atctgctctgatgccgcatagttaagccagtatacactccgctatcgctacgtgactgggtcat
ggctgcgccccgacacccgccaacacccgctgacgcgccctgacgggcttgtctgctcccggca
tccgcttacagacaagctgtgaccgtctccgggagctgcatgtgtcagaggttttcaccgtcat
caccgaaacgcgcgaggcagcagatcaattcgcgcgcgaaggcgaagcggcatgcatttacgtt
gacaccatcgaatggtgcaaaacctttcgcggtatggcatgatagcgcccggaagagagtcaat
tcagggtggtgaatgtgaaaccagtaacgttatacgatgtcgcagagtatgccggtgtctctta
tcagaccgtttcccgcgtggtgaaccaggccagccacgtttctgcgaaaacgcgggaaaaagtg
gaagcggcgatggcggagctgaattacattcccaaccgcgtggcacaacaactggcgggcaaac
agtcgttgctgattggcgttgccacctccagtctggccctgcacgcgccgtcgcaaattgtcgc
ggcgattaaatctcgcgccgatcaactgggtgccagcgtggtggtgtcgatggtagaacgaagc
ggcgtcgaagcctgtaaagcggcggtgcacaatcttctcgcgcaacgcgtcagtgggctgatca
ttaactatccgctggatgaccaggatgccattgctgtggaagctgcctgcactaatgttccggc
gttatttcttgatgtctctgaccagacacccatcaacagtattattttctcccatgaagacggt
acgcgactgggcgtggagcatctggtcgcattgggtcaccagcaaatcgcgctgttagcgggcc
cattaagttctgtctcggcgcgtctgcgtctggctggctggcataaatatctcactcgcaatca
aattcagccgatagcggaacgggaaggcgactggagtgccatgtccggttttcaacaaaccatg
caaatgctgaatgagggcatcgttcccactgcgatgctggttgccaacgatcagatggcgctgg
gcgcaatgcgcgccattaccgagtccgggctgcgcgttggtgcggatatctcggtagtgggata
cgacgataccgaagacagctcatgttatatcccgccgtcaaccaccatcaaacaggatttcgc
ctgctggggcaaaccagcgtggaccgcttgctgcaactctctcagggccaggcggtgaagggca
atcagctgttgcccgtctcactggtgaaagaaaaaccacctggcgcccaatacgcaaaccgc
ctctccccgcgcgttggccgattcattaatgcagctggcacgacaggtttcccgactggaaagc
gggcagtgagcgcaacgcaattaatgtgagttagcgcgaattgatctg
```
(SEQ ID NO:33)

Figure 27A

5'-
cccgtcttactgtcgggaattcgcgttggccgattcattaatgcagattctgaaatgagctgtt
gacaattaatcatccggctcgtataatgtgtggaattgtgagcggataacaatttcacacagga
aacagcgccgctgagaaaaagcgaagcggcactgctctttaacaatttatcagacaatctgtgt
gggcactcgaccggaattatcgattaactttattattaaaaattaaagaggtatatattaatgt
atcgattaaataaggaggaataaaccatggatccgagctcaggaggtaaaaaaacatgaaaaca
gtagttattattgatgcattacgaacaccaattggaaaatataaaggcagcttaagtcaagtaa
gtgccgtagacttaggaacacatgttacaacacaacttttaaaaagacattccactatttctga
agaaattgatcaagtaatctttggaaatgttttacaagctggaaatggccaaaatcccgcacga
caaatagcaataaacagcggtttgtctcatgaaattccgcaatgacggttaatgaggtctgcg
gatcaggaatgaaggccgttatttggcgaaacaattgattcaattaggagaagcggaagtttt
aattgctggcgggattgagaatatgtcccaagcacctaaattacaacgttttaattacgaaaca
gaaagctacgatgcgcctttttctagtatgatgtatgatggattaacggatgcctttagtggtc
aggcaatgggcttaactgctgaaaatgtggccgaaaagtatcatgtaactagagaagagcaaga
tcaatttctgtacattcacaattaaaagcagctcaagcacaagcagaagggatattcgctgac
gaaatagccccattagaagtatcaggaacgcttgtggagaaagatgaagggattcgccctaatt
cgagcgttgagaagctaggaacgcttaaaacagtttttaaagaagacggtactgtaacagcagg
gaatgcatcaaccattaatgatggggcttctgctttgattattgcttcacaagaatatgccgaa
gcacacggtcttccttatttagctattattcgagacagtgtggaagtcggtattgatccagcct
atatgggaatttcgccgattaaagccattcaaaaactgttagcgcgcaatcaacttactacgga
agaaattgatctgtatgaaatcaacgaagcatttgcagcaacttcaatcgtggtccaaagagaa
ctggctttaccagaggaaaaggtcaacatttatggtggcggtatttcattaggtcatgcgattg
gtgccacaggtgctcgtttattaacgagtttaagttatcaattaaatcaaaagaaaagaaata
tggagtggcttctttatgtatcggcggtggcttaggactcgctatgctactagagagacctcag
caaaaaaaaacagccgatttatcaaatgagtcctgaggaacgcctggcttctcttcttaatg
aaggccagatttctgctgatacaaaaaaagaatttgaaaatacggctttatcttcgcagattgc
caatcatatgattgaaaatcaaatcagtgaaacagaagtgccgatgggcgttggcttacattta
acagtggacgaaactgattatttggtaccaatggcgacagaagagccctcagttattgcggctt
tgagtaatggtgcaaaaatagcacaaggatttaaaacagtgaatcaacaacgcttaatgcgtgg
acaaatcgttttttacgatgttgcagatcccgagtcattgattgataaactacaagtaagagaa
gcggaagttttttcaacaagcagagttaagttatccatctatcgttaaacggggcggcggcttaa
gagatttgcaatatcgtacttttgatgaatcatttgtatctgtcgacttttagtagatgttaa
ggatgcaatgggggcaaatatcgttaacgctatgttggaaggtgtggccgagttgttccgtgaa
tggtttgcggagcaaaagattttattcagtattttaagtaattatgccacggagtcggttgtta
cgatgaaaacggctattccagtttcacgtttaagtaaggggagcaatggccgggaaattgctga
aaaaattgttttagcttcacgctatgcttcattagatccttatcgggcagtcacgcataacaaa
ggaatcatgaatggcattgaagctgtagttttagctacaggaaatgatacacgcgctgttagcg
cttcttgtcatgcttttgcggtgaaggaaggtcgctaccaaggcttgactagttggacgctgga
tggcgaacaactaattggtgaaatttcagttccgcttgctttagccacggttggcggtgccaca
aaagtcttacctaaatctcaagcagctgctgatttgttagcagtgacggatgcaaaagaactaa
gtcgagtagtagcggctgttggtttggcacaaaatttagcggcgttacgggccttagtctctga
aggaattcaaaaggacacatggctctacaagcacgttctttagcgatgacggtcggagctact
ggtaaagaagttgaggcagtcgctcaacaattaaaacgtcaaaaaacgatgaaccaagaccgag
ccatggctatttttaaatgatttaagaaaacaataaggaggtaaaaaaacatgacaattgggat

Figure 27B

```
tgataaaattagttttttttgtgccccettattatattgatatgacggcactggctgaagccaga
aatgtagacctggaaaatttcatattggtattgggcaagaccaaatggcggtgaacccaatca
gccaagatattgtgacatttgcagccaatgccgcagaagcgatcttgaccaaagaagataaaga
ggccattgatatggtgattgtcgggactgagtccagtatcgatgagtcaaaagcggccgcagtt
gtcttacatcgtttaatggggattcaaccttctgctcgctctttcgaaatcaaggaagcttgtt
acggagcaacagcaggcttacagttagctaagaatcacgtagccttacatccagataaaaagt
cttggtcgtagcggcagatattgcaaaatatggcttaaattctggcggtgagcctacacaagga
gctggggcggttgcaatgttagttgctagtgaaccgcgcattttggctttaaaagaggataatg
tgatgctgacgcaagatatctatgactttggcgtccaacaggccaccgtatcctatggtcga
tggtcctttgtcaaacgaaacctacatccaatcttttgcccaagtctgggatgaacataaaaaa
cgaaccggtcttgatttttgcagattatgatgctttagcgttccatattccttacacaaaaatgg
gcaaaaaagccttattagcaaaaatctccgaccaaactgaagcagaacaggaacgaattttagc
ccgttatgaagaaagtatcgtctatagtcgtcgcgtaggaaacttgtatacgggttcactttat
ctgggactcatttcccttttagaaaatgcaacgactttaaccgcaggcaatcaaattggtttat
tcagttatggttctggtgctgtcgctgaattttttcactggtgaattagtagctggttatcaaaa
tcatttacaaaaagaaactcatttagcactgctggataatcggacagaactttctatcgctgaa
tatgaagccatgtttgcagaaactttagacacagacattgatcaaacgttagaagatgaattaa
aatatagtatttctgctattaataataccgttcgttcttatcgaaactaagagatctgcagctg
gtaccatatgggaattcgaagcttgggcccgaacaaaaactcatctcagaagaggatctgaata
gcgccgtcgaccatcatcatcatcatcattgagtttaaacggtctccagcttggctgttttggc
ggatgagagaagattttcagcctgatacagattaaatcagaacgcagaagcggtctgataaaac
agaatttgcctggcggcagtagcgcggtggtcccacctgaccccatgccgaactcagaagtgaa
acgccgtagcgccgatggtagtgtggggtctcccatgcgagagtagggaactgccaggcatca
aataaaacgaaaggctcagtcgaaagactgggcctttcgttttatctgttgtttgtcggtgaac
gctctcctgagtaggacaaatccgccgggagcggatttgaacgttgcgaagcaacggcccggag
ggtggcgggcaggacgcccgccataaactgccaggcatcaaattaagcagaaggccatcctgac
ggatggcctttttgcgtttctacaaactcttttttgtttatttttctaaatacattcaaatatgt
atccgctcatgagacaataaccctgataaatgcttcaataatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc
tgatgccgcatagttaagccagccccgacacccgccaacacccgctgacgagcttagtaaagcc
ctcgctagattttaatgcggatgttgcgattacttcgccaactattgcgataacaagaaaaagc
cagcctttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
```

Lower Pathway Bacillus Cassette
9371 bp

Figure 29A

5'-
tgtaacctttgctttcaaatgagtagaaataatgcacatccatgtttgtatcgtgcaaataaag
tgtttcatccgtaggaaaaaatgactttagtatctgttccgcttttctgatgaaatgtgctcc
ccgacaaaattgaatgaatcatggacatttgctggctttgatacagcgaaagcagccgttccta
tgttatatatcggatttaacagcaggacaaaaaacaccatgacagccatcgtcacccacttatt
cacacgcacataaaccttttcctgacttttggaacagatgatagctcatcaaaaatcccgccatt
gccaaataaatcgtatatggcattactgcaccataatcttttgagatttgattgggatatggcg
caagcagcaagacaagcagtccgataatcagcgtataaaataagcctagtaagatcttatccgt
tctccaatacagcttgaaaaacactacattcaacgcaatgggaagagtgatgatgaaaaacaga
aacacgaatgcaatcggctccatccatccgggtattccttccaatacgaaagaaactaaaaa
tcatttgtacgatcggcaaactgacaacagcaaggtcgaacgtataaaacttacccttccgcc
atgatcacgcggcatcagcatatagtgaaagccgtcagcagcacatatccgtataacaaaaaa
tgcagcagcggcagcagttcttttccgtcctctcttaagtaagcgctggtgaagtttgttgatt
gcacctggtgaataagttcaacagacactccgccagcagcacaatccgcaatataacacccgc
caagaacattgtgcgctgccggtttatttgggatgatgcaccaaaagatataagcccgccaga
acaacaattgaccattgaatcagcagggtgctttgtctgcttaatataaaataacgttcgaaat
gcaatacataatgactgaataactccaacacgaacaacaactccattttcttctgctatcaaaa
taacagactcgtgattttccaaacgagctttcaaaaagcctctgcccttgcaaatcggatgc
ctgtctataaaattcccgatattggttaaacagcggcgcaatggcggccgcatctgatgtcttt
gcttggcgaatgttcatcttatttcttcctccctctcaataatttttcattctatcccttttc
tgtaaagtttattttcagaatactttttatcatcatgctttgaaaaaatatcacgataatatcc
attgttctcacggaagcacacgcaggtcatttgaacgaattttttcgacaggaatttgccggga
ctcaggagcatttaacctaaaaagcatgacatttcagcataatgaacatttactcatgtctat
tttcgttcttttctgtatgaaaatagttatttcgagtctctacggaaatagcgagagatgatat
acctaaatagagataaaatcatctcaaaaaatgggtctactaaaatattattccatctattac
aataaattcacagaatagtcttttaagtaagtctactctgaattttttaaaggagagggtaa
agagtgtcattaccgttcttaacttctgcaccgggaaaggttattattttggtgaacactctg
ctgtgtacaacaagcctgccgtcgctgctagtgtgtctgcgttgagaacctacctgctaataag
cgagtcatctgcaccagatactattgaattggacttcccggacattagctttaatcataagtgg
tccatcaatgatttcaatgccatcaccgaggatcaagtaaactcccaaaaattggccaaggctc
aacaagccaccgatggcttgtctcaggaactcgttagtcttttggatccgttgttagctcaact
atccgaatccttccactaccatgcagcgttttgtttcctgtatatgtttgtttgcctatgcccc
catgccaagaatattaagttttctttaaagtctactttacccatcggtgctgggttgggctcaa
gcgcctctatttctgtatcactggccttagctatggcctacttggggggttaataggatctaa
tgacttggaaaagctgtcagaaaacgataagcatatagtgaatcaatgggccttcataggtgaa
aagtgtattcacggtaccccttcaggaatagataacgctgtggccacttatggtaatgccctgc
tatttgaaaagactcacataatggaacaataaacacaaacaattttaagttcttagatgattt
cccagccattccaatgatcctaacctatactagaattccaaggtctacaaagatcttgttgct
cgcgttcgtgtgttggtcaccgagaaattcctgaagttatgagccaattctagatgccatgg
gtgaatgtgccctacaaggcttagagatcatgactaagttaagtaaatgtaaaggcaccgatga
cgaggctgtagaaactaataatgaactgtatgaacaactattggaattgataagaataaatcat
ggactgcttgtctcaatcggtgtttctcatcctggattagaacttattaaaaatctgagcgatg
atttgagaattggctccacaaaacttaccggtgctggtggcggcggttgctcttgactttgtt
acgaagagacattactcaagagcaaattgacagcttcaaaaagaaattgcaagatgattttagt

Figure 29B

```
tacgagacatttgaaacagacttgggtgggactggctgctgtttgttaagcgcaaaaaatttga
ataaagatcttaaaatcaaatccctagtattccaattatttgaaaataaaactaccacaaagca
acaaattgacgatctattattgccaggaaacacgaatttaccatggacttcataaaaggagagg
gtgtcagagttgagagccttcagtgccccagggaaagcgttactagctggtggatatttagttt
tagatacaaaatatgaagcatttgtagtcggattatcggcaagaatgcatgctgtagcccatcc
ttacggttcattgcaagggtctgataagtttgaagtgcgtgtgaaaagtaaacaatttaaagat
ggggagtggctgtaccatataagtcctaaaagtggcttcattcctgtttcgataggcggatcta
agaaccctttcattgaaaaagttatcgctaacgtatttagctactttaaacctaacatggacga
ctactgcaatagaaacttgttcgttattgatattttctctgatgatgcctaccattctcaggag
gatagcgttaccgaacatcgtggcaacagaagattgagttttcattcgcacagaattgaagaag
ttcccaaaacagggctgggctcctcggcaggtttagtcacagttttaactacagctttggcctc
ctttttgtatcggacctggaaaataatgtagacaaatatagagaagttattcataatttagca
caagttgctcattgtcaagctcagggtaaaattggaagcgggtttgatgtagcggcggcagcat
atggatctatcagatatagaagattcccacccgcattaatctctaatttgccagatattggaag
tgctacttacggcagtaaactggcgcatttggttgatgaagaagactggaatattacgattaaa
agtaaccatttaccttcgggattaactttatggatgggcgatattaagaatggttcagaaacag
taaaactggtccagaaggtaaaaaattggtatgattcgcatatgccagaaagcttgaaaatata
tacagaactcgatcatgcaaattctagatttatggatggactatctaaactagatcgcttacac
gagactcatgacgattacagcgatcagatatttgagtctcttgagaggaatgactgtacctgtc
aaaagtatcctgaaatcacagaagttagagatgcagttgccacaattagacgttcctttagaaa
aataactaaagaatctggtgccgatatcgaacctcccgtacaaactagcttattggatgattgc
cagaccttaaaaggagttcttacttgcttaatacctggtgctggtggttatgacgccattgcag
tgattactaagcaagatgttgatcttagggctcaaaccgctaatgacaaaagatttttctaaggt
tcaatggctggatgtaactcaggctgactggggtgttaggaaagaaaaagatccggaaacttat
cttgataaataaaaggagagggtgaccgtttacacagcatccgttaccgcacccgtcaacatcg
caacccttaagtattgggggaaaagggacacgaagttgaatctgcccaccaattcgtccatatc
agtgactttatcgcaagatgacctcagaacgttgacctctgcggctactgcacctgagtttgaa
cgcgacactttgtggttaaatggagaaccacacagcatcgacaatgaaagaactcaaaattgtc
tgcgcgacctacgccaattaagaaaggaaatggaatcgaaggacgcctcattgcccacattatc
tcaatggaaactccacattgtctccgaaaataactttcctacagcagctggtttagcttcctcc
gctgctggctttgctgcattggtctctgcaattgctaagttataccaattaccacagtcaactt
cagaaatatctagaatagcaagaaaggggtctggttcagcttgtagatcgttgtttggcggata
cgtggcctgggaaatgggaaagctgaagatggtcatgattccatggcagtacaaatcgcagac
agctctgactggcctcagatgaaagcttgtgtcctagttgtcagcgatattaaaaaggatgtga
gttccactcagggtatgcaattgaccgtggcaacctccgaactatttaaagaaagaattgaaca
tgtcgtaccaagagatttgaagtcatgcgtaaagccattgttgaaaaagatttcgccacctttt
gcaaaggaaacaatgatggattccaactctttccatgccacatgtttggactctttccctccaa
tattctacatgaatgacacttccaagcgtatcatcagttggtgccacaccattaatcagtttta
cggagaaacaatcgttgcatacacgtttgatgcaggtccaaatgctgtgttgtactacttagct
gaaaatgagtcgaaactctttgcatttatctataaattgtttggctctgttcctggatgggaca
agaaatttactactgagcagcttgaggctttcaaccatcaatttgaatcatctaactttactgc
acgtgaattggatcttgagttgcaaaaggatgttgccagagtgattttaactcaagtcggttca
ggcccacaagaaacaaacgaatctttgattgacgcaaagactggtctaccaaaggaataaaagg
agagggtgactgccgacaacaatagtatgccccatggtgcagtatctagttacgccaaattagt
```

Figure 29C gcaaaaccaaacacctgaagacatttggaagagtttcctgaaattattccattacaacaaaga
cctaatacccgatctagtgagacgtcaaatgacgaaagcggagaaacatgtttttctggtcatg
atgaggagcaaattaagttaatgaatgaaaattgtattgttttggattgggacgataatgctat
tggtgccggtaccaagaaagtttgtcatttaatggaaaatattgaaaagggtttactacatcgt
gcattctccgtctttatttttcaatgaacaaggtgaattacttttacaacaaagagccactgaaa
aaataactttccctgatctttggactaacacatgctgctctcatccactatgtattgatgacga
attaggtttgaagggtaagctagacgataagattaagggcgctattactgcggcggtgagaaaa
ctagatcatgaattaggtattccagaagatgaaactaagacaagggggtaagtttcactttttaa
acagaatccattacatggcaccaagcaatgaaccatggggtgaacatgaaattgattacatcct
attttataagatcaacgctaaagaaaacttgactgtcaacccaaacgtcaatgaagttagagac
ttcaaatgggtttcaccaaatgatttgaaaactatgtttgctgacccaagttacaagtttacgc
cttggtttaagattatttgcgagaattacttattcaactggtgggagcaattagatgacctttc
tgaagtggaaaatgacaggcaaattcatagaatgctataaaaaaaaccggccttggccccgccg
gttttttattatttttcttcctccgcatgttcaatccgctccataatcgacggatggctccctc
tgaaaattttaacgagaaacggcgggttgacccggctcagtcccgtaacggccaagtcctgaaa
cgtctcaatcgccgcttcccggtttccggtcagctcaatgccgtaacggtcggcggcgttttcc
tgataccgggagacggcattcgtaatttgaatacatacgaacaaattaataaagtgaaaaaaat
acttcggaaacatttaaaaaataaccttattggtacttacatgtttggatcaggagttgagagt
ggactaaaaccaaatagtgatcttgacttttttagtcgtcgtatctgaaccattgacagatcaaa
gtaaagaaatacttatacaaaaaattagacctatttcaaaaaaaataggagataaaagcaactt
acgatatattgaattaacaattattattcagcaagaaatggtaccgtggaatcatcctcccaaa
caagaatttatttatggagaatggttacaagagctttatgaacaaggatacattcctcagaagg
aattaaattcagatttaaccataatgctttaccaagcaaaacgaaaaaataaaagaatatacgg
aaattatgacttagaggaattactacctgatattccatttctgatgtgagaagagccattatg
gattcgtcagaggaattaatagataattatcaggatgatgaaaccaactctatattaactttat
gccgtatgattttaactatggacacgggtaaaatcataccaaaagatattgcgggaaatgcagt
ggctgaatcttctccattagaacatagggagagaatttttgttagcagttcgtagttatcttgga
gagaatattgaatggactaatgaaaatgtaaatttaactataaactatttaaataacagattaa
aaaaattataatgtaaccttgctttcaaatgagtagaaataatgcacatccatgtttgtatcg
tgcaaataaagtgtttcatccgtaggaaaaaatgactttagtatctgttccgcttttctgatg
aaatgtgctccccgacaaaattgaatgaatcatggacatttgctggctttgatacagcgaaagc
agccgttcctatgttatatatcggatttaacagcaggacaaaaaacaccatgacagccatcgtc
acccacttattcacacgcacataaacctttcctgacttttggaacagatgatagctcatcaaaa
atcccgccattgccaaataaatcgtatatggcattactgcaccataatcttttgagatttgatt
gggatatggcgcaagcagcaagacaagcagtccgataatcagcgtataaaataagcctagtaag
atcttatccgttctccaatacagcttgaaaaacactacattcaacgcaatgggaagagtgatga
tgaaaaacagaaacacgaatgcaatcggctccatcccatccgggtattccttccaatacgaaaa
gaaactaaaaatcatttgtacgatcggcaaactgacaacagcaaggtcgaacgtataaaactta
cccttccgccatgatcacgcggcatcagcatatagtgaaaagccgtcagcagcacatatccgt
ataacaaaaatgcagcagcggcagcagttcttttccgtcctctcttaagtaagcgctggtgaa
gttgttgattgcacctggtgaataagttcaacagacactcccgccagcagcacaatccgcaat
ataacacccgccaagaacattgtgcgctgccggttttattttgggatgatgcaccaaaagatata
agcccgccagaacaacaattgaccattgaatcagcagggtgctttgtctgcttaatataaaata
acgttcgaaatgcaatacataatgactgaataactccaacacgaacaacaaaagtgcgcatttt

Figure 29D

```
Ataaaagctaatgattcagtccacataattgatagacgaattctgctacaggtcacgtggctat
gtgaaggatcgcgcgtccagttaagagcaaaaacattgacaaaaaaatttatttatgctaaaat
ttactattaatatatttgtatgtataataagattctcctggccaggggaatcttattttttgtg
gaggatcatttcatgaggaaaaatgagtccagcttaacgtctctaatttcagcttttgcccgtg
catatcacagccgatatgacacacctcttattttgatgattttatcgcaaaagatctcattaa
cgaaaaagagtttatcgacatcagtaaaaatatgattcaagaaatatcgttttcaacaaagag
atcgccgaacgtcttcaaaatgatcctgaaaaaatattaaaatggggttgcacaaatccagctgt
ctccaacgcccctagcacgtgcttcttattgtgaaaaagtcttgcacaacgaattaatcctggg
ggcaaaacagtatgtcattcttggagcgggactggatactttctgctttcggcatccagaatta
gaaaacagcttacaggttttcgaggttgatcatccggccacacagcaattgaaaaaaaataagc
tgaaggatgcaaatctgacaattccgggtcatcttcattttgttcctatggatttcaccaaaac
gttttcgtatgatcctctcttagatgaaggatttaaaaacacaaaaacattcttcagccttctc
ggagtgtcttattatgtaacacgggaagaaaatgcaagcttgatcagcaatttattttctcatg
tcccgcttggaagctctattgttttgattatgcggacgaaacacttttacagcaaaagggac
gtcgaatcgagttgaacatatggtgaagatggctgccgcaagcggggaaccgatgaaatcatgt
ttcacttatcaagagattgaacatctg
```
(SEQ ID NO:47)

Figure 31A

5'-
tagaaaaactcatcgagcatcaaatgaaactgcaatttattcatatcaggattatcaataccat
atttttgaaaaagccgtttctgtaatgaaggagaaaactcaccgaggcagttccataggatggc
aagatcctggtatcggtctgcgattccgactcgtccaacatcaatacaacctattaatttcccc
tcgtcaaaaataaggttatcaagtgagaaatcaccatgagtgacgactgaatccggtgagaatg
gcaaaagtttatgcatttctttccagacttgttcaacaggccagccattacgctcgtcatcaaa
atcactcgcatcaaccaaaccgttattcattcgtgattgcgcctgagcgaggcgaaatacgcga
tcgctgttaaaggacaattacaaacaggaatcgagtgcaaccggcgcaggaacactgccagcg
catcaacaatattttcacctgaatcaggatattcttctaatacctggaacgctgttttccggg
gatcgcagtggtgagtaaccatgcatcatcaggagtacggataaaatgcttgatggtcggaagt
ggcataaattccgtcagccagtttagtctgaccatctcatctgtaacatcattggcaacgctac
ctttgccatgtttcagaaacaactctggcgcatcgggcttcccatacaagcgatagattgtcgc
acctgattgcccgacattatcgcgagcccatttatacccatataaatcagcatccatgttggaa
tttaatcgcggcctcgacgtttccgttgaatatggctcatattcttcctttttcaatattatt
gaagcatttatcagggttattgtctcatgagcggatacatatttgaatgtatttagaaaaataa
acaaatagggggtcagtgttacaaccaattaaccaattctgaacattatcgcgagcccattata
cctgaatatggctcataacaccccttgtttgcctggcggcagtagcgcggtggtcccacctgac
cccatgccgaactcagaagtgaaacgccgtagcgccgatggtagtgtggggactccccatgcga
gagtagggaactgccaggcatcaaataaaacgaaaggctcagtcgaaagactgggcctttcgcc
cgggctaattagggggtgtcgcccttagtcgctgaacatgtgctctgtttctaccgagaacgt
ttccttcactgagacggaaaccgaggcacgtcgtagcgcgaactacgagccgatagctgggac
tacgatttcctgctgtcttccgatactgacgaatctattgaggtgtacaaagacaaagcaaaga
aactggaggctgaagtgcgccgcgaaattaacaacgagaaagctgaattcctgactctgctgga
gctgatcgataacgtacagcgcctggtctgggttaccgcttcgaatctgatatccgtcgcgca
ctggatcgtttcgtaagcagcggcggtttcgatggcgtgaccaaaacgagcctgcacgctaccg
cgctgtccttccgtctgctgcgtcagcacggcttcgaagtttctcaggaagcattctccggttt
caaagatcaaaacggtaacttcctggaaaacctgaaagaagacactaaggcgatcctgagcctg
tatgaggcaagctttctggccctggagggtgagaacatcctggatgaggcgcgcgtattcgcca
tctcccatctgaaagagctgtctgaagagaaatcggtaaggaactggcagagcaggttaatca
cgcactggaactgccgctgcatcgtcgtacccagcgtctggaggcggtttggtccatcgaagcg
taccgcaaaaaggaggatgctaaccaggttctgctggaactggccatcctggactacaacatga
tccagtccgtttaccagcgtgatctgcgtgaaacctcccgttggtggcgccgtgtgggcctggc
gaccaaactgcacttcgctaaggaccgcctgattgagtcttttactgggcagtcggcgttgcg
ttcgaacctcagtattctgactgccgtaacagcgttgcgaaaatgttcagcttcgttactatta
tcgacgacatctacgacgtttacggtactctggacgagctggaactgtttaccgacgctgtcga
acgttgggatgttaacgccatcaacgatctgcctgactacatgaaactgtgcttcctggcactg
tataacacgatcaacgaaattgcatacgacaacctgaaagacaaaggtgaaaacatcctgccgt
acctgactaaagcgtgggcggatctgtgtaacgcttttctgcaagaagcgaatggctgtataa
caaatccactccgacctttgacgattatttcggcaatgcctggaaatccagctctggcccgctg
caactgatcttcgcttattttgcggttgtccaaaacatcaaaaaggaggaaattgaaaacctgc
aaaaataccacgatatcattagccgtccttctcatatctttcgcctgtgcaacgacctggcaag
cgcgtccgcagagatcgcacgtggcgaaaccgctaactctgtttcctgctacatgcgcaccaag
ggcatttccgaagagctggcaaccgagagcgtaatgaatctgatcgacgaaacctgtaagaaaa
tgaacaaagaaaaactgggtggctccctgttcgctaaaccgttcgtagagactgctattaacct

Figure 31B

```
ggcacgtcagagccactgcacctaccacaatggtgacgcacatactagcccggatgaactgact
cgtaaacgtgtactgtctgttatcaccgaaccgattctgccgttcgaacgttaactgcagcgtc
aatcgaaagggcgacacaaaatttattctaaatgcataataaatactgataacatcttatagtt
tgtattatattttgtattatcgttgacatgtataatttttgatatcaaaaactgattttcccttt
attattttcgagatttatttttcttaattctctttaacaaactagaaatattgtatatacaaaaa
atcataaataatagatgaatagtttaattataggtgttcatcaatcgaaaaagcaacgtatctt
atttaaagtgcgttgctttttttctcatttataaggttaaataattctcatatatcaagcaaagt
gacaggcgcccttaaatattctgacaaatgctcttccctaaactcccccataaaaaaacccg
ccgaagcgggttttttacgttatttgcggattaacgattactcgttatcagaaccgcccaggggg
cccgagcttaagactggccgtcgttttacaacacagaaagagtttgtagaaacgcaaaaaggcc
atccgtcagggccttctgcttagtttgatgcctggcagttccctactctcgccttccgcttcc
tcgctcactgactcgctgcgctcggtcgttcggctgcggcgagcggtatcagctcactcaaagg
cggtaatacggttatccacagaatcaggggataacgcaggaaagaacatgtgagcaaaaggcca
gcaaaaggccaggaaccgtaaaaaggccgcgttgctggcgttttttccataggctccgccccct
gacgagcatcacaaaaatcgacgctcaagtcagaggtggcgaaacccgacaggactataaagat
accaggcgtttccccctggaagctccctcgtgcgctctcctgttccgaccctgccgcttaccgg
atacctgtccgcctttctcccttcgggaagcgtggcgctttctcatagctcacgctgtaggtat
ctcagttcggtgtaggtcgttcgctccaagctgggctgtgtgcacgaaccccccgttcagcccg
accgctgcgccttatccggtaactatcgtcttgagtccaacccggtaagacacgacttatcgcc
actggcagcagccactggtaacaggattagcagagcgaggtatgtaggcggtgctacagagttc
ttgaagtggtgggctaactacggctacactagaagaacagtatttggtatctgcgctctgctga
agccagttaccttcggaaaaagagttggtagctcttgatccggcaaacaaaccaccgctggtag
cggtggtttttttgtttgcaagcagcagattacgcgcagaaaaaaaggatctcaagaagatcct
ttgatcttttctacggggtctgacgctcagtggaacgacgcgcgcgtaactcacgttaagggat
tttggtcatgagcttgcgccgtcccgtcaagtcagcgtaatgctctgcttt
```
(SEQ ID NO:48)

Figure 33A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgctctgtttctaccgagaacgtttccttcact
gagacggaaaccgaggcacgtcgtagcgcgaactacgagccgaatagctgggactacgatttcc
tgctgtcttccgatactgacgaatctattgaggtgtacaaagacaaagcaaagaaactggaggc
tgaagtgcgccgcgaaattaacaacgagaaagctgaattcctgactctgctggagctgatcgat
aacgtacagcgcctgggtctgggttaccgcttcgaatctgatatccgtcgcgcactggatcgtt
tcgtaagcagcggcggtttcgatggcgtgaccaaaacgagcctgcacgctaccgcgctgtcctt
ccgtctgctgcgtcagcacggcttcgaagtttctcaggaagcattctccggtttcaaagatcaa
aacggtaacttcctggaaaacctgaaagaagacactaaggcgatcctgagcctgtatgaggcaa
gctttctggccctggagggtgagaacatcctggatgaggcgcgcgtattcgccatctcccatct
gaaagagctgtctgaagagaaaatcggtaaggaactggcagagcaggttaatcacgcactggaa
ctgccgctgcatcgtcgtacccagcgtctggaggcggtttggtccatcgaagcgtaccgcaaaa
aggaggatgctaaccaggttctgctggaactggccatcctggactacaacatgatccagtccgt
ttaccagcgtgatctgcgtgaaacctcccgttggtggcgccgtgtgggcctggcgaccaaactg
cacttcgctaaggaccgcctgattgagtcttttactgggcagtcggcgttgcgttcgaacctc
agtattctgactgccgtaacagcgttgcgaaaatgttcagcttcgttactattatcgacgacat
ctacgacgtttacggtactctggacgagctggaactgtttaccgacgctgtcgaacgttgggat
gttaacgccatcaacgatctgcctgactacatgaaactgtgcttcctggcactgtataacacga
tcaacgaaattgcatacgacaacctgaaagacaaggtgaaaacatcctgccgtacctgactaa
agcgtgggcggatctgtgtaacgcttttctgcaagaagcgaaatggctgtataacaaatccact
ccgaccttgacgattatttcggcaatgcctggaaatccagctctggcccgctgcaactgatct
tcgcttatttgcggttgtccaaaacatcaaaaggaggaaattgaaaacctgcaaaaatacca
cgatatcattagccgtccttctcatatctttcgcctgtgcaacgacctggcaagcgcgtccgca
gagatcgcacgtggcgaaaccgctaactctgtttcctgctacatgcgcaccaagggcatttccg
aagagctggcaaccgagagcgtaatgaatctgatcgacgaaacctgtaagaaaatgaacaaaga
aaaactgggtggctccctgttcgctaaaccgttcgtagagactgctattaacctggcacgtcag
agccactgcacctaccacaatggtgacgcacatactagcccggatgaactgactcgtaaacgtg
tactgtctgttatcaccgaaccgattctgccgttcgaacgttaactgcagctggtaccatatgg
gaattcgaagctttctagaacaaaaactcatctcagaagaggatctgaatagcgccgtcgacca
tcatcatcatcattgagtttaaacggtctccagcttggctgttttggcggatgagagaaga
ttttcagcctgatacagattaaatcagaacgcagaagcggtctgataaaacagaatttgcctgg
cggcagtagcgcggtggtcccacctgaccccatgccgaactcagaagtgaaacgccgtagcgcc
gatggtagtgtggggtctccccatgcgagagtagggaactgccaggcatcaaataaaacgaaag
gctcagtcgaaagactgggcctttcgttttatctgttgtttgtcggtgaacgctctcctgagta
ggacaaatccgccgggagcggatttgaacgttgcgaagcaacggcccggagggtggcgggcagg
acgcccgccataaactgccaggcatcaaattaagcagaaggccatcctgacggatggccttttt
gcgtttctacaaactcttttgtttattttctaaatacattcaaatatgtatccgctcatgag
acaataaccctgataaatgcttcaataatattgaaaaaggaagagtatgagtattcaacatttc

Figure 33B cgtgtcgcccttattccttttttgcggcattttgccttcctgttttttgctcacccagaaacgc
tggtgaaagtaaaagatgctgaagatcagttgggtgcacgagtgggttacatcgaactggatct
caacagcggtaagatccttgagagttttcgccccgaagaacgttttccaatgatgagcactttt
aaagttctgctatgtggcgcggtattatcccgtgttgacgccgggcaagagcaactcggtcgcc
gcatacactattctcagaatgacttggttgagtactccagtcacagaaaagcatcttacgga
tggcatgacagtaagagaattatgcagtgctgccataaccatgagtgataacactgcggccaac
ttacttctgacaacgatcggaggaccgaaggagctaaccgcttttttgcacaacatgggggatc
atgtaactcgccttgatcgttgggaaccggagctgaatgaagccataccaaacgacgagcgtga
caccacgatgcctgtagcaatggcaacaacgttgcgcaaactattaactggcgaactacttact
ctagcttcccggcaacaattaatagactggatggaggcggataaagttgcaggaccacttctgc
gctcggcccttccggctggctggtttattgctgataaatctggagccggtgagcgtgggtctcg
cggtatcattgcagcactggggccagatggtaagccctcccgtatcgtagttatctacacgacg
gggagtcaggcaactatggatgaacgaaatagacagatcgctgagataggtgcctcactgatta
agcattggtaactgtcagaccaagtttactcatatatactttagattgatttaaaacttcattt
ttaatttaaaaggatctaggtgaagatcctttttgataatctcatgaccaaaatcccttaacgt
gagttttcgttccactgagcgtcagacccgtagaaaagatcaaaggatcttcttgagatcctt
ttttctgcgcgtaatctgctgcttgcaaacaaaaaaaccaccgctaccagcggtggtttgttt
gccggatcaagagctaccaactctttttccgaaggtaactggcttcagcagagcgcagatacca
aatactgtccttctagtgtagccgtagttaggccaccacttcaagaactctgtagcaccgccta
catacctcgctctgctaatcctgttaccagtggctgctgccagtggcgataagtcgtgtcttac
cgggttggactcaagacgatagttaccggataaggcgcagcggtcgggctgaacggggggttcg
tgcacacagcccagcttggagcgaacgacctacaccgaactgagatacctacagcgtgagctat
gagaaagcgccacgcttcccgaagggagaaaggcggacaggtatccggtaagcggcagggtcgg
aacaggagagcgcacgagggagcttccaggggggaaacgcctggtatctttatagtcctgtcggg
tttcgccacctctgacttgagcgtcgatttttgtgatgctcgtcaggggggcggagcctatgga
aaaacgccagcaacgcggcctttttacggttcctggccttttgctggccttttgctcacatgtt
ctttcctgcgttatcccctgattctgtggataaccgtattaccgcctttgagtgagctgatacc
gctcgccgcagccgaacgaccgagcgcagcgagtcagtgagcgaggaagcggaagagcgcctga
tgcggtattttctccttacgcatctgtgcggtatttcacaccgcatatggtgcactctcagtac
aatctgctctgatgccgcatagttaagccagtatacactccgctatcgctacgtgactgggtca
tggctgcgccccgacacccgccaacacccgctgacgcgccctgacgggcttgtctgctcccggc
atccgcttacagacaagctgtgaccgtctccgggagctgcatgtgtcagaggttttcaccgtca
tcaccgaaacgcgcgaggcagcagatcaattcgcgcgcgaaggcgaagcggcatgcatttacgt
tgacaccatcgaatggtgcaaaacctttcgcggtatggcatgatagcgcccggaagagagtcaa
ttcagggtggtgaatgtgaaaccagtaacgttatacgatgtcgcagagtatgccggtgtctctt
atcagaccgtttccgcgtggtgaaccaggccagccacgtttctgcgaaaacgcgggaaaaagt
ggaagcggcgatggcggagctgaattacattcccaaccgcgtggcacaacaactggcgggcaaa
cagtcgttgctgattggcgttgccacctccagtctggccctgcacgcgccgtcgcaaattgtcg
cggcgattaaatctcgcgccgatcaactgggtgccagcgtggtggtgtcgatggtagaacgaag
cggcgtcgaagcctgtaaagcggcggtgcacaatcttctcgcgcaacgcgtcagtgggctgatc
attaactatccgctggatgaccaggatgccattgctgtggaagctgcctgcactaatgttccgg
cgttatttcttgatgtctctgaccagacacccatcaacagtattattttctcccatgaagacgg
tacgcgactgggcgtggagcatctggtcgcattgggtcaccagcaaatcgcgctgttagcgggc
ccattaagttctgtctcggcgcgtctgcgtctggctggctggcataaatatctcactcgcaatc

Figure 33C aaattcagccgatagcggaacgggaaggcgactggagtgccatgtccggttttcaacaaaccat
gcaaatgctgaatgagggcatcgttcccactgcgatgctggttgccaacgatcagatggcgctg
ggcgcaatgcgcgccattaccgagtccgggctgcgcgttggtgcggatatctcggtagtgggat
acgacgataccgaagacagctcatgttatatcccgccgtcaaccaccatcaaacaggattttcg
cctgctggggcaaaccagcgtggaccgcttgctgcaactctctcagggccaggcggtgaagggc
aatcagctgttgcccgtctcactggtgaaaagaaaaaccaccctggcgcccaatacgcaaaccg
cctctccccgcgcgttggccgattcattaatgcagctggcacgacaggtttcccgactggaaag
cgggcagtgagcgcaacgcaattaatgtgagttagcgcgaattgatctg
(SEQ ID NO:49)

Figure 35A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaagaacaaatctgacctgcacgcaaccgctctgtctttccgtctgct
gcgtcagcacggtttcgaggtttctcaggatgttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt

Figure 35B

```
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
tcgcccttaggaggtaaaaaaaatgactgccgacaacaatagtatgccccatggtgcagtatc
tagttacgccaaattagtgcaaaaccaaacacctgaagacatttggaagagtttcctgaaatt
attccattacaacaaagacctaatacccgatctagtgagacgtcaaatgacgaaagcggagaaa
catgtttttctggtcatgatgaggagcaaattaagttaatgaatgaaaattgtattgttttgga
ttgggacgataatgctattggtgccggtaccaagaaagtttgtcatttaatggaaaatattgaa
aagggtttactacatcgtgcattctccgtctttatttcaatgaacaaggtgaattacttttac
aacaaagagccactgaaaaataactttccctgatctttggactaacacatgctgctctcatcc
actatgtattgatgacgaattaggtttgaagggtaagctagacgataagattaagggcgctatt
actgcggcggtgagaaaactagatcatgaattaggtattccagaagatgaaactaagacaaggg
gtaagtttcactttttaaacagaatccattacatggcaccaagcaatgaaccatggggtgaaca
tgaaattgattacatcctatttataagatcaacgctaaagaaaacttgactgtcaacccaaac
gtcaatgaagttagagacttcaaatgggtttcaccaaatgatttgaaaactatgtttgctgacc
caagttacaagtttacgccttggtttaagattatttgcgagaattacttattcaactggtggga
gcaattagatgacctttctgaagtggaaaatgacaggcaaattcatagaatgctataacaacgc
gtcctgcagctggtaccatatgggaattcgaagctttctagaacaaaaactcatctcagaagag
gatctgaatagcgccgtcgaccatcatcatcatcattgagtttaaacggtctccagcttgg
ctgttttggcggatgagagaagattttcagcctgatacagattaaatcagaacgcagaagcggt
ctgataaaacagaatttgcctggcggcagtagcgcggtggtcccacctgaccccatgccgaact
cagaagtgaaacgccgtagcgccgatggtagtgtggggtctcccatgcgagagtagggaactg
ccaggcatcaaataaaacgaaaggctcagtcgaaagactgggcctttcgttttatctgttgttt
gtcggtgaacgctctcctgagtaggacaaatccgccgggagcggatttgaacgttgcgaagcaa
cggccggagggtggcgggcaggacgcccgccataaactgccaggcatcaaattaagcagaagg
ccatcctgacggatggcctttttgcgtttctacaaactcttttgtttattttctaaatacat
tcaaatatgtatccgcttaaccggaattgccagctggggcgccctctggtaaggttgggaagcc
ctgcaaagtaaactggatggctttctcgccgccaaggatctgatggcgcaggggatcaagctct
gatcaagagacaggatgaggatcgtttcgcatgattgaacaagatggattgcacgcaggttctc
cggccgcttggtggagaggctattcggctatgactgggcacaacagacaatcggctgctctga
tgccgccgtgttccggctgtcagcgcaggggcgcccggttcttttgtcaagaccgacctgtcc
ggtgccctgaatgaactgcaagacgaggcagcgcggctatcgtggctggccacgacgggcgttc
cttgcgcagctgtgctcgacgttgtcactgaagcgggaagggactggctgctattgggcgaagt
gccggggcaggatctcctgtcatctcaccttgctcctgccgagaaagtatccatcatggctgat
```

Figure 35C gcaatgcggcggctgcatacgcttgatccggctacctgcccattcgaccaccaagcgaaacatc
gcatcgagcgagcacgtactcggatggaagccggtcttgtcgatcaggatgatctggacgaaga
gcatcaggggctcgcgccagccgaactgttcgccaggctcaaggcgagcatgcccgacggcgag
gatctcgtcgtgacccatggcgatgcctgcttgccgaatatcatggtggaaaatggccgctttt
ctggattcatcgactgtggccggctgggtgtggcggaccgctatcaggacatagcgttggctac
ccgtgatattgctgaagagcttggcggcgaatgggctgaccgcttcctcgtgctttacggtatc
gccgctcccgattcgcagcgcatcgccttctatcgccttcttgacgagttcttctgacatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactcttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccaggggggaaacgcctggtatctt
tatagtcctgtcgggtttcgccacctctgacttgagcgtcgattttgtgatgctcgtcagggg
ggcggagcctatggaaaaacgccagcaacgcggccttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtatttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
(SEQ ID NO:50)

Figure 37A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggatttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctcccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaagaacaaatctgacctgcacgcaaccgctctgtctttccgtctgct
gcgtcagcacggtttcgaggtttctcaggatgttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtacctttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct

Figure 37B attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacacccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaaccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg
cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgcagctggtaccatatgggaattcgaagctt
tctagaacaaaaactcatctcagaagaggatctgaatagcgccgtcgaccatcatcatcatcat
cattgagtttaaacggtctccagcttggctgttttggcggatgagagaagattttcagcctgat
acagattaaatcagaacgcagaagcggtctgataaaacagaatttgcctggcggcagtagcgcg

Figure 37C

```
gtggtcccacctgaccccatgccgaactcagaagtgaaacgccgtagcgccgatggtagtgtgg
ggtctccccatgcgagagtagggaactgccaggcatcaaataaaacgaaaggctcagtcgaaag
actgggcctttcgtttatctgttgtttgtcggtgaacgctctcctgagtaggacaaatccgcc
gggagcggatttgaacgttgcgaagcaacggcccggagggtggcgggcaggacgccgccataa
actgccaggcatcaaattaagcagaaggccatcctgacggatggccttttgcgtttctacaaa
ctcttttgtttatttttctaaatacattcaaatatgtatccgcttaaccggaattgccagctg
gggcgccctctggtaaggttgggaagccctgcaaagtaaactggatggctttctcgccgccaag
gatctgatggcgcaggggatcaagctctgatcaagagacaggatgaggatcgtttcgcatgatt
gaacaagatggattgcacgcaggttctccggccgcttgggtggagaggctattcggctatgact
gggcacaacagacaatcggctgctctgatgccgccgtgttccggctgtcagcgcaggggcgccc
ggttcttttgtcaagaccgacctgtccggtgccctgaatgaactgcaagacgaggcagcgcgg
ctatcgtggctggccacgacgggcgttccttgcgcagctgtgctcgacgttgtcactgaagcgg
gaagggactggctgctattgggcgaagtccggggcaggatctcctgtcatctccacttgctcc
tgccgagaaagtatccatcatggctgatgcaatgcggcggctgcatacgcttgatccggctacc
tgcccattcgaccaccaagcgaaacatcgcatcgagcgagcacgtactcggatggaagccggtc
ttgtcgatcaggatgatctggacgaagagcatcaggggctcgcgccagccgaactgttcgccag
gctcaaggcgagcatgcccgacggcgaggatctcgtcgtgacccatggcgatgcctgcttgccg
aatatcatggtggaaaatggccgcttttctggattcatcgactgtggccggctgggtgtggcgg
accgctatcaggacatagcgttggctacccgtgatattgctgaagagcttggcggcgaatgggc
tgaccgcttcctcgtgctttacggtatcgccgctcccgattcgcagcgcatcgccttctatcgc
cttcttgacgagttcttctgacgcatgaccaaaatcccttaacgtgagttttcgttccactgag
cgtcagaccccgtagaaaagatcaaaggatcttcttgagatcctttttttctgcgcgtaatctg
ctgcttgcaaacaaaaaaccaccgctaccagcggtggtttgtttgccggatcaagagctacca
actctttttccgaaggtaactggcttcagcagagcgcagataccaaatactgtccttctagtgt
agccgtagttaggccaccacttcaagaactctgtagcaccgcctacatacctcgctctgctaat
cctgttaccagtggctgctgccagtggcgataagtcgtgtcttaccgggttggactcaagacga
tagttaccggataaggcgcagcggtcgggctgaacggggggttcgtgcacacagcccagcttgg
agcgaacgacctacaccgaactgagatacctacagcgtgagctatgagaaagcgccacgcttcc
cgaagggagaaaggcggacaggtatccggtaagcggcagggtcggaacaggagagcgcacgagg
gagcttccaggggaaacgcctggtatctttatagtcctgtcgggtttcgccacctctgacttg
agcgtcgatttttgtgatgctcgtcaggggggcggagcctatggaaaaacgccagcaacgcggc
cttttacggttcctggccttttgctggccttttgctcacatgttctttcctgcgttatcccct
gattctgtggataaccgtattaccgcctttgagtgagctgataccgctcgccgcagccgaacga
ccgagcgcagcgagtcagtgagcgaggaagcggaagagcgcctgatgcggtattttctccttac
gcatctgtgcggtatttcacaccgcatatggtgcactctcagtacaatctgctctgatgccgca
tagttaagccagtatacactccgctatcgctacgtgactgggtcatggctgcgccccgacaccc
gccaacaccgctgacgcgcctgacgggc
```
(SEQ ID NO:51)

Figure 39A

5'-
ctggcgtaatagcgaagaggcccgcaccgatcgcccttcccaacagttgcgcagcctgaatggc
gaatggcgcctgatgcggtatttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcagggaattaattcccacggg
ttttgctgcccgcaaacgggctgttctggtgttgctagtttgttatcagaatcgcagatccggc
ttcagccggtttgccggctgaaagcgctatttcttccagaattgccatgattttttcccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaagctctgatgtatctat
ctttttttacaccgttttcatctgtgcatatggacagttttccctttgatatgtaacggtgaaca
gttgttctacttttgtttgttagtcttgatgcttcactgatagatacaagagccataagaacct
cagatccttccgtatttagccagtatgttctctagtgtggttcgttgttttgcgtgagccatg
agaacgaaccattgagatcatacttactttgcatgtcactcaaaaattttgcctcaaaactggt
gagctgaattttgcagttaaagcatcgtgtagtgttttcttagtccgttatgtaggtaggaa
tctgatgtaatggttgttggtattttgtcaccattcattttatctggttgttctcaagttcgg

Figure 39B

```
ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
ttttttaactggaaaagataaggcaatatctcttcactaaaaactaattctaattttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtctttttcgtgacattcagttc
gctgcgctcacggctctggcagtgaatgggggtaaatggcactacaggcgccttttatggattc
atgcaaggaaactacccataatacaagaaaagcccgtcacgggcttctcagggcgtttatggc
gggtctgctatgtggtgctatctgacttttttgctgttcagcagttcctgccctctgatttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaagacatcattaaa
gccctggaaaacatcgtactgctggacgaaaacaaaagaacaaatctgacctgcacgcaaccg
ctctgtctttccgtctgctgcgtcagcacggtttcgaggtttctcaggatgttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct
```

Figure 39C

```
atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcagctggtaccatatgggaattcgaagctttctagaacaaaaactca
tctcagaagaggatctgaatagcgccgtcgaccatcatcatcatcatcattgagtttaaacggt
ctccagcttggctgttttggcggatgagagaagattttcagcctgatacagattaaatcagaac
gcagaagcggtctgataaaacagaatttgcctggcggcagtagcgcggtggtcccacctgaccc
catgccgaactcagaagtgaaacgccgtagcgccgatggtagtgtggggtctccccatgcgaga
gtagggaactgccaggcatcaaataaaacgaaaggctcagtcgaaagactgggcctttcgtttt
atctgttgtttgtcggtgaacgctctcctgagtaggacaaatccgccgggagcggatttgaacg
ttgcgaagcaacggcccggagggtggcggcaggacgcccgccataaactgccaggcatcaaat
taagcagaaggccatcctgacggatggcctttttgcgtttctacaaactcttttgtttatttt
tctaaatacattcaaatatgtatccgctcatgagacaataaccctgataaatgcttcaataat
(SEQ ID NO:52)
```

Figure 41A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagttttttgttctagaaa
gcttcgaattcccatatggtaccagctgcagttagacatacatcagctggttaatcgggaaagg
gtcaatcagcagcagtttgatgcggttttcagtcgcgtagtctgggcgacccagaccatcgcca
tactggtaggtgcagtgggaaacacgtgccatgttaactgcgatttccatgaacgctttaggca
gcagggtggagtcgctaacgcgttcacgattcatctttttccattcggcgtcgatcagtttacg
cagttcttcgcgggcctgttcctcgctggtaccatcgttttcgtgcatgtagctaatgatagaa
ttggtagtctcgccacgttccagctccgccgcagaggtggccagatcgttgcacaggcggaaga
taacgcagctagaacgcaccagaccatggaagtcggtcagggaacgcagcgcgtggtcggagat
gtcttcctgctgctggcatacggaaaagtaagacggcgccagcagcgctacaccggaggaggaa
acgctggcgttttccaggtacttggagaaagccgggataatttgttgttggaccatttcgcct
cttgcagaaaggctttgcacagttcacgccagcttttcgtcagataggacaggttgttatgacc
tttctctttcagaatagaataggacgtgtcgttaacggtgttgtacagtgccaggaaacacagt
ttcatatagtccggcagggtgttaatagcgttaacgtcccagcgctctacagcatcggtgaaca
gttgcagttcgtccagagtgccataaacgtcatacacgtcatcgatgatcgtcaccagaccaaa
catttagtaacagctttgcgacattcaccaaactgcgggtctggcgccatacccagtgcccag
aaataaacttccatcaggcggtcgcgtacaaaatccagtttgctagccaggcccatctcggtcc
accagcgggacagatcttgcagctctttctggtgcagggtctgtaccatgttaaaatccagctt
cgccagctccagcagcagctggtgatgcggttctttcggttcgtatttatccaggaaccaacgt
gcctccagacggtgcagacgctggtgatatggcagttccagggcgtggctcacttgttctgcaa
ccttggtattaatgccttctttcaggttgttcttcaggtgggtgatggaaaaggtacgcgcctc
ctccagcaggttctcaccctcgaaacccaggtaagacgcttcatacaggctcagcaggccttgg
acgtcacctttcagttcaccgctgaaaccaccttctttatccttgaaacgctcaaaaacatcct
gagaaacctcgaaaccgtgctgacgcagcagacggaaagacagagcggttgcgtgcaggtcaga
tttgttcttttttgttttcgtccagcagtacgatgttttccagggctttaatgatgtcttttca
aatttgtaggtcagacccaggcgctgcacatcgtcgatcagctccagcagggacagcggctggg
tgtctacacggttgatcatgcagcgaacttcttcctccagtttggtcgctttctcctccagctt
ttccactttcaggtcgttctccaggattgcaggaattcgaaattccacaggtttggctgatag
tttgcggaacgacgggaattatgctcggtaatctgagtaaattgagaagaggtcgcacacatgg
tttattcctccttatttaatcgatacattaatatatacctctttaatttttaataataaagtta
atcgataattccggtcgagtgcccacacagattgtctgataaattgttaaagagcagtgccgct
tcgcttttctcagcggcgctgtttcctgtgtgaaattgttatccgctcacaattccacacatt
atacgagccggatgattaattgtcaacagctcatttcagaatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc

Figure 41B

```
tgatgccgcatagttaagccagccccgacacccgccaacacccgctgacgagcttagtaaagcc
ctcgctagattttaatgcggatgttgcgattacttcgccaactattgcgataacaagaaaaagc
cagcctttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttcccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttacaccgttttcatct
gtgcatatggacagttttccctttgatatgtaacggtgaacagttgttctactttgtttgtta
gtcttgatgcttcactgatagatacaagagccataagaacctcagatccttccgtatttagcca
gtatgttctctagtgtggttcgttgtttttgcgtgagccatgagaacgaaccattgagatcata
cttactttgcatgtcactcaaaaattttgcctcaaaactggtgagctgaatttttgcagttaaa
gcatcgtgtagtgttttcttagtccgttatgtaggtaggaatctgatgtaatggttgttggta
ttttgtcaccattcattttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc
```

Figure 41C cttgtgagttttcttttgtgttagttcttttaataaccactcataaatcctcatagagtatttg
ttttcaaaagacttaacatgttccagattatattttatgaattttttaactggaaaagataag
gcaatatctcttcactaaaaactaattctaattttttcgcttgagaacttggcatagtttgtcca
ctggaaaatctcaaagcctttaaccaaaggattcctgatttccacagttctcgtcatcagctct
ctggttgctttagctaatacaccataagcatttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtccttttcctttgagttgtgggtat
ctgtaaattctgctagacctttgctggaaaacttgtaaattctgctagaccctctgtaaattcc
gctagacctttgtgtgttttttttgtttatattcaagtggttataatttatagaataaagaaag
aataaaaaaagataaaagaatagatcccagccctgtgtataactcactactttagtcagttcc
gcagtattacaaaaggatgtcgcaaacgctgtttgctcctctacaaaacagaccttaaaaccct
aaaggcttaagtagcaccctcgcaagctcgggcaaatcgctgaatattccttttgtctccgacc
atcaggcacctgagtcgctgtcttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgtttatggcgggtctgctatgtggtgctatc
tgacttttgctgttcagcagttcctgccctctgattttccagtctgaccacttcggattatcc
cgtgacaggtcattcagactggctaatgcacccagtaaggcagcggtatcatcaacaggctta
(SEQ ID NO:53)

Figure 43A

5'-
ctggcgtaatagcgaagaggcccgcaccgatcgcccttcccaacagttgcgcagcctgaatggc
gaatggcgcctgatgcggtatttTctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgattttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctacttttgtttgttagtcttgatgcttcactgatagatacaagagccataagaacct
cagatccttccgtatttagccagtatgttctctagtgtggttcgttgtttttgcgtgagccatg
agaacgaaccattgagatcatacttactttgcatgtcactcaaaaatttttgcctcaaaactggt
gagctgaattttttgcagttaaagcatcgtgtagtgttttcttagtccgttatgtaggtaggaa
tctgatgtaatggttgttggtatttttgtcaccattcatttttatctggttgttctcaagttcgg

Figure 43B

```
ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatatttatgaat
tttttaactggaaaagataaggcaatatctcttcactaaaaactaattctaattttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtcttttcgtgacattcagttc
gctgcgctcacggctctggcagtgaatggggtaaatggcactacaggcgccttttatggattc
atgcaaggaaactacccataatacaagaaagcccgtcacgggcttctcagggcgtttatggc
gggtctgctatgtggtgctatctgactttttgctgttcagcagttcctgccctctgatttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaagaacaaatctgacctgcacgcaaccg
ctctgtctttccgtctgctgcgtcagcacggtttcgaggtttctcaggatgttttgagcgttt
caaggataaagaaggtggtttcagcggtgaactgaaaggtgacgtccaaggcctgctgagcctg
tatgaacgtcttacctgggtttcgagggtgagaacctgctggaggaggcgcgtaccttttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagaccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct
```

Figure 43C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctggtcgc
ccagactacgcgactgaaaaccgcatcaaactgctgctgattgacccttcccgattaaccagc
tgatgtatgtctaactgcatcgcccttaggaggtaaaaaaaatgactgccgacaacaatagta
tgccccatggtgcagtatctagttacgccaaattagtgcaaaaccaaacacctgaagacattt
ggaagagtttcctgaaattattccattacaacaaagacctaatacccgatctagtgagacgtca
aatgacgaaagcggagaaacatgttttctggtcatgatgaggagcaaattaagttaatgaatg
aaaattgtattgttttggattgggacgataatgctattggtgccggtaccaagaaagtttgtca
tttaatggaaaatattgaaaagggtttactacatcgtgcattctccgtctttatttcaatgaa
caaggtgaattacttttacaacaaagagccactgaaaaaataactttccctgatctttggacta
acacatgctgctctcatccactatgtattgatgacgaattaggtttgaagggtaagctagacga
taagattaagggcgctattactgcggcggtgagaaaactagatcatgaattaggtattccagaa
gatgaaactaagacaaggggtaagtttcactttttaaacagaatccattacatggcaccaagca
atgaaccatggggtgaacatgaaattgattacatcctatttataagatcaacgctaaagaaaa
cttgactgtcaacccaaacgtcaatgaagttagagacttcaaatgggtttcaccaaatgatttg
aaaactatgtttgctgacccaagttacaagtttacgccttggtttaagattatttgcgagaatt
acttattcaactggtgggagcaattagatgacctttctgaagtggaaaatgacaggcaaattca
tagaatgctataacgacgcgtcctgcagctggtaccatatgggaattcgaagctttctagaacg
aaaactcatctcagaagaggatctgaatagcgccgtcgaccatcatcatcatcatcattgagtt
taaacggtctccagcttggctgttttggcggatgagagaagatttcagcctgatacagattaa
atcagaacgcagaagcggtctgataaaacagaatttgcctggcggcagtagcgcggtggtccca
cctgacccccatgccgaactcagaagtgaaacgccgtagcgccgatggtagtgtggggtctcccc
atgcgagagtagggaactgccaggcatcaaataaaacgaaaggctcagtcgaaagactgggcct
ttcgttttatctgttgtttgtcggtgaacgctctcctgagtaggacaaatccgccgggagcgga
tttgaacgttgcgaagcaacggcccggagggtggcgggcaggacgcccgccataaactgccagg
catcaaattaagcagaaggccatcctgacggatggcctttttgcgtttctacaaactcttttg
tttattttctaaatacattcaaatatgtatccgctcatgagacaataaccctgataaatgctt
caataat
(SEQ ID NO:54)

Figure 45A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgccgccaccctccgggccgttgcttcgcaacgttcaaatccgctcccgg
cggatttgtcctactcaggagagcgttcaccgacaaacaacagataaaacgaaaggcccagtct
ttcgactgagccttctcgtttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagtttttgttctagaaa
gcttcgaattcccatatggtaccagctgcagttatgccagccaggccttgatttggcttccat
accagcggcatcgaggccgagttcggcgcgcatttcttcctgagttccttgcggaataaagaag
tccggcaggccaatgttcagcacgggtactggtttacgatgggccatcagcacttcgttcacgc
cgctgcctgcgccgcccataatggcgttttcttctacggtgaccagcgcttcatggctggcggc
catttccagaattaacgcttcatcaagcggtttcacaaaacgcatatcgaccagcgtggcgttc
agcgattcggcgactttcgccgcttctggcatcagcgtaccaaagttaaggatcgccagtttct
cgccacgacgcttcacaatgcctttgccaattggtagttttccagcggcgtcagttccacgcc
gaccgcgttgccacgcgggtagcgcaccgctgacgggccatcgttatagtgatagccggtatag
agcatctggcgacattcgttttcatcgctcggggtcataatgaccatttccggtatgcagcgca
ggtaagagagatcaaaagcaccctgatgggtttgaccgtcagcaccaacaatgcccgcgcggtc
gatggcgaacaggaccggaagcttttgaatcgccacgtcatgcagcacctgatcataggcgcgt
tgcaggaaagtggagtaaatcgcgacaatgggtttgtacccaccaatcgccagacccgcagcaa
aggtcaccgcgtgttgctcggcaattgccacgtcgaagtagcgatccgggaatttacgtgaaaa
ctcgaccatgccggaaccttcacgcatcgccggagtaatcgccatcagcttgttgtctttcgct
gccgtttcgcacaaccagtcgccaaagatttttgaatagctcggcaaaccgccgctacttttcg
gcaaacaaccgctggagggatcaaatttaggcacggcgtggaaagtgatcgggtctttttctgc
cggttcataaccacgacctttttggtcatgatatgcaggaactgcgggccttcaggtcgcgc
atgttctttagcgtggtgataagccccagcacatcgtgaccgtccaccgggccgatgtagttaa
agcccagctcttcaaacaacgtgccaggcactaccatgcctttaatatgttcttcggtgcgttt
gagcagctctttaattggcggcacgccagagaaaacttttttcccgccttcgcgcagtgaagag
taaagcttaccggaaagcagctgtgccagatggttgttgagcgcgccgacattttcggaaatcg
acatttcattgtcgttgagaatcaccagcatatcaggacggatatcgcccgcgtgattcatcgc
ttcaaacgccatgcctgcggtaatcgcgccatcgccaatgacacagacggtgcggcgattttg
ccttcttttcggcagcaaccgcaataccaattccggcactgatggaggttgatgaatgcccga
cgcttaatacgtcatattcgctttcgccgcgccacgggaacgggtgcagaccgcctttctgacg
gatggtgccgattttgtcgcggcgtccggtcaaaatttatgcggataagcctgatgccccaca
tcccaaatcaattggtcaaacgggtgttgtagacatagtgcagcgccacggtcagttcgaccg
tgcccagcccggaggcgaagtgcccgctggaacggctcacgctgtcgagtaaatagcggcgcag
ttcgtcgcagagtttcggtaaactctctttcggcaacagtcgtaactcctgggtggagtcgacc
agtgccagggtcgggtatttggcaatatcaaaactcatgttttttacctcctaagggcgaatg
cagttagacatacatcagctggttaatcgggaaagggtcaatcagcagcagtttgatgcggttt
tcagtcgcgtagtctgggcgacccagaccatcgccatactggtaggtgcagtgggaaacacgtg
ccatgttaactgcgatttccatgaacgctttaggcagcagggtggagtcgctaacgcgttcacg

Figure 45B

```
attcatcttttccattcggcgtcgatcagtttacgcagttcttcgcgggcctgttcctcgctg
gtaccatcgttttcgtgcatgtagctaatgatagaattggtagtctcgccacgttccagctccg
ccgcagaggtggccagatcgttgcacaggcggaagataacgcagctagaacgcaccagaccatg
gaagtcggtcagggaacgcagcgcgtggtcggagatgtcttcctgctgctggcatacggaaaag
taagacggcgccagcagcgctacaccggaggaggaaacgctggcgttttccaggtacttggaga
aagccgggataattttgttgttggaccatttcgcctcttgcagaaaggctttgcacagttcacg
ccagcttttcgtcagataggacaggttgttatgacctttctctttcagaatagaataggacgtg
tcgttaacggtgttgtacagtgccaggaaacacagtttcatatagtccggcagggtgttaatag
cgttaacgtcccagcgctctacagcatcggtgaacagttgcagttcgtccagagtgccataaac
gtcatacacgtcatcgatgatcgtcaccagaccaaacattttagtaacagctttgcgacattca
ccaaactgcgggtctggcgccatacccagtgcccagaaataaacttccatcaggcggtcgcgta
caaaatccagtttgctagccaggcccatctcggtccaccagcgggacagatcttgcagctcttt
ctggtgcagggtctgtaccatgttaaaatccagcttcgccagctccagcagcagctggtgatgc
ggttctttcggttcgtatttatccaggaaccaacgtgcctccagacggtgcagacgctggtgat
atggcagttccagggcgtggctcacttgttctgcaaccttggtattaatgccttctttcaggtt
gttcttcaggtgggtgatggaaaaggtacgcgcctcctccagcaggttctcaccctcgaaaccc
aggtaagacgcttcatacaggctcagcaggccttggacgtcacctttcagttcaccgctgaaac
caccttctttatccttgaaacgctcaaaaacatcctgagaaacctcgaaaccgtgctgacgcag
cagacggaaagacagagcggttgcgtgcaggtcagatttgttcttttttgttttcgtccagcagt
acgatgttttccagggctttaatgatgtcttttttcaaatttgtaggtcagacccaggcgctgca
catcgtcgatcagctccagcagggacagcggctgggtgtctacacggttgatcatgcagcgaac
ttcttcctccagtttggtcgctttctcctccagcttttccactttcaggtcgttctccagggat
tgcaggaattcgaaattccacaggtttggctgatagtttgcggaacgacgggaattatgctcgg
taatctgagtaaattgagaagaggtcgcacacatggtttattcctccttatttaatcgatacat
taatatatacctctttaattttaataataaagttaatcgataattccggtcgagtgcccacac
agattgtctgataaattgttaaagagcagtgccgcttcgcttttctcagcggcgctgtttcct
gtgtgaaattgttatccgctcacaattccacacattatacgagccggatgattaattgtcaaca
gctcatttcagaatctggcgtaatagcgaagaggcccgcaccgatcgcccttcccaacagttgc
gcagcctgaatggcgaatggcgcctgatgcggtattttctccttacgcatctgtgcggtatttc
acaccgcatatggtgcactctcagtacaatctgctctgatgccgcatagttaagccagccccga
cacccgccaacacccgctgacgagcttagtaaagccctcgctagattttaatgcggatgttgcg
attacttcgccaactattgcgataacaagaaaagccagcctttcatgatatatctcccaattt
gtgtagggcttattatgcacgcttaaaaataataaaagcagacttgacctgatagtttggctgt
gagcaattatgtgcttagtgcatctaacgcttgagttaagccgcgccgcgaagcggcgtcggct
tgaacgaattgttagacattatttgccgactaccttggtgatctcgcctttcacgtagtggaca
aattcttccaactgatctgcgcgcgaggccaagcgatcttcttcttgtccaagataagcctgtc
tagcttcaagtatgacgggctgatactgggccggcaggcgctccattgcccagtcggcagcgac
atccttcggcgcgattttgccggttactgcgctgtaccaaatgcgggacaacgtaagcactaca
tttcgctcatcgccagcccagtcgggcggcgagttccatagcgttaaggtttcatttagcgcct
caaatagatcctgttcaggaaccggatcaaagagttcctccgccgctggacctaccaaggcaac
gctatgttctcttgcttttgtcagcaagatagccagatcaatgtcgatcgtggctggctcgaag
atacctgcaagaatgtcattgcgctgccattctccaaattgcagttcgcgcttagctggataac
gccacggaatgatgtcgtcgtgcacaacaatggtgacttctacagcgcggagaatctcgctctc
tccaggggaagccgaagtttccaaaaggtcgttgatcaaagctcgccgcgttgtttcatcaagc
```

Figure 45C

```
cttacggtcaccgtaaccagcaaatcaatatcactgtgtggcttcaggccgccatccactgcgg
agccgtacaaatgtacggccagcaacgtcggttcgagatggcgctcgatgacgccaactacctc
tgatagttgagtcgatacttcggcgatcaccgcttccctcatgatgtttaactttgttttaggg
cgactgccctgctgcgtaacatcgttgctgctccataacatcaaacatcgacccacggcgtaac
gcgcttgctgcttggatgcccgaggcatagactgtacccaaaaaaacagtcataacaagccat
gaaaaccgccactgcgccgttaccaccgctgcgttcggtcaaggttctggaccagttgcgtgag
cgcatacgctacttgcattacagcttacgaaccgaacaggcttatgtccactgggttcgtgcct
tcatccgtttccacggtgtgcgtcacccggcaaccttgggcagcagcgaagtcgaggcatttct
gtcctggctggcgaacgagcgcaaggtttcggtctccacgcatcgtcaggcattggcggccttg
ctgttcttctacggcaaggtgctgtgcacggatctgccctggcttcaggagatcggaagacctc
ggccgtcgcggcgcttgccggtggtgctgacccggatgaagtggttcgcatcctcggttttct
ggaaggcgagcatcgtttgttcgcccagcttctgtatggaacgggcatgcggatcagtgaggt
ttgcaactgcgggtcaaggatctggatttcgatcacggcacgatcatcgtgcgggagggcaagg
gctccaaggatcgggccttgatgttacccgagagcttggcacccagcctgcgcgagcaggggaa
ttaattcccacgggttttgctgcccgcaaacgggctgttctggtgttgctagtttgttatcaga
atcgcagatccggcttcagccggtttgccggctgaaagcgctatttcttccagaattgccatga
ttttttccccacgggaggcgtcactggctccgtgttgtcggcagctttgattcgataagcagc
atcgcctgtttcaggctgtctatgtgtgactgttgagctgtaacaagttgtctcaggtgttcaa
tttcatgttctagttgctttgttttactggtttcacctgttctattaggtgttacatgctgttc
atctgttacattgtcgatctgttcatggtgaacagctttgaatgcaccaaaaactcgtaaaagc
tctgatgtatctatcttttttacaccgttttcatctgtgcatatggacagttttccctttgata
tgtaacggtgaacagttgttctacttttgtttgttagtcttgatgcttcactgatagatacaag
agccataagaacctcagatccttccgtatttagccagtatgttctctagtgtggttcgttgttt
ttgcgtgagccatgagaacgaaccattgagatcatacttactttgcatgtcactcaaaaatttt
gcctcaaaactggtgagctgaattttttgcagttaaagcatcgtgtagtgttttttcttagtccgt
tatgtaggtaggaatctgatgtaatggttgttggtattttgtcaccattcattttttatctggtt
gttctcaagttcggttacgagatccatttgtctatctagttcaacttggaaaatcaacgtatca
gtcgggcggcctcgcttatcaaccaccaatttcatattgctgtaagtgtttaaatctttactta
ttggtttcaaaacccattggttaagccttttaaactcatggtagttattttcaagcattaacat
gaacttaaattcatcaaggctaatctctatatttgccttgtgagttttcttttgtgttagttct
tttaataaccactcataaatcctcatagagtatttgttttcaaaagacttaacatgttccagat
tatatttatgaatttttttaactggaaaagataaggcaatatctcttcactaaaaactaattc
taattttcgcttgagaacttggcatagtttgtccactggaaaatctcaaagcctttaaccaaa
ggattcctgatttccacagttctcgtcatcagctctctggttgctttagctaatacaccataag
catttccctactgatgttcatcatctgagcgtattggttataagtgaacgataccgtccgttc
tttccttgtagggttttcaatcgtggggttgagtagtgccacacagcataaaattagcttggtt
tcatgctccgttaagtcatagcgactaatcgctagttcatttgctttgaaaacaactaattcag
acatacatctcaattggtctaggtgattttaatcactataccaattgagatgggctagtcaatg
ataattactagtccttttcctttgagttgtgggtatctgtaaattctgctagacctttgctgga
aaacttgtaaattctgctagaccctctgtaaattccgctagacctttgtgtgttttttttgttt
atattcaagtggttataatttatagaataaagaagaataaaaaagataaaagaatagatcc
cagccctgtgtataactcactactttagtcagttccgcagtattacaaaaggatgtcgcaaacg
ctgtttgctcctctacaaaacagaccttaaaaccctaaaggcttaagtagcaccctcgcaagct
cgggcaaatcgctgaatattccttttgtctccgaccatcaggcacctgagtcgctgtcttttc
```

Figure 45D

Gtgacattcagttcgctgcgctcacggctctggcagtgaatgggggtaaatggcactacaggcg
ccttttatggattcatgcaaggaaactacccataatacaagaaaagcccgtcacgggcttctca
gggcgttttatggcgggtctgctatgtggtgctatctgacttttgctgttcagcagttcctgc
cctctgattttccagtctgaccacttcggattatcccgtgacaggtcattcagactggctaatg
cacccagtaaggcagcggtatcatcaacaggctta
(SEQ ID NO:55)

5'-
tcgctgcgctcggtcgttcggctgcggcgagcggtatcagctcactcaaaggcggtaatacggt
tatccacagaatcaggggataacgcaggaaagaacatgtgagcaaaaggccagcaaaaggccag
gaaccgtaaaaaggccgcgttgctggcgtttttccataggctccgcccccctgacgagcatcac
aaaaatcgacgctcaagtcagaggtggcgaaacccgacaggactataaagataccaggcgtttc
cccctggaagctccctcgtgcgctctcctgttccgaccctgccgcttaccggatacctgtccgc
ctttctcccttcgggaagcgtggcgctttctcatagctcacgctgtaggtatctcagttcggtg
taggtcgttcgctccaagctgggctgtgtgcacgaaccccccgttcagcccgaccgctgcgcct
tatccggtaactatcgtcttgagtccaacccggtaagacacgacttatcgccactggcagcagc
cactggtaacaggattagcagagcgaggtatgtaggcggtgctacagagttcttgaagtggtgg
cctaactacggctacactagaagaacagtatttggtatctgcgctctgctgaagccagttacct
tcggaaaaagagttggtagctcttgatccggcaaacaaaccaccgctggtagcggtggttttt
tgtttgcaagcagcagattacgcgcagaaaaaaaggatctcaagaagatcctttgatcttttct
acggggtctgacgctcagtggaacgaaaactcacgttaagggattttggtcatgagattatcaa
aaaggatcttcacctagatccttttaaattaaaaatgaagttttaaatcaatctaaagtatata
tgagtaaacttggtctgacagttaccaatgcttaatcagtgaggcacctatctcagcgatctgt
ctatttcgttcatccatagttgcctgactccccgtcgtgtagataactacgatacgggagggct
taccatctggccccagtgctgcaatgataccgcgagacccacgctcaccggctccagatttatc
agcaataaaccagccagccggaagggccgagcgcagaagtggtcctgcaactttatccgcctcc
atccagtctattaattgttgccgggaagctagagtaagtagttcgccagttaatagtttgcgca
acgttgttgccattgctacaggcatcgtggtgtcacgctcgtcgtttggtatggcttcattcag
ctccggttcccaacgatcaaggcgagttacatgatcccccatgttgtgcaaaaaagcggttagc
tccttcggtcctccgatcgttgtcagaagtaagttggccgcagtgttatcactcatggttatgg
cagcactgcataattctcttactgtcatgccatccgtaagatgcttttctgtgactggtgagta
ctcaaccaagtcattctgagaatagtgtatgcggcgaccgagttgctcttgcccggcgtcaata
cgggataataccgcgccacatagcagaactttaaaagtgctcatcattggaaaacgttcttcgg
ggcgaaaactctcaaggatcttaccgctgttgagatccagttcgatgtaacccactcgtgcacc
caactgatcttcagcatcttttactttcaccagcgtttctgggtgagcaaaaacaggaaggcaa
aatgccgcaaaaaagggaataagggcgacacggaaatgttgaatactcatactcttccttttc
aatattattgaagcatttatcagggttattgtctcatgagcggatacatatttgaatgtattta
gaaaaataaacaaatagggggttccgcgcacatttccccgaaaagtgccacctgacgtctaagaa
accattattatcatgacattaacctataaaaataggcgtatcacgaggccctttcgtctcgcgc
gtttcggtgatgacggtgaaaacctctgacacatgcagctcccggagacggtcacagcttgtct
gtaagcggatgccgggagcagacaagcccgtcagggcgcgtcagcgggtgttggcgggtgtcgg
ggctggcttaactatgcggcatcagagcagattgtactgagagtgcaccatagatctggagctg
taatataaaaaccttcttcaactaacggggcaggttagtgacattagaaaaccgactgtaaaaa
gtacagtcggcattatctcatattataaaagccagtcattaggcctatctgacaattcctgaat
agagttcataaacaatcctgcatgataaccatcacaaacagaatgatgtacctgtaaagatagc
ggtaaatatattgaattacctttattaatgaattttcctgctgtaataatgggtagaaggtaat
tactattattattgatatttaagttaaacccagtaaatgaagtccatggaataatagaaagaga
aaaagcattttcaggtataggtgttttgggaaacaatttccccgaaccattatatttctctaca
tcagaaaggtataaatcataaaactctttgaagtcattctttacaggagtccaaataccagaga
atgttttagatacaccatcaaaaattgtataaagtggctctaacttatcccaataacctaactc
tccgtcgctattgtaaccagttctaaaagctgtatttgagtttatcacccttgtcactaagaaa
ataaatgcagggtaaaatttatatccttcttgttttatgtttc

Figure 51B

```
ggtataaaacactaatatcaatttctgtggttatactaaaagtcgtttgttggttcaaataatg
attaaatatctcttttctcttccaattgtctaaatcaattttattaaagttcatttgatatgcc
tcctaaattttatctaaagtgaatttaggaggcttacttgtctgctttcttcattagaatcaa
tccttttttaaaagtcaatattactgtaacataaatatatattttaaaaatatcccactttatc
caatttcgtttgttgaactaatgggtgctttagttgaagaataaaagacctatgcggtgtgaa
ataccgcacagatgcgtaaggagaaaataccgcatcaggcgccattcgccattcaggctgcgca
actgttgggaagggcgatcggtgcgggcctcttcgctattacgccagctggcgaaaggggatg
tgctgcaaggcgattaagttgggtaacgccagggttttcccagtcacgacgttgtaaaacgacg
gccagtgccaagcttgcatgcctgcactccatttcttctgctatcaaaataacagactcgtga
ttttccaaacgagctttcaaaaaagcctctgcccttgcaaatcggatgcctgtctataaaatt
cccgatattggttaaacagcggcgcaatggcggccgcatctgatgtctttgcttggcgaatgtt
catcttatttcttcctccctctcaataattttttcattctatcccttttctgtaaagtttattt
ttcagaatactttatcatcatgctttgaaaaaatatcacgataatatccattgttctcacgga
agcacacgcaggtcatttgaacgaattttttcgacaggaatttgccgggactcaggagcattta
acctaaaaaagcatgacatttcagcataatgaacatttactcatgtctattttcgttcttttct
gtatgaaaatagttatttcgagtctctacggaaatagcgagagatgatatacctaaatagagat
aaaatcatctcaaaaaatgggtctactaaaatattattccatctattacaataaattcacaga
atagtcttttaagtaagtctactctgaattttttaaaaggagagggtaaagagtgaaaacagt
agttattattgatgcattacgaacaccaattggaaaatataaaggcagcttaagtcaagtaagt
gccgtagacttaggaacacatgttacaacacaacttttaaaaagacattccactatttctgaag
aaattgatcaagtaatctttggaaatgttttacaagctggaaatggccaaaatcccgcacgaca
aatagcaataaacagcggtttgtctcatgaaattcccgcaatgacggttaatgaggtctgcgga
tcaggaatgaaggccgttatttggcgaaacaattgattcaattaggagaagcggaagttttaa
ttgctggcgggattgagaatatgtcccaagcacctaaattacaacgttttaattacgaaacaga
aagctacgatgcgcctttttctagtatgatgtatgatggattaacggatgcctttagtggtcag
gcaatgggcttaactgctgaaaatgtggccgaaaagtatcatgtaactagagaagagcaagatc
aatttctgtacattcacaattaaaagcagctcaagcacaagcagaagggatattcgctgacga
aatagccccattagaagtatcaggaacgcttgtggagaaagatgaagggattcgcctaattcg
agcgttgagaagctaggaacgcttaaaacagttttaaagaagacggtactgtaacagcaggga
atgcatcaaccattaatgatggggcttctgctttgattattgcttcacaagaatatgccgaagc
acacggtcttccttatttagctattattcgagacagtgtggaagtcggtattgatccagcctat
atgggaatttcgccgattaaagccattcaaaaactgttagcgcgcaatcaacttactacggaag
aaattgatctgtatgaaatcaacgaagcatttgcagcaacttcaatcgtggtccaaagagaact
ggctttaccagaggaaaaggtcaacatttatggtggcggtatttcattaggtcatgcgattggt
gccacaggtgctcgtttattaacgagtttaagttatcaattaaatcaaaagaaaagaaatatg
gagtggcttctttatgtatcggcggtggcttaggactcgctatgctactagagagacctcagca
aaaaaaaaacagccgatttatcaaatgagtcctgaggaacgcctggcttctcttcttaatgaa
ggccagatttctgctgatacaaaaaaagaatttgaaaatacggctttatcttcgcagattgcca
atcatatgattgaaaatcaaatcagtgaaacagaagtgccgatgggcgttggcttacatttaac
agtggacgaaactgattatttggtaccaatggcgacagaagagccctcagttattgcggctttg
agtaatggtgcaaaaatagcacaaggatttaaaacagtgaatcaacaacgcttaatgcgtggac
aaatcgttttttacgatgttgcagatcccgagtcattgattgataaactacaagtaagagaagc
ggaagttttcaacaagcagagttaagttatccatctatcgttaaacggggcggcggcttaaga
gatttgcaatatcgtacttttgatgaatcatttgtatctgtcgactttttagtagatgttaagg
atgcaatggggcaaatatcgttaacgctatgttggaaggtgtg
```

Figure 51C gccgagttgttccgtgaatggtttgcggagcaaaagatttttattcagtatttttaagtaattatg
ccacggagtcggttgttacgatgaaaacggctattccagtttcacgtttaagtaaggggagcaa
tggccgggaaattgctgaaaaaattgttttagcttcacgctatgcttcattagatccttatcgg
gcagtcacgcataacaaaggaatcatgaatggcattgaagctgtagttttagctacaggaaatg
atacacgcgctgttagcgcttcttgtcatgcttttgcggtgaaggaaggtcgctaccaaggctt
gactagttggacgctggatggcgaacaactaattggtgaaatttcagttccgcttgctttagcc
acggttggcggtgccacaaaagtcttacctaaatctcaagcagctgctgatttgttagcagtga
cggatgcaaaagaactaagtcgagtagtagcggctgttggtttggcacaaaatttagcggcgtt
acgggccttagtctctgaaggaattcaaaaggacacatggctctacaagcacgttcttagcg
atgacggtcggagctactggtaaagaagttgaggcagtcgctcaacaattaaaacgtcaaaaaa
cgatgaaccaagaccgagccatggctatttttaaatgatttaagaaaacaataaaaggagagggt
gacaattgggattgataaaattagtttttttgtgccccttattatattgatatgacggcactg
gctgaagccagaaatgtagaccctggaaaatttcatattggtattgggcaagaccaaatggcgg
tgaacccaatcagccaagatattgtgacatttgcagccaatgccgcagaagcgatcttgaccaa
agaagataaagaggccattgatatggtgattgtcgggactgagtccagtatcgatgagtcaaaa
gcggccgcagttgtcttacatcgtttaatggggattcaacctttcgctcgctctttcgaaatca
aggaagcttgttacggagcaacagcaggcttacagttagctaagaatcacgtagccttacatcc
agataaaaaagtcttggtcgtagcggcagatattgcaaaatatggcttaaattctggcggtgag
cctacacaaggagctggggcggttgcaatgttagttgctagtgaaccgcgcatttttggctttaa
aagaggataatgtgatgctgacgcaagatatctatgacttttggcgtccaacaggccacccgta
tcctatggtcgatggtcctttgtcaaacgaaacctacatccaatcttttgcccaagtctgggat
gaacataaaaaacgaaccggtcttgattttgcagattatgatgctttagcgttccatattcctt
acacaaaaatgggcaaaaaagccttattagcaaaatctccgaccaaactgaagcagaacagga
acgaattttagcccgttatgaagaaagtatcgtctatagtcgtcgcgtaggaaacttgtatacg
ggttcactttatctgggactcatttcccttttagaaaatgcaacgactttaaccgcaggcaatc
aaattggtttattcagttatggttctggtgctgtcgctgaattttcactggtgaattagtagc
tggttatcaaaatcatttacaaaagaaactcatttagcactgctggataatcggacagaactt
tctatcgctgaatatgaagccatgtttgcagaaactttagacacagacattgatcaaacgttag
aagatgaattaaaatatagtatttctgctattaataataccgttcgttcttatcgaaactaaaa
aaaaccggccttggccccgccggttttttattatttttcttcctccgcatgttcaatccgctcc
ataatcgacggatggctccctctgaaaattttaacgagaaacggcgggttgacccggctcagtc
ccgtaacggccaagtcctgaaacgtctcaatcgccgcttcccggtttccggtcagctcaatgcc
gtaacggtcggcggcgttttcctgataccgggagacggcattcgtaatcgggatccccgggtac
cgagctcgaattcgtaatcatgtcatagctgtttcctgtgtgaaattgttatccgctcacaatt
ccacacaacatacgagccggaagcataaagtgtaaagcctggggtgcctaatgagtgagctaac
tcacattaattgcgttgcgctcactgcccgctttccagtcgggaaacctgtcgtgccagctgca
ttaatgaatcggccaacgcgcggggagaggcggtttgcgtattgggcgctcttccgcttcctcg
ctcactgac
(SEQ ID NO:56)

Figure 55A 1-
tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgggggctcccttagggttcc
gatttagtgctttacggcacctcgaccccaaaaaacttgattagggtgatggttcacgtagtgggccatcgccctgatagacggtttttcgccc
tttgacgttggagtccacgttctttaatagtggactcttgttccaaactggaacaacactcaaccctatctcggtctattcttttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaaccccctatttgtttattttttctaaatacattcaaatatgtatccgctcatgaattaattcttagaaaaactcatcg
agcatcaaatgaaactgcaatttattcatatcaggattatcaataccatattttgaaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgtttcccggggatcgcagtggtgagtaaccatgcatcatcaggagtacggataaaatgcttgatggtcggaagag
gcataaattccgtcagccagttagtctgaccatctcatctgtaacatcattggcaacgctacctttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacaccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccaggggggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttctttcctgcgttatccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
gggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcaggggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag

Figure 55B ccagccagacgcagacgcgccgagacagaacttaatgggcccgctaacagcgcgatttgctggtgacccaatgcgaccagatgctccac
gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccacttttttcccgcgtttccgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
taggggaattgtgagcggataacaattcccctctagaaataattttgtttaactttaagaaggagatatacatatgcgttgtagcgtgtccaccg
aaaatgtgtctttcaccgaaactgaaaccgaagctcgtcgttctgcgaactacgaacctaacagctgggactatgattacctgctgtcctccga
cacggacgagtccatcgaagtatacaaagacaaagcgaaaaagctggaagccgaagttcgtcgcgagattaataacgaaaaagcagaat
ttctgaccctgctggaactgattgacaacgtccagcgcctgggcctgggttaccgtttcgagtctgatatccgtggtgcgctggatcgcttcgt
ttcctccggcggcttcgatgcggtaaccaagacttccctgcacggtacggcactgtctttccgtctgctgcgtcaacacggttttgaggtttctc
aggaagcgttcagcggcttcaaagaccaaaacggcaacttcctggagaacctgaaggaagatatcaaagctatcctgagcctgtacgagg
ccagcttcctggctctggaaggcgaaaacatcctggacgaggcgaaggttttcgcaatctctcatctgaaagaactgtctgaagaaaagatc
ggtaaagagctggcagaacaggtgaaccatgcactggaactgccactgcatcgccgtactcagcgtctggaagcagtatggtctatcgag
gcctaccgtaaaaaggaggacgcgaatcaggttctgctggagctggcaattctggattacaacatgatccagtctgtataccagcgtgatct
gcgtgaaacgtcccgttggtggcgtcgtgtgggtctggcgaccaaactgcactttgctcgtgaccgcctgattgagagcttctactgggccg
tgggtgtagcattcgaaccgcaatactccgactgccgtaactccgtcgcaaaaatgttttctttcgtaaccattatcgacgatatctacgatgtat
acggcaccctggacgaactggagctgtttactgatgcagttgagcgttgggacgtaaacgccatcaacgacctgccggattacatgaaact
gtgctttctggctctgtataacactattaacgaaatcgcctacgacaacctgaaagataaaggtgagaacatcctgccgtatctgaccaaagc
ctgggctgacctgtgcaacgctttcctgcaagaagccaagtggcgtgtacaacaaatctactccgacctttgacgactacttcggcaacgcatg
gaaatcctcttctggcccgctgcaactggtgttcgcttacttcgctgtcgtgcagaacattaaaaaggaagagatcgaaaacctgcaaaaata
ccatgacaccatctctcgtccttcccatatcttccgtctgtgcaatgacctggctagcgcgtctgcggaaattgcgcgtggtgaaaccgcaaat
agcgtttcttgttacatgcgcactaaaggtatctccgaagaactggctaccgaaagcgtgatgaatctgatcgatgaaacctggaaaaagatg
aacaaggaaaaactgggtggtagcctgttcgcgaaaccgttcgtggaaaccgcgatcaacctggcacgtcaatctcactgcacttatcataa
cggcgacgcgcataccctctccggatgagctgacccgcaaacgcgttctgtctgtaatcactgaaccgattctgccgtttgaacgctaaggat
ccgaattcgagctccgtcgacaagcttgcggccgcactcgagcaccaccaccaccactgagatccggctgctaacaaagcccgaaa
ggaagctgagttggctgctgccaccgctgagcaataactagcataacccttggggcctctaaacgggtcttgaggggttttttgctgaaag
gaggaactatatccggat (SEQ ID NO:87)

Figure 58A 1-
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctggggttaccgtttcgagtctgatatccgtggtgcgctggatcgcttcgtttcctccggcggcttcgatgcggtaaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggtttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgttttctttcgtaaccattatcgacgatatctacgatgtatacggcaccctggacgaactggagctgtttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgctttcctgcaagaagcca
agtggctgtacaacaaatctactccgacctttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttcccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcatacctctccggatgagctgaccc
gcaaacgcgttctgtctgtaatcactgaaccgattctgccgtttgaacgctaactgcagctggtaccatatgggaattcgaagctttctagaac
aaaaactcatctcagaagaggatctgaatagcgccgtcgaccatcatcatcatcatcattgagtttaaacgctctccagcttggctgttttggcg
gatgagagaagatttcagcctgatacagattaaatcagaacgcagaagcggtctgataaaacagaatttgcctggcggcagtagcgcggt
ggtcccacctgaccccatgccgaactcagaagtgaaacgccgtagcgccgatggtagtgtggggtctcccatgcgagagtagggaact
gccaggcatcaaataaaacgaaaggctcagtcgaaagactgggcctttcgttttatctgttgtttgtcggtgaacgctctcctgagtaggacaa
atccgccgggagcggatttgaacgttgcgaagcaacggcccggagggtggcgggcaggacgcccgccataaactgccaggcatcaaat
taagcagaaggccatcctgacggatggcctttttgcgtttctacaaactcttttgtttattttctaaatacattcaaatatgtatccgctcatgaga
caataaccctgataaatgcttcaataatattgaaaaaggaagagtatgagtattcaacatttccgtgtcgcccttattccctttttttgcggcattttg
ccttcctgtttttgctcacccagaaacgctggtgaaagtaaaagatgctgaagatcagttgggtgcacgagtgggttacatcgaactggatctc
aacagcggtaagatccttgagagttttcgccccgaagaacgttttccaatgatgagcacttttaaagttctgctatgtggcgcggtattatcccg
tgttgacgccgggcaagagcaactcggtcgccgcatacactattctcagaatgacttggttgagtactcaccagtcacagaaaagcatcttac
ggatggcatgacagtaagagaattatgcagtgctgccataaccatgagtgataacactgcggccaacttacttctgacaacgatcggagga
ccgaaggagctaaccgctttttgcacaacatgggggatcatgtaactcgccttgatcgttgggaaccggagctgaatgaagccataccaaa
cgacgagcgtgacaccacgatgcctgtagcaatggcaacaacgttgcgcaaactattaactggcgaactacttactctagcttcccggcaac
aattaatagactggatggaggcggataaagttgcaggaccacttctgcgctcggcccttccggctggctggtttattgctgataaatctggag
ccggtgagcgtgggtctcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcagaccaagtttactcatatata
ctttagattgatttaaaacttcattttaatttaaaaggatctaggtgaagatcctttttgataatctcatgaccaaaatcccttaacgtgagttttcgtt
ccactgagcgtcagaccccgtagaaaagatcaaaggatcttcttgagatcctttttttctgcgcgtaatctgctgcttgcaaacaaaaaaacca
ccgctaccagcggtggtttgtttgccggatcaagagctaccaactctttttccgaaggtaactggcttcagcagagcgcagataccaaatact
gtccttctagtgtagccgtagttaggccaccacttcaagaactctgtagcaccgcctacatacctcgctctgctaatcctgttaccagtggctgc

Figure 58B tgccagtggcgataagtcgtgtcttaccgggttggactcaagacgatagttaccggataaggcgcagcggtcgggctgaacggggggttc
gtgcacacagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccagggggaaacgcctggtat
ctttatagtcctgtcgggtttcgccacctctgacttgagcgtcgatttttgtgatgctcgtcaggggggcggagcctatggaaaaacgccagca
acgcggccttttacggttcctggcctttgctggcctttgctcacatgttctttcctgcgttatccctgattctgtggataaccgtattaccgcct
ttgagtgagctgataccgctcgccgcagccgaacgaccgagcgcagcgagtcagtgagcgaggaagcggaagagcgcctgatgcggt
atttctccttacgcatctgtgcggtatttcacaccgcatatggtgcactctcagtacaatctgctctgatgccgcatagttaagccagtatacact
ccgctatcgctacgtgactgggtcatggctgcgccccgacaccgccaacacccgctgacgcgccctgacgggcttgtctgctcccggca
tccgcttacagacaagctgtgaccgtctccgggagctgcatgtgtcagaggttttcaccgtcatcaccgaaacgcgcgaggcagcagatca
attcgcgcgcgaaggcgaagcggcatgcatttacgttgacaccatcgaatggtgcaaaacctttcgcggtatggcatgatagcgcccggaa
gagagtcaattcagggtggtgaatgtgaaaccagtaacgttatacgatgtcgcagagtatgccggtgtctcttatcagaccgtttcccgcgtg
gtgaaccaggccagccacgtttctgcgaaaacgcgggaaaaagtggaagcggcgatggcggagctgaattacattcccaaccgcgtggc
acaacaactggcgggcaaacagtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaagcctgtaaagcggcggtgcacaa
tcttctcgcgcaacgcgtcagtgggctgatcattaactatccgctggatgaccaggatgccattgctgtggaagctgcctgcactaatgttccg
gcgttatttcttgatgtctctgaccagacacccatcaacagtattattttctcccatgaagacggtacgcgactgggcgtggagcatctggtcgc
attgggtcaccagcaaatcgcgctgttagcgggcccattaagttctgtctcggcgcgtctgcgtctggctggctggcataaatatctcactcg
caatcaaattcagccgatagcggaacgggaaggcgactggagtgccatgtccggttttcaacaaaccatgcaaatgctgaatgagggcatc
gttcccactgcgatgctggttgccaacgatcagatggcgctgggcgcaatgcgcgccattaccgagtccgggctgcgcgttggtgcggat
atctcggtagtgggatacgacgataccgaagacagctcatgttatatcccgccgtcaaccaccatcaaacaggatttttcgcctgctggggca
aaccagcgtggaccgcttgctgcaactctctcagggccaggcggtgaagggcaatcagctgttgcccgtctcactggtgaaaagaaaaac
caccctggcgcccaatacgcaaaccgcctctccccgcgcgttggccgattcattaatgcagctggcacgacaggtttcccgactggaaagc
gggcagtgagcgcaacgcaattaatgtgagttagcgcgaattgatctg (SEQ ID NO:88)

Figure 61A 1-
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctgggttaccgtttcgagtctgatatccgtggtgcgctggatcgcttcgtttcctccggcggcttcgatgcggtaaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggttttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgttttctttcgtaaccattatcgacgatatctacgatgtatacggcaccctggacgaactggagctgtttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgctttcctgcaagaagcca
agtggctgtacaacaaatctactccgacctttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttccatatcttccgtctg
tgcaatgacctggctagcgcgtctgcggaaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcatacctctccggatgagctgaccc
gcaaacgcgttctgtctgtaatcactgaaccgattctgccgtttgaacgctaactgcataaaggaggtaaaaaaacatggtatcctgttctgcg
ccgggtaagatttacctgttcggtgaacacgccgtagtttatggcgaaactgcaattgcgtgtgcggtggaactgcgtacccgtgttcgcgcg
gaactcaatgactctatcactattcagagccagatcggccgcaccggtctggatttcgaaaagcacccttatgtgtctgcggtaattgagaaa
atgcgcaaatctattcctattaacggtgttttcttgaccgtcgtcgattccgacatcccggtgggctccggtctgggtagcagcgcagccgttactat
cgcgtctattggtgcgctgaacgagctgttcggctttggcctcagcctgcaagaaatcgctaaactgggccacgaaatcgaaattaaagtac
agggtgccgcgtccccaaccgatacgtatgtttctaccttcggcggcgtggttaccatcccggaacgtcgcaaactgaaaactccggactg
cggcattgtgattggcgataccggcgtttctcctccaccaaagagttagtagctaacgtacgtcagctgcgcgaaagctacccggatttgat
cgaaccgctgatgacctctattggcaaaatctctcgtatcggcgaacaactggttctgtctggcgactacgcatccatcggccgcctgatgaa
cgtcaaccagggtctcctggacgccctgggcgttaacatcttagaactgagccagctgatctattccgctcgtgcggcaggtgcgtttggcg
ctaaaatcacgggcgctggcggcggtggctgtatggttgcgctgaccgctccggaaaaatgcaaccaagtggcagaagcggtagcaggc
gctggcggtaaagtgactatcactaaaccgaccgagcaaggtctgaaagtagattaaagtctagttaaagtttaaacggtctccagcttggct
gttttggcggatgagagaagattttcagcctgatacagattaaatcagaacgcagaagcggtctgataaaacagaatttgcctggcggcagt
agcgcggtggtcccacctgaccccatgccgaactcagaagtgaaacgccgtagcgccgatggtagtgtggggtctcccatgcgagagt
agggaactgccaggcatcaaataaaacgaaaggctcagtcgaaagactgggccttcgttttatctgttgtttgtcggtgaacgctctcctgag
taggacaaatccgccgggagcggatttgaacgttgcgaagcaacggcccggagggtggcgggcaggacgcccgccataaactgccag
gcatcaaattaagcagaaggccatcctgacggatggccttttgcgtttctacaaactcttttgttattttctaaatacattcaaatatgtatccg
ctcatgagacaataaccctgataaatgcttcaataatattgaaaaaggaagagtatgagtattcaacatttccgtgtcgcccttattcccttttttg
cggcattttgccttcctgtttttgctcacccagaaacgctggtgaaagtaaaagatgctgaagatcagttgggtgcacgagtgggttacatcga
actggatctcaacagcggtaagatccttgagagttttcgccccgaagaacgttttccaatgatgagcacttttaaagttctgctatgtggcgcg
gtattatcccgtgttgacgccgggcaagagcaactcggtcgccgcatacactattctcagaatgacttggttgagtactcaccagtcacagaa
aagcatcttacggatggcatgacagtaagagaattatgcagtgctgccataaccatgagtgataacactgcggccaacttacttctgacaacg

Figure 61B atcggaggaccgaaggagctaaccgcttttttgcacaacatgggggatcatgtaactcgccttgatcgttgggaaccggagctgaatgaag
ccataccaaacgacgagcgtgacaccacgatgcctgtagcaatggcaacaacgttgcgcaaactattaactggcgaactacttactctagct
tcccggcaacaattaatagactggatggaggcggataaagttgcaggaccacttctgcgctcggcccttccggctggctggtttattgctgat
aaatctggagccggtgagcgtgggtctcgcggtatcattgcagcactggggccagatggtaagccctcccgtatcgtagttatctacacgac
gggagtcaggcaactatggatgaacgaaatagacagatcgctgagataggtgcctcactgattaagcattggtaactgtcagaccaagttt
actcatatatactttagattgatttaaaacttcatttttaatttaaaaggatctaggtgaagatcctttttgataatctcatgaccaaaatcccttaacgt
gagttttcgttccactgagcgtcagaccccgtagaaaagatcaaaggatcttcttgagatccttttttctgcgcgtaatctgctgcttgcaaaca
aaaaaaccaccgctaccagcggtggtttgtttgccggatcaagagctaccaactcttttccgaaggtaactggcttcagcagagcgcagat
accaaatactgtccttctagtgtagccgtagttaggccaccacttcaagaactctgtagcaccgcctacatacctcgctctgctaatcctgttac
cagtggctgctgccagtggcgataagtcgtgtcttaccgggttggactcaagacgatagttaccggataaggcgcagcggtcgggctgaa
cggggggttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccagggggaa
acgcctggtatctttatagtcctgtcgggtttcgccacctctgacttgagcgtcgatttttgtgatgctcgtcagggggcggagcctatggaaa
aacgccagcaacgcggcctttttacggttcctggccttttgctggccttttgctcacatgttctttcctgcgttatcccctgattctgtggataacc
gtattaccgcctttgagtgagctgataccgctcgccgcagccgaacgaccgagcgcagcgagtcagtgagcgaggaagcggaagagcg
cctgatgcggtattttctccttacgcatctgtgcggtatttcacaccgcatatggtgcactctcagtacaatctgctctgatgccgcatagttaag
ccagtatacactccgctatcgctacgtgactgggtcatggctgcgccccgacacccgccaacacccgctgacgcgccctgacgggcttgt
ctgctcccggcatccgcttacagacaagctgtgaccgtctccgggagctgcatgtgtcagaggttttcaccgtcatcaccgaaacgcgcga
ggcagcagatcaattcgcgcgcgaaggcgaagcggcatgcatttacgttgacaccatcgaatggtgcaaaacctttcgcggtatggcatga
tagcgcccggaagagagtcaattcagggtggtgaatgtgaaaccagtaacgttatacgatgtcgcagagtatgccggtgtctcttatcagac
cgtttcccgcgtggtgaaccaggccagccacgttctgcgaaaacgcgggaaaaagtggaagcggcgatggcggagctgaattacattcc
caaccgcgtggcacaacaactggcgggcaaacagtcgttgctgattggcgttgccacctccagtctggccctgcacgcgccgtcgcaaatt
gtcgcggcgattaaatctcgcgccgatcaactgggtgccagcgtggtggtgtcgatggtagaacgaagcggcgtcgaagcctgtaaagcg
gcggtgcacaatcttctcgcgcaacgcgtcagtgggctgatcattaactatccgctggatgaccaggatgccattgctgtggaagctgcctg
cactaatgttccgcgcgttatttcttgatgtctctgaccagacacccatcaacagtattatttctcccatgaagacggtacgcgactgggcgtgg
agcatctggtcgcattgggtcaccagcaaatcgcgctgttagcgggcccattaagttctgtctcggcgcgtctgcgtctggctggctggcata
aatatctcactcgcaatcaaattcagccgatagcggaacgggaaggcgactggagtgccatgtccggttttcaacaaaccatgcaaatgctg
aatgagggcatcgttcccactgcgatgctggttgccaacgatcagatggcgctgggcgcaatgcgcgccattaccgagtccgggctgcgc
gttggtgcggatatctcggtagtgggatacgacgataccgaagacagctcatgttatatcccgccgtcaaccaccatcaaacaggattttcgc
ctgctggggcaaaccagcgtggaccgcttgctgcaactctctcagggccaggcggtgaagggcaatcagctgttgcccgtctcactggtg
aaagaaaaaccaccctggcgcccaatacgcaaaccgcctctccccgcgcgttggccgattcattaatgcagctggcacgacaggtttccc
gactggaaagcgggcagtgagcgcaacgcaattaatgtgagttagcgcgaattgatctg (SEQ ID NO:89)

Figure 63A 1-
aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcactttcggggaaatgtgcgcggaaccccctatttgttt
attttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgtctgatgccg
ccgtgttccggctgtcagcgcaggggcgcccggttcttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcattttttaatttaaaaaggatctaggtgaagatccttttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaaggggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

Figure 63B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggtttttcttttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccactt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactatagggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagcccgctgggcacttggcgctacacaagt
ggcctctggcctcgcacacattccacatccaccggtaggcgccaacggctccgttctttggtggcccctcgcgccaccttccactcctcc
cctagtcaggaagttccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaaggggtgggtccggggcgggctcaggggcgggctcagggcggggcggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggccttttaaag
accgtaaagaaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagctttattttcatgatctgtgtgttggttttttgtgtgcggcgcggaagttcctattctctag
aaagtataggaacttcctcgagccctatagtgagtcgtattagatcgcggccgcgcccttgacaatgccacatcctgagcaaataattcaacc
actaattgtgagcggataacaaaggaggtaaaaaaacatggtatcctgttctgcgccgggtaagatttacctgttcggtgaacacgccgtagt
ttatggcgaaactgcaattgcgtgtgcggtggaactgcgtaccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaaattaaagtacagggtgccgcgtccccaaccgatacgtatgttctacc
ttcggcggcgtggttaccatcccggaacgtcgcaaactgaaaactccggactgcggcattgtgattggcgataccggcgttttctcctccac
caaagagttagtagctaacgtacgtcagctgcgcgaaagctaccggatttgatcgaaccgctgatgacctctattggcaaaatctctcgtat
cggcgaacaactggttctgtctggcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

Figure 63C tgcgctgaccgctccggaaaaatgcaaccaagtggcagaagcggtagcaggcgctggcggtaaagtgactatcactaaaccgaccgag
caaggtctgaaagtagattaa (SEQ ID NO:90)

Figure 64A 1-
aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagagcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcacttttcggggaaatgtgcgcggaaccccctatttgttt
atttttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgtctgatgccg
ccgtgttccggctgtcagcgcaggggcgcccggttcttttgtcaagaccgacctgtccggtgccctgaatgaactgcaggacgaggcagc
gcggctatcgtggctggccacgacgggcgttccttgcgcagctgtgctcgacgttgtcactgaagcggggaagggactggctgctattggg
cgaagtgccgggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcattttttaatttaaaaggatctaggtgaagatcctttttgataatct
catgaccaaaatcccttaacgtgagttttcgttccactgagcgtcagacccgctagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

Figure 64B

```
tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggttttctttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactataggggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagcccgctgggcacttggcgctacacaagt
ggcctctggcctcgcacacattccacatccaccggtaggcgccaaccggctccgttctttggtggcccttcgcgccaccttccactcctcc
cctagtcaggaagttccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaagggtgggtccgggggcgggctcagggggcgggctcagggggcggggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggcctttttaaag
accgtaaagaaaaataagcacaagttttatccggcctttattcacattcttgcccgcctgatgaatgctcatccggaattccgtatggcaatgaa
agacggtgagctggtgatatgggatagtgttcaccccttgttacaccgttttccatgagcaaactgaaacgtttcatcgctctggagtgaatacc
acgacgatttccggcagtttctacacatatattcgcaagatgtggcgtgttacggtgaaaacctggcctatttccctaaagggtttattgagaat
atgttttcgtctcagccaatccctgggtgagtttcaccagttttgatttaaacgtggccaatatggacaacttcttcgcccccgtttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagctttatttcatgatctgtgtgttggttttgtgtgcggcgcggaagttcctattctctag
aaagtataggaacttcctcgagccctatagtgagtcgtattagatcgcggccgcgcccttgaccatgccacatcctgagcaaataattcaacc
actaattgtgagcggataacaaaggaggtaaaaaaacatggtatccgttctgcgccgggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaaattaaagtacagggtgccgcgtcccaaccgatacgtatgtttctacc
ttcggcggcgtggttaccatcccggaacgtcgcaaactgaaaactccggactgcggcattgtgattggcgataccggcgttttctcctccac
caaagagttagtagctaacgtacgtcagctgcgcgaaagctacccggatttgatcgaaccgctgatgacctctattggcaaaatctctcgtat
cggcgaacaactggttctgtctggcgactacgcatccatcggccgcctgatgaacgtcaaccaggtctcctggacgccctgggcgttaac
atcttagaactgagccagctgatctattccgctcgtgcggcaggtgcgtttggcgctaaaatcacgggcgctggcggcggtggctgtatggt
```

Figure 64C tgcgctgaccgctccggaaaaatgcaaccaagtggcagaagcggtagcaggcgctggcggtaaagtgactatcactaaaccgaccgag
caaggtctgaaagtagattaa (SEQ ID NO:91)

Figure 65A 1-
aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaaactaccgcattaaagcttatcgatgataagctgtcaaacatgagaattaattcttgaagacgaaagggcctcgtg
atacgcctattttataggttaatgtcatgataataatggtttcttagacgtcaggtggcacttttcggggaaatgtgcgcggaacccctatttgttt
attttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttcttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcg
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagacccgctagaaaagatcaaaggatcttcttgagatccttttttctgcg
cgtaatctgctgcttgcaaacaaaaaaaccaccgctaccagccggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aaggggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

Figure 65B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggttttctttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccacttt
ttcccgcgtttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactataggggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttctttggtgcccccttcgcgccaccttccactcctcc
cctagtcaggaagttccccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaagggggtgggtccggggcgggctcaggggcgggctcaggggcggggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggcctttttaaag
accgtaaagaaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagctttattttcatgatctgtgtgttggttttgtgtgcggcgcggaagttcctattctctag
aaagtataggaacttcctcgagcccatagtgagtcgtattagatcgcggccgcgcccttgacgatgccacatcctgagcaaataattcaacc
actaattgtgagcggataacaaaggaggtaaaaaaacatggtatcctgttctgcgccgggtaagatttacctgttcggtgaacacgccgtagt
ttatggcgaaactgcaattgcgtgtgcggtggaactgcgtaccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaaattaaagtacagggtgccgcgtccccaaccgatacgtatgtttctacc
ttcggcggcgtggttaccatcccggaacgtcgcaaactgaaaactccggactgcggcattgtgattggcgataccggcgttttctcctccac
caaagagttagtagctaacgtacgtcagctgcgcgaaagctaccggatttgatcgaaccgctgatgacctctattggcaaaatctctcgtat
cggcgaacaactggttctgtctggcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

Figure 65C tgcgctgaccgctccggaaaaatgcaaccaagtggcagaagcggtagcaggcgctggcggtaaagtgactatcactaaaccgaccgag
caaggtctgaaagtagattaa (SEQ ID NO:92)

Figure 66A

1- aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctattttataggttaatgtcatgataataatggtttcttagacgtcaggtggcacttttcggggaaatgtgcgcggaaccccctatttgttt
attttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttcttttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcattttaatttaaaaggatctaggtgaagatccttttgataatct
catgaccaaaatcccttaacgtgagttttcgttccactgagcgtcagaccccgtagaaaagatcaaaggatcttcttgagatccttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttcttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtatttttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtataggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

Figure 66B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggttttcttttcaccagtgagacgggcaacagctgattgcccttcaccgcc
tggccctgagagagttgcagcaagcggtccacgctggtttgccccagcaggcgaaaatcctgtttgatggtggttaacgcgcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggtttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacgggcctgccaccataccacgccgaaacaagcgctcatgagcccg
aagtggcgagcccgatcttcccatcggtgatgtcggcgatataggcgccagcaaccgcacctgtggcgccggtgatgccggccacgat
gcgtccggcgtagaggatcgagatctcgatcccgcgaaattaatacgactcactataggggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagcccgctgggcacttggcgctacacaagt
ggcctctggcctcgcacacattccacatccaccggtaggcgccaaccggctccgttctttggtggccccttcgcgccaccttccactcctcc
cctagtcaggaagttcccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaaggggtgggtccggggcgggctcaggggcgggctcagggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggccttttaaag
accgtaaagaaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctgggggttcgaataaagaccgaccaagcgacgtct
gagagctccctggcgaattcggtaccaataaaagagctttattttcatgatctgtgtgttggtttttgtgtgcggcgcggaagttcctattctctag
aaagtataggaacttcctcgagccctatagtgagtcgtattagatcgcggccgcgcccttgactatgccacatcctgagcaaataattcaacc
actaattgtgagcggataacaaaggaggtaaaaaaacatggtatcctgttctgcgccgggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaaattaaagtacagggtgccgcgtccccaaccgatacgtatgttctacc
ttcggcggcgtggttaccatcccggaacgtcgcaaactgaaaactccggactgcggcattgtgattggcgataccggcgttttctcctccac
caaaagagttagtagctaacgtacgtcagctgcgcgaaagctaccggatttgatcgaaccgctgatgacctctattggcaaaatctctcgtat
cggcgaacaactggttctgtctggcgactacgcatccatcggccgcctgatgaacgtcaaccaggtctcctggacgccctgggcgttaac
atcttagaactgagccagctgatctattccgctcgtgcggcaggtgcgtttggcgctaaaatcacgggcgctggcggcggtggctgtatggt

Figure 66C tgcgctgaccgctccggaaaaatgcaaccaagtggcagaagcggtagcaggcgctggcggtaaagtgactatcactaaaccgaccgag
caaggtctgaaagtagattaa (SEQ ID NO:93)

Figure 73B gcggccgcgcccttgacgatgccacatcctgagcaaataattcaaccactaattgtgagcggataacacaaggaggaaacagc
catggtatcctgttctgcgccgggtaagatttacctgttcggtgaacacgccgtagtttatggcgaaactgcaattgcgtgtgcggt
ggaactgcgtacccgtgttcgcgcggaactcaatgactctatcactattcagagccagatcggccgcaccggtctggatttcgaa
aagcacccttatgtgtctgcggtaattgagaaaatgcgcaaatctattcctattaacggtgttttcttgaccgtcgattccgacatccc
ggtgggctccggtctgggtagcagcgcagccgttactatcgcgtctattggtgcgctgaacgagctgttcggctttggcctcagc
ctgcaagaaatcgctaaactgggccacgaaatcgaaattaaagtacagggtgccgcgtccccaaccgatacgtatgtttctacct
tcggcggcgtggttaccatcccggaacgtcgcaaactgaaaactccggactgcggcattgtgattggcgataccggcgttttctc
ctccaccaaagagttagtagctaacgtacgtcagctgcgcgaaagctacccggatttgatcgaaccgctgatgacctctattggc
aaaatctctcgtatcggcgaacaactggttctgtctggcgactacgcatccatcggccgcctgatgaacgtcaaccagggtctcct
ggacgccctgggcgttaacatcttagaactgagccagctgatctattccgctcgtgcggcaggtgcgtttggcgctaaaatcacg
ggcgctggcggcggtggctgtatggttgcgctgaccgctccggaaaaatgcaaccaagtggcagaagcggtagcaggcgct
ggcggtaaagtgactatcactaaaccgaccgagcaaggtctgaaagtagattaagccttgacttaatagctgcttatttcgcccta
tggtacctagtaggaggaaaaaaacatggaaatgcgtcaaccggctgtcgcaggtcaattctacccactgcgttgcgagaacct
ggaaaacgaactgaaacgctgcttcgaaggcctggagatccgcgaacaagaagtgctgggcgcagtctgtccgcacgccggt
tatatgtactctggcaaagttgcggcgcacgtctatgccactctgccggaagctgatacctacgtaatcttcggcccgaaccacac
cggctacggtagccctgtctctgtgagccgtgaaacttggaagaccccgttgggcaatatcgatgttgacctggaactggcgga
cggcttcctgggttccatcgtagatgcggatgaactcggtcacaaatacgaacactctatcgaagttcagctgccgtttctgcaata
ccgttttgaacgcgatttcaaaattctgccaatctgcatgggtatgcaagacgaagaaaccgcggtcgaagtaggtaacctgctg
gcggatctgatcagcgagtccggtaaacgtgctgtgatcatcgcaagctctgatttcacccactatgagacggctgaacgtgcca
aagaaatcgattccgaagttattgattctatcctgaactttgacatctctggcatgtacgatcgcctgtatcgccgtaacgcctctgttt
gcggttacggcccgatcaccgctatgctgacggcaagcaaaaagctgggcggctctcgtgcgactttgctgaaatacgcaaac
agcggtgacgtgtccggtgataaagacgctgtggtgggctacgccgccatcatcgttgagtaagctgattaaaggttgaacagat
aggatttcgtcatggatcctacaaggaggaaaaaaacatgaatgcttctaatgaaccggtgattctgaaactgggtggctctgcta
ttaccgacaaaggtgcctacgaaggcgtagttaaggaagctgatttgctgcgcatcgcacaggaagttagcggtttccgtggca
agatgatcgtggttcatggtgctggtagcttcggccatacgtacgcgaagaaatacggcctggaccgtaccttcgacccagagg
gcgcaattgttactcatgaatctgttaaaaagctcgcctccaaagttgtaggtgctctgaatagcttcggcgtgcgtgctatcgcgg
tgcatcctatggactgcgcagtatgccgtaacggtcgtatcgaaacgatgtatctggactccatcaagttaatgctggaaaaaggt
ctggtgccggttctgcacggcgacgtcgcaatggatattgaactgggcacttgtatcctgtccggtgatcaaatcgttcctacctg
gccaaagaactgggtatctcccgcctcggcctgggcagcgcagaggatggtgtgctggatatggagggcaaacctgtaccgg
aaaatcaccccagaaactttcgaagagttccgccactgcatcggtggttctggttctactgatgtaaccggtggcatgctgggcaaa
gtgctggaacttctggaattgagcaaaaattcttccattactagctacattttcaacgctggtaaagcagacaacatctaccgctttct
gaatggtgagtccatcggcactcgcatcagcccggacaagcgtgtttaagctagttattaacctaaatgctctaaaccagttatga
gctctacaaggaggaaaaaaacatgattaacactaccagccgccgcaaaattgaacacctgaaactctgcgcagaatccccgg
ttgaagcgcgtcaggtatctgccggctttgaagacgttactctgatccaccgcgctttaccggagctgaacatggatgaactgga
cctcagcgttgatttcctgggtaaacgcatcaaagcgccgttcctgattgcgtctatcacgggtggtcacccagataccatccgg
ttaacgctgcgctggcagctgctgctgaggagctgggtgttggcatcggcgttggctctcagcgcgcggccattgatgatccga
gccaggaagacagcttccgtgtagtgcgtgatgaagcccagatgcgtttgtttatggcaacgtcggcgcagcacagatccgtc
agtatggtgttgaaggtgttgaaaaactgatcgaaatgattgacgcagatgccttggcaatccacctgaactttctgcaagaagcg
gtccaaccggaaggtgaccgcgacgcgaccggttgcctggacatgattaccgaaatttgctctcagattaaaactccggtaatcg
tgaaagaaaccggtgcaggcattagccgtgaagatgcgattctgttccagaaagctggcgtgagcgcaatcgacgttggcggc
gcgggcggcacctcctgggctggcgtcgaggtctaccgtgctaaagaaagccgtgactctgttagcgagcgtttaggtgagct
gttttgggatttcggcattccgacggtagcttctctgattaatcccgcgtttccttgccgctgatcgcaaccggcggtatccgtaac
ggtctggacattgctaaaagcattgctctcggcgcaagcgctgccagcgccgctctgccgttcgttggtccgtccctggagggc
aaagaatccgttgtacgtgtgctgagctgcatgctggaagaatttaaagcagcaatgttttgtgcggttgcggcaacatcaaaga

Figure 73C cctgcacaactctccagtagtggtaactggttggacccgcgaatacctggagcagcgcggttttaacgttaaggacctctccctg
ccgggcaacgctctgtaagcttcaacgcgtctacaaataaaaaaggcacgtcagatgacgtgcctttttcttgtctaga
(SEQ ID NO:113)

MCM376 - MMK from M. mazei archeal Lower in pET200D
6647 bp

Figure 74B aagggcgagctcaacgatccggctgctaacaaagcccgaaaggaagctgagttggctgctgccaccgctgagcaataactag
cataaccccttggggcctctaaacgggtcttgaggagttttttgctgaaaggaggaactatatccggatatcccgcaagaggccc
ggcagtaccggcataaccaagcctatgcctacagcatccagggtgacggtgccgaggatgacgatgagcgcattgttagatttc
atacacggtgcctgactgcgttagcaatttaactgtgataaactaccgcattaaagcttatcgatgataagctgtcaaacatgagaa
ttaattcttgaagacgaaagggcctcgtgatacgcctatttttataggttaatgtcatgataataatggtttcttagacgtcaggtggca
cttttcggggaaatgtgcgcggaaccccctatttgtttatttttctaaatacattcaaatatgtatccgctcatgagacaataaccctgat
aaatgcttcaataatattgaaaaaggaagagtatgattgaacaagatggattgcacgcaggttctccggccgcttgggtggagag
gctattcggctatgactgggcacaactgacaatcggctgctctgatgccgccgtgttccggctgtcagcgcaggggcgcccggt
tcttttgtcaagaccgacctgtccggtgccctgaatgaactgcaggacgaggcagcgcggctatcgtggctggccacgacgg
gcgttccttgcgcagctgtgctcgacgttgtcactgaagcgggaagggactggctgctattgggcgaagtgccggggcaggat
ctcctgtcatctcaccttgctcctgccgagaaagtatccatcatggctgatgcaatgcggcggctgcatacgcttgatccggctac
ctgcccattcgaccaccaagcgaaacatcgcatcgagcgggcacgtactcggatggaagccggtcttgtcgatcaggatgatct
ggacgaagagcatcaggggctcgcgccagccgaactgttcgccaggctcaaggcgcgcatgcccgacggcgaggatctcgt
cgtgacacatggcgatgcctgcttgccgaatatcatggtggaaaatggccgcttttctggattcatcgactgtggccggctgggtg
tggcggaccgctatcaggacatagcgttggctacccgtgatattgctgaagagcttggcggcgaatgggctgaccgcttcctcgt
gctttacggtatcgccgctcccgattcgcagcgcatcgccttctatcgccttcttgacgagttcttctgagcgggactctggggttc
gaaatgaccgaccaagcgacgcctaactgtcagaccaagtttactcatatatactttagattgatttaaaacttcatttttaatttaaaa
ggatctaggtgaagatcctttttgataatctcatgaccaaaatcccttaacgtgagttttcgttccactgagcgtcagacccgtaga
aaagatcaaaggatcttcttgagatccttttttctgcgcgtaatctgctgcttgcaaacaaaaaaaccaccgctaccagcggtggtt
tgtttgccggatcaagagctaccaactctttttccgaaggtaactggcttcagcagagcgcagataccaaatactgtccttctagtgt
agccgtagttaggccaccacttcaagaactctgtagcaccgcctacatacctcgctctgctaatcctgttaccagtggctgctgcc
agtggcgataagtcgtgtcttaccgggttggactcaagacgatagttaccggataaggcgcagcggtcgggctgaacggggg
gttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcaggggg
cggagcctatggaaaaacgccagcaacgcggcctttttacggttcctggccttttgctggccttttgctcacatgttctttcctgcgtt
atcccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcaatggtgca
ctctcagtacaatctgctctgatgccgcatagttaagccagtatacactccgctatcgctacgtgactgggtcatggctgcgcccc
gacacccgccaacacccgctgacgcgccctgacgggcttgtctgctcccggcatccgcttacagacaagctgtgaccgtctcc
gggagctgcatgtgtcagaggttttcaccgtcatcaccgaaacgcgcgaggcagctgcggtaaagctcatcagcgtggtcgtg
aagcgattcacagatgtctgcctgttcatccgcgtccagctcgttgagtttctccagaagcgttaatgtctggcttctgataaagcgg
gccatgttaagggcggttttttcctgtttggtcactgatgcctccgtgtaagggggatttctgttcatgggggtaatgataccgatga
aacgagagaggatgctcacgatacgggttactgatgatgaacatgcccggttactggaacgttgtgagggtaaacaactggcg
gtatggatgcggcgggaccagagaaaaatcactcagggtcaatgccagcgcttcgttaatacagatgtaggtgttccacaggggt
agccagcagcatcctgcgatgcagatccggaacataatggtgcagggcgctgacttccgcgtttccagactttacgaaacacgg
aaaccgaagaccattcatgttgttgctcaggtcgcagacgttttgcagcagcagtcgcttcacgttcgctcgcgtatcggtgattca
ttctgctaaccagtaaggcaaccccgccagcctagccgggtcctcaacgacaggagcacgatcatgcgcacccgtggccagg
acccaacgctgcccgagatgcgccgcgtgcggctgctggagatggcggacgcgatggatatgttctgccaagggttggtttgc
gcattcacagttctccgcaagaattgattggctccaattcttggagtggtgaatccgttagcgaggtgccgccggcttccattcagg
tcgaggtggcccggctccatgcaccgcgacgcaacgcggggaggcagacaaggtatagggcggcgcctacaatccatgcc
aacccgttccatgtgctcgccgaggcggcataaatcgccgtgacgatcagcggtccaatgatcgaagttaggctggtaagagc
cgcgagcgatccttgaagctgtccctgatggtcgtcatctacctgcctggacagcatggcctgcaacgcgggcatcccgatgcc
gccggaagcgagaagaatcataatggggaaggccatccagcctcgcgtcgcgaacgccagcaagacgtagcccagcgcgt

Figure 74C cggccgccatgccggcgataatggcctgcttctcgccgaaacgtttggtggcgggaccagtgacgaaggcttgagcgagggc
gtgcaagattccgaataccgcaagcgacaggccgatcatcgtcgcgctccagcgaaagcggtcctcgccgaaaatgacccag
agcgctgccggcacctgtcctacgagttgcatgataaagaagacagtcataagtgcggcgacgatagtcatgccccgcgccca
ccggaaggagctgactgggttgaaggctctcaagggcatcggtcgagatcccggtgcctaatgagtgagctaacttacattaatt
gcgttgcgctcactgcccgctttccagtcgggaaacctgtcgtgccagctgcattaatgaatcggccaacgcgcggggagagg
cggtttgcgtattgggcgccagggtggttttctttttcaccagtgagacgggcaacagctgattgcccttcaccgcctggccctga
gagagttgcagcaagcggtccacgctggtttgccccagcaggcgaaaatcctgtttgatggtggttaacggcgggatataacat
gagctgtcttcggtatcgtcgtatcccactaccgagatatccgcaccaacgcgcagcccggactcggtaatggcgcgcattgcg
cccagcgccatctgatcgttggcaaccagcatcgcagtgggaacgatgccctcattcagcatttgcatggtttgttgaaaaccgg
acatggcactccagtcgccttcccgttccgctatcggctgaatttgattgcgagtgagatatttatgccagccagccagacgcaga
cgcgccgagacagaacttaatgggcccgctaacagcgcgatttgctggtgacccaatgcgaccagatgctccacgcccagtcg
cgtaccgtcttcatgggagaaaataatactgttgatgggtgtctggtcagagacatcaagaaataacgccggaacattagtgcag
gcagcttccacagcaatggcatcctggtcatccagcggatagttaatgatcagcccactgacgcgttgcgcgagaagattgtgc
accgccgctttacaggcttcgacgccgcttcgttctaccatcgacaccaccacgctggcacccagttgatcggcgcgagatttaa
tcgccgcgacaatttgcgacggcgcgtgcagggccagactggaggtggcaacgccaatcagcaacgactgtttgcccgccag
ttgttgtgccacgcggttgggaatgtaattcagctccgccatcgccgcttccacttttccgcgttttcgcagaaacgtggctggc
ctggttcaccacgcgggaaacggtctgataagagacaccggcatactctgcgacatcgtataacgttactggtttcacattcacca
ccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatg
caaggagatggcgcccaacagtccccggccacggggcctgccaccatacccacgccgaaacaagcgctcatgagcccga
agtggcgagcccgatcttccccatcggtgatgtcggcgatataggcgccagcaaccgcacctgtggcgccggtgatgccggc
cacgatgcgtccggcgtagaggatcgagatctcgatcccgcgaaattaatacgactcactatagggggaattgtgagcggataac
aattcccctctagaaataattttgtttaactttaagaaggagatatacatatgcggggttctcatcatcatcatcatcatggtatggcta
gcatgactggtggacagcaaatgggtcgggatctgtacgacgatgacgataaggatcatcccttcaccatggtatcctgttctgc
gccgggtaagatttacctgttcggtgaacacgccgtagtttatggcgaaactgcaattgcgtgtgcggtggaactgcgtacccgt
gttcgcgcggaactcaatgactctatcactattcagagccagatcggccgcaccggtctggatttcgaaaagcacccttatgtgtc
tgcggtaattgagaaaatgcgcaaatctattcctattaacggtgttttcttgaccgtcgattccgacatcccggtgggctccggtctg
ggtagcagcgcagccgttactatcgcgtctattggtgcgctgaacgagctgttcggctttggcctcagcctgcaagaaatcgcta
aactgggccacgaaatcgaaattaaagtacagggtgccgcgtccccaaccgatacgtatgtttctaccttcggcggcgtggttac
catcccggaacgtcgcaaactgaaaactccggactgcggcattgtgattggcgataccggcgttttctcctccaccaaagagtta
gtagctaacgtacgtcagctgcgcgaaagctacccggatttgatcgaaccgctgatgacctctattggcaaaatctctcgtatcgg
cgaacaactggttctgtctggcgactacgcatccatcggccgcctgatgaacgtcaaccagggtctcctggacgccctgggcgt
taacatcttagaactgagccagctgatctattccgctcgtgcggcaggtgcgtttggcgctaaaatcacgggcgctggcggcggt
ggctgtatggttgcgctgaccgctccggaaaaatgcaaccaagtggcagaagcggtagcaggcgctggcggtaaagtgactat
cactaaaccgaccgagcaaggtctgaaagtagattaa
(SEQ ID NO:114)

CDS 2: Gentamycin resistance gene; CDS: 1 *E. coli* replication protein

Figure 77A 1-
ctcgggccgtctcttgggcttgatcggccttcttgcgcatctcacgcgctcctgcggcggcctgtagggcaggctcataccctgccgaacc
gcttttgtcagccggtcggccacggcttccggcgtctcaacgcgctttgagattccagcttttcggccaatccctgcggtgcataggcgcgt
ggctcgaccgcttgcgggctgatggtgacgtggcccactggtggccgctccagggcctcgtagaacgcctgaatgcgcgtgtgacgtgc
cttgctgccctcgatgccccgttgcagccctagatcggccacagcggccgcaaacgtggtctggtcgcgggtcatctgcgctttgttgccga
tgaactccttggccgacagcctgccgtcctgcgtcagcggcaccacgaacgcggtcatgtgcgggctggtttcgtcacggtggatgctggc
cgtcacgatgcgatccgccccgtacttgtccgccagccacttgtgcgccttctcgaagaacgccgcctgctgttcttggctggccgacttcca
ccattccgggctggccgtcatgacgtactcgaccgccaacacagcgtccttgcgccgcttctctggcagcaactcgcgcagtcggcccatc
gcttcatcggtgctgctggccgccagtgctcgttctctggcgtcctgctggcgtcagcgttgggcgtctcgcgctcgcggtaggcgtgctt
gagactggccgccacgttgcccattttcgccagcttcttgcatcgcatgatcgcgtatgccgccatgcctgccccctcccttttggtgtccaacc
ggctcgacgggggcagcgcaaggcggtgcctccggcgggccactcaatgcttgagtatactcactagactttgcttcgcaaagtcgtgac
cgcctacggcggctgcggcgccctacgggcttgctctccgggcttcgccctgcgcggtcgctgcgctcccttgccagcccgtggatatgtg
gacgatggccgcgagcggccaccggctggctcgcttcgctcggcccgtggacaaccctgctggacaagctgatggacaggctgcgcct
gcccacgagcttgaccacagggattgcccaccggctaccagccttcgaccacataccaccggctccaactgcgcggcctgcggcctt
gccccatcaatttttttaattttctctggggaaaagcctccggcctgcggcctgcgcgcttcgcttgccggttggacaccaagtggaaggcgg
gtcaaggctcgcgcagcgaccgcgcagcggcttggccttgacgcgcctggaacgacccaagcctatgcgagtgggggcagtcgaagg
cgaagcccgcccgcctgccccccgagcctcacggcggcgagtgcggggggttccaaggggggcagcgccaccttgggcaaggccgaag
gccgcgcagtcgatcaacaagccccggaggggccacttttttgccggaggggggagccgcgccgaaggcgtgggggaaccccgcaggg
gtgcccttcttgggcaccaaagaactagatatagggcgaaatgcgaaagacttaaaaatcaacaacttaaaaaaggggggtacgcaacag
ctcattgcggcaccccccgcaatagctcattgcgtaggttaaagaaaatctgtaattgactgccacttttacgcaacgcataattgttgtcgcgc
tgccgaaaagttgcagctgattgcgcatggtgccgcaaccgtgcggcaccctaccgcatggagataagcatggccacgcagtccagaga
aatcggcattcaagccaagaacaagcccggtcactgggtgcaaacggaacgcaaagcgcatgaggcgtgggccgggcttattgcgagg
aaacccacggcggcaatgctgctgcatcacctcgtggcgcagatgggccaccagaacgccgtggtggtcagccagaagacactttccaa
gctcatcggacgttcttgcggacggtccaatacgcagtcaaggacttggtggccgagcgctggatctccgtcgtgaagctcaacggcccc
ggcaccgtgtcggcctacgtggtcaatgaccgcgtggcgtggggccagccccgcgaccagttgcgcctgtcggtgttcagtgccgccgt
ggtggttgatcacgacgaccaggacgaatcgctgttggggcatggcgacctgcgccgcatcccgaccctgtatccgggcgagcagcaac
taccgaccggccccggcgaggagccgcccagccagcccggcattccgggcatggaaccagacctgccagccttgaccgaaacggag
gaatgggaacggcgcgggcagcagcgcctgccgatgcccgatgagccgtgttttctggacgatggcgagccgttggagccgccgacac
gggtcacgctgccgcgccggtagcacttgggttgcgcagcaaccgtaagtgcgctgttccagactatcggctgtagccgcctcgccgcc
ctataccttgtctgcctccccgcgttgcgtcgcggtgcatggagccgggccacctcgacctgaatggaagccggcggcacctcgctaacg
gattcaccgttttatcaggctctggagaggcagaataaatgatcatatcgtcaattattacctccacggggagagcctgagcaaactggcctca
ggcatttgagaagcacacggtcacactgcttccggtagtcaataaaccggtaaaccagcaatagacataagcggctatttaacgaccctgcc
ctgaaccgacgaccgggtcgaatttgctttcgaatttctgccattcatccgcttattatcacttattcaggcgtagcaccaggcgtttaagggca
ccaataactgccttaaaaaaattacgccccgccctgccactcatcgcagtcggcctattggttaaaaaatgagctgatttaacaaaaatttaac
gcgaattttaacaaaatattaacgcttacaatttccattcgccattcaggctgcgcaactgttgggaagggcgatcggtgcgggcctcttcgct
attacgccagctggcgaaagggggatgtgctgcaaggcgattaagttgggtaacgccagggttttcccagtcacgacgttgtaaaacgacg
gccagtgagcgcgcgtaatacgactcactatagggcgaattggagctccaccgcggtggcggccgctctagaactagtggatccccgg
gctgcatgctcgagcggccgccagtgtgatggatatctgcagaattcgcccttcttgatatcttagtgtgcgttaaccaccaccacattggtc
cctgcccgaccgcatagcggccttttcatgcagtagcccctgctcgccaacaatttcgtataccgagatgtggtgagattttttgcccggcgg
caatcagatacttgccgctgtgatcaacattgaagccgcgcggctgggtttccgttggctggaagccttctttactcaacacgctgccatcttc
cgaaacgctgaaaacggtaatcaggctggcgggtacggtcgcaggcgtataaatggcgaccatccggggtgatatgaatatcagccgccc
aacgggtgtcggagaagttttccggcatcatatccagcgtctggacacattcgatattaccgtgcggatctttcagttcccagacatccactga
gctgtttaactcattgacgcaatacgcatattgttcgtttggatggaataccatatgacgcgggccggcccccttcaacggtggtcacttccgca
gggtcctgcgccacgagatgaccatcatcgctgaccgtaaacaggcaaatgcgatcctgctttaatgccggaacccacagcgtacggttgt

Figure 77B ccggtgagatattggcggaatggcaaccgtccagcccctcgaccacatcgacgacgcccactggcaggccatcttccagacgcgttacgc
tcacgttacccgcattgtaagaacctacaaagacaaactgcccctggtgatcggtggaaatatgcgtcggactacccggcagcgcagactc
tgcggcaaaggtcagtgcgccatcgtccggggcgatacgatacgccaggacgcgaaactcagggcgaacaccaacatagagataacgt
ttgtccgggctgaccaccatcggctgcacctgccccggcacatcgacaacctgtgtcagcgtcagtgcgccttcatgattcagattccagac
gtgaatttgctggctctcagggctggcgatataaactgtttgcttcatgaatgctcctttgggttacctccgggaaacgcggttgatttgtttagtg
gttgaattatttgctcaggatgtggcatagtcaagggcgtgacggctcgctaatacaactcactatagggctcgaggaagttcctatactttcta
gagaataggaacttccgcgccgcacacaaaaaccaacacacagatcatgaaaataaagctcttttattggtaccgaattcgccagggagct
ctcagacgtcgcttggtcggtctttattcgaaccccagagtcccgcttacgccccgccctgccactcatcgcagtactgttgtaattcattaagc
attctgccgacatggaagccatcacaaacggcatgatgaacctgaatcgccagcggcatcagcaccttgtcgccttgcgtataatatttgccc
atggtgaaaacggggcgaagaagttgtccatattggccacgtttaaatcaaaactggtgaaactcacccagggattggctgagacgaaaa
acatattctcaataaaccctttagggaaataggccaggttttcaccgtaacacgccacatcttgcgaatatatgtgtagaaactgccggaaatc
gtcgtggtattcactccagagcgatgaaaacgtttcagtttgctcatggaaaacggtgtaacaagggtgaacactatcccatatcaccagctc
accgtctttcattgccatacggaattccggatgagcattcatcaggcgggcaagaatgtgaataaaggccggataaaacttgtgcttattttct
ttacggtctttaaaaaggccgtaatatccagctgaacggtctggttataggtacattgagcaactgactgaaatgcctcaaaatgttctttacgat
gccattgggatatatcaacggtggtatatccagtgatttttttctccatggtttagttcctcaccttgtcgtattatactatgccgatatactatgccg
atgattaattgtcaacacgtgctgctgcaggtcgaaaggcccggagatgaggaagaggagaacagcgcggcagacgtgcgcttttgaag
cgtgcagaatgccgggcctccggaggaccttcggggcgcccgccccgccctgagcccgccctgagcccgccccggaccacccctt
cccagcctctgagcccagaaagcgaaggagcaaagctgctattggccgctgccccaaaggcctacccgcttccattgctcagcggtgctg
tccatctgcacgagactagtgagacgtgctacttccatttgtcacgtcctgcacgacgcgagctgcggggcgggggggaacttcctgacta
ggggaggagtggaaggtggcgcgaaggggccaccaaagaacggagccggttggcgcctaccggtggatgtggaatgtgtgcgaggc
cagaggccacttgtgtagcgccaagtgcccagcgggctgctaaagcgcatgctccagactgccttgggaaaagcgcctcccctacccg
gtagaatgaagttcctatactttctagagaataggaacttcgcggccgcccttagtgagggttaattcaactgactgtaacagctaaaattagt
cgcttttggcggtaagggcgaattccagcacactggcggccgttactagtggatccgagctcggtaccaagcttgatgcaggaattcgatat
caagcttatcgataccgtcgacctcgagggggggcccggtacccagcttttgttccctttagtgagggttaattgcgcgcttggcgtaatcatg
gtcatagctgtttcctgtgtgaaattgttatccgctcacaattccacacaacatacgagccggaagcataaagtgtaaagcctggggtgcctaa
tgagtgagctaactcacattaattgcgttgcgctcactgcccgctttccagtcgggaaacctgtcgtgccagctgcattaatgaatcggccaac
gcgcggggagaggcggtttgcgtattgggcgcatgcataaaaactgttgtaattcattaagcattctgccgacatggaagccatcacaaacg
gcatgatgaacctgaatcgccagcggcatcagcaccttgtcgccttgcgtataatatttgcccatggacgcacaccgtggaaacggatgaa
ggcacgaacccagttgacataagcctgttcggttcgtaaactgtaatgcaagtagcgtatgcgctcacgcaactggtccagaaccttgaccg
aacgcagcggtggtaacggcgcagtggcggttttcatggcttgttatgactgtttttttgtacagtctatgcctcgggcatccaagcagcaagc
gcgttacgccgtgggtcgatgtttgatgttatggagcagcaacgatgttacgcagcagcaacgatgttacgcagcagggcagtcgccctaa
aacaaagttaggtggctcaagtatgggcatcattcgcacatgtaggctcggccctgaccaagtcaaatccatgcgggctgctcttgatctttc
ggtcgtgagttcggagacgtagccacctactcccaacatcagccggactccgattacctcgggaacttgctccgtagtaagacattcatcgc
gcttgctgccttcgaccaagaagcggttgttggcgctctcgcggcttacgttctgccaggtttgagcagccgcgtagtgagatctatatctat
gatctcgcagtctccggcgagcaccggaggcagggcattgccaccgcgctcatcaatctcctcaagcatgaggccaacgcgcttggtgct
tatgtgatctacgtgcaagcagattacggtgacgatcccgcagtggctctctatacaaagttgggcatacgggaagaagtgatgcactttgat
atcgacccaagtaccgccacctaacaattcgttcaagccgagatcggcttcccggccgcggagttgttcggtaaattgtcacaacgccgcc
aggtggcacttttcgggaaatgtgcgcgcccgcgttcctgctggcgctgggcctgtttctggcgctggacttcccgctgttccgtcagcag
cttttcgcccacggccttgatgatcgcggcggccttggcctgcatatcccgattcaacggccccagggcgtccagaacgggcttcaggcgc
tcccgaaggt (SEQ ID NO:122).

Figure 78B
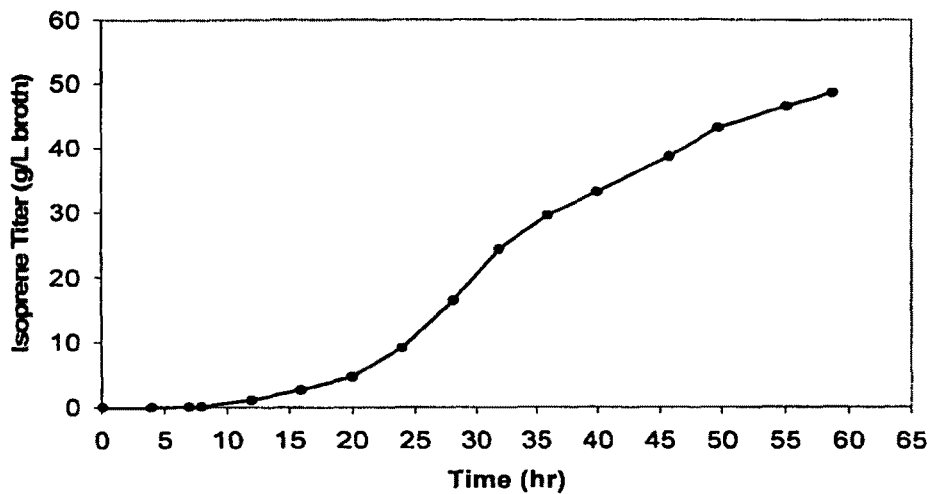
Titer 78C
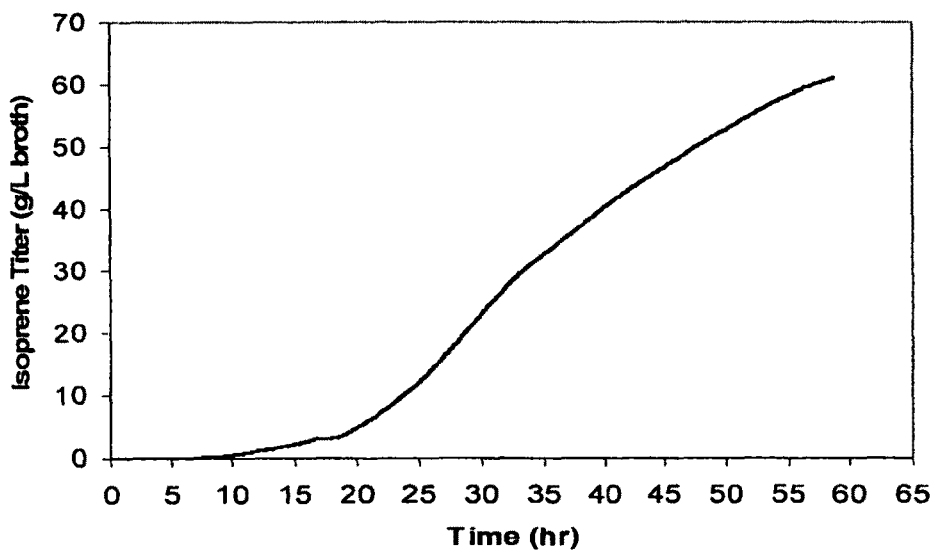

Figure 79B

5'-
tagaaaaactcatcgagcatcaaatgaaactgcaatttattcatatcaggattatcaataccatatttttgaaaaagccgtttctgtaatgaagga
gaaaactcaccgaggcagttccataggatggcaagatcctggtatcggtctgcgattccgactcgtccaacatcaatacaacctattaatttcc
cctcgtcaaaaataaggttatcaagtgagaaatcaccatgagtgacgactgaatccggtgagaatggcaaaagtttatgcatttctttccagac
ttgttcaacaggccagccattacgctcgtcatcaaaatcactcgcatcaaccaaaccgttattcattcgtgattgcgcctgagcgaggcgaaat
acgcgatcgctgttaaaaggacaattacaaacaggaatcgagtgcaaccggcgcaggaacactgccagcgcatcaacaatattttcacctg
aatcaggatattcttctaatacctggaacgctgtttttccggggatcgcagtggtgagtaaccatgcatcatcaggagtacggataaaatgctt
gatggtcggaagtggcataaaattccgtcagccagtttagtctgaccatctcatctgtaacatcattggcaacgctacctttgccatgtttcagaa
acaactctggcgcatcgggcttcccatacaagcgatagattgtcgcacctgattgcccgacattatcgcgagcccatttatacccatataaatc
agcatccatgttggaatttaatcgcggcctcgacgtttcccgttgaatatggctcatattcttcctttttcaatattattgaagcatttatcaggttat
tgtctcatgagcggatacatatttgaatgtatttagaaaaataaacaataggggtcagtgttacaaccaattaaccaattctgaacattatcgcg
agcccatttatacctgaatatggctcataacaccccttgtttgcctggcggcagtagcgcggtggtcccacctgaccccatgccgaactcaga
agtgaaacgccgtagcgccgatggtagtgtggggactccccatgcgagagtagggaactgccaggcatcaaatcaaaacgaaaggctcag
tcgaaagactgggccttcgcccgggctaattaggggggtgtcgcccttcgattgacggttacgggatcctcacacgtacatcagctggttgat
gggggaacgggtcgatgagcagcagcttgatgcggttctcggtggcgtaatccgggcggcccagcccgtccccatattggtaggtgcagtg
gctcacgcgggccatgttcacggcgatctccatgaacgccttcggcagcagggtgctgtccgacacgcgctcgcggttcattttcttccact
cggcgtcgatcagcttgcgcagctcttcgcgggcctgttcctcgctcgtgccgtcgttctcgtgcatgtagctgatgatgctgttggtggtttcg
ccgcgttcgagttccgccgccgaggtcgccagatcgttgcacagccgaaagatcacgcaggacgagcgcaccaggccgtggaagtcgg
tcagggagcggagggcgtggtccgagatatcttcctgctgctggcagaccgagaagtagctcggcgccagcagcgcgacccccgctgga
ggacacgctggcgttctccaggtacttgctgaaggcggggatgatcttgttattgctccacttggcttcttgcaggaaggccttgcacagttcg
cgccagcttttggtcagatagctcaggttattgtggccttctccttcaggatggagtaggacgtgtcgttcacggtgttgtacagggccagga
agcacagcttcatatagtcgggcagcgtgttgatggcgttcacgtcccagcgttccaccgcgtcggtgaagagctgcagttcgtccagggta
ccgtacacgtcatagacgtcatcgataatggtgaccagaccgaacatcttggtgacggccttgcggcattcgccgaactgcgggtccggcg
ccatgcccagcgcccagaagtacacttccatcaggcggtcccgcacgaaatccagcttgctggcgaggcccatctcggtccaccaccgg
ctcaggtcctgcagctctttttggtgcagggtctggaccatgttgaaatcgagtttggccagttccagcagcagctggtgatgcggctccttgg
gttcgtacttgtccagaaaccaccgcgcctccaggcggtgcaggcgttgatgatacggcagctccagcgcgtgggacacctgctcggcca
ccttcgtgttgatcccctccttgaggttgttcttcagatgggtgatgctgaaggtacgggcctcctccagcagattttcgccttcgaaaccgaga
tagctggcctcgtacaggctcagcaggccctgcacgtcacccttcagttccccggagaagcccccttctttgtccttgaagcgctcgaacac
gtcctggctcacctcaaagccatgctgccgcagcaggcggaagctcagggcggtcgcgtgcagatcgcttttgttcttcttattctcgtccag
caggacgatgttctccagcgccttgatgatatcttctcaaacttgtaggtcaggcccaggcgctgcacgtcgtcgatgagctccagcaggct
caggggctgggtgtccacccggttgatcatgcaacgcacctcctcctccagcttggtggccttctcttcgagcttctccaccttcaggtcgtttt
ccaggctctgcaggaactcgaagttccacaggttgggctggtagttcgcggaccgacggctattatgctcggtgatctgggtgaactggctg
ctggtggcgcacatatgtatatctccttcttaaagttaaacaagcttaagatgttcagcgacaagggcgacacaaaattattctaaatgcataat
aaatactgataacatcttatagtttgtattatatttgtattatcgttgacatgtataattttgatatcaaaaactgattttccctttattatttttcgagattta
ttttcttaattctctttaacaaactagaaatattgtatatacaaaaaatcataaataatagatgaatagtttaattataggtgttcatcaatcgaaaaag
caacgtatcttatttaaagtgcgttgcttttttctcatttataaggttaaataattctcatatatcaagcaaagtgacaggcgcccttaaatattctga
caaatgctctttccctaaactcccccataaaaaaacccgccgaagcgggttttacgttatttgcggattaacgattactcgttatcagaaccg
cccaggggcccgagcttaagactggccgtcgttttacaacacagaaagagtttgtagaaacgcaaaaaggccatccgtcagggccttct
gcttagtttgatgcctggcagttccctactctcgccttccgcttcctcgctcactgactcgctgcgctcggtcgttcggctgcggcgagcggtat
cagctcactcaaaggcggtaatacggttatccacagaatcaggggataacgcaggaaagaacatgtgagcaaaaggccagcaaaaggc
caggaaccgtaaaaaggccgcgttgctggcgtttttccataggctccgcccccctgacgagcatcacaaaaatcgacgctcaagtcagag
gtggcgaaacccgacaggactataaagataccaggcgtttccccctggaagctccctcgtgcgctctcctgttccgaccctgccgcttaccg
gatacctgtccgcctttctcccttcgggaagcgtggcgctttctcatagctcacgctgtaggtatctcagttcggtgtaggtcgttcgctccaag
ctgggctgtgtgcacgaaccccccgttcagcccgaccgctgcgccttatccggtaactatcgtcttgagtccaacccggtaagacacgactt

Figure 79C atcgccactggcagcagccactggtaacaggattagcagagcgaggtatgtaggcggtgctacagagttcttgaagtggtgggctaactac
ggctacactagaagaacagtatttggtatctgcgctctgctgaagccagttaccttcggaaaaagagttggtagctcttgatccggcaaacaa
accaccgctggtagcggtggttttttttgtttgcaagcagcagattacgcgcagaaaaaaaggatctcaagaagatcctttgatcttttctacgg
ggtctgacgctcagtggaacgacgcgcgcgtaactcacgttaagggattttggtcatgagcttgcgccgtcccgtcaagtcagcgtaatgct
ctgcttt (SEQ ID NO:123)

POLYMERS OF ISOPRENE FROM RENEWABLE RESOURCES

This application claims benefit of U.S. Provisional Patent Application Ser. No. 61/133,521, filed on Jun. 30, 2008. The teachings of U.S. Provisional Patent Application Ser. No. 61/133,521 are incorporated herein by reference in their entirety.

BACKGROUND OF THE INVENTION

Isoprene (2-methyl-buta-1,3-diene) is an extremely important organic compound that is used in a wide array of applications. For instance, isoprene is employed as an intermediate or a starting material in the synthesis of numerous chemical compositions and polymers. Isoprene is also an important biological material that is synthesized naturally by many plants and animals, including humans. Isoprene is a colorless liquid at room temperature and is highly flammable. The structural formula of isoprene is:

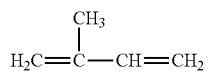

Isoprene became in important monomer for utilization in the synthesis of cis-1,4-polybutadiene when its stereo-regulated polymerization became commercially possible in the early 1960s. Cis-1,4-polyisoprene made by such stereo-regulated polymerizations is similar in structure and properties to natural rubber. Even though it is not identical to natural rubber it can be used as a substitute for natural rubber in many applications. For instance, synthetic cis-1,4-polyisoprene rubber is widely used in manufacturing tires and other rubber products. This demand for synthetic cis-1,4-polyisoprene rubber consumes a majority of the isoprene available in the worldwide market. The remaining isoprene is used in making other synthetic rubbers, block copolymers, and other chemical products. For instance, isoprene is used in making butadiene-isoprene rubbers, styrene-isoprene copolymer rubbers, styrene-isoprene-butadiene rubbers, styrene-isoprene-styrene block copolymers, and styrene-isoprene block copolymers.

Over the years many synthesis routes for producing isoprene have been investigated. For instance, the synthesis of isoprene by reacting isobutylene with formaldehyde in the presence of a catalyst is described in U.S. Pat. Nos. 3,146,278, 3,437,711, 3,621,072, 3,662,016, 3,972,955, 4,000,209, 4,014,952, 4,067,923, and 4,511,751. U.S. Pat. No. 3,574,780 discloses another process for the manufacture of isoprene by passing a mixture of methyl-tert-butyl ether and air over mixed oxide catalysts. The methyl-tert-butyl ether is then cracked into isobutylene and methanol over the catalyst. The methanol produced is oxidized into formaldehyde which then reacts with the isobutylene over the same catalyst to produce the isoprene. U.S. Pat. No. 5,177,290 discloses a process for producing dienes, including isoprene, which involves reacting a reaction mixture of a tertiary alkyl ether and a source of oxygen over two functionally distinct catalysts under reaction conditions sufficient to produce high yields of the dienes with minimal recycle of the ether.

The isoprene used in industrial applications is typically produced as a by-product of the thermal cracking of petroleum or naphtha or is otherwise extracted from petrochemical streams. This is a relatively expensive energy-intensive process. With the worldwide demand for petrochemical based products constantly increasing, the cost of isoprene is expected to rise to much higher levels in the long-term and its availability is limited in any case. In other words, there is a concern that future supplies of isoprene from petrochemical based sources will be inadequate to meet projected needs and that prices will rise to unprecedented levels. Accordingly, there is a current need to procure a source of isoprene from a low cost, renewable source which is environmentally friendly.

SUMMARY OF THE INVENTION

It has been found that certain cells in culture can convert more than about 0.002 percent of the carbon available in the cell culture medium into isoprene. These cells have a heterologous nucleic acid that (i) encodes an isoprene synthase polypeptide and (ii) is operably linked to a promoter. In some cases, these cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. The isoprene produced in such a cultured medium can then be recovered and polymerized into synthetic rubbers and other useful polymeric materials.

It is anticipated that there will be a significant demand for synthetic rubber and other isoprene containing polymers that are synthesized using isoprene of this type which is made from renewable, non-petrochemical based resources. In fact, it is believed that industrial customers and consumers would prefer to purchase isoprene containing polymers that are derived from such environmentally friendly sources to those that are made with isoprene derived from a petrochemical process. It is further believed that customers would be willing to pay premium prices for such environmentally friendly products that are made with renewable resources. However, it is important to be able to verify that such isoprene containing polymers are actually made from non-petrochemical based resources. The synthetic isoprene containing polymers of this invention offer the benefit of being verifiable as to being derived from non-petrochemical based resources. They can also be analytically distinguished from rubbers that come from natural sources.

The present invention more specifically discloses a polyisoprene polymer which is comprised of repeat units that are derived from isoprene monomer, wherein the polyisoprene polymer has $\delta^{13}C$ value of greater than −22‰. This type of polyisoprene can be a polyisoprene homopolymer.

The subject invention further reveals a polyisoprene polymer which is comprised of repeat units that are derived from isoprene monomer, wherein the polyisoprene polymer has $\delta^{13}C$ value which is within the range of −30‰ to −28.5‰. This type of polyisoprene can also be a polyisoprene homopolymer.

The present invention also discloses a polyisoprene polymer which is comprised of repeat units that are derived from isoprene monomer, wherein the polyisoprene is free of protein, and wherein the polyisoprene polymer has $\delta^{13}C$ value which is within the range of −34‰ to −24‰.

This invention further reveals a polyisoprene polymer which is comprised of repeat units that are derived from isoprene monomer, wherein the polyisoprene polymer has a cis-1,4-microstructure content of less than 99.9%, wherein the polyisoprene polymer has a trans-1,4-microstructure content of less than 99.9%, and wherein the polyisoprene polymer has $\delta^{13}C$ value of which is within the range of −34‰ to −24‰.

The subject invention also discloses a polyisoprene polymer which is comprised of repeat units that are derived from isoprene monomer, wherein the polyisoprene polymer has a 3,4-microstructure content of greater than 2%, and wherein the polyisoprene polymer has $\delta^{13}C$ value of which is within the range of −34‰ to −24‰.

The present invention further reveals a polyisoprene polymer which is comprised of repeat units that are derived from isoprene monomer, wherein the polyisoprene polymer has a 1,2-microstructure content of greater than 2%, and wherein the polyisoprene polymer has $\delta^{13}C$ value of which is within the range of −34‰ to −24‰.

The subject invention also discloses a polymer which is comprised of repeat units that are derived from isoprene monomer and at least one additional monomer, wherein the polymer includes blocks of repeat units that are derived from isoprene, and wherein the blocks of repeat units that are derived from isoprene have a $\delta^{13}C$ value of greater than −22‰.

The present invention further reveals a polymer which is comprised of repeat units that are derived from isoprene monomer and at least one additional monomer, wherein the polymer includes blocks of repeat units that are derived from isoprene, and wherein the blocks of repeat units that are derived from isoprene have a $\delta^{13}C$ value which is within the range of −34‰ to −24‰.

The subject invention also discloses a liquid polyisoprene polymer which is comprised of repeat units that are derived from isoprene monomer, wherein the polyisoprene polymer has weight average molecular weight which is within the range of 5,000 to 100,000, and wherein the liquid polyisoprene polymer has $\delta^{13}C$ value of which is within the range of −34‰ to −24‰.

The present invention further reveals a liquid polyisoprene polymer which is comprised of repeat units that are derived from isoprene monomer, wherein the liquid polyisoprene polymer has a weight average molecular weight which is within the range of 5,000 to 100,000, and wherein the liquid polyisoprene polymer has $\delta^{13}C$ value of which is within the range of −34‰ to −24‰.

The subject invention also disloses a method for verifying that a polyisoprene homopolymer is from a sustainable renewable non-petroleum derived source which comprises: (I) determining the $\delta^{13}C$ value of the polyisoprene homopolymer; (II) if the polyisoprene homopolymer has a $\delta^{13}C$ value within the range of −34‰ to −30‰ or within the range of −28.5‰ to −24‰ additionally analyzing the polyisoprene homopolymer to determine (1) its cis-microstructure content, (2) its 3,4-microstructure content, (3) its 1,2-microstructure content, (4) its a weight average molecular weight, or (5) the presence or absence of residual proteins, soaps, lipids, resins, or sugars indicative of natural rubber; and (III) verifying that the polyisoprene homopolymer is from a sustainable renewable non-petroleum derived source if it has (i) a $\delta^{13}C$ value of greater than −22‰, (ii) a $\delta^{13}C$ value which is within the range of −30‰ to −28.5‰, or (iii) a $\delta^{13}C$ value within the range of −34‰ to −30‰ or within the range of −28.5‰ to −24‰ and if it (a) has a cis-microstructure content of less than 100%, (b) contains 3,4-microstructure, (c) contains 1,2-microstructure, (d) has a weight average molecular weight of less than 100,000, or (e) is free of residual proteins, soaps, lipids, resins, or sugars indicative of natural rubber.

The present invention further reveals a method for verifying that a copolymer having repeat units that are derived from isoprene contains isoprene that is from a sustainable renewable non-petroleum derived source, said method comprising: (I) determining the $\delta^{13}C$ value of at least one polyisoprene block in the copolymer; and (II) verifying that the isoprene in the copolymer is from a sustainable renewable non-petroleum derived source if the polyisoprene block has (i) a $\delta^{13}C$ value of greater than −22‰, or (ii) a $\delta^{13}C$ value which is within the range of −34‰ to −28.5.

BRIEF DESCRIPTION OF THE DRAWINGS

FIG. 1 is the nucleotide sequence of a kudzu isoprene synthase gene codon-optimized for expression in *E. coli* (SEQ ID NO:1). The atg start codon is in italics, the stop codon is in bold and the added PstI site is underlined.

FIG. 3 is the nucleotide sequence of pTrcKudzu (SEQ ID NO:2). The RBS is underlined, the kudzu isoprene synthase start codon is in bold capitol letters and the stop codon is in bold, capitol, italics, letters. The vector backbone is pTrcHis2B.

FIG. 5 is the nucleotide sequence of pETNHisKudzu (SEQ ID NO:5).

FIG. 7 is the nucleotide sequence of pCL-lac-Kudzu (SEQ ID NO:7).

FIG. 12 is the nucleotide sequence of pBS Kudzu #2 (SEQ ID NO:57).

FIG. 13 is the nucleotide sequence of kudzu isoprene synthase codon-optimized for expression in *Yarrowia* (SEQ ID NO:8).

FIG. 15 is the nucleotide sequence of vector pSPZ1 (MAP29Spb) (SEQ ID NO:11).

FIG. 16 is the nucleotide sequence of the synthetic kudzu (*Pueraria montana*) isoprene gene codon-optimized for expression in *Yarrowia* (SEQ ID NO:12).

FIG. 17 is the nucleotide sequence of the synthetic hybrid poplar (*Populus alba×Populus tremula*) isoprene synthase gene (SEQ ID NO:13). The ATG start codon is in bold and the stop codon is underlined.

FIG. 18A1 and FIG. 18A2 show a schematic outlining construction of vectors pYLA 1, pYL1 and pYL2. In FIG. 18A1, YURA51 represents SEQ ID NO:79; YURA3 represents SEQ ID NO:77; Y18S5 represents SEQ ID NO:76; and Y18S3 represents SEQ ID NO:75. In FIG. 18A2, XPRT5 represents SEQ ID NO:74; and XPRT3 represents SEQ ID NO:73.

In FIG. 18B, XPR5 represents SEQ ID NO:72; and XPR3 represents SEQ ID NO:71).

In FIG. 18D, ICL15 represents SEQ ID NO:70; and ICL13 represents SEQ ID NO:69.

FIG. 22 is the nucleotide sequence of pTrcKudzu yIDI DXS Kan (SEQ ID NO:20).

FIG. 25 is a nucleotide sequence of pTrcKKDyIkIS kan (SEQ ID NO:33).

FIG. 27 is a nucleotide sequence of pCL PtrcUpperPathway (SEQ ID NO:46).

FIG. 29 is a nucleotide sequence of cassette containing the lower MVA pathway and yeast idi for integration into the *B. subtilis* chromosome at the nprE locus (SEQ ID NO:47).

FIG. 31 is a nucleotide sequence of p9796-poplar (SEQ ID NO:48).

FIG. 33 is a nucleotide sequence of pTrcPoplar (SEQ ID NO:49).

FIG. 35 is a nucleotide sequence of pTrcKudzu yIDI Kan (SEQ ID NO:50).

FIG. 37 is a nucleotide sequence of pTrcKudzuDXS Kan (SEQ ID NO:51).

FIG. 39 is a nucleotide sequence of pCL PtrcKudzu (SEQ ID NO:52).

FIG. 41 is a nucleotide sequence of pCL PtrcKudzu A3 (SEQ ID NO:53).

FIG. 43 is a nucleotide sequence of pCL PtrcKudzu yIDI (SEQ ID NO:54).

FIG. 45 is a nucleotide sequence of pCL PtrcKudzu DXS (SEQ ID NO:55).

FIG. 51 is the nucleotide sequence of pJMupperpathway2 (SEQ ID NO:56).

FIGS. 55A and 55B are the nucleotide sequence of plasmid pET24 *P. alba* HGS (SEQ ID NO:87).

FIGS. 58A and 58B are the nucleotide sequence of plasmid EWL230 (SEQ ID NO:88).

FIGS. 61A and 61B are the nucleotide sequence of plasmid EWL244 (SEQ ID NO:89).

FIGS. 63A-63C are the nucleotide sequence of plasmid MCM484 (SEQ ID NO:90).

FIGS. 64A-64C are the nucleotide sequence of plasmid MCM485 (SEQ ID NO:91).

FIGS. 65A-65C are the nucleotide sequence of plasmid MCM486 (SEQ ID NO:92).

FIGS. 66A-66C are the nucleotide sequence of plasmid MCM487 (SEQ ID NO:93).

FIG. 67A shows the time course of optical density within the 15-L bioreactor fed with glucose. FIG. 67B shows the time course of isoprene titer within the 15-L bioreactor fed with glucose. The titer is defined as the amount of isoprene produced per liter of fermentation broth. FIG. 67C shows the time course of total isoprene produced from the 15-L bioreactor fed with glucose. FIG. 67D shows the total carbon dioxide evolution rate (TCER), or metabolic activity profile, within the 15-L bioreactor fed with glucose.

FIG. 68A shows the time course of optical density within the 15-L bioreactor fed with glucose. FIG. 68B shows the time course of isoprene titer within the 15-L bioreactor fed with glucose. The titer is defined as the amount of isoprene produced per liter of fermentation broth. FIG. 68C shows the time course of total isoprene produced from the 15-L bioreactor fed with glucose. FIG. 68D shows the volumetric productivity within the 15-L bioreactor fed with glucose. An average value of 1.1 g/L/hr was maintained for a 40-hour period (23-63 hours) with yeast extract feeding. FIG. 68E shows the carbon dioxide evolution rate (CER), or metabolic activity profile, within the 15-L bioreactor fed with glucose.

FIG. 69A shows growth of *E. coli* EWL256, which contains both the MVA pathway and isoprene synthase, on either glucose, biomass hydrolysate, glycerol, or acetate as the only carbon source. The different carbon sources were added to a concentration of 1% in the media. A negative control with no added carbon source was included. Growth was measured as optical density at 600 nM. FIG. 69B shows specific productivity of isoprene from *E. coli* EWL256 containing both the MVA pathway and isoprene synthase when grown on either glucose, biomass hydrolysate, glycerol, or acetate as only carbon source. The different carbon sources were added to a concentration of 1% in the media. A negative control with no added carbon source was included. Samples were taken 190 minutes, 255 minutes and 317 minutes after inoculation and isoprene produced by the bacteria was measured using GC-MS. FIG. 69C shows growth of *E. coli* EWL256 on either glucose or xylose as the only carbon source. The different carbon sources were added to a concentration of 1% in the media. A negative control with no added carbon source was included. Growth was measured as optical density at 600 nM. FIG. 69D shows specific productivity of isoprene from *E. coli* EWL256 when grown on either glucose or xylose as only carbon source. The carbon sources were added to a concentration of 1% in the media. A negative control with no added carbon source was included. Samples were taken 260 minutes, 322 minutes and 383 minutes after inoculation and isoprene produced by the bacteria was measured using GC-MS.

FIGS. 73B and 73C are the nucleotide sequence of the *M. mazei* archaeal lower Pathway operon (SEQ ID NO:113).

FIGS. 74B and 74C are the nucleotide sequence of MCM376-MVK from *M. mazei* archaeal Lowerin pET200D (SEQ ID NO:114).

FIGS. 77A and 77B are the nucleotide sequence of plasmid pBBRCMPGI1.5-pgl (SEQ ID NO:122).

FIGS. 78A-78F are graphs of isoprene production by *E. coli* strain expressing *M. mazei* mevalonate kinase, *P. alba* isoprene synthase, and pgl (RHM111608-2), and grown in fed-batch culture at the 15-L scale. FIG. 78A shows the time course of optical density within the 15-L bioreactor fed with glucose. FIG. 78B shows the time course of isoprene titer within the 15-L bioreactor fed with glucose. The titer is defined as the amount of isoprene produced per liter of fermentation broth. Method for calculating isoprene: cumulative isoprene produced in 59 hrs, g/Fermentor volume at 59 hrs, L [=] g/L broth. FIG. 78C also shows the time course of isoprene titer within the 15-L bioreactor fed with glucose. Method for calculating isoprene: ∫(Instantaneous isoprene production rate, g/L/hr)dt from t=0 to 59 hours [=] g/L broth. FIG. 78D shows the time course of total isoprene produced from the 15-L bioreactor fed with glucose. FIG. 78E shows volumetric productivity within the 15-L bioreactor fed with glucose. FIG. 78F shows carbon dioxide evolution rate (CER), or metabolic activity profile, within the 15-L bioreactor fed with glucose.

FIGS. 79B and 79C are the nucleotide sequence of pJ201:19813 (SEQ ID NO:123).

DETAILED DESCRIPTION OF THE INVENTION

Figure 2:
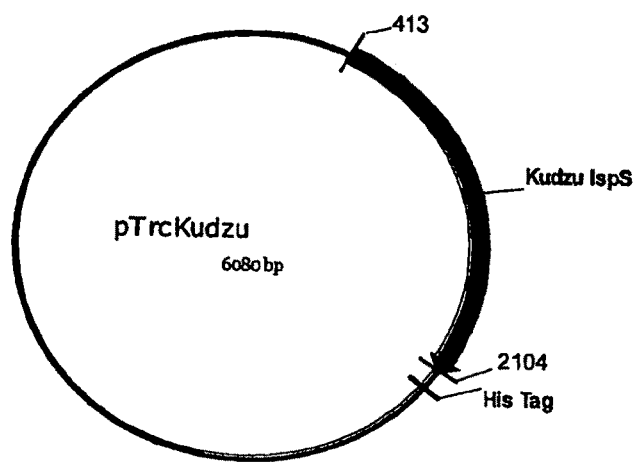
FIG. 2 is a map of pTrcKudzu.

A technique for producing isoprene in a culture of cells that produce isoprene is described in U.S. Provisional Patent Application Ser. No. 61/013,574, filed on Dec. 13, 2007, and in U.S. Provisional Patent Application Ser. No. 61/013,386, filed on Dec. 13, 2007, and in U.S. patent application Ser. No. 12/335,071. The teachings of U.S. Provisional Patent Application Ser. No. 61/013,574 (now published as United States Patent Publication No. 2009/0203102A1), U.S. Provisional Patent Application Ser. No. 61/013,386, and U.S. patent application Ser. No. 12/335,071 (now published as United States Patent Publication No. 2009/0203102A1) are incorporated herein by reference for the purpose of teaching techniques for producing and recovering isoprene by such a process. In any case, U.S. Provisional Patent Application Ser. No. 61/013,574, U.S. Provisional Patent Application Ser. No. 61/013,386, and U.S. patent application Ser. No. 12/335,071 teach compositions and methods for the production of increased amounts of isoprene in cell cultures. In particular, these compositions and methods increase the rate of isoprene production and increase the total amount of isoprene that is produced. For example, cell culture systems that generate $4.8 \times 10^4$ nmole/$g_{wcm}$/hr of isoprene have been produced (Table 1). The efficiency of these systems is demonstrated by the conversion of ~23.6 molar % yield (10.7 weight % yield) of the carbon that the cells consume from a cell culture medium into isoprene (% carbon yield). As shown in the Examples and Table 2, approximately 60.5 g of isoprene per liter of broth was generated. Isoprene was produced at a peak specific rate of $1.88 \times 10^5$ nmol/OD/hr ($1.88 \times 10^5$ nmole/$g_{wcm}$/hr). If desired, even greater amounts of isoprene can be obtained using other conditions, such as those described herein. In some embodiments, a renewable carbon source is used for the production of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further below, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) or *Populus alba* (Poplar) isoprene synthase polypeptide was expressed in a variety of host cells, such as *Escherichia coli, Panteoa citrea, Bacillus subtilis, Yarrowia lipolytica*, and *Trichoderma reesei*. As also shown in the Examples, a heterologous *Methanosarcina mazei* (*M. mazei*) mevalonate kinase (MVK) was expressed in host cells such as *Escherichia coli* to increase isoprene production. All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 60.5 g of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

TABLE 1

Exemplary yields of isoprene from a shake flask using the cell cultures and methods of the invention.

| | Isoprene Production in a Headspace vial* | |
|---|---|---|
| Strain | Headspace concentration µg/$L_{gas}$ | Specific Rate µg/$L_{broth}$/hr/OD (nmol/$g_{wcm}$/hr) |
| *E. coli* BL21/pTrcKudzu IS | 1.40 | 53.2 (781.2) |
| *E. coli* BL21/Pcl DXS yidi Kudzu IS | 7.61 | 289.1 ($4.25 \times 10^3$) |
| *E. coli* BL21/MCM127 with kudzu IS and entire MVA pathway | 23.0 | 874.1 ($1.28 \times 10^4$) |
| *E. coli* BL21/Pet N-HisKudzu IS | 1.49 | 56.6 (831.1) |
| *Pantoea citrea*/pTrcKudzu IS | 0.66 | 25.1 (368.6) |
| *E. coli* w/Poplar IS [Miller (2001)] | — | 5.6 (82.2) |
| *Bacillis licheniformis* Fall U.S. Pat. No. 5,849,970 | — | 4.2 (61.4) |
| *Yarrowia lipolytica* with kudzu isoprene synthase | ~0.05 µg/L | ~2 (~30) |
| *Trichoderma reesei* with kudzu isoprene synthase | ~0.05 µg/L | ~2 (~30) |
| *E. coli* BL21/ | 85.9 | $3.2 \times 10^3$ |

TABLE 1-continued

Exemplary yields of isoprene from a shake flask using the cell cultures and methods of the invention.

| Strain | Isoprene Production in a Headspace vial* | |
|---|---|---|
| | Headspace concentration $\mu g/L_{gas}$ | Specific Rate $\mu g/L_{broth}/hr/OD$ $(nmol/g_{wcm}/hr)$ |
| pTrcKKDyIkIS with kudzu IS and lower MVA pathway | | $(4.8 \times 10^4)$ |

The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.
*Normalized to 1 mL of 1 OD$_{600}$, cultured for 1 hour in a sealed headspace vial with a liquid to headspace volume ratio of 1:19.

TABLE 2

Exemplary yields of isoprene in a fermentor using the cell cultures and methods of the invention.

| Strain | Isoprene Production in Fermentors | | |
|---|---|---|---|
| | Peak Headspace concentration** $(ug/L_{gas})$ | Titer $(mg/L_{broth})$ | Peak Specific rate $\mu g/L_{broth}/hr/OD$ $(nmol/g_{wcm}/hr)$ |
| E. coli BL21/ pTrcKudzu with Kudzu IS | 52 | 41.2 | 37 (543.3) |
| E. coli FM5/pTrcKudzu IS | 3 | 3.5 | 21.4 (308.1) |
| E. coli BL21/triple strain (DXS, yidi, IS) | 285 | 300 | 240 $(3.52 \times 10^3)$ |
| E. coli FM5/triple strain (DXS, yidi, IS) | 50.8 | 29 | 180.8 $(2.65 \times 10^3)$ |
| E. coli/MCM127 with Kudzu IS and entire MVA pathway | 1094 | 250 | 875 $(1.28 \times 10^4)$ |
| Bacillus subtilis wild-type | 1.5 | 2.5 | 0.8 (11.7) |
| Bacillus pBS Kudzu IS | 16.6 | ~30 (over 100 hours) | 5 (73.4) |
| Bacillus Marburg 6051 [Wagner and Fall (1999)] | 2.04 | 0.61 | 24.5 (359.8) |
| Bacillus Marburg 6051 Fall U.S. Pat. No. 5,849,970 | 0.7 | 0.15 | 6.8 (100) |
| E. coli BL21/pCLPtrcUpper Pathway and gi1.2KKDyI and pTrcAlba-mMVK | $2.03 \times 10^4$ | $3.22 \times 10^4$ | $5.9 \times 10^3$ $(8.66 \times 10^4)$ |
| E. coli BL21/pCLPtrcUpper Pathway and gi1.2KKDyI and pTrcAlba-mMVK plus pBBRCMPGI1.5pgl | $3.22 \times 10^4$ | $6.05 \times 10^4$ | $1.28 \times 10^4$ $(1.88 \times 10^5)$ |

The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.
**Normalized to an off-gas flow rate of 1 vvm (1 volume off-gas per 1 L$_{broth}$ per minute).

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 19A:
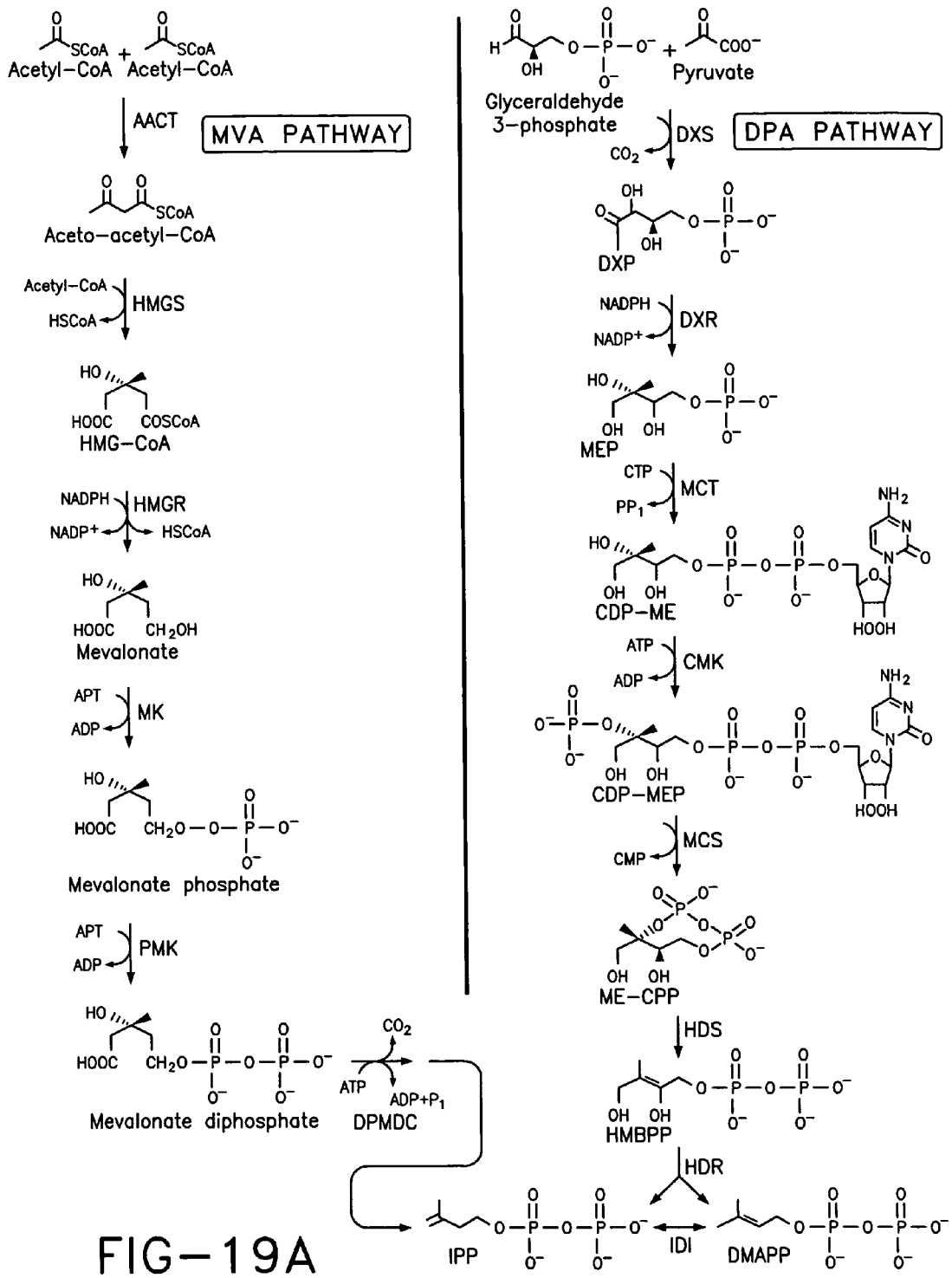
FIG. 19 shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERGS, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

The encoded DXS and IDI polypeptides are part of the DXP pathway for the biosynthesis of isoprene (FIG. 19A). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

For example, fermentation of E. coli cells with a kudzu isoprene synthase, S. cerevisia IDI, and E. coli DXS nucleic acids was used to produce isoprene. The levels of isoprene varied from 50 to 300 μg/L over a time period of 15 hours (Example 7, part VII).

As another example, fermentation of E. coli with M. mazei mevalonate kinase (MVK), P. alba isoprene synthase, the upper MVA pathway, and the integrated lower MVA pathway was used to produce isoprene. The levels of isoprene varied from 32 to 35.6 g/L over a time period of 67 hours (Example 10, part III).

In yet another example, fermentation of E. coli with M. mazei mevalonate kinase (MVK), P. alba isoprene synthase, pgl over-expression (RHM111608-2), the upper MVA pathway, and the integrated lower MVA pathway were used to produce isoprene. The levels of isoprene vary from 33.2 g/L to 40.0 g/L over a time period of 40 hours or 48.6 g/L to 60.5 g/L over a time period of 59 hours (Example 13, part (ii)).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by E. coli cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

Figure 19B:
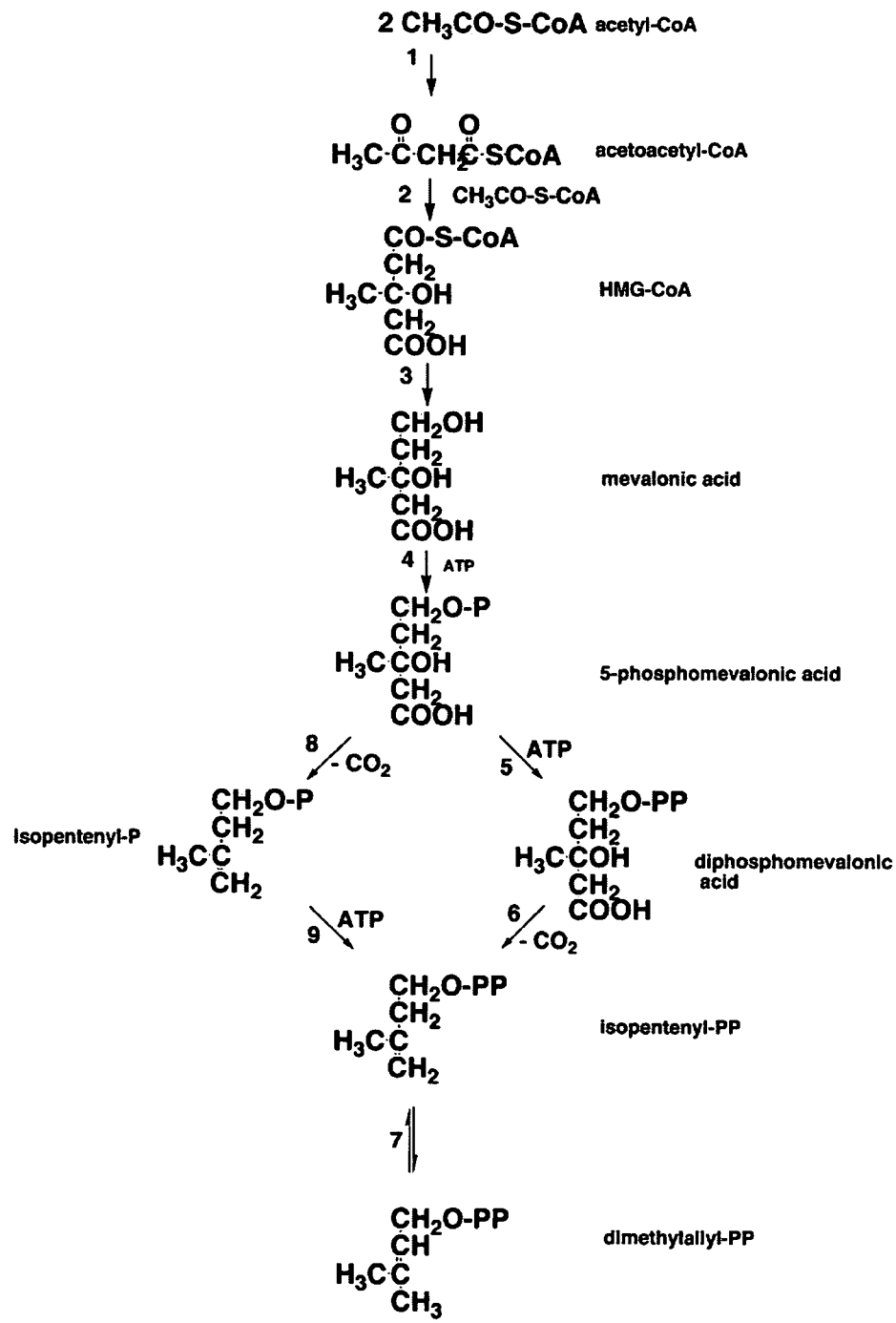

In some embodiments, the production of isoprene by cells that contain a heterologous isoprene synthase nucleic acid is augmented by increasing the amount of a MVA polypeptide expressed by the cells (FIGS. 19A and 19B). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. In some embodiments, the cells contain an entire MVA pathway that includes AA-CoA thiolase, HMG-CoA synthase, HMG-CoA reductase, MVK, PMDC, IPK, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, E. coli cells containing a nucleic acid encoding a kudzu isoprene synthase polypeptide and nucleic acids encoding Saccharomyces cerevisia MVK, PMK, MVD, and IDI polypeptides generated isoprene at a rate of $6.67 \times 10^4$ nmol/$L_{broth}$/$OD_{600}$/hr (see Example 8). Additionally, a 14 liter fermentation of E. coli cells with nucleic acids encoding Enterococcus faecalis AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in E. coli. E. coli cells that contain nucleic acids for both the upper MVA pathway and the lower MVA pathway as well as a kudzu isoprene synthase (strain MCM 127) produced significantly more isoprene (874 µg/$L_{broth}$/hr/OD) compared to E. coli cells with nucleic acids for only the lower MVA pathway and the kudzu isoprene synthase (strain MCM 131) (see Table 3 ni isoprene synthase polypeptide and a nucleic acid encoding M. mazei MVK polypeptide generated 320.6 g (at a peak specific rate of $9.54 \times 10^4$ nmol/$L_{broth}$/$OD_{600}$/hr (i.e. $9.5 \times 10^{-5}$ mol/$L_{broth}$/$OD_{600}$/hr)) of isoprene during a 67 hour fermentation in the absence of yeast extract feeding or 395.5 g (at a peak specific rate of $8.66 \times 10^4$ nmol/$L_{broth}$/$OD_{600}$/hr during a 68 hour fermentation in the presence of yeast extract feeding (see Example 10).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Figure 48A:
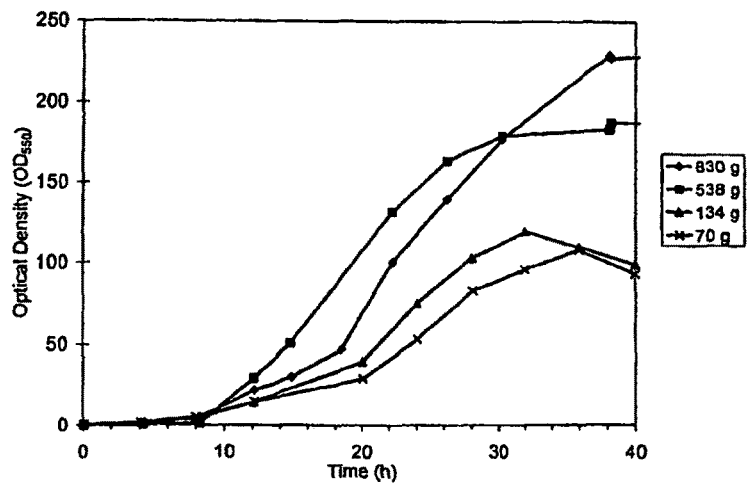
FIG. 48 shows graphs demonstrating the effect of yeast extract of isoprene production. Panel A shows the time course of optical density within fermentors fed with varying amounts of yeast extract. Panel B shows the time course of isoprene titer within fermentors fed with varying amounts of yeast extract. The titer is defined as the amount of isoprene produced per liter of fermentation broth. Panel C shows the effect of yeast extract on isoprene production in *E. coli* grown in fed-batch culture.
Figure 48B:
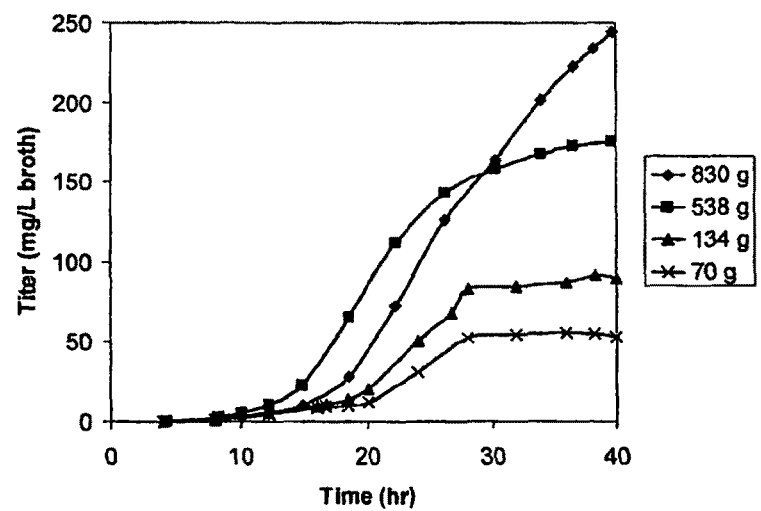
Figure 48C:
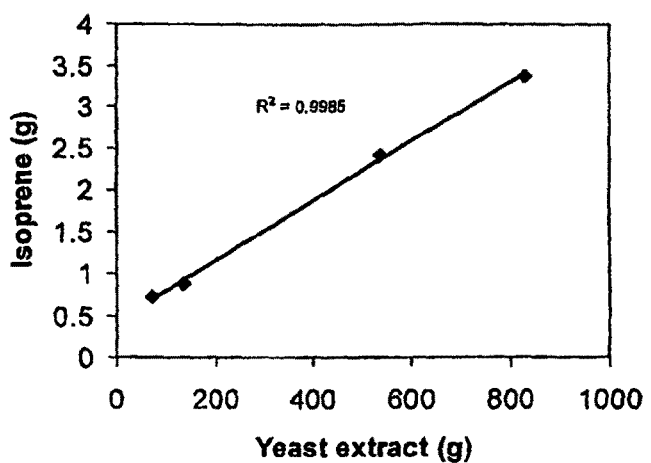

As indicated in Example 7, part VI, the amount of isoprene produced can be further increased by adding yeast extract to the cell culture medium using E. coli cells with kudzu isoprene synthase, S. cerevisia IDI, and E. coli DXS nucleic acids to produce isoprene. In particular, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 7, part VIII). Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Figure 69A:
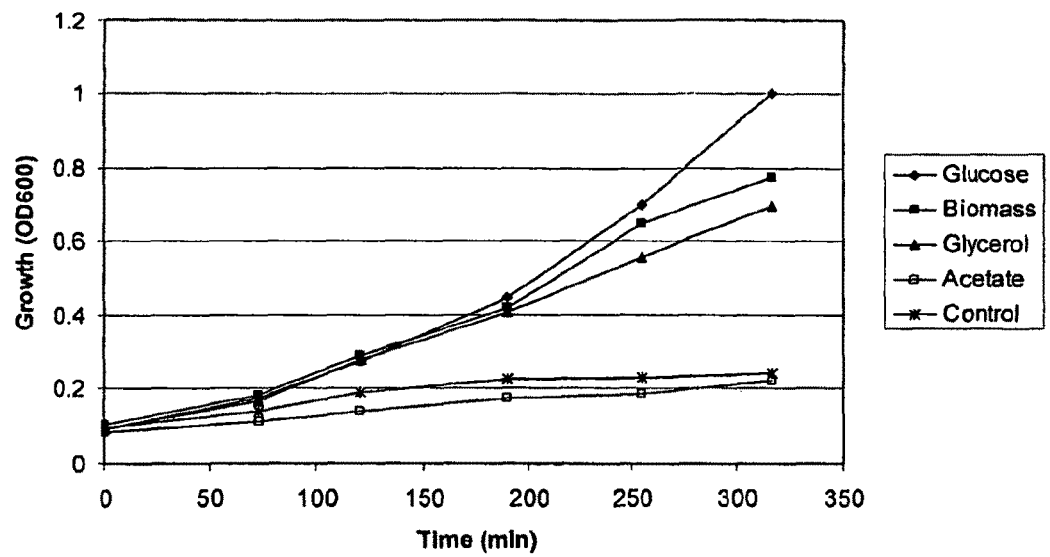
FIGS. 69A-69D shows production of isoprene from different carbon sources via the MVA (pathway).
Figure 69B:
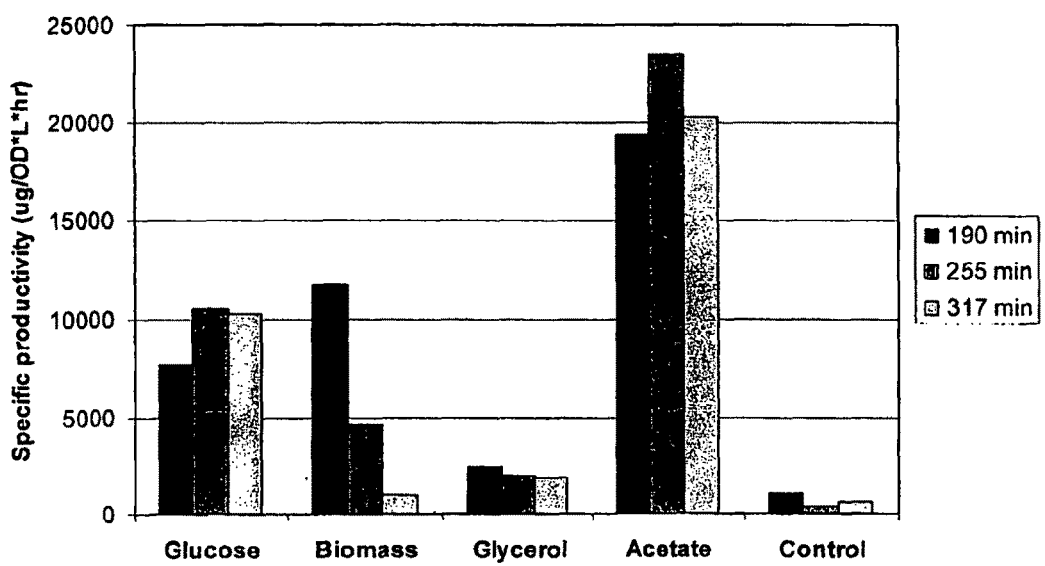
Figure 69C:
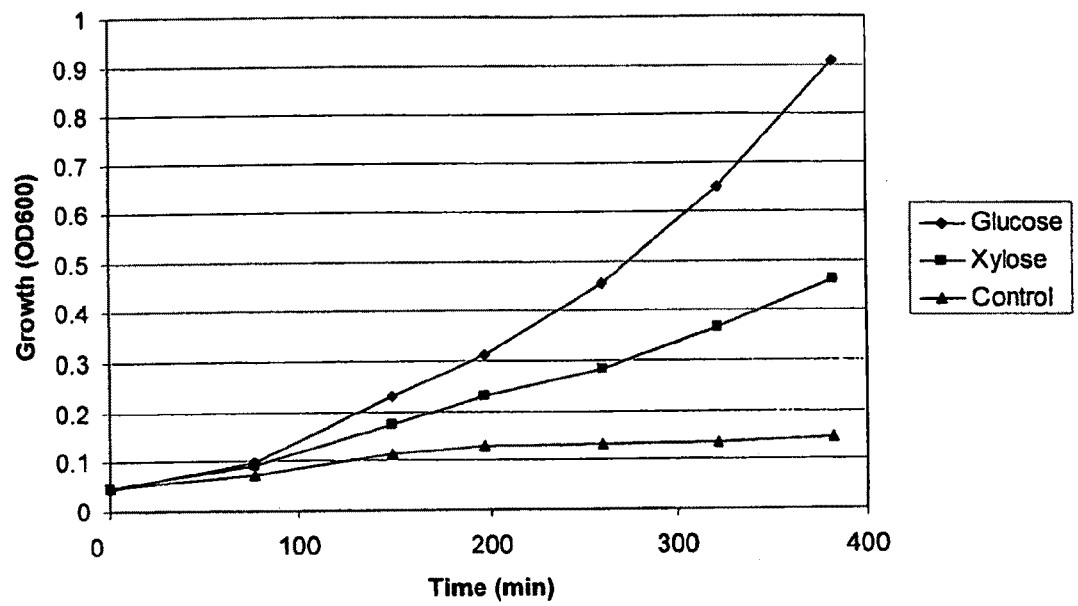

Isoprene production was also demonstrated using three types of hydrolyzed biomass (bagasse, corn stover, and soft wood pulp) as the carbon source (FIGS. 46A-C and FIGS. 69A and 69B). E. coli cells with kudzu isoprene synthase, S. cerevisia IDI, and E. coli DXS nucleic acids produced as much isoprene from these hydrolyzed biomass carbon sources as from the equivalent amount of glucose (e.g., 1% glucose, w/v). E. coli cells expressing P. alba isoprene synthase and the MVA pathway produced isoprene at a higher initial growth rate from ammonia fiber expansion (AFEX) pretreated corn stover than from the equivalent amount of glucose. (FIGS. 69A and 69B). If desired, any other biomass carbon source can be used in the compositions and methods of the invention. Biomass carbon sources are desirable because they are cheaper than many conventional cell mediums, thereby facilitating the economical production of isoprene.

Figure 47A:
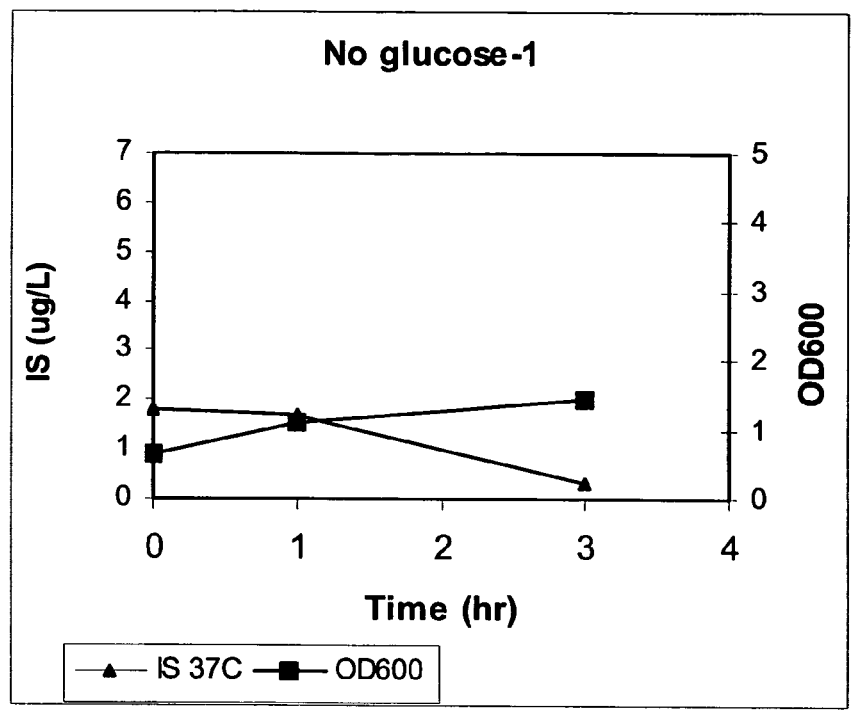
FIG. 47A shows a graph representing isoprene production by BL21 (XDE3) pTrcKudzu yIDI DXS (kan) in a culture with no glucose added. Squares represent OD600, and triangles represent isoprene produced (μg/ml).
Figure 47B:
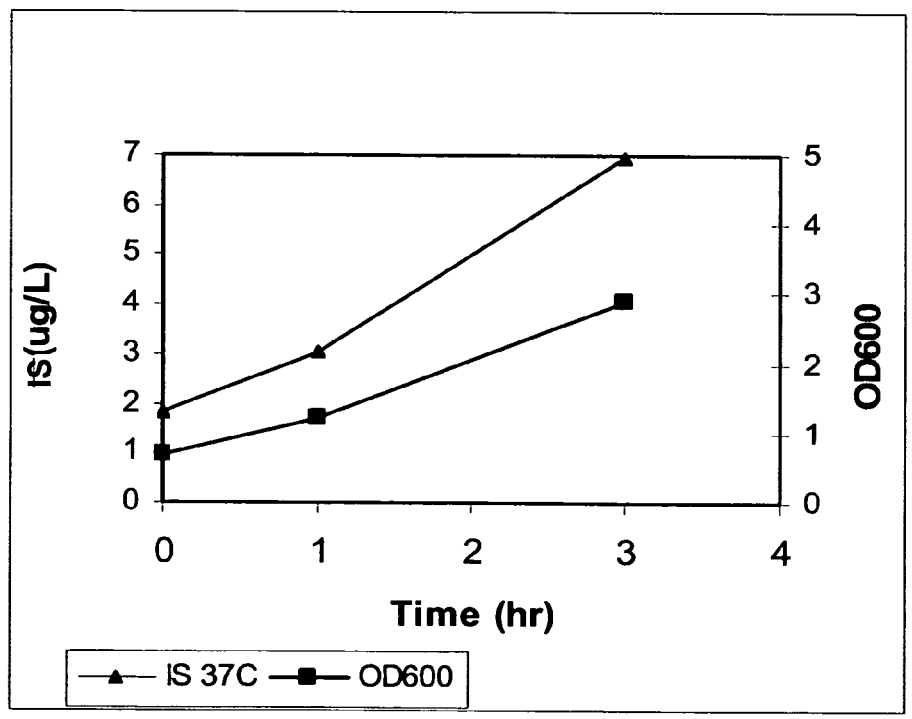
FIG. 47B shows a graph representing isoprene production from 1% glucose feedstock invert sugar by BL21 (XDE3) pTrcKudzu yIDI DXS (kan). Squares represent OD600, and triangles represent isoprene produced (μg/ml).
Figure 47C:
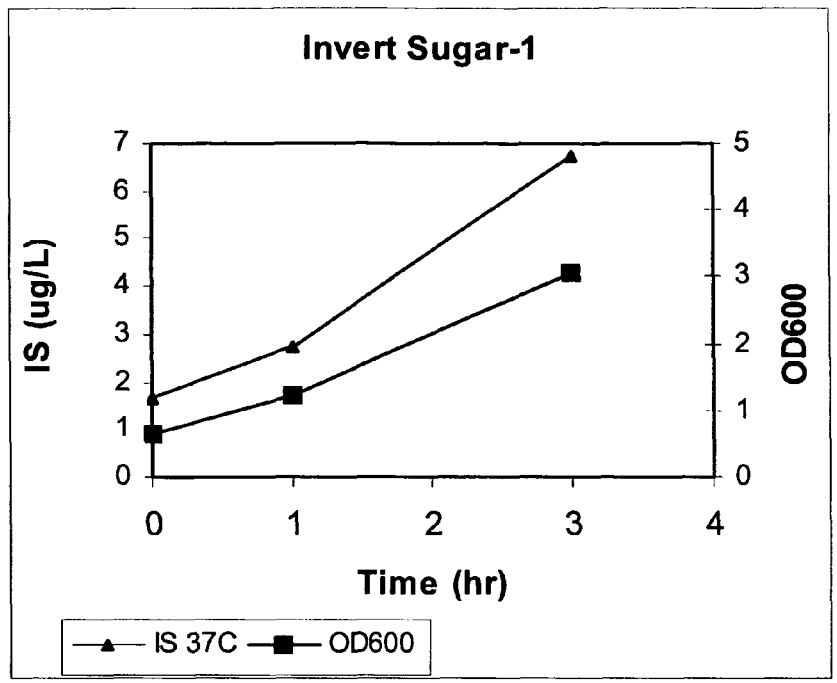
FIG. 47C shows a graph representing isoprene production from 1% invert sugar feedstock by BL21 (λDE3) pTrcKudzu yLDI DXS (kan). Squares represent OD600, and triangles represent isoprene produced (μg/ml).
Figure 47D:
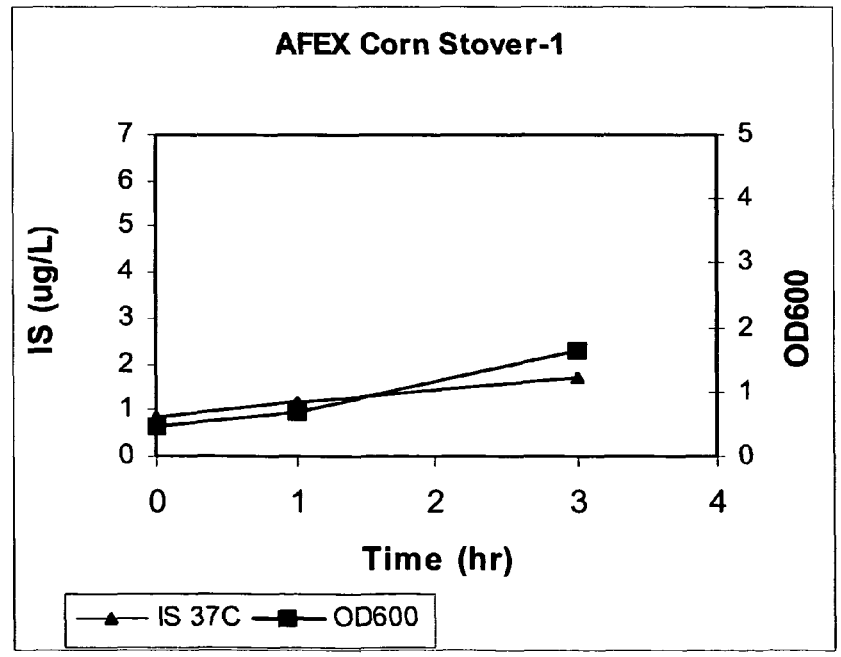
FIG. 47D shows a graph representing isoprene production from 1% AFEX corn stover feedstock by BL21 (λDE3) pTrcKudzu yIDI DXS (kan). Squares represent OD600, and triangles represent isoprene produced (μg/ml).

Additionally, invert sugar was shown to function as a carbon source for the generation of isoprene (FIG. 47D).

Additionally, xylose, acetate, and glycerol were also shown to function as a carbon source for the generation of isoprene (FIGS. 69A-69D). For example, E. coli cells with P. alba isoprene synthase and the MVA pathway grown on acetate as the only carbon source had a specific productivity of isoprene about twice as high as during growth on glucose (Example 10, Part IV; FIGS. 69A and 69B).

In some embodiments, an oil is included in the cell medium. For example, B. subtilis cells containing a kudzu isoprene synthase nucleic acid produced isoprene when cultured in a cell medium containing an oil and a source of glucose (Example 4, part III). As another example, E. coli fadR atoC mutant cells containing the upper and lower MVA pathway plus kudzu isoprene synthase produced isoprene when cultured in a cell medium containing palm oil and a source of glucose (Example 12, part II). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since a lot of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides that include part or all of a first polypeptide (e.g., an isoprene synthase, DXS, IDI, or MVA pathway polypeptide) and part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized.

In some embodiments, the nucleic acid is a heterologous nucleic acid. By "heterologous nucleic acid" is meant a nucleic acid whose nucleic acid sequence is not identical to that of another nucleic acid naturally found in the same host cell. In particular embodiments, the nucleic acid includes a segment of or the entire nucleic acid sequence of any naturally-occurring isoprene synthase, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, BM, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the worldwide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007 or Dec. 11, 2008, such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the E. coli/pTrcKudzu strain described herein) in the shake flask method as described in Example 1. After induction is complete, approximately 10 mLs of cells are pelleted by centrifugation at 7000xg for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 µl of 1M $MgCl_2$, 1 mM (250 µg/ml) DMAPP, 65 µl of Plant Extract Buffer (PEB) (50 mM Tris-HCl, pH 8.0, 20 mM $MgCl_2$, 5% glycerol, and 2 mM DTT) is added to 25 µl of cell extract in a 20 ml Headspace vial with a metal screw cap and teflon coated silicon septum (Agilent Technologies) and cultured at 37° C. for 15 minutes with shaking. The reaction is quenched by adding 200 µl of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa, Populus albaxtremula* (CAC35696), or *Populus alba*) (Sasaki et al., FEBS Letters 579(11): 2514-2518, 2005; Miller et al., Planta 213: 483-487, 2001), aspen (such as *Populus tremuloides*) (Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo. 3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo. Mevalonate kinase (MVK) polypeptide phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Phosphomevalonate decarboxylase (PMDC) polypeptides convert mevalonate-5-phosphate into isopentenyl phosphate (IP). Standard methods (such as those described herein) can be used to determine whether a polypeptide has PMDC polypeptide activity by measuring the ability of the polypeptide to convert mevalonate-5-phosphate into IP in vitro, in a cell extract, or in vivo.

Isopentenyl phosphate kinase (IPK) polypeptides phosphorylate isopentyl phosphate (IP) to form isopentenyl diphosphate (IPP). Standard methods (such as those described herein) can be used to determine whether a polypeptide has IPK polypeptide activity by measuring the ability of the polypeptide to convert IP into IPP in vitro, in a cell extract, or in vivo.

Exemplary IDI polypeptides and nucleic acids are described above.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids which may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, $2^{nd}$ ed., Cold Spring Harbor, 1989, which is hereby incorporated by reference in its entirety, particularly with respect to transformation methods. Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as *E. coli*. Once injected into the cell, the heterologous DNA circularizes under the influence of the cos sticky ends. In this manner, large segments of heterologous DNA can be introduced and expressed in host cells.

Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., *Applied. Microbiol. Biotechnol.* 75: 1377-84, 2007; Withers et al., *Appl Environ Microbiol.* 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (worldwide web at "expasy.org", Swiss Institute of Bioinformatics Swiss-Prot group CMU-1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of *Trichoderma* are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an *A. nidulans* amdS nucleic acid as a selective marker is described in Kelley et al., EMBO J. 4:475-479, 1985 and Penttila et al., *Gene* 61:155-164, 1987 (which are each hereby incorporated by reference in their entireties, particularly with respect to selective markers). In some embodiments, an isoprene synthase, DXS, IDI, or MVA pathway nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in *Saccharomyces*); AOX1 (useful for expression in *Pichia*); and lac, trp, ☒ $P_L$, ☒ $P_R$, T7, tac, and trc (useful for expression in *E. coli*).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132, 527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous *Escherichia, Panteoa, Bacillus, Yarrowia, Streptomyces,* or *Trichoderma* promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid.

In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, 2$^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, an isoprene synthase, DXS, IDI, or MVA pathway nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., *Mol. Cell. Biol.* 4:2306-2315, 1984 and Boel et al., *EMBO J.* 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei* cellobiohydrolase 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a *Trichoderma* strain (such as *T. reesei*). Other useful fungal terminators include the terminator from an *A. niger* or *A. awamori* glucoamylase nucleic acid (Nunberg et al., *Mol. Cell Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, 2$^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for overexpressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIG. 19). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, DI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens*, *H. lanuginose*, or *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans,* or *A. awamori*) (Ward et al., Appl. Microbiol. Biotechnol. 39: 7380743, 1993 and Goedegebuur et al., Genet. 41: 89-98, 2002), *Fusarium* sp., (e.g., *F. roseum, F. graminum F. cerealis, F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., Sci. 228: 21-26, 1985). The term "*Trichoderma*" or "*Trichoderma* sp." or "*Trichoderma* spp." refer to any fungal genus previously or currently classified as *Trichoderma*.

In some embodiments, the fungus is *A. nidulans, A. awamori, A. oryzae, A. aculeatus, A. niger, A. japonicus, T. reesei, T. viride, F. oxysporum,* or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei*.

In some embodiments, the source organism is a yeast, such as *Saccharomyces* sp., *Schizosaccharomyces* sp., *Pichia* sp., or *Candida* sp. In some embodiments, the source organism is a bacterium, such as strains of *Bacillus* such as *B. licheniformis* or *B. subtilis*, strains of *Pantoea* such as *P. citrea*, strains of *Pseudomonas* such as *P. alcaligenes*, strains of *Streptomyces* such as *S. albus, S. lividans,* or *S. rubiginosus*, or strains of *Escherichia* such as *E. coli*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named

*Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus.*

In some embodiments, the source organism is a gram-positive bacterium. Non-limiting examples include strains of *Streptomyces* (e.g., *S. albus, S. lividans, S. coelicolor*, or *S. griseus*) and *Bacillus*. In some embodiments, the source organism is a gram-negative bacterium, such as *E. coli* or *Pseudomonas* sp.

In some embodiments, the source organism is a plant, such as a plant from the family Fabaceae, such as the Faboideae subfamily. In some embodiments, the source organism is kudzu, poplar (such as *Populus albaxtremula* CAC35696 or *Populus alba*) (Sasaki et al., *FEBS Letters* 579(11): 2514-2518, 2005), aspen (such as *Populus tremuloides*), or *Quercus robur.*

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: Chroococcales, Pleurocapsales, Oscillatoriales, Nostocales, or Stigonematales.

Exemplary Host Cells

A variety of host cells can be used to express isoprene synthase, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. Nos. 6,022,725; 6,268,328; 7,262,041; WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes*," in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (*Sci.* 9:991-1001, 2000; EP 238023; and Yelton et al., *Proceedings. Natl. Acad. Sci. USA* 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2 \times 10^6$/mL) are used in the transformation. A volume of 100 µL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharids), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), acetate, animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose. In some embodiment, the carbohydrate is xylose or glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include acetate, glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassaya, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. Nos. 6,176,176; 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., Bioresource Technology 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.*, 53(2) 541-543, 1989, which is hereby incorporated by reference in its entirety, particularly with respect to carbon sources) and in bacteria (Hunter et. al., *Biochemistry*, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, Bacterial Metabolism, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylene-tetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd., [Int. Symp.]*, $7^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell media). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in Manual of Methods for General Bacteriology Gerhardt et al., eds), American Society for Microbiology, Washington, D.C. (1994) or Brock in Biotechnology: A Textbook of Industrial Microbiology, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: A Textbook of Industrial Microbiology, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: A Textbook of Industrial Microbiology, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, DXS, IDI, or MVA pathway nucleic acid(s) operably linked to the promoter. In some embodiments, a compound (such as IPTG) is added to induce expression of the isoprene synthase, DXS, IDI, or MVA pathway nucleic acid (s) operably linked to the promoter.

Exemplary Production of Isoprene

In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The peak specific productivity is determined by dividing the total productivity by the amount of cells, as determined by optical density at 600 nm ($OD_{600}$). In some embodiments, the isoprene amount is measured at the peak specific productivity time point. In some embodiments, the peak specific productivity for the cells is about any of the isoprene amounts per cell disclosed herein.

By "peak volumetric productivity" is meant the maximum amount of isoprene produced per volume of broth (including the volume of the cells and the cell medium) during the culturing of cells for a particular period of time (e.g., the culturing of cells during a particular fermentation run). By "peak specific volumetric productivity time point" is meant the time point during the culturing of cells for a particular period of time (e.g., the culturing of cells during a particular fermentation run) when the amount of isoprene produced per volume of broth is at a maximum. The peak specific volumetric productivity is determined by dividing the total productivity by the volume of broth and amount of time. In some embodiments, the isoprene amount is measured at the peak specific volumetric productivity time point. In some embodiments, the peak specific volumetric productivity for the cells is about any of the isoprene amounts per volume per time disclosed herein.

By "peak concentration" is meant the maximum amount of isoprene produced during the culturing of cells for a particular period of time (e.g., the culturing of cells during a particular fermentation run). By "peak concentration time point" is meant the time point during the culturing of cells for a particular period of time (e.g., the culturing of cells during a particular fermentation run) when the amount of isoprene produced per cell is at a maximum. In some embodiments, the isoprene amount is measured at the peak concentration time point. In some embodiments, the peak concentration for the cells is about any of the isoprene amounts disclosed herein.

By "average volumetric productivity" is meant the average amount of isoprene produced per volume of broth (including the volume of the cells and the cell medium) during the culturing of cells for a particular period of time (e.g., the culturing of cells during a particular fermentation run). The average volumetric productivity is determined by dividing the total productivity by the volume of broth and amount of time. In some embodiments, the average specific volumetric productivity for the cells is about any of the isoprene amounts per volume per time disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 12,500, 20,000, 30,000, 40,000, 50,000, 75,000, 100,000, 125,000, 150,000, 188,000, or more nmole of isoprene/gram of cells for the wet weight of the cells/hour (nmole/$g_{wcm}$/hr). In some embodiments, the amount of isoprene is between about 2 to about 200,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, about 2,000 to about 5,000 nmole/$g_{wcm}$/hr, about 5,000 to about 10,000 nmole/$g_{wcm}$/hr, about 10,000 to about 50,000 nmole/$g_{wcm}$/hr, about 50,000 to about 100,000 nmole/$g_{wcm}$/hr, about 100,000 to about 150,000 nmole/$g_{wcm}$/hr, or about 150,000 to about 200,000 nmole/$g_{wcm}$. In some embodiments, the amount of isoprene is between about 20 to about 200,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, about 400 to about 1,000 nmole/$g_{wcm}$/hr, about 1,000 to about 5,000 nmole/$g_{wcm}$/hr, about 2,000 to about 20,000 nmole/$g_{wcm}$/hr, about 5,000 to about 50,000 nmole/$g_{wcm}$/hr, about 10,000 to about 100,000 nmole/$g_{wcm}$/hr, about 20,000 to about 150,000 nmole/$g_{wcm}$/hr, or about 20,000 to about 200,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some embodiments, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example I, part II). If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

In some embodiments, the cells in culture have an average volumetric productivity of isoprene at greater than or about 0.1, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, or more mg of isoprene/L of broth/hr (mg/$L_{broth}$/hr, wherein the volume of broth includes the volume of the cells and the cell medium). In some embodiments, the average volumetric productivity of isoprene is between about 0.1 to about 3,500 mg/$L_{broth}$/hr, such as between about 0.1 to about 100 mg/$L_{broth}$/hr, about 100 to about 500 mg/$L_{broth}$/hr, about 500 to about 1,000 mg/$L_{broth}$/hr, about 1,000 to about 1,500 mg/$L_{broth}$/hr, about 1,500 to about 2,000 mg/$L_{broth}$/hrr, about 2,000 to about 2,500 mg/$L_{broth}$/hr, about 2,500 to about 3,000 mg/$L_{broth}$/hr, or about 3,000 to about 3,500 mg/$L_{broth}$/hr. In some embodiments, the average volumetric productivity of isoprene is between about 10 to about 3,500 mg/$L_{broth}$/hr, about 100 to about 3,500 mg/$L_{broth}$/hr, about 200 to about 1,000 mg/$L_{broth}$/hr, about 200 to about 1,500 mg/$L_{broth}$/hr, about 1,000 to about 3,000 mg/$L_{broth}$/hr, or about 1,500 to about 3,000 mg/$L_{broth}$/hr.

In some embodiments, the cells culture have a peak volumetric productivity of isoprene at greater than or about 0.5, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 12,500, 15,000, or more mg of isoprene/L of broth/hr (mg/$L_{broth}$/hr, wherein the volume of broth includes the volume of the cells and the cell medium). In some embodiments, the peak volumetric productivity of isoprene is between about 0.5 to about 15,000 mg/$L_{broth}$/hr, such as between about 0.5 to about 10 mg/$L_{broth}$/hr, about 1.0 to about 100 mg/$L_{broth}$/hr, about 100 to about 500 mg/$L_{broth}$/hr, about 500 to about 1,000 mg/$L_{broth}$/hr, about 1,000 to about 1,500 mg/$L_{broth}$/hr, about 1,500 to about 2,000 mg/$L_{broth}$/hr, about 2,000 to about 2,500 mg/$L_{broth}$/hr, about 2,500 to about 3,000 mg/$L_{broth}$/hr, about 3,000 to about 3,500 mg/$L_{broth}$/hr, about 3,500 to about 5,000 mg/$L_{broth}$/hr, about 5,000 to about 7,500 mg/$L_{broth}$/hr, about 7,500 to about 10,000 mg/$L_{broth}$/hr, about 10,000 to about 12,500 mg/$L_{broth}$/hr, or about 12,500 to about 15,000 mg/$L_{broth}$/hr. In some embodiments, the peak volumetric productivity of isoprene is between about 10 to about 15,000 mg/$L_{broth}$/hr, about 100 to about 2,500 mg/$L_{broth}$/hr, about 1,000 to about 5,000 mg/$L_{broth}$/hr, about 2,500 to about 7,500 mg/$L_{broth}$/hr, about 5,000 to about 10,000 mg/$L_{broth}$/hr, about 7,500 to about 12,500 mg/$L_{broth}$/hr, or about 10,000 to about 15,000 mg/$L_{broth}$/hr.

The instantaneous isoprene production rate in mg/$L_{broth}$ hr/hr in a fermentor can be measured by taking a sample of the fermentor off-gas, analyzing it for the amount of isoprene (in units such as mg of isoprene per $L_{gas}$) as described, for example, in Example I, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 2.0, 2.2, 2.4, 2.6, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 23.2, 23.4, 23.6, 23.8, 24.0, 25.0, 30.0, 31.0, 32.0, 33.0, 35.0, 37.5, 40.0, 45.0, 47.5, 50.0, 55.0, 60.0, 65.0, 70.0, 75.0, 80.0, 85.0, or 90.0 molar % of the carbon in the cell culture medium into isoprene. In some embodiments, the percent conversion of carbon into isoprene is between about 0.002 to about 90.0 molar %, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, about 1.0 to about 1.6%, about 1.6 to about 3.0%, about 3.0 to about 5.0%, about 5.0 to about 8.0%, about 8.0 to about 10.0%, about 10.0 to about 15.0%, about 15.0 to about 20.0%, about 20.0 to about 25.0%, about 25.0% to 30.0%, about 30.0% to 35.0%, about 35.0% to 40.0%, about 45.0% to 50.0%, about 50.0% to 55.0%, about 55.0% to 60.0%, about 60.0% to 65.0%, about 65.0% to 70.0%, about 75.0% to 80.0%, about 80.0% to 85.0%, or about 85.0% to 90.0%. In some embodiments, the percent conversion of carbon into isoprene is between about 0.002 to about 0.4 molar %, 0.002 to about 0.16 molar %, 0.04 to about 0.16 molar %, about 0.005 to about 0.3 molar %, about 0.01 to about 0.3 molar %, about 0.05 to about 0.3 molar %, about 0.1 to 0.3 molar %, about 0.3 to about 1.0 molar %, about 1.0 to about 5.0 molar %, about 2 to about 5.0 molar %, about 5.0 to about 10.0 molar %, about 7 to about 10.0 molar %, about 10.0 to about 20.0 molar %, about 12 to about 20.0 molar %, about 16 to about 20.0 molar %, about 18 to about 20.0 molar %, about 18 to 23.2 molar %, about 18 to 23.6 molar %, about 18 to about 23.8 molar %, about 18 to about 24.0 molar %, about 18 to about 25.0 molar %, about 20 to about 30.0 molar %, about 30 to about 40.0 molar %, about 30 to about 50.0 molar %, about 30 to about 60.0 molar %, about 30 to about 70.0 molar %, about 30 to about 80.0 molar %, or about 30 to about 90.0 molar %.

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

$$\text{Carbon Yield} = \frac{\text{moles carbon in isoprene produced}}{(\text{moles carbon in carbon source}) \times 100} \quad \text{Equation 1}$$

For this calculation, yeast extract can be assumed to contain 50% w/w carbon. As an example, for the 500 liter described in Example 7, part VIII, the percent conversion of carbon into isoprene can be calculated as shown in Equation 2.

$$\text{\% Carbon Yield} = \frac{39.1 \text{ g isoprene} \times 1/68.1 \text{ mol/g} \times 5 \text{ C/mol}}{[(181{,}221 \text{ g glucose} \times 1/180 \text{ mol/g} \times 6 \text{ C/mol}) + (17{,}780 \text{ g yeast extract} \times 0.5 \times 1/12 \text{ mol/g})] \times 100} \quad \text{Equation 2}$$

$$= 0.042\%$$

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein.

One skilled in the art can readily convert the rates of isoprene production or amount of isoprene produced into any other units. Exemplary equations are listed below for inter-converting between units.

Units for Rate of Isoprene production (total and specific)

$$1 \text{ g isoprene}/L_{broth}/\text{hr} = 14.7 \text{ mmol isoprene}/L_{broth}/\text{hr} \text{ (total volumetric rate)} \quad \text{Equation 3}$$

$$1 \text{ nmol isoprene}/g_{wcm}/\text{hr} = 1 \text{ nmol isoprene}/L_{broth}/\text{hr}/OD_{600} \text{ (This conversion assumes that one liter of broth with an } OD_{600} \text{ value of 1 has a wet cell weight of 1 gram.)} \quad \text{Equation 4}$$

$$1 \text{ nmol isoprene}/g_{wcm}/\text{hr} = 68.1 \text{ ng isoprene}/g_{wcm}/\text{hr} \text{ (given the molecular weight of isoprene)} \quad \text{Equation 5}$$

$$1 \text{ nmol isoprene}/L_{gas} \, O_2/\text{hr} = 90 \text{ nmol isoprene}/L_{broth}/\text{hr (at an } O_2 \text{ flow rate of 90 L/hr per L of culture broth)} \quad \text{Equation 6}$$

$$1 \text{ ug isoprene}/L_{gas} \text{ in off-gas} = 60 \text{ ug isoprene}/L_{broth}/\text{hr at a flow rate of 60 } L_{gas} \text{ per } L_{broth} \text{ (1 vvm)} \quad \text{Equation 7}$$

Units for Titer (Total and Specific)

$$1 \text{ nmol isoprene/mg cell protein} = 150 \text{ nmol isoprene}/L_{broth}/O_{600} \text{ (This conversion assumes that one liter of broth with an } OD_{600} \text{ value of 1 has a total cell protein of approximately 150 mg) (specific productivity)} \quad \text{Equation 8}$$

$$1 \text{ g isoprene}/L_{broth} = 14.7 \text{ mmol isoprene}/L_{broth} \text{ (total titer)} \quad \text{Equation 9}$$

If desired, Equation 10 can be used to convert any of the units that include the wet weight of the cells into the corresponding units that include the dry weight of the cells.

$$\text{Dry weight of cells} = (\text{wet weight of cells})/3.3 \quad \text{Equation 10}$$

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques. such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, any of the methods described herein further include polymerizing the isoprene. For example, standard methods can be used to polymerize the purified isoprene to form cis-polyisoprene or other down stream products using standard methods.

Additional methods and compositions are described in U.S. Provisional patent application No. 61/097,186, filed on Sep. 15, 2008 (now published as United States Patent Publication No. 2010/0086978 A1), U.S. Provisional patent application No. 61/097,189, filed on Sep. 15, 2008 (now published as United States Patent Publication No. 2010/0184178 A1), U.S. Provisional patent application No. 61/097,163, filed on Sep. 15, 2008, and U.S. patent application Ser. No. 12/335,071 (now published as United States Patent Publication No. 2009/0203102 A1) all of which are incorporated by reference in their entirties, particularly with respect to compositions and methods for producing isoprene.

The isoprene of this invention can be polymerized into useful polymers, including synthetic rubber, utilizing the same techniques that are applicable to isoprene that is derived from petrochemical sources. The polymerization and recovery of such isoprene containing polymers are suitably carried out according to various methods suitable for diene monomer polymerization processes. This includes batchwise, semi-continuous, or continuous operations under conditions that exclude air and other atmospheric impurities, particularly oxygen and moisture. The polymerization of the isoprene monomer may also be carried out in a number of different polymerization reactor systems, including but not limited to bulk polymerization, vapor phase polymerization, solution polymerization, suspension polymerization, emulsion polymerization, and precipitation polymerization systems. The commercially preferred methods of polymerization are typically solution polymerization and emulsion polymerization.

The polymerization reaction can also be initiated using a vast array of different polymerization initiators or catalyst systems. The initiator or catalyst system used will be dependent upon the desired characteristics of the isoprene containing polymer being synthesized. For instance, in cases where cis-1,4-polyisoprene rubber is being made a Ziegler Natta catalyst system which is comprised of titanium tetrachloride and triethyl aluminum can be utilized. In synthesizing other types of isoprene containing polymers other types of initiator systems may be needed. For instance, isoprene containing polymers can be made using a free radical initiator, a redox initiator, an anionic initiator, or a cationic initiator. The preferred initiation or catalyst system will depend upon the polymer microstructure, molecular weight, molecular weight distribution, and chain branching desired. The preferred initiators will also depend upon whether the isoprene is being homopolymerized or copolymerized with additional monomers. In the case of copolymers the initiator used will also depend upon whether it is desirable for the polymer being made to have a random, non-random, or tapered distribution of repeat units that are derived of the particular monomers. For instance, anionic initiators or controlled free radical initiators are typically used in synthesizing block copolymers having isoprene blocks.

It is important for the initiator or catalyst system employed to be compatible with the type of polymerization system used. For instance, in emulsion polymerizations free radical initiators are typically utilized. In solution polymerizations anionic initiators, such as alkyl lithium compounds, are typically employed to initiate the polymerization. An advantage of free radical polymerization is that reactions can typically be carried out under less rigorous conditions than ionic polymerizations. Free radical initiation systems also exhibit a greater tolerance of trace impurities.

Conventional emulsion recipes may also be employed in polymerizing isoprene in accordance with the present invention; however, some restrictions and modifications may arise either from the inclusion of additional comonomers, or the restrictions on polymerization parameters. Ionic surfactants, known in the art, including sulfonate detergents and carboxylate, sulfate, and phosphate soaps are useful in this invention. The level of ionic surfactant is computed based upon the total weight of the organic components and may range from about 2 to 30 parts by weight of ionic surfactant per 100 parts by weight of organic components.

Examples of free radical initiators that are useful in the practice of the present invention are those known as "redox" initiators, such as combinations of chelated iron salts, sodium formaldehyde sulfoxylate, and organic hydroperoxides. Representative of organic hydroperoxides are cumene hydroperoxide, paramenthane hydroperoxide, and tertiary butyl hydroperoxide. Tertiary butyl hydroperoxide (t-BHP), tertiary butyl peracetate (t-BPA) and "azo" initiators, such as azobisiobutyronitrile (AIBN), are preferred. The reaction temperature utilized in free radical polymerizations is typically maintained in the range of 0° C. to 150° C. Temperatures between about 20° C. and 120° C. are generally preferred and temperatures within the range of 60° C. to 100° C. are normally most preferred. The reaction pressure is not critical. It is typically only sufficiently high to maintain liquid phase reaction conditions; it may be autogenic pressure, which will vary depending upon the components of the reaction mixture and the temperature, or it may be higher, e.g., up to 1000 psi.

In batch operations, the polymerization time can be varied as desired from as little as a few minutes to as lone as several days. Polymerization in batch processes may be terminated when monomer is no longer absorbed, or earlier, if desired, e.g., if the reaction mixture becomes too viscous. In continuous operations, the polymerization mixture may be passed through a reactor or series of reactors of any suitable design. The polymerization reactions in such cases are suitably adjusted by varying the residence time in the reactor system. Residence times vary with the type of reactor system and range from 10 to 15 minutes to 24 or more hours. The concentration of monomer in the reaction mixture may vary upwards from 5 percent by weight of the reaction mixture, depending on the conditions employed; the range from 20 to 80 percent by weight is preferred.

The polymerization of isoprene may also be carried out in a suitable organic solvent that is liquid under the conditions of reaction and which is relatively inert. The solvent may have the same number of carbon atoms per molecule as the diene reactant or it may be in a different boiling range. Preferred organic solvents are normally alkanes and cycloalkanes.

The solvents can be comprised of one or more aromatic, paraffinic or cycloparaffinic compounds. These solvents will normally contain from about 4 carbon atoms per mole to about 10 carbon atoms per molecule and will be liquid under the conditions of the polymerization. Some representative examples of suitable organic solvents include pentane, isooctane, cyclohexane, methylcyclohexane, isohexane, n-heptane, n-octane, n-hexane, benzene, toluene, xylene, ethylbenzene, diethylbenzene, isobutylbenzene, petroleum ether, kerosene, petroleum spirits, petroleum naphtha, and the like, alone or in admixture. Aromatic hydrocarbons, such as benzene, toluene, isopropylbenzene, xylene, or halogenated aromatic compounds, such as chlorobenzene, bromobenzene, or orthodichlorobenzene, may also be employed, but are not preferred in most cases. Other useful solvents include tetrahydrofuran and dioxane.

In the solution polymerization, there will normally be from 5 to 30 weight percent monomers in the polymerization medium. Such polymerization media are, of course, comprised of the organic solvent and monomers. In most cases, it will be preferred for the polymerization medium to contain from 10 to 25 weight percent monomers. It is generally more preferred for the polymerization medium to contain 15 to 20 weight percent monomers.

The polymerization is typically carried out to attain an essentially complete conversion of monomers into polymer. Incremental monomer addition, or a chain transfer agent, may be used in order to avoid excessive gel formation. Such minor modifications are within the skill of the artisan. After the polymerization is complete, the polymer is recovered from a slurry or solution of the polymer. A simple filtration may be adequate to separate polymer from diluent. Other means for separating polymer from diluent may be employed. The polymer may be treated, separately or while slurried in the reaction mixture, in order to separate residues. Such treatment may be with alcohols such as methanol, ethanol, or isopropanol, with acidified alcohols, or with other similar polar liquids. In many cases the polymers are obtained in hydrocarbon solutions and the polymer can be recovered by coagulation with acidified alcohol, e.g., rapidly stirred methanol or isopropanol containing 2% hydrochloric acid. Following this initial coagulation, the polymers may be washed with an appropriate liquid, such as methanol.

As has been previously noted, the isoprene can also be copolymerized with one or more additional comonomers to make useful copolymers. Some adjustments in the polymerization recipe or reaction conditions may be necessary to obtain a satisfactory rate of polymer formation, depending on the relative amount of isoprene included and the other monomers involved. Examples of comonomers that are useful in the practice of this invention include other diene monomers, such as 1,3-butadiene and hexadienes. Vinyl aromatic monomers can also be copolymerizable with isoprene to make useful polymers. Such vinyl aromatic monomers include styrene, α-methylstyrene, divinyl benzene, vinyl chloride, vinyl acetate, vinylidene chloride, methyl methacrylate, ethyl acrylate, vinylpyridine, acrylonitrile, methacrylonitrile, methacrylic acid, itaconic acid and acrylic acid. Mixtures of different comonomers can also be employed at differing levels.

The isoprene monomer can also be copolymerized with one or more additional conjugated diolefin monomers. Those containing from 4 to 8 carbon atoms are generally preferred for commercial purposes. Some specific representative examples of conjugated diolefin monomers that can be copolymerized with isoprene include 1,3-butadiene, 2,3-dimethyl-1,3-butadiene, piperylene, 3-butyl-1,3-octadiene, 2-phenyl-1,3-butadiene, and the like, alone or in admixture.

Some representative examples of ethylenically unsaturated monomers that can copolymerized with isoprene include alkyl acrylates, such as methyl acrylate, ethyl acrylate, butyl acrylate, methyl methacrylate and the like; vinylidene monomers having one or more terminal $CH_2=CH-$ groups; vinyl aromatics such as styrene, .alpha.-methylstyrene, bromostyrene, chlorostyrene, fluorostyrene and the like; α-olefins such as ethylene, propylene, 1-butene and the like; vinyl halides, such as vinylbromide, chloroethene (vinylchloride), vinylfluoride, vinyliodide, 1,2-dibromoethene, 1,1-dichloroethene (vinylidene chloride), 1,2-dichloroethene and the like; vinyl esters, such as vinyl acetate; α, β-olefinically unsaturated nitriles, such as acrylonitrile and methacrylonitrile; α,β-olefinically unsaturated amides, such as acrylamide, N-methyl acrylamide, N,N-dimethylacrylamide, methacrylamide and the like. Functionalized monomers can also optionally be copolymerized with the isoprene in making useful rubbery polymers. Functionalized monomers of this type and methods by which they can be incorporated into rubbery polymers are described in U.S. Pat. Nos. 6,627,721 and 6,936,669. The teachings of U.S. Pat. Nos. 6,627,721 and 6,936,669 are incorporated herein by reference for the purpose of describing such functionalized monomers and their incorporation into isoprene containing polymers.

Rubbery polymers which are copolymers of one or more diene monomers with one or more other ethylenically unsaturated monomers will normally contain from about 50 weight percent to about 99 weight percent conjugated diolefin monomers (including isoprene) and from about 1 weight percent to about 50 weight percent of the other ethylenically unsaturated monomers in addition to the conjugated diolefin monomers. For example, rubbery copolymers of isoprene monomer with vinylaromatic monomers, such as styrene-isoprene rubbers will normally which contain from 50 to 95 weight percent isoprene and from 5 to 50 weight percent vinylaromatic monomers.

Vinyl aromatic monomers are probably the most important group of ethylenically unsaturated monomers which are commonly incorporated into isoprene containing rubbers. Such vinyl aromatic monomers typically contain from 8 to 20 carbon atoms. Usually, the vinyl aromatic monomer will contain from 8 to 14 carbon atoms. The most widely used vinyl aromatic monomer is styrene. Some examples of vinyl aromatic monomers that can be utilized include styrene, 1-vinylnaphthalene, 2-vinylnaphthalene, α-methylstyrene, 4-phenylstyrene, 3-methylstyrene and the like.

Some representative examples of isoprene containing rubbery polymers include cis-1,3-polyisoprene homopolymer rubber, 3,4-polyisoprene rubber, styrene-isoprene rubber (SIR), β-methylstyrene-isoprene rubber, styrene-isoprene-butadiene rubber (SIBR), styrene-isoprene rubber (SIR), isoprene-butadiene rubber (IBR), α-methylstyrene-isoprene-butadiene rubber and α-methylstyrene-styrene-isoprene-butadiene rubber. In cases where the rubbery polymer is comprised of repeat units that are derived from two or more monomers, the repeat units which are derived from the different monomers, including the isopren, will normally be distributed in an essentially random manner. The repeat units that are derived from the monomers differ from the monomer in that a double bond is normally consumed in by the polymerization reaction.

The rubbery polymer can be made by solution polymerization in a batch process by in a continuous process by continuously charging the isoprene monomer and optionally additional monomers into a polymerization zone. The polymerization zone will typically be a polymerization reactor or a series of polymerization reactors. The polymerization zone will normally provide agitation to keep the monomers, polymer, initiator, and modifier well dispersed throughout the organic solvent the polymerization zone. Such continuous polymerizations are typically conducted in a multiple reactor system. The rubbery polymer synthesized is continuously withdrawn from the polymerization zone. The monomer conversion attained in the polymerization zone will normally be at least about 85 percent. It is preferred for the monomer conversion to be at least about 90 percent.

The polymerization can be initiated with an anionic initiator, such as an alkyl lithium compound. The alkyl lithium compounds that can be used will typically contain from 1 to about 8 carbon atoms, such as n-butyl lithium. The amount of the lithium initiator utilized will vary with the monomers being polymerized and with the molecular weight that is desired for the polymer being synthesized. However, as a general rule, from 0.01 to 1 phm (parts per 100 parts by weight of monomer) of the lithium initiator will be utilized. In most cases, from 0.01 to 0.1 phm of the lithium initiator will be utilized with it being preferred to utilize 0.025 to 0.07 phm of the lithium initiator.

Such anionic polymerizations are optionally conducted in the presence of polar modifiers, such as alkyltetrahydrofurfuryl ethers. Some representative examples of specific polar modifiers that can be used include methyltetrahydrofurfuryl ether, ethyltetrahydrofurfuryl ether, propyltetrahydrofurfuryl ether, butyltetrahydrofurfuryl ether, hexyltetrahydrofurfuryl ether, octyltetrahydrofurfuryl ether, dodecyltetrahydrofurfuryl ether, diethyl ether, di-n-propyl ether, diisopropyl ether, di-n-butyl ether, tetrahydrofuran, dioxane, ethylene glycol dimethyl ether, ethylene glycol diethyl ether, diethylene glycol dimethyl ether, diethylene glycol diethyl ether, triethylene glycol dimethyl ether, trimethylamine, triethylamine, N,N,N',N'-tetramethylethylenediamine, N-methyl morpholine, N-ethyl morpholine, or N-phenyl morpholine.

The polar modifier will typically be employed at a level wherein the molar ratio of the polar modifier to the lithium initiator is within the range of about 0.01:1 to about 5:1. The molar ratio of the polar modifier to the lithium initiator will more typically be within the range of about 0.1:1 to about 4:1. It is generally preferred for the molar ratio of polar modifier to the lithium initiator to be within the range of about 0.25:1 to about 3:1. It is generally most preferred for the molar ratio of polar modifier to the lithium initiator to be within the range of about 0.5:1 to about 3:2.

The polymerization temperature utilized in such anionic polymerizations can vary over a broad range of from about −20° C. to about 180° C. In most cases, a polymerization temperature within the range of about 30° C. to about 125° C. will be utilized. It is typically preferred for the polymerization temperature to be within the range of about 45° C. to about 100° C. It is typically most preferred for the polymerization temperature to be within the range of about 60° C. to about 90° C. The pressure used will normally be sufficient to maintain a substantially liquid phase under the conditions of the polymerization reaction.

Such anionic polymerizations of isoprene are normally conducted for a length of time sufficient to permit substantially complete polymerization of the isoprene and any additional monomers that are present. In other words, the polymerization is normally carried out until high conversions of at least about 85 percent are attained. The polymerization is then normally terminated by the addition of an agent, such as an alcohol, a terminating agent, or a coupling agent. For example, a tin halide and/or silicon halide can be used as a coupling agent. The tin halide and/or the silicon halide are continuously added in cases where asymmetrical coupling is desired. This continuous addition of tin coupling agent and/or the silicon coupling agent is normally done in a reaction zone separate from the zone where the bulk of the polymerization is occurring. The coupling agents will normally be added in a separate reaction vessel after the desired degree of conversion has been attained. The coupling agents can be added in a hydrocarbon solution, e.g., in cyclohexane, to the polymerization admixture with suitable mixing for distribution and reaction. In other words, the coupling will typically be added only after a high degree of conversion has already been attained. For instance, the coupling agent will normally be added only after a monomer conversion of greater than about 85 percent has been realized. It will typically be preferred for the monomer conversion to reach at least about 90 percent before the coupling agent is added.

The tin halides used as coupling agents will normally be tin tetrahalides, such as tin tetrachloride, tin tetrabromide, tin tetrafluoride or tin tetraiodide. However, tin trihalides can also optionally be used. Polymers coupled with tin trihalides having a maximum of three arms. This is, of course, in contrast to polymers coupled with tin tetrahalides which have a maximum of four arms. To induce a higher level of branching, tin tetrahalides are normally preferred. As a general rule, tin tetrachloride is most preferred.

The silicon coupling agents that can be used will normally be silicon tetrahalides, such as silicon tetrachloride, silicon tetrabromide, silicon tetrafluoride or silicon tetraiodide. However, silicon trihalides can also optionally be used. Polymers coupled with silicon trihalides having a maximum of three arms. This is, of course, in contrast to polymers coupled with silicon tetrahalides which have a maximum of four arms. To induce a higher level of branching, silicon tetrahalides are normally preferred. As a general rule, silicon tetrachloride is most preferred of the silicon coupling agents.

A combination of a tin halide and a silicon halide can optionally be used to couple the rubbery polymer. By using such a combination of tin and silicon coupling agents improved properties for tire rubbers, such as lower hysteresis, can be attained. It is particularly desirable to utilize a combination of tin and silicon coupling agents in tire tread compounds that contain both silica and carbon black. In such cases, the molar ratio of the tin halide to the silicon halide employed in coupling the rubbery polymer will normally be within the range, of 20:80 to 95:5. The molar ratio of the tin halide to the silicon halide employed in coupling the rubbery polymer will more typically be within the range of 40:60 to 90:10. The molar ratio of the tin halide to the silicon halide employed in coupling the rubbery polymer will preferably be within the range of 60:40 to 85:15. The molar ratio of the tin halide to the silicon halide employed in coupling the rubbery polymer will most preferably be within the range of 65:35 to 80:20.

Broadly, and exemplary, a range of about 0.01 to 4.5 milliequivalents of tin coupling agent (tin halide and silicon halide) is employed per 100 grams of the rubbery polymer. It is normally preferred to utilize about 0.01 to about 1.5 milliequivalents of the coupling agent per 100 grams of polymer to obtain the desired Mooney viscosity. The larger quantities tend to result in production of polymers containing terminally reactive groups or insufficient coupling. One equivalent of tin coupling agent per equivalent of lithium is considered an optimum amount for maximum branching. For instance, if a mixture tin tetrahalide and silicon tetrahalide is used as the coupling agent, one mole of the coupling agent would be utilized per four moles of live lithium ends. In cases where a mixture of tin trihalide and silicon trihalide is used as the coupling agent, one mole of the coupling agent will optimally be utilized for every three moles of live lithium ends. The coupling agent can be added in a hydrocarbon solution, e.g., in cyclohexane, to the polymerization admixture in the reactor with suitable mixing for distribution and reaction.

After the coupling has been completed, a tertiary chelating alkyl 1,2-ethylene diamine or a metal salt of a cyclic alcohol can optionally be added to the polymer cement to stabilize the coupled rubbery polymer. In most cases, from about 0.01 phr (parts by weight per 100 parts by weight of dry rubber) to about 2 phr of the chelating alkyl 1,2-ethylene diamine or metal salt of the cyclic alcohol will be added to the polymer cement to stabilize the rubbery polymer. Typically, from about 0.05 phr to about 1 phr of the chelating alkyl 1,2-ethylene diamine or metal salt of the cyclic alcohol will be added. More typically, from about 0.1 phr to about 0.6 phr of the chelating alkyl 1,2-ethylene diamine or the metal salt of the cyclic alcohol will be added to the polymer cement to stabilize the rubbery polymer.

The terminating agents that can be used to stop the polymerization and to "terminate" the living rubbery polymer include tin monohalides, silicon monohalides, N,N,N',N'-tetradialkyldiamino-benzophenones (such as tetramethyldiaminobenzophenone and the like), N,N-dialkylamino-benzaldehydes (such as dimethylaminobenzaldehyde and the like), 1,3-dialkyl-2-imidazolidinones (such as 1,3-dimethyl-2-imidazolidinone and the like), 1-alkyl substituted pyrrolidinones; 1-aryl substituted pyrrolidinones, dialkyl-dicycloalkyl-carbodiimides containing from about 5 to about 20 carbon atoms, and dicycloalkyl-carbodiimides containing from about 5 to about 20 carbon atoms.

After the termination step, and optionally the stabilization step, has been completed, the rubbery polymer can be recovered from the organic solvent. The coupled rubbery polymer can be recovered from the organic solvent and residue by means such as chemical (alcohol) coagulation, thermal desolventization, or other suitable method. For instance, it is often desirable to precipitate the rubbery polymer from the organic solvent by the addition of lower alcohols containing from about 1 to about 4 carbon atoms to the polymer solution. Suitable lower alcohols for precipitation of the rubber from the polymer cement include methanol, ethanol, isopropyl alcohol, normal-propyl alcohol and t-butyl alcohol. The utilization of lower alcohols to precipitate the rubbery polymer from the polymer cement also "terminates" any remaining living polymer by inactivating lithium end groups. After the coupled rubbery polymer is recovered from the solution, steam-stripping can be employed to reduce the level of volatile organic compounds in the coupled rubbery polymer. Additionally, the organic solvent can be removed from the rubbery polymer by drum drying, extruder drying, vacuum drying, and the like.

As has previously been explained, synthetic cis-1,3-polyisoprene rubber that is similar enough to allow for free substitution with natural rubber can be produced by the solution polymerization of isoprene with a Ziegler Natta catalyst system that is comprised of titanium tetrachloride (TiCl$_4$) and an organoaluminum compound, such as triethyl aluminum, Al—(CH$_2$—CH$_3$)$_3$. The polyisoprene rubber that is made with this Ziegler Natta catalyst system has a high cis-microstructure contain of up to 98 percent that closely assimilates that of natural rubber from *Hevea Brasiliensis* (the common rubber tree) which has a cic-microstructure content of virtually 100 percent. However, this slight difference in polymer microstructure results of physical properties that are inferior to those of natural rubber is certain respects. For instance, natural rubber typically exhibits green strength that is superior to that of synthetic cis-1,4-polyisprene rubber. On the other hand, in certain other respects synthetic cis-1,4-polyisprene rubber is superior to natural rubber from the *Hevea Brasiliensis*, guayule, and *Taraxacum kok-Saghyz* (Russian dandelion). For instance, natural rubber contains residual proteins, soaps, resins, and sugars since it comes from plants. The presence of these residual impurities can be extremely detrimental in some applications. For instance, the presence of residual proteins in rubber products can cause serious allergic reactions in some people and are a major concern for manufacturers of some rubber-containing products, such as rubber gloves, condoms, syringe plungers, and the like. In any case, the synthetic polyisoprene homopolymer rubbers of this invention that are free from proteins, soaps, resins, and sugars present in natural rubber, including natural rubber from the *Hevea Brasiliensis*.

U.S. Pat. No. 3,931,136 discloses a process for producing high molecular weight cis-1,4-polyisoprene. The catalyst used in this process is a three-component mixture of (A) a titanium tetrachloride, (B) an organoaluminum compound of the formula AlR$_3$, where each R represents an alkyl group, preferably an alkyl group containing 1 to 8 carbon atoms, an aryl group, preferably a phenyl group, or a cycloalkyl group, preferably a cyclohexyl group, and (C) a beta-diketone of the formula:

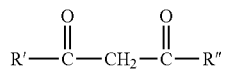

where R' and R" can be the same or different and represent an alkyl group or a aryl group. R' and R" will preferably represent an alkyl group containing from 1 to 5 carbon atoms or a phenyl group. The teachings of U.S. Pat. No. 3,931,136 are incorporated herein by reference for the purpose of teaching catalyst systems and polymerization techniques that can be used in synthesizing cis-1,4-polyisoprene.

A solution polymerization technique for synthesizing cis-1,4-polyisoprene with a catalyst system that is comprised of a mixture of titanium tetrachloride and a trialkylaluminum compound is disclosed by U.S. Pat. No. 4,430,487. In this process the polymerization is shortstopped with 4,7-diazadecane-1,10-diamine. The teachings of U.S. Pat. No. 4,430,487 are incorporated herein by reference for the purpose of teaching catalyst systems and polymerization techniques that can be used in synthesizing cis-1,4-polyisoprene.

The synthesis of cis-1,4-polyisoprene by polymerizing isoprene with a catalyst system which is comprised of a titanium tetrahalide, a trialkylaluminum compound and diphenylether can result in the formation of unwanted gel. U.S. Pat. No. 5,919,876 discloses that gel formation can be reduced by conducting such polymerizations in the presence of a diarylamine, such as para-styrenated diphenylamine. U.S. Pat. No. 5,919,876 more specifically discloses a process for synthesizing cis-1,4-polyisoprene having a low gel content which comprises polymerizing isoprene in an inert organic solvent with a preformed catalyst system which is made by reacting an organoaluminum compound with titanium tetrahalide, such as titanium tetrachloride, in the presence of at least one ether, wherein said polymerization is conducted at a temperature which is within the range of about 0° C. to about 100° C., and wherein said polymerization is conducted in the presence of a diarylamine. The teachings of U.S. Pat. No. 5,919,867 are incorporated herein by reference for the purpose of teaching catalyst systems and solution polymerization techniques that can be used in synthesizing cis-1,4-polyisoprene rubber.

Cis-1,4-polyisoprene can be made by vapor phase polymerization utilizing a preformed catalyst that is made by reacting an organoaluminum compound with titanium tetrachloride. U.S. Pat. No. 6,066,705 discloses a method for vapor phase polymerizing isoprene into cis-1,4-polyisoprene in a process comprising the steps of: (1) charging into a reaction zone said isoprene and a preformed catalyst system which is made by reacting an organoaluminum compound with titanium tetrachloride, preferably in the presence of at least one ether; wherein the isoprene is maintained in the vapor phase in said reaction zone by a suitable combination of temperature and pressure; (2) allowing said isoprene to polymerize into cis-1,4-polyisoprene at a temperature within the range of about 35° C. to about 70° C.; and (3) withdrawing said cis-1,4-polyisoprene from said reaction zone. It has been determined that gel formation can be reduced in such vapor phase polymerizations by conducting the polymerization of the isoprene monomer in the presence of a diarylamine, such as para-styrenated diphenylamine. The teachings of U.S. Pat. No. 6,066,705 are incorporated herein by reference for the purpose of teaching catalyst systems and vapor phase polymerization techniques that can be used in synthesizing cis-1,4-polyisoprene rubber.

Polyisoprene rubber that is clear (transparent) and of high purity can be synthesized utilizing a neodymium catalyst system. U.S. Pat. No. 6,780,948 relates to such a process for the synthesis of polyisoprene rubber which comprises polymerizing isoprene monomer in the presence of a neodymium catalyst system, wherein the neodymium catalyst system is prepared by (1) reacting a neodymium carboxylate with an organoaluminum compound in the presence of isoprene for a period of about 10 minutes to about 30 minutes to produce neodymium-aluminum catalyst component, and (2) subsequently reacting the neodymium-aluminum catalyst component with a dialkyl aluminum chloride for a period of at least 30 minutes to produce the neodymium catalyst system. The teachings of U.S. Pat. No. 5,919,867 are incorporated herein by reference for the purpose of teaching catalyst systems and polymerization techniques that can be used in synthesizing cis-1,4-polyisoprene rubber that is of high purity.

U.S. Pat. Nos. 7,091,150 and 7,199,201 disclose the use of a neodymium catalyst system to polymerize isoprene monomer into synthetic polyisoprene rubber having an extremely high cis-microstructure content and high stereo regularity. This polyisoprene rubber will crystallize under strain and can be compounded into rubber formulations in a manner similar to natural rubber. This technique more specifically discloses a process for the synthesis of polyisoprene rubber which comprises polymerizing isoprene monomer in the presence of a neodymium catalyst system, wherein the neodymium catalyst system is prepared by a process that comprises (1) reacting a neodymium carboxylate with an organoaluminum compound in an organic solvent to produce neodymium-aluminum catalyst component, and (2) subsequently reacting the neodymium-aluminum catalyst component with an elemental halogen to produce the neodymium catalyst system. In practicing this process, the neodymium catalyst system is typically void of nickel-containing compounds.

The synthetic polyisoprene rubber made by this process is comprised of repeat units that are derived from isoprene, wherein the synthetic polyisoprene rubber has a cis-microstructure content which is within the range of 98.0% to 99.5%, a 3,4-microstructure content which is within the range of 0.5% to 2.0%, and a trans-microstructure content which is within the range of 0.0% to 0.5%. The teachings of U.S. Pat. Nos. 7,091,150 and 7,199,201 are incorporated herein by reference for the purpose of teaching neodymium catalyst systems and polymerization techniques that can be used in synthesizing cis-1,4-polyisoprene rubber of extremely high cis-microstructure content and high stereo regularity.

Single component lanthanide catalysts, such as lanthanide diiodides, can also be used in the synthesis of polyisoprene having extremely high cis-microstructure contents. For instance, thulium diiodide, dysprosium diiodide, and neodymium diiodide can initiate the polymerization of isoprene into high cis-1,4-polyisoprene rubber without the need for any additional catalyst components. Lanthanide diiodides can accordingly be used to initiate the polymerization of isoprene monomer into high cis-1,4-polyisoprene under solution polymerization conditions.

U.S. Pat. No. 4,894,425 reveals a process for synthesizing polyisoprene that may possess functional groups and that contains more than 70 percent 1,2- and 3,4-structural units. This process involves the anionic polymerization of isoprene in an inert hydrocarbon solvent in the presence of an organolithium compound as the catalyst and an ether as the cocatalyst, wherein the cocatalyst used is an ethylene glycol dialkyl ether of the formula $R^1$—O—$CH_2$—$CH_2$—O—$R^2$ wherein $R^1$ and $R^2$ are alkyl groups having different numbers of carbon atoms, selected from the group consisting of methyl, ethyl, n-propyl, iso-propyl, n-butyl, iso-butyl, sec-butyl, and tert-butyl, and wherein the sum of the carbon atoms in the two alkyl groups $R^1$ and $R^2$ is within the range of 5 to 7. The teachings of U.S. Pat. No. 4,894,425 are incorporated herein by reference for the purpose of teaching catalyst systems and polymerization techniques that can be used in synthesizing polyisoprene having a high 1,2- and 3,4-microstructure content.

Crystallizable 3,4-polyisoprene can be synthesized in organic solvents to quantitative yields after short polymerization times by utilizing the catalyst systems described by U.S. Pat. No. 5,082,906. The 3,4-polyisoprene made utilizing this catalyst system is strain crystallizable and can be employed in tire treads which provide improved traction and improved cut growth resistance. U.S. Pat. No. 5,082,906 specifically discloses a process for the synthesis of 3,4-polyisoprene which comprises polymerizing isoprene monomer in an organic solvent at a temperature which is within the range of about −10° C. to about 100° C. in the presence of a catalyst system which is composed of (a) an organoiron compound, (b) an organoaluminum compound, (c) a chelating aromatic amine, and (d) a protonic compound; wherein the molar ratio of the chelating amine to the organoiron compound is within the range of about 0.1:1 to about 1:1, wherein the molar ratio of the organoaluminum compound to the organoiron compound is within the range of about 5:1 to about 200:1, and wherein the molar ratio of the protonic compound to the organoaluminum compound is within the range of about 0.001:1 to about 0.2:1. The teachings of U.S. Pat. No. 5,082,906 are incorporated herein by reference for the purpose of teaching catalyst systems and polymerization techniques that can be used in synthesizing polyisoprene having a high 3,4-microstructure content and which is strain crystallizable.

U.S. Pat. No. 5,356,997 also relates to a process for the synthesis of strain crystallizable 3,4-polyisoprene. This 3,4-polyisoprene has a 3,4-microstructure content which is within the range of about 65% to about 85%, a cis-1,4-microstructure content which is within the range of about 15% to about 35%, and essentially no trans-1,4-microstructure or 1,2-microstructure. It can be synthesized in organic solvents to quantitative yields after short polymerization times. U.S. Pat. No. 5,356,997 specifically discloses a process for the synthesis of 3,4-polyisoprene which comprises polymerizing isoprene monomer in an organic solvent at a temperature which is within the range of about −10° C. to about 100° C. in the presence of a catalyst system which is comprised of (a) an organoiron compound which is soluble in the organic solvent, wherein the iron in the organoiron compound is in the +3 oxidation state, (b) a partially hydrolyzed organoaluminum compound which was prepared by adding a protonic compound selected from the group consisting of water, alcohols and carboxylic acids to the organoaluminum compound, and (c) a chelating aromatic amine; wherein the molar ratio of the chelating amine to the organoiron compound is within the range of about 0.1:1 to about 1:1, wherein the molar ratio of the organoaluminum compound to the organoiron compound is within the range of about 5:1 to about 200:1, and wherein the molar ratio of the protonic compound to the organoaluminum compound is within the range of about 0.001:1 to about 0.2:1. The teachings of U.S. Pat. No. 5,356,997 are incorporated herein by reference for the purpose of teaching catalyst systems and polymerization techniques that can be used in synthesizing polyisoprene having a high 3,4-microstructure content and which is strain crystallizable.

U.S. Pat. No. 5,677,402 reveals a process for preparing 3,4-polyisoprene rubber which comprises polymerizing isoprene monomer with an organolithium initiator at a temperature which is within the range of about 30° C. to about 100° C. in the presence of a sodium alkoxide and a polar modifier, wherein the molar ratio of the sodium alkoxide to the organolithium initiator is within the range of about 0.05:1 to about 3:1; and wherein the molar ratio of the polar modifier to the organolithium initiator is within the range of about 0.25:1 to about 5:1. The teachings of U.S. Pat. No. 5,677,402 are incorporated herein by reference for the purpose of teaching catalyst systems and polymerization techniques that can be used in synthesizing 3,4-polyisoprene.

U.S. Pat. No. 7,351,768 discloses the synthesis of liquid polyisoprene having a weight average molecular weight which is within the range of 5,000 to 100,000 and preferable within the range of 20,000 to 80,000. The teachings of U.S. Pat. No. 5,677,402 are incorporated herein by reference for the purpose illustrating the synthesis of liquid polyisoprene.

U.S. Pat. No. 6,576,728 discloses a process for the copolymerization of styrene and isoprene to produce low vinyl styrene-isoprene rubber having a random distribution of repeat units that are derived from styrene. The initiator systems employed in these polymerizations are comprised of (a) a lithium initiator and (b) a member selected from the group consisting of (1) a sodium alkoxide, (2) a sodium salt of a sulfonic acid, and (3) a sodium salt of a glycol ether. It is important for the initiator system used in these polymerzations to be free of polar modifiers, such as Lewis bases. The teachings of U.S. Pat. No. 6,576,728 are incorporated herein by reference for the purpose illustrating the synthesis of styrene-isoprene rubber.

U.S. Pat. No. 6,313,216 discloses a process for synthesizing random styrene-isoprene rubber comprising: (1) continuously charging isoprene, styrene, an initiator, and a solvent into a first polymerization zone, (2) allowing the isoprene and styrene to copolymerize in the first polymerization zone to total conversion of 60 to 95 percent to produce a polymer cement containing living styrene-isoprene chains, (3) continuously charging the polymer cement containing living styrene-isoprene chains and additional isoprene monomer into a second polymerization zone, wherein from 5 to 40 percent of the total amount of isoprene changed is charged into the second polymerization zone, (4) allowing the copolymerization to continue in the second polymerization zone to a conversion of the isoprene monomer of at least 90 percent wherein the total conversion of styrene and isoprene in the second polymerization zone is limited to a maximum of 98 percent, (5) withdrawing a polymer cement of random styrene-isoprene rubber having living chain ends from the second reaction zone, (6) killing the living chain ends on the random styrene-isoprene rubber, and (7) recovering the random styrene-isoprene rubber from the polymer cement, wherein the copolymerizations in the first polymerization zone and the second polymerization zone are carried out at a temperature which is within the range of 70° C. to 100° C., and wherein the amount of styrene charged into the first polymerization zone is at least 2 percent more than the total amount of styrene bound into the rubber. The teachings of U.S. Pat. No. 6,313,216 are incorporated herein by reference for the purpose illustrating the synthesis of styrene-isoprene rubber.

Isoprene-butadiene copolymers having high vinyl contents can be synthesized in organic solvents to high yields after short polymerization times by utilizing the process disclosed in U.S. Pat. No. 5,061,765. The isoprene-butadiene copolymers made utilizing this process have a glass transition temperature which is within the range of about 0° C. to about −60° C. and can be employed in tire treads which provide improved traction and improved cut growth resistance. U.S. Pat. No. 5,061,765 more specifically discloses a process for the synthesis of isoprene-butadiene copolymers having a high vinyl content which comprises copolymerizing isoprene monomer and butadiene monomer in an organic solvent at a temperature which is within the range of about −10° C. to about 100° C. in the presence of a catalyst system which is comprised of (a) an organoiron compound, (b) an organoaluminum compound, (c) a chelating aromatic amine, and (d) a protonic compound; wherein the molar ratio of the chelating amine to the organoiron compound is within the range of about 0.1:1 to about 1:1, wherein the molar ratio of the organoaluminum compound to the organoiron compound is within the range of about 5:1 to about 200:1, and wherein the molar ratio of the protonic compound to the organoaluminum compound is within the range of about 0.001:1 to about 0.2:1. The teachings of U.S. Pat. No. 5,061,765 are incorporated herein by reference for the purpose illustrating the synthesis of isoprene-butadiene rubber.

A technique for synthesizing rubbery terpolymers of styrene, isoprene and butadiene is disclosed in U.S. Pat. No. 5,137,998. These rubbery terpolymers exhibit an excellent combination of properties for utilization in tire tread rubber compounds. By utilizing such terpolymers in tire treads, tires having improved wet skid resistance can be built without sacrificing rolling resistance or tread wear characteristics. U.S. Pat. No. 5,137,998 more specifically discloses a process for preparing a rubbery terpolymer of styrene, isoprene, and butadiene having multiple glass transition temperatures and having an excellent combination of properties for use in making tire treads which comprises: terpolymerizing styrene, isoprene and 1,3-butadiene in an organic solvent at a temperature of no more than about 40° C. in the presence of (a) at least one member selected from the group consisting of tripiperidino phosphine oxide and alkali metal alkoxides and (b) an organolithium compound. The teachings of U.S. Pat. No. 5,137,998 are incorporated herein by reference for the purpose illustrating the synthesis of styrene-isoprene-butadiene rubber.

A liquid isoprene-butadiene rubber (IBR) which is particularly valuable for use in making treads for high performance automobile tires, including race tires, that exhibit superior dry traction characteristics and durability, can be made by the process disclosed in U.S. Pat. No. 6,562,895. This isoprene-butadiene rubber is a liquid at room temperature and is comprised of repeat units which are derived from about 5 weight percent to about 95 weight percent isoprene and from about 5 weight percent to about 95 weight percent 1,3-butadiene, wherein the repeat units derived from isoprene and 1,3-butadiene are in essentially random order. This IBR also has a low number average molecular weight which is within the range of about 3,000 to about 50,000 and has a glass transition temperature which is within the range of about −50° C. to about 20° C.

These isoprene-butadiene copolymers are synthesized utilizing an organolithium initiator and a polar modifier. The level of organolithium initiator employed will be dependent upon the molecular weight which is desired for the liquid isoprene-butadiene polymer being synthesized. As a general rule, in all anionic polymerizations the molecular weight of the polymer produced is inversely proportional to the amount of initiator utilized. Since liquid isoprene-butadiene polymer having a relatively low molecular weight is being synthesized, the amount of initiator employed will be relatively large. As a general rule, from about 0.1 to about 2 phm (parts per hundred parts of monomer by weight) of the organolithium compound will be employed. In most cases, it will be preferred to utilize from about 0.2 to about 1 phm of the organolithium compound with it being most preferred to utilize from about 0.4 phm to 0.6 phm of the organolithium compound. In any case, an amount of organolithium initiator will be selected to result in the production of liquid isoprene-butadiene polymer having a number average molecular weight which is within the range of about 3,000 to about 50,000.

The amount of organolithium initiator will preferably be selected to result in the production of liquid isoprene-butadiene polymer having a number average molecular weight which is within the range of about 5,000 to about 30,000. The amount of organolithium initiator will most preferably be selected to result in the production of liquid isoprene-butadiene polymer having a number average molecular weight that is within the range of about 8,000 to about 18,000. In any case, it is critical to carry out the copolymerization of the 1,3-butadiene and the styrene in the presence of a polar modifier, such as N,N,N',N'-tetramethylethylenediamine (TMEDA), to attain a high glass transition temperature which is within the range of about −50° C. to 20° C. The teachings of U.S. Pat. No. 6,562,895 are incorporated herein by reference for the purpose illustrating the synthesis of liquid isoprene-butadiene polymers.

Block copolymers containing a block of polyisoprene can be made by the process described in U.S. Pat. No. 5,242,984. For instance, linear diblock polymers of styrene and isoprene (S-I block copolymers) and linear triblock polymers of styrene and isoprene (S-I-S triblock polymers) can be made by this process. In this technique, the monomers are polymerized sequentially by anionic polymerization in an inert organic solvent. Normally an organoalkali metal compound, such as an alkyl lithium compound, is used to initiate the polymerization which can be conducted over a broad temperature range.

Methods of controlling the molecular weights of the blocks and the overall polymer are described in U.S. Pat. Nos. 3,149,182 and 3,231,635 which state that the amount of monomer can be kept constant and different molecular weights can be achieved by changing the amount of catalyst or that the amount of catalyst can be kept constant and different molecular weights can be achieved by varying the amount of the monomer. Following the sequential polymerization, the product is terminated such as by the addition of a protic terminating agent, e.g. water, alcohol or other reagents or with hydrogen, for the purpose of removing the lithium radical forming the nucleus for the condensed polymer product. The block polymer product is then recovered such as by coagulation utilizing hot water or steam or both. The teachings of U.S. Pat. Nos. 5,242,984, 3,149,182, and 3,231,635 are incorporated herein by reference for the purpose of teaching methods for synthesizing S-I block copolymers and S-I-S triblock polymers.

All types of polymers made with the isoprene of this invention are verifiable as being made with isoprene that did not originate from a petrochemical source. Additionally, the isoprene containing polymers of this invention can also be distinguished from isoprene containing polymers that come from natural sources, such as natural rubber. Accordingly, the isoprene containing polymers of this invention are analytically verifiable as coming from the bio-renewable, environmentally friendly, sources delineated herein.

The ratio of carbon isotopes $^{13}C$ and $^{12}C$ can be used to identify or rule out potential origins for many carbon-containing samples. This method works well because: (1) both isotopes are stable on geological time frames; (2) the ratio of $^{13}C$ to $^{12}C$ can be measured with great precision using combinations of combustion analysis, gas chromatography, and isotope ratio mass spectrometry; (3) $^{13}C/^{12}C$ ratios for many naturally occurring materials occur within narrow ranges characteristic of those materials; and (4) $^{13}C/^{12}C$ ratios for many materials change in predictable ways as these materials undergo chemical reactions.

Studies involving $^{13}C/^{12}C$ ratios at or near natural abundance levels usually report isotopic data as "delta values", which are represented by the symbol $\delta^{13}C$ and given in parts per thousand (‰) relative to a standard reference sample. For carbon, the reference sample typically is Pee Dee Belemite, which has a $^{13}C$ natural abundance of 1.112328% and is assigned $\delta^{13}C$ 0.00‰. The formula relating $^{13}C/^{12}C$ ratios to delta values is:

$\delta^{13}C$ (in ‰) versus standard=$[(R_{sample}-R_{standard})$
$R_{standard}](1000)$, where $R_{sample}$ is the $^{13}C/^{12}C$
ration for the sample and $R_{standard}$ is the ratio for
Pee Dee Belemite.

Although isotopes of carbon (i.e., $^{13}C$ and $^{12}C$) take part in the same physical processes and same chemical reactions, the slight mass difference between $^{13}C$ and $^{12}C$ can be manifested in very slight differences in rates for many reactions and processes. This leads to small differences between $^{13}C/^{12}C$ ratios for samples subjected to chemical reactions or physical processes. For example, physical processes such as evaporation or diffusion discriminate against heavier isotopes and typically lead to slight enrichment of the heavier isotope in the original sample as the lighter isotope evaporates or diffuses away more rapidly. The $^{13}C/^{12}C$ ratio therefore increases slightly as evaporation or diffusion occurs. For chemical reactions, including enzymatic reactions, the situation is more complex, but there often is a slight discrimination of one isotope over another, which can be detected by measuring $^{13}C/^{12}C$ ratios or $\delta^{13}C$ values. For example, atmospheric $CO_2$ can be converted into plant matter via two very different mechanisms for photosynthesis: the Calvin-Benson pathway, which occurs in $C_3$ plants, and the Hatch-Slack pathway, which occurs in $C_4$ plants. These two mechanisms are sufficiently different to produce a measureable difference in $\delta^{13}C$ from the same $CO_2$. For $C_4$ plants, $\delta^{13}C$ typically ranges from −9‰ to −17‰ with a mean near −13‰. For $C_3$ plants, $\delta^{13}C$ typically ranges from −20‰ to −32‰ with a mean near −27‰. Because these ranges are so different and $\delta^{13}C$ values can be routinely measured within 0.02‰, it is relatively easy to distinguish between plant residues derived from $C_3$ versus $C_4$ plants. This has myriad applications in archeology and other fields where analysis of carbon-containing residues from cooking or skeletal remains can be used to track the evolution, activities and diets of humans and other animals.

More recently, $\delta^{13}C$ values have been utilized to detect economic fraud, especially the adulteration of foodstuffs by other materials—including potentially harmful synthetics derived from petrochemicals. For example, maize (corn) oil is considered to be a premium vegetable oil and there is a temptation for unscrupulous producers to dilute maize oil with cheaper oils. Fortunately, maize oil is derived from a $C_4$ plant while most of the cheaper alternatives are derived from $C_3$ plants or animals. The $\delta^{13}C$ for authentic maize oil is therefore −13.7‰ to −16.4‰ compared to −25‰ to −32‰ for the alternatives. Any significant dilution of maize oil by a cheaper alternative can be detected by measuring $\delta^{13}C$. Similarly, the addition of cane sugar (a product of $C_4$ photosynthesis) to fruit juices, wines, spirits, and honey (all products of $C_3$ photosynthesis) can be detected by measuring $\delta^{13}C$ values. It is even possible to detect the adulteration of natural flavors by synthetic analogs and the use of illegal synthetic hormone supplements via $\delta^{13}C$ values.

The current invention utilizes the ability to accurately measure $\delta^{13}C$ values in order to produce new, isotopically unique isoprenic polymers that can be readily distinguished from polymers derived from petroleum-based feedstocks. The current invention also utilizes the ability to accurately measure $\delta^{13}C$ values in order to produce new, isotopically unique isoprenic polymers that can be readily distinguished from natural rubber. A salient feature of the current invention is that it provides new polymers with a broad range of $\delta^{13}C$ values that can be tailored and subsequently verified for authenticity. As described earlier, these new polymers satisfy an increasing need from customers for verifiable products that contain neither potential proteinaceous allergens nor feedstocks derived from petroleum.

The polymers represented by the current invention contain isoprene units that are isotopically unique compared to both natural rubber and synthetic polymers containing petroleum-derived isoprene. In the case of natural rubber derived from Hevea brasiliensis (i.e., the common natural rubber tree), $\delta^{13}C$ values typically range from about −27‰ to about −28‰. Guayule rubber, which is derived from a desert shrub, has $\delta^{13}C$ of about −31‰. Both rubbers exhibit $\delta^{13}C$ values expected for products of $C_3$ photosynthesis, and both rubbers are known to contain polymer-bound proteins.

Traditional synthetic polyisoprene can have different $\delta^{13}C$ values depending on the source of isoprene. For isoprene derived from extractive distillation of $C_5$ streams from petroleum refineries, $\delta^{13}C$ is about −22‰ to about −24‰. This range is typical for light, unsaturated hydrocarbons derived from petroleum, and polymers containing petroleum-based isoprene typically contain isoprenic units with the same $\delta^{13}C$. For polymers containing isoprene derived from the reaction of isobutylene with formaldehyde, $\delta^{13}C$ values can be about −34.4‰ because formaldehyde is often derived from feedstocks with much more negative $\delta^{13}C$ values.

The current invention provides isoprene-containing polymers with very different $\delta^{13}C$ values. For example, fermentation of corn-derived glucose ($\delta^{13}C$ −10.73‰ with minimal amounts of other carbon-containing nutrients (e.g., yeast extract) produces isoprene which can be polymerized into polyisoprene with $\delta^{13}C$ −14.66‰ to −14.85‰. The $\delta^{13}C$ for this polymer clearly is in a new range that is well outside the normal ranges for natural rubber and all previously known synthetic polyisoprene, and it is within the range normally associated with products derived from $C_4$ plants. The unique $\delta^{13}C$ value for this polymer is a direct consequence of the fact that the isoprene in the polymer is derived from corn-based glucose, which indeed is a product derived from $C_4$ plants.

It is recognized by those with ordinary skill in the art that similar results can be obtained using other sugars or fermentable derived from $C_4$ plants. For example, sucrose from sugar cane ($\delta^{13}C$ −10.4‰, invert sugar from sugar cane ($\delta^{13}C$ −15.3‰, glucose from cornstarch ($\delta^{13}C$ −11.1‰, and glucose from hydrolytic degradation of either corn stover ($\delta^{13}C$ −11.3‰ or sugar cane bagasse ($\delta^{13}C$ −13.0‰ should all produce isoprene that can be used to produce isoprene polymers with $\delta^{13}C$ values that are less negative than either natural rubber or synthetic polymers containing petroleum-based isoprene. Those with ordinary skill in the art also will recognize that it should be possible to produce isoprene and isoprene polymers with $\delta^{13}C$ less negative than about −22‰ from fermentable feedstocks with $\delta^{13}C$ approximately greater (i.e., less negative) than about −18‰, including mixtures of fermentable feedstocks with an average $\delta^{13}C$ approximately greater than about −18‰.

In addition to producing isoprene-containing polymers with $\delta^{13}C$ values characteristic of products derived from $C_4$ plants, those skilled in the art will recognize that uniquely isotopically labeled isoprene-containing polymers can be made from fermentable non-$C_4$ feedstocks. For example, glucose from hydrolyzed softwood pulp ($\delta^{13}C$ −23‰) should yield isoprene and polyisoprene with $\delta^{13}C$ near −27‰, which is in a unique range between the normal ranges observed for isoprene derived from extractive distillation of $C_5$ fractions and isoprene derived from the reaction of isobutylene with formaldehyde. Those skilled in the art also will recognize that fermentation of other sugars with $\delta^{13}C$ ranges of approximately −20‰ to about −28‰ should produce isoprene and isoprenic polymers with $\delta^{13}C$ ranging from about −24‰ to about −32‰. These other sugars might include (but are not limited to) glucose from hydrolyzed cellulose ($\delta^{13}C$ −25±2‰), invert sugar from beet sugar ($\delta^{13}C$ −26‰ to −27‰), and lactose ($\delta^{13}C$ −27‰ to −28‰. Fermentation of plant oils ($\delta^{13}C$ −26‰ to −32‰), including palm oil ($\delta^{13}C$ −30‰) could provide access to isoprene polymers with $\delta^{13}C$ more negative than −30‰.

Those skilled in the art will recognize that cofermentation of two or more feedstocks can be used to produce isoprene and therefore isoprene-containing polymers with intermediate $\delta^{13}C$ values. For example, a 1:1 mixture of sucrose from sugar cane ($\delta^{13}C$ −10.4‰) and sucrose from beet sugar ($\delta^{13}C$ −26‰ to −27‰) should produce isoprene and therefore isoprene-containing polymers with approximately the same $\delta^{13}C$ value as polymer produced from sucrose derived from a single source with the average $\delta^{13}C$ value (i.e., approx −18.5‰). The same should be true for invert sugars derived from sugar and beets. In both cases, it should be obvious that the same polymers could be synthesized by mixing and then (co)polymerizing equal amounts of isoprene separately prepared from sucrose or invert sugar derived from sugar cane and beets. It also should be obvious that cofermentation of sugars with other fermentable feedstocks—such as yeast extract and plant oils—can be used to produce isoprene and therefore isoprene-containing polymers with intermediate $\delta^{13}C$ values. For example, cofermentation of glucose ($\delta^{13}C$ −10.73‰) and yeast extract ($\delta^{13}C$ −26‰ to −27‰) in a ratio of 181.2:17.6 produces isoprene which can be polymerized to polyisoprene with $\delta^{13}C$ values of −18‰ to −20‰. In contrast, fermentation of glucose with a minimal amount of yeast extract and subsequent polymerization of the isoprene produces polyisoprene with $\delta^{13}C$ values of −14‰ to −15‰.

For copolymers of isoprene with other monomers, those skilled in the art recognize that there is a finite amount of isoprene that is incorporated into the polymer background as "blocks" of polyisoprene. The tendency of isoprene to form blocks of two or more isoprenic units—even in "random copolymers"—depends on many factors, including the amount of isoprene relative to other monomers, the type of catalyst used for polymerization, and the specific reaction conditions for polymerization. The presence of these blocks along the polymer backbone can usually be detected by NMR spectroscopy. By using a combination of chemical degradation (e.g., ozonolysis) and chromatography, it is possible to isolate fragments of these blocks for chemical analysis, including measurement of $\delta^{13}C$ values for the blocks derived from isoprene. This provides a way for determining whether copolymers of isoprene with other monomers contain isoprene derived from renewable/sustainable feedstocks, especially feedstocks derived from $C_4$ plants.

The polyisoprene polymers of this invention which are made with isoprene monomer from the cells cultures that utilize bio-renewable carbon sources can be identified as such by virtue of their $\delta^{13}C$ value and other polymer characteristics. For instance, the following isoprene containing polymers are verifiable as containing isoprene monomer that was produced utilizing the method of this invention:

(1) Polyisoprene polymer which is comprised of repeat units that are derived from isoprene monomer, wherein the polyisoprene polymer has $\delta^{13}C$ value of greater than −22‰. Such polyisoprene polymers can have a $\delta^{13}C$ value which is greater than −21‰, and can also have a $\delta^{13}C$ value which is greater than −20‰. In some cases, the polyisoprene polymer will has a $\delta^{13}C$ value which is within the range of −22% to −10‰, and in other cases it will have a $\delta^{13}C$ value which is within the range of −21% to −12‰. In still other cases the polyisoprene polymer will have a $\delta^{13}C$ value which is within the range of −20‰ to −14‰. In many cases, the polyisoprene polymer will be polyisoprene homopolymer rubber.

(2) A polyisoprene polymer which is comprised of repeat units that are derived from isoprene monomer, wherein the polyisoprene polymer has $\delta^{13}C$ value which is within the range of −30‰ to −28.5‰. Such polyisoprene polymers can have a $\delta^{13}C$ value which is within the range of −30‰ to −29‰. In some cases, the polyisoprene polymer will have a $\delta^{13}C$ value which is within the range of −30‰ to −29‰, and in other cases the polyisoprene polymer will have a $\delta^{13}C$ value which is within the range of −30‰ to −29.5‰. In still other cases the polyisoprene polymer can have a $\delta^{13}C$ value which is within the range of −29.5‰ to −28.5‰ and in still further cases the polyisoprene polymer can have a $\delta^{13}C$ value which is within the range of −29.0‰ to −28.5‰. In many cases, the polyisoprene polymer will be polyisoprene homopolymer rubber.

(3) A polyisoprene polymer which is comprised of repeat units that are derived from isoprene monomer, wherein the polyisoprene is free of protein, and wherein the polyisoprene polymer has $\delta^{13}C$ value which is within the range of −34‰ to −24‰. In some cases this polyisoprene polymer has $\delta^{13}C$ value which is within the range of −34‰ to −25‰. In other cases the polyisoprene polymer has a $\delta^{13}C$ value which is within the range of −33‰ to −25‰, and in still other cases the polyisoprene polymer has a $\delta^{13}C$ value which is within the range of −32‰ to −25‰. In many cases, the polyisoprene polymer will be polyisoprene homopolymer rubber.

(4) A polyisoprene polymer which is comprised of repeat units that are derived from isoprene monomer, wherein the polyisoprene polymer has a cis-1,4-microstructure content of less than 99.9%, wherein the polyisoprene polymer has a trans-1,4-microstructure content of less than 99.9%, and wherein the polyisoprene polymer has $\delta^{13}C$ value of which is within the range of −34‰ to −24‰. Such polyisoprene can have a $\delta^{13}C$ value which is within the range of −34‰ to −25‰. In some cases the polyisoprene polymer will have a $\delta^{13}C$ value which is within the range of −33‰ to −25‰. In other cases the polyisoprene polymer will have a $\delta^{13}C$ value which is within the range of −32‰ to −25‰. The polyisoprene polymer can have a cis-1,4-microstructure content of less than 99.8%. In other cases the polyisoprene polymer will have a cis-1,4-microstructure content of less than 99.7%. In still other cases the polyisoprene polymer will have a cis-1,4-microstructure content of less than 99.5% or even less than 99%. In many cases the polyisoprene polymer will have a cis-1,4-microstructure content of less than 98.5% or even less than 98%. This polyisoprene polymer can also have a polydispersity of less than 2.0 or even less than 1.8. In some cases the polyisoprene polymer has a polydispersity of less than 1.6 or even less than 1.5. In still other cases the polyisoprene polymer can have a polydispersity of less than 1.4 or even less than 1.2. In many cases the polyisoprene polymer will have a polydispersity of less than 1.1.

(5) A polyisoprene polymer which is comprised of repeat units that are derived from isoprene monomer, wherein the polyisoprene polymer has a 3,4-microstructure content of greater than 2%, and wherein the polyisoprene polymer has $\delta^{13}C$ value of which is within the range of −34‰ to −24‰. Such polyisoprene polymers can have a $\delta^{13}C$ value which is within the range of −34‰ to −25‰. In some cases the polyisoprene polymer will have a $\delta^{13}C$ value which is within the range of −33‰ to −25‰. In other cases polyisoprene polymer will have a $\delta^{13}C$ value which is within the range of −32‰ to −25‰. The polyisoprene polymer can have a 3,4-microstructure content of greater than 5%. In some cases the polyisoprene polymer will have a 3,4-microstructure content of greater than 10%. In other cases the polyisoprene polymer will have a 3,4-microstructure content of greater than 15%. In still other the polyisoprene polymer will have a 3,4-microstructure content of greater than 20%. In many cases the polyisoprene polymer will have a 3,4-microstructure content of greater than 25%. This polyisoprene polymer can have a polydispersity of less than 2.0. In some cases the polyisoprene polymer will have a polydispersity of less than 1.8. In other cases the polyisoprene polymer will have a polydispersity of less than 1.6. In still other cases the polyisoprene polymer will have a polydispersity of less than 1.5 or even than 1.4. In many cases the polyisoprene polymer will have a polydispersity of less than 1.2 or even less than 1.1.

(6) A polyisoprene polymer which is comprised of repeat units that are derived from isoprene monomer, wherein the polyisoprene polymer has a 1,2-microstructure content of greater than 2%, and wherein the polyisoprene polymer has $\delta^{13}C$ value of which is within the range of −34‰ to −24‰. Polyisoprene polymers of this type can have a $\delta^{13}C$ value which is within the range of −34‰ to −25‰. In some cases, the polyisoprene polymer will have a $\delta^{13}C$ value which is within the range of −33‰ to −25‰. In other cases, the polyisoprene polymer will have a $\delta^{13}C$ value which is within the range of −32‰ to −25‰. The polyisoprene polymer can have a 1,2-microstructure content of greater then than 5%. In some cases, the polyisoprene polymer will have a 1,2-microstructure content of greaterthan 10%. In other cases, the polyisoprene polymer will have a 1,2-microstructure content of greater than 15%. In still other cases, the polyisoprene polymer will have a 1,2-microstructure content of greater than 20%. In many cases, the polyisoprene polymer will have a 1,2-microstructure content of greater than 25%. The polyisoprene polymer can have a polydispersity of less than 2.0. In some cases, the polyisoprene polymer will have a polydispersity of less than 1.8. In other cases, the polyisoprene polymer will have a polydispersity of less than 1.6. In still other cases, the polyisoprene polymer will have a polydispersity of less than 1.5. In many cases, the polyisoprene polymer will have a polydispersity of less than 1.4 or even less than 1.2. It is possible for the polyisoprene polymer to have a polydispersity of less than 1.1.

(7) A polymer which is comprised of repeat units that are derived from isoprene monomer and at least one additional monomer, wherein the polymer includes blocks of repeat units that are derived from isoprene, and wherein the blocks of repeat units that are derived from isoprene have a $\delta^{13}C$ value of greater than −22‰. Such polyisoprene polymers can have a $\delta^{13}C$ value which is greater than −21‰. In some cases, the polyisoprene polymer will have a $\delta^{13}C$ value which is greater than −20‰. In other cases, the polyisoprene polymer will have a $\delta^{13}C$ value which is within the range of −22‰ to −10‰. In still other cases, the polyisoprene polymer will have a $\delta^{13}C$ value which is within the range of −21‰ to −12‰. In many cases, the polyisoprene polymer will have a $\delta^{13}C$ value that is within the range of −20‰ to −14‰.

(8) A polymer which is comprised of repeat units that are derived from isoprene monomer and at least one additional monomer, wherein the polymer includes blocks of repeat units that are derived from isoprene, and wherein the blocks of repeat units that are derived from isoprene have a $\delta^{13}C$ value which is within the range of −34‰ to −24‰. Such copolymers can have a $\delta^{13}C$ value is within the range of −34‰ to −25‰. In some cases, copolymer of this type will have a $\delta^{13}C$ value which is within the range of −33‰ to −25‰. In other cases, copolymers of this type will have a $\delta^{13}C$ value is within the range of −32‰ to −25‰. Copolymers of this type can be rubbery copolymers of isoprene and 1,3-butadiene, rubbery copolymer of isoprene and styrene, rubbery copolymers of isoprene and α-methyl styrene, and the like.

(9) A liquid polyisoprene polymer which is comprised of repeat units that are derived from isoprene monomer, wherein the polyisoprene polymer has weight average molecular weight which is within the range of 5,000 to 100,000, and wherein the liquid polyisoprene polymer has $\delta^{13}C$ value of which is within the range of −34‰ to −24‰. Such liquid polyisoprene polymers can have a $\delta^{13}C$ value which is within the range of −34% to −25‰. In some cases, the liquid polyisoprene polymer will have a $\delta^{13}C$ value which is within the range of −33‰ to −25‰. In other cases, the liquid polyisoprene polymer will have a $\delta^{13}C$ value which is within the range of −32‰ to −25‰. Such liquid polyisoprene polymers can have a weight average molecular weight that is within the range of 20,000 to 80,000. In some cases, the liquid polyisoprene polymer will have a weight average molecular weight which is within the range of 30,000 to 50,000. In other cases, the polyisoprene polymer will have a polydispersity of less than 2.0 or even less than 1.8. In still other cases, the liquid polyisoprene polymer will have a polydispersity of less than 1.6 or even less than 1.5. In many cases, the liquid polyisoprene polymer will have a polydispersity of less than 1.4 or even less than 1.2. It is possible for the liquid polyisoprene polymer to have a polydispersity of less than 1.1.

(10) A liquid polyisoprene polymer which is comprised of repeat units that are derived from isoprene monomer, wherein the liquid polyisoprene polymer has a weight average molecular weight which is within the range of 5,000 to 100,000, and wherein the liquid polyisoprene polymer has $\delta^{13}C$ value of which is within the range of −34‰ to −24‰. Such liquid polyisoprene polymers can have a $\delta^{13}C$ value which is within the range of −34‰ to −25‰. In some cases, the liquid polyisoprene polymer will have a $\delta^{13}C$ value which is within the range of −33‰ to −25‰. In still other cases, the liquid polyisoprene polymer will have a $\delta^{13}C$ value which is within the range of −32‰ to −25‰. Such liquid polyisoprene can have a weight average molecular weight that is within the range of 20,000 to 80,000. The liquid polyisoprene will typically have a weight average molecular weight which is within the range of 30,000 to 50,000. Such liquid polyisoprene can have a polydispersity of less than 2.0. In some cases, the liquid polyisoprene polymer will have a polydispersity of less than 1.8. In other cases, the liquid polyisoprene polymer has a polydispersity of less than 1.6. In still other cases, the liquid polyisoprene polymer will have a polydispersity of less than 1.5 or even less than 1.4. In many cases, the liquid polyisoprene polymer will have a polydispersity of less than 1.2 or even less than 1.1.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric pressure. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

In the practice of this invention $^{13}C$ analysis can be done by loading 0.5 to 1.0 mg samples into tin cups for carbon isotopic analysis using a Costech ECS4010 Elemental Analyzer as an inlet for a ThermoFinnigan Delta Plus XP isotope ratio mass spectrometer. Samples are dropped into a cobaltous/cobaltic oxide combustion reactor at 1020° C. with combustion gases being passed in a helium stream at 85mL/min through a copper reactor (650° C.) to convert $NO_x$ $N_2$. $CO_2$ and $N_2$ are separated using a 3-m 5 Å molecular sieve column. Then, $^{13}C/^{12}C$ ratios are calibrated to the VPDB scale using two laboratory standards (Acetanilide B, −29.52±0.02‰m and cornstarch A, −11.01±0.02‰) which have been carefully calibrated to the VPDB scale by off-line combustion and dual-inlet analysis using the 2-standard approach of T. B. Coplen et al, New Guidelines for $\delta^{13}C$ Measurements, Anal. Chem., 78, 2439-2441 (2006). The teachings of Coplen are incorporated herein by reference for the purpose of teaching the technique for determining $\delta^{13}C$ values.

Example 1

Production of Isoprene in *E. coli* Expressing Recombinant Kudzu Isoprene Synthase I. Construction of Vectors for Expression of the Kudzu Isoprene Synthase in *E. coli*

The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (SEQ ID NO:1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3).

Figure 4:
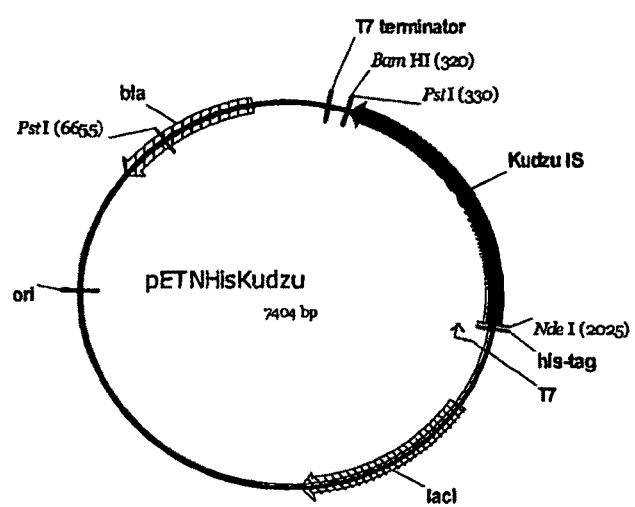
FIG. 4 is a map of pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGAT-CATATGTGTGCGACCTCTTCTCAATTTAC (SEQ ID NO:3) and pET-His-Kudzu-R: 5'-CGGTCGACGGATC-CCTGCAGTTAGACATACATCAGCTG (SEQ ID NO:4). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 μl. The PCR product was digested with NdeI/BamH1 and cloned into pET16b digested with the same enzymes. The ligation mix was transformed into *E. coli* Top10 (Invitrogen)

and the correct clone selected by sequencing. The resulting plasmid, in which the kudzu isoprene synthase gene was expressed from the T7 promoter, was designated pET-NHisKudzu (FIGS. 4 and 5).

Figure 6:
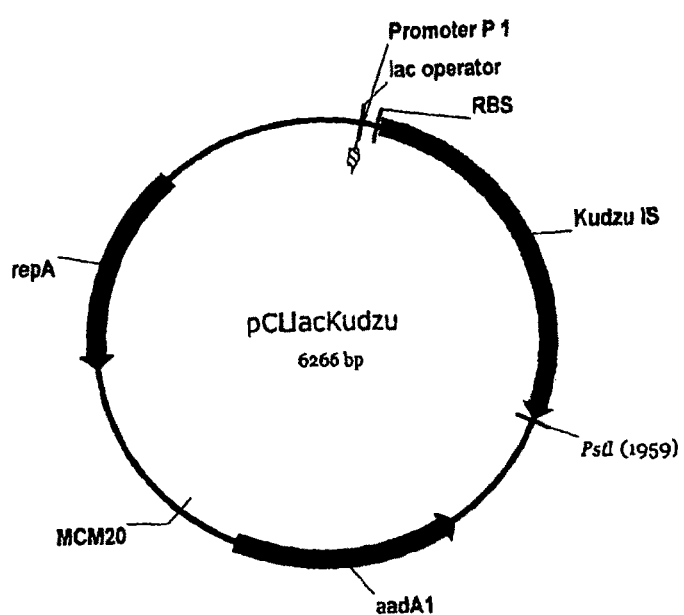
FIG. 6 is a map of pCL-lac-Kudzu.
Figure 8A:
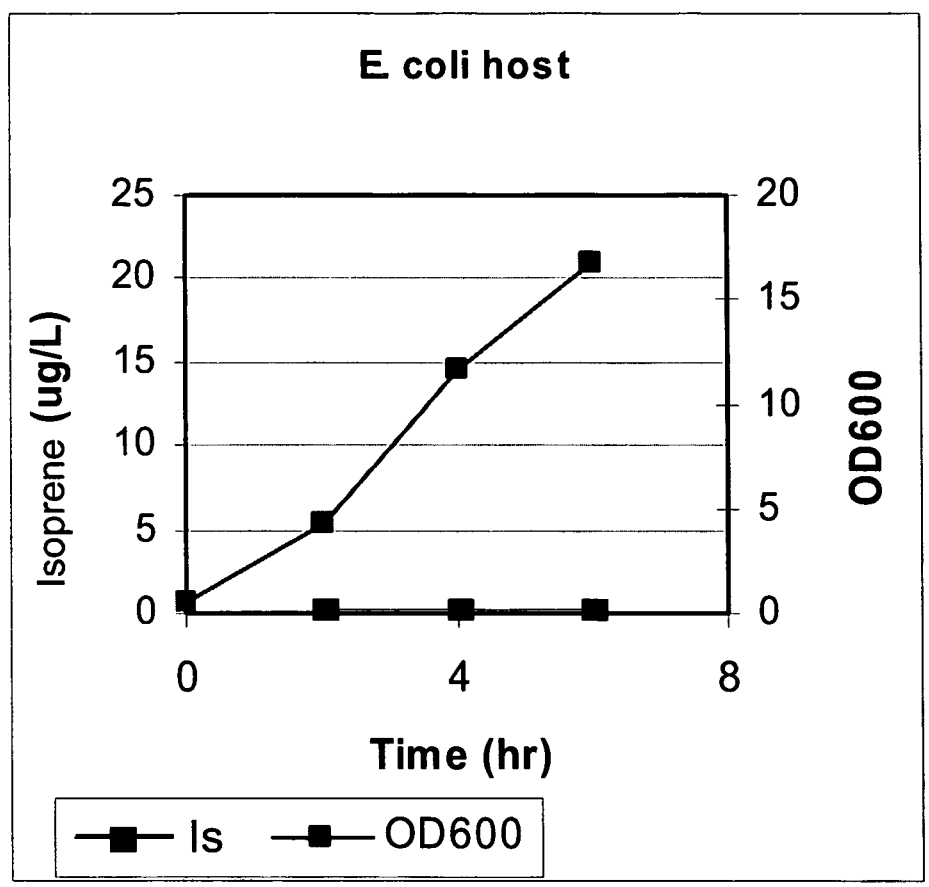
FIG. 8A is a graph showing the production of isoprene in *E. coli* BL21 cells with no vector.
Figure 8B:
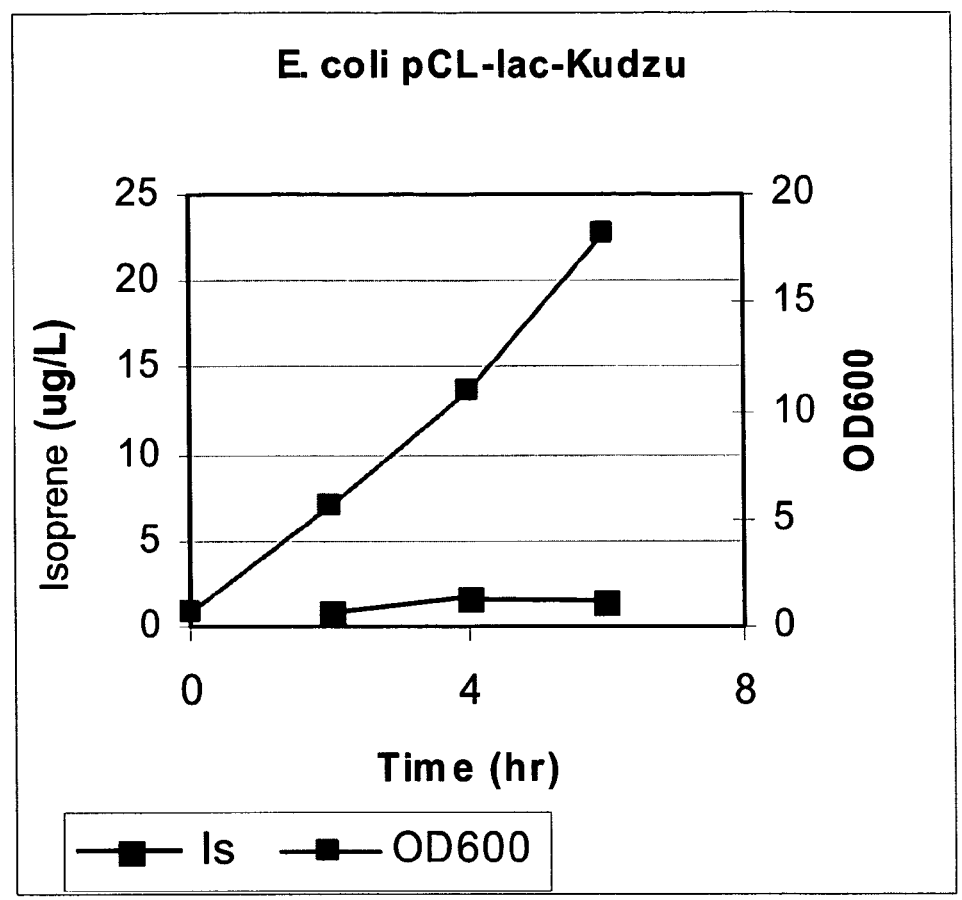
FIG. 8B is a graph showing the production of isoprene in *E. coli* BL21 cells with pCL-lac-Kudzu
Figure 8C:
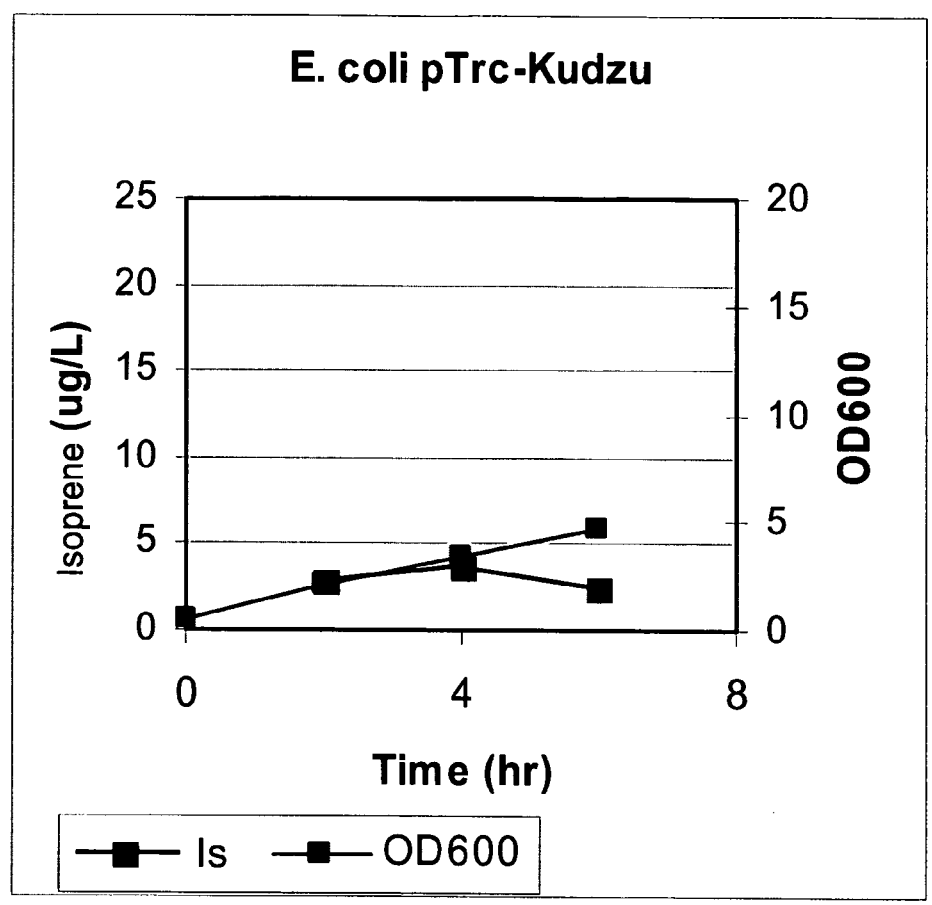
FIG. 8C is a graph showing the production of isoprene in *E. coli* BL21 cells with pTrcKudzu.
Figure 8D:
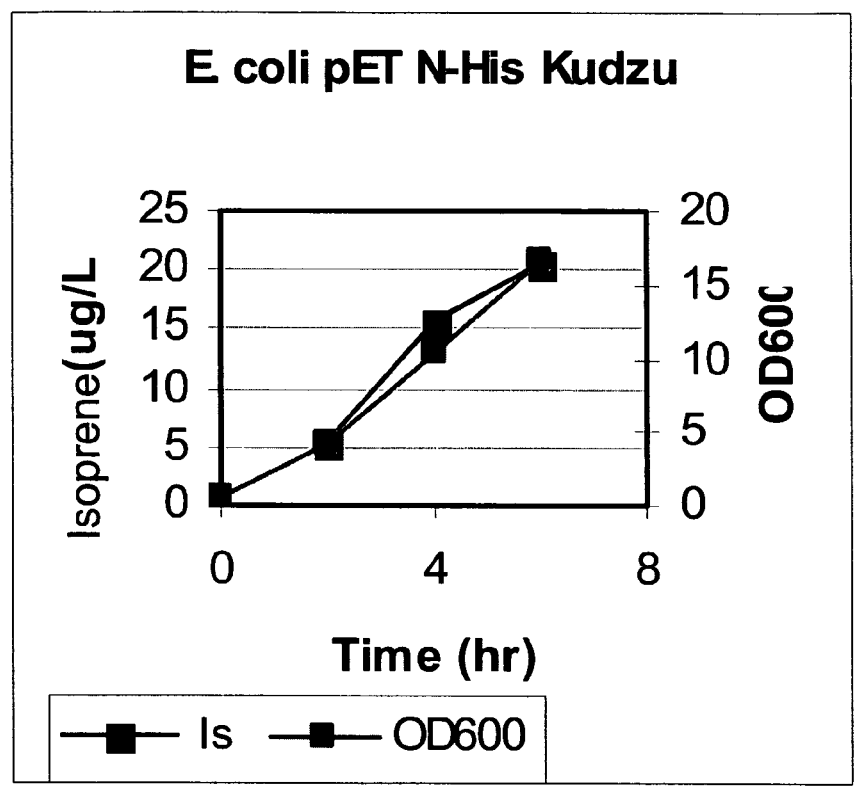
FIG. 8D is a graph showing the production of isoprene in *E. coli* BL21 cells with pETN-HisKudzu.

The kudzu isoprene synthase gene was also cloned into the low copy number plasmid pCL1920. Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAGCTTGTATC-GATTAAATAAGGAGGAATAAACC (SEQ ID NO:6) and BamH1-Kudzu R: 5'-CGGTCGACGGATCCCTGCAGT-TAGACATACATCAGCTG (SEQ ID NO:4). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into *E. coli* Top10. Several transformants were checked by sequencing. The resulting plasmid was designated pCL-lac-Kudzu (FIGS. 6 and 7).

II. Determination of Isoprene Production

For the shake flask cultures, one ml of a culture was transferred from shake flasks to 20 ml CTC headspace vials (Agilent vial cat# 5188 2753; cap cat# 5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/minutes. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 200 µg/L. The limit of detection was estimated to be 50 to 100 ng/L using this method.

III. Production of Isoprene in Shake Flasks Containing *E. coli* Cells Expressing Recombinant Isoprene Synthase The vectors described above were introduced to *E. coli* strain BL21 (Novagen) to produce strains BL21/ptrcKudzu, BL21/pCL-lac-Kudzu and BL21/pETHisKudzu. The strains were spread for isolation onto LA (Luria agar) and carbenicillin (50 µg/ml) and incubated overnight at 37° C. Single colonies were inoculated into 250 ml baffled shake flasks containing 20 ml Luria Bertani broth (LB) and carbenicillin (100 µg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen) and carbenicillin (100 µg/ml) to an $OD_{600}$~0.05. The culture was incubated at 30° C. with shaking at 200 rpm. When the $OD_{600}$~0.5-0.8, 400 µM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIG. 8.

IV. Production of Isoprene from BL21/ptrcKudzu in 14 Liter Fermentation

Large scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in $diH_2O$. The pH was adjusted to 6.8 with potassium hydroxide (KOH) and q.s. to volume. The final product was filter sterilized with 0.22µ filter (only, not autoclaved). The recipe for 1000× Modified Trace Metal Solution was as follows: Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component was dissolved one at a time in $diH_2O$, pH to 3.0 with HCl/NaOH, then q.s. to volume and filter sterilized with a 0.22µ filter.

Figure 9A:
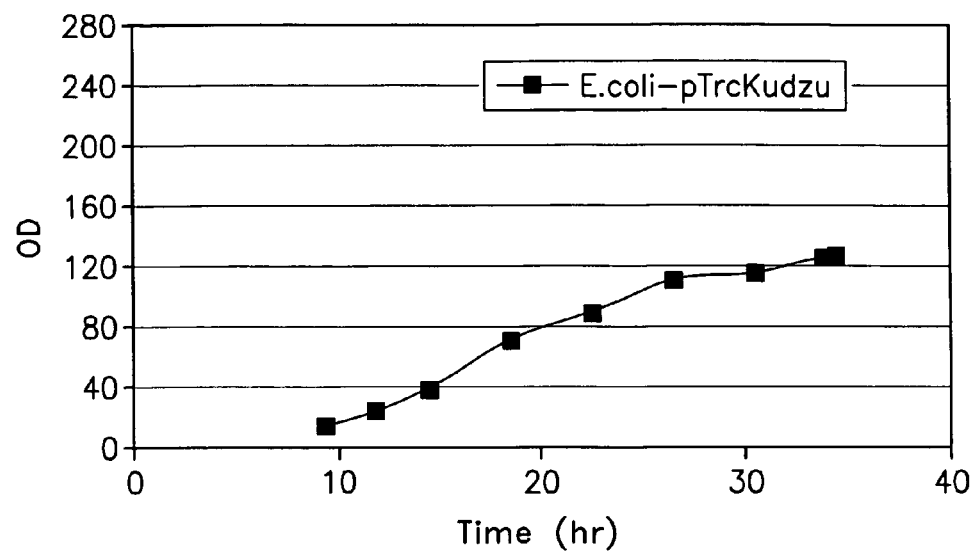
FIG. 9A is a graph showing OD over time of fermentation of *E. coli* BL21/pTrcKudzu in a 14 liter fed batch fermentation.
Figure 9B:
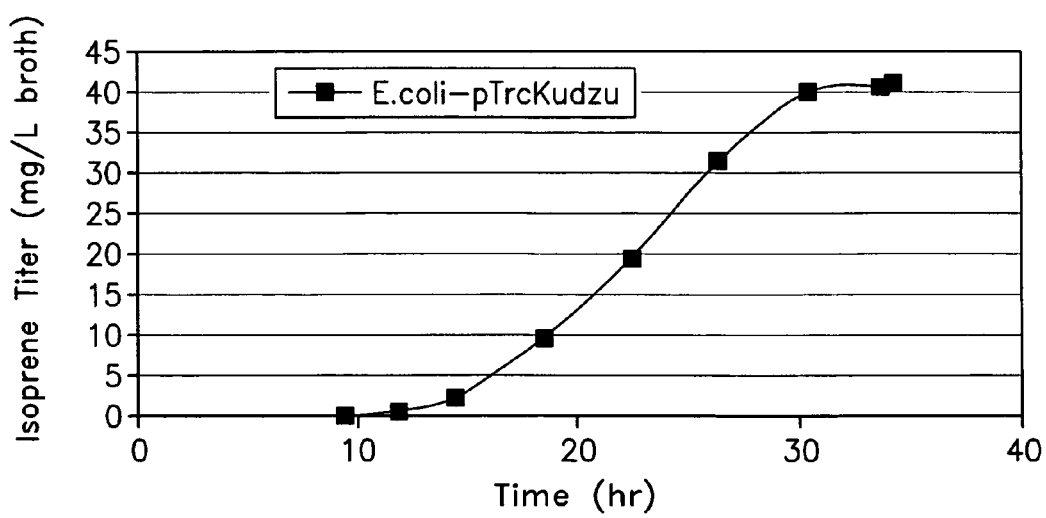
FIG. 9B is a graph showing isoprene production over time of fermentation of *E. coli* BL21/pTrcKudzu in a 14 liter fed batch fermentation.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIG. 9.

Example 2

Figure 30:
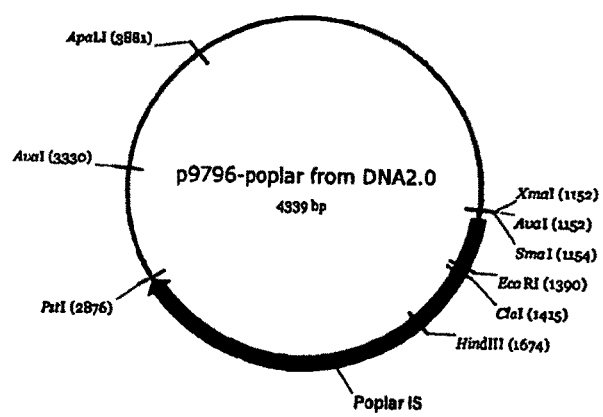
FIG. 30 is a map of p9796-poplar.
Figure 32:
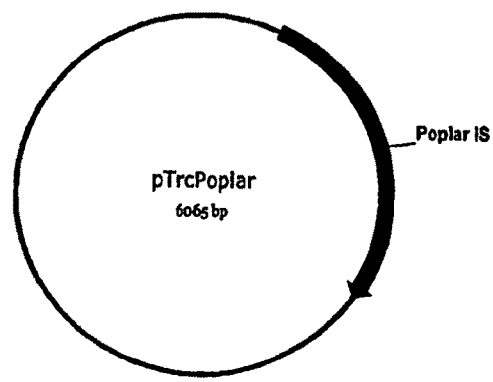
FIG. 32 is a map of pTrcPoplar.

Production of Isoprene in *E. coli* Expressing Recombinant Poplar Isoprene Synthase The protein sequence for the poplar (*Populus alba×Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIGS. 30 and 31). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 32 and 33), was verified by sequencing.

Example 3

Production of Isoprene in *Panteoa citrea* Expressing Recombinant Kudzu Isoprene Synthase The pTrcKudzu and pCL-lac Kudzu plasmids described in Example 1 were electroporated into *P. citrea* (U.S. Pat. No.

Figure 10A:
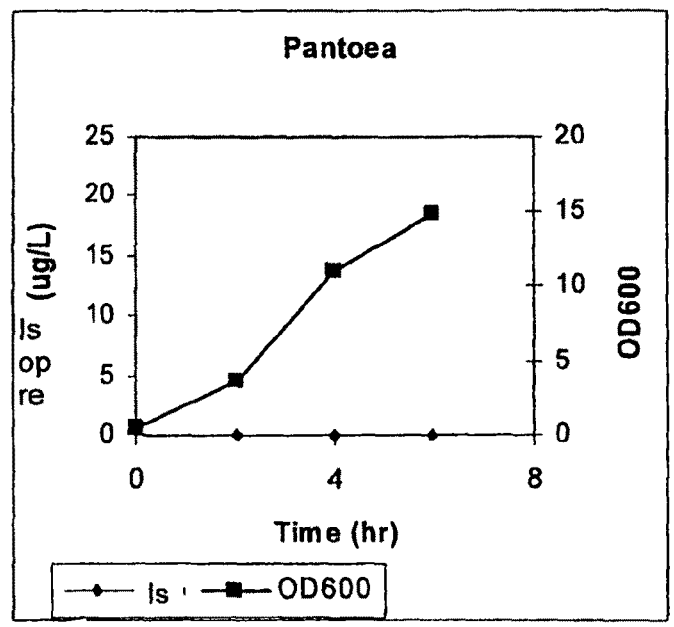
FIG. 10A is a graph showing the production of isoprene in *Panteoa citrea*. Control cells without recombinant kudzu isoprene synthase. Grey diamonds represent isoprene synthesis, black squares represent OD600.
Figure 10B:
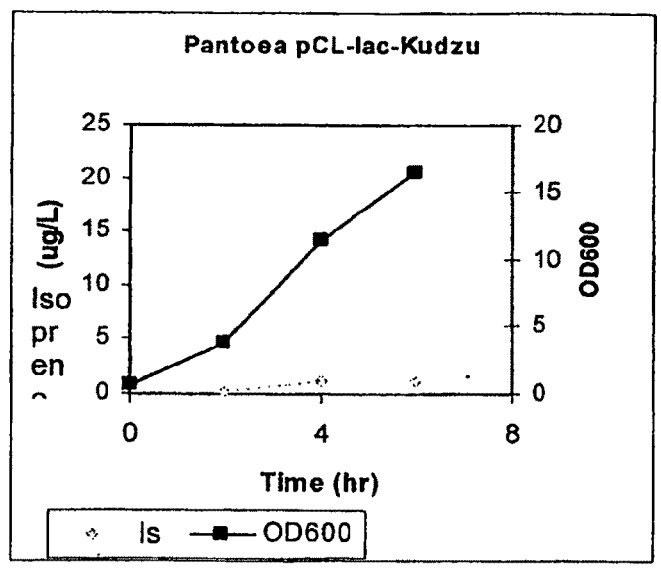
FIG. 10B is a graph showing the production of isoprene in *Panteoa citrea* expressing pCL-lac Kudzu. Grey diamonds represent isoprene synthesis, black squares represent OD600.
Figure 10C:
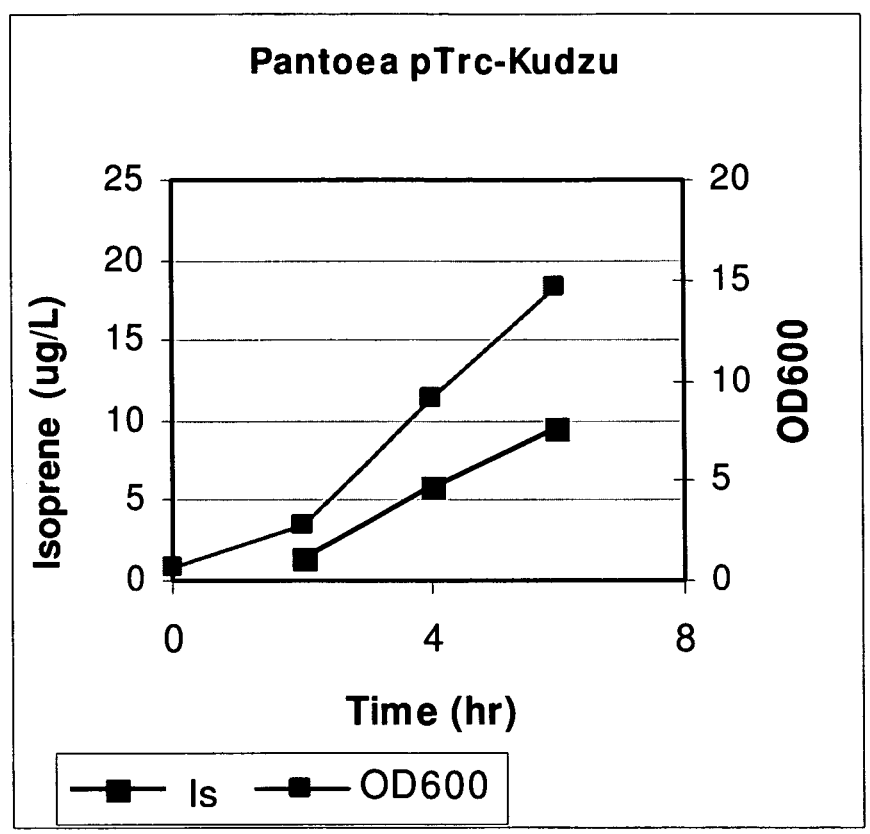
FIG. 10C is a graph showing the production of isoprene in *Panteoa citrea* expressing pTrcKudzu. Grey diamonds represent isoprene synthesis, black squares represent OD600.

7,241,587). Transformants were selected on LA containing carbenicillin (200 μg/ml) or spectinomycin (50 μg/ml) respectively. Production of isoprene from shake flasks and determination of the amount of isoprene produced was performed as described in Example 1 for *E. coli* strains expressing recombinant kudzu isoprene synthase. Results are shown in FIG. 10.

Example 4

Production of Isoprene in *Bacillus subtilis* Expressing Recombinant Kudzu Isoprene Synthase I. Construction of a *B. subtilis* Replicating Plasmid for the Expression of Kudzu Isoprene Synthase The kudzu isoprene synthase gene was expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator were amplified separately and fused using PCR. The construct was then cloned into pBS19 and transformed into *B. subtilis*.
a) Amplification of the aprE Promoter The aprE promoter was amplified from chromosomal DNA from *Bacillus subtilis* using the following primers:

```
CF 797 (+) Start aprE promoter MfeI
                                 (SEQ ID NO: 58)
5'- GACATCAATTGCTCCATTTTCTTCTGCTATC CF 07-43 (-) Fuse aprE promoter to Kudzu ispS
                                 (SEQ ID NO: 59)
5'- ATTGAGAAGAGGTCGCACACACTCTTTACCCTCTCCTTTTA
``` b) Amplification of the Isoprene Synthase Gene

The kudzu isoprene synthase gene was amplified from plasmid pTrcKudzu (SEQ ID NO:2). The gene had been codon optimized for *E. coli* and synthesized by DNA 2.0. The following primers were used:

```
CF 07-42 (+) Fuse the aprE promoter to kudzu
isoprene synthase gene (GTG start codon)
                                 (SEQ ID NO: 60)
5'-TAAAAGGAGAGGGTAAAGAGTGTGTGCGACCTCTTCTCAAT CF 07-45 (-) Fuse the 3' end of kudzu isoprene
synthase gene to the terminator
                                 (SEQ ID NO: 61)
5'-CCAAGGCCGGTTTTTTTTAGACATACATCAGCTGGTTAATC
``` c) Amplification of the Transcription Terminator

The terminator from the alkaline serine protease of *Bacillus amyliquefaciens* was amplified from a previously sequenced plasmid pJHPms382 using the following primers:

```
CF 07-44 (+) Fuse the 3' end of kudzu isoprene
synthase to the terminator
                                 (SEQ ID NO: 62)
5'-GATTAACCAGCTGATGTATGTCTAAAAAAAACCGGCCTTGG CF 07-46 (-) End of B. amyliquefaciens terminator
(BamHI)
                                 (SEQ ID NO: 63)
5'-GACATGACGGATCCGATTACGAATGCCGTCTC
```

The kudzu fragment was fused to the terminator fragment using PCR with the following primers:

```
CF 07-42 (+) Fuse the aprE promoter to kudzu
isoprene synthase gene (GTG start codon)
                                 (SEQ ID NO: 60)
5'-TAAAAGGAGAGGGTAAAGAGTGTGTGCGACCTCTTCTCAAT CF 07-46 (-) End of B. amyliquefaciens terminator
(BamHI)
                                 (SEQ ID NO: 63)
5'-GACATGACGGATCCGATTACGAATGCCGTCTC
```

The kudzu-terminator fragment was fused to the promoter fragment using PCR with the following primers:

```
CF 797 (+) Start aprE promoter MfeI
                                 (SEQ ID NO: 64)
5'-GACATCAATTGCTCCATTTTCTTCTGCTATC CF 07-46 (-) End of B. amyliquefaciens terminator
(BamHI)
                                 (SEQ ID NO: 63)
5'-GACATGACGGATCCGATTACGAATGCCGTCTC
```

The fusion PCR fragment was purified using a Qiagen kit and digested with the restriction enzymes MfeI and BamHI. This digested DNA fragment was gel purified using a Qiagen kit and ligated to a vector known as pBS19, which had been digested with EcoRI and BamHI and gel purified.

The ligation mix was transformed into *E. coli* Top 10 cells and colonies were selected on LA and 50 carbenicillin plates. A total of six colonies were chosen and grown overnight in LB and 50 carbenicillin and then plasmids were isolated using a Qiagen kit. The plasmids were digested with EcoRI and BamHI to check for inserts and three of the correct plasmids were sent in for sequencing with the following primers:

```
CF 149 (+) EcoRI start of aprE promoter
                                 (SEQ ID NO: 65)
5'-GACATGAATTCCTCCATTTTCTTCTGC CF 847 (+) Sequence in pXX 049 (end of aprE
promoter)
                                 (SEQ ID NO: 66)
5'-AGGAGAGGGTAAAGAGTGAG CF 07-45 (-) Fuse the 3' end of kudzu isoprene
synthase to the terminator
                                 (SEQ ID NO: 61)
5'-CCAAGGCCGGTTTTTTTTAGACATACATCAGCTGGTTAATC CF 07-48 (+) Sequencing primer for kudzu
isoprene synthase
                                 (SEQ ID NO: 67)
5'-CTTTTCCATCACCCACCTGAAG CF 07-49 (+) Sequencing in kudzu isoprene
synthase
                                 (SEQ ID NO: 68)
5'-GGCGAAATGGTCCAACAACAAAATTATC
```

Figure 52:
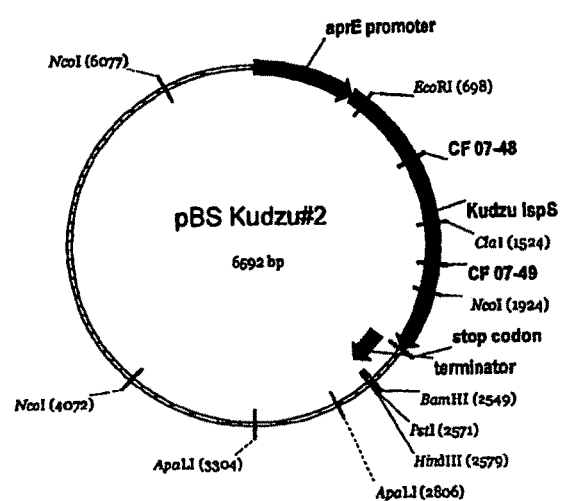
FIG. 52 is a map of pBS Kudzu #2.

The plasmid designated pBS Kudzu #2 (FIGS. 52 and 12) was correct by sequencing and was transformed into BG 3594 comK, a *Bacillus subtilis* host strain. Selection was done on LA and 5 chloramphenicol plates. A transformant was chosen and struck to single colonies on LA and 5 chloramphenicol, then grown in LB and 5 chloramphenicol until it reached an $OD_{600}$ of 1.5. It was stored frozen in a vial at −80° C. in the presence of glycerol. The resulting strain was designated CF 443.
II. Production of Isoprene in Shake Flasks Containing *B. subtilis* Cells Expressing Recombinant Isoprene Synthase Overnight cultures were inoculated with a single colony of CF 443 from a LA and Chloramphenicol (Cm, 25 μg/ml).

Figure 11:
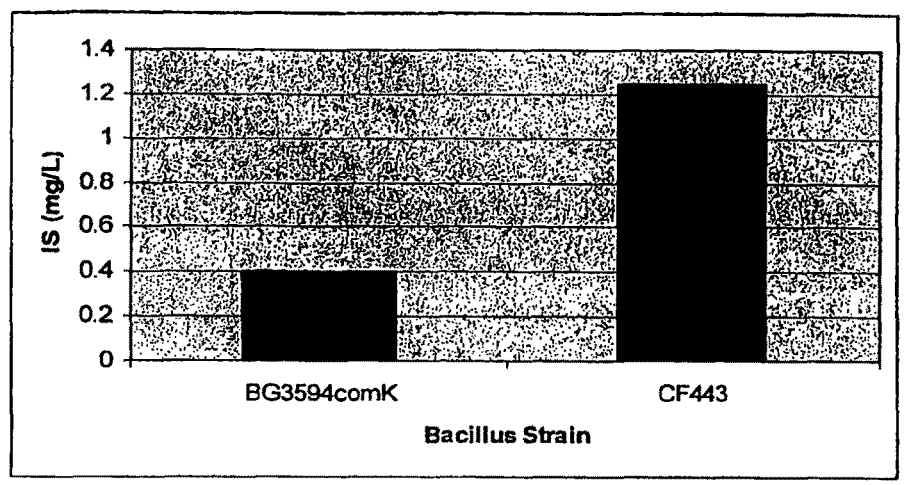
FIG. 11 is a graph showing the production of isoprene in *Bacillus subtilis* expressing recombinant isoprene synthase. BG3594comK is a *B. subtilis* strain without plasmid (native isoprene production). CF443-BG3594comK is a *B. subtilis* strain with pBSKudzu (recombinant isoprene production). IS on the y-axis indicates isoprene.

Cultures were grown in LB and Cm at 37° C. with shaking at 200 rpm. These overnight cultures (1 ml) were used to inoculate 250 ml baffled shake flasks containing 25 ml Grants II media and chloramphenicol at a final concentration of 25 µg/ml. Grants II Media recipe was 10 g soytone, 3 ml 1M $K_2HPO_4$, 75 g glucose, 3.6 g urea, 100 ml 10×MOPS, q.s. to 1 L with $H_2O$, pH 7.2; 10×MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100× micronutrients recipe was 1.47 g $CaCl_2*2H_2O$, 0.4 g $FeSO_4.7H_2O$, 0.1 g $MnSO_4*H_2O$, 0.1 g $ZnSO_4*H_2O$, 0.05 g $CuCl_2*2H_2O$, 0.1 g $CoCl_2*6H_2O$, 0.1 g $Na_2MoO_4.2H_2O$, q.s. to 1 L with $H_2O$, Shake flasks were incubated at 37° C. and samples were taken at 18, 24, and 44 hours. At 18 hours the headspaces of CF443 and the control strain were sampled. This represented 18 hours of accumulation of isoprene. The amount of isoprene was determined by gas chromatography as described in Example 1. Production of isoprene was enhanced significantly by expressing recombinant isoprene synthase (FIG. 11).

III. Production of Isoprene by CF443 in 14 L Fermentation

Figure 53A:
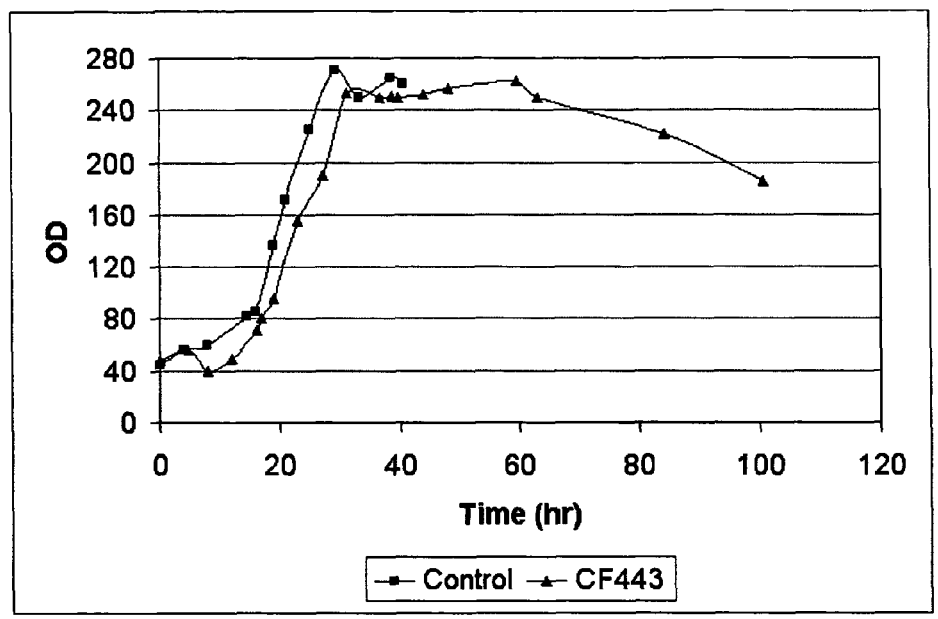
FIG. 53A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).
Figure 53B:
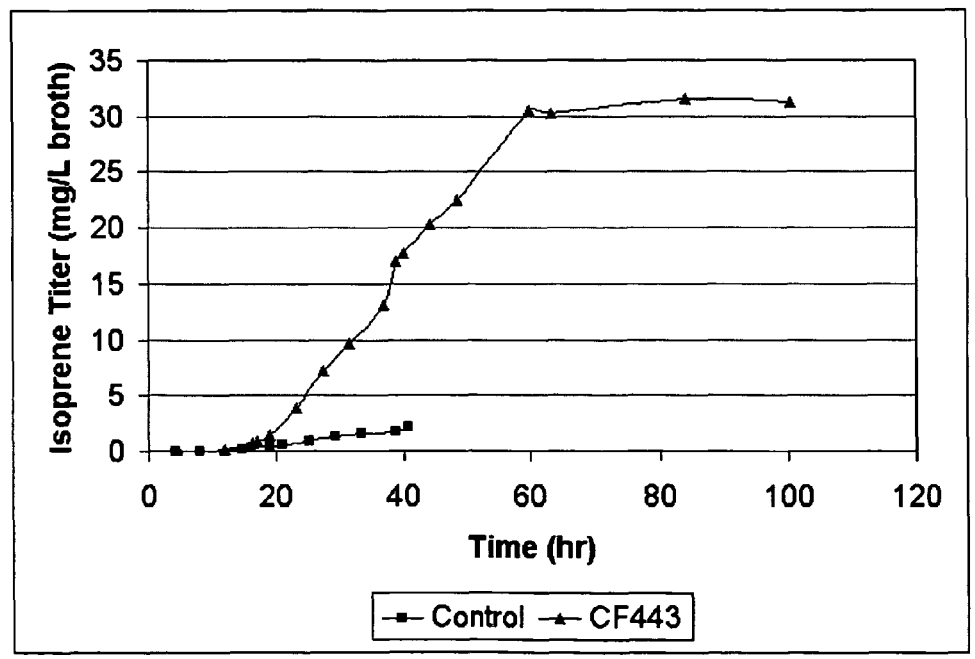
FIG. 53B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Large scale production of isoprene from *B. subtilis* containing the recombinant kudzu isoprene synthase gene on a replication plasmid was determined from a fed-batch culture. *Bacillus* strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, DO %, airflow, and pressure were monitored throughout the entire process. The DO % is maintained above 20. Samples were taken over the time course of 36 hours and analyzed for cell growth ($OD_{550}$) and isoprene production. Results of these experiments are presented in FIGS. 53A and 53B.

IV. Integration of the Kudzu Isoprene Synthase (ispS) in *B. subtilis*.

The kudzu isoprene synthase gene was cloned in an integrating plasmid (pJH101-cmpR) under the control of the aprE promoter. Under the conditions tested, no isoprene was detected.

Example 5

Production of Isoprene in *Trichoderma*

I. Construction of Vectors for Expression of the Kudzu Isoprene Synthase in *Trichoderma reesei*

The *Yarrowia lipolytica* codon-optimized kudzu IS gene was synthesized by DNA 2.0 (SEQ ID NO:8) (FIG. 13). This plasmid served as the template for the following PCR amplification reaction: 1 µl plasmid template (20 ng/ul), 1 µl Primer EL-945 (10 uM) 5'-GCTTATGGATCCTCTAGACTATTA-CACGTACATCAATTGG (SEQ ID NO:9), 1 µl Primer EL-965 (10 uM) 5'-CACCATGTGTGCAACCTCCTC-CCAGTTTAC (SEQ ID NO:10), 1 µl dNTP (10 mM), 5 µl 10× PfuUltra II Fusion HS DNA Polymerase Buffer, 1 µl PfuUltra II Fusion HS DNA Polymerase, 40 µl water in a total reaction volume of 50 µl. The forward primer contained an additional 4 nucleotides at the 5'-end that did not correspond to the *Y. lipolytica* codon-optimized kudzu isoprene synthase gene, but was required for cloning into the pENTR/D-TOPO vector. The reverse primer contained an additional 21 nucleotides at the 5'-end that did not correspond to the *Y. lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the *Y. lipolytica* codon-optimized kudzu isoprene synthase gene.

The PCR product was then cloned using the TOPO pENTR/D-TOPO Cloning Kit following manufacturer's protocol: 1 µl PCR reaction, 1 µl Salt solution, 1 µl TOPO pENTR/D-TOPO vector and 3 µl water in a total reaction volume of 6 µl. The reaction was incubated at room temperature for 5 minutes. One microliter of TOPO reaction was transformed into TOP10 chemically competent *E. coli* cells. The transformants were selected on LA and 50 µg/ml kanamycin plates. Several colonies were picked and each was inoculated into a 5 ml tube containing LB and 50 µg/ml kanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid, encoding a *Y. lipolytica* codon-optimized kudzu isoprene synthase gene, was used for Gateway Cloning into a custom-made pTrex3g vector. Construction of pTrex3g is described in WO 2005/001036 A2. The reaction was performed following manufacturer's protocol for the Gateway LR Clonase II Enzyme Mix Kit (Invitrogen): 1 µl *Y. lipolytica* codon-optimized kudzu isoprene synthase gene pENTR/D-TOPO donor vector, 1 µl pTrex3g destination vector, 6 µl TE buffer, pH 8.0 in a total reaction volume of 8 µl. The reaction was incubated at room temperature for 1 hour and then 1 µl proteinase K solution was added and the incubation continued at 37° C. for 10 minutes. Then 1 µl of reaction was transformed into TOP10 chemically competent *E. coli* cells. The transformants were selected on LA and 50 µg/ml carbenicillin plates. Several colonies were picked and each was inoculated into a 5 ml tube containing LB and 50 µg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Figure 14:
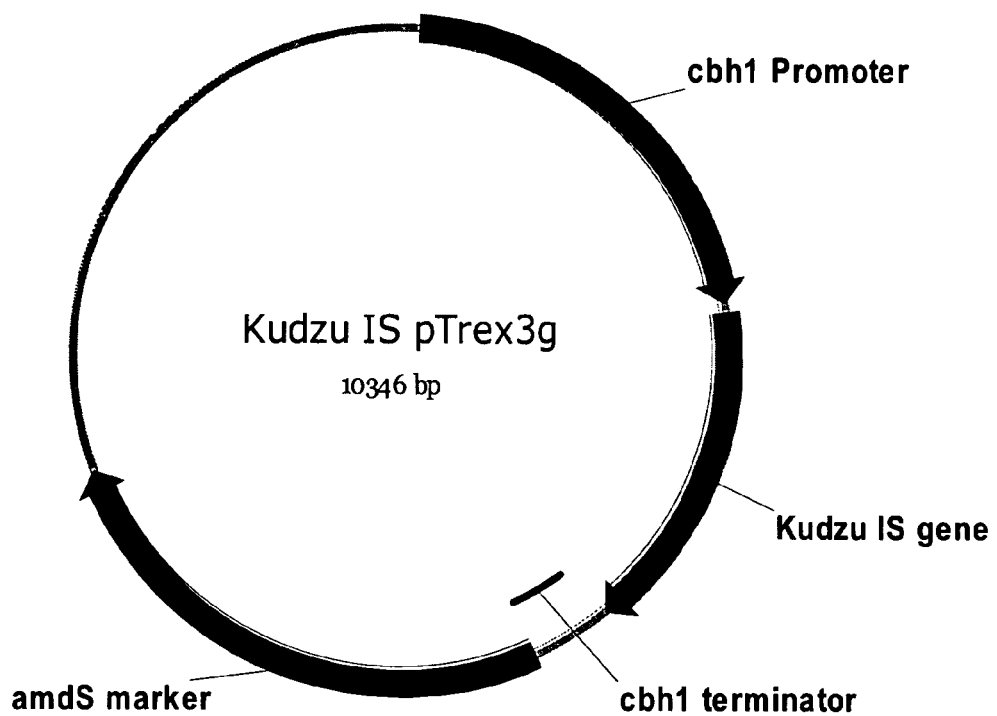
FIG. 14 is a map of pTrex3g comprising a kudzu isoprene synthase gene codon-optimized for expression in *Yarrowia*.

Biolistic transformation of Y lipolytica codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2).

Isolation of stable transformants and shake flask evaluation was performed using protocol listed in Example 11 of patent publication WO 2005/001036 A2.

II. Production of Isoprene in Recombinant Strains of *T. reesei*

One ml of 15 and 36 hour old cultures of isoprene synthase transformants described above were transferred to head space vials. The vials were sealed and incubated for 5 hours at 30° C. Head space gas was measured and isoprene was identified by the method described in Example 1. Two of the transformants showed traces of isoprene. The amount of isoprene could be increased by a 14 hour incubation. The two positive samples showed isoprene at levels of about 0.5 μg/L for the 14 hour incubation. The untransformed control showed no detectable levels of isoprene. This experiment shows that *T. reesei* is capable of producing isoprene from endogenous precursor when supplied with an exogenous isoprene synthase.

Example 6

Production of Isoprene in *Yarrowia*

I. Construction of Vectors for Expression of the Kudzu Isoprene Synthase in *Yarrowia lipolytica*.

The starting point for the construction of vectors for the expression of the kudzu isoprene synthase gene in *Yarrowia lipolytica* was the vector pSPZ1(MAP29Spb). The complete sequence of this vector (SEQ ID No:11) is shown in FIG. 15.

The following fragments were amplified by PCR using chromosomal DNA of a Y lipolytica strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

```
ICL1 3
                                  (SEQ ID NO: 69)
5'-GGTGAATTCAGTCTACTGGGGATTCCCAAATCTATATATACTGCA
GGTGAC

ICL1 5
                                  (SEQ ID NO: 70)
5'-GCAGGTGGGAAACTATGCACTCC

XPR 3
                                  (SEQ ID NO: 71)
5'-CCTGAATTCTGTTGGATTGGAGGATTGGATAGTGGG

XPR 5
                                  (SEQ ID NO: 72)
5'-GGTGTCGACGTACGGTCGAGCTTATTGACC

XPRT3
                                  (SEQ ID NO: 73)
5'-GGTGGGCCCGCATTTTGCCACCTACAAGCCAG

XPRT 5
                                  (SEQ ID NO: 74)
5'-GGTGAATTCTAGAGGATCCCAACGCTGTTGCCTACAACGG

Y18S3
                                  (SEQ ID NO: 75)
5'-GGTGCGGCCGCTGTCTGGACCTGGTGAGTTTCCCCG

Y18S 5
                                  (SEQ ID NO: 76)
5'-GGTGGGCCCATTAAATCAGTTATCGTTTATTTGATAG

YURA3
                                  (SEQ ID NO: 77)
5'-GGTGACCAGCAAGTCCATGGGTGGTTTGATCATGG

YURA 50
                                  (SEQ ID NO: 78)
5'-GGTGCGGCCGCCTTTGGAGTACGACTCCAACTATG

YURA 51
                                  (SEQ ID NO: 79)
5'-GCGGCCGCAGACTAAATTTATTTCAGTCTCC
```

For PCR amplification the PfuUltraII polymerase (Stratagene), supplier-provided buffer and dNTPs, 2.5 μM primers and the indicated template DNA were used in accordance with the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Figure 18B:
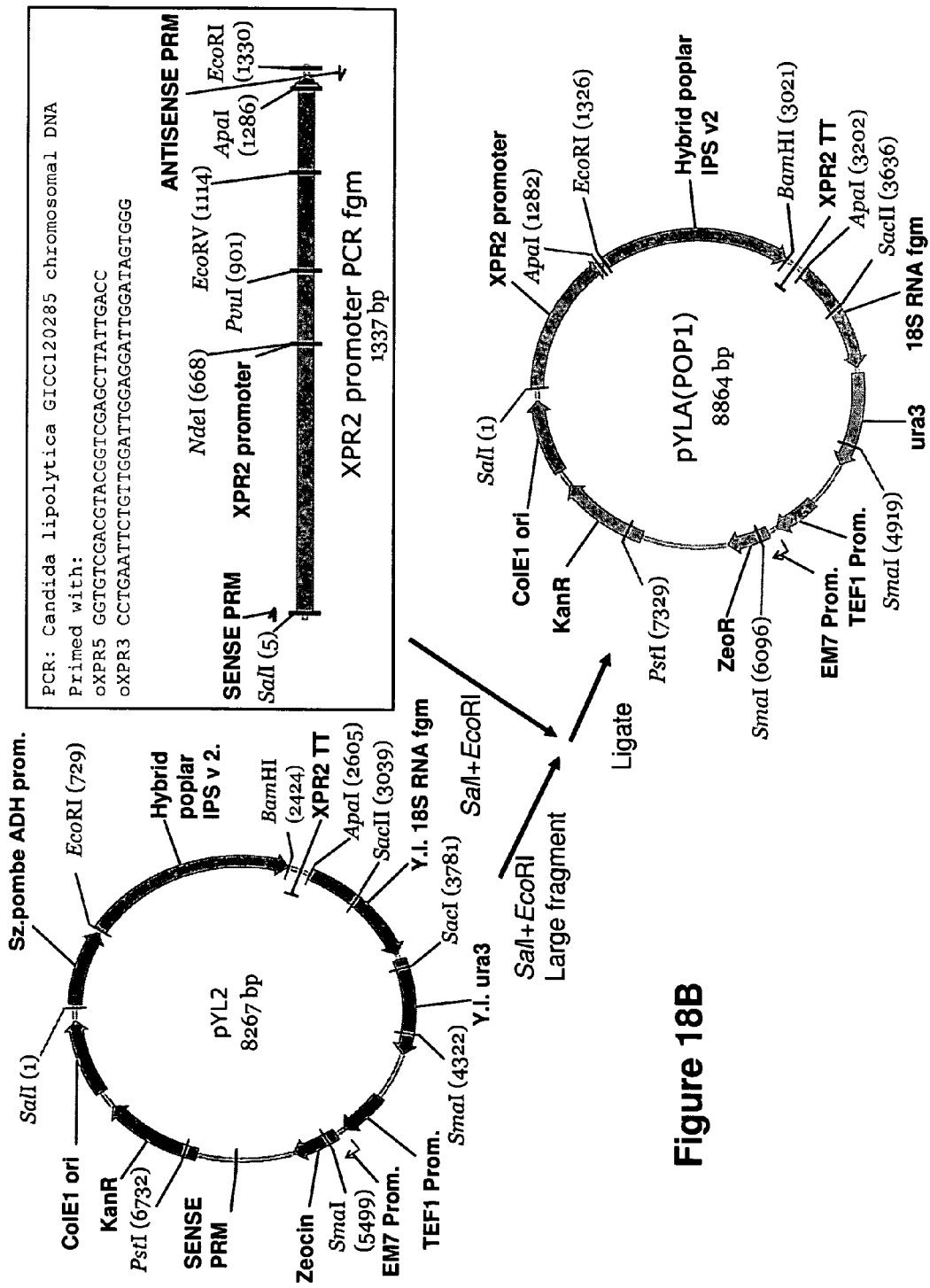
FIG. 18B shows a schematic outlining construction of the vector pYLA(POP1).
Figure 18C:
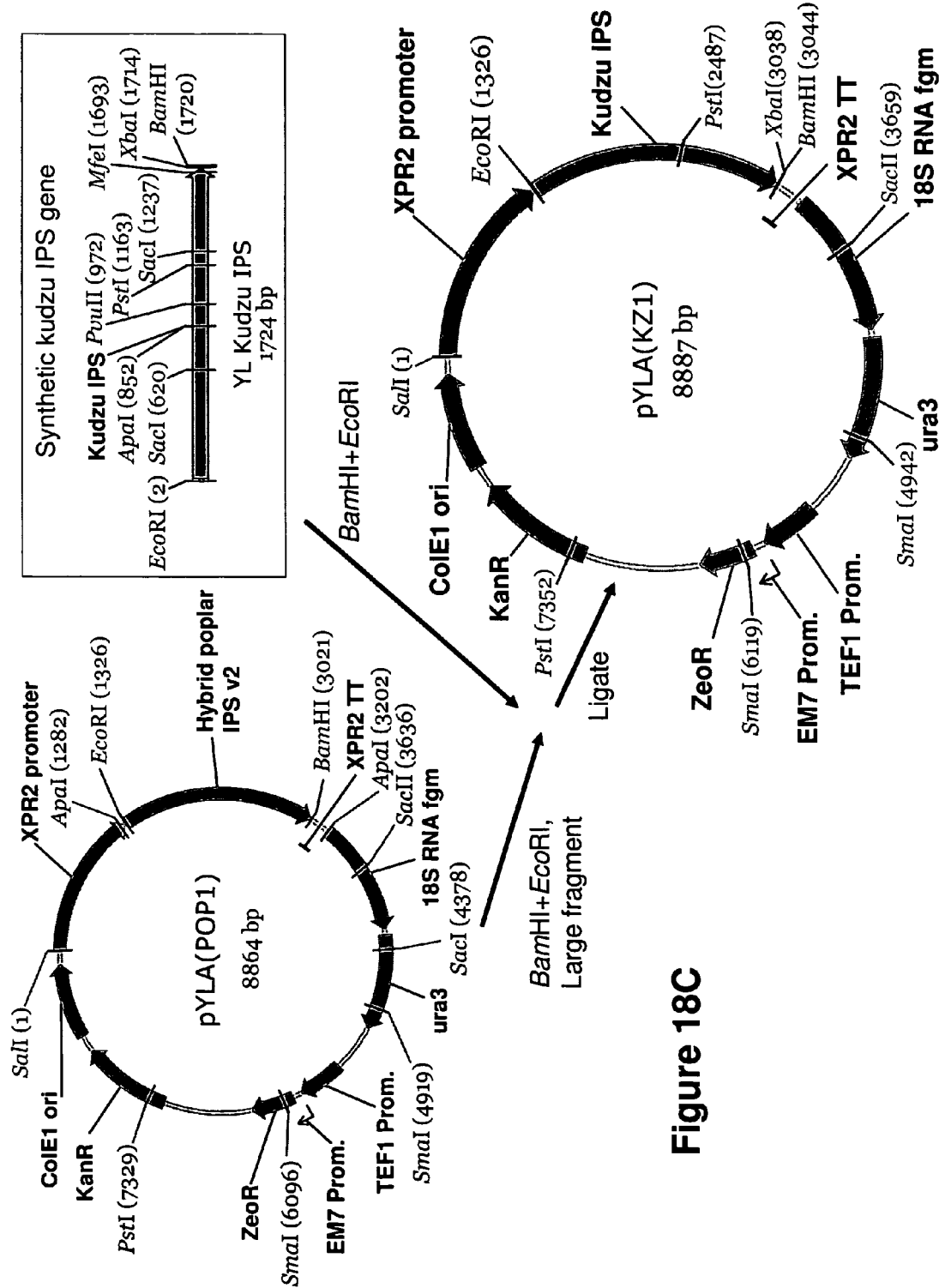
FIG. 18C shows a schematic outlining construction of the vector pYLA(KZ1)
Figure 18D:
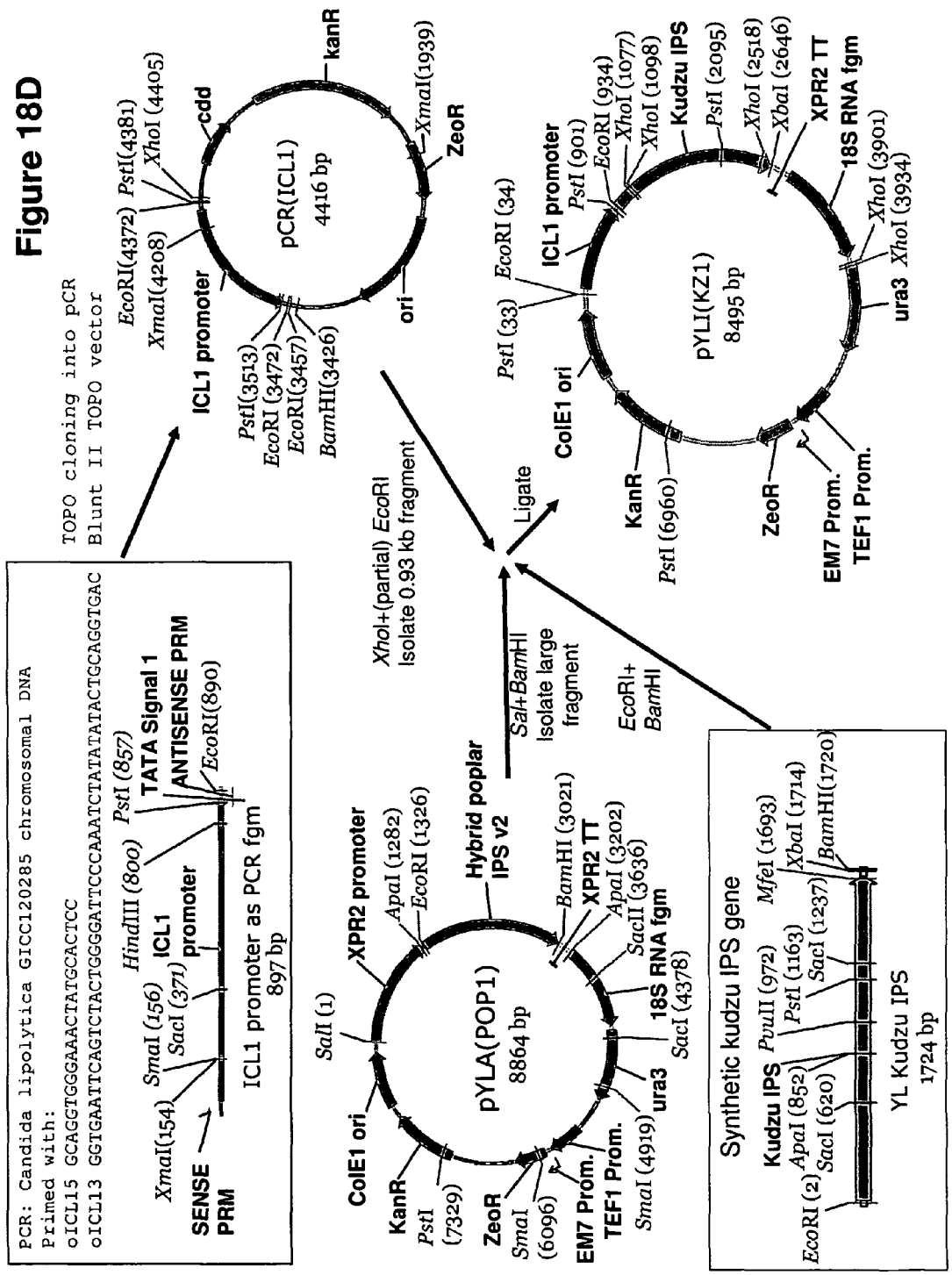
FIG. 18D shows a schematic outlining construction of the vector pYLI(KZ1).
Figure 18E:
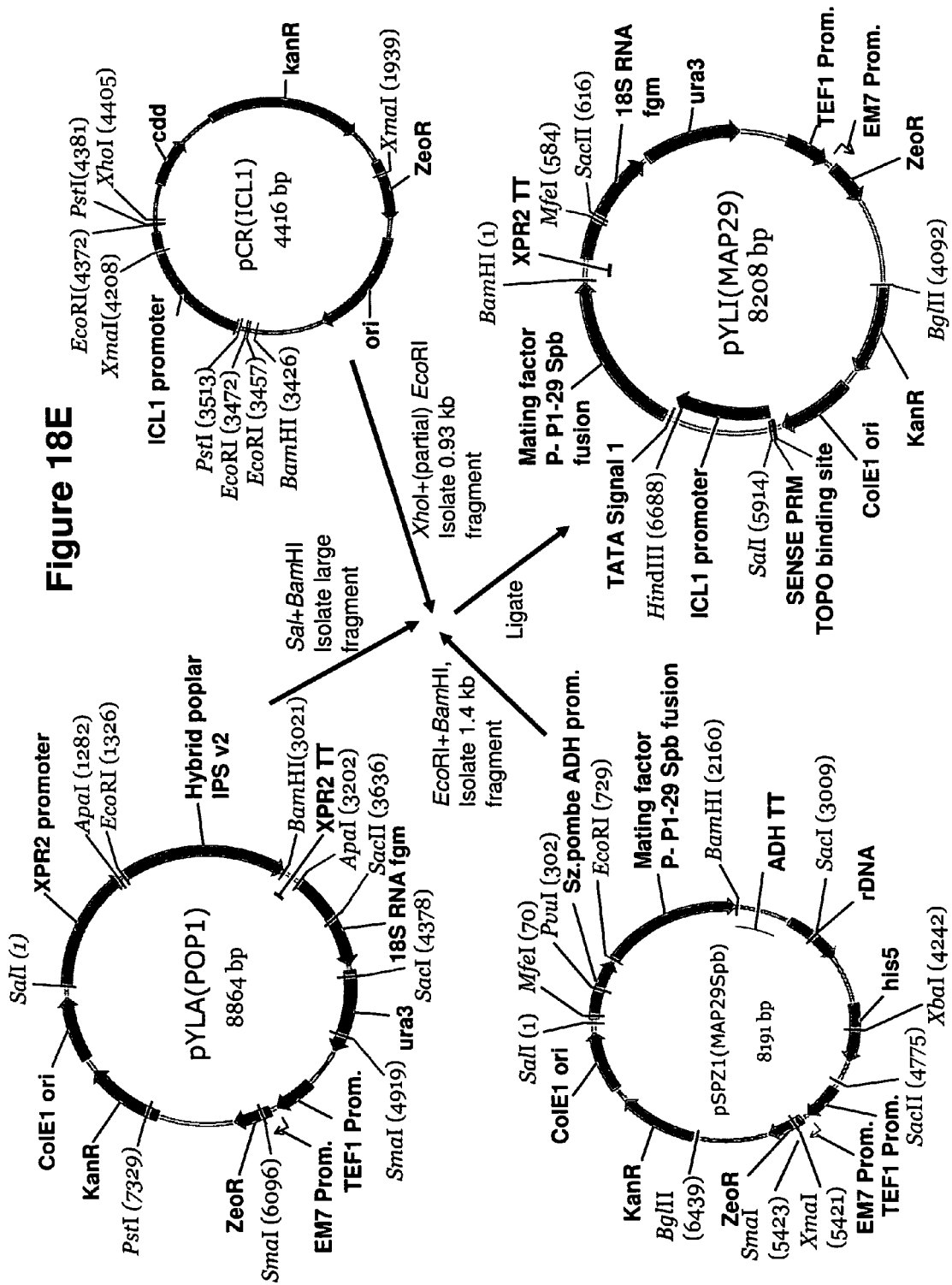
FIG. 18E shows a schematic outlining construction of the vector pYLI(MAP29)
Figure 18F:
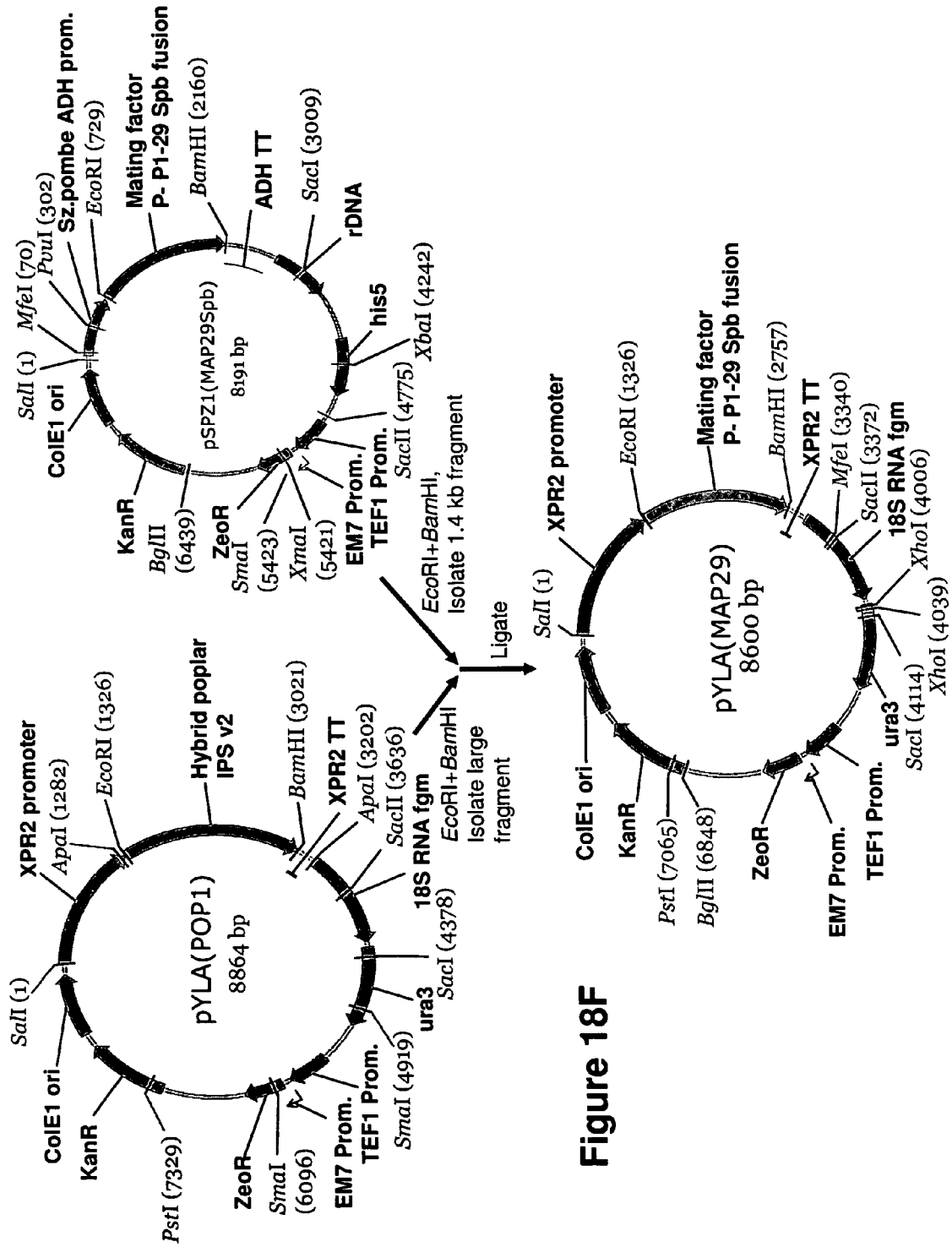
FIG. 18F shows a schematic outlining construction of the vector pYLA(MAP29)

Synthetic DNA molecules encoding the kudzu isoprene synthase gene, codon-optimized for expression in *Yarrowia*, was obtained from DNA 2.0 (FIG. 16; SEQ ID NO:12). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18. Control plasmids in which a mating factor gene (MAP29) is inserted in place of an isoprene synthase gene were also constructed (FIGS. 18E and 18F).

A similar cloning procedure can be used to express a poplar (*Populus alba×Populus tremula*) isoprene synthase gene. The sequence of the poplar isoprene is described in Miller B. et al. (2001) *Planta* 213, 483-487 and shown in FIG. 17 (SEQ ID NO:13). A construction scheme for the generation the plasmids pYLA(POP1) and pYLI(POP1) carrying synthetic poplar isoprene synthase gene under control of XPR2 and ICL1 promoters respectively is presented in FIGS. 18A and B.

II. Production of Isoprene by Recombinant Strains of *Y. lipolytica*.

Vectors pYLA(KZ1), pYLI(KZ1), pYLA(MAP29) and pYLI(MAP29) were digested with SacI and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred μl aliquots of the cell suspension were mixed with linearized plasmid DNA solution (10-20 μg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Figure 20A:
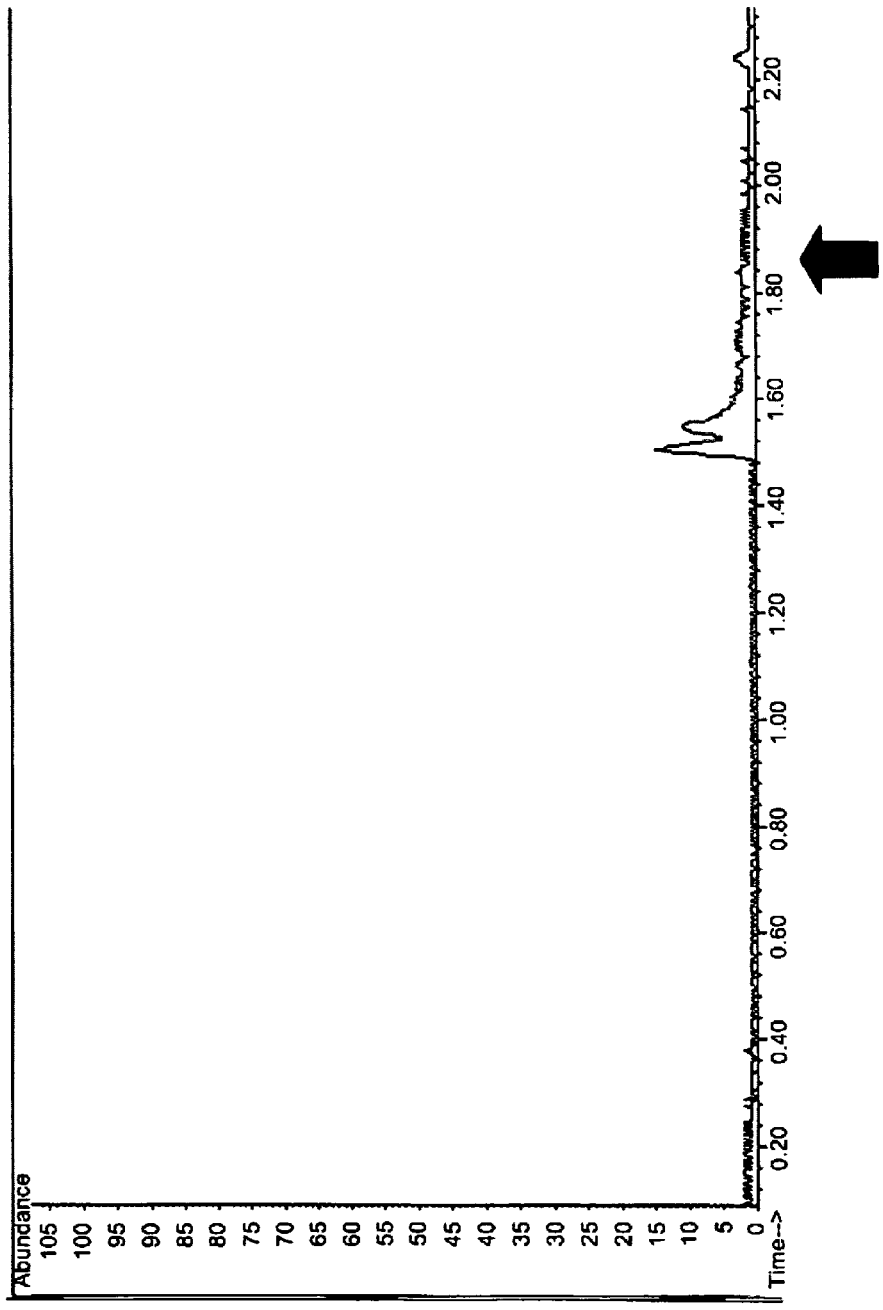
FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.
Figure 20B:
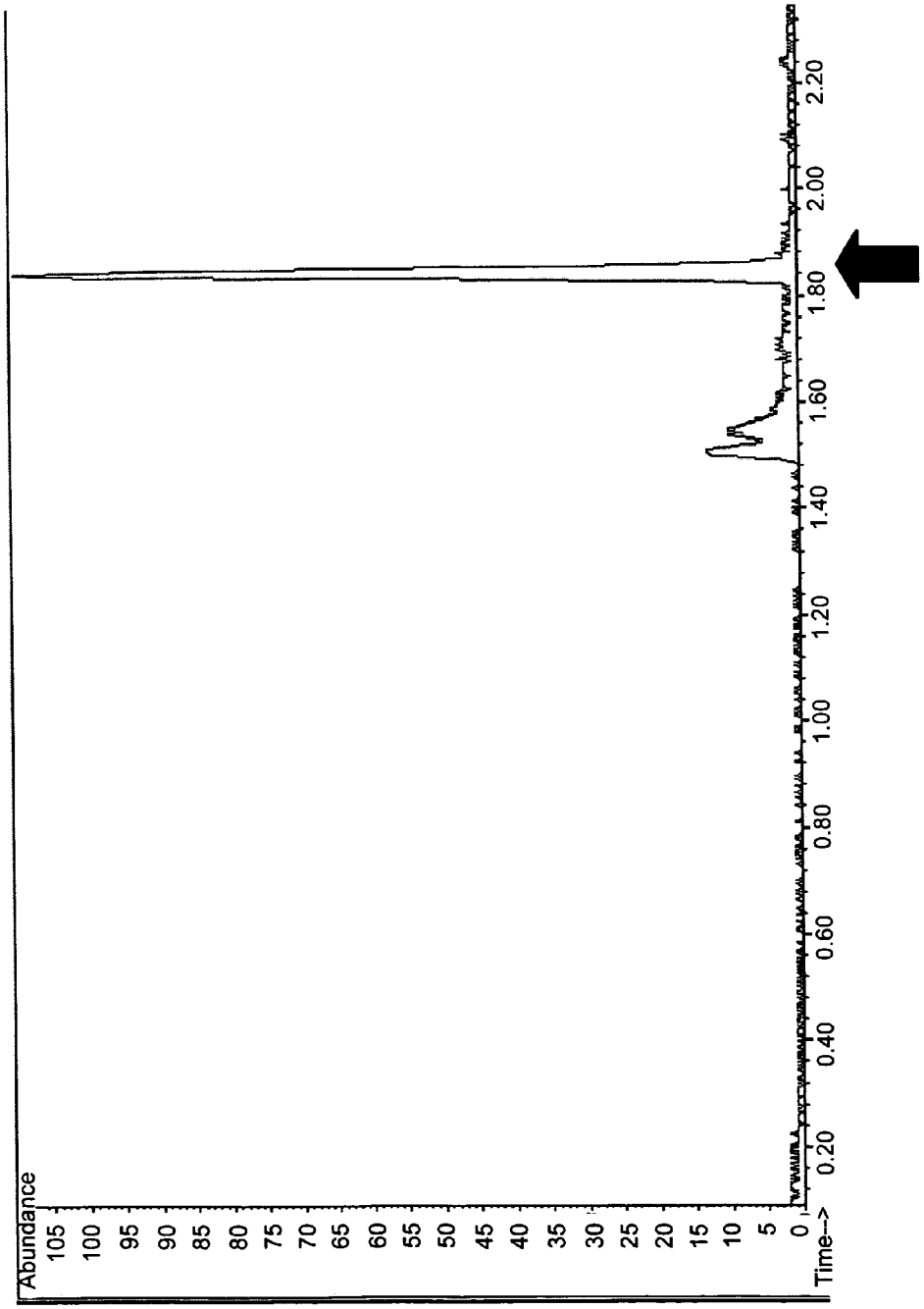

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 1. All transformants obtained with pYLA(KZ1) and pYLI(KZ1) produced readily detectable amounts of isoprene (0.5 μg/L to 1 μg/L, FIG. 20). No isoprene was detected in the headspace of the control strains carrying phytase gene instead of an isoprene synthase gene.

Example 7

Production of Isoprene in *E. coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli* i) Construction of pTrcKudzuKan

Figure 34:
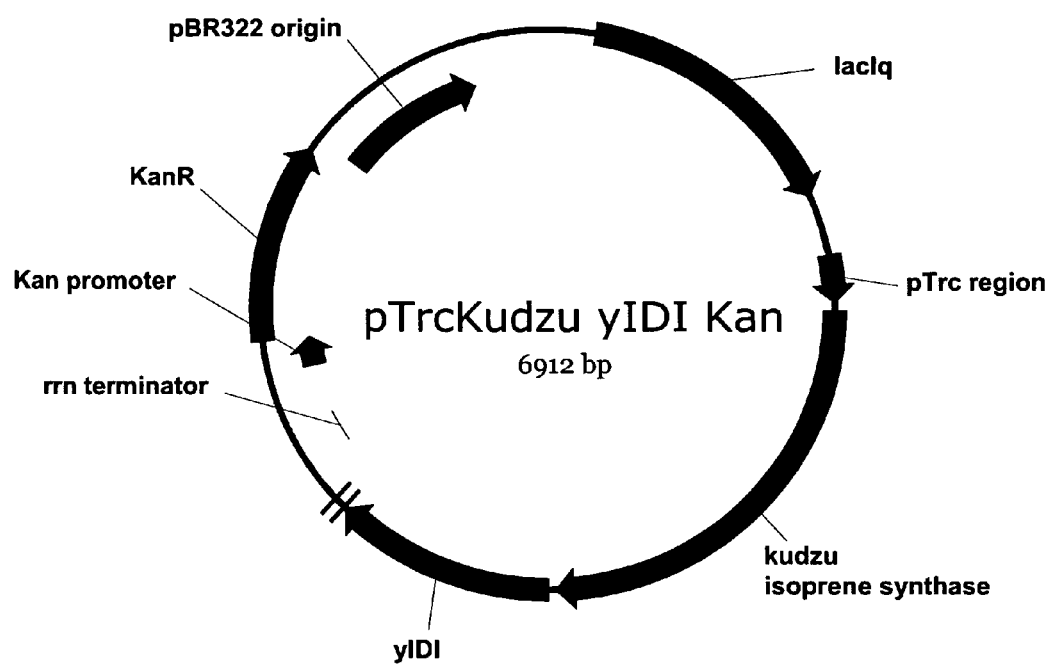
FIG. 34 is a map of pTrcKudzu yIDI Kan.

The bla gene of pTrcKudzu (described in Example 1) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the kan$^r$ gene which had been PCR amplified from pCR-Blunt-II-TOPO using primers MCM22 5'-GAT-CAAGCTTAACCGGAATTGCCAGCTG (SEQ ID NO:14) and MCM23 5'-GATCCGATCGTCAGAAGAACTCGT-CAAGAAGGC (SEQ ID NO:15), digested with HindIII and PvuI, and end-filled. A transformant carrying a plasmid conferring kanamycin resistance (pTrcKudzuKan) was selected on LA containing kanamycin 50 µg/ml.

ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATG-CATCGCCCTTAGGAGGTAAAAAAAAATGAC (SEQ ID NO:16) and PstI-YIDI 1R 5'-CCTTCTGCAGGACGCGT-TGTTATAGC (SEQ ID NO:17); and the template was *S. cerevisiae* genomic DNA. The PCR product was digested with NsiI and PstI and gel purified prior to ligation. The ligation mixture was transformed into chemically competent TOP10 cells and selected on LA containing 50 µg/ml kanamycin. Several transformants were isolated and sequenced and the resulting plasmid was called pTrcKudzu-yIDI(kan) (FIGS. 34 and 35).

iii) Construction of pTrcKudzu DXS Kan

Plasmid pTrcKudzuKan was digested with PstI, treated with SAP, heat killed and gel purified. It was ligated to a PCR product encoding dxs from *E. coli* with a synthetic RBS.

Figure 21:
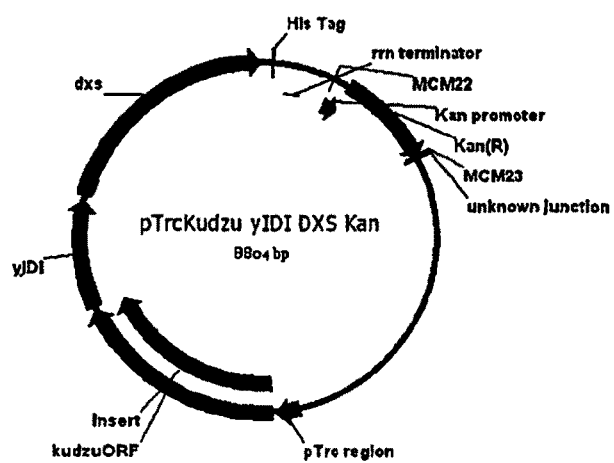
FIG. 21 is a map of pTrcKudzu yIDI DXS Kan.
Figure 36:
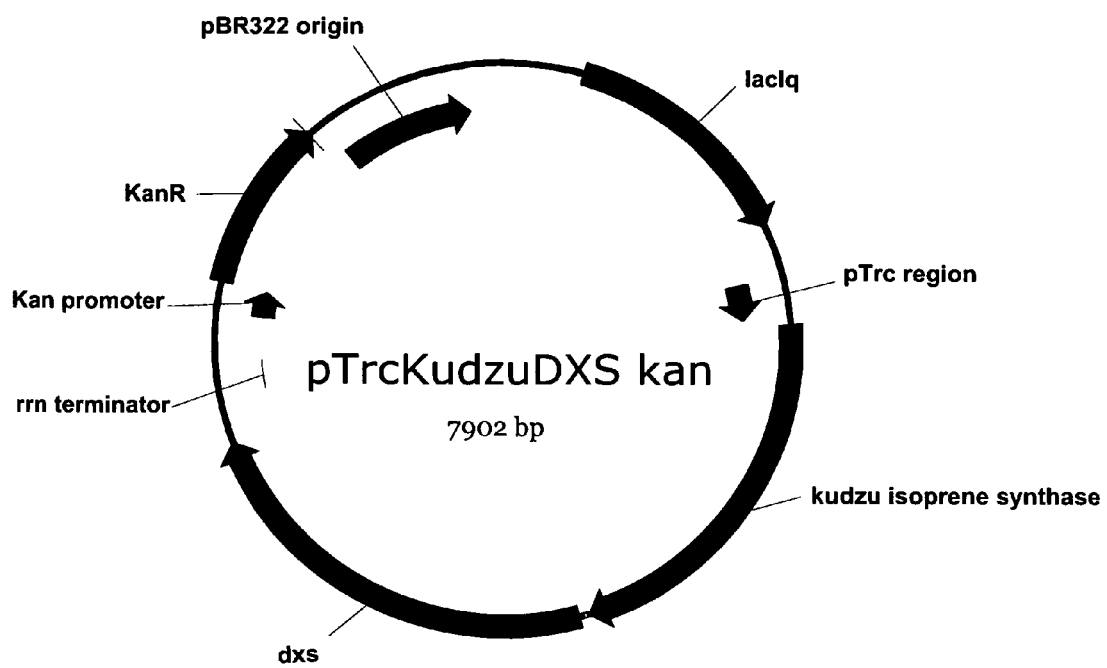
FIG. 36 is a map of pTrcKudzuDXS Kan.
Figure 38:
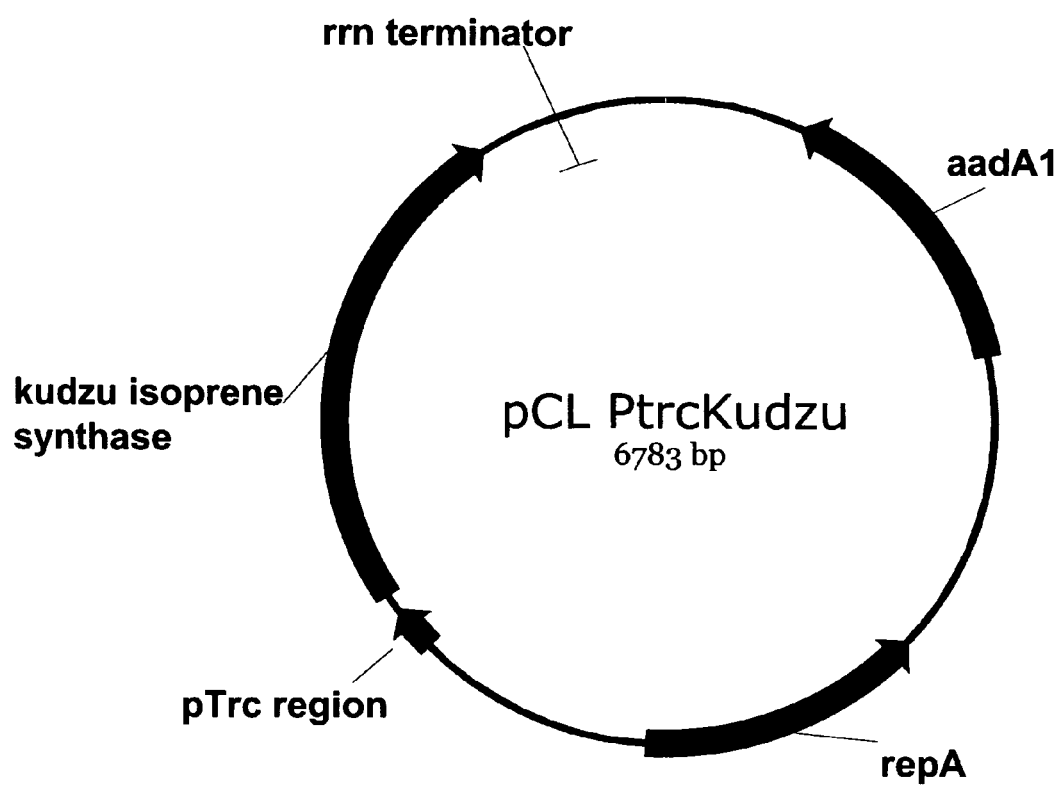
FIG. 38 is a map of pCL PtrcKudzu.
Figure 40:
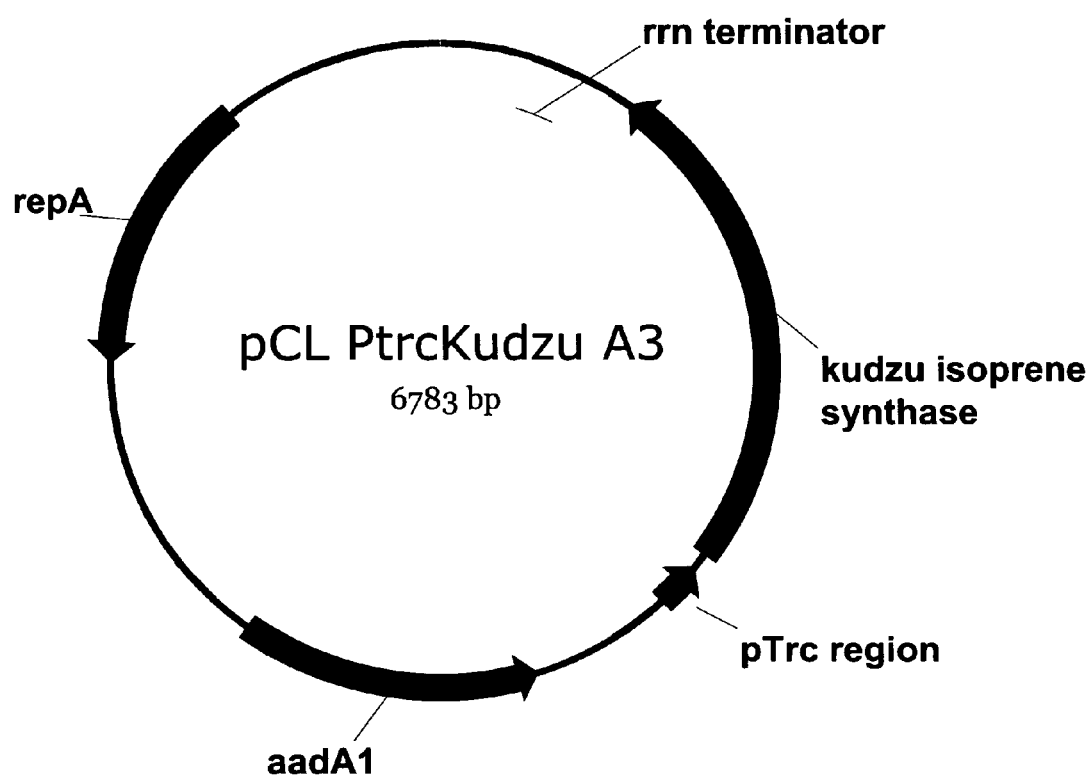
FIG. 40 is a map of pCL PtrcKudzu A3.

The primers for PCR were MCM13 5'-GATCATGCAT-TCGCCCTTAGGAGGTAAAAAAACAT-GAGTTTTGATATTGCCAAA TACCCG (SEQ ID NO:18) and MCM14 5'-CATGCTGCAGTTATGCCAGCCAGGC-CTTGAT (SEQ ID NO:19); and the template was *E. coli* genomic DNA. The PCR product was digested with NsiI and PstI and gel purified prior to ligation. The resulting transformation reaction was transformed into TOP10 cells and selected on LA with kanamycin 50 µg/ml. Several transformants were isolated and sequenced and the resulting plasmid was called pTrcKudzu-DXS(kan) (FIGS. 36 and 37).

iv) Construction of pTrcKudzu-yIDI-dxs (kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAGG-TAAAAAAACATGAGTTTTGATATTGCCAAA TACCCG (SEQ ID NO:18) and MCM14 5'-CATGCTGCAGTTATGC-CAGCCAGGCCTTGAT (SEQ ID NO:19); template TOP10 cells) which had been digested with NsiI and PstI and gel purified. The final plasmid was called pTrcKudzu-yIDI-dxs (kan) (FIGS. 21 and 22).

v) Construction of pCL PtrcKudzu

A fragment of DNA containing the promoter, structural gene and terminator from Example 1 above was digested from pTrcKudzu using SspI and gel purified. It was ligated to pCL1920 which had been digested with PvuII, treated with SAP and heat killed. The resulting ligation mixture was transformed into TOP10 cells and selected in LA containing spectinomycin 50 µg/ml. Several clones were isolated and sequenced and two were selected. pCL PtrcKudzu and pCL PtrcKudzu (A3) have the insert in opposite orientations (FIGS. 38-41).

vi) Construction of pCL PtrcKudzu yIDI

Figure 42:
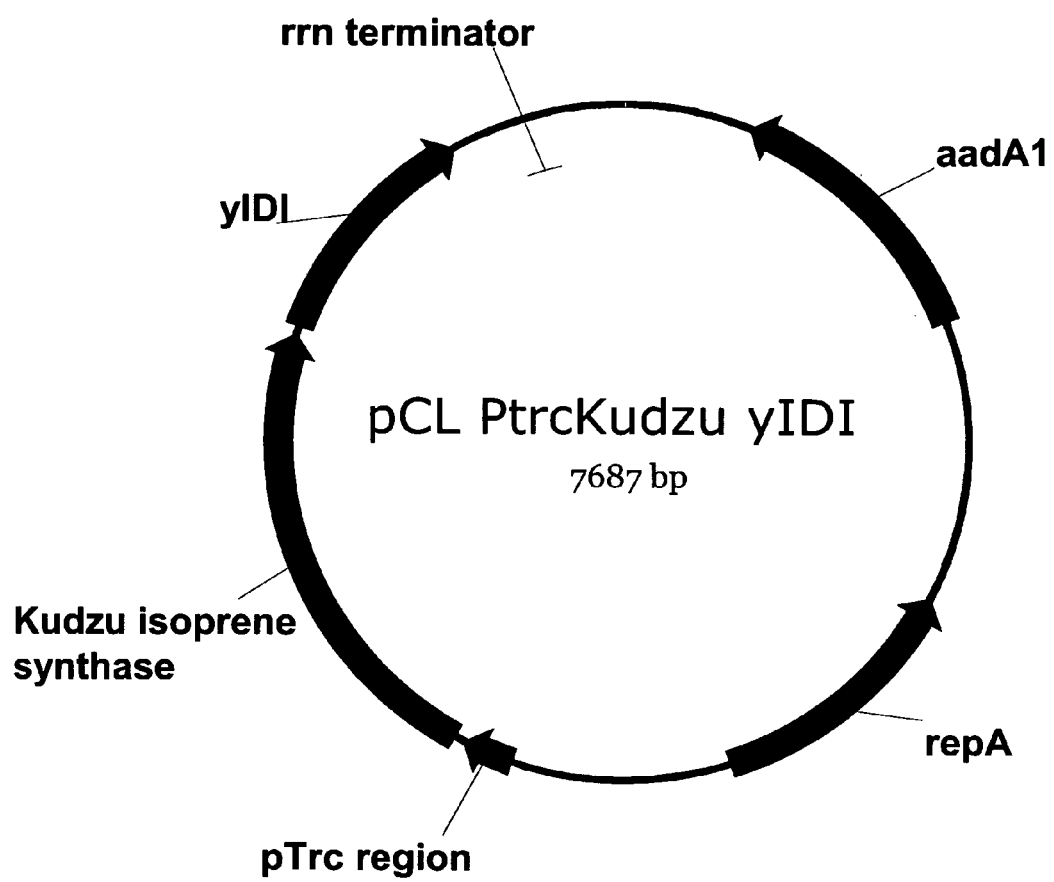
FIG. 42 is a map of pCL PtrcKudzu yIDI.

The NsiI-PstI digested, gel purified, IDI PCR amplicon from (ii) above was ligated into pCL PtrcKudzu which had been digested with PstI, treated with SAP, and heat killed. The ligation mixture was transformed into TOP10 cells and selected in LA containing spectinomycin 50 µg/ml. Several clones were isolated and sequenced and the resulting plasmid is called pCL PtrcKudzu yIDI (FIGS. 42 and 43).

vii) Construction of pCL PtrcKudzu DXS

Figure 44:
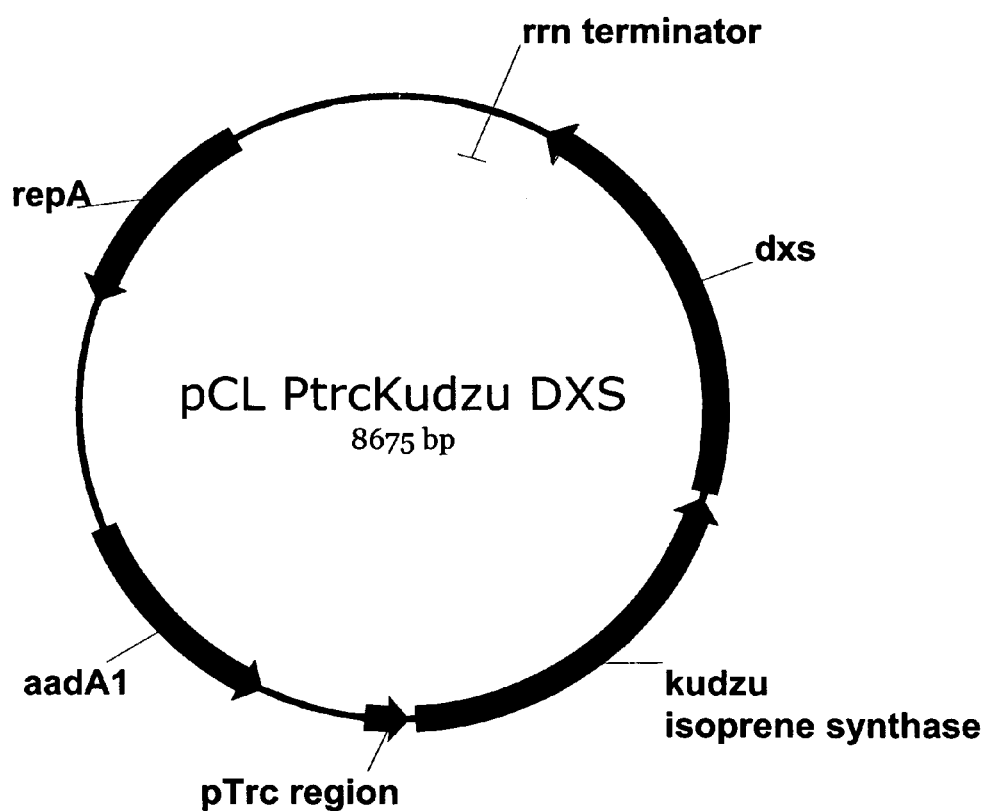
FIG. 44 is a map of pCL PtrcKudzu DXS.
Figure 46A:
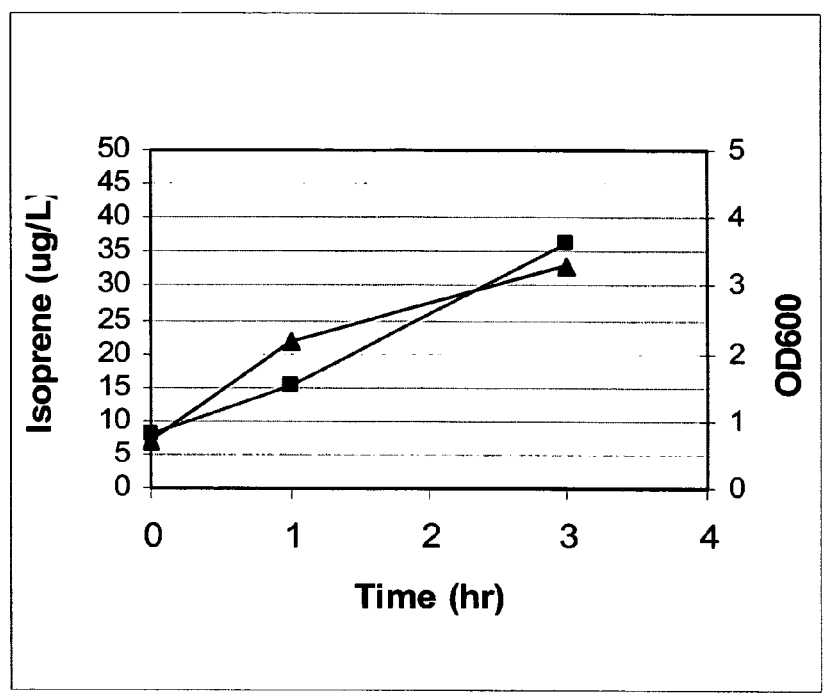
FIG. 46 shows graphs representing isoprene production from biomass feedstocks. Panel A shows isoprene production from corn stover, Panel B shows isoprene production from bagasse, Panel C shows isoprene production from softwood pulp, Panel D shows isoprene production from glucose, and Panel E shows isoprene production from cells with no additional feedstock. Grey squares represent OD600 measurements of the cultures at the indicated times post-inoculation and black triangles represent isoprene production at the indicated times post-inoculation.
Figure 46B:
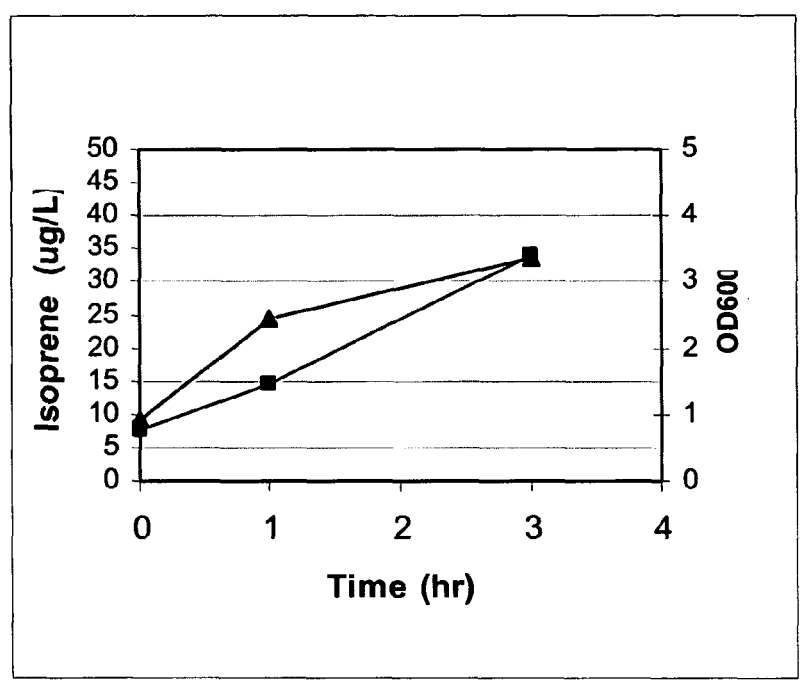
Figure 46C:
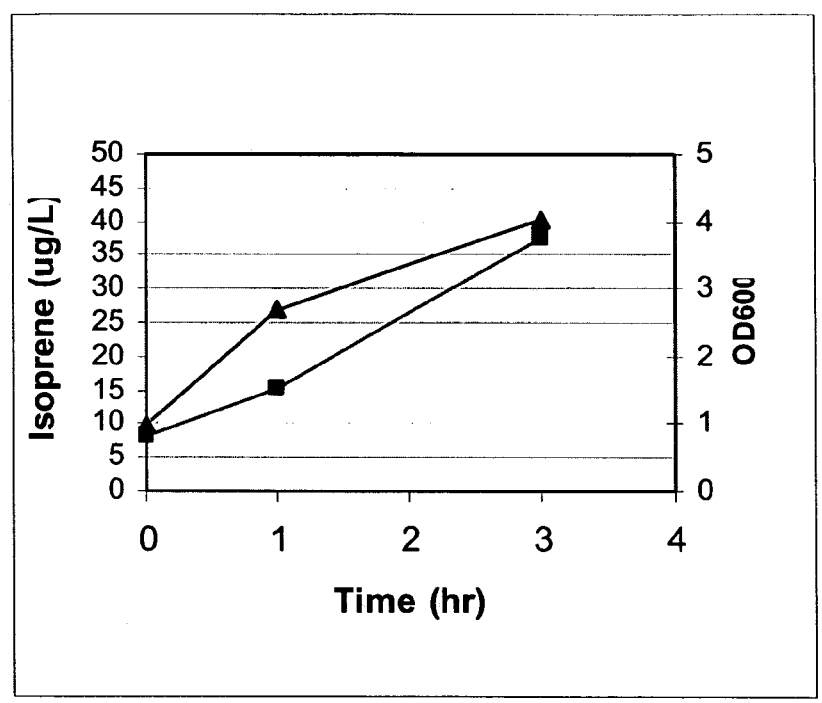
Figure 46D:
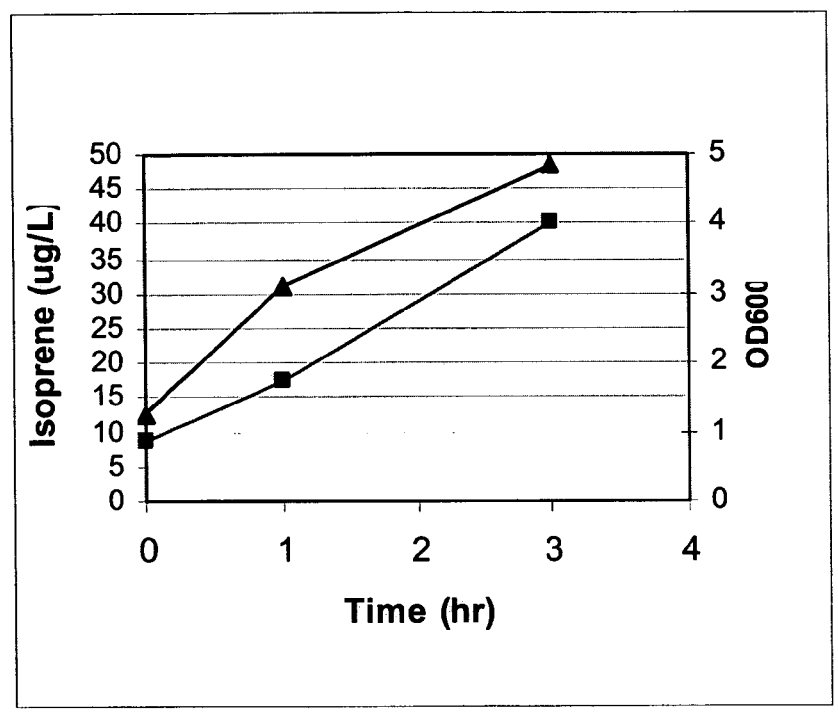

The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP10 cells and selected in LA containing spectinomycin 50 µg/ml. Several clones were isolated and sequenced and the resulting plasmid is called pCL PtrcKudzu DXS (FIGS. 44 and 45).

II. Measurement of Isoprene in Headspace from Cultures Expressing Kudzu Isoprene Synthase, idi, and/or dxs at Different Copy Numbers.

Cultures of *E. coli* BL21(λADE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 µg/mL. Cultures of pCL PtrcKudzu (E), pCL PtrcKudzu, pCL PtrcKudzu-yIDI (F) and pCL PtrcKudzu-DXS (G) were grown in LB spectinomycin 50 µg/mL. Cultures were induced with 400 µM IPTG at time 0 ($OD_{600}$ approximately 0.5) and samples taken for isoprene headspace measurement (see Example 1). Results are shown in FIG. 23A-23G.

Figure 23A:
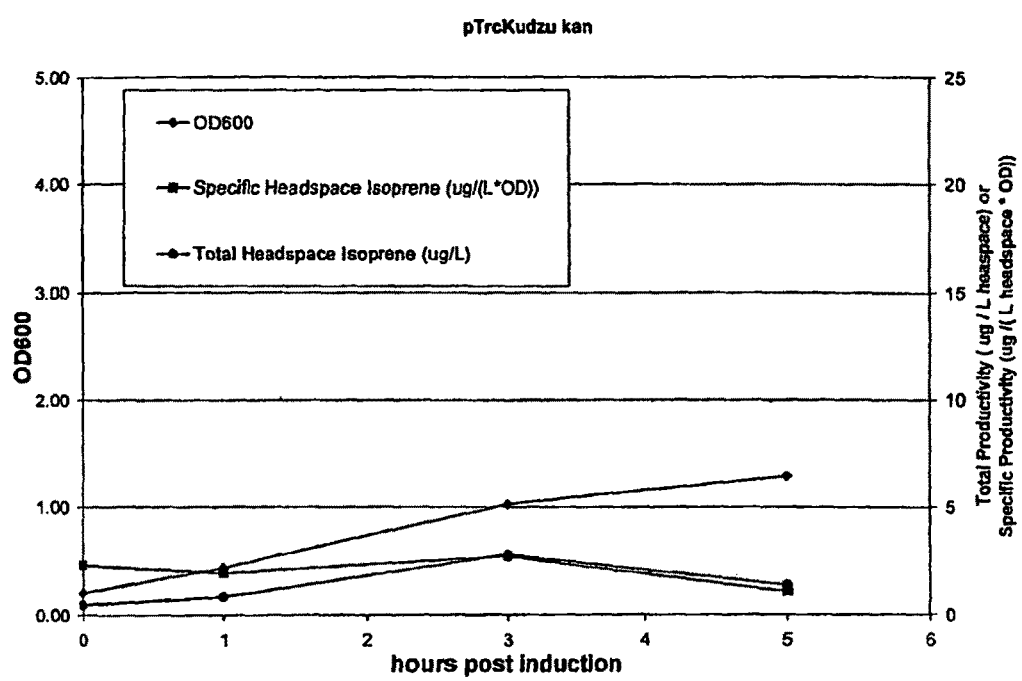
FIG. 23A is a graph showing production of isoprene from glucose in BL21/pTrcKudzukan. Time 0 is the time of induction with IPTG (400 µmol). The x-axis is time after induction; the y-axis is OD600 and the y2-axis is total productivity of isoprene (µg/L headspace or specific productivity (µg/L headspace/OD). Diamonds represent OD600, circles represent total isoprene productivity (µg/L) and squares represent specific productivity of isoprene (µg/L/OD).
Figure 23B:
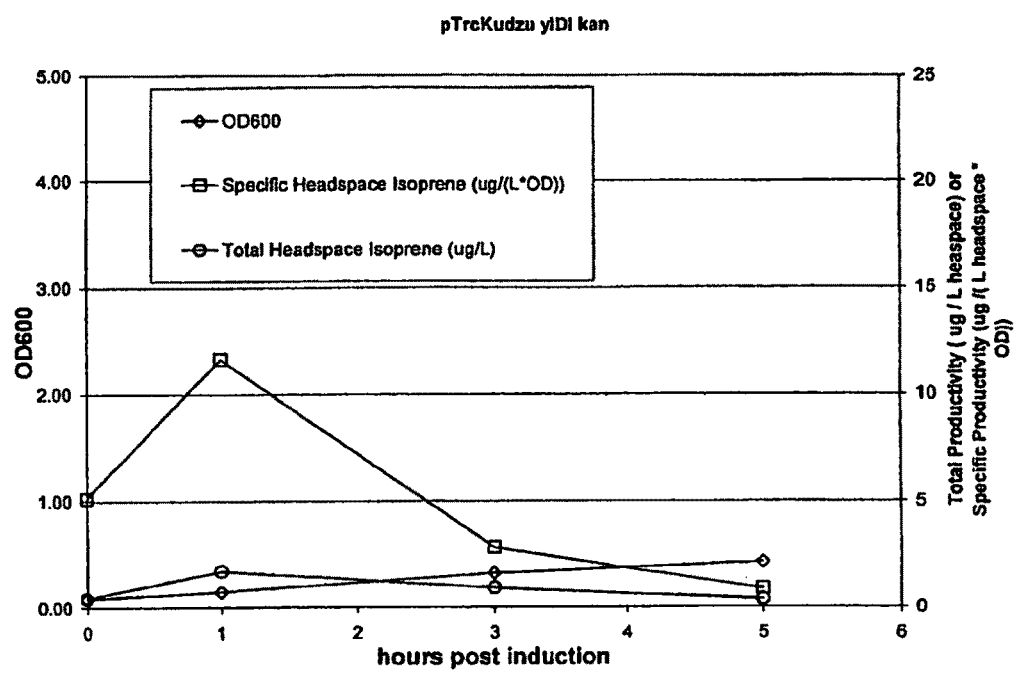
FIG. 23B is a graph showing production of isoprene from glucose in BL21/pTrcKudzu yIDI kan. Time 0 is the time of induction with IPTG (400 µmol). The x-axis is time after induction; the y-axis is OD600 and the y2-axis is total productivity of isoprene (µg/L headspace or specific productivity (µg/L headspace/OD). Diamonds represent OD600, circles represent total isoprene productivity (µg/L) and squares represent specific productivity of isoprene (µg/L/OD).
Figure 23C:
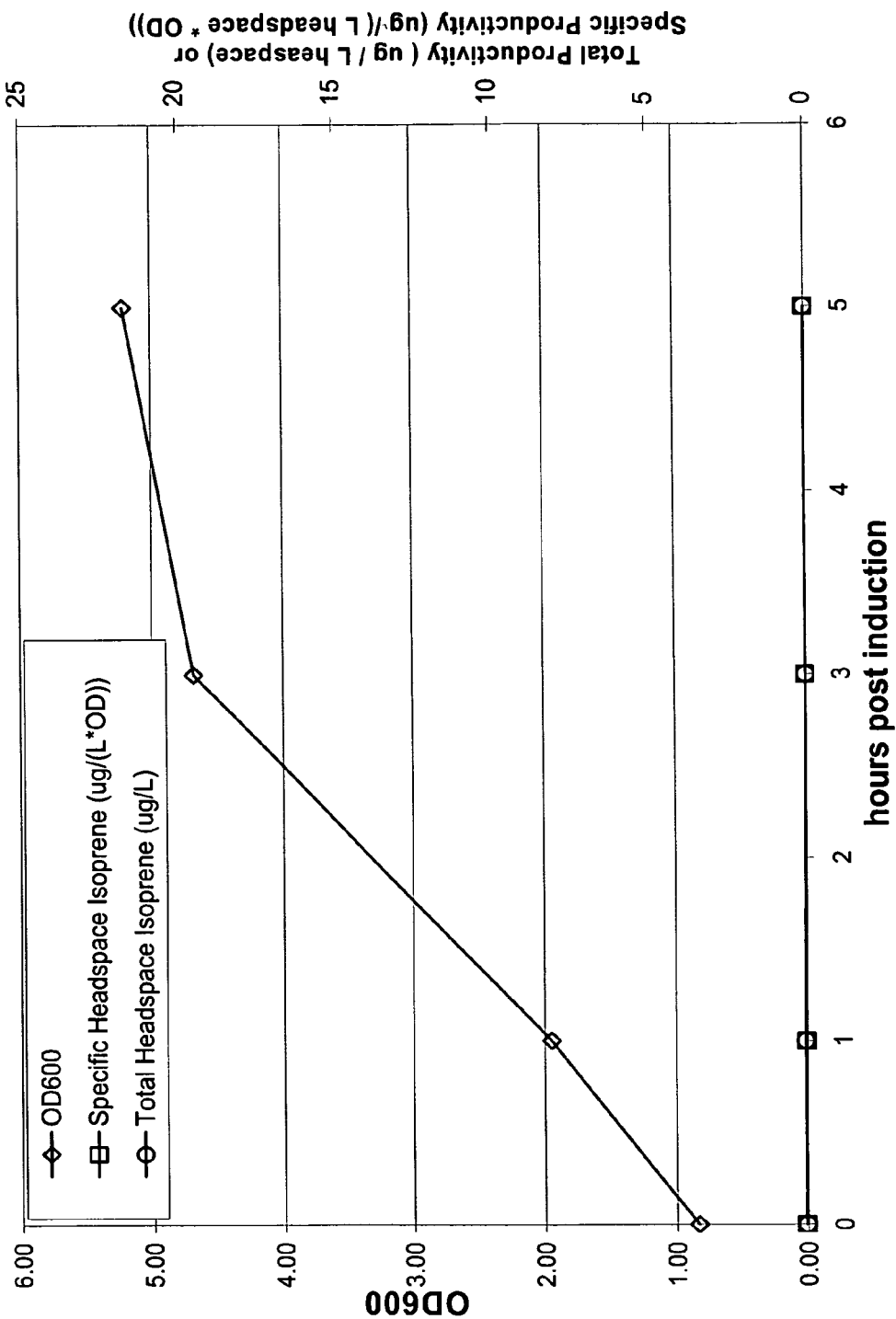
FIG. 23C is a graph showing production of isoprene from glucose in BL21/pTrcKudzu DXS kan. Time 0 is the time of induction with IPTG (400 µmol). The x-axis is time after induction; the y-axis is OD600 and the y2-axis is total productivity of isoprene (µg/L headspace or specific productivity (µg/L headspace/OD). Diamonds represent OD600, circles represent total isoprene productivity (µg/L) and squares represent specific productivity of isoprene (µg/L/OD).
Figure 23D:
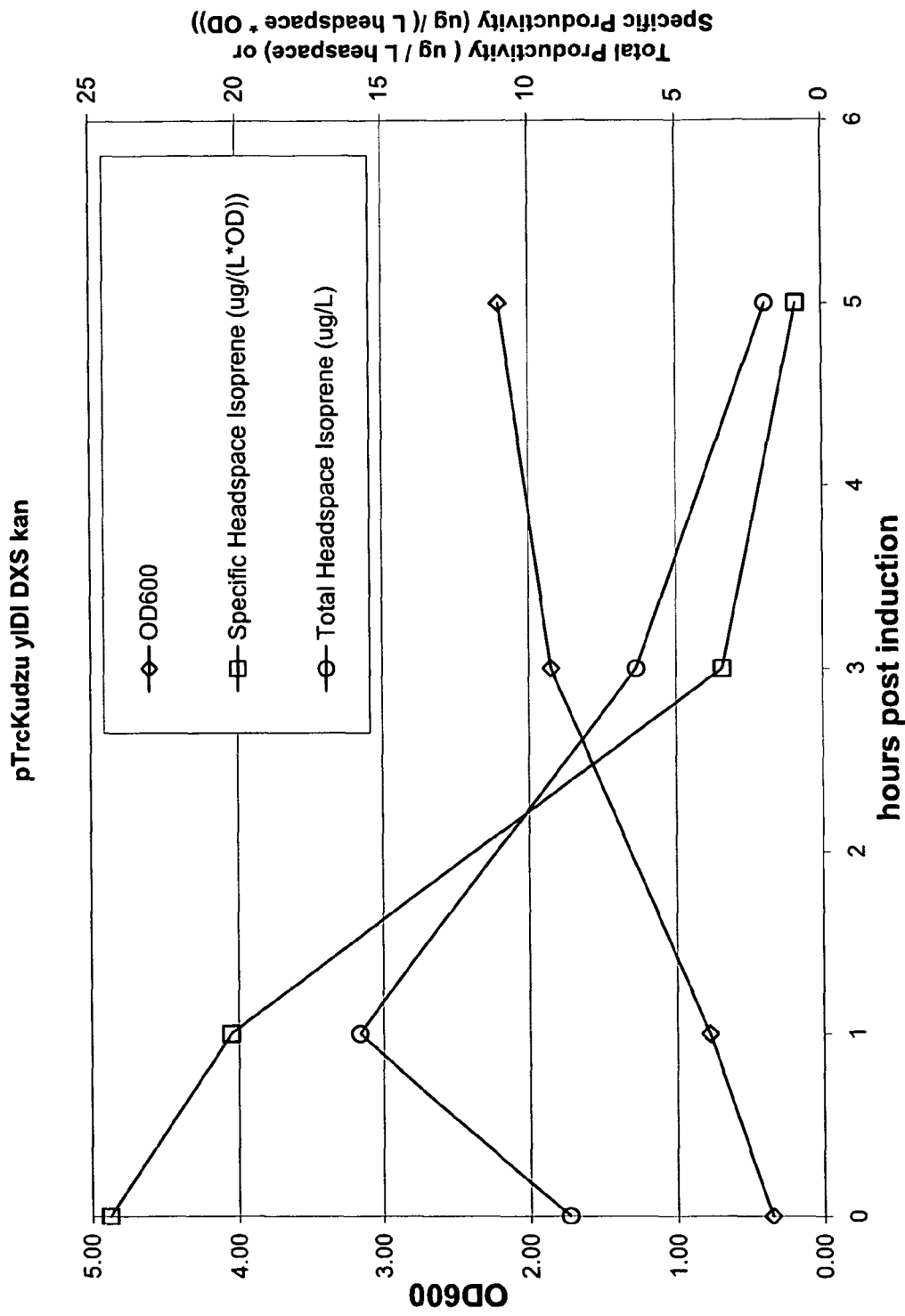
FIG. 23D is a graph showing production of isoprene from glucose in BL21/pTrcKudzu yIDI DXS kan. Time 0 is the time of induction with IPTG (400 µmol). The x-axis is time after induction; the y-axis is OD600 and the y2-axis is total productivity of isoprene (µg/L headspace or specific productivity (µg/L headspace/OD). Diamonds represent OD600, circles represent total isoprene productivity (µg/L) and squares represent specific productivity of isoprene (µg/L/OD).
Figure 23E:
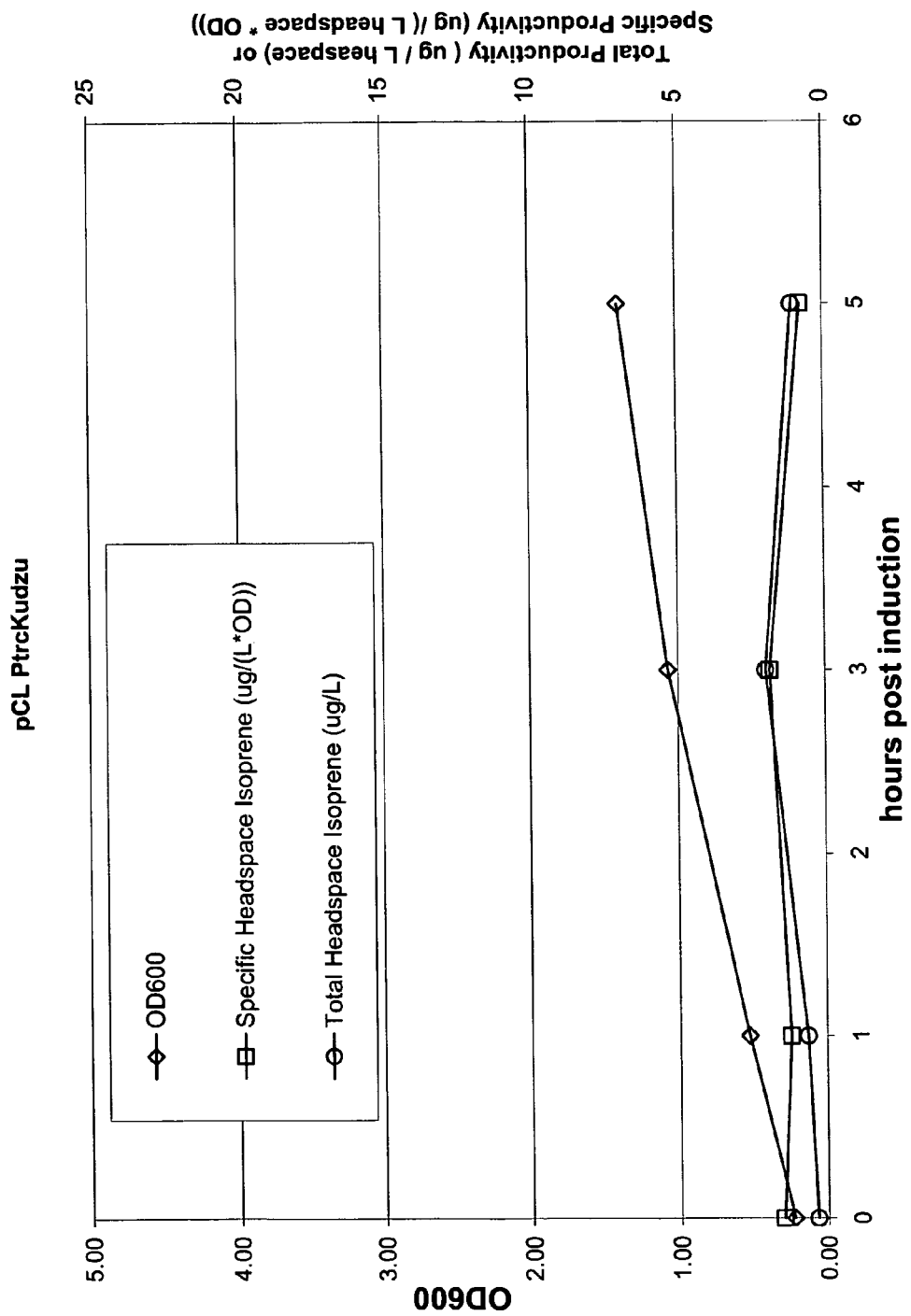
FIG. 23E is a graph showing production of isoprene from glucose in BL21/pCL PtrcKudzu. Time 0 is the time of induction with IPTG (400 µmol). The x-axis is time after induction; the y-axis is OD600 and the y2-axis is total productivity of isoprene (µg/L headspace or specific productivity (µg/L headspace/OD). Diamonds represent OD600, circles represent total isoprene productivity (µg/L) and squares represent specific productivity of isoprene (µg/L/OD).
Figure 23F:
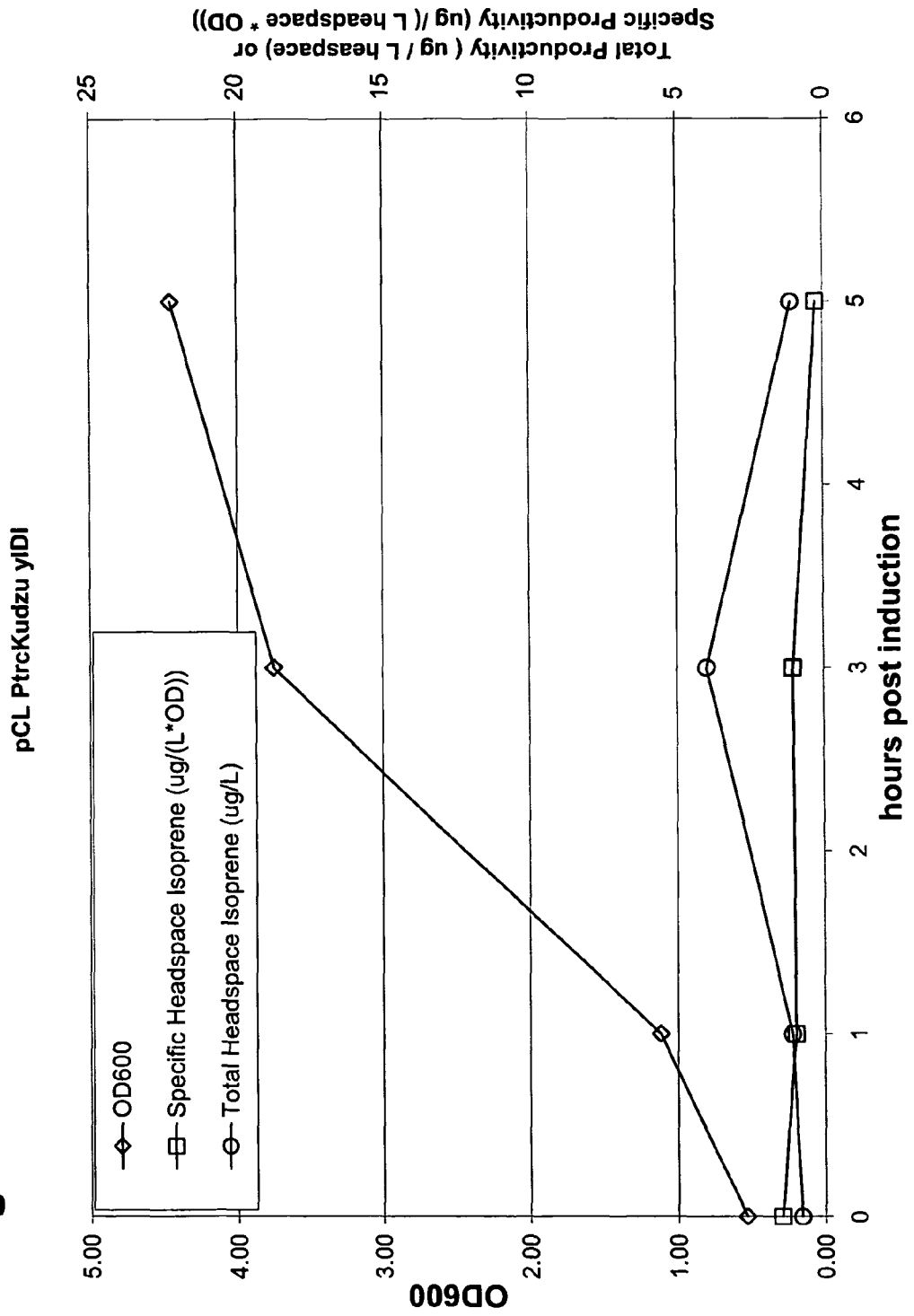
FIG. 23F is a graph showing production of isoprene from glucose in BL21/pCL PtrcKudzu yIDI. Time 0 is the time of induction with IPTG (400 µmol). The x-axis is time after induction; the y-axis is OD600 and the y2-axis is total productivity of isoprene (µg/L headspace or specific productivity (µg/L headspace/OD). Diamonds represent OD600, circles represent total isoprene productivity (µg/L) and squares represent specific productivity of isoprene (µg/L/OD).
Figure 23G:
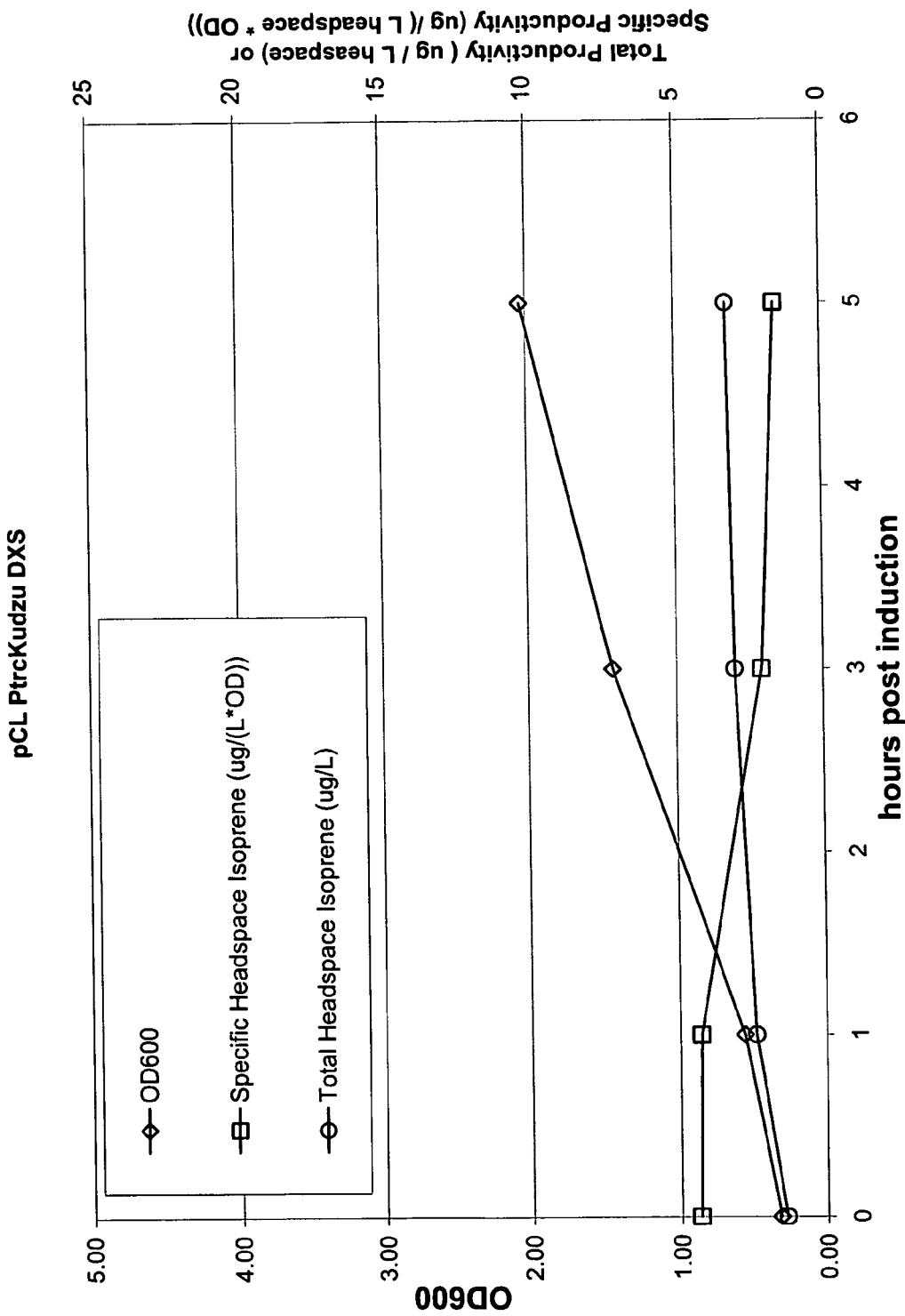
FIG. 23G is a graph showing production of isoprene from glucose in BL21/pCL PtrcKudzu DXS. Time 0 is the time of induction with IPTG (400 µmol). The x-axis is time after induction; the y-axis is OD600 and the y2-axis is total productivity of isoprene (µg/L headspace or specific productivity (µg/L headspace/OD). Diamonds represent OD600, circles represent total isoprene productivity (µg/L) and squares represent specific productivity of isoprene (µg/UOD).
Figure 23H:
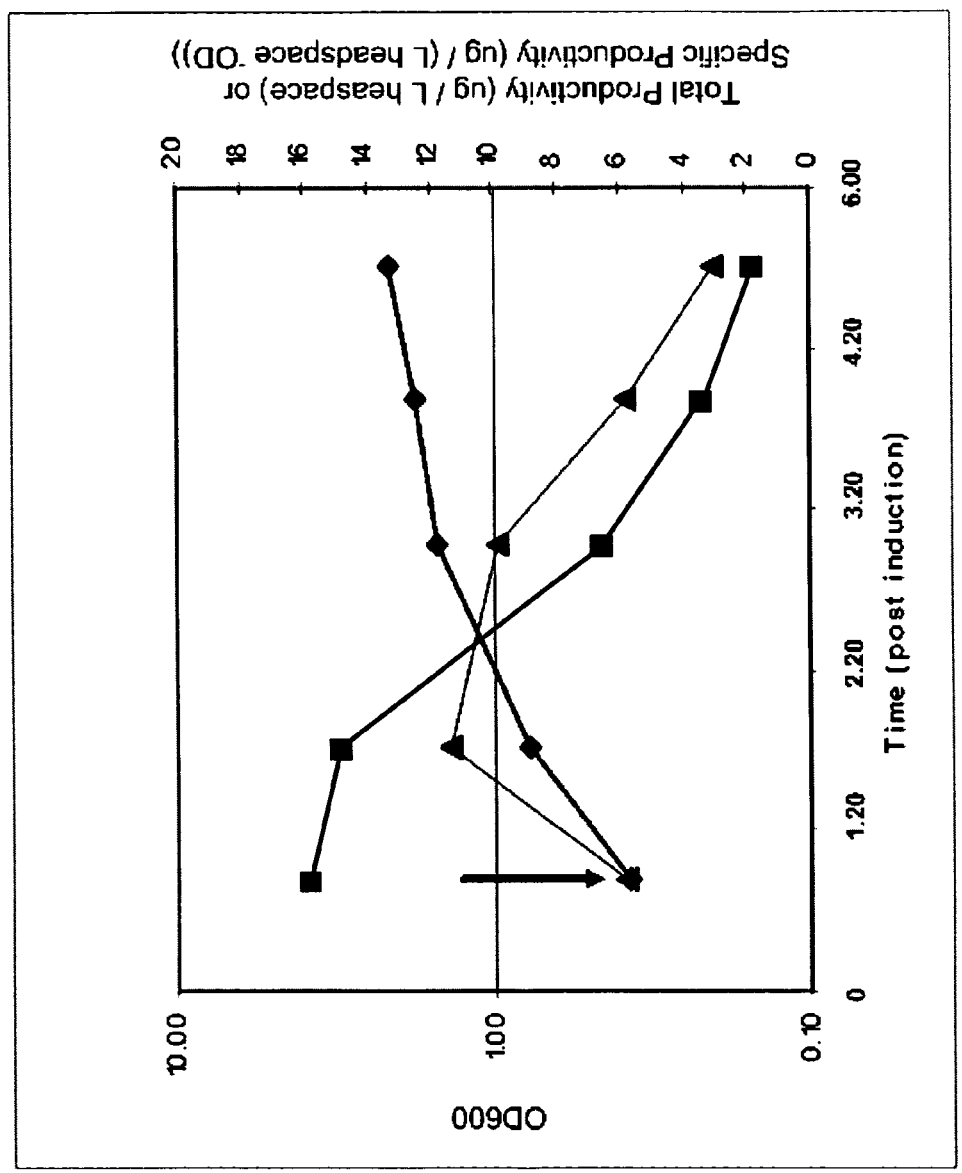
FIG. 23H is a graph showing production of isoprene from glucose in BL21/pTrcKudzuIDIDXSkan. The arrow indicates the time of induction with IPTG (400 µmol). The x-axis is time after induction; the y-axis is OD600 and the y2-axis is total productivity of isoprene (μg/L headspace or specific productivity (μg/L headspace/OD). Black diamonds represent OD600, black triangles represent isoprene productivity (μg/L) and white squares represent specific productivity of isoprene (μg/L/OD).

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 µg/ml) at 20° C. and used to inoculate shake flasks of TM3 (13.6 g $K_2PO_4$, 13.6 g $KH_2PO_4$, 2.0 g $MgSO_4\cdot 7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks were incubated at 30° C. until an $OD_{600}$ of 0.8 was reached, and then induced with 400 µM IPTG. Samples were taken at various times after induction and the amount of isoprene in the head space was measured as described in Example 1. Results are shown in FIG. 23H.

III. Production of Isoprene from Biomass in *E. coli*/pTrcKudzu yIDI DXS

The strain BL21 pTrcKudzuIDIDXS was tested for the ability to generate isoprene from three types of biomass; bagasse, corn stover and soft wood pulp with glucose as a control. Hydrolysates of the biomass were prepared by enzymatic hydrolysis (Brown, L. and Torget, R., 1996, NREL standard assay method Lap-009 "Enzymatic Saccharification of Lignocellulosic Biomass") and used at a dilution based upon glucose equivalents. In this example, glucose equivalents were equal to 1% glucose. A single colony from a plate freshly transformed cells of BL21 (DE3) pTrcKudzu yIDI DXS (kan) was used to inoculate 5 ml of LB plus kanamycin (50 µg/ml). The culture was incubated overnight at 25° C. with shaking. The following day the overnight culture was diluted to an $OD_{600}$ of 0.05 in 25 ml of TM3 and 0.2% YE and 1% feedstock. The feedstock was corn stover, bagasse, or softwood pulp. Glucose was used as a positive control and no glucose was used as a negative control. Cultures were incubated at 30° C. with shaking at 180 rpm. The culture was monitored for $OD_{600}$ and when it reached an $OD_{600}$ of ~0.8, cultures were analyzed at 1 and 3 hours for isoprene production as described in Example 1. Cultures are not induced. All cultures containing added feedstock produce isoprene equivalent to those of the glucose positive control. Experiments were done in duplicate and are shown in FIG. 46.

IV. Production of Isoprene from Invert Sugar in *E. coli*/pTrcKudzuIDIDXS

A single colony from a plate freshly transformed cells of BL21 (λDE3)/pTrcKudzu yIDI DXS (kan) was used to inoculate 5 mL of LB and kanamycin (50 µg/ml). The culture was incubated overnight at 25° C. with shaking. The following day the overnight culture was diluted to an $OD_{600}$ of 0.05 in 25 ml of TM3 and 0.2% YE and 1% feedstock. Feedstock was glucose, inverted glucose or corn stover. The invert sugar feedstock (Danisco Invert Sugar) was prepared by enzymatically treating sucrose syrup. AFEX corn stover was prepared as described below (Part V). The cells were grown at 30° C. and the first sample was measured when the cultures reached an $OD_{600}$~0.8-1.0 (0 hour). The cultures were analyzed for growth as measured by $OD_{600}$ and for isoprene production as in Example 1 at 0, 1 and 3 hours. Results are shown in FIG. 47.

V. Preparation of Hydrolysate from AFEX Pretreated Corn Stover

AFEX pretreated corn stover was obtained from Michigan Biotechnology Institute. The pretreatment conditions were 60% moisture, 1:1 ammonia loading, and 90° C. for 30 minutes, then air dried. The moisture content in the AFEX pretreated corn stover was 21.27%. The contents of glucan and xylan in the AFEX pretreated corn stover were 31.7% and 19.1% (dry basis), respectively. The saccharification process was as follows; 20 g of AFEX pretreated corn stover was added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for bread-making industry), and 72.65 ml of DI water. The flask was put in an orbital shaker and incubated at 50° C. for 96 hours. One sample was taken from the shaker and analyzed using HPLC. The hydrolysate contained 38.5 g/l of glucose, 21.8 g/l of xylose, and 10.3 g/l of oligomers of glucose and/or xylose.

VI. The Effect of Yeast Extract on Isoprene Production in *E. coli* Grown in Fed-Batch Culture Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 48A). The isoprene level in the off-gas from the fermentor was determined as previously described. The isoprene titer increased over the course of the fermentation (FIG. 48B). The amount of isoprene produced was linearly proportional to the amount of fed yeast extract (FIG. 48C).

VII. Production of Isoprene in 500 L Fermentation of pTrcKudzu DXS yIDI

A 500 liter fermentation of *E. coli* cells with a kudzu isoprene synthase, *S. cerevisiae* IDI, and *E. coli* DXS nucleic acids (*E. coli* BL21 (λDE3) pTrc Kudzu dxs yidi) was used to produce isoprene. The levels of isoprene varied from 50 to 300 µg/L over a time period of 15 hours. On the basis of the average isoprene concentrations, the average flow through the device and the extent of isoprene breakthrough, the amount of isoprene collected was calculated to be approximately 17 g.

VIII. Production of Isoprene in 500 L Fermentation of *E. coli* Grown in Fed-Batch Culture Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium gas ($NH_3$) and q.s. to volume. Glucose 10 g, thiamine*HCl 0.1 g, and antibiotic were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in DI $H_2O$, pH to 3.0 with HCl/NaOH, then q.s. to volume and filter sterilized with 0.22 micron filter.

Fermentation was performed in a 500-L bioreactor with *E. coli* cells containing the pTrcKudzu yIDI DXS plasmid. This experiment was carried out to monitor isoprene formation from glucose and yeast extract at the desired fermentation pH 7.0 and temperature 30° C. An inoculum of *E. coli* strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Figure 49A:
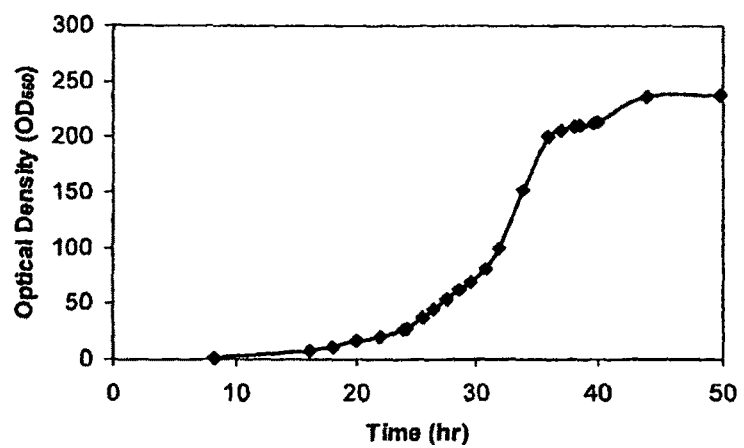
FIG. 49 shows graphs demonstrating isoprene production from a 500 L bioreactor with *E. coli* cells containing the pTrcKudzu+yIDI+DXS plasmid. Panel A shows the time course of optical density within the 500-L bioreactor fed with glucose and yeast extract. Panel B shows the time course of isoprene titer within the 500-L bioreactor fed with glucose and yeast extract. The titer is defined as the amount of isoprene produced per liter of fermentation broth. Panel C shows the time course of total isoprene produced from the 500-L bioreactor fed with glucose and yeast extract.
Figure 49B:
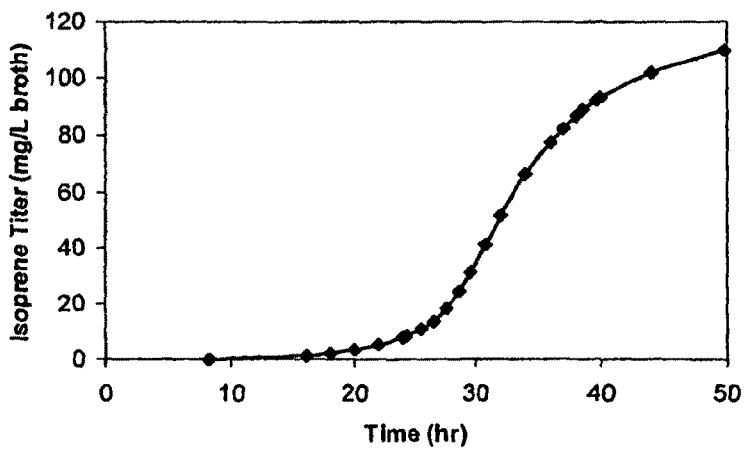
Figure 49C:
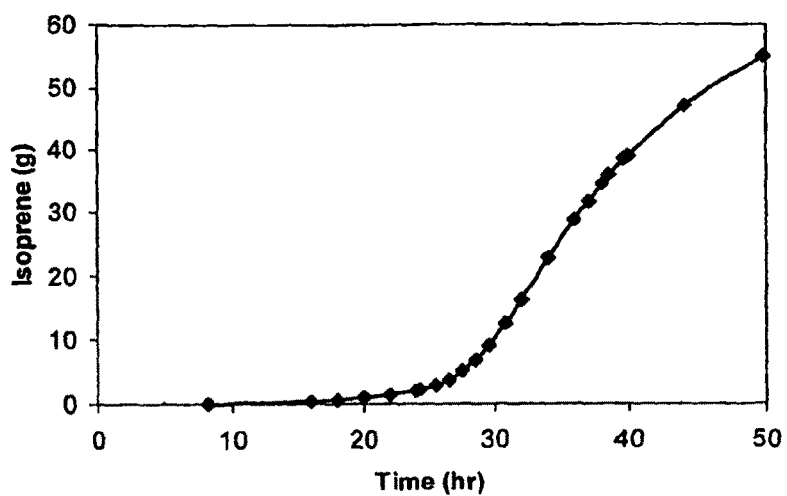

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 49A. The isoprene level in the off-gas from the bioreactor was determined as previously described. The isoprene titer increased over the course of the fermentation (FIG. 49B). The total amount of isoprene produced during the 50 hour fermentation was 55.1 g and the time course of production is shown in FIG. 49C.

Example 8

Production of Isoprene in *E. coli* Expressing Kudzu Isoprene Synthase and Recombinant Mevalonic Acid Pathway Genes I. Cloning the Lower MVA Pathway The strategy for cloning the lower mevalonic pathway was as follows. Four genes of the mevalonic acid biosynthesis pathway; mevalonate kinase (MVK), phosphomevalonate kinase (PMK), diphosphomevalonte decarboxylase (MVD) and isopentenyl diphosphate isomerase genes were amplified by PCR from *S. cerevisiae* chromosomal DNA and cloned individually into the pCR BluntII TOPO plasmid (Invitrogen). In some cases, the idi gene was amplified from *E. coli* chromosomal DNA. The primers were designed such that an *E. coli* consensus RBS (AGGAGGT (SEQ ID NO:80) or AAGGAGG (SEQ ID NO:81)) was inserted at the 5' end, 8 by upstream of the start codon and a PstI site was added at the 3' end. The genes were then cloned one by one into the pTrcHis2B vector until the entire pathway was assembled.

Chromosomal DNA from *S. cerevisiae* S288C was obtained from ATCC (ATCC 204508D). The MVK gene was amplified from the chromosome of *S. cerevisiae* using primers MVKF (5'-AGGAGGTAAAAAAACATGTCATTAC-CGTTCTTAACTTCTGC, SEQ ID NO:21) and MVK-PstI-R (5'-ATGGCTGCAGGCCTATCGCAAATTAGCT-TATGAAGTCCATGGTAAATTCGTG, SEQ ID NO:22) using PfuTurbo as per manufacturer's instructions. The correct sized PCR product (1370 bp) was identified by electrophoresis through a 1.2% E-gel (Invitrogen) and cloned into pZeroBLUNT TOPO. The resulting plasmid was designated pMVK1. The plasmid pMVK1 was digested with SadI and TaqI restriction endonucleases and the fragment was gel purified and ligated into pTrcHis2B digested with SadI and BstBI. The resulting plasmid was named pTrcMVK1.

The second gene in the mevalonic acid biosynthesis pathway, PMK, was amplified by PCR using primers: PstI-PMK1 R (5'-GAATTCGCCCTTCTGCAGCTACC, SEQ ID NO:23) and BsiHKA I-PMK1 F (5'-CGACTGGTGCAC-CCTTAAGGAGGAAAAAAACATGTCAG, SEQ ID NO:24). The PCR reaction was performed using Pfu Turbo polymerase (Stratagene) as per manufacturer's instructions. The correct sized product (1387 bp) was digested with PstI and BsiHKI and ligated into pTrcMVK1 digested with PstI. The resulting plasmid was named pTrcKK. The MVD and the idi genes were cloned in the same manner. PCR was carried out using the primer pairs PstI-MVD 1 R (5'-GTGCTG-GAATTCGCCCTTCTGCAGC, SEQ ID NO:25) and NsiI-MVD 1 F (5'-GTAGATGCATGCAGAATTCGCCCTTAAG-GAGG, SEQ ID NO:26) to amplify the MVD gene and PstI-YIDI 1 R (5'-CCTTCTGCAGGACGCGTTGTTATAGC, SEQ ID NO:27) and NsiI-YIDI 1 F (5'-CATCAATG-CATCGCCCTTAGGAGGTAAAAAAAAATGAC, SEQ ID NO:28) to amplify the yIDI gene. In some cases the IPP isomerase gene, idi from *E. coli* was used. To amplify idi from *E. coli* chromosomal DNA, the following primer set was used: PstI-CIDI 1 R (5'-GTGTGATGGATATCTGCAGAAT-TCG, SEQ ID NO:29) and NsiI-CIDI 1 F (5'-CATCAATG-CATCGCCCTTAGGAGGTAAAAAAACATG, SEQ ID NO:30). Template DNA was chromosomal DNA isolated by standard methods from *E. coli* FM5 (WO 96/35796 and WO 2004/033646, which are each hereby incorporated by reference in their entireties, particularly with respect to isolation of nucleic acids). The final plasmids were named pKKDIy for the construct encoding the yeast idi gene or pKKDIc for the construct encoding the *E. coli* idi gene. The plasmids were transformed into *E. coli* hosts BL21 for subsequent analysis. In some cases the isoprene synthase from kudzu was cloned into pKKDIy yielding plasmid pKKDIyIS.

The lower MVA pathway was also cloned into pTrc containing a kanamycin antibiotic resistance marker. The plasmid pTrcKKDIy was digested with restriction endonucleases ApaI and PstI, the 5930 by fragment was separated on a 1.2% agarose E-gel and purified using the Qiagen Gel Purification kit according to the manufacturer's instructions. The plasmid pTrcKudzuKan, described in Example 7, was digested with restriction endonucleases ApaI and PstI, and the 3338 by fragment containing the vector was purified from a 1.2% E-gel using the Qiagen Gel Purification kit. The 3338 by vector fragment and the 5930 by lower MVA pathway fragment were ligated using the Roche Quick Ligation kit. The ligation mix was transformed into *E. coli* TOP10 cells and tranformants were grown at 37° C. overnight with selection on LA containing kanamycin (50 μg/ml). The transformants were verified by restriction enzyme digestion and one was frozen as a stock. The plasmid was designated pTrcK-anKKDIy.

II. Cloning a Kudzu Isoprene Synthase Gene into pTrcK-anKKDIy

Figure 24:
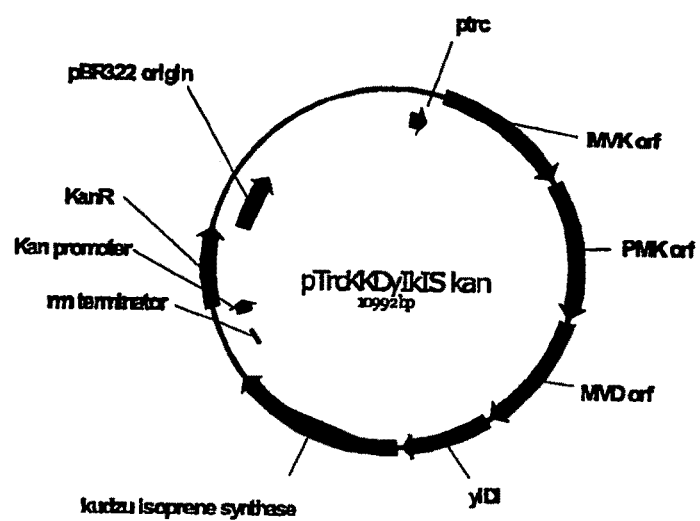
FIG. 24 is a map of pTrcKKDyIkIS kan.

The kudzu isoprene synthase gene was amplified by PCR from pTrcKudzu, described in Example 1, using primers MCM50 5'-GATCATGCATTCGCCCTTAGGAGG-TAAAAAAACATGTGTGCGACCTCTTCTCAA TTTACT (SEQ ID NO:31) and MCM53 5'-CGGTCGACGGATCCCT-GCAGTTAGACATACATCAGCTG (SEQ ID NO:32). The resulting PCR fragment was cloned into pCR2.1 and transformed into *E. coli* TOP10. This fragment contains the coding sequence for kudzu isoprene synthase and an upstream region containing a RBS from *E. coli*. Transformants were incubated overnight at 37° C. with selection on LA containing carbenicillin (50 μg/ml). The correct insertion of the fragment was verified by sequencing and this strain was designated MCM93. The plasmid from strain MCM93 was digested with restriction endonucleases NsiI and PstI to liberate a 1724 by insert containing the RBS and kudzu isoprene synthase. The 1724 by fragment was separated on a 1.2% agarose E-gel and purified using the Qiagen Gel Purification kit according to the manufacturer's instructions. Plasmid pTrcKanKKDIy was digested with the restriction endonuclease PstI, treated with SAP for 30 minutes at 37° C. and purified using the Qiagen PCR cleanup kit. The plasmid and kudzu isoprene synthase encoding DNA fragment were ligated using the Roche Quick Ligation kit. The ligation mix was transformed into *E. coli* TOP10 cells and transformants were grown overnight at 37° C. with selection on LA containing Kanamycin at 50 μg/ml. The correct transformant was verified by restriction digestion and the plasmid was designated pTrcKKDIyIkISKan (FIGS. 24 and 25). This plasmid was transformed into BL21(XDE3) cells (Invitrogen).

III. Isoprene Production from Mevalonate in *E. coli* Expressing the Recombinant Lower Mevalonate Pathway and Isoprene Synthase from Kudzu.

Strain BL21/pTrcKKDyIkISKan was cultured in MOPS medium (Neidhardt et al., (1974) *J. Bacteriology* 119:736-747) adjusted to pH 7.1 and supplemented with 0.5% glucose and 0.5% mevalonic acid. A control culture was also set up using identical conditions but without the addition of 0.5% mevalonic acid. The culture was started from an overnight seed culture with a 1% inoculum and induced with 500 μM IPTG when the culture had reached an $OD_{600}$ of 0.3 to 0.5. The cultures were grown at 30° C. with shaking at 250 rpm. The production of isoprene was analyzed 3 hours after induction by using the head space assay described in Example 1. Maximum production of isoprene was $6.67 \times 10^4$ nmol/$L_{broth}$/$OD_{600}$/hr where $L_{broth}$ is the volume of broth and includes both the volume of the cell medium and the volume of the cells. The control culture not supplemented with mevalonic acid did not produce measurable isoprene.

IV. Cloning the Upper MVA Pathway

The upper mevalonate biosynthetic pathway, comprising two genes encoding three enzymatic activities, was cloned from *Enterococcus faecalis*. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes second enzyme in the pathway, HMG-CoA synthase. The mvaE gene was amplified from *E. faecalis* genomic DNA (ATCC 700802D-5) with an *E. coli* ribosome binding site and a spacer in front using the following primers:

CF 07-60 (+) Start of mvaE w/ RBS + ATG start codon SacI
(SEQ ID NO: 34)
5'-GAGACATGAGCTCAGGAGGTAAAAAAACATGAAAACAGTAGTTAT
TATTG CF 07-62 (-) Fuse mvaE to mvaS with RBS in between
(SEQ ID NO: 35)
5'-TTTATCAATCCCAATTGTCATGTTTTTTTACCTCCTTTATTGTTT
TCTTAAATC The mvaS gene was amplified from *E. faecalis* genomic DNA (ATCC 700802D-5) with a RBS and spacer from *E. coli* in front using the following primers:

CF 07-61 (+) Fuse mvaE to mvaS with RBS in between
(SEQ ID NO: 36)
5'-GATTTAAGAAAACAATAAAGGAGGTAAAAAAACATGACAATTGGG
ATTGATAAA CF 07-102 (-) End of mvaS gene BglII
(SEQ ID NO: 37)
5'-GACATGACATAGATCTTTAGTTTCGATAAGAACGAACGGT The PCR fragments were fused together with PCR using the following primers:

CF 07-60 (+) Start of mvaE w/ RBS + ATG start codon SacI
(SEQ ID NO: 34)
5'-GAGACATGAGCTCAGGAGGTAAAAAAACATGAAAACAGTAGTTAT
TATTG CF 07-102 (-) End of mvaS gene BglII
(SEQ ID NO: 37)
5'-GACATGACATAGATCTTTAGTTTCGATAAGAACGAACGGT The fusion PCR fragment was purified using a Qiagen kit and digested with the restriction enzymes SacI and BglII. This digested DNA fragment was gel purified using a Qiagen kit and ligated into the commercially available vector pTrcHis2A, which had been digested with SacI and BglII and gel purified.

The ligation mix was transformed into *E. coli* Top 10 cells and colonies were selected on LA and 50 µg/ml carbenicillin plates. A total of six colonies were chosen and grown overnight in LB and 50 µg/ml carbenicillin and plasmids were isolated using a Qiagen kit. The plasmids were digested with SacI and BglII to check for inserts and one correct plasmid was sequenced with the following primers:

CF 07-58 (+) Start of mvaE gene
(SEQ ID NO: 38)
5'-ATGAAAACAGTAGTTATTATTGATGC

CF 07-59 (-) End of mvaE gene
(SEQ ID NO: 39)
5'-ATGTTATTGTTTTCTTAAATCATTTAAAATAGC CF 07-82 (+) Start of mvaS gene
(SEQ ID NO: 40)
5'-ATGACAATTGGGATTGATAAAATTAG CF 07-83 (-) End of mvaS gene
(SEQ ID NO: 41)
5'-TTAGTTTCGATAAGAACGAACGGT CF 07-86 (+) Sequence in mvaE
(SEQ ID NO: 42)
5'-GAAATAGCCCCATTAGAAGTATC CF 07-87 (+) Sequence in mvaE
(SEQ ID NO: 43)
5'-TTGCCAATCATATGATTGAAAATC CF 07-88 (+) Sequence in mvaE
(SEQ ID NO: 44)
5'-GCTATGCTTCATTAGATCCTTATCG CF 07-89 (+) Sequence mvaS
(SEQ ID NO: 45)
5'-GAAACCTACATCCAATCTTTTGCCC The plasmid called pTrcHis2AUpperPathway#1 was correct by sequencing and was transformed into the commercially available *E. coli* strain BL21. Selection was done on LA and 50 µg/ml carbenicillin. Two transformants were chosen and grown in LB and 50 µg/ml carbenicillin until they reached an $OD_{600}$ of 1.5. Both strains were frozen in a vial at –80° C. in the presence of glycerol. Strains were designated CF 449 for pTrcHis2AUpperPathway#1 in BL21, isolate #1 and CF 450 for pTrcHis2AUpperPathway#1 in BL21, isolate #2. Both clones were found to behave identically when analyzed.

V. Cloning of UpperMVA Pathway into pCL1920

Figure 26:
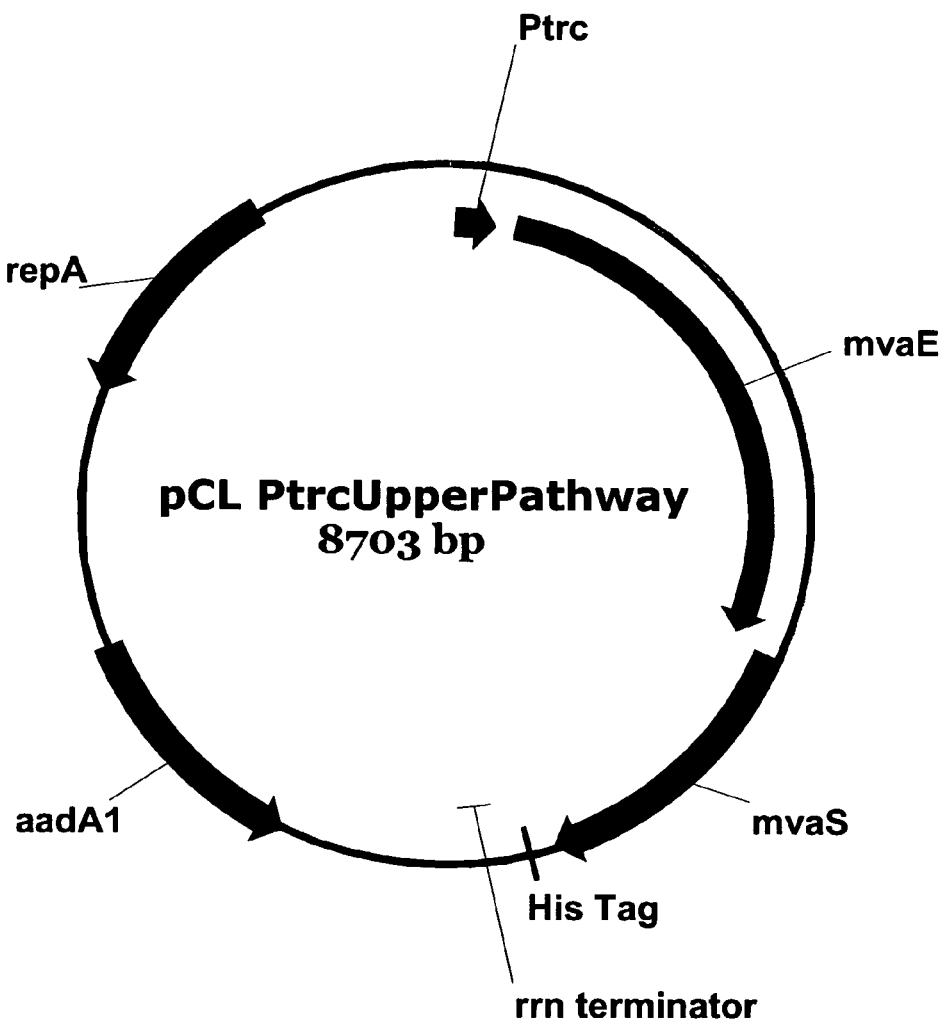
FIG. 26 is a map of pCL PtrcUpperPathway.

The plasmid pTrcHis2AUpperPathway was digested with the restriction endonuclease SspI to release a fragment containing pTrc-mvaE-mvaS-(His tag)-terminator. In this fragment, the his-tag was not translated. This blunt ended 4.5 kbp fragment was purified from a 1.2% E-gel using the Qiagen Gel Purification kit. A dephosphorylated, blunt ended 4.2 kbp fragment from pCL1920 was prepared by digesting the vector with the restriction endonuclease PvuII, treating with SAP and gel purifying from a 1.2% E-gel using the Qiagen Gel Purification kit. The two fragments were ligated using the Roche Quick Ligation Kit and transformed into TOP10 chemically competent cells. Transformants were selected on LA containing spectinomycin (50 µg/ml). A correct colony was identified by screening for the presence of the insert by PCR. The plasmid was designated pCL PtrcUpperPathway (FIGS. 26 and 27).

VI. Strains Expressing the Combined Upper and Lower Mevalonic Acid Pathways

To obtain a strain with a complete mevalonic acid pathway plus kudzu isoprene synthase, plasmids pTrcKKDyIkISkan and pCLpTrcUpperPathway were both transformed into BL21(λDE3) competent cells (Invitrogen) and transformants were selected on LA containing kanamycin (50 µg/ml) and Spectinomycin (50 µg/ml). The transformants were checked by plasmid prep to ensure that both plasmids were retained in the host. The strain was designated MCM127.

VII. Production of Mevalonic Acid from Glucose in *E. coli*/pUpperpathway

Single colonies of the BL21/pTrcHis2A-mvaE/mvaS or FM5/p pTrcHis2A-mvaE/mvaS are inoculated into LB and carbenicillin (100 µg/ml) and are grown overnight at 37° C. with shaking at 200 rpm. These cultures were diluted into 50 ml medium in 250 ml baffled flasks to an $OD_{600}$ of 0.1. The medium was TM3, 1 or 2% glucose, carbenicillin (100 ug/ml) or TM3, 1% glucose. hydrolyzed soy oil, and carbenicillin (100 ug/ml) or TM3 and biomass (prepared bagasse, corn stover or switchgrass). Cultures were grown at 30° C. with shaking at 200 rpm for approximately 2-3 hours until an $OD_{600}$ of 0.4 was reached. At this point the expression from the mvaE mvaS construct was induced by the addition of IPTG (400 µM). Cultures were incubated for a further 20 or 40 hours with samples taken at 2 hour intervals to 6 hour post induction and then at 24, 36 and 48 hours as needed. Sampling was done by removing 1 ml of culture, measuring the $OD_{600}$, pelleting the cells in a microfuge, removing the supernatant and analyzing it for mevalonic acid.

A 14 liter fermentation of *E. coli* cells with nucleic acids encoding *Enterococcus faecalis* AA-CoA thiolase, HMG- CoA synthase, and HMG-CoA reductase polypeptides produced 22 grams of mevalonic acid with TM3 medium and 2% glucose as the cell medium. A shake flask of these cells produced 2-4 grams of mevalonic acid per liter with LB medium and 1% glucose as the cell culture medium. The production of mevalonic acid in these strains indicated that the MVA pathway was functional in *E. coli*.

VIII. Production of Isoprene from *E. coli* BL21 Containing the Upper and Lower MVA Pathway Plus Kudzu Isoprene Synthase.

The following strains were created by transforming in various combinations of plasmids containing the upper and lower MVA pathway and the kudzu isoprene synthase gene as described above and the plasmids containing the idi, dxs, and dxr and isoprene synthase genes described in Example 7. The host cells used were chemically competent BL21(λDE3) and the transformations were done by standard methods. Transformants were selected on L agar containing kanamycin (50 μg/ml) or kanamycin plus spectinomycin (both at a concentration of 50 μg/ml). Plates were grown at 37° C. The resulting strains were designated as follows:

Grown on Kanamycin Plus Spectinomycin (50 μg/ml each)
MCM127—pCL Upper MVA and pTrcKKDyIkIS (kan) in BL21(λDE3)
MCM131—pCL1920 and pTrcKKDyIkIS (kan) in BL21 (λDE3)
MCM125—pCL Upper MVA and pTrcHis2B (kan) in BL21 (λDE3)

Grown on Kanamycin (50 μg/ml)
MCM64—pTrcKudzu yIDI DXS (kan) in BL21(λDE3)
MCM50—pTrcKudzu (kan) in BL21(λDE3)
MCM123—pTrcKudzu yIDI DXS DXR (kan) in BL21 (λDE3)

The above strains were streaked from freezer stocks to LA and appropriate antibiotic and grown overnight at 37° C. A single colony from each plate was used to inoculate shake flasks (25 ml LB and the appropriate antibiotic). The flasks were incubated at 22° C. overnight with shaking at 200 rpm. The next morning the flasks were transferred to a 37° C. incubator and grown for a further 4.5 hours with shaking at 200 rpm. The 25 ml cultures were centrifuged to pellet the cells and the cells were resuspended in 5 ml LB and the appropriate antibiotic. The cultures were then diluted into 25 ml LB, % glucose, and the appropriate antibiotic to an $OD_{600}$ of 0.1. Two flasks for each strain were set up, one set for induction with IPTG (800 μM) the second set was not induced. The cultures were incubated at 37° C. with shaking at 250 rpm. One set of the cultures were induced after 1.50 hours (immediately following sampling time point 1). At each sampling time point, the $OD_{600}$ was measured and the amount of isoprene determined as described in Example 1. Results are presented in Table 3. The amount of isoprene made is presented as the amount at the peak production for the particular strain.

TABLE 3

Production of isoprene in *E. coli* strains

| Strain | Isoprene ($\mu g/L_{broth}$/hr/OD) |
| --- | --- |
| MCM50 | 23.8 |
| MCM64 | 289 |
| MCM125 | ND |
| MCM131 | Trace |
| MCM127 | 874 |

ND: not detected
Trace: peak present but not integrable.

IX. Analysis of Mevalonic Acid

Mevalonolactone (1.0 g, 7.7 mmol) (CAS# 503-48-0) was supplied from Sigma-Aldrich (WI, USA) as a syrup that was dissolved in water (7.7 mL) and was treated with potassium hydroxide (7.7 mmol) in order to generate the potassium salt of mevalonic acid. The conversion to mevalonic acid was confirmed by $^1$H NMR analysis. Samples for HPLC analysis were prepared by centrifugation at 14,000 rpm for 5 minutes to remove cells, followed by the addition of a 300 μl aliquot of supernatant to 900 μl of $H_2O$. Perchloric acid (36 μl of a 70% solution) was then added followed by mixing and cooling on ice for 5 minutes. The samples were then centrifuged again (14,000 rpm for 5 min) and the supernatant transferred to HPLC. Mevalonic acid standards (20, 10, 5, 1 and 0.5 g/L) were prepared in the same fashion. Analysis of mevalonic acid (20 uL injection volume) was performed by HPLC using a BioRad Aminex 87-H+ column (300 mm by 7.0 mm) eluted with 5 mM sulfuric acid at 0.6 mL/min with refractive index (RI) detection. Under these conditions mevalonic acid eluted as the lactone form at 18.5 minutes.

Example 9

Construction of the Upper and Lower MVA Pathway for Integration into *Bacillus subtilis*

I. Construction of the Upper MVA Pathway in *Bacillus subtilis*

The upper pathway from *Enterococcus faecalis* is integrated into *B. subtilis* under control of the aprE promoter. The upper pathway consists of two genes; mvaE, which encodes for AACT and HMGR, and mvaS, which encodes for HMGS. The two genes are fused together with a stop codon in between, an RBS site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allow them to be fused together by a PCR reaction. PCR amplifications are carried out using Herculase polymerase according to manufacturer's instructions.

1: PaprE
CF 07-134 (+) Start of aprE promoter PstI
(SEQ ID NO: 82)
5'-GACATCTGCAGCTCCATTTTCTTCTGC CF 07-94 (-) Fuse PaprE to mvaE
(SEQ ID NO: 83)
5'-CAATAATAACTACTGTTTTCACTCTTTACCCTCTCCTTTTAA Template: *Bacillus subtilis* chromosomal DNA 2: mvaE
CF 07-93 (+) fuse mvaE to the aprE promoter (GTG start codon)
(SEQ ID NO: 84)

```
-continued
5'-TTAAAAGGAGAGGGTAAAGAGTGAAAACAGTAGTTATTATTG

CF 07-62 (-) Fuse mvaE to mvaS with RBS in
between
                                   (SEQ ID NO: 35)
5'-TTTATCAATCCCAATTGTCATGTTTTTTTACCTCCTTTATTGTTT
TCTTAAATC Template: Enterococcus faecalis chromosomal DNA
(from ATCC)

3. mvaS
CF 07-61 (+) Fuse mvaE to mvaS with RBS in
between
                                   (SEQ ID NO: 36)
5'-GATTTAAGAAAACAATAAAGGAGGTAAAAAAACATGACAATTGGG
ATTGATAAA CF 07-124 (-) Fuse the end of mvaS to the
terminator
                                   (SEQ ID NO: 85)
5'-CGGGGCCAAGGCCGGTTTTTTTTAGTTTCGATAAGAACGAACGGT Template: Enterococcus faecalis chromosomal DNA 4. B. amyliquefaciens alkaline serine protease
terminator CF 07-123 (+) Fuse the end of mvaS to the
terminator
                                   (SEQ ID NO: 86)
5'-ACCGTTCGTTCTTATCGAAACTAAAAAAAACCGGCCTTGGCCCCG CF 07-46 (-) End of B. amyliquefaciens terminator
BamHI
                                   (SEQ ID NO: 63)
5'-GACATGACGGATCCGATTACGAATGCCGTCTC Template: Bacillus amyliquefaciens chromosomal
DNA PCR Fusion Reactions 5. Fuse mvaE to mvaS
CF 07-93 (+) fuse mvaE to the aprE promoter
(GTG start codon)
                                   (SEQ ID NO: 84)
5'-TTAAAAGGAGAGGGTAAAGAGTGAAAACAGTAGTTATTATTG CF 07-124 (-) Fuse the end of mvaS to the
terminator
                                   (SEQ ID NO: 85)
5'-CGGGGCCAAGGCCGGTTTTTTTTAGTTTCGATAAGAACGAACGGT Template: #2 and 3 from above 6. Fuse mvaE-mvaS to aprE promoter
CF 07-134 (+) Start of aprE promoter PstI
                                   (SEQ ID NO: 82)
5'-GACATCTGCAGCTCCATTTTCTTCTGC CF 07-124 (-) Fuse the end of mvaS to the
terminator
                                   (SEQ ID NO: 85)
5'-CGGGGCCAAGGCCGGTTTTTTTTAGTTTCGATAAGAACGAACGGT Template #1 and #4 from above 7. Fuse PaprE-mvaE-mvaS to terminator
CF 07-134 (+) Start of aprE promoter PstI
                                   (SEQ ID NO: 82)
5'-GACATCTGCAGCTCCATTTTCTTCTGC CF 07-46 (-) End of B. amyliquefaciens terminator
BamHI
                                   (SEQ ID NO: 63)
5'-GACATGACGGATCCGATTACGAATGCCGTCTC Template: #4 and #6
```

Figure 50:
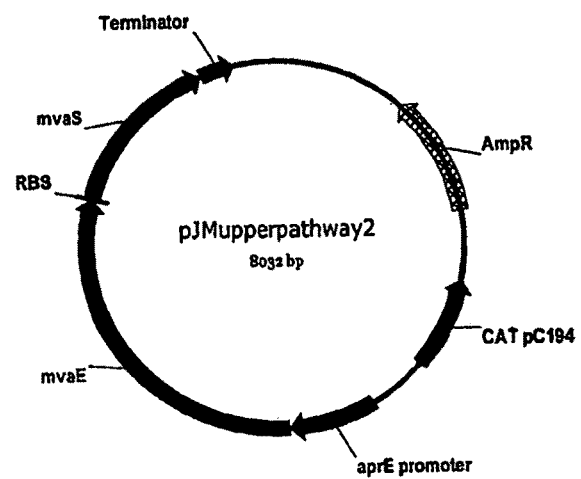
FIG. 50 is a map of pJMupperpathway2.

The product is digested with restriction endonucleases PstI/BamHI and ligated to pJM102 (Perego, M. 1993. Integrational vectors for genetic manipulation in *Bacillus subtilis*, p. 615-624. In A. L. Sonenshein, J. A. Hoch, and R. Losick (ed.), *Bacillus subtilis* and other gram-positive bacteria: biochemistry, physiology, and molecular genetics. American Society for Microbiology, Washington, D.C.) which is digested with PstI/BamHI. The ligation is transformed into *E. coli* TOP 10 chemically competent cells and transformants are selected on LA containing carbenicillin (50 µg/ml). The correct plasmid is identified by sequencing and is designated pJMUpperpathway2 (FIGS. 50 and 51). Purified plasmid DNA is transformed into *Bacillus subtilis* aprEnprE PxylcomK and transformants are selected on L agar containing chloramphenicol (5 µg/ml). A correct colony is selected and is plated sequentially on L agar containing chloramphenicol 10, 15 and 25 µg/ml to amplify the number of copies of the cassette containing the upper pathway.

The resulting strain is tested for mevalonic acid production by growing in LB containing 1% glucose and 1%. Cultures are analyzed by GC for the production of mevalonic acid.

This strain is used subsequently as a host for the integration of the lower mevalonic acid pathway.

The following primers are used to sequence the various constructs above.

```
Sequencing primers:

CF 07-134 (+) Start of aprE promoter PstI
                                   (SEQ ID NO: 82)
5'-GACATCTGCAGCTCCATTTTCTTCTGC CF 07-58 (+) Start of mvaE gene
                                   (SEQ ID NO: 38)
5'-ATGAAAACAGTAGTTATTATTGATGC CF 07-59 (-) End of mvaE gene
                                   (SEQ ID NO: 39)
5'-ATGTTATTGTTTTCTTAAATCATTTAAAATAGC CF 07-82 (+) Start of mvaS gene
                                   (SEQ ID NO: 40)
5'-ATGACAATTGGGATTGATAAAATTAG CF 07-83 (-) End of mvaS gene
                                   (SEQ ID NO: 41)
5'-TTAGTTTCGATAAGAACGAACGGT CF 07-86 (+) Sequence in mvaE
                                   (SEQ ID NO: 42)
5'-GAAATAGCCCCATTAGAAGTATC CF 07-87 (+) Sequence in mvaE
                                   (SEQ ID NO: 43)
5'-TTGCCAATCATATGATTGAAAATC CF 07-88 (+) Sequence in mvaE
                                   (SEQ ID NO: 44)
5'-GCTATGCTTCATTAGATCCTTATCG CF 07-89 (+) Sequence mvaS
                                   (SEQ ID NO: 45)
5'-GAAACCTACATCCAATCTTTTGCCC
```

Transformants are selected on LA containing chloramphenicol at a concentration of 5 µg/ml. One colony is confirmed to have the correct integration by sequencing and is plated on LA containing increasing concentrations of chloramphenicol over several days, to a final level of 25 µg/ml. This results in amplification of the cassette containing the genes of interest. The resulting strain is designated CF 455: pJMupperpathway#1×*Bacillus subtilis* aprEnprE Pxyl comK (amplified to grow on LA containing chloramphenicol 25 µg/ml).

II. Construction of the Lower MVA Pathway in *Bacilus subtilis*

Figure 28:
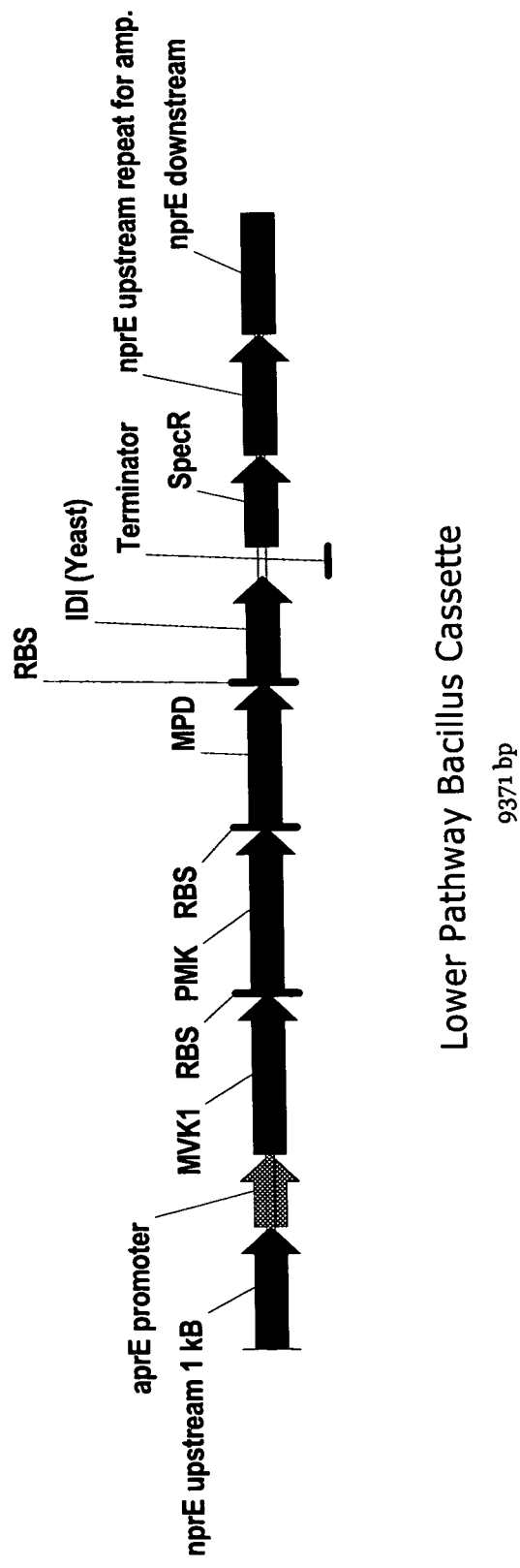
FIG. 28 shows a map of the cassette containing the lower MVA pathway and yeast idi for integration into the *B. subtilis* chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonte kinase gene with a *Bacillus* RBS upstream of the start site. RBS-MPD indicates the yeast diphosphomevalonate decarboxylase gene with a *Bacillus* RBS upstream of the start site. RBS-IDI indicates the yeast idi gene with a *Bacillus* RBS upstream of the start site. Terminator indicates the terminator alkaline serine protease transcription terminator from *B. amyliquefaciens*. SpecR indicates the spectinomycin resistance marker. "nprE upstream repeat for amp." indicates a direct repeat of the upstream region used for amplification.

The lower MVA pathway, consisting of the genes mvk1, pmk, mpd and idi are combined in a cassette consisting of flanking DNA regions from the nprE region of the *B. subtilis* chromosome (site of integration), the aprE promoter, and the spectinomycin resistance marker (see FIGS. 28 and 29). This cassette is synthesized by DNA2.0 and is integrated into the chromosome of *B. subtilis* containing the upper MVA pathway integrated at the aprE locus. The kudzu isoprene synthase gene is expressed from the replicating plasmid described in Example 4 and is transformed into the strain with both upper and lower pathways integrated.

Example 10

Production of Isoprene in *E. coli* Expressing *M. mazei* Mevalonate Kinase and *P. alba* Isoprene Synthase I. Construction of Vectors and Strains Encoding *M. mazei* Mevalonate Kinase (MVK) and *P. alba* Isoprene Synthase
(i) Construction of Strain EWL201 (BL21, Cm-GI1.2-KKDyI)

*E. coli* BL21 (Novagen brand, EMD Biosciences, Inc.) was a recipient strain, transduced with MCM331 P1 lysate (lysate prepared according to the method described in Ausubel, et al., Current Protocols in Molecular Biology. John Wiley and Sons, Inc.). Transductants were selected for by spreading cells onto L Agar and 20 µg/µl chloramphenicol. The plates were incubated overnight at 30° C. Analysis of transductants showed no colonies on control plates (water+cells control plate for reversion and water and P1 lysate control plate for lysate contamination.

Four transductants were picked and used to inoculate 5 mL L Broth and 20 µg/µl chloramphenicol. The cultures were grown overnight at 30° C. with shaking at 200 rpm. To make genomic DNA preps of each transductant for PCR analysis, 1.5 mL of overnight cell culture were centrifuged. The cell pellet was resuspended with 400 µl Resuspension Buffer (20 mM Tris, 1 mM EDTA, 50 mM NaCl, pH 7.5) and 4 µl RNase, DNase-free (Roche) was added. The tubes were incubated at 37° C. for 30 minutes followed by the addition of 4 µl 10% SDS and 4 µl of 10 mg/ml Proteinase K stock solution (Sigma-Aldrich). The tubes were incubated at 37° C. for 1 hour. The cell lysate was transferred into 2 ml Phase Lock Light Gel tubes (Eppendorf) and 200 µl each of saturated phenol pH7.9 (Ambion Inc.) and chloroform were added. The tubes were mixed well and microcentrifuged for 5 minutes. A second extraction was done with 400 µl chloroform and the aqueous layer was transferred to a new eppendorf tube. The genomic DNA was precipitated by the addition of 1 ml of 100% ethanol and centrifugation for 5 minutes. The genomic DNA pellet was washed with 1 ml 70% ethanol. The ethanol was removed and the genomic DNA pellet was allowed to air dry briefly. The genomic DNA pellet was resuspended with 200 µl TE.

Using Pfu Ultra II DNA polymerase (Stratagene) and 200 ng/µl of genomic DNA as template, 2 different sets of PCR reaction tubes were prepared according to manufacturer's protocol. For set 1, primers MCM130 and GB Cm-Rev (Table 4) were used to ensure transductants were successfully integrated into the attTn7 locus. PCR parameters for set 1 were 95° C. for 2 minutes (first cycle only), 95° C. for 25 seconds, 55° C. for 25 seconds, 72° C. for 25 seconds (repeat steps 2-4 for 28 cycles), 72° C. for 1 minute. For set 2, primers MVD For and MVD Rev (Table 4) were used to ensure that the gi1.2-KKDyI operon integrated properly. PCR parameters for set 2 were 95° C. for 2 minutes (first cycle only), 95° C. for 25 seconds, 55° C. for 25 seconds, 72° C. for 10 seconds (repeat steps 2-4 for 28 cycles), 72° C. for 1 minute. Analysis of PCR amplicons on a 1.2% E-gel (Invitrogen Corp.) showed that all 4 transductant clones were correct (picked one and designated as strain EWL201).
ii) Construction of Strain EWL204 (BL21, loopout-GI1.2-KKDyI)

The chloramphenicol marker was looped out of strain EWL201 using plasmid pCP20 as described by Datsenko and Wanner (2000) (Datsenko et al., *Proc Natl. Acad. Sci.* USA 97:6640-6645, 2000). One-step inactivation of chromosomal genes in *Escherichia coli* K-12 using PCR products. (Datsenko et al., *PNAS*, 97: 6640-6645, 2000). EWL201 cells were grown in L Broth to midlog phase and then washed three times in ice-cold, sterile water. An aliquot of 50 µl of cell suspension was mixed with 1 µl of pCP20 and the cell suspension mixture was electroporated in a 2 mm cuvette (Invitrogen Corp.) at 2.5 Volts and 25 uFd using a Gene Pulser Electroporator (Bio-Rad Inc.). 1 ml of LB was immediately added to the cells, then transferred to a 14 ml polypropylene tube (Sarstedt) with a metal cap.

Cells were allowed to recover by growing for 1 hour at 30° C. Transformants were selected on L Agar and 20 µg/µl chloramphenicol and 50 µg/µl carbenicillin and incubated at 30° C. overnight. The next day, a single clone was grown in 10 ml L Broth and 50 µg/µl carbenicillin at 30° C. until early log phase. The temperature of the growing culture was then shifted to 42° C. for 2 hours. Serial dilutions were made, the cells were then spread onto LA plates (no antibiotic selection), and incubated overnight at 30° C. The next day, 20 colonies were picked and patched onto L Agar (no antibiotics) and LA and 20 µg/µl chloramphenicol plates. Plates were then incubated overnight at 30° C. Cells able to grow on LA plates, but not LA and 20 µg/µl chloramphenicol plates, were deemed to have the chloramphenicol marker looped out (picked one and designated as strain EWL204).
iii) Construction of Plasmid pewl230 (pTrc *P. alba*)

Figure 54:
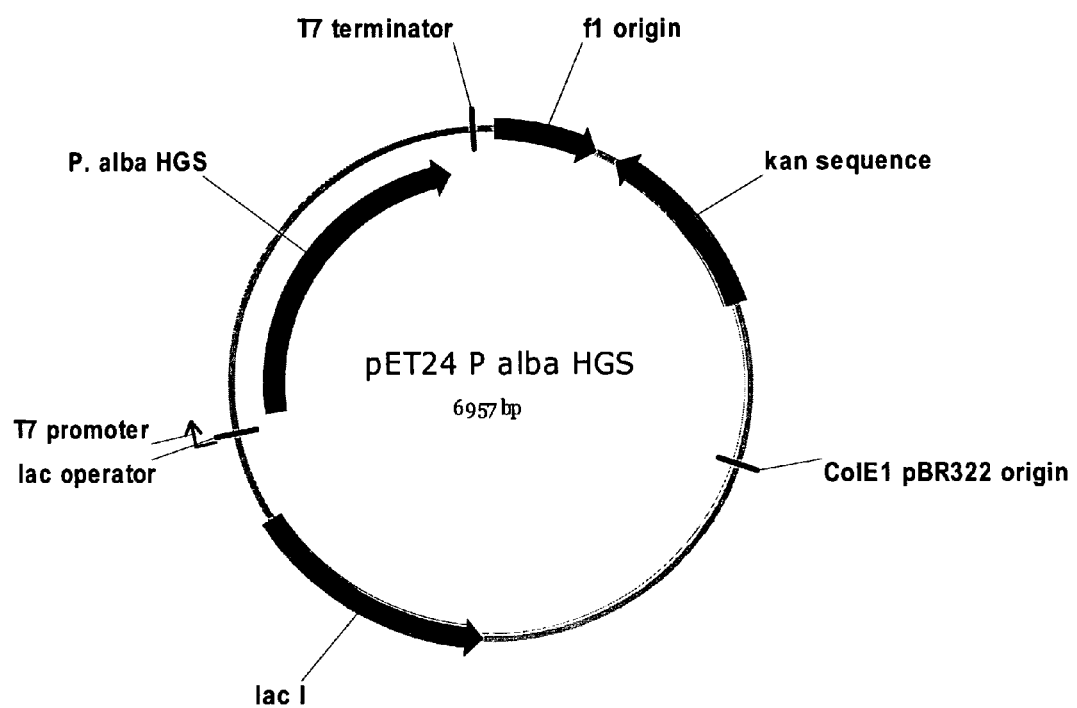
FIG. 54 is a map of plasmid pET24 *P. alba* HGS.

Generation of a synthetic gene encoding *Populus alba* isoprene synthase (*P. alba* HGS) was outsourced to DNA2.0 Inc. (Menlo Park, Calif.) based on their codon optimization method for *E. coli* expression. The synthetic gene was custom cloned into plasmid pET24a (Novagen brand, EMD Biosciences, Inc.) and delivered lyophilized (FIGS. 54, 55A and 55B).

A PCR reaction was performed to amplify the *P. alba* isoprene synthase (*P. alba* HGS) gene using pET24 *P. alba* HGS as the template, primers MCM182 and MCM192, and Herculase II Fusion DNA polymerase (Stratagene) according to manufacturer's protocol. PCR conditions were as follows: 95° C. for 2 minutes (first cycle only), 95° C. for 25 seconds, 55° C. for 20 seconds, 72° C. for 1 minute, repeat for 25 cycles, with final extension at 72° C. for 3 minutes. The *P. alba* isoprene synthase PCR product was purified using QIAquick PCR Purification Kit (Qiagen Inc.).

Figure 56:
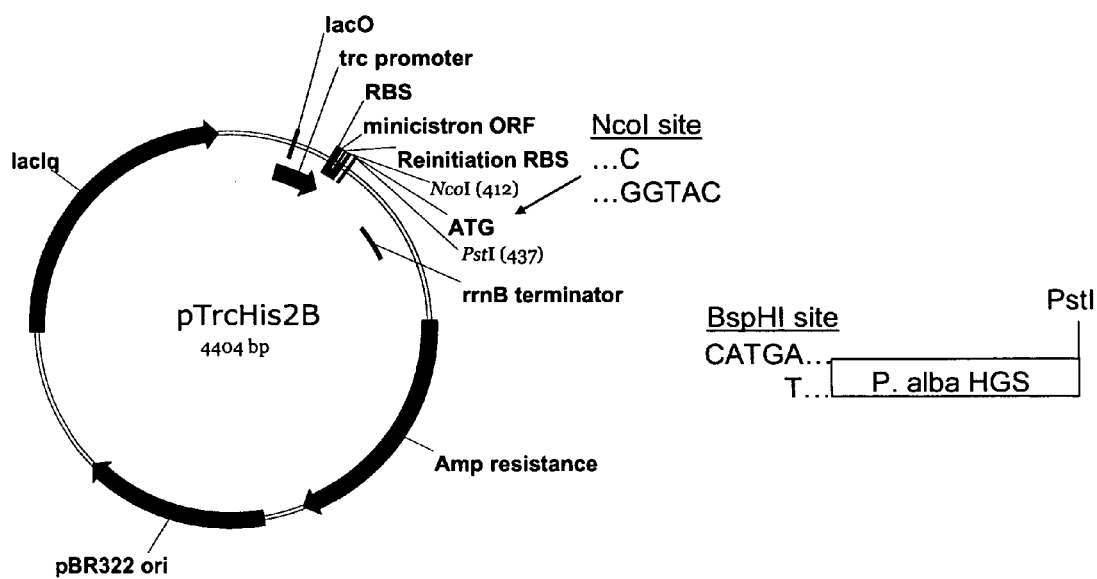
FIG. 56 is a schematic diagram showing restriction sites used for endonuclease digestion to construct plasmid EWL230 and compatible cohesive ends between BspHI and NcoI sites.

*P. alba* isoprene synthase PCR product was then digested in a 20 µl reaction containing 1 µl BspHI endonuclease (New England Biolabs) with 2 µl 10×NEB Buffer 4. The reaction was incubated for 2 hours at 37° C. The digested PCR fragment was then purified using the QIAquick PCR Purification Kit. A secondary restriction digest was performed in a 20 µl reaction containing 1 µl PstI endonuclease (Roche) with 2 µl 10× Buffer H. The reaction was incubated for 2 hours at 37° C. The digested PCR fragment was then purified using the QIAquick PCR Purification Kit. Plasmid pTrcHis2B (Invitrogen Corp.) was digested in a 20 µl reaction containing 1 µl NcoI endonuclease (Roche), 1 µl PstI endonuclease, and 2 µl 10× Buffer H. The reaction was incubated for 2 hours at 37° C. The digested pTrcHis2B vector was gel purified using a 1.2% E-gel (Invitrogen Corp.) and extracted using the QIAquick Gel Extraction Kit (Qiagen) (FIG. 56). Using the compatible cohesive ends of BspHI and NcoI sites, a 20 µl ligation reaction was prepared containing 5 µl *P. alba* isoprene synthase insert, 2 µl pTrc vector, 1 µl T4 DNA ligase (New England Biolabs), 2 µl 10× ligase buffer, and 10 µl ddH₂O. The ligation mixture was incubated at room temperature for 40 minutes. The ligation mixture was desalted by floating a 0.025 µm nitrocellulose membrane filter (Millipore) in a petri dish of ddH₂O and applying the ligation mixture gently on top of the nitrocellulose membrane filter for 30 minutes at room temperature. MCM446 cells (See section II) were grown in LB to midlog phase and then washed three times in ice-cold, sterile water. An aliquot of 50 µl of cell suspension was mixed with 5 µl of desalted pTrc *P. alba* HGS ligation mix. The cell suspension mixture was electroporated in a 2 mm cuvette at 2.5 Volts and 25 uFd using a Gene Pulser Electroporator. 1 ml of LB is immediately added to the cells, then transferred to a 14 ml polypropylene tube (Sarstedt) with a metal cap.

Figure 57:
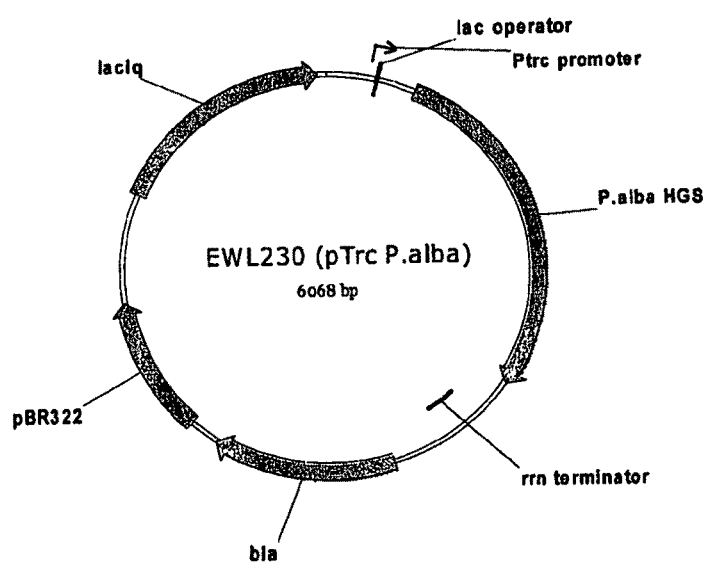
FIG. 57 is a map of plasmid EWL230.

Cells were allowed to recover by growing for 2 hour at 30° C. Transformants were selected on L Agar and 50 µg/µl carbenicillin and 10 mM mevalonic acid and incubated at 30° C. The next day, 6 transformants were picked and grown in 5 ml L Broth and 50 µg/µl carbenicillin tubes overnight at 30° C. Plasmid preps were performed on the overnight cultures using QIAquick Spin Miniprep Kit (Qiagen). Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. All 6 plasmids were the correct size and shipped to Quintara Biosciences (Berkeley, Calif.) for sequencing with primers MCM65, MCM66, EL1000 (Table 4). DNA sequencing results showed all 6 plasmids were correct. Picked one and designated plasmid as EWL230 (FIGS. 57, 58A and 58B).

iv) Construction of Plasmid pEWL244 (pTrc *P. alba*-mMVK)

A PCR reaction was performed to amplify the *Methanosarcina mazei* (*M. mazei*) MVK gene using MCM376 as the template (see section v), primers MCM165 and MCM177 (see Table 4), and Pfu Ultra II Fusion DNA polymerase (Stratagene) according to manufacturer's protocol. PCR conditions were as follows: 95° C. for 2 minutes (first cycle only), 95° C. for 25 seconds, 55° C. for 25 seconds, 72° C. for 18 seconds, repeat for 28 cycles, with final extension at 72° C. for 1 minute. The *M. mazei* MVK PCR product was purified using QIAquick PCR Purification Kit (Qiagen Inc.).

Figure 59:
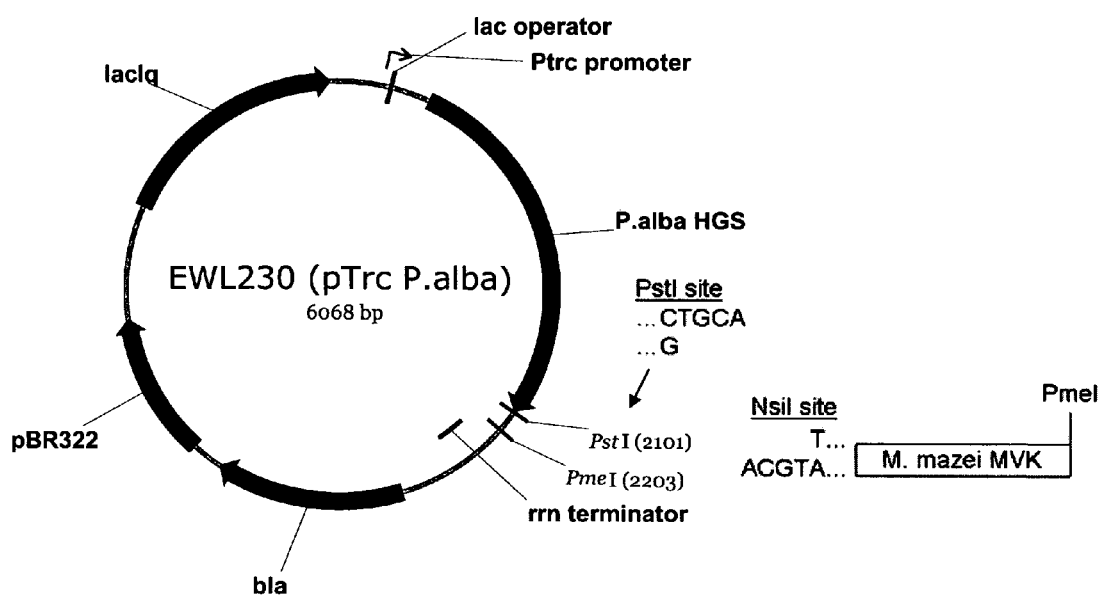
FIG. 59 is a schematic diagram showing restriction sites used for endonuclease digestion to construct plasmid EWL244 and compatible cohesive ends between NsiI and PstI sites.
Figure 60:
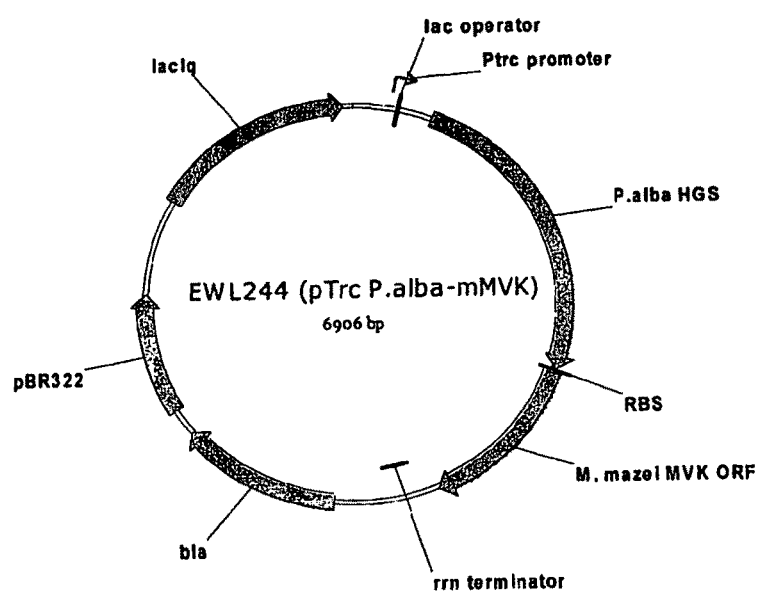
FIG. 60 is a map of EWL244.
Figure 62:
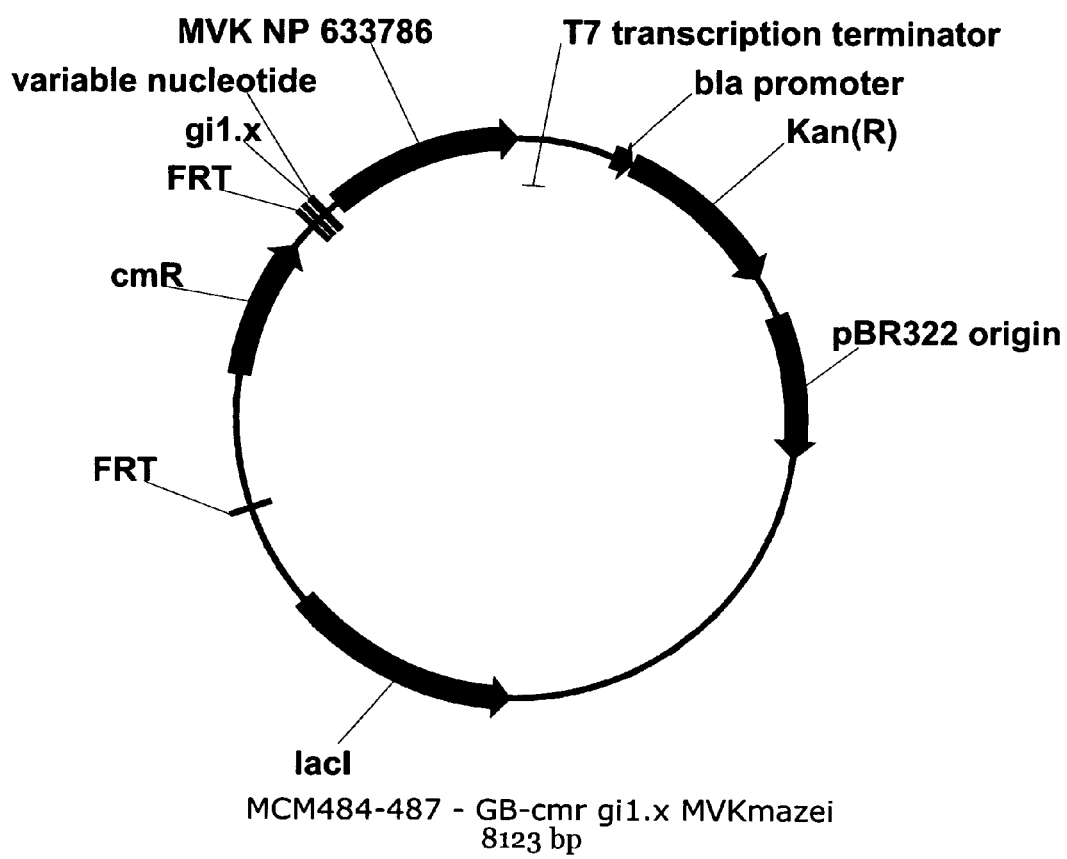
FIG. 62 is a map of plasmids MCM484-487.

The *M. mazei* MVK PCR product was then digested in a 40 µl reaction containing 8 µl PCR product, 2 µl PmeI endonuclease (New England Biolabs), 4 µl 10×NEB Buffer 4, 4 µl 10×NEB BSA, and 22 µl of ddH₂O. The reaction was incubated for 3 hours at 37° C. The digested PCR fragment was then purified using the QIAquick PCR Purification Kit. A secondary restriction digest was performed in a 47 µl reaction containing 2 µl NsiI endonuclease (Roche), 4.7 µl 10× Buffer H, and 40 µl of PmeI digested *M. mazei* MVK fragment. The reaction was incubated for 3 hours at 37° C. The digested PCR fragment was then gel purified using a 1.2% E-gel and extracted using the QIAquick Gel Extraction Kit. Plasmid EWL230 was digested in a 40 µl reaction containing 10 µl plasmid, 2 µl PmeI endonuclease, 4 µl 10×NEB Buffer 4, 4 µl 10×NEB BSA, and 20 µl of ddH₂O. The reaction was incubated for 3 hours at 37° C. The digested PCR fragment was then purified using the QIAquick PCR Purification Kit. A secondary restriction digest was performed in a 47 µl reaction containing 2 µl PstI endonuclease, 4.7 µl 10× Buffer H, and 40 µl of PmeI digested EWL230 linear fragment. The reaction was incubated for 3 hours at 37° C. The digested PCR fragment was then gel purified using a 1.2% E-gel and extracted using the QIAquick Gel Extraction Kit (FIG. 59). Using the compatible cohesive ends of NsiI and PstI sites, a 20 µl ligation reaction was prepared containing 8 µl *M. mazei* MVK insert, 3 µl EWL230 plasmid, 1 µl T4 DNA ligase, 2 µl 10× ligase buffer, and 4 µl ddH₂O. The ligation mixture was incubated at overnight at 16° C. The next day, the ligation mixture was desalted by floating a 0.024 µm nitrocellulose membrane filter in a petri dish of ddH₂O and applying the ligation mixture gently on top of the nitrocellulose membrane filter for 30 minutes at room temperature. MCM446 cells were grown in LB to midlog phase and then washed three times in ice-cold, sterile water. An aliquot of 50 µl of cell suspension was mixed with 5 µl of desalted pTrc *P. alba*-mMVK ligation mix. The cell suspension mixture was electroporated in a 2 mm cuvette at 2.5 Volts and 25 uFd using a Gene Pulser Electroporator. 1 ml of LB is immediately added to the cells, then the cells are transferred to a 14 ml polypropylene tube with a metal cap. Cells were allowed to recover by growing for 2 hour at 30° C. Transformants were selected on LA and 50 µg/µl carbenicillin and 5 mM mevalonic acid plates and incubated at 30° C. The next day, 6 transformants were picked and grown in 5 ml LB and 50 µg/µl carbenicillin tubes overnight at 30° C. Plasmid preps were performed on the overnight cultures using QIAquick Spin Miniprep Kit. Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. Three of the 6 plasmids were the correct size and shipped to Quintara Biosciences for sequencing with primers MCM65, MCM66, EL1000, EL1003, and EL1006 (Table 4). DNA sequencing results showed all 3 plasmids were correct. Picked one and designated plasmid as EWL244 (FIGS. 60 and 61A-B).

v) Construction of Plasmid MCM376—MVK from *M. mazei* Archaeal Lower in pET200D

Figure 73A:
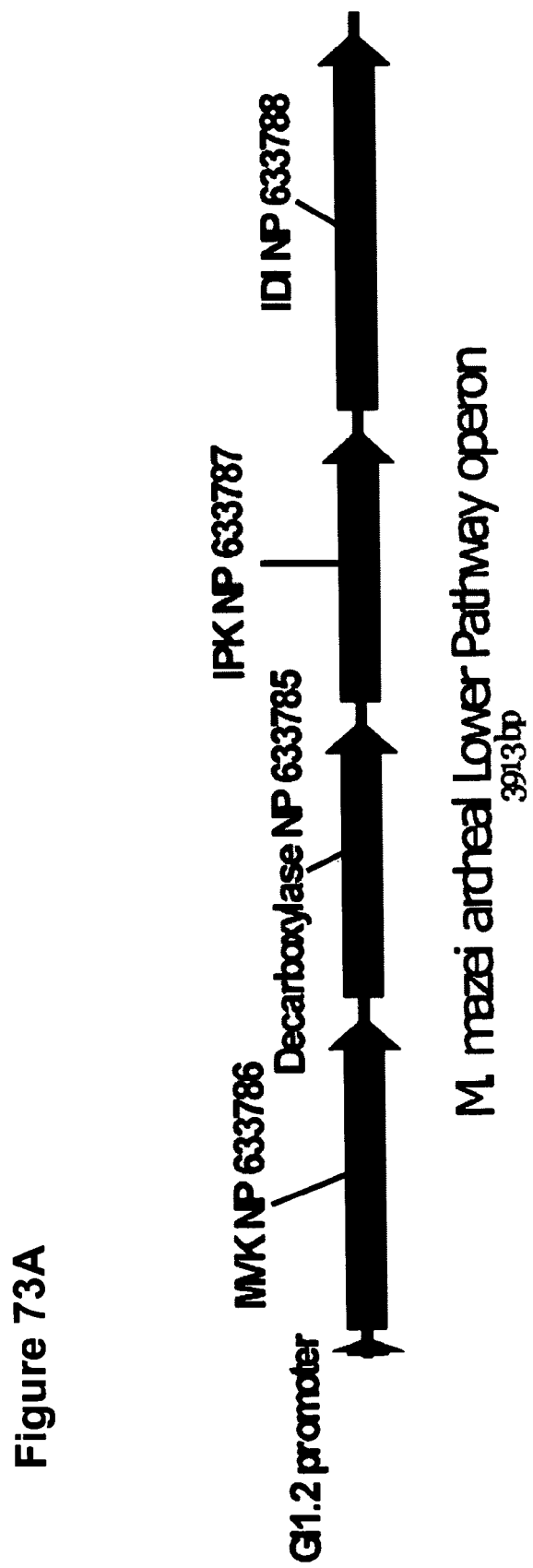
FIG. 73A is a map of the *M. mazei* archaeal Lower Pathway operon.
Figure 74A:
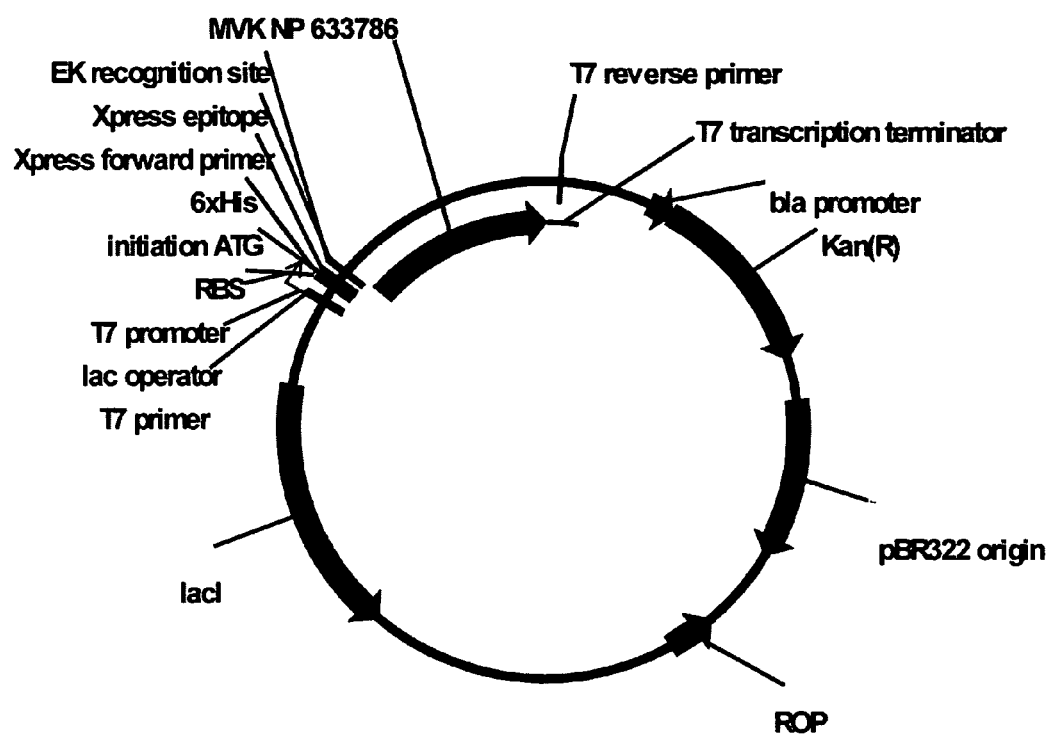
FIG. 74A is a map of MCM376-MVK from *M. mazei* archaeal Lowerin pET200D.
Figure 75A:
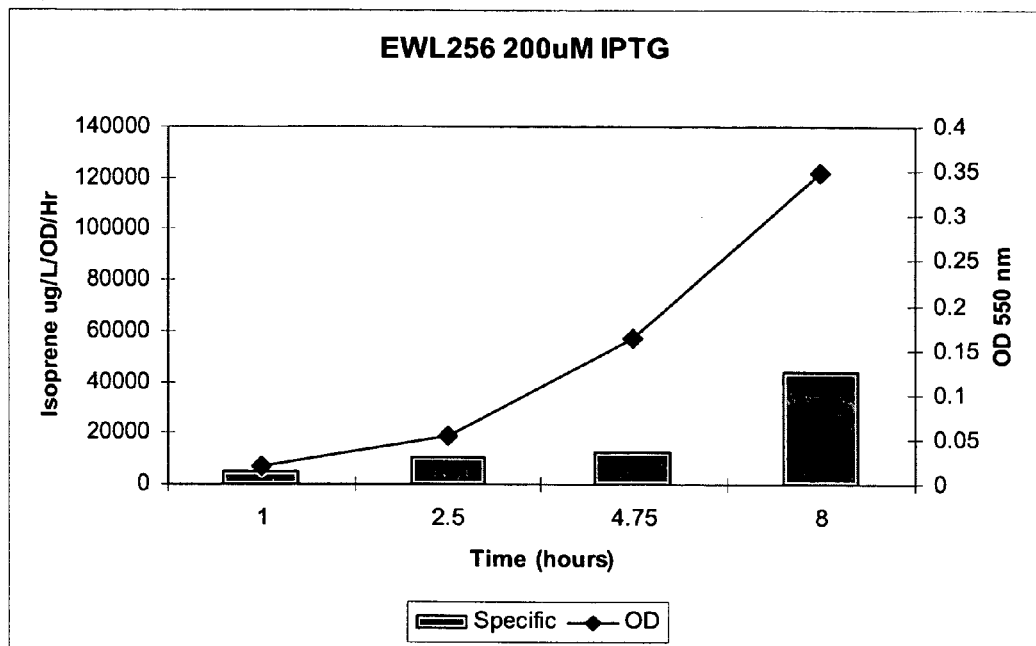
FIGS. 75A-75D show growth and specific productivity of isoprene production for EWL256 compared to RM11608-2. Growth (OD550) is represented by the white diamonds; specific productivity of isoprene is represented by the solid bars. The x-axis is time (hours) post-induction with either 200 (FIGS. 75A and 75B) or 400 (FIGS. 75C and 75D) uM IPTG. Y-1 axis is productivity of isoprene (ug/L/OD/hr) and Y-2 is arbitrary units of optical density at a wavelength of 550. These values for the OD550 must be multiplied by 6.66 to obtain the actual OD of the culture.
Figure 75B:
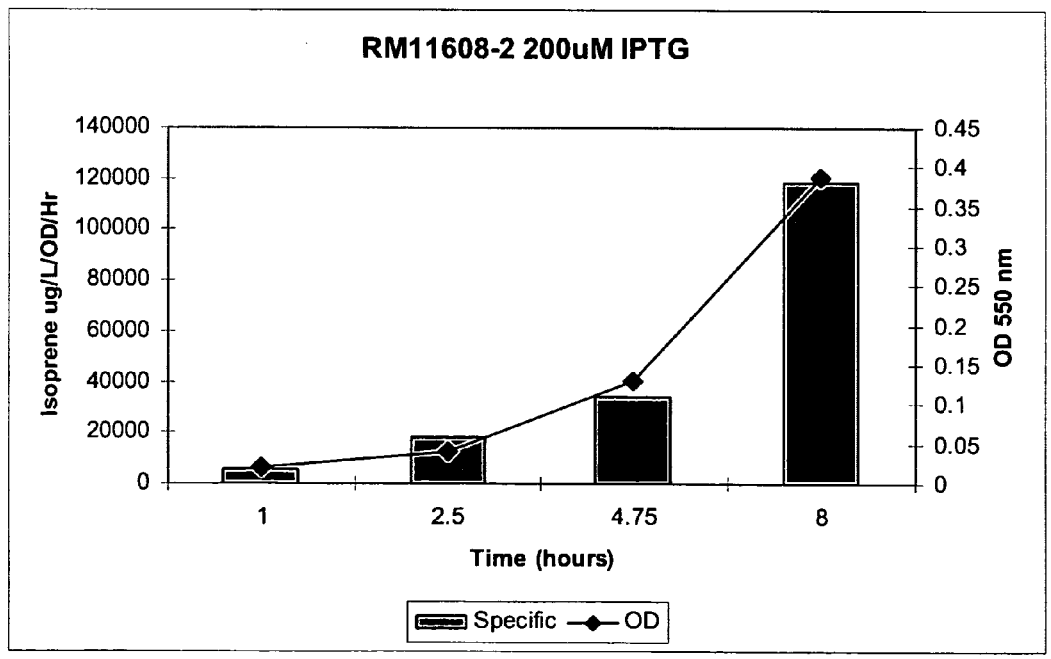
Figure 75C:
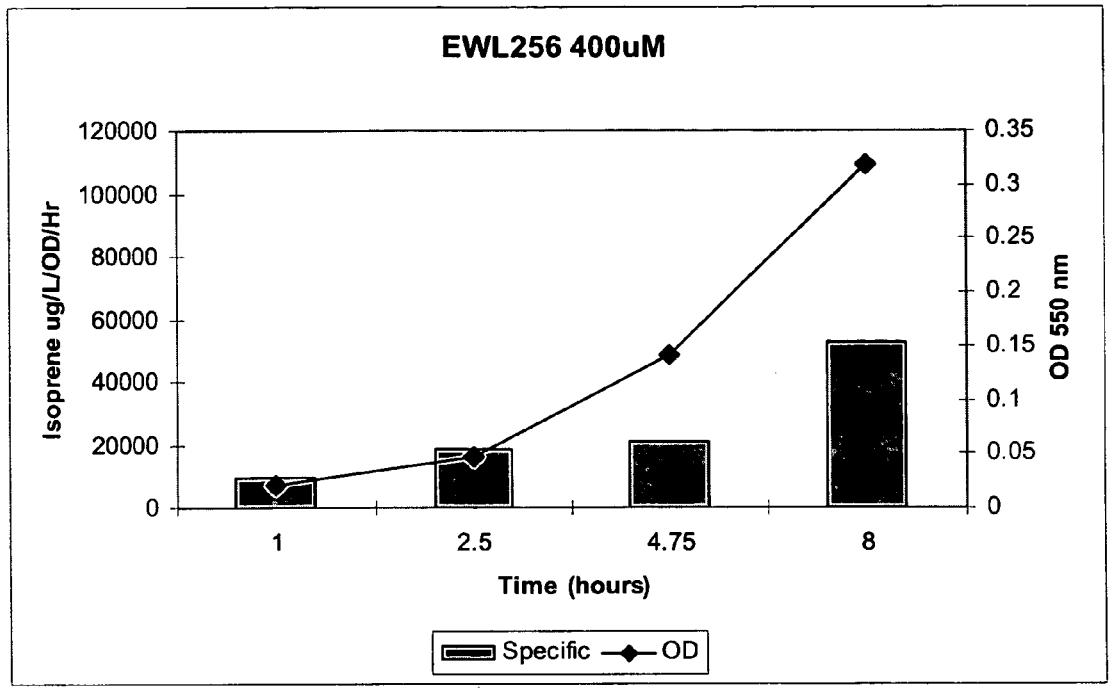
Figure 75D:
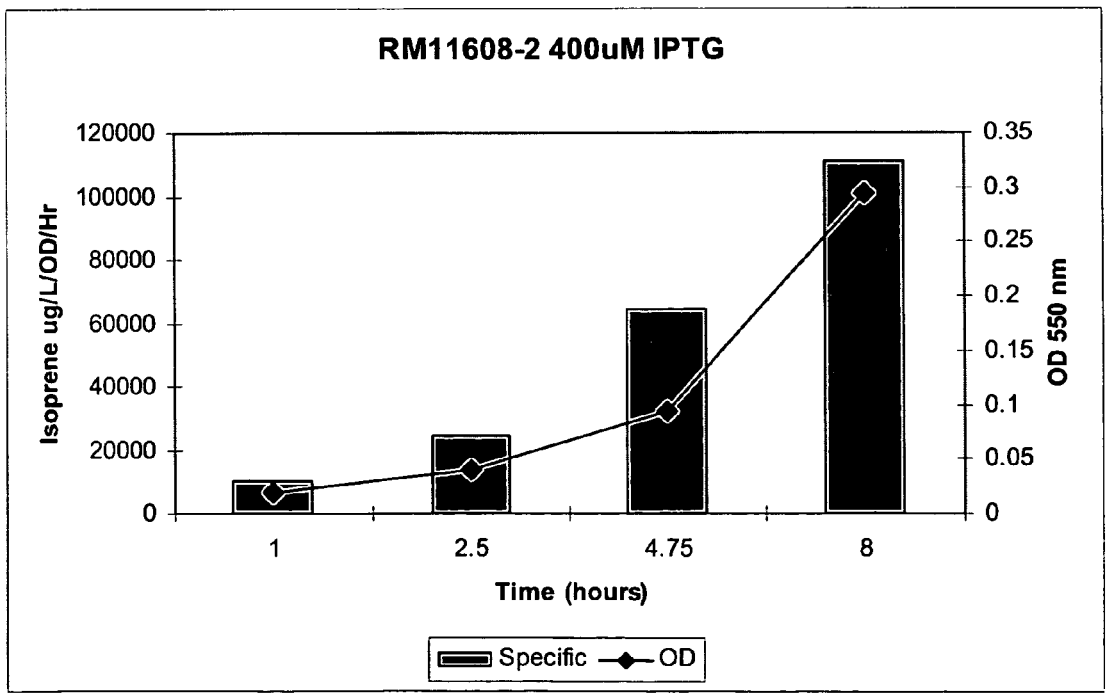
Figure 76:
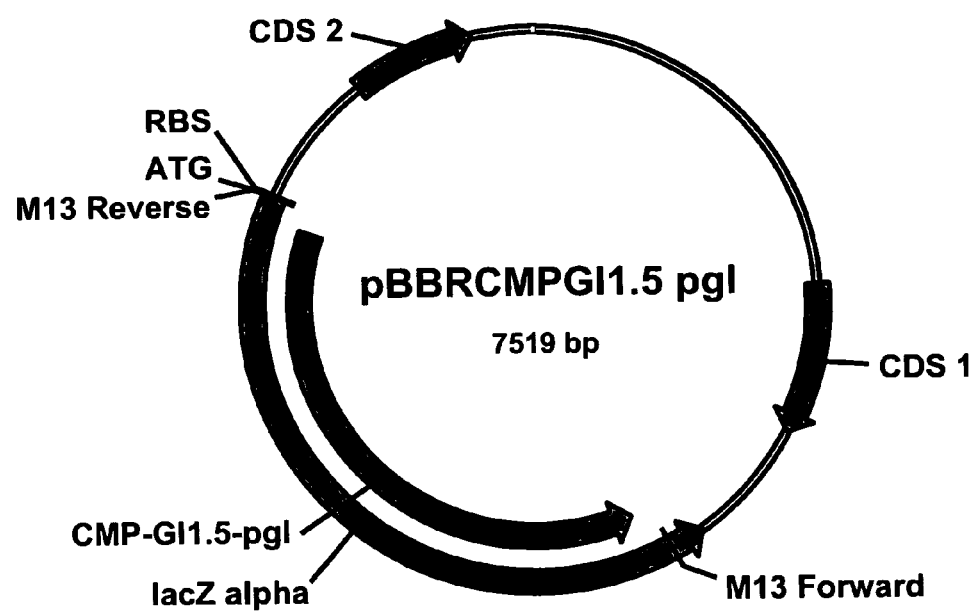
FIG. 76 is a map of plasmid pBBRCMPGI1.5-pgl.

The MVK ORF from the *M. mazei* archaeal Lower Pathway operon (FIGS. 73A-C) was PCR amplified using primers MCM161 and MCM162 (Table 4) using the Invitrogen Platinum HiFi PCR mix. 45 uL of PCR mix was combined with 1 uL template, 1 uL of each primer at 10 uM, and 2 uL water. The reaction was cycled as follows: 94° C. for 2:00 minutes; 30 cycles of 94° C. for 0:30 minutes, 55° C. for 0:30 minutes and 68° C. for 1:15 minutes; and then 72° C. for 7:00 minutes, and 4° C. until cool. 3 uL of this PCR reaction was ligated to Invitrogen pET200D plasmid according to the manufacturer's protocol. 3 uL of this ligation was introduced into Invitrogen TOP10 cells, and transformants were selected on LA/kan50. A plasmid from a transformant was isolated and the insert sequenced, resulting in MCM376 (FIGS. 74A-C).

vi) Construction of Strain EWL251 (BL21(DE3), Cm-GI1.2-KKDyI, pTrc *P. alba*-mMVK)

MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) were grown in LB to midlog phase and then washed three times in ice-cold, sterile water. Mixed 50 µl of cell suspension with 1 µl of plasmid EWL244. The cell suspension mixture was electroporated in a 2 mm cuvette at 2.5 Volts and 25 uFd using a Gene Pulser Electroporator. 1 ml of LB is immediately added to the cells, then the cells were transferred to a 14 ml polypropylene tube with a metal cap. Cells were allowed to recover by growing for 2 hours at 30° C. Transformants were selected on LA and 50 µg/µl carbenicillin and 5 mM mevalonic acid plates and incubated at 37° C. One colony was selected and designated as strain EWL251.

vii) Construction of Strain EWL256 (BL21(DE3), pTrc *P. alba*-mMVK, pCL Upper MVA)

EWL251 cells were grown in LB to midlog phase and then washed three times in ice-cold, sterile water. Mixed 50 µl of cell suspension with 1 µl of plasmid MCM82 (which is pCL PtrcUpperPathway encoding *E. faecalis* mvaE and mvaS). The cell suspension mixture was electroporated in a 2 mm cuvette at 2.5 Volts and 25 uFd using a Gene Pulser Electroporator. 1 ml of LB was immediately added to the cells, then transferred to a 14 ml polypropylene tube with a metal cap. Cells were allowed to recover by growing for 2 hour at 30° C. Transformants were selected on LA and 50 µg/µl carbenicillin and 50 µg/µl spectinomycin plates and incubated at 37° C. Picked one colony and designated as strain EWL256.

TABLE 4

Primer Sequences

| Primer name | Primer sequence |
|---|---|
| MCM130 | ACCAATTGCACCCGGCAGA (SEQ ID NO: 94) |
| GB Cm Rev | GCTAAAGCGCATGCTCCAGAC (SEQ ID NO: 95) |
| MVD For | GACTGGCCTCAGATGAAAGC (SEQ ID NO: 96) |
| MVD Rev | CAAACATGTGGCATGGAAAG (SEQ ID NO: 97) |
| MCM182 | GGGCCCGTTTAAACTTTAACTAGACTCTGCAGTTAGCGTTCAAACGGCAGAA (SEQ ID NO: 98) |
| MCM192 | CGCATGCATGTCATGAGATGTAGCGTGTCCACCGAAAA (SEQ ID NO: 99) |
| MCM65 | ACAATTTCACACAGGAAACAGC (SEQ ID NO: 100) |
| MCM66 | CCAGGCAAATTCTGTTTTATCAG (SEQ ID NO: 101) |
| EL1000 | GCACTGTCTTTCCGTCTGCTGC (SEQ ID NO: 102) |
| MCM165 | GCGAACGATGCATAAAGGAGGTAAAAAAACATGGTATCCTGTTCTGCGCCGGGTAAGATTTACCTG (SEQ ID NO: 103) |
| MCM177 | GGGCCCGTTTAAACTTTAACTAGACTTTAATCTACTTTCAGACCTTGC (SEQ ID NO: 104) |
| EL1003 | GATAGTAACGGCTGCGCTGCTACC (SEQ ID NO: 105) |
| EL1006 | GACAGCTTATCATCGACTGCACG (SEQ ID NO: 106) |
| MCM161 | CACCATGGTATCCTGTTCTGCG (SEQ ID NO: 107) |
| MCM162 | TTAATCTACTTTCAGACCTTGC (SEQ ID NO: 108) |

II. Construction of MCM442-449: BL21 and BL21(DE3) with FRT-cmR-FRT-gi1.x-mKKDyI i) Construction of Template for Recombination FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers MCM193 and MCM195 were used to amplify the resistance cassette from the FRT-gb2-Cm-FRT template using Stratagene Herculase II Fusion kit according to the manufacturer's protocol. The 50 uL reaction was cycled as follows: 95° C., 2 minutes; (95° C., 20 seconds, 55° C., 20 seconds, 72° C., 1 minute)×5, (95° C., 20 seconds, 60° C., 20 seconds, 72° C., 1 minute)×25; 72° C., 3 minutes; 4° C. until cool. The amplicon was purified by a Qiagen PCR column according to the manufacturer's protocol and eluted in 30 uL EB (Elution Buffer). DNA was digested with NdeI and PciI in a 20 uL reaction with 1× Roche H buffer and 0.5 uL BSA. Plasmid MCM376 was digested in a 10 uL reaction containing 1 uL each of N del, N col, and Roche H buffer. Reactions proceeded overnight at 37° C., and then cut DNA was purified on Qiagen PCR columns and eluted in 30 uL EB. The PCR product was ligated into MCM376 in a reaction containing 1 uL vector, 3 uL PCR product, 1 uL Roche Quick Ligase Buffer 2, 5 uL Buffer1, and 1 uL Ligase. The reaction proceeded at room temperature for 3 hours and then 5 uL was transformed into Invitrogen TOP10 cells according to the manufacturer's protocol. Transformants were selected on L agar (LA) and chloramphenicol (10 ug/mLO) at 37° C. overnight.

Transformant colonies were patched onto LA containing chloramphenicol (30 ug/mL) and kanamycin (50 ug/ml) for storage and sent to Quintara (Berkeley, Calif.) for sequencing. Four clones, one each with the four different nucleotides at the "N" in primer MCM195, were found to have the correct sequence for the inserted promoter. Clones were grown in 5 mL LB containing chloramphenicol (30 ug/mL) and kanamycin (50 ug/mL) and used for the preparation of plasmid DNA. This plasmid was retransformed into TOP10 cells and strains were frozen as:

TABLE 5

| MCM484-487 | |
|---|---|
| MCM484 | cmR-gi1.6-MVK(mazei) in pET (clone A1-3, variable nt A) |
| MCM485 | cmR-gi1.0-MVK(mazei) in pET (clone B4-6, variable nt C) |
| MCM486 | cmR-gi1.2-MVK(mazei) in pET (clone C1-5, variable nt G) |
| MCM487 | cmR-gi1.5-MVK(mazei) in pET (clone C3-3, variable nt T) | ii) Creation of Recombination Target Strains MCM349 and MCM441

The chloramphenicol resistance (cmR) marker was looped out of strain MCM331 using plasmid pGB706 (GeneBridges) according to Manufacturer's instructions. MCM331 cells were grown to mid-log in LB and washed three times in iced, sterile water. A 1 uL aliquot of pGB706 DNA was added to 50 uL of cell suspension and this mixture was electroporated in a 2 mm cuvette at 2.5 volts, 25 uFd followed immediately by recovery in 500 uL LB for one hour at 30 C. Transformants were selected on LB containing tetracycline (5 ug/ml) at 30° C. The following day, a clone was grown up at 30° C. in LB containing tetracycline (5 ug/ml) until visibly turbid (OD600~0.5-0.8). This culture was streaked onto LB and grown overnight at 37° C. A clone that was unable to grow on LB containing chloramphenicol (10 ug/mL) or LB containing tetracycline (5 ug/mL) was frozen as MCM348. Plasmid MCM356 (pRedET carbencillin; GeneBridges) was electroporated in as described above and transformants were selected on LB containing carbenicillin (50 ug/mL) at 30° C. A clone was grown in LB carbenicillin (50 ug/mL) at 30° C. and frozen as MCM349.

Strain MCM441 was created by electrotransforming plasmid MCM356 into EWL204 as above.

iii) Recombination of FRT-cmR-FRT-gi1.x-mMVK into MCM349 and MCM441

Plasmids MCM484-487 were used as template for PCR amplification with primers MCM120 and MCM196 and Herculase II Fusion kit, according to the manufacturer's protocol. Three reactions per template were carried out, with 0, 1, or 3 uL DMSO. The 50 uL reactions were cycled as follows: 95° C., 2 minutes; (95° C., 20 seconds; 55° C. 20 seconds; 72° C., 1.5 minutes) for five cycles; (95° C., 20 seconds; 60° C. 20 seconds; 72° C., 1.5 minutes) for 25 cycles; 72° C. for 3 minutes; 4° C., overnight. The three reactions from a given template were pooled and purified on Qiagen PCR columns and eluted with 30 uL EB at 60° C. 5 uL DNA was digested with 1 uL DpnI in 1×Roche Buffer A for 3 hours at 37° C. This DNA was then microdialyzed against excess water for 30 minutes.

Strains were grown in 5 mL LB containing carbenicillin (50 ug/mL) from fresh streaks at 30 C to an OD600 of ~0.5. 40 mM L-arabinose was added and cultures were incubated at 37 C for 1.5 hours. Cells were harvested and electroporated with 3 uL dialyzed amplicons above, and then recovered in 500 uL SOC at 37 C for 1.5-3 hours. Transformants were selected on LA plates containing chloramphenicol (5 ug/mL) at 37° C.

Kanamycin sensitive clones were screened by PCR for insertion of the amplicon. PCR products from positive clones were sequenced to verify the sequence of inserted DNA. Amplicons were consistent with the FRT-gi1.2-yKKDyI at attTn7 in MCM441 and 348 being replaced by FRT-cmR-FRT-gi1.x-mKKDyI (The yK and mK designations refer to the mevalonate kinase from *Saccharomyces cerevisiae* and *Methanosarcina mazei* respectively).

TABLE 6A

The following strains were grown in LB containing chloramphenicol (5 ug/mL) and frozen.

| Strain ID | Name | Parent | Recombination Amplicon Template |
|---|---|---|---|
| MCM442 | BL21(DE3) cmR-gi1.6mKKDyI A1, clone37 (A) | MCM349 | MCM484 |
| MCM443 | BL21(DE3) cmR-gi1.0mKKDyI B4, clone27 (C) | MCM349 | MCM485 |
| MCM444 | BL21(DE3) cmR-gi1.2mKKDyI C1, clone16 (G) | MCM349 | MCM486 |
| MCM445 | BL21(DE3) cmR-gi1.5mKKDyI C3, clone7 (T) | MCM349 | MCM487 |
| MCM446 | BL21 cmR-gi1.6mKKDyI A1-3 (A) | MCM441 | MCM484 |
| MCM447 | BL21 cmR-gi1.0mKKDyI B4-6 (C) | MCM441 | MCM485 |
| MCM448 | BL21 cmR-gi1.2mKKDyI C1-5 (G) | MCM441 | MCM486 |
| MCM449 | BL21 cmR-gi1.5mKKDyI C3-3 (T) | MCM441 | MCM487 |

TABLE 6B

Primers

| MCM120 | AAAGTAGCCGAAGATGACGGTTTGTCACATGGAGTTGGCAGG ATGTTTGATTAAAAGCAATTAACCCTCACTAAAGGGCGG (SEQ ID NO: 109) |
|---|---|
| MCM193 | GATATACATATGAATTAACCCTCACTAAAGG (SEQ ID NO: 110) |

TABLE 6B-continued

Primers

| MCM195 | GCATGCATGACATGTTTTTTTACCTCCTTTGTTATCCGCTCA CAATTAGTGGTTGAATTATTTGCTCAGGATGTGGCATNGTCA AGGGCGCGGCCGCGATCTAATACGACTCACTATAGGGCTCG (SEQ ID NO: 111) |
|---|---|
| MCM196 | AGGCTCTCAACTCTGACATGTTTTTTTCCTCCTTAAGGGTGC AGGCCTATCGCAAATTAGCTTAATCTACTTTCAGACCTTGCT CGG (SEQ ID NO: 112) |

III. The Effect of Yeast Extract on Isoprene Production in *E. coli* Expressing Genes from the Mevalonic Acid Pathway and Grown in Fed-Batch Culture at the 15-L Scale Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in Di $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL Upper), the integrated lower MVA pathway (gi1.2KKDyI), and high expression of mevalonate kinase from *M. mazei* and isoprene synthase from *P. alba* (pTrcAlba-mMVK). This experiment was carried out to monitor isoprene formation from glucose at the desired fermentation pH 7.0 and temperature 30° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

i) Production of Isoprene in *E. coli* Cells (EL256) Grown in Fed-Batch Culture without Yeast Extract Feeding Glucose was fed at an exponential rate until cells reached the stationary phase. After this time the glucose feed was decreased to meet metabolic demands. The total amount of glucose delivered to the bioreactor during the 67 hour fermentation was 3.9 kg.

Figure 67A:
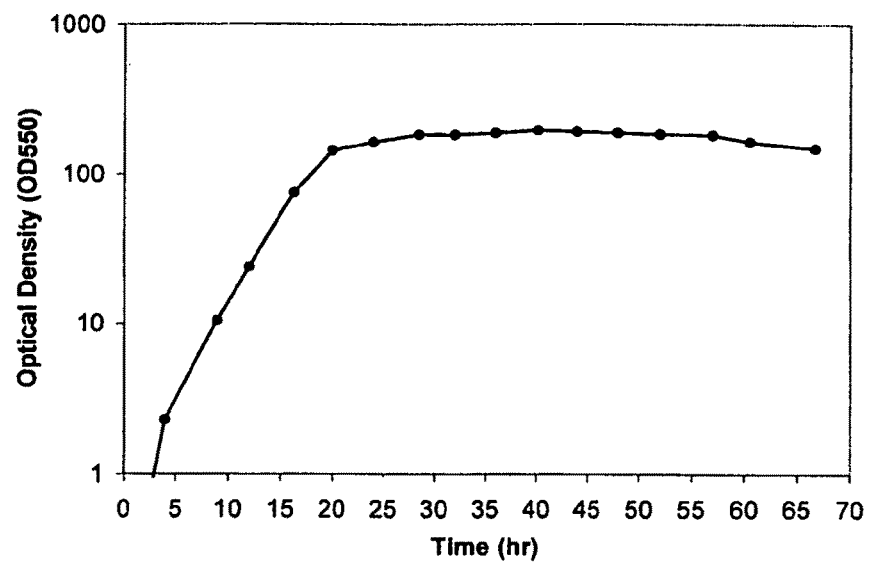
FIGS. 67A-67D are graphs of isoprene production by *E. coli* strain (EWL256) expressing genes from the MVA pathway and grown in fed-batch culture at the 15-L scale without yeast extract feeding.
Figure 67B:
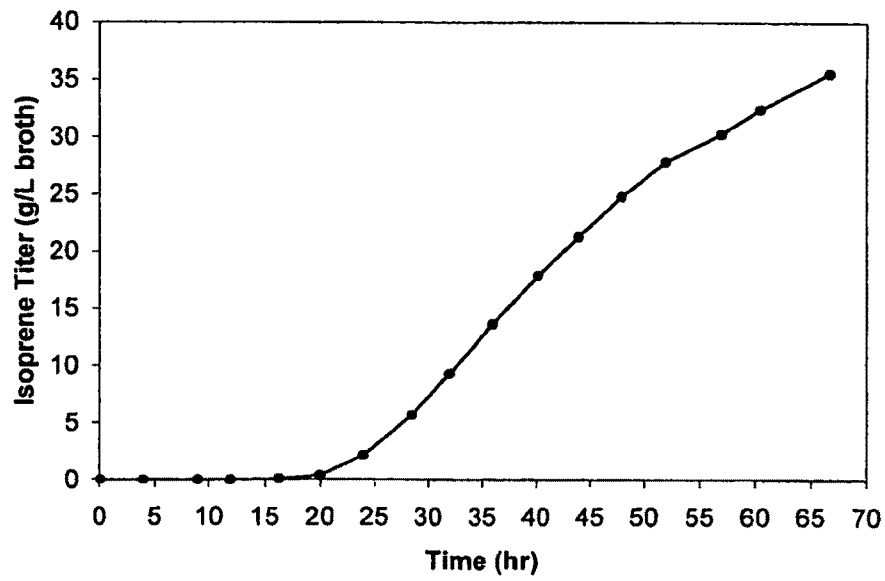
Figure 67C:
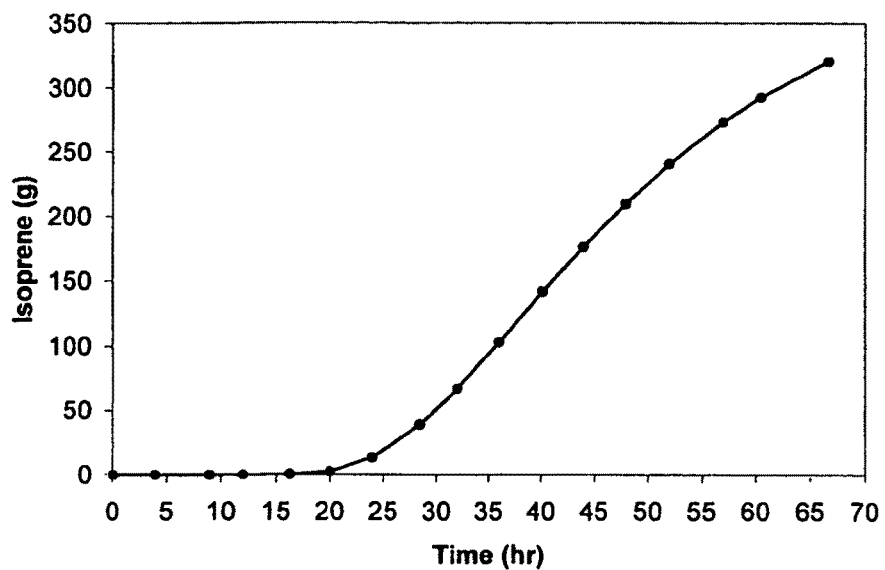
Figure 67D:
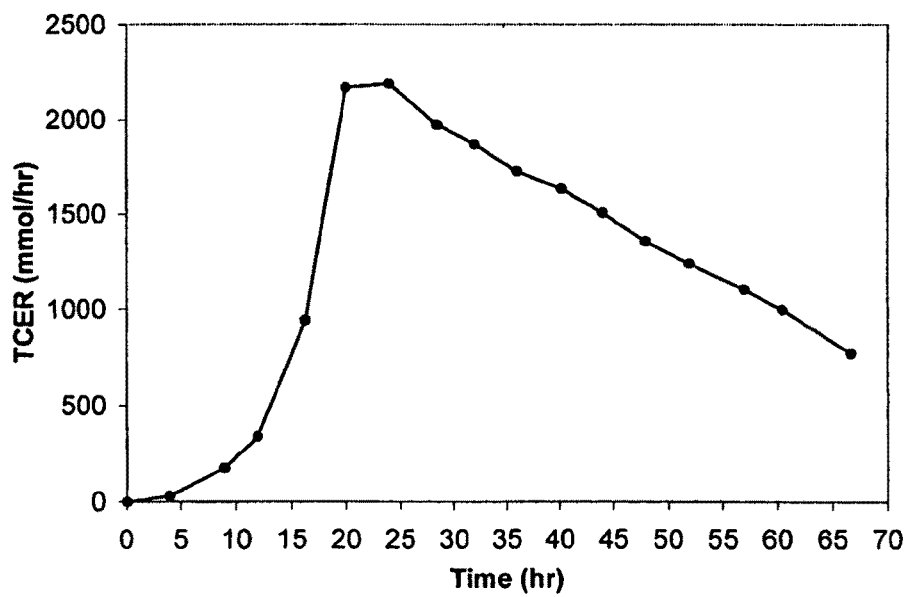

Induction was achieved by adding isopropyl-beta-D-1-thiogalactopyranoside (IPTG). The IPTG concentration was brought to 102 uM when the optical density at 550 nm ($OD_{550}$) reached a value of 9. The IPTG concentration was raised to 192 uM when $OD_{550}$ reached 140. The $OD_{550}$ profile within the bioreactor over time is shown in FIG. 67A. The isoprene level in the off gas from the bioreactor was determined using a Hiden mass spectrometer. The isoprene titer increased over the course of the fermentation to a final value of 35.6 g/L (FIG. 67B). The total amount of isoprene produced during the 67 hour fermentation was 320.6 g and the time course of production is shown in FIG. 67C. The metabolic activity profile, as measured by TCER, is shown in FIG. 67D. The molar yield of utilized carbon that went into producing isoprene during fermentation was 17.9%. The weight percent yield of isoprene from glucose was 8.1%.

Figure 68A:
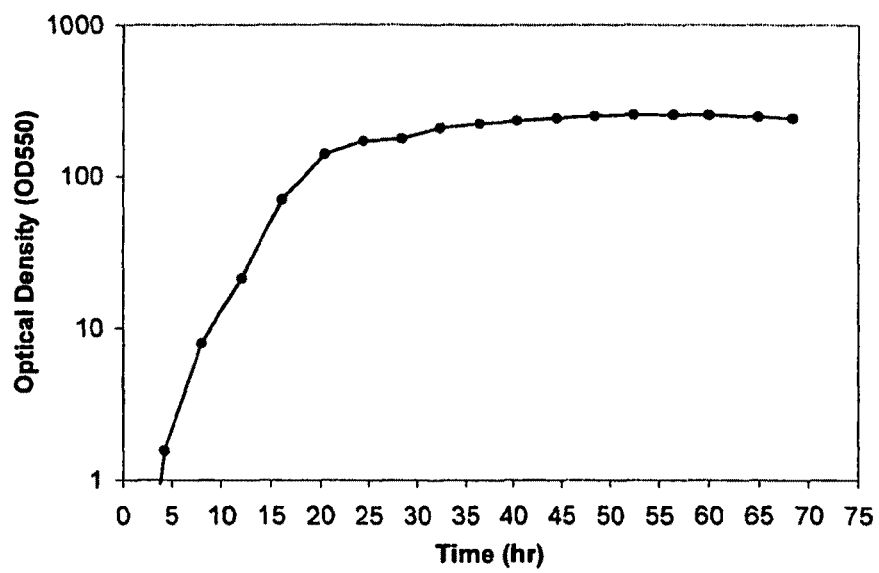
FIGS. 68A-68E are graphs of isoprene production by *E. coli* strain (EWL256) expressing genes from the MVA pathway and grown in fed-batch culture at the 15-L scale with yeast extract feeding.
Figure 68B:
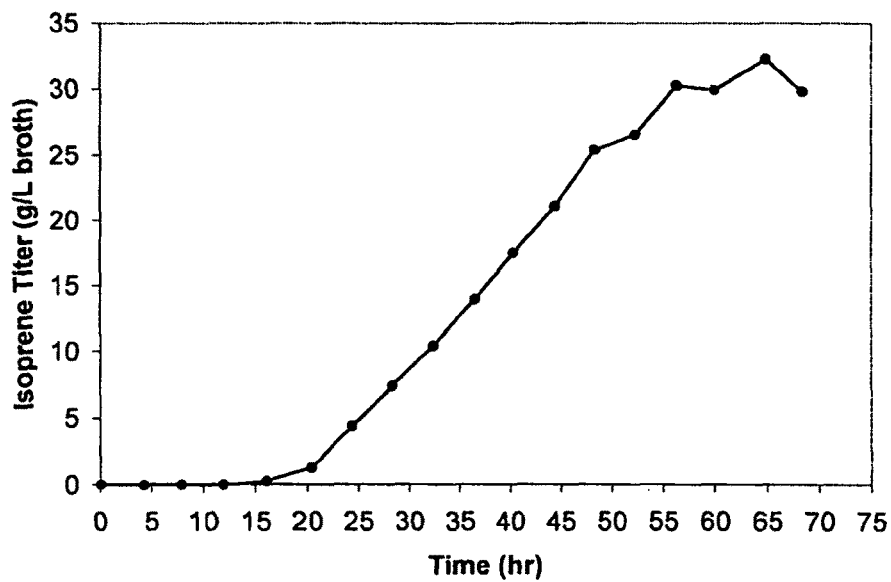
Figure 68C:
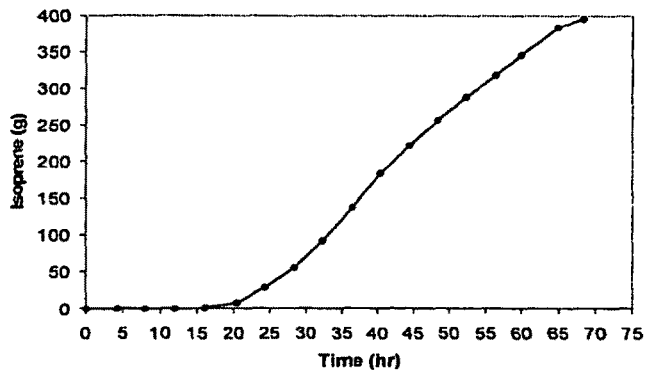
Figure 68D:
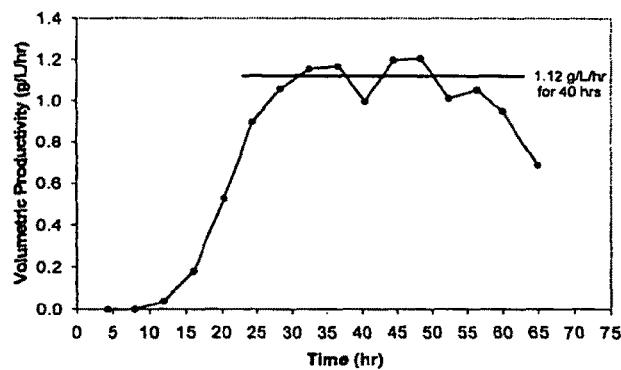
Figure 68E:
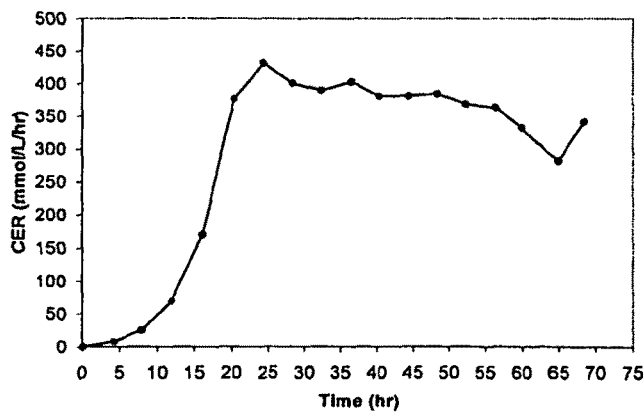

Production of Isoprene in *E. coli* Cells (EL256) Grown in Fed-Batch Culture with Yeast Extract Feeding Glucose was fed at an exponential rate until cells reached the stationary phase. After this time the glucose feed was decreased to meet metabolic demands. The total amount of glucose delivered to the bioreactor during the 68 hour fermentation was 7.1 kg. A total of 1.06 kg of yeast extract was also fed during the fermentation. Induction was achieved by adding IPTG. The IPTG concentration was brought to 208 uM when the optical density at 550 nm ($OD_{550}$) reached a value of 7. The IPTG concentration was raised to 193 uM when $OD_{550}$ reached 180. The $OD_{550}$ profile within the bioreactor over time is shown in FIG. 68A. The isoprene level in the off gas from the bioreactor was determined using a Hiden mass spectrometer. The isoprene titer increased over the course of the fermentation to a maximum value of 32.2 g/L (FIG. 68B). The total amount of isoprene produced during the 68 hour fermentation was 395.5 g and the time course of production is shown in FIG. 68C. The time course of volumetric productivity is shown in FIG. 68D and shows that an average rate of 1.1 g/L/hr was maintained for between 23 and 63 hours. The metabolic activity profile, as measured by CER, is shown in FIG. 68E The molar yield of utilized carbon that went into producing isoprene during fermentation was 10.3%. The weight percent yield of isoprene from glucose was 5.2%.

IV. Production of Isoprene from Different Carbon Sources in *E. coli* Harboring the Mevalonic Acid (MVA) Pathway and Isoprene Synthase (EWL256)

Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Modified Trace Metal Solution 1 ml. All of the components were dissolved sequentially in $diH_2O$. The pH was adjusted to 6.8 with ammonium hydroxide (30%) and brought to volume. Media was filter sterilized with a 0.22 micron filter. Carbon source was added to a final concentration of 1%. Required antibiotics were added after sterilization and pH adjustment.

1000× Trace Metal Solution (Per Liter Fermentation Media):

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component was dissolved one at a time in $diH_2O$, pH to 3.0 with HCl/NaO H, and then brought to volume and filter sterilized with a 0.22 micron filter.

i) Preparation of AFEX Biomass Hydrolysate

AFEX pretreated corn stover was hydrolyzed to prepare biomass hydrolysate containing both xylose, glucose and acetate.

AFEX pretreated corn stover, received from Michigan Biotechnology Institute, was used. The pretreatment conditions were, 60% moisture, 1:1 ammonia loading, and 90° C. for 30 minutes, then air dried. The moisture content in the AFEX pretreated corn stover was 21.27%. Content of glucan and xylan in the AFEX pretreated corn stover were 31.7% and 19.1% (dry basis) respectively. The enzyme used was accellerase 1000, Grindamyl H121 (Danisco xylanase product from *Aspergillus niger* for bread-making industry).

For saccharification, 20 g of AFEX pretreated corn stover was added into a 500 ml flask, together with 5 ml of 1 M pH 4.8 sodium citrate buffer, 2.25 ml of Accellerase 1000, 0.1 ml of Grindamyl H121, and 72.65 ml of DI water. The flask was put in an orbital shaker, and incubated at 50° C. for 96 hours.

For analysis, one sample was taken from the shaker, and analyzed using HPLC. The hydrolysate contained 37.2 g/l of glucose and 24.3 g/L of xylose, and 7.6 g/L of oligomers of glucose and/or xylose. Additionally, the hydrolysate also contains 1.17 g/L acetate.

ii) Experimental Procedure

An inoculum of the *E. coli* strain EWL256 containing the MVA pathway and isoprene synthase was taken from a frozen vial and streaked onto an LB broth agar plate containing spectinomycin (50 ug/mL) and carbinicllin (50 ug/mL) and incubated at 30° C. overnight. A single colony was inoculated into TM3 media containing glucose, xylose, glycerol, acetate or biomass as only carbon source and grown overnight at 30° C. Cells grow on acetate reached a significantly lower optical density. Cells grown on glucose, glycerol, biomass hydrolysate or acetate were diluted into 20 mL of TM3 media containing the respective carbon sources to reach an optical density of between 0.1 measured at 600 nM. A negative control not containing any carbon source was prepared from the glucose overnight culture. A separate experiment was performed with glucose and xylose, where the cultures were diluted to an optical density of 0.05. All culture conditions (except for acetate and glycerol) were tested in duplicates and the presented results are averaged between these cultures. Production of isoprene was induced with 200 µM IPTG from the beginning of the experiment. The flasks were incubated at 30° C. in an orbital shaker (200 rpm) and growth was followed by measuring optical density. After the glucose fed cultures had reached an optical density of approximately 0.4, samples were analyzed for isoprene production from all the tested carbon sources every hour for three hours. Samples of 100 µL were transferred in duplicates to 2 mL glass vials, sealed and incubated for 30 min at 30° C. The bacteria were then heat killed by incubation at 80° C. for 8 minutes. The amount of produced isoprene was measured using GC-MS and specific productivity (µg/L*hr) was calculated.

iii) Results

Significant production of isoprene could be demonstrated during growth on all the tested carbon sources. These carbon sources are examples of common alcohols, organic acids, sugars containing 5 or 6 carbon units ($C_5$ or $C_6$), and biomass hydrolysate.

Figure 69D:
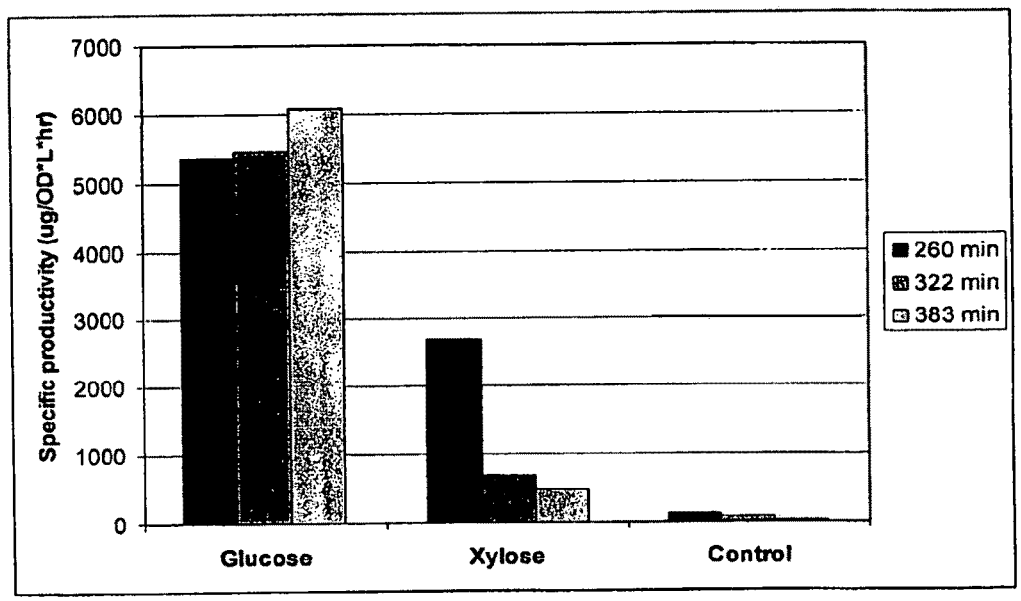

The initial growth rate on biomass hydrolysate was comparable to the growth rate on glucose (FIG. 69A). The initial specific productivity during growth on biomass hydrolysate was significantly higher than during growth on glucose. This demonstrates that biomass hydrolysate can be used as an efficient source of carbon for the production of isoprene. The specific productivity declined after 255 minutes of growth on biomass hydrolysate (FIG. 69B). The bacteria had a slower growth rate with xylose as only carbon source when compared to glucose (FIG. 69C), but a significant specific isoprene productivity was measured (FIG. 69D). This shows that both $C_5$ and $C_6$ sugars can be utilized for the production of isoprene via the mevalonate acid pathway.

Surprisingly, bacteria grown on acetate as the only carbon source had a specific productivity of isoprene approximately twice as high as during growth on glucose (FIG. 69A). The bacteria grew slower on acetate when compared to glucose (FIG. 69B), but the performed experiment demonstrates that acetate can also be used as a carbon source for the production of isoprene. Acetate was also present in the biomass hydrolysate as measured by HPLC.

The bacteria grew well with glycerol as only carbon source (FIG. 69A) and significant production of isoprene was demonstrated (FIG. 69B). This shows that common alcohols may also be used as carbon sources for production of isoprene via the mevalonate acid pathway.

Example 11

Expression of Isoprene-synthase from Plant in Streptomyces sp.

Figure 71:
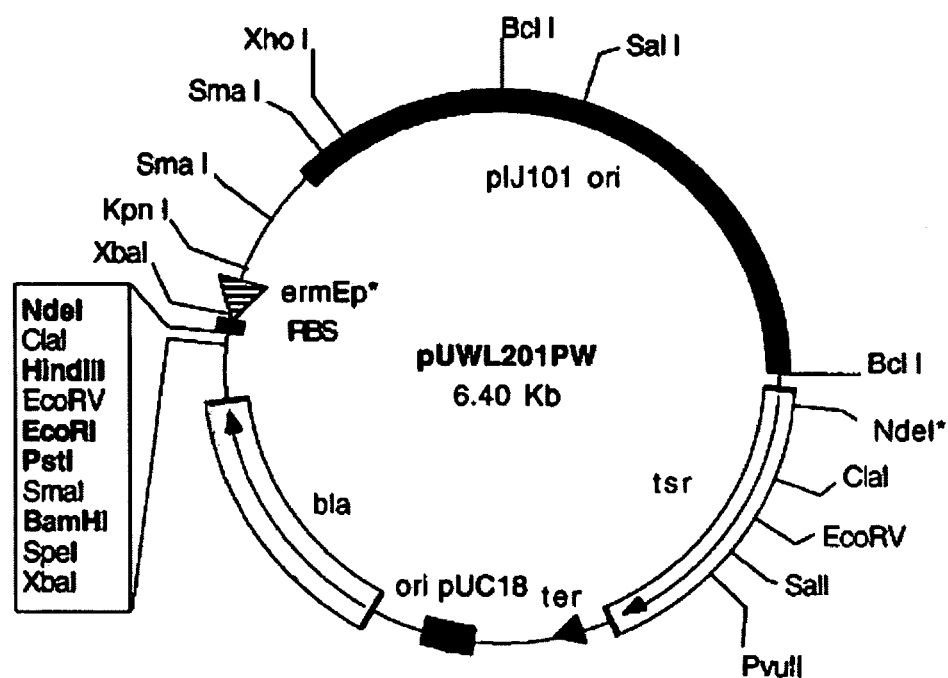
FIG. 71 is a map of the *E. coli*-Streptomyces shuttle vector pUWL201PW (6400 bp) used for cloning isoprene synthase from Kudzu. Tsr, thiostrepton resistance gene. Picture is taken from Doumith et al., Mol. Gen. Genet. 264: 477-485, 2000.
Figure 79A:
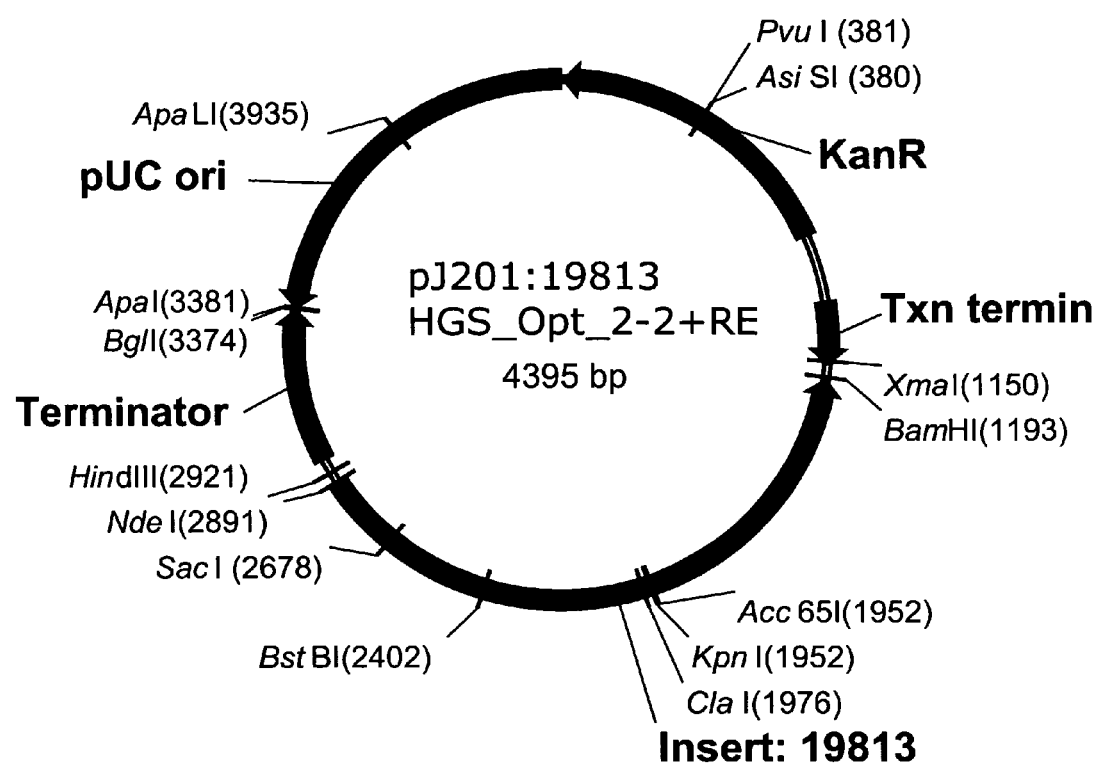
FIG. 79A is a map of plasmid pJ201:19813.

The gene for isoprene synthase Kudzu was obtained from plasmid pJ201:19813. Plasmid pJ201:19813 encodes isoprene synthase from *Pueraia lobata* (Kudzu plant) and was codon-optimized for *Pseudomonas fluorescens*, *Pseudomonas putida*, *Rhodopseudomonas palustris* and *Corynebacterium* (FIGS. 79A-79C (SEQ ID NO:123)). Digestion of plasmid pJ201:19813 with restriction enzymes NdeI and BamHI liberated gene iso19813 that was ligated into the *Streptomyces*-*E. coli* shuttle vector pUWL201PW (Doumith et al., *Mol. Gen. Genet.* 264: 477-485, 2000; FIG. 71) to generate pUWL201_iso. Successful cloning was verified by restriction analysis of pUWL201_iso. Expression of isoprene synthase iso19813 was under control of the erm-promoter which allows for constitutive expression in *Streptomycetes* species, but not for expression in *E. coli*.

PUWL201PW (no insert) and pUWL201_iso were introduced in *Streptomyces albus* J1074 (Sanchez et al., *Chem. Biol.* 9:519-531, 2002) by transformation of protoplasts as described by Hopwood et al., *The John innes foundation*, Norwich, 1985.

A 200 µl aliquot of protoplast suspensions was transformed with 1.9 µg pUWL201PW or 2.9 µg pUWL201_iso. After incubation overnight at 28° C. on non-selective R5-agar-plates, positive transformants were selected by further incubation for 4 days in R3-overlay agar containing thiostrepton (250 µg/ml). Thiostrepton resistant transformants were examined for presence of the pUWL-plasmids by plasmid preparation using Plasmid Mini Kit (Qiagen). Prepared plasmid DNA was reintroduced in *E. coli* DH5a to generate sufficient amounts of plasmid DNA to be analyzed by restriction analysis. Positive transformants were selected on ampicillin-containing L-agar plates and insert analysis was done by digestion of plasmid DNA with NdeI and BamHI endonucleases. Isoprene synthase was identified as a 1.7 kb fragment in positive pUWL201 iso clones while in the control strains (pUWL201PW) no such fragment was observed.

Figure 72:
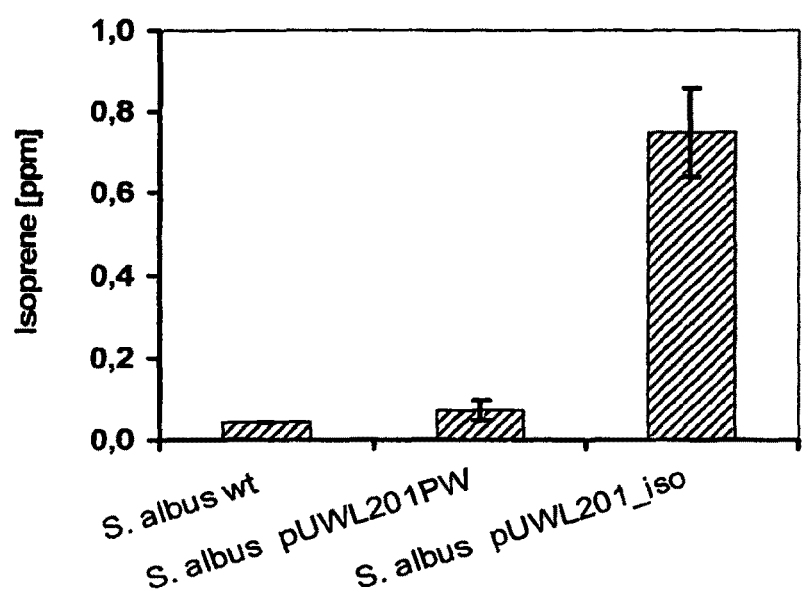
FIG. 72 shows isoprene formation by *Streptomyces albus* wild type strain ("wt") and strains harboring plasmid pUWL201PW (negative control) or pUWL201_iso (encoding isoprene synthase from Kudzu).

Wild type strain and transformants of *S. albus* containing control plasmid pUWL201PW or isoprene synthase encoding pUWL201_iso were analyzed for isoprene formation. Strains were cultivated in duplicate on solid media (tryptic soy broth agar, TSB; 2.5 ml) in presence or absence of thiostrepton (200 µg/ml) and incubated for 4 days at 28° C. in sealed head-space vials (total volume 20 ml). 500 µl head-space samples (end point measurements) were analyzed by GC-MS in SIM-mode and isoprene was identified according to reference retention times and molecular masses (67 m/z). Isoprene present in head-space samples was quantified by previously generated calibration curves. While wild-type *S. albus* and control strains harboring pUWL201PW produced isoprene in concentrations slightly higher than the detection limit (0.04-0.07 ppm), *S. albus* harboring pUWL201_iso produced isoprene in at least tenfold excess compared to controls (0.75 ppm; FIG. 72). The results demonstrate successful expression of plant-derived isoprene synthase in a prokaryotic organism of the Actinomycetes group.

Example 12

Production of Isoprene or Mevalonate from Fatty Acid or Palm Oil in *E. coli* fadR atoC LS5218 Containing the Upper or Upper and Lower Mevalonic Acid Pathway Plus Kudzu Isoprene Synthase

*Escherichia coli* fadR atoC strain LS5218 (#6966) was obtained from the Coli Genetic Stock Center. FadR encodes a transcription repressor that negatively regulates expression of the genes encoding fatty acid degradation enzymes (Campbell et al., *J. Bacteriol.* 183: 5982-5990, 2001). AtoC is a response regulator in a two-component regulatory system wherein AtoS regulates acetolactate metabolism. The fadR atoC strain allows constitutive expression of the fatty acid degradation genes and incorporates long chain fatty acids into long-chain-length polyhydroxyalkanoates. When palm oil is used as a carbon source for either mevalonate or isoprene production, the palm oil was converted to glycerol plus fatty acid. Methods for this are well known in the art, and it can be done either enzymatically by incubation with a lipase (for example Porcine pancreatic lipase, *Candida rugosa* lipase, or other similar lipases) or chemically by saponification with a base such as sodium hydroxide.

i) *E. coli* fadR atoC Strain Expressing the Upper Mevalonic Acid Pathway

Strain WW4 was created by electroporating pCLPtrcUpperPathway into LS5218 using standard methods (Sambrooke et al., Molecular Cloning: A Laboratory Manual, $2^{nd}$ ed., Cold Spring Harbor, 1989). Incorporation of the plasmid was demonstrated by the production of mevalonic acid (MVA) when cells were cultured in TM3 medium supplemented with either C12 fatty acid (FA) or palm oil as the carbon source. To demonstrate production of MVA by WW4 from fatty acid, cells from an overnight culture were diluted 1 to 100 into 5 mL of modified TM3 medium (TM3 without yeast extract) supplemented with 0.25% C12 FA (Sigma cat #L9755). The first sign of MVA production (24 mg/L) was apparent after overnight incubation at 30° C. of the IPTG induced culture. Production increased over three days with the final level of 194 mg/L of MVA produced. To demonstrate production of MVA by WW4 from oil, cells from an overnight culture were diluted 1 to 100 into modified TM3 medium supplemented with 200 mg of digested palm oil per 5 mL of TM3 medium. The first sign of MVA production (50 mg/L) was apparent after overnight incubation of the IPTG induced culture at 30° C. Production increased over three days with a final level of 500 mg/L of MVA produced.

ii) *E. coli* fadR atoC Strain Expressing the Upper and Lower MVA Pathway Plus Kudzu Isoprene Synthase

Figure 70A:
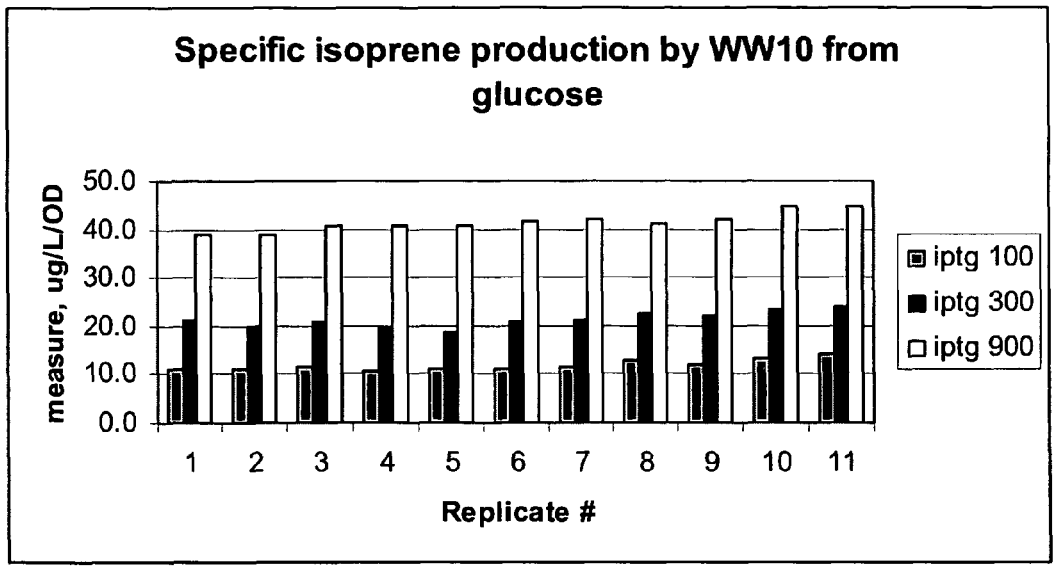
FIGS. 70A and 70B show the production of isoprene by *E. coli* strains from glucose and from fatty acid, respectively. For FIG. 70A, eleven colonies from the transformation of WW4 with pMCM118, the plasmid bearing the lower mevalonic acid pathway, were picked to verify the presence of the lower pathway. Cell from the colonies were cultured in TM3 medium containing 0.1% yeast extract and 2% glucose. Aliquots of induced culture were assayed for isoprene production after 4 hours of induction. All colonies showed the production of isoprene. The inducer IPTG had a strong growth inhibitory effect as was evident from the 3 to 4.6-fold reduced cell density in going from 50 to 900 uM concentration of the inducer (data not shown). The graph shows that higher induction, yields a higher specific titer of isoprene. For FIG. 70B, the production culture was inoculated from a washed overnight culture at 1 to 10 dilution. The culture was grown for several hours and induced with 50 uM IPTG. The left bar shows isoprene assay results four hours after induction followed by a one hour isoprene accumulation assay. The middle bar shows the one hour normalized value for the same culture with the same induction period but analyzed by a 12 hour isoprene accumulation assay. The right bar shows the value for a one hour isoprene accumulation assay of the culture that was induced for 13 hours.

*Escherichia coli* strain WW4 (LS5218 fadR atoC pCLPtrcUpperPathway) was transformed with pMCM118 [pTrcK-KDyIkIS] to yield WW10. The incorporation of the plasmid was demonstrated by evidence of production of isoprene when the strain was cultured in TM3 and glucose and induced with IPTG (100, 300, or 900 uM). The strain was relatively sensitive to IPTG and showed a significant growth defect even at 100 uM IPTG. These results are shown in FIG. 70A.

To test isoprene production from dodecanoic acid, WW10 was cultured overnight in L broth containing spectinomycin (50 ug/ml), and kanamycin (50 ug/ml) at 37 C with shaking at 200 rpm. The cells were washed with modified TM3 medium by centrifugation and resuspension in their original culture volume with this medium. The washed and resuspended cells from this starter culture were diluted 1 to 100 and 1 to 10 into 5 mL of modified TM3 medium containing 0.125% C12 Fatty Acid (Sigma cat #L9755).

To demonstrate production of mevalonate from palm oil, the oil was predigested with lipase at 37° C. and 250 rpm for several days to release the fatty acids (evidence of hydrolysis was judged by the foam formed when tubes were shaken).

In addition, a culture was set up by diluting the washed cells at 1 to 10 into modified TM3 medium contained in test tubes with palm oil. A further tube was set up by the addition of 0.125% C12FA to the remainder (2.5 mL) of the washed cells without further dilution (bioconversion). After 3.75 hours of growth at 30° C. with shaking at 250 rpm all of the cultures were induced by the addition of 50 uM IPTG. Incubation was continued for 4 hours after which time 200 uL of each of the cultures was assayed for isoprene accumulation with a modified head space assay (1 hour accumulation at 30°

Figure 70B:
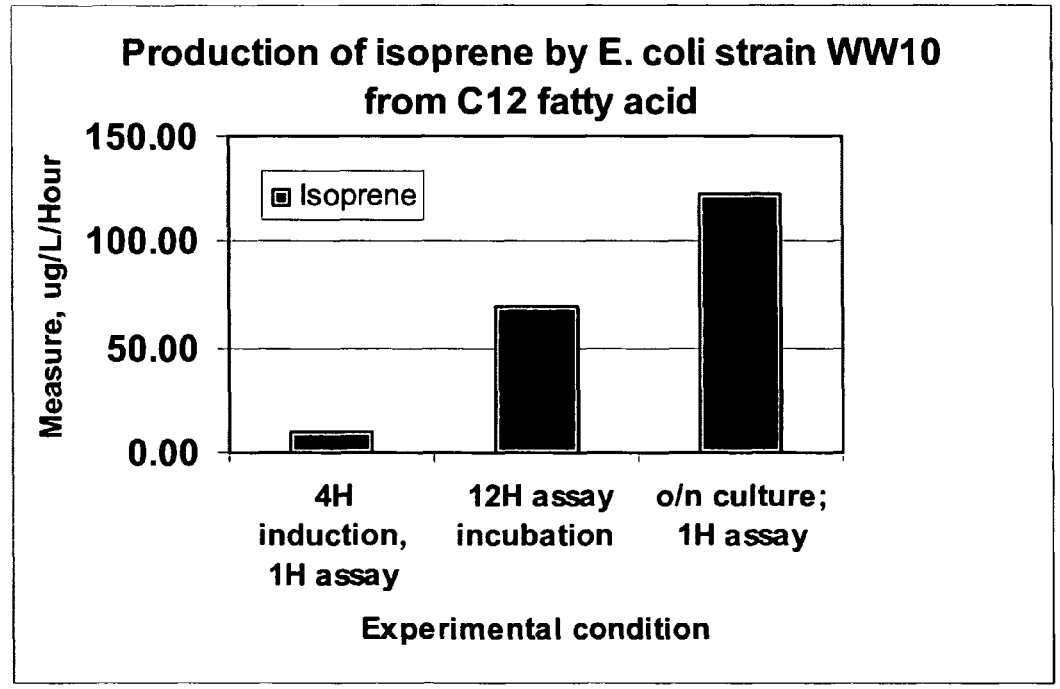

C. with shaking at 500 rpm). An additional isoprene assay was conducted by a 12 hour incubation of the assay glass block prior to GCMS analysis. Incubation of the induced cultures was continued overnight and 200 uL aliquots were again assayed for isoprene production (1 hour, 30 deg, 500 rpm Shel-shaker) the following morning. Analysis of these cultures showed the production of significant levels of isoprene. The highest levels of isoprene were observed in the culture which was seeded at 1/10 dilution from the overnight starter culture after it had been incubated and induced overnight. This result suggests that this culture continued to grow and increase in cell density. These results are shown in FIG. 70B. Cell density could not be measured directly because the fatty acid suspension had a turbid appearance. Cell density of this culture was therefore determined by plating an aliquot of the culture and showed 8×10$^7$ colony forming units. This corresponds approximately to an OD$_{600}$ of 0.1. Nevertheless, this culture provided significant isoprene production; no isoprene is observed for similar strains without the pathway described in this example.

Example 13

Improvement of Isoprene Production by Constitutive Expression of ybhE in *E. coli*.

This example shows production of isoprene in a strain constitutively expressing ybhE (pgl) compared to a control strain with wild type ybhE. The gene ybhE (pgl) encodes a 6-phosphogluconolactonase that suppresses posttranslational gluconylation of heterologously expressed proteins and improves product solubility and yield while also improving biomass yield and flux through the pentose phosphate pathway (Aon et al. *Applied and Environmental Microbiology*, 74(4): 950-958, 2008).

The BL21 strain of *E. coli* producing isoprene (EWL256) was constructed with constitutive expression of the ybhE gene on a replicating plasmid pBBR1MCS5(Gentamycin) (obtained from Dr. K. Peterson, Louisiana State University).

FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers Pgl-F and PglGI1.5-R were used to amplify the resistance cassette from the FRT-gb2-Cm-FRT template using Stratagene Herculase II Fusion kit according to the manufacturer's protocol. The PCR reaction (50 uL final volume) contained: 5 uL buffer, 1 uL template DNA (FRT-gb2-Cm-F from Gene Bridges), 10 pmols of each primer, and 1.5 uL 25 mM dNTP mix, made to 50 uL with dH$_2$O. The reaction was cycled as follows: 1×2 minutes, 95° C. then 30 cycles of (30 seconds at 95° C.; 30 seconds at 63° C.; 3 minutes at 72° C.).

The resulting PCR product was purified using the QiaQick PCR purification kit (Qiagen) and electroporated into electrocompetent MG1655 cells harboring the pRed-ET recombinase-containing plasmid as follows. Cells were prepared by growing in 5 mLs of L broth to and OD600-0.6 at 30° C. The cells were induced for recombinase expression by the addition of 4% arabinose and allowed to grow for 30 minutes at 30° C. followed by 30 minutes of growth at 37° C. An aliquot of 1.5 mLs of the cells was washed 3-4 times in ice cold dH$_2$O. The final cell pellet was resuspended in 40 uL of ice cold dH$_2$O and 2-5 uL of the PCR product was added. The electroporation was carried out in 1-mm gap cuvettes, at 1.3 kV in a Gene Pulser Electroporator (Bio-Rad Inc.). Cells were recovered for 1-2 hours at 30° C. and plated on L agar containing chloramphenicol (5 ug/mL). Five transformants were analyzed by PCR and sequencing using primers flanking the integration site (2 primer sets: pgl and 49 rev and 3' EcoRV-pglstop; Bottom Pgb2 and Top GB's CMP (946)). A correct transformant was selected and this strain was designated MG1655 GI1.5-pgl::CMP.

The chromosomal DNA of MG1655 GI1.5-pgl::CMP was used as template to generate a PCR fragment containing the FRT-CMP-FRT-GI1.5—ybhE construct. This construct was cloned into pBBR1MCS5(Gentamycin) as follows. The fragment, here on referred to as CMP-GI1.5-pgl, was amplified using the 5' primer Pglconfirm-F and 3' primer 3' EcoRV-pglstop. The resulting fragment was cloned using the Invitrogen TOPO-Blunt cloning kit into the plasmid vector pCR-Blunt II-TOPO as suggested from the manufacturer. The NsiI fragment harboring the CMP-GI1.5-pgl fragment was cloned into the PstI site of pBBR1MCS5(Gentamycin). A 20 µl ligation reaction was prepared containing 5 µl CMP-GI1.5-pgl insert, 2 µl pBBR1MCS5(Gentamycin) vector, 1 µl T4 DNA ligase (New England Biolabs), 2 µl 10× ligase buffer, and 10 µl ddH$_2$O. The ligation mixture was incubated at room temperature for 40 minutes then 2-4 uL were electroporated into electrocompetent Top10 cells (Invitrogen) using the parameters disclosed above. Transformants were selected on L agar containing 10 ug/ml chloramphenicol and 5 ug/ml Gentamycin. The sequence of the selected clone was determined using a number of the primers described above as well as with the in-house T3 and Reverse primers provided by Sequetech, Calif. This plasmid was designated pBBRC-MPGI1.5-pgl (FIGS. 77A-B and SEQ ID NO:122).

Plasmid pBBRCMPGI1.5-pgl was electroporated into EWL256, as described above in Example 10 and transformants were plated on L agar containing Chloramphenicol (10 ug/mL), Gentamycin (5 ug/mL), spectinomycin (50 ug/mL), and carbenicillin (50 ug/mL). One transformant was selected and designated RM11608-2.

```
Primers:

Pgl-F
                                         (SEQ ID NO: 115)
5'-ACCGCCAAAAGCGACTAATTTTAGCTGTTACAGTCAGTTGAATTA
ACCCTCACTAAAGGGCGGCCGC-3'

PglGI1.5-R
                                         (SEQ ID NO: 116)
5'-GCTGGCGATATAAACTGTTTGCTTCATGAATGCTCCTTTGGGTTA
CCTCCGGGAAACGCGGTTGATTTGTTTAGTGGTTGAATTATTTGCTCA
GGATGTGGCATAGTCAAGGGCGTGACGGCTCGCTAATACGACTCACTA
TAGGGCTCGAG-3'

3' EcoRV-pglstop:
                                         (SEQ ID NO: 117)
5'-CTT GAT ATC TTA GTG TGC GTT AAC CAC CAC pgl +49rev:
                                         (SEQ ID NO: 118)
CGTGAATTTGCTGGCTCTCAG Bottom Pgb2:
                                         (SEQ ID NO: 119)
GGTTTAGTTCCTCACCTTGTC Top GB's CMP (946):
                                         (SEQ ID NO: 120)
ACTGAAACGTTTTCATCGCTC Pglconfirm-F
                                         (SEQ ID NO: 121)
5'-ACCGCCAAAAGCGACTAATTTTAGCT-3'
``` i) Small Scale Analysis

Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 1 g, 1000× Trace Metals Solution 1 ml. All of the components were added together and dissolved in $diH_2O$. The pH was adjusted to 6.8 with ammonium hydroxide (30%) and brought to volume. Media was filter-sterilized with a 0.22 micron filter. Glucose 5.0 g and antibiotics were added after sterilization and pH adjustment.

1000× Trace Metal Solution (Per Liter Fermentation Media):

Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

a) Experimental Procedure

Isoprene production was analyzed by growing the strains in a Cellerator™ from MicroReactor Technologies, Inc. The working volume in each of the 24 wells was 4.5 mL. The temperature was maintained at 30° C., the pH setpoint was 7.0, the oxygen flow setpoint was 20 sccm and the agitation rate was 800 rpm. An inoculum of E. coli strain taken from a frozen vial was streaked onto an LB broth agar plate (with antibiotics) and incubated at 30° C. A single colony was inoculated into media with antibiotics and grown overnight. The bacteria were diluted into 4.5 mL of media with antibiotics to reach an optical density of 0.05 measured at 550 nm.

Off-gas analysis of isoprene was performed using a gas chromatograph-mass spectrometer (GC-MS) (Agilent) headspace assay. Sample preparation was as follows: 100 µL of whole broth was placed in a sealed GC vial and incubated at 30° C. for a fixed time of 30 minutes. Following a heat kill step, consisting of incubation at 70° C. for 5 minutes, the sample was loaded on the GC.

Optical density (OD) at a wavelength of 550 nm was obtained using a microplate reader (Spectramax) during the course of the run. Specific productivity was obtained by dividing the isoprene concentration (µg/L) by the OD reading and the time (hour).

The two strains EWL256 and RM11608-2 were assessed at 200 and 400 uM IPTG induction levels. Samples were analyzed for isoprene production and cell growth (OD550) at 1, 2.5, 4.75, and 8 hours post-induction. Samples were done in duplicate.

b) Results

The experiment demonstrated that at 2 different concentrations of IPTG the strain expressing the ybhE (pgl) had a dramatic 2-3 fold increase in specific productivity of isoprene compared to the control strain.

ii) Isoprene Fermentation from E. coli Expressing M. mazei Mevalonate Kinase, P. alba Isoprene Synthase, and pgl Over-Expression (RHM111608-2) and Grown in Fed-Batch Culture at the 15-L Scale Medium Recipe (Per Liter Fermentation Medium)

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in Di $H_2O$, pH to 3.0 with HCl/NaOH, then q.s. to volume and filter sterilized with a 0.22 micron filter.

Fermentation was performed in a 15-L bioreactor with BL21 (DE3) E. coli cells containing the upper mevalonic acid (MVA) pathway (pCL Upper), the integrated lower MVA pathway (gi1.2KKDyI), high expression of mevalonate kinase from M. mazei and isoprene synthase from P. alba (pTrcAlba-mMVK), and high expression of pgl (pBBR-pgl). This experiment was carried out to monitor isoprene formation from glucose at the desired fermentation pH 7.0 and temperature 34° C. A frozen vial of the E. coli strain was thawed and inoculated into tryptone-yeast extract medium. After the inoculum grew to OD 1.0, measured at 550 nm, 500 mL was used to inoculate a 15-L bioreactor bringing the initial volume to 5-L.

Figure 78A:
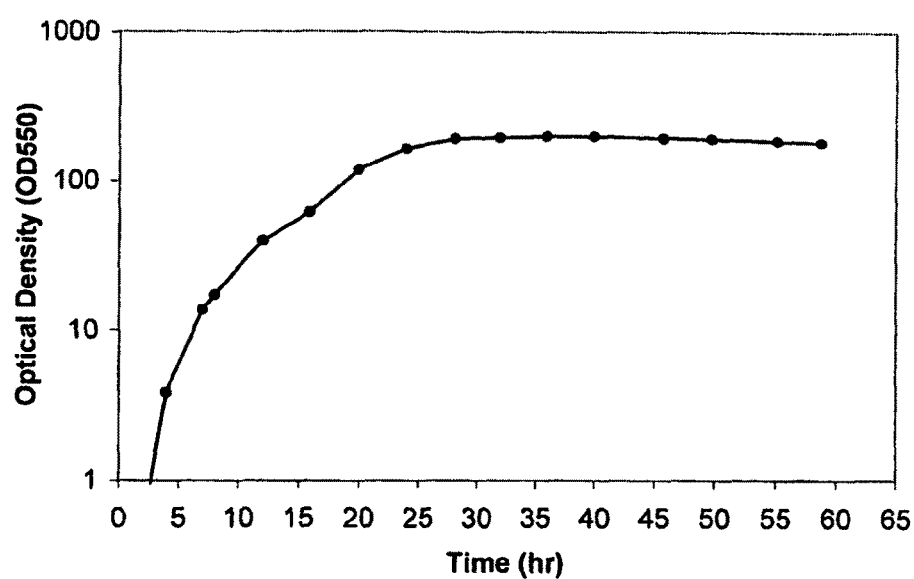
Figure 78D:
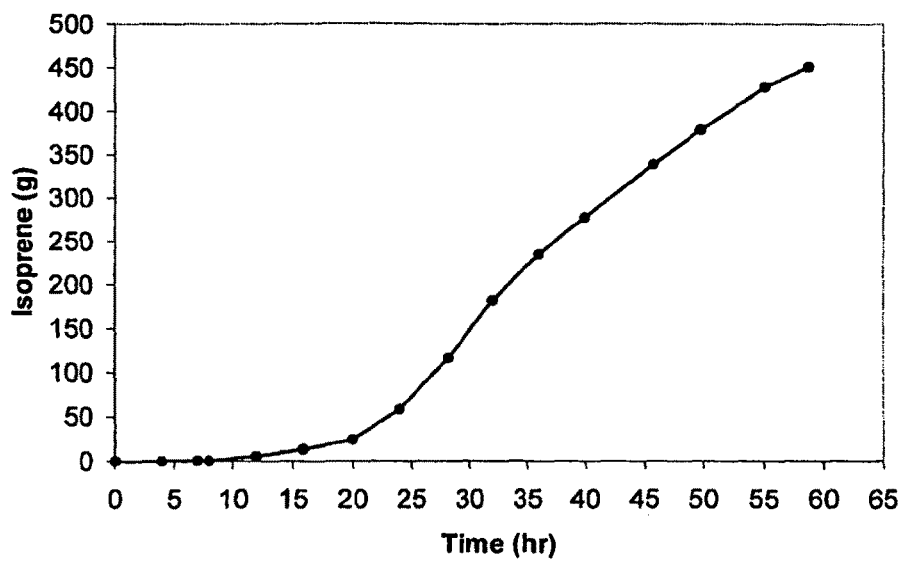
Figure 78E:
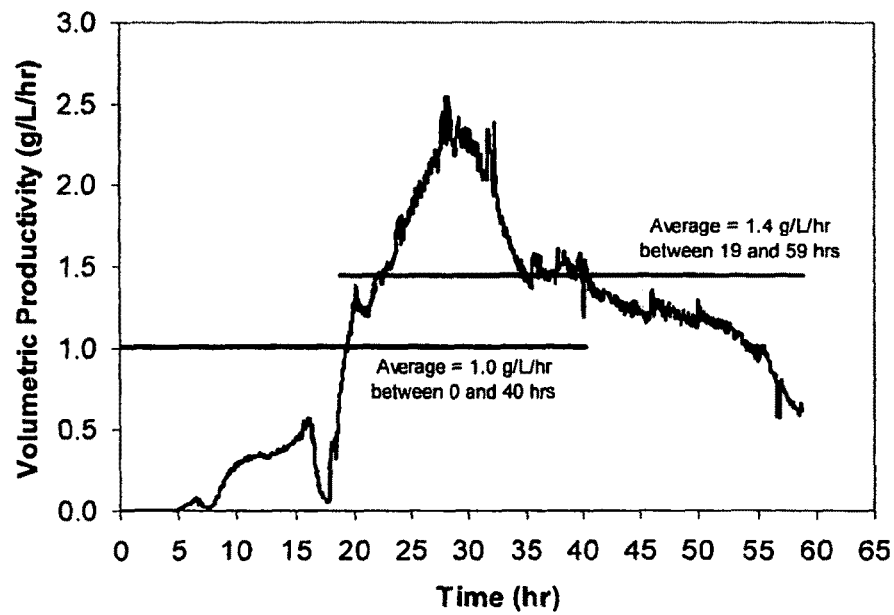
Figure 78F:
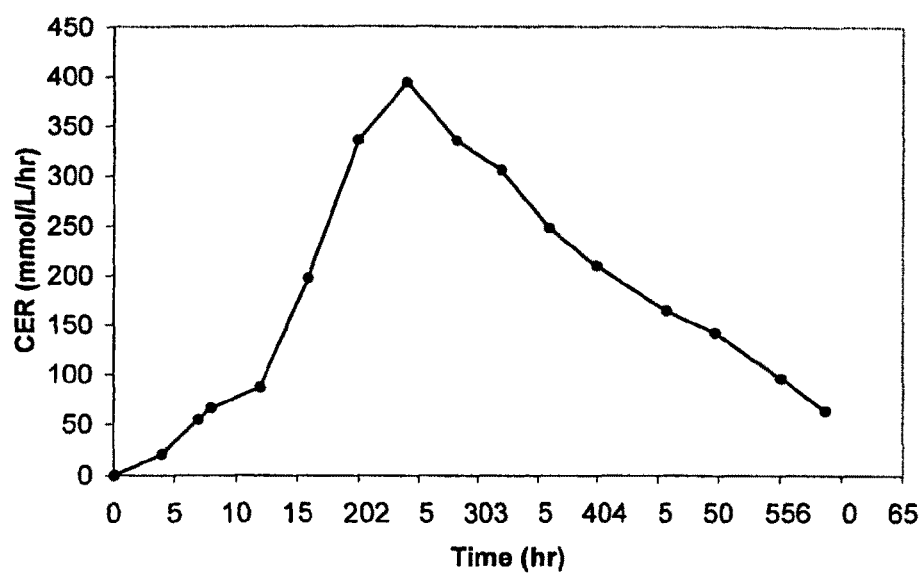

Glucose was fed at an exponential rate until cells reached the stationary phase. After this time the glucose feed was decreased to meet metabolic demands. The total amount of glucose delivered to the bioreactor during the 40 hour (59 hour) fermentation was 3.1 kg (4.2 kg at 59 hour). Induction was achieved by adding IPTG. The IPTG concentration was brought to 110 uM when the optical density at 550 nm ($OD_{550}$) reached a value of 4. The IPTG concentration was raised to 192 uM when $OD_{550}$ reached 150. The $OD_{550}$ profile within the bioreactor over time is shown in FIG. 78A. The isoprene level in the off gas from the bioreactor was determined using a Hiden mass spectrometer. The isoprene titer increased over the course of the fermentation to a maximum value of 33.2 g/L at 40 hours (48.6 g/L at 59 hours) (FIG. 78B). The isoprene titer increased over the course of the fermentation to a maximum value of 40.0 g/L at 40 hours (60.5 g/L at 59 hours) (FIG. 78C). The total amount of isoprene produced during the 40-hour (59-hour) fermentation was 281.3 g (451.0 g at 59 hours) and the time course of production is shown in FIG. 78D. The time course of volumetric productivity is shown in FIG. 78E and shows that an average rate of 1.0 g/L/hr was maintained between 0 and 40 hours (1.4 g/L/hour between 19 and 59 hour). The metabolic activity profile, as measured by CER, is shown in FIG. 78F. The molar yield of utilized carbon that went into producing isoprene during fermentation was 19.6% at 40 hours (23.6% at 59 hours). The weight percent yield of isoprene from glucose was 8.9% at 40 hours (10.7% at 59 hours).

Preparation of Isoprene Samples for Polymerization (a) Preparation of 1000× Modified Trace Metal Solution:

Each of the following components is dissolved one at a time in Di $H_2O$: Citric Acid*$H_2O$ (40 g), $MnSO_4*H_2O$ (30 g), NaCl (10 g), $FeSO_4*7H_2O$ (1 g), $CoCl_2*6H_2O$ (1 g), $ZnSO*7H_2O$ (1 g), $CuSO_4*5H_2O$ (100 mg), $H_3BO_3$ (100 mg), $NaMoO_4*2H_2O$ (100 mg). The pH was adjusted to 3.0 with HCl/NaOH, then q.s. to volume and filter sterilized with a 0.22 micron filter.

(b) Preparation of Fermentation Medium:

Each liter of fermentation medium contained $K_2HPO_4$ (7.5 g), $MgSO_4*7H_2O$ (2 g), citric acid monohydrate (2 g), ferric ammonium citrate (0.3 g), yeast extract (0.5 g), 1000× Modified Trace Metal Solution (1 ml). All of the components were added together and dissolved in diH2O. This solution was autoclaved. The pH was adjusted to 7.0 with ammonium gas (NH3) and q.s. to volume. Glucose (10 g), thiamine*HCl (0.1 g), and antibiotic were added after sterilization and pH adjustment.

(c) Collection of Isoprene Samples for Purification and Polymerization:

Isoprene was collected by adsorption on activated charcoal by passing the fermentation exhaust across canisters of activated charcoal arranged in parallel on an exhaust manifold.

(d) Preparation of Isoprene Polymerization Sample A from Glucose using *E. coli*

Fermentation was performed at pH 7.0 and 30° C. in a 15-L bioreactor with BL21 (DE3) *E. coli* cells containing the pCL PtrcUpperMVA and pTrc KKDyIkIS plasmids. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Figure 80:
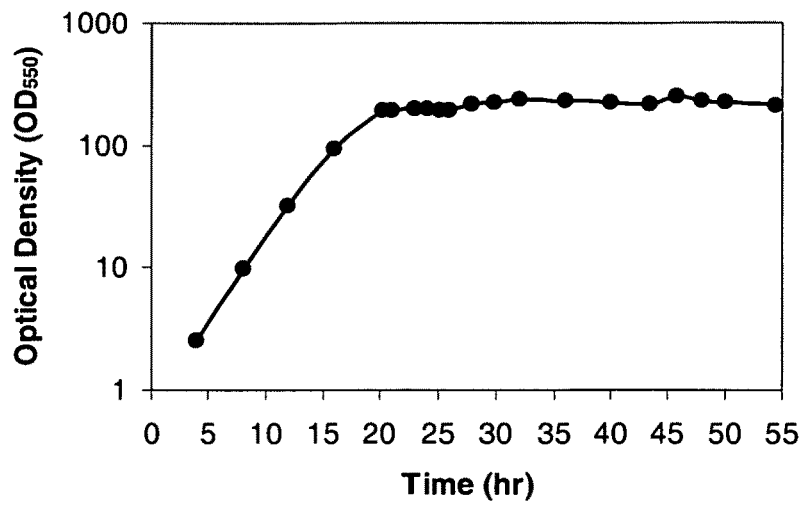
FIG. 80 shows the time course of optical density within the 15-L bioreactor fed with glucose.
Figure 81:
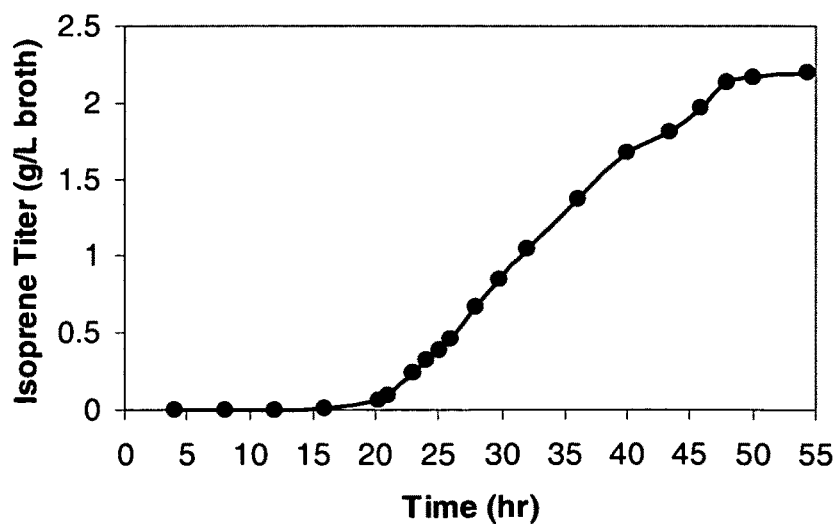
FIG. 81 shows the time course of isoprene titer within the 15-L bioreactor fed with glucose. The titer is defined as the amount of isoprene produced per liter of fermentation broth.
Figure 82:
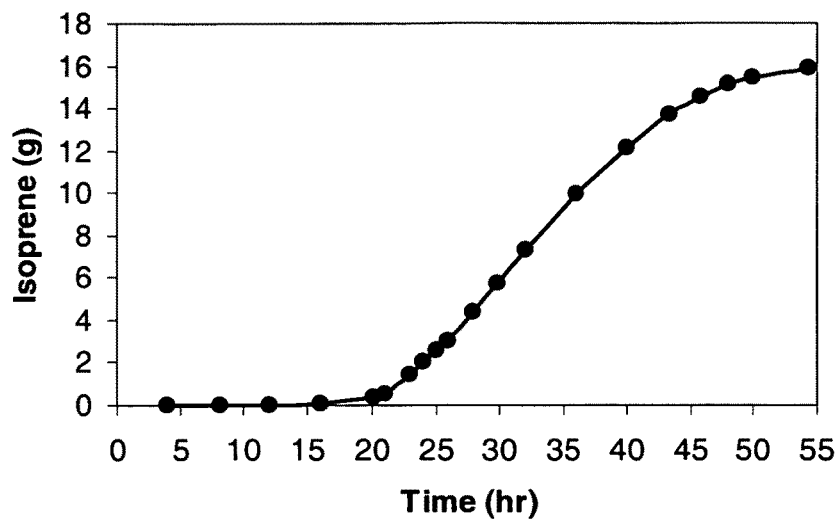
FIG. 82 shows the time course of total isoprene produced from the 15-L bioreactor fed with glucose.
Figure 83:
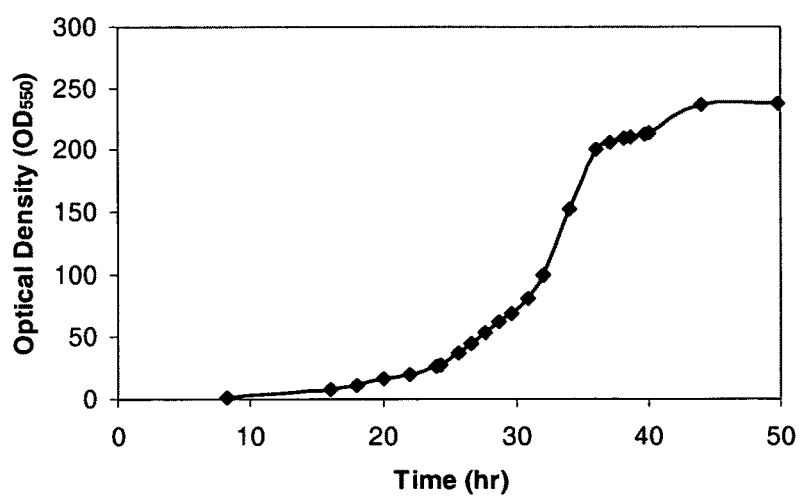
FIG. 83 is a graph illustrating the time course of optical density within the 500-L bioreactor fed with glucose and yeast extract.
Figure 84:
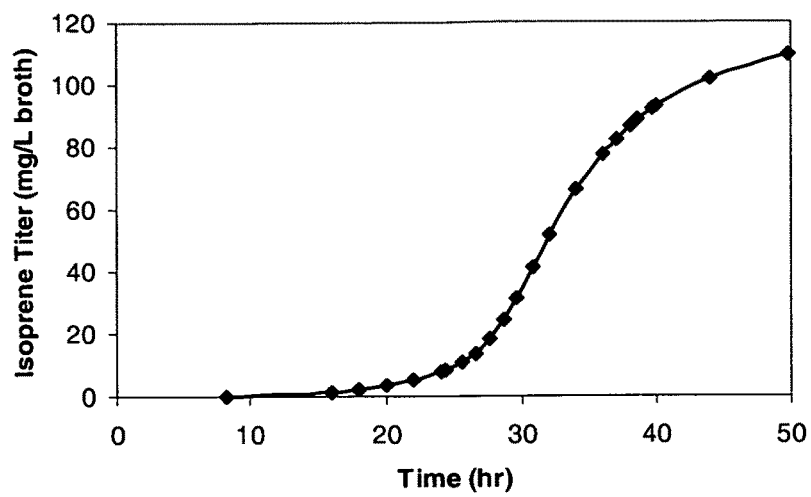
FIG. 84 is a graph illustrating the time course of isoprene titer within the 500-L bioreactor fed with glucose and yeast extract. The titer is defined as the amount of isoprene produced per liter of fermentation broth.
Figure 85:
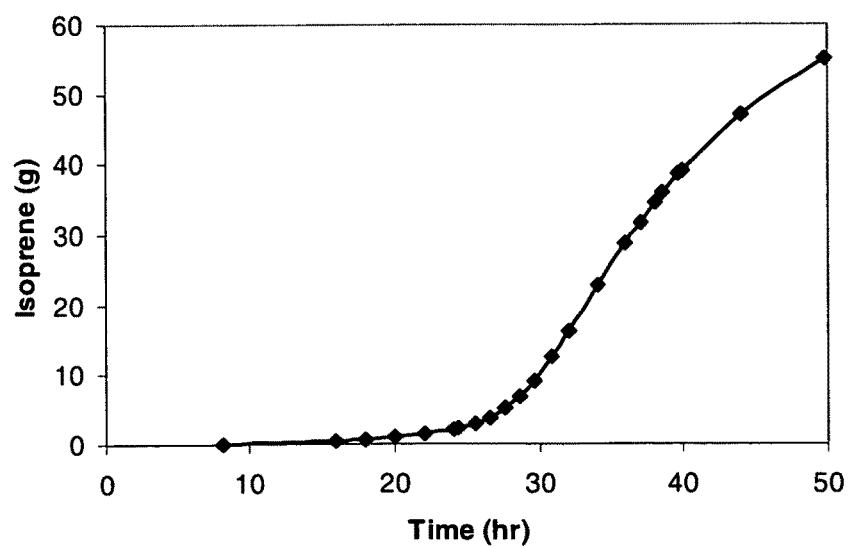
FIG. 85 is a graph illustrating the time course of total isoprene produced form the 500-L bioreactor fed with glucose and yeast extract.

Glucose was fed at an exponential rate until cells reached the stationary phase. After this time the glucose feed was decreased to meet metabolic demands. The total amount of glucose delivered to the bioreactor during the 54 hour fermentation was 3.7 kg. Induction was achieved by adding isopropyl-beta-D-1-thiogalactopyranoside (IPTG). The IPTG concentration was brought to 25 μM when the optical density at 550 nm ($OD_{550}$) reached a value of 10. The IPTG concentration was raised to 50 uM when OD550 reached 190. IPTG concentration was raised to 100 uM at 38 hours of fermentation. The OD550 profile within the bioreactor over time is shown in FIG. 1. The isoprene titer increased over the course of the fermentation to a final value of 2.2 g/L (FIG. 2). The total amount of isoprene produced during the 54 hour fermentation was 15.9 g and the time course of production is shown in FIG. 3. The molar yield of utilized carbon that went into producing isoprene during fermentation was 1.53%. (See FIGS. 80, 81 and 82).

(e) Preparation of Isoprene Polymerization Sample B from Glucose and Yeast Extract Using *E. coli*

Isoprene formation from glucose and yeast extract was performed at pH 7.0 and 30° C. in a 500-L bioreactor with *E. coli* cells containing the pTrcKudzu+yIDI+DXS plasmid. An inoculum of *E. coli* strain taken from a frozen vial was prepared in soytone-yeast extract-glucose medium. After the inoculum grew to OD 0.15, measured at 550 nm, 20 mL was used to inoculate a bioreactor containing 2.5-L tryptone-yeast extract medium. The 2.5-L bioreactor was grown at 30° C. to OD 1.0 and 2.0-L was transferred to the 500-L bioreactor. Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 4. The isoprene titer increased over the course of the fermentation (FIG. 5). The total amount of isoprene produced during the 50 hour fermentation was 55.1 g and the time course of production is shown in FIG. 6.

Isoprene Desorption from Activated Charcoal (Method A)

Activated charcoal (130 g), which had been exposed to a stream of fermentor off-gas, was placed into a 1000 mL flask along with a stir bar. Cyclohexane (563 mL) was added to the flask and the slurry was agitated for 2 hours. Vacuum was applied (100 mbar) via an in-line cryogenic trap (30 mL capacity, immersed in liq. nitrogen). Four fractions were collected and combined to yield an isoprene/cyclohexane solution (2.1 wt % isoprene, total volume=53.1 g). This solution was vacuum distilled at 100 mbar and a new isoprene/cyclohexane solution was collected (yield=10.1 g), which was dried over 3 A molecular sieves. GC analysis of this solution indicated an isoprene content of 7.7 wt. %.

Isoprene Desorption from Activated Charcoal (Method B)

Activated charcoal (65 g), which had been exposed to a stream of fermentor off-gas, was placed into a 500 mL flask along with a stir bar. Jarytherm DBT (250 g) was added to the charcoal and the slurry was agited for 2 hours. Vacuum was applied (5 mbar) via an in-line cryogenic trap (30 mL capacity, immersed in liq. nitrogen). After 1 hour the trap was warmed to ambient temperature. Two liquid phases were present in the trap (total weight 1.82 g). The organic phase was diluted with cyclohexane (3.26 g), decanted, and dried over 3 A molecular sieves. GC analysis of this solution indicated an isoprene content of 27.3 wt. %, or 1.22 g).

Preparation of Neodymium Catalyst

Neodymium versatate (2.68 mL, 0.51 M in hexane,), triisobutylaluminum (54 mL, 1.0 M in hexane), and diethylaluminum chloride (3.40 mL, 1.0 M in hexane) were drawn up into plastic syringes fitted with steel cannula. The first two components were added to a solution of 1,3-butadiene in hexane (22.4 mL, 15 wt. % 1,3-butadiene, placed into a 100 mL glass vessel with septum top, and agitated for 0.5 h at ambient temperature. The last component was added to the solution after which it was heat-aged for 0.5 h at 65° C. The final solution was clear and yellow. The concentration of the solution based on neodymium was 0.0164 M.

Preparation of Titanium Catalyst

A 100 mL glass reaction vessel with septum inlet and containing a magnetic stirbar was placed in an ice bath at 0° C., charged with n-hexane (5.07 mL, anhydrous), and with neat $TiCl_4$ (1.5 mL, 13.7 mmol) under vigorous agitation. Separately, a solution was generated consisting of diphenyl ether (1.2 mL, 7.6 mmol) and triisobutylaluminum (14.6 mL, 12.6 mmol, 25 wt. % solution in hexane). The solution was added to the reaction vessel over the course of 5 minutes. A brown precipitate formed during the addition. The suspension was stirred for 10 minutes and was then stored at −40° C. for future use.

Polymerization

Samples of polyisoprene derived primarily from glucose were produced by polymerizing Isoprene Polymerization Sample A with Neodymium catalyst and n-BuLi. Samples of polyisoprene derived from cofermentation of glucose and yeast extract were produced by polymerizing Isoprene Polymerization Sample B with Neodymium catalyst, titatium catalyst, n-BuLi catalyst, and emulsion free radical polymerization. Representative polymerization conditions are described below.

Solution Polymerization of Isoprene with Neodymium Catalyst

A 4 mL screw top glass vial with Teflon coated stir bar was annealed in an oven for 3 h at 150° C. The vial was fitted with a Teflon faced silicone septum and open-top cap. Using a syringe, it was then charged with an isoprene solution (1.5 g, 7.7 wt. % in cyclohexane, anhydrous). Neodymium catalyst solution (60 uL) was injected into the vial with a microsyringe. The vial was placed onto a stirrer/hotplate regulated to 65° C., with the stir bar spinning at 500 rpm. After 15 minutes the solution became noticeably more viscose. After a reaction time of 1.5 h the reaction was quenched with a solution of isopropanol and butylated hydroxytoluene, (BHT), (30 uL, 10 wt. % BHT). A 100 mg sample of the cement was removed for GPC analysis. The remaining polymer cement was dried under ambient conditions. The isolated polymer weighed 110 mg, was determined to have a weight average molecular weight of 935,000 (by GPC) and a cis-mirrostructure content of greater than 90% (by $^{13}$C-NMR).

Solution Polymerization of Isoprene with Ti Catalyst

A 4 mL screw top glass vial and Teflon coated stir bar was annealed in an oven for 3 h at 150° C. The vial was fitted with a pre-scored Teflon faced silicone septum and open-top cap. Using a syringe, it was then charged with an isoprene solution (1.5 g, 7.7 wt. % in cyclohexane, anhydrous). The titanium catalyst suspension was magnetically stirred and a sample was removed (70 uL) with a disposable tip pipette, which was then added to the reaction vial through the pre-scored septum. The reaction vial septum was replaced with a solid cap, and the vial was placed onto a stirrer/hotplate'regulated to 65° C., with the stir bar spinning at 500 rpm. After 5 minutes the solution became noticeably more viscose. After a reaction time of 1.5 h the reaction was quenched with a solution of isopropanol and butylated hydroxytoluene, (BHT), (30 uL. 10 wt. % BHT). A 100 mg sample of the cement was removed for GPC analysis. The remaining polymer cement was dried under ambient conditions. The isolated polymer weighed 108 mg, had a weight average molecular weight of 221,000 (by GPC), and had a cis-mirocstructure content of greater than 94% (by $^{13}$C-NMR).

Emulsion Polymerization of Isoprene

A 20 mL vial was used as a polymerization vessel. The metal cap was pierced twice with an awl and cardboard linear was replaced with a rubber gasket and Teflon linear. The vial was rinsed with deionied water and dried under nitrogen.

To the vial was added 7.05 g deionized water, 1.14 g of 10% soap (potassium salt of mixed fatty acids), 174 mg of 10% ammonium persulfate solution, and 24 mg of n-dodecane thiol. The flask was purge for 30 seconds with nitrogen and capped. To the vial through the rubber/Teflon gasket was charged 3 mL of bio-HG (2.033 grams of isoprene). The vial was placed in a standard bottle polymerization bath (a second blank vial allows the vial to fit in a 4 oz bottle holder). The mixture was tumbled for 25.5 hours at 65° C. (+/−0.2° C.).

Work-Up:

The latex was transferred to 50 mL pear shaped flask and diluted with 10 mL of water. Un-reacted volatile organic was removed by evaporating 2 mL of water under vacuum (54 mmHg, 40-50° C.). To the latex was added an antioxidant dispersion, 140 mg of 50% active polyphenolic AO (Bostex 24). The latex was coagulated by adding it to a dilute acid solution (12 mL of 18% sulfuric acid in 150 mL RO water). The polymer coagulated into a single large piece which was pressed and washed with RO water. The sample was off white soft rubbery mass. The yield was 1.24 grams of wet crumb.

The final total solids content (TSC=100*dried weight/wet weight) was 18.9 wt % or an approximate conversion of 84%.

Polymerization of Isoprene with Butyllithium

Butyllithium (1.6 M in hexane) was diluted with n-hexane (anhydrous) in a ratio of 1:10. The solution was titrated against a standard N-pivalolyl-o-benzylaniline in THF. A solution of isoprene in cyclohexane (4 mL) was dried by passing it through a small column containing heat treated silica gel.

A 4 mL glass vial (oven dried at 150° C.) was charged with a small Teflon coated magnetic stir bar and a solution of isoprene in cyclohexane (1.35 g, 21.5 wt %). Butyllithium (0.14 M, hexane) was added via syringe and the vial was heated to 65° C. on a stirrer/hot plate for 3 h. The polymer reaction was quenched with a BHT/iso-propanol solution (10 wt % BHT in iso-propanol). All volatiles were removed under vacuum. This procedure yielded 290 mg of polymer which reprecsents a theoretical yield of about 100%. This polymer was determined by GPC analysis to have a weight average molecular weight ($M_w$) of 17,880 and was determined by $^{13}$C NMR to have a cis-microstructure content of 67%; a trans-microstructure content of 25%, and a 3,4-microstructure content of 8%.

GPC Analysis of Polymers

Size Exclusion Chromatography (SEC) is a well established technique to measure polymer molecular weight and polydispersity (Mw/Mn). Two Polymer Laboratories C microgel columns in series were utilized with tetrahydrofuran as the carrier solvent at a flow rate of 0.7 ml/min and a column temperature of 40° C. SEC was performed using a Wyatt Technologies miniDawn light scattering detector coupled with a Hewlett Packard 1047A refractive index detector. Polystyrene standards were used to calibrate the instrument.

NMR Analysis of Polymers

Polymer microstructures were determined by $^{13}$C-NMR analysis on a Varian Unity-Plus 400 MHz spectrometer in chloroform-di solvent.

Data from $^{13}$C/$^{12}$C Isotope Analyses

| Entry | Sample | $\delta^{13}$C |
|---|---|---|
| 1 | PI from sugar beet invert sugar | −34.98 |
| 2 | Commercial PI from isobutylene | −34.43 |
| 3 | Commercial PI from isobutylene | −34.42 |
| 4 | Guayule rubber | −31.10 |
| 5 | Palm oil | −30.03 |
| 6 | Palm oil | −30.00 |
| 7 | Natural rubber (Neco) | −28.11 |
| 8 | Natural rubber (Pumpic) | −27.92 |
| 9 | Natural rubber (Negato) | −27.86 |
| 10 | Natural rubber (Nivco) | −27.79 |
| 11 | Natural rubber (Naplo) | −27.74 |
| 12 | Natural rubber (Krado 1) | −27.68 |
| 13 | Natural rubber (Krado 1) | −27.55 |
| 14 | Natural rubber (Krado 2) | −27.54 |
| 15 | Natural rubber (Krado 2) | −27.52 |
| 16 | Natural rubber (Krado 2) | −27.49 |
| 17 | Natural rubber (Nolo) | −27.38 |
| 18 | Yeast extract | −25.70 |
| 19 | Yeast extract | −25.68 |
| 20 | Commercial PI from extractive distillation (Sample 2) | −23.83 |
| 21 | Commercial PI from extractive distillation (Sample 2) | −23.83 |
| 22 | Sugar from softwood pulp (Sample 2) | −23.25 |
| 23 | Sugar from softwood pulp (Sample 1) | −23.00 |
| 24 | Sugar from softwood pulp (Sample 1) | −22.96 |
| 25 | Commercial PI from extractive distillation (Sample 3) | −22.95 |
| 26 | Commercial PI from extractive distillation (Sample 3) | −22.95 |
| 27 | Commercial PI from extractive distillation (Sample 3) | −22.94 |
| 28 | Commercial PI from extractive distillation (Sample 3) | −22.92 |
| 29 | Commercial PI from extractive distillation (Sample 3) | −22.90 |
| 30 | Commercial PI from extractive distillation (Sample 3) | −22.89 |
| 31 | Commercial PI from extractive distillation (Sample 3) | −22.89 |
| 32 | Commercial PI from extractive distillation (Sample 3) | −22.89 |
| 33 | Commercial PI from extractive distillation (Sample 3) | −22.87 |
| 34 | Commercial PI from extractive distillation (Sample 3) | −22.84 |
| 35 | Commercial PI from extractive distillation (Sample 1) | −22.63 |
| 36 | Commercial PI from extractive distillation (Sample 1) | −22.62 |
| 37 | Commercial PI from extractive distillation (Sample 1) | −22.54 |
| 38 | PI from Isoprene Sample B (emulsion polymerization) | −19.67 |
| 39 | PI from Isoprene Sample B (Neodymium catalyst) | −19.14 |
| 40 | PI from Isoprene Sample B (Neodymium catalyst) | −18.80 |
| 41 | PI from Isoprene Sample B (Neodymium catalyst) | −18.37 |
| 42 | PI from Isoprene Sample B (n-BuLi catalyst) | −18.12 |
| 43 | PI from Isoprene Sample B (n-BuLi catalyst) | −18.12 |
| 44 | Invert Sugar (Sample 1) | −15.37 |
| 45 | Invert Sugar (Sample 2) | −15.36 |
| 46 | Invert Sugar (Sample 1) | −15.34 |
| 47 | Invert Sugar (Sample 1) | −15.31 |
| 48 | Invert Sugar (Sample 1) | −15.25 |
| 49 | PI from Isoprene Sample A (Neodymium catalyst) | −14.85 |
| 50 | PI from Isoprene Sample A (n-BuLi catalyst) | −14.69 |
| 51 | PI from Isoprene Sample A (n-BuLi catalyst) | −14.69 |
| 52 | PI from Isoprene Sample A (n-BuLi catalyst) | −14.66 |
| 53 | Glucose from bagasse (sample 2) | −13.19 |
| 54 | Glucose from bagasse (sample 1) | −13.00 |
| 55 | Glucose from bagasse (sample 1) | −12.93 |
| 56 | Glucose from corn stover (sample 2) | −11.42 |
| 57 | Glucose from corn stover (sample 1) | −11.23 |
| 58 | Glucose from corn stover (sample 1) | −11.20 |
| 59 | Cornstarch | −11.12 |

-continued

| Entry | Sample | δ¹³C |
|---|---|---|
| 60 | Cornstarch | −11.11 |
| 61 | Cornstarch | −11.10 |
| 62 | Cornstarch | −11.07 |
| 63 | Glucose | −10.73 |

(note:
PI = polyisoprene)

Unless defined otherwise, the meanings of all technical and scientific terms used herein are those commonly understood by one of skill in the art to which this invention pertains. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide general definitions for many of the terms used herein.

The headings provided herein are not limitations of the various aspects or embodiments of the invention which can be had by reference to the specification as a whole. For use herein, unless clearly indicated otherwise, use of the terms "a", "an," and the like refers to one or more. Reference to "about" a value or parameter herein includes (and describes) embodiments that are directed to that value or parameter per se. For example, description referring to "about X" includes description of "X." Numeric ranges are inclusive of the numbers defining the range. It is understood that aspects and embodiments of the invention described herein include "comprising," "consisting," and "consisting essentially of" aspects and embodiments.

While certain representative embodiments and details have been shown for the purpose of illustrating the subject invention, it will be apparent to those skilled in this art that various changes and modifications can be made therein without departing from the scope of the subject invention. It is to be understood that this invention is not limited to the particular methodology, protocols, and reagents described, as these may vary. One of skill in the art will also appreciate that any methods and materials similar or equivalent to those described herein can also be used to practice or test the invention.

Appendix 1

Exemplary 1-deoxy-D-xylulose-5-phosphate Synthase Nucleic Acids and Polypeptides ATH: AT3G21500(DXPS1) AT4G15560(CLA1) AT5G11380(DXPS3)
OSA: 4338768 4340090 4342614
CME: CMF089C
PFA: MAL13P1.186
TAN: TA20470
TPV: TP01_0516
ECO: b0420(dxs)
ECJ: JW0410(dxs)
ECE: Z0523(dxs)
ECS: ECs0474
ECC: c0531(dxs)
ECI: UTI89_C0443(dxs)
ECP: ECP_0479
ECV: APECO1_1590(dxs)
ECW: EcE24377A_0451(dxs)
ECX: EcHS_A0491
STY: STY0461(dxs)
STT: t2441(dxs)
SPT: SPA2301(dxs)
SEC: SC0463(dxs)
STM: STM0422(dxs)
YPE: YPO3177(dxs)
YPK: y1008(dxs)
YPM: YP_0754(dxs)
YPA: YPA_2671
YPN: YPN_0911
YPP: YPDSF_2812
YPS: YPTB0939(dxs)
YPI: YpsIP31758_3112(dxs)
SFL: SF0357(dxs)
SFX: S0365(dxs)
SFV: SFV_0385(dxs)
SSN: SSON_0397(dxs)
SBO: SBO_0314(dxs)
SDY: SDY_0310(dxs)
ECA: ECA1131(dxs)
PLU: plu3887(dxs)
BUC: BU464(dxs)
BAS: BUsg448(dxs)
WBR: WGLp144(dxs)
SGL: SG0656
KPN: KPN_00372(dxs)
BFL: Bfl238(dxs)
BPN: BPEN_244(dxs)
HIN: HI1439(dxs)
HIT: NTHI1691(dxs)
HIP: CGSHiEE_04795
HIQ: CGSHiGG_01080
HDU: HD0441(dxs)
HSO: HS_0905(dxs)
PMU: PM0532(dxs)
MSU: MS1059(dxs)
APL: APL_0207(dxs)
XFA: XF2249
XFT: PD1293(dxs)
XCC: XCC2434(dxs)
XCB: XC_1678
XCV: XCV2764(dxs)
XAC: XAC2565(dxs)
XOO: XOO2017(dxs)
XOM: XOO_1900(XOO1900)
VCH: VC0889
VVU: VV1_0315
VVY: VV0868
VPA: VP0686
VFI: VF0711
PPR: PBPRA0805
PAE: PA4044(dxs)
PAU: PA14_11550(dxs)
PAP: PSPA7_1057(dxs)
PPU: PP_0527(dxs)
PST: PSPTO_0698(dxs)
PSB: Psyr_0604
PSP: PSPPH_0599(dxs)
PFL: PFL_5510(dxs)
PFO: Pfl_5007
PEN: PSEEN0600(dxs)
PMY: Pmen_3844
PAR: Psyc_0221(dxs)
PCR: Pcryo_0245
ACI: ACIAD3247(dxs)
SON: SO_1525(dxs)
SDN: Sden_2571
SFR: Sfri_2790
SAZ: Sama_2436

SBL: Sbal_1357
SLO: Shew_2771
SHE: Shewmr4_2731
SHM: Shewmr7_2804
SHN: Shewana3_2901
SHW: Sputw3181_2831
ILO: IL2138(dxs)
CPS: CPS_1088(dxs)
PHA: PSHAa2366(dxs)
PAT: Patl_1319
SDE: Sde_3381
PIN: Ping_2240
MAQ: Maqu_2438
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
NOC: Noc_1743
AEH: Mlg_1381
HCH: HCH_05866(dxs)
CSA: Csal_0099
ABO: ABO_2166(dxs)
AHA: AHA_3321(dxs)
BCI: BCI_0275(dxs)
RMA: Rmag_0386
VOK: COSY_0360(dxs)
NME: NMB1867
NMA: NMA0589(dxs)
NMC: NMC0352(dxs)
NGO: NGO0036
CVI: CV_2692(dxs)
RSO: RSc2221(dxs)
REU: Reut_A0882
REH: H16_A2732(dxs)
RME: Rmet_2615
BMA: BMAA0330(dxs)
BMV: BMASAVP1_1512(dxs)
BML: BMA10299_1706(dxs)
BMN: BMA10247_A0364(dxs)
BXE: BxeB2827
BUR: Bcep18194_B2211
BCN: Bcen_4486
BCH: Bcen2424_3879
BAM: Bamb_3250
BPS: BPSS1762(dxs)
BPM: BURPS1710b_A0842(dxs)
BPL: BURPS1106A_A2392(dxs)
BPD: BURPS668_A2534(dxs)
BTE: BTH_II0614(dxs)
BPE: BP2798(dxs)
BPA: BPP2464(dxs)
BBR: BB1912(dxs)
RFR: Rfer_2875
POL: Bpro_1747
PNA: Pnap_1501
AJS: Ajs_1038
MPT: Mpe_A2631
HAR: HEAR0279(dxs)
MMS: mma_0331
NEU: NE1161(dxs)
NET: Neut_1501
NMU: Nmul_A0236
EBA: ebA4439(dxs)
AZO: azo1198(dxs)
DAR: Daro_3061
TBD: Tbd_0879
MFA: Mfla_2133
HPY: HP0354(dxs)
HPJ: jhp0328(dxs)
HPA: HPAG1_0349
HHE: HH0608(dxs)
HAC: Hac_0968(dxs)
WSU: WS1996
TDN: Tmden_0475
CJE: Cj0321(dxs)
CJR: CJE0366(dxs)
CJJ: CJJ81176_0343(dxs)
CJU: C8J_0298(dxs)
CJD: JJD26997_1642(dxs)
CFF: CFF8240_0264(dxs)
CCV: CCV52592_1671(dxs) CCV52592_1722
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
PCA: Pcar_1667
PPD: Ppro_1191 Ppro_2403
DVU: DVU1350(dxs)
DVL: Dvul_1718
DDE: Dde_2200
LIP: LI0408(dsx)
DPS: DP2700
ADE: Adeh_1097
MXA: MXAN_4643(dxs)
SAT: SYN_02456
SFU: Sfum_1418
PUB: SAR11_0611(dxs)
MLO: mlr7474
MES: Meso_0735
SME: SMc00972(dxs)
ATU: Atu0745(dxs)
ATC: AGR_C_1351
RET: RHE_CH00913(dxs)
RLE: RL0973(dxs)
BME: BMEI1498
BMF: BAB1_0462(dxs)
BMS: BR0436(dxs)
BMB: BruAb1_0458(dxs)
BOV: BOV_0443(dxs)
BJA: bll2651(dxs)
BRA: BRADO2161(dxs)
BBT: BBta_2479(dxs)
RPA: RPA0952(dxs)
RPB: RPB_4460
RPC: RPC_1149
RPD: RPD_4305
RPE: RPE_1067
NWI: Nwi_0633
NHA: Nham_0778
BHE: BH04350(dxs)
BQU: BQ03540(dxs)
BBK: BARBAKC583_0400(dxs)
CCR: CC_2068
SIL: SPO0247(dxs)
SIT: TM1040_2920
RSP: RSP_0254(dxsA) RSP_1134(dxs)
JAN: Jann_0088 Jann_0170

RDE: RD1_0101(dxs) RD1_0548(dxs)
MMR: Mmar10_0849
HNE: HNE_1838(dxs)
ZMO: ZMO1234(dxs) ZMO1598(dxs)
NAR: Saro_0161
SAL: Sala_2354
ELI: ELI_12520
GOX: GOX0252
GBE: GbCGDNIH1_0221 GbCGDNIH1_2404
RRU: Rru_A0054 Rru_A2619
MAG: amb2904
MGM: Mmc1_1048
SUS: Acid_1783
BSU: BG11715(dxs)
BHA: BH2779
BAN: BA4400(dxs)
BAR: GBAA4400(dxs)
BAA: BA_4853
BAT: BAS4081
BCE: BC4176(dxs)
BCA: BCE_4249(dxs)
BCZ: BCZK3930(dxs)
BTK: BT9727_3919(dxs)
BTL: BALH_3785(dxs)
BLI: BL01523(dxs)
BLD: BL102598(dxs)
BCL: ABC2462(dxs)
BAY: RBAM_022600
BPU: BPUM_2159
GKA: GK2392
GTN: GTNG_2322
LMO: lmo1365(tktB)
LMF: LMOf2365_1382(dxs)
LIN: lin1402(tktB)
LWE: lwe1380(tktB)
LLA: L108911(dxsA) L123365(dxsB)
LLC: LACR_1572 LACR_1843
LLM: llmg0749(dxsB)
SAK: SAK_0263
LPL: lp_2610(dxs)
LJO: LJ0406
LAC: LBA0356
LSL: LSL_0209(dxs)
LGA: LGAS_0350
STH: STH1842
CAC: CAC2077 CA_P0106(dxs)
CPE: CPE1819
CPF: CPF_2073(dxs)
CPR: CPR_1787(dxs)
CTC: CTC01575
CNO: NT01CX_1983
CTH: Cthe_0828
CDF: CD1207(dxs)
CBO: CBO1881(dxs)
CBA: CLB_1818(dxs)
CBH: CLC_1825(dxs)
CBF: CLI_1945(dxs)
CKL: CKL_1231(dxs)
CHY: CHY_1985(dxs)
DSY: DSY2348
DRM: Dred_1078
PTH: PTH_1196(dxs)
SWO: Swol_0582
CSC: Csac_1853
TTE: TTE1298(dxs)
MTA: Moth_1511
MPE: MYPE730

MGA: MGA_1268(dxs)
MTU: Rv2682c(dxs1) Rv3379c(dxs2)
MTC: MT2756(dxs)
MBO: Mb2701c(dxs1) Mb3413c(dxs2)
MLE: ML1038(dxs)
MPA: MAP2803c(dxs)
MAV: MAV_3577(dxs)
MSM: MSMEG_2776(dxs)
MMC: Mmcs_2208
CGL: NCgl1827(cgl1902)
CGB: cg2083(dxs)
CEF: CE1796
CDI: DIP1397(dxs)
CJK: jk1078(dxs)
NFA: nfa37410(dxs)
RHA: RHA1_ro06843
SCO: SCO6013(SC1C3.01) SCO6768(SC6A5.17)
SMA: SAV1646(dxs1) SAV2244(dxs2)
TWH: TWT484
TWS: TW280(Dxs)
LXX: Lxx10450(dxs)
CMI: CMM_1660(dxsA)
AAU: AAur_1790(dxs)
PAC: PPA1062
TFU: Tfu_1917
FRA: Francci3_1326
FAL: FRAAL2088(dxs)
ACE: Acel_1393
SEN: SACE_1815(dxs) SACE_4351
BLO: BL1132(dxs)
BAD: BAD_0513(dxs)
FNU: FN1208 FN1464
RBA: RB2143(dxs)
CTR: CT331(dxs)
CTA: CTA_0359(dxs)
CMU: TC0608
CPN: CPn1060(tktB_2)
CPA: CP0790
CPJ: CPj1060(tktB_2)
CPT: CpB1102
CCA: CCA00304(dxs)
CAB: CAB301(dxs)
CFE: CF0699(dxs)
PCU: pc0619(dxs)
TPA: TP0824
TDE: TDE1910(dxs)
LIL: LA3285(dxs)
LIC: LIC10863(dxs)
LBJ: LBJ_0917(dxs)
LBL: LBL_0932(dxs)
SYN: sll1945(dxs)
SYW: SYNW1292(Dxs)
SYC: syc1087_c(dxs)
SYF: Synpcc7942_0430
SYD: Syncc9605_1430
SYE: Syncc9902_1069
SYG: sync_1410(dxs)
SYR: SynRCC307_1390(dxs)
SYX: SynWH7803_1223(dxs)
CYA: CYA_1701(dxs)
CYB: CYB_1983(dxs)
TEL: tll0623
GVI: gll0194
ANA: alr0599
AVA: Ava_4532
PMA: Pro0928(dxs)
PMM: PMM0907(Dxs)

PMT: PMT0685(dxs)
PMN: PMN2A_0300
PMI: PMT9312_0893
PMB: A9601_09541(dxs)
PMC: P9515_09901(dxs)
PMF: P9303_15371(dxs)
PMG: P9301_09521(dxs)
PMH: P9215_09851
PMJ: P9211_08521
PME: NATL1_09721(dxs)
TER: Tery_3042
BTH: BT_1403 BT_4099
BFR: BF0873 BF4306
BFS: BF0796(dxs) BF4114
PGI: PG2217(dxs)
CHU: CHU_3643(dxs)
GFO: GFO_3470(dxs)
FPS: FP0279(dxs)
CTE: CT0337(dxs)
CPH: Cpha266_0671
PVI: Cvib_0498
PLT: Plut_0450
DET: DET0745(dxs)
DEH: cbdb_A720(dxs)
DRA: DR_1475
DGE: Dgeo_0994
TTH: TTC1614
TTJ: TTHA0006
AAE: aq_881
TMA: TM1770
PMO: Pmob_1001

Exemplary Acetyl-CoA-Acetyltransferase Nucleic
Acids and Polypeptides

HSA: 38(ACAT1) 39(ACAT2)
PTR: 451528(ACAT1)
MCC: 707653(ACAT1) 708750(ACAT2)
MMU: 110446(Acat1) 110460(Acat2)
RNO: 25014(Acat1)
CFA: 484063(ACAT2) 489421(ACAT1)
GGA: 418968(ACAT1) 421587(RCJMB04_34i5)
XLA: 379569(MGC69098) 414622(MGC81403) 414639(MGC81256) 444457(MGC83664)
XTR: 394562(acat2)
DRE: 30643(acat2)
SPU: 759502(LOC759502)
DME: Dmel_CG10932 Dmel_CG9149
CEL: T02G5.4 T02G5.7 T02G5.8(kat-1)
ATH: AT5G48230(ACAT2/EMB1276)
OSA: 4326136 4346520
CME: CMA042C CME087C
SCE: YPL028W(ERG10)
AGO: AGOS_ADR165C
PIC: PICST_31707(ERG10)
CAL: CaO19.1591(erg10)
CGR: CAGL0L12364g
SPO: SPBC215.09c
MGR: MGG_01755 MGG_13499
ANI: AN1409.2
AFM: AFUA_6G14200 AFUA_8G04000
AOR: AO090103000012 AO090103000406
CNE: CNC05280
UMA: UM03571.1
DDI: DDB_0231621
PFA: PF14_0484

TET: TTHERM_00091590 TTHERM00277470 TMERM_00926980
TCR: 511003.60
ECO: b2224(atoB)
ECJ: JW2218(atoB) JW5453(yqeF)
ECE: Z4164(yqeF)
ECS: ECs3701
ECC: c2767(atoB) c3441(yqeF)
ECI: UTI89_C2506(atoB) UTI89_C3247(yqeF)
ECP: ECP_2268 ECP_2857
ECV: APECO1_3662(yqeF) APECO1_4335(atoB) APECO1_43352(atoB)
ECX: EcHS_A2365
STY: STY3164(yqeF)
STT: t2929(yqeF)
SPT: SPA2886(yqeF)
SEC: SC2958(yqeF)
STM: STM3019(yqeF)
SFL: SF2854(yqeF)
SFX: S3052(yqeF)
SFV: SFV_2922(yqeF)
SSN: SSON_2283(atoB) SSON_3004(yqeF)
SBO: SBO_2736(yqeF)
ECA: ECA1282(atoB)
ENT: Ent638_3299
SPE: Spro_0592
HIT: NTHI0932(atoB)
XCC: XCC1297(atoB)
XCB: XC_2943
XCV: XCV1401(thlA)
XAC: XAC1348(atoB)
XOO: XOO1881(atoB)
XOM: XOO_1778(XOO1778)
VCH: VCA0690
VCO: VCO395_0630
VVU: VV2_0494 VV2_0741
VVY: VVA1043 VVA1210
VPA: VPA0620 VPA1123 VPA1204
PPR: PBPRB1112 PBPRB1840
PAE: PA2001(atoB) PA2553 PA3454 PA3589 PA3925
PAU: PA14_38630(atoB)
PPU: PP_2051(atoB) PP_2215(fadAx) PP_3754 PP_4636
PPF: Pput_2009 Pput_2403 Pput_3523 Pput_4498
PST: PSPTO_0957(phbA-1) PSPTO_3164(phbA-2)
PSB: Psyr_0824 Psyr_3031
PSP: PSPPH0850(phbA1) PSPPH_2209(phbA2)
PFL: PFL_1478(atoB-2) PFL_2321 PFL_3066 PFL_4330(atoB-2) PFL_5283
PFO: Pfl_1269 Pfl_1739 Pfl_2074 Pfl_2868
PEN: PSEEN3197 PSEEN3547(fadAx) PSEEN4635(phbA)
PMY: Pmen_1138 Pmen_2036 Pmen_3597 Pmen_3662 Pmen_3820
PAR: Psyc_0252 Psyc_1169
PCR: Pcryo_0278 Pcryo_1236 Pcryo_1260
PRW: PsycPRwf_2011
ACI: ACIAD0694 ACIAD1612 ACIAD2516(atoB)
SON: SO_1677(atoB)
SDN: Sden_1943
SFR: Sfri_1338 Sfri_2063
SAZ: Sama_1375
SBL: Sbal_1495
SBM: Shew185_1489
SBN: Sbal195_1525
SLO: Shew_1667 Shew_2858 SPC: Sputcn32_1397
SSE: Ssed_1473 Ssed_3533
SPL: Spea_2783
SHE: Shewmr4_2597

SHM: Shewmr7_2664
SHN: Shewana3_2771
SHW: Sputw3181_2704
ILO: IL0872
CPS: CPS_1605 CPS_2626
PHA: PSHAa0908 PSHAa1454(atoB) PSHAa1586(atoB)
PAT: Patl_2923
SDE: Sde_3149
PIN: Ping0659 Ping_2401
MAQ: Maqu_2117 Maqu_2489 Maqu_2696 Maqu_3162
CBU: CBU_0974
LPN: lpg1825(atoB)
LPF: lpl1789
LPP: lpp 1788
NOC: Noc_1891
AEH: Mlg0688 Mlg_2706
HHA: Hhal_1685
HCH: HCH_05299
CSA: Csal_0301 Csal_3068
ABO: ABO_0648(fadAx)
MMW: Mmwyl1_0073 Mmwyl1_3021 Mmwyl1_3053 Mmwyl1_3097 Mmwyl1_4182
AHA: AHA_2143(atoB)
CVI: CV_2088(phaA) CV_2790(phaA)
RSO: RSc0276(atoB) RSc 1632(phbA) RSc1637(bktB) RSc1761(RS02948)
REU: Reut_A0138 Reut_A1348 Reut_A1353 Reut_B4561 Reut_B4738 Reut_B5587 Reut_C5943 Reut_C6062
REH: H16_A0170 H16_A0867 H16_A0868 H16_A0872 H16_A1297 H16_A1438(phaA) H16_A1445(bktB) H16_A1528 H16_A1713 H16_A1720 H16_A1887 H16_A2148 H16_B0380 H16_B0381 H16_B0406 H16_B0662 H16_B0668 H16_B0759 H16_B1369 H16_B1771
RME: Rmet_0106 Rmet_1357 Rmet_1362 Rmet_5156
BMA: BMA1316 BMA1321(phbA) BMA1436
BMV: BMASAVP1_A1805(bktB) BMASAVP1_A1810 (phbA)
BML: BMA10299_A0086(phbA) BMA10299_A0091
BMN: BMA10247_1076(bktB) BMA10247_1081(phbA)
BXE: Bxe_A2273 Bxe_A2335 Bxe_A2342 Bxe_A4255 Bxe_B0377 Bxe_B0739 Bxe_C0332 Bxe_C0574 Bxe_C0915
BVI: Bcep1808_0519 Bcep1808_1717 Bcep1808_2877 Bcep1808_3594 Bcep1808_4015 Bcep1808_5507 Bcep1808_5644
BUR: Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332
BCN: Bcen_1553 Bcen_1599 Bcen_2158 Bcen_2563 Bcen_2998 Bcen_6289
BCH: Bcen2424_0542 Bcen2424_1790 Bcen2424_2772 Bcen2424_5368 Bcen2424_6232 Bcen2424_6276
BAM: Bamb_0447 Bamb_1728 Bamb_2824 Bamb_4717 Bamb_5771 Bamb_5969
BPS: BPSL1426 BPSL1535(phbA) BPSL1540
BPM: BURPS1710b_2325(bktB) BURPS1710b_2330 (phbA) BURPS1710b_2453(atoB-2)
BPL: BURPS1106A_2197(bktB) BURPS1106A_2202 (phbA)
BPD: BURPS668_2160(bktB) BURPS668_2165(phbA)
BTE: BTH_12144 BTH_12256 BTH_12261
PNU: Pnuc_0927
BPE: BP0447 BP0668 BP2059
BPA: BPP0608 BPP1744 BPP3805 BPP4216 BPP4361
BBR: BB0614 BB3364 BB4250 BB4804 BB4947
RFR: Rfer_0272 Rfer_1000 Rfer_1871 Rfer_2273 Rfer_2561 Rfer_2594 Rfer_3839
POL: Bpro_1577 Bpro_2140 Bpro_3113 Bpro_4187
PNA: Pnap_0060 Pnap_0458 Pnap_0867 Pnap_1159 Pnap_2136 Pnap_2804
AAV: Aave_0031 Aave_2478 Aave_3944 Aave_4368
AJS: Ajs_0014 Ajs_0124 Ajs_1931 Ajs_2073 Ajs_2317 Ajs_3548 Ajs_3738 Ajs_3776
VEI: Veis_1331 Veis_3818 Veis_4193
DAC: Daci_0025 Daci_0192 Daci_3601 Daci_5988
MPT: Mpe_A1536 Mpe_A1776 Mpe_A1869 Mpe_A3367
HAR: HEAR0577(phbA)
MMS: mma0555
NEU: NE2262(bktB)
NET: Neut_0610
EBA: ebA5202 p2A409(tioL)
AZO: azo0464(fadA1) azo0469(fadA2) azo2172(thlA)
DAR: Daro_0098 Daro_3022
HPA: HPAG10675
HAC: Hac_0958(atoB)
GME: Gmet_1719 Gmet_2074 Gmet_2213 Gmet_2268 Gmet_3302
GUR: Gura_3043
BBA: Bd0404(atoB) Bd2095
DOL: Dole_0671 Dole_1778 Dole_2160 Dole_2187
ADE: Adeh_0062 Adeh_2365
AFW: Anae109_0064 Anae109_1504
MXA: MXAN_3791
SAT: SYN_02642
SFU: Sfum_2280 Sfum_3582
RPR: RP737
RCO: RC1134 RC1135
RFE: RF_0163(paaJ)
RBE: RBE_0139(paaJ)
RAK: A1C_05820
RBO: A1I_07215
RCM: A1E_04760
PUB: SAR11_0428(thlA)
MLO: mlr3847
MES: Meso_3374
PLA: Plav_1573 Plav_2783
SME: SMa1450 SMc03879(phbA)
SMD: Smed_0499 Smed_3117 Smed_5094 Smed_5096
ATU: Atu2769(atoB) Atu3475
ATC: AGR_C_5022(phbA) AGR_L_2713
RET: RHE_CH04018(phbAch) RHE_PC00068(ypc00040) RHE_PF00014(phbAf)
RLE: RL4621(phaA) pRL100301 pRL120369
BME: BMEIO274 BMEH0817
BMF: BAB1_1783(phbA-1) BAB2_0790(phbA-2)
BMS: BR1772(phbA-1) BRA0448(phbA-2)
BMB: BruAb1_1756(phbA-1) BruAb2_0774(phbA-2)
BOV: BOV_1707(phbA-1)
OAN: Oant_1130 Oant_3107 Oant_3718 Oant_4020
BJA: bll0226(atoB) bll3949 bll7400 bll7819 blr3724(phbA)
BRA: BRADO0562(phbA) BRADO0983(pimB) BRADO3110 BRADO3134(atoB)
BBT: BBta_3558 BBta_3575(atoB) BBta_5147(pimB) BBta_7072(pimB) BBta_7614(phbA)
RPA: RPA0513(pcaF) RPA0531 RPA3715(pimB)
RPB: RPB_0509 RPB_0525 RPB_1748
RPC: RPC_0504 RPC_0636 RPC_0641 RPC_0832 RPC_1050 RPC_2005 RPC_2194 RPC_2228
RPD: RPD_0306 RPD_0320 RPD_3105 RPD_3306

RPE: RPE_0168 RPE_0248 RPE_3827
NWI: Nwi_3060
XAU: Xaut_3108 Xaut_4665
CCR: CC_0510 CC_0894 CC_3462
SIL: SPO0142(bktB) SPO0326(phbA) SPO0773 SPO3408
SIT: TM1040_0067 TM1040_2790 TM1040_3026 TM1040_3735
RSP: RSP_0745 RSP_1354 RSP_3184
RSH: Rsph17029_0022 Rsph17029_2401 Rsph17029_3179 Rsph17029_3921
RSQ: Rsph17025_0012 Rsph17025_2466 Rsph17025_2833
JAN: Jann_0262 Jann_0493 Jann_4050
RDE: RD1_0025 RD1_0201(bktB) RD1_3394(phbA)
PDE: Pden_2026 Pden_2663 Pden_2870 Pden_2907 Pden_4811 Pden_5022
DSH: Dshi_0074 Dshi_3066 Dshi_3331
MMR: Mmar10_0697
HNE: HNE_2706 HNE_3065 HNE_3133
NAR: Saro_0809 Saro_1069 Saro_1222 Saro_2306 Saro_2349
SAL: Sala_0781 Sala_1244 Sala_2896 Sala_3158
SWI: Swit_0632 Swit_0752 Swit_2893 Swit_3602 Swit_4887 Swit 5019 Swit_5309
ELI: ELI_01475 ELI_06705 ELI_12035
GBE: GbCGDNIH1_0447
ACR: Acry_1847 Acry_2256
RRU: Rru_A0274 Rru_A1380 Rru_A1469 Rru_A1946 Rru_A3387
MAG: amb0842
MGM: Mmc1_1165
ABA: Acid345_3239
BSU: BG11319(mmgA) BG13063(yhfS)
BHA: BH1997 BH2029 BH3801(mmgA)
BAN: BA3687 BA4240 BA5589
BAR: GBAA3687 GBAA4240 GBAA5589
BAA: BA_0445 BA_4172 BA_4700
BAT: BAS3418 BAS3932 BAS5193
BCE: BC3627 BC4023 BC5344
BCA: BCE_3646 BCE_4076 BCE_5475
BCZ: BCZK3329(mmgA) BCZK3780(thl) BCZK5044(atoB)
BCY: Bcer98_2722 Bcer98_3865
BTK: BT9727_3379(mmgA) BT9727_3765(thl) BT9727_5028(atoB)
BTL: BALH_3262(mmgA) BALH_3642(fadA) BALH_4843(atoB)
BLI: BL03925(mmgA)
BLD: BLi03968(mmgA)
BCL: ABC0345 ABC2989 ABC3617 ABC3891(mmgA)
BAY: RBAMO22450
BPU: BPUM_2374(yhfS) BPUM_2941 BPUM_3373
OIH: OB0676 OB0689 OB2632 OB3013
GKA: GK1658 GK3397
SAU: SA0342 SA0534(vraB)
SAV: SAV0354 SAV0576(vraB)
SAM: MW0330 MW0531(vraB)
SAR: SAR0351(thl) SAR0581
SAS: SAS0330 SAS0534
SAC: SACOL0426 SACOL0622(atoB)
SAB: SAB0304(thl) SAB0526
SAA: SAUSA300_0355 SAUSA300_0560(vraB)
SAO: SAOUHSC_00336 SAOUHSC_00558
SAJ: SaurJH9_0402
SAH: SaurJH1_0412
SEP: SE0346 SE2384
SER: SERP0032 SERP0220
SHA: SH0510(mvaC) SH2417
SSP: SSP0325 SSP2145
LMO: lmo 1414
LMF: LMOf2365_1433
LIN: lin1453
LWE: lwe1431
LLA: L11745(thiL) L25946(fadA)
LLC: LACR_1665 LACR_1956
LLM: llmg_0930(thiL)
SPY: SPy_0140 SPy_1637(atoB)
SPZ: M5005_Spy_0119 M5005_Spy_0432 M5005_Spy_1344(atoB)
SPM: spyM18_0136 spyM18_1645(atoB)
SPG: SpyM3_0108 SpyM3_1378(atoB)
SPS: SPs0110 SPs0484
SPH: MGAS10270_Spy0121 MGAS10270_Spy0433 MGAS10270_Spy1461(atoB)
SPI: MGAS10750_Spy0124 MGAS10750_Spy0452 MGAS10750_Spy1453(atoB)
SPJ: MGAS2096_Spy0123 MGAS2096_Spy0451 MGAS2096_Spy1365(atoB)
SPK: MGAS9429_Spy0121 MGAS9429_Spy0431 MGAS9429_Spy1339(atoB)
SPF: SpyM50447(atoB2)
SPA: M6_Spy0166 M6_Spy0466 M6_Spy1390
SPB: M28_Spy0117 M28_Spy0420 M28_Spy1385(atoB)
SAK: SAK_0568
LJO: 111609
LAC: LBA0626(thiL)
LSA: LSA1486
LDB: Ldb0879
LBU: LBUL_0804
LBR: LVIS_2218
LCA: LSEI_1787
LGA: LGAS_1374
LRE: Lreu_0052
EFA: EF1364
OOE: OEOE_0529
STH: STH2913 STH725 STH804
CAC: CAC2873 CA_P0078(thiL)
CPE: CPE2195(atoB)
CPF: CPF_2460
CPR: CPR_2170
CTC: CTC00312
CNO: NT01CX_0538 NT01CX_0603
CDF: CD1059(thlA1) CD2676(thlA2)
CBO: CB03200(thl)
CBE: Cbei_0411 Cbei_3630
CKL: CKL_3696(thlA1) CKL_3697(thlA2) CKL_3698(thlA3)
AMT: Amet_4630
AOE: Clos0084 Clos0258
CHY: CHY_1288 CHY_1355(atoB) CHY_1604 CHY_1738
DSY: DSY0632 DSY0639 DSY1567 DSY1710 DSY2402 DSY3302
DRM: Dred_0400 Dred_1491 Dred_1784 Dred_1892
SWO: Swol_0308 Swol_0675 Swol_0789 Swol_1486 Swol_1934 Swol_2051
TTE: TTE0549(paaJ)
MTA: Moth_1260
MTU: Rv1135A Rv1323(fadA4) Rv3546(fadA5)
MTC: MT1365(phbA)
MBO: Mb1167 Mb1358(fadA4) Mb3576(fadA5) Mb3586c(fadA6)
MBB: BCG_1197 BCG_1385(fadA4) BCG_3610(fadA5) BCG_3620c(fadA6)

MLE: ML1158(fadA4)
MPA: MAP2407c(fadA3) MAP2436c(fadA4)
MAV: MAV_1544 MAV_1573 MAV_1863 MAV_5081
MSM: MSMEG_2224 MSMEG_4920
MUL: MUL_0357
MVA: Mvan_1976 Mvan_1988 Mvan_4305 Mvan_4677 Mvan_4891
MGI: Mflv_1347 Mflv_1484 Mflv_2040 Mflv_2340 Mflv_4356 Mflv_4368
MMC: Mmcs_1758 Mmcs_1769 Mmcs_3796 Mmcs_3864
MKM: Mkms_0251 Mkms_1540 Mkms_1805 Mkms_1816 Mkms_2836 Mkms_3159 Mkms_3286 Mkcms_3869 Mkms_3938 Mkms_4227 Mkms_4411 Mkms_4580 Mkms_4724 Mkms_4764 Mkms_4776
MJL: Mjls_0231 Mjls_1739 Mjls_1750 Mjls_2819 Mjls_3119 Mjls_3235 Mjls_3800 Mjls_3850 Mjls_4110 Mjls_4383 Mjls_4705 Mjls_4876 Mjls_5018 Mjls_5063 Mjls_5075
CGL: NCgl2309(cgl2392)
CGB: cg2625(pcaF)
CEF: CE0731 CE2295
CJK: jk1543(fadA3)
NFA: nfa10750(fadA4)
RHA: RHA1_ro01455 RHA1_ro01623 RHA1_ro01876 RHA1_ro02517(catF) RHA1_ro03022 RHA1_ro03024 RHA1_ro03391 RHA1_ro03892 RHA1_ro04599 RHA1_ro05257 RHA1_ro08871
SCO: SCO5399(SC8F4.03)
SMA: SAV1384(fadA5) SAV2856(fadAl)
ART: Arth_1160 Arth_2986 Arth_3268 Arth_4073
NCA: Noca_1371 Noca_1797 Noca_1828 Noca_2764 Noca_4142
TFU: Tfu_1520 Tfu_2394
FRA: Francci3_3687
FRE: Franean1_1044 Franean1_2711 Franean1_2726 Franean1_3929 Franean1_4037 Franean14577
FAL: FRAAL2514 FRAAL2618 FRAAL5910(atoB)
ACE: Acel_0626 Acel_0672
SEN: SACE_1192(mmgA) SACE_2736(fadA6) SACE_4011(catF) SACE_6236(fadA4)
STP: Strop_3610
SAQ: Sare_1316 Sare_3991
RXY: Rxyl_1582 Rxyl_1842 Rxyl_2389 Rxyl_2530
FNU: FN0495
BGA: BG0110(fadA)
BAF: BAPKO_0110(fadA)
LIL: LA0457(thiL1) LA0828(thiL2) LA4139(fadA)
LIC: LIC10396(phbA)
LBJ: LBJ_2862(paaJ-4)
LBL: LBL_0209(paaJ-4)
SYN: slr1993(phaA)
SRU: SRU_1211(atoB) SRU_1547
CHU: CHU_1910(atoB)
GFO: GFO_1507(atoB)
FJO: Fjoh_4612
FPS: FP0770 FP1586 FP1725
RRS: RoseRS_3911 RoseRS_4348
RCA: Rcas_0702 Rcas_3206
HAU: Haur_0522
DRA: DR_1072 DR_1428 DR_1960 DR_2480 DR_A0053
DGE: Dgeo_0755 Dgeo_1305 Dgeo_1441 Dgeo_1883
TTH: TTC0191 TTC0330
TTJ: TTHA0559
TME: Tmel_1134
FNO: Fnod0314
PMO: Pmob_0515
HMA: rrnAC0896(acaB3) rrnAC2815(aca2) rrnAC3497(yqeF) rrnB0240(aca1) rrnB0242(acaB2) rrnB0309(acaB1)
TAC: Ta0582
TVO: TVN0649
PTO: PTO1505
APE: APE_2108
SSO: SSO2377(acaB-4)
STO: ST0514
SAI: Saci_0963 Saci_1361(acaB1)
MSE: Msed_0656
PAI: PAE1220
PIS: Pisl_0029 Pisl_1301
PCL: Pcal_0781
PAS: Pars_0309 Pars_1071
CMA: Cmaq_1941

Exemplary HMG-CoA Synthase Nucleic Acids and Polypeptides

HSA: 3157(HMGCS1) 3158(HMGCS2)
PTR: 457169(HMGCS2) 461892(HMGCS1)
MCC: 702553(HMGCS1) 713541(HMGCS2)
MMU: 15360(Hmgcs2) 208715(Hmgcs1)
RNO: 24450(Hmgcs2) 29637(Hmgcs1)
CFA: 479344(HMGCS1) 607923(HMGCS2)
BTA: 407767(HMGCS1)
SSC: 397673(CH242-38B5.1)
GGA: 396379(HMGCS1)
XLA: 380091(hmgcs1) 447204(MGC80816)
DRE: 394060(hmgcs1)
SPU: 578259(L00578259)
DME: Dmel_CG4311(Hmgs)
CEL: F25B4.6
ATH: AT4G11820(BAP1)
OSA: 4331418 4347614
CME: CMM189C
SCE: YML126C(ERG13)
AGO: AGOS_ADL356C
PIC: PICST_83020
CAL: CaO19_7312(CaO19.7312)
CGR: CAGL0H04081g
SPO: SPAC4F8.14c(hcs)
MGR: MGG_01026
ANI: AN4923.2
AFM: AFUA_3G10660 AFUA_8G07210
AOR: AO0003000611 AO090010000487
CNE: CNC05080 CNG02670
UMA: UM05362.1
ECU: ECU10_0510
DDI: DDBDRAFT_0217522 DDB_0219924(hgsA)
TET: TTHERM_00691190
TBR: Tb927.8.6110
YPE: YP01457
YPK: y2712(pksG)
YPM: YP_1349(pksG)
YPA: YPA_0750
YPN: YPN_2521
YPP: YPDSF_1517
YPS: YPTB1475
CBD: COXBU7E912_1931
TCX: Tcr_1719
DNO: DNO_0799
BMA: BMAA1212
BPS: BPSS1002
BPM: BURPS1710b_A2613

BPL: BURPS1106A_A1384
BPD: BURPS668_A1470
BTE: BTH_II1670
MXA: MXAN_3948(tac) MXAN_4267(mvaS)
BSU: BG10926(pksG)
OIH: OB2248
SAU: SA2334(mvaS)
SAV: SAV2546(mvaS)
SAM: MW2467(mvaS)
SAR: SAR2626(mvaS)
SAS: SAS2432
SAC: SACOL2561
SAB: SAB2420(mvaS)
SAA: SAUSA300_2484
SAO: SAOUHSC_02860
SAJ: SaurJH9_2569
SAH: SaurJH1_2622
SEP: SE2110
SER: SERP2122
SHA: SH0508(mvaS)
SSP: SSP0324
LMO: lmo1415
LMF: LMOf2365_1434(mvaS)
LIN: lin1454
LWE: lwe1432(mvaS)
LLA: L13187(hmcM)
LLC: LACR_1666
LLM: llmg_0929(hmcM)
SPY: SPy_0881(mvaS.2)
SPZ: M5005_Spy0687(mvaS.1)
SPM: spyM18_0942(mvaS2)
SPG: SpyM3_0600(mvaS.2)
SPS: SPs1253
SPH: MGAS10270_Spy0745(mvaS1)
SPI: MGAS10750_Spy0779(mvaS1)
SPJ: MGAS2096_Spy0759(mvaS1)
SPK: MGAS9429_Spy0743(mvaS1)
SPF: SpyM51121(mvaS)
SPA: M6_Spy0704
SPB: M28_Spy0667(mvaS.1)
SPN: SP_1727
SPR: spr1571(mvaS)
SPD: SPD_1537(mvaS)
SAG: SAG1316
SAN: gbs1386
SAK: SAK_1347
SMU: SMU.943c
STC: str0577(mvaS)
STL: stu0577(mvaS)
STE: STER_0621
SSA: SSA_0338(mvaS)
SSU: SSU05_1641
SSV: SSU98_1652
SGO: SGO_0244
LPL: lp_2067(mvaS)
LJO: LJ1607
LAC: LBA0628(hmcS)
LSA: LSA1484(mvaS)
LSL: LSL_0526
LDB: Ldb0881(mvaS)
LBU: LBUL_0806
LBR: LVIS_1363
LCA: LSEI_1785
LGA: LGAS_1372
LRE: Lreu_0676
PPE: PEPE_0868
EFA: EF1363
OOE: OEOE0968
LME: LEUM_1184
NFA: nfa22120
SEN: SACE_4570(pksG)
BBU: BB0683
BGA: BG0706
BAF: BAPKO_0727
FJO: Fjoh_0678
HAL: VNG1615G(mvaB)
HMA: rrnAC1740(mvaS)
HWA: HQ2868A(mvaB)
NPH: NP2608A(mvaB_1) NP4836A(mvaB_2)

Exemplary Hydroxymethylglutaryl-CoA Reductase
Nucleic Acids and Polypeptides

HSA: 3156(HMGCR)
PTR: 471516(HMGCR)
MCC: 705479(HMGCR)
MMU: 15357(Hmgcr)
RNO: 25675(Hmgcr)
CFA: 479182(HMGCR)
BTA: 407159(HMGCR)
GGA: 395145(RCJMB04_14 m24)
SPU: 373355(LOC373355)
DME: Dmel_CG10367(Hmgcr)
CEL: F08F8.2
OSA: 4347443
SCE: YLR450W(HMG2) YML075C(HMG1)
AGO: AGOS_AER152W
CGR: CAGL0L11506g
SPO: SPCC162.09c(hmg1)
ANI: AN3817.2
AFM: AFUA_1G11230 AFUA_2G03700
AOR: AO090103000311 AO090120000217
CNE: CNF04830
UMA: UM03014.1
ECU: ECU10_1720
DDI: DDB_0191125(hmgA) DDB_0215357(hmgB)
TBR: Tb927.6.4540
TCR: 506831.40 509167.20
LMA: LmjF30.3190
VCH: VCA0723
VCO: VC0395_0662
VVU: VV2_0117
VVY: VVA0625
VPA: VPA0968
VFI: VFA0841
PAT: Patl_0427
CBU: CBU_0030 CBU_0610
CBD: COXBU7E912_0151 COXBU7E912_0622(hmgA)
TCX: Tcr_1717
DNO: DNO_0797
CVI: CV_1806
SUS: Acid_5728 Acid_6132
SAU: SA2333(mvaA)
SAV: SAV2545(mvaA)
SAM: MW2466(mvaA)
SAB: SAB2419c(mvaA)
SEP: SE2109
LWE: lwe0819(mvaA)
LLA: L10433(mvaA)
LLC: LACR_1664
LLM: llmg_0931(mvaA)
SPY: SPy_0880(mvaS.1)
SPM: spyM18_0941(mvaS1)
SPG: SpyM3_0599(mvaS.1)

SPS: SPs1254
SPH: MGAS10270_Spy0744
SPI: MGAS10750_Spy0778
SPJ: MGAS2096_Spy0758
SPK: MGAS9429_Spy0742
SPA: M6_Spy0703
SPN: SP_1726
SAG: SAG1317
SAN: gbs1387
STC: str0576(mvaA)
STL: stu0576(mvaA)
STE: STER_0620
SSA: SSA_0337(mvaA)
LPL: lp_0447(mvaA)
LJO: LJ1608
LSL: LSL_0224
LBR: LVIS_0450
LGA: LGAS_1373
EFA: EF1364
NFA: nfa22110
BGA: BG0708(mvaA)
SRU: SRU_2422
FPS: FP2341
MMP: MMP0087(hmgA)
MMQ: MmarC5_1589
MAC: MA3073(hmgA)
MBA: Mbar_A1972
MMA: MM_0335
MBU: Mbur_1098
MHU: Mhun_3004
MEM: Memar_2365
MBN: Mboo_0137
MTH: MTH562
MST: Msp_0584(hmgA)
MSI: Msm_0227
MKA: MK0355(HMG1)
AFU: AF1736(mvaA)
HAL: VNG1875G(mvaA)
HMA: rrnAC3412(mvaA)
HWA: HQ3215A(hmgR)
NPH: NP0368A(mvaA_2) NP2422A(mvaA_1)
TAC: Ta0406m
TVO: TVN1168
PTO: PT01143
PAB: PAB2106(mvaA)
PFU: PF1848
TKO: TK0914
RCI: RCIX1027(hmgA) RCIX376(hmgA)
APE: APE_1869
IHO: Igni_0476
HBU: Hbut_1531
SSO: SSO0531
STO: ST1352
SAI: Saci_1359
PAI: PAE2182
PIS: Pisl_0814
PCL: Pcal_1085
PAS: Pars_0796

Exemplary Mevalonate Kinase Nucleic Acids and Polypeptides

HSA: 4598(MVK)
MCC: 707645(MVK)
MMU: 17855(Mvk)
RNO: 81727(Mvk)
CFA: 486309(MVK)
BTA: 505792(MVK)
GGA: 768555(MVK)
DRE: 492477(zgc:103473)
SPU: 585785(LOC585785)
DME: Dmel_CG33671
OSA: 4348331
SCE: YMR208W(ERG12)
AGO: AGOS_AER335W
PIC: PICST_40742(ERG12)
CGR: CAGL0F03861g
SPO: SPAC13G6.11c
MGR: MGG_06946
ANI: AN3869.2
AFM: AFUA_4G07780
AOR: AO090023000793
CNE: CNK01740
ECU: ECU09_1780
DDI: DDBDRAFT_0168621
TET: TTHERM_00637680
TBR: Tb927.4.4070
TCR: 436521.9 509237.10
LMA: LmjF31.0560
CBU: CBU_0608 CBU_0609
CBD: COXBU7E912_0620(mvk)
LPN: lpg2039
LPF: lpl2017
LPP: lpp 2022
BBA: Bd1027(1 mbP) Bd1630(mvk)
MXA: MXAN_5019(mvk)
OIH: OB0225
SAU: SA0547(mvaK1)
SAV: SAV0590(mvaK1)
SAM: MW0545(mvaK1)
SAR: SAR0596(mvaK1)
SAS: SAS0549
SAC: SACOL0636(mvk)
SAB: SAB0540(mvaK1)
SAA: SAUSA300_0572(mvk)
SAO: SAOUHSC_00577
SEP: SE0361
SER: SERP0238(mvk)
SHA: SH2402(mvaK1)
SSP: SSP2122
LMO: lmo0010
LMF: LMOf2365_0011
LIN: lin0010
LWE: lwe0011(mvk)
LLA: L7866(yeaG)
LLC: LACR_0454
LLM: llmg_0425(mvk)
SPY: SPy_0876(mvaK1)
SPZ: M5005_Spy_0682(mvaK1)
SPM: spyM18_0937(mvaK1)
SPG: SpyM3_0595(mvaK1)
SPS: SPs1258
SPH: MGAS10270_Spy0740(mvaK1)
SPI: MGAS10750_Spy0774(mvaK1)
SPJ: MGAS2096_Spy0753(mvaK1)
SPK: MGAS9429_Spy0737(mvaK1)
SPF: SpyM51126(mvaK1)
SPA: M6_Spy0699
SPB: M28_Spy0662(mvaK1)
SPN: SP_0381
SPR: spr0338(mvk)
SPD: SPD_0346(mvk)
SAG: SAG1326
SAN: gbs1396

SAK: SAK_1357(mvk)
SMU: SMU.181
STC: str0559(mvaK1)
STL: stu0559(mvaK1)
STE: STER_0598
SSA: SSA_0333(mvaK1)
SSU: SSU05_0289
SSV: SSU980285
SGO: SGO_0239(mvk)
LPL: lp_1735(mvaK1)
LJO: LJ1205
LAC: LBA1167(mvaK)
LSA: LSA0908(mvaK1)
LSL: LSL_0685(eRG)
LDB: Ldb0999(mvk)
LBU: LBUL_0906
LBR: LVIS_0858
LCA: LSEI_1491
LGA: LGAS_1033
LRE: Lreu_0915
PPE: PEPE_0927
EFA: EF0904(mvk)
OOE: OEOE_1100
LME: LEUM_1385
NFA: nfa22070
BGA: BG0711
BAF: BAPKO_0732
FPS: FP0313
MMP: MMP1335
MAE: Maeo_0775
MAC: MA0602(mvk)
MBA: Mbar_A1421
MMA: MM_1762
MBU: Mbur_2395
MHU: Mhun_2890
MEM: Memar_1812
MBN: Mboo_2213
MST: Msp_0858(mvk)
MSI: Msm_1439
MKA: MK0993(ERG12)
HAL: VNG1145G(mvk)
HMA: rrnAC0077(mvk)
HWA: HQ2925A(mvk)
NPH: NP2850A(mvk)
PTO: PT01352
PHO: PH1625
PAB: PAB0372(mvk)
PFU: PF1637(mvk)
TKO: TK1474
RCI: LRC399(mvk)
APE: APE_2439
HBU: Hbut_0877
SSO: SS00383
STO: ST2185
SAI: Saci_2365(mvk)
MSE: Msed_1602
PAI: PAE3108
PIS: Pisl_0467
PCL: Pcal_1835

Exemplary Phosphomevalonate Kinase Nucleic
Acids and Polypeptides

HSA: 10654(PMVK)
PTR: 457350(PMVK)
MCC: 717014(PMVK)
MMU: 68603(Pmvk)
CFA: 612251(PMVK)
BTA: 513533(PMVK)
DME: Dmel_CG10268
ATH: AT1G31910
OSA: 4332275
SCE: YMR220W(ERG8)
AGO: AGOS_AER354W
PIC: PICST_52257(ERG8)
CGR: CAGL0F03993g
SPO: SPAC343.01c
MGR: MGG_05812
ANI: AN2311.2
AFM: AFUA_5G10680
AOR: AO090010000471
CNE: CNM00100
UMA: UM00760.1
DDI: DDBDRAFT_0184512
TBR: Tb09.160.3690
TCR: 507913.20 508277.140
LMA: LmjF15.1460
MXA: MXAN_5017
OIH: OB0227
SAU: SA0549(mvaK2)
SAV: SAV0592(mvaK2)
SAM: MWO547(mvaK2)
SAR: SAR0598(mvaK2)
SAS: SAS0551
SAC: SACOL0638
SAB: SAB0542(mvaK2)
SAA: SAUSA300_0574
SAO: SAOUHSC_00579
SAJ: SauJH9_0615
SEP: SE0363
SER: SERP0240
SHA: SH2400(mvaK2)
SSP: SSP2120
LMO: lmo0012
LMF: LMOf2365_0013
LIN: lin0012
LWE: lwe0013
LLA: L10014(yebA)
LLC: LACR_0456
LLM: llmg0427
SPY: SPy_0878(mvaK2)
SPZ: M5005_Spy_0684(mvaK2)
SPM: spyM18_0939
SPG: SpyM3_0597(mvaK2)
SPS: SPs1256
SPH: MGAS10270_Spy0742(mvaK2)
SPI: MGAS10750_Spy0776(mvaK2)
SPJ: MGAS2096_Spy0755(mvaK2)
SPK: MGAS9429_Spy0739(mvaK2)
SPF: SpyM51124(mvaK2)
SPA: M6_Spy0701
SPB: M28_Spy0664(mvaK2)
SPN: SP_0383
SPR: spr0340(mvaK2)
SPD: SPD_0348(mvaK2)
SAG: SAG1324
SAN: gbs1394
SAK: SAK_1355
SMU: SMU.938
STC: str0561(mvaK2)
STL: stu0561(mvaK2)
STE: STER_0600
SSA: SSA_0335(mvaK2)
SSU: SSU050291

SSV: SSU98_0287
SGO: SGO_0241
LPL: lp_1733(mvaK2)
LJO: LJ1207
LAC: LBA1169
LSA: LSA0906(mvaK2)
LSL: LSL_0683
LDB: Ldb0997(mvaK)
LBU: LBUL0904
LBR: LVIS_0860
LCA: LSEI_1092
LGA: LGAS_1035
LRE: Lreu_0913
PPE: PEPE_0925
EFA: EF0902
NFA: nfa22090
BGA: BG0710
BAF: BAPKO_0731
NPH: NP2852A
SSO: SSO2988
STO: ST0978
SAI: Saci_1244

Exemplary Diphosphomevalonate Decarboxylase Nucleic Acids and Polypeptides

HSA: 4597(MVD)
PTR: 468069(MVD)
MCC: 696865(MVD)
MMU: 192156(Mvd)
RNO: 81726(Mvd)
CFA: 489663(MVD)
GGA: 425359(MVD)
DME: Dmel_CG8239
SCE: YNR043W(MVD1)
AGO: AGOS_AGL232C
PIC: PICST_90752
CGR: CAGL0C03630g
SPO: SPAC24C9.03
MGR: MGG_09750
ANI: AN4414.2
AFM: AFUA_4G07130
AOR: AO090023000862
CNE: CNL04950
UMA: UM05179.1
DDI: DDBDRAFT_0218058
TET: TTHERM_00849200
TBR: Tb10.05.0010 Tb10.61.2745
TCR: 507993.330 511281.40
LMA: LmjF18.0020
CBU: CBU_0607(mvaD)
CBD: COXBU7E912_0619(mvaD)
LPN: lpg2040
LPF: lpl2018
LPP: lpp2023
TCX: Tcr_1734
DNO: DNO_0504(mvaD)
BBA: Bd1629
MXA: MXAN_5018(mvaD)
OIH: OB0226
SAU: SA0548(mvaD)
SAV: SAV0591(mvaD)
SAM: MWO546(mvaD)
SAR: SAR0597(mvaD)
SAS: SAS0550
SAC: SACOL0637(mvaD)
SAB: SAB0541(mvaD)
SAA: SAUSA300_0573(mvaD)
SAO: SAOUHSC_00578
SAJ: SaurJH9_0614
SAH: SaurJH1_0629
SEP: SE0362
SER: SERP0239(mvaD)
SHA: SH2401(mvaD)
SSP: SSP2121
LMO: lmo0011
LMF: LMOf2365_0012(mvaD)
LIN: lin0011
LWE: lwe0012(mvaD)
LLA: L9089(yeaH)
LLC: LACR_0455
LLM: llmg0426(mvaD)
SPY: SPy_0877(mvaD)
SPZ: M5005_Spy_0683(mvaD)
SPM: spyM18_0938(mvd)
SPG: SpyM3_0596(mvaD)
SPS: SPs1257
SPH: MGAS10270_Spy0741(mvaD)
SPI: MGAS10750_Spy0775(mvaD)
SPJ: MGAS2096_Spy0754(mvaD)
SPK: MGAS9429_Spy0738(mvaD)
SPF: SpyM51125(mvaD)
SPA: M6_Spy0700
SPB: M28_Spy0663(mvaD)
SPN: SP_0382
SPR: spr0339(mvd1)
SPD: SPD_0347(mvaD)
SAG: SAG1325(mvaD)
SAN: gbs1395
SAK: SAK_1356(mvaD)
SMU: SMU.937
STC: str0560(mvaD)
STL: stu0560(mvaD)
STE: STER_0599
SSA: SSA_0334(mvaD)
SSU: SSU05_0290
SSV: SSU98_0286
SGO: SGO_0240(mvaD)
LPL: lp_1734(mvaD)
LJO: LJ1206
LAC: LBA1168(mvaD)
LSA: LSA0907(mvaD)
LSL: LSL_0684
LDB: Ldb0998(mvaD)
LBU: LBUL_0905
LBR: LVIS_0859
LCA: LSEI_1492
LGA: LGAS_1034
LRE: Lreu_0914
PPE: PEPE_0926
EFA: EF0903(mvaD)
LME: LEUM_1386
NFA: nfa22080
BBU: BB0686
BGA: BG0709
BAF: BAPKO0730
GFO: GFO_3632
FPS: FP0310(mvaD)
HAU: Haur_1612
HAL: VNG0593G(dmd)
HMA: rrnAC1489(dmd)
HWA: HQ1525A(mvaD)
NPH: NP1580A(mvaD)
PTO: PT00478 PT01356

SSO: SSO2989
STO: ST0977
SAI: Saci_1245(mvd)
MSE: Msed_1576

Exemplary Isopentenyl Phosphate Kinases (IPK) Nucleic Acids and Polypeptides

*Methanobacterium thermoautotrophicum* gi|2621082
*Methanococcus jannaschii* DSM 2661 gi|1590842;
*Methanocaldococcus jannaschii* gi|1590842
*Methanothermobacter thermautotrophicus* gi|2621082
*Picrophilus torridus* DSM9790 (IG-57) gi|48477569
*Pyrococcus abyssi* gi|14520758
*Pyrococcus horikoshii* OT3 gi|3258052
*Archaeoglobus fulgidus* DSM4304 gi|2648231

Exemplary Isopentenyl-Diphosphate Delta-Isomerase (IDI) Nucleic Acids and Polypeptides HSA: 3422(IDI1) 91734(IDI2)
PTR: 450262(ID12) 450263(IDI1)
MCC: 710052(LOC710052) 721730(LOC721730)
MMU: 319554(Idi1)
RNO: 89784(Idi1)
GGA: 420459(IDI1)
XLA: 494671(LOC494671)
XTR: 496783(idi2)
SPU: 586184(LOC586184)
CEL: K06H7.9(idi-1)
ATH: AT3G02780(IPP2)
OSA: 4338791 4343523
CME: CMB062C
SCE: YPL117C(IDI1)
AGO: AGOS_ADL268C
PIC: PICST_68990(IDI1)
CGR: CAGL0J06952g
SPO: SPBC106.15(idi1)
ANI: AN0579.2
AFM: AFUA_6G11160
AOR: AO090023000500
CNE: CNA02550
UMA: UM04838.1
ECU: ECU02_0230
DDI: DDB_0191342(ipi)
TET: TTHERM_00237280 TTHERM_00438860
TBR: Tb09.211.0700
TCR: 408799.19 510431.10
LMA: LmjF35.5330
EHI: 46.t00025
ECO: b2889(idi)
ECJ: JW2857(idi)
ECE: Z4227
ECS: ECs3761
ECC: c3467
ECI: UTI89_C3274
ECP: ECP_2882
ECV: APECO1_3638
ECW: EcE24377A_3215(idi)
ECX: EcHS_A3048
STY: STY3195
STT: t2957
SPT: SPA2907(idi)
SEC: SC2979(idi)
STM: STM3039(idi)
SFL: SF2875(idi)
SFX: S3074
SFV: SFV_2937
SSN: SSON_3042 SSON_3489(yhfK)
SBO: SBO_3103
SDY: SDY_3193
ECA: ECA2789
PLU: plu3987
ENT: Ent638_3307
SPE: Spro_2201
VPA: VPA0278
VFI: VF0403
PPR: PBPRA0469(mvaD)
PEN: PSEEN4850
CBU: CBU_0607(mvaD)
CBD: COXBU7E912_0619(mvaD)
LPN: lpg2051
LPF: lpl2029
LPP: lpp2034
TCX: Tcr_1718
HHA: Hhal_1623
DNO: DNO_0798
EBA: ebA5678 p2A143
DVU: DVU1679(idi)
DDE: Dde_1991
LIP: Ll1134
BBA: Bd1626
AFW: Anae109_4082
MXA: MXAN_5021(fni)
RPR: RP452
RTY: RT0439(idi)
RCO: RC0744
RFE: RF_0785(fni)
RBE: RBE_0731(fni)
RAK: A1C_04190
RBO: A1I_04755
RCM: A1E_02555
RRI: A1G_04195
MLO: mlr6371
RET: RHE_PD00245(ypd00046)
XAU: Xaut_4134
SIL: SP00131
SIT: TM1040_3442
RSP: RSP_0276
RSH: Rsph17029_1919
RSQ: Rsph17025_1019
JAN: Jann_0168
RDE: RD1_0147(idi)
DSH: Dshi_3527
BSU: BG11440(ypgA)
BAN: BA1520
BAR: GBAA1520
BAA: BA_2041
BAT: BAS1409
BCE: BC1499
BCA: BCE_1626
BCZ: BCZK1380(fni)
BCY: Bcer98_1222
BTK: BT9727_1381(fni)
BTL: BALH_1354
BLI: BL02217(fni)
BLD: BLi02426
BAY: RBAM_021020(fni)
BPU: BPUM_2020(fni)
OIH: OB0537
SAU: SA2136(fni)
SAV: SAV2346(fni)
SAM: MW2267(fni)

SAR: SAR2431(fni)
SAS: SAS2237
SAC: SACOL2341(fni)
SAB: SAB2225c(fni)
SAA: SAUSA300_2292(fni)
SAO: SAOUHSC_02623
SEP: SE1925
SER: SERP1937(fni-2)
SHA: SH0712(fni)
SSP: SSP056
LMO: lmo 1383
LMF: LMOf2365_1402(fni)
LIN: lin1420
LWE: lwe1399(fni)
LLA: L11083(yebB)
LLC: LACR_0457
LLM: llmg_0428(fni)
SPY: SPy_0879
SPZ: M5005_Spy_0685
SPM: spyM18_0940
SPG: SpyM3_0598
SPS: SPs1255
SPH: MGAS10270_Spy0743
SPI: MGAS10750_Spy0777
SPJ: MGAS2096_Spy0756
SPK: MGAS9429_Spy0740
SPF: SpyM51123(fni)
SPA: M6_Spy0702
SPB: M28_Spy0665
SPN: SP_0384
SPR: spr0341(fni)
SPD: SPD_0349(fni)
SAG: SAG1323
SAN: gbs1393
SAK: SAK_1354(fni)
SMU: SMU.939
STC: str0562(idi)
STL: stu0562(idi)
STE: STER_0601
SSA: SSA_0336
SGO: SGO_0242
LPL: lp_1732(idi1)
LJO: LJ1208 LAC: LBA1171
LSA: LSA0905(idi)
LSL: LSL_0682
LDB: Ldb0996(fni)
LBU: LBUL_0903
LBR: LVIS_0861
LCA: LSEI_1493
LGA: LGAS_1036
LRE: Lreu_0912
EFA: EF0901
OOE: OEOE_1103
STH: STH1674
CBE: Cbei_3081
DRM: Dred_0474
SWO: Swol_1341
MTA: Moth_1328
MTU: Rv1745c(idi)
MTC: MT1787(idi)
MBO: Mb1774c(idi)
MBB: BCG_1784c(idi)
MPA: MAP3079c
MAV: MAV_3894(fni)
MSM: MSMEG_1057(fni) MSMEG_2337(fni)
MUL: MUL_0380(idi2)
MVA: Mvan_1582 Mvan_2176

MGI: Mflv_1842 Mflv_4187
MMC: Mmcs_1954
MKM: Mkms_2000
MJL: Mjls_1934
CGL: NCgl2223(cg12305)
CGB: cg2531(idi)
CEF: CE2207
CDI: DIP1730(idi)
NFA: nfa19790 nfa22100
RHA: RHA1_ro00239
SCO: SCO6750(SC5F2A.33c)
SMA: SAV1663(idi)
LXX: Lxx23810(idi)
CMI: CMM_2889(idiA)
AAU: AAur_0321(idi)
PAC: PPA2115
FRA: Francci3_4188
FRE: Franean1_5570
FAL: FRAAL6504(idi)
KRA: Krad_3991
SEN: SACE_2627(idiB_2) SACE_5210(idi)
STP: Strop_4438
SAQ: Sare_4564 Sare_4928
RXY: Rxy10400
BBU: BB0684
BGA: BG0707
SYN: sll1556
SYC: syc2161_c
SYF: Synpcc7942_1933
CYA: CYA_2395(fni)
CYB: CYB_2691(fni)
TEL: tll1403
ANA: all4591
AVA: Ava_2461 Ava_B0346
TER: Tery_1589
SRU: SRU_1900(idi)
CHU: CHU_0674(idi)
GFO: GFO_2363(idi)
FJO: Fjoh_0269
FPS: FP1792(idi)
CTE: CT0257
CCH: Cag_1445
CPH: Cpha266_0385
PVI: Cvib_1545
PLT: Plut_1764
RRS: RoseRS_2437
RCA: Rcas_2215
HAU: Haur_4687
DRA: DR_1087
DGE: Dgeo_1381
TTH: TT_P0067
TTJ: TTHB110
MJA: MJ0862
MMP: MMP0043
MMQ: MmarC5_1637
MMX: MmarC6_0906
MMZ: MmarC7_1040
MAE: Maeo_1184
MVN: Mevan_1058
MAC: MA0604(idi)
MBA: Mbar_A1419
MMA: MM_1764
MBU: Mbur_2397
MTP: Mthe_0474
MHU: Mhun_2888
MLA: Mlab_1665
MEM: Memar_1814

| | |
|---|---|
| MBN: Mboo 2211 | SMR: Smar_0822 |
| MTH: MTH48 | IHO: Igni_0804 |
| MST: Msp_0856(fni) | HBU: Hbut_0539 |
| MSI: Msm_1441 | SSO: SS00063 |
| MKA: MK0776(lldD) | STO: ST2059 |
| AFU: AF2287 | SAI: Saci_0091 |
| HAL: VNG1818G(idi) VNG6081G(crt_1) VNG6445G (crt_2) VNG7060 VNG7149 | MSE: Msed_2136 |
| | PAI: PAE0801 |
| HMA: rrnAC3484(idi) | PIS: Pisl_1093 |
| HWA: HQ2772A(idiA) HQ2847A(idiB) | PCL: Pcal_0017 |
| NPH: NP0360A(idiB_1) NP4826A(idiA) NP5124A(idiB_2) | PAS: Pars_0051 |
| | TPE: Tpen_0272 |

Exemplary isoprene synthase nucleic acids and polypeptides

Genbank Accession Nos.
AY341431
AY316691
AY279379
AJ457070
AY182241

TAC: Ta0102
TVO: TVN0179
PTO: PT00496
PHO: PH1202
PAB: PAB1662
PFU: PF0856
TKO: TK1470
RCI: LRC397(fni)
APE: APE_1765.1

---

What is claimed is:

1. A polyisoprene polymer which is comprised of repeat units that are derived from isoprene monomer, wherein the polyisoprene polymer has $\delta^{13}C$ value of greater than −22‰ or which is within the range of −30‰ to −28.5‰.

2. A polyisoprene polymer as specified in claim 1 wherein the polyisoprene polymer has $\delta^{13}C$ value which is within the range of −21‰ to −12‰.

3. A polyisoprene polymer as specified in claim 1 wherein the polyisoprene polymer has $\delta^{13}C$ value which is within the range of −29.5‰ to −28.5‰.

4. A polyisoprene polymer as specified in claim 1 wherein the polyisoprene polymer has $\delta^{13}C$ value which is within the range of −30‰ to −29‰.

5. A polyisoprene polymer as specified in claim 1 wherein the polyisoprene polymer is a homopolymer.

6. A polymer as specified in claim 1 wherein the polymer which is comprised of repeat units which are derived from isoprene, wherein the isoprene is produced by (a) culturing cells comprising a heterologous nucleic acid encoding an isoprene synthase polypeptide under suitable culture conditions for the production of the isoprene, (b) producing the isoprene, and (c) recovering the isoprene from the culture.

7. A polyisoprene polymer as specified in claim 1 wherein the polyisoprene polymer has a 3,4-microstructure content of greater than 10 percent.

8. A polyisoprene polymer as specified in claim 1 wherein the polyisoprene polymer has a 1,2-microstructure content of greater than 10 percent.

9. A polyisoprene polymer which is comprised of repeat units that are derived from isoprene monomer, wherein the polyisoprene polymer has $\delta^{13}C$ value which is within the range of −34‰ to −24‰, and wherein the polyisoprene (i) has a cis-1,4-microstructure content of less than 99.9% and a trans-1,4-microstructure content of less than 99.9%, or (ii) has a 3,4-microstructure content of greater than 2%, or (iii) has a 1,2-microstructure content of greater than 2%, or (iv) has weight average molecular weight which is within the range of 5,000 to 100,000.

10. A polyisoprene polymer as specified in claim 9 wherein the polyisoprene polymer has $\delta^{13}C$ value which is within the range of −33‰ to −25‰.

11. A polyisoprene polymer as specified in claim 10 wherein the polyisoprene polymer has a 1,2-microstructure content of greater than 5%.

12. A polyisoprene polymer as specified in claim 11 wherein the polyisoprene polymer has a polydispersity of less than 2.0.

13. A polyisoprene polymer as specified in claim 9 wherein the polyisoprene polymer is a liquid polyisoprene polymer having a weight average molecular weight which is within the range of 30,000 to 50,000.

14. A polymer as specified in claim 9 wherein the polymer which is comprised of repeat units which are derived from isoprene, wherein the isoprene is produced by (a) culturing cells comprising a heterologous nucleic acid encoding an isoprene synthase polypeptide under suitable culture conditions for the production of the isoprene, (b) producing the isoprene, and (c) recovering the isoprene from the culture.

15. A polymer which is comprised of repeat units that are derived from isoprene monomer and at least one additional monomer, wherein the polymer includes blocks of repeat units that are derived from isoprene, and wherein the blocks of repeat units that are derived from isoprene have a $\delta^{13}C$ value of greater than −22‰ or which is within the range of −34‰ to −24‰.

16. A polymer as specified in claim 15 wherein the polymer is a copolymer selected from the group consistion of (i) copolymers of isoprene and 1,3-butadiene, (ii) copolymers of isoprene and styrene, (iii) copolymers of isoprene, 1,3-butadiene, and styrene, and (iv) copolymers of isoprene and α-methyl styrene.

17. A polyisoprene polymer as specified in claim 13 wherein the liquid polyisoprene polymer has a polydispersity of less than 1.8.

18. A method for verifying that a polyisoprene homopolymer is from a sustainable renewable non-petroleum derived source which comprises: (I) determining the $\delta^{13}C$ value of the polyisoprene homopolymer; (II) if the polyisoprene homopolymer has a $\delta^{13}C$ value within the range of −34‰ to −30‰ or within the range of −28.5‰ to −24‰ additionally analyzing the polyisoprene homopolymer to determine (1) its cis-microstructure content, (2) its 3,4-microstructure content, (3) its 1,2-microstructure content, (4) its a weight average molecular weight, or (5) the presence or absence of residual proteins, soaps, lipids, resins, or sugars indicative of natural rubber; and (III) verifying that the polyisoprene homopolymer is from a sustainable renewable non-petroleum derived source if it has (i) a $\delta^{13}C$ value of greater than −22‰, (ii) a $\delta^{13}C$ value which is within the range of −30‰ to −28.5‰, or (iii) a $\delta^{13}C$ value within the range of −34‰ to −30‰ or within the range of −28.5% to −24‰ and if it (a) has a cis-microstructure content of less than 100%, (b) contains 3,4-microstructure, (c) contains 1,2-microstructure, (d) has a weight average molecular weight of less than 100,000, or (e) is free of residual proteins, soaps, lipids, resins, or sugars indicative of natural rubber.

19. A method as specified in claim 18 wherein the verification is made by showing that the polyisoprene homopolymer has a $\delta^{13}C$ value which is within the range of −34‰ to −30‰ and by showing that the polyisoprene homopolymer is free of residual proteins, soaps, lipids, resins, or sugars indicative of natural rubber.

20. A method for verifying that a copolymer having repeat units that are derived from isoprene contains isoprene that is from a sustainable renewable non-petroleum derived source, said method comprising: (I) determining the $\delta^{13}C$ value of at least one polyisoprene block in the copolymer; and (II) verifying that the isoprene in the copolymer is from a sustainable renewable non-petroleum derived source if the polyisoprene block has (i) a $\delta^{13}C$ value of greater than −22‰, or (ii) a $\delta^{13}C$ value which is within the range of −34‰ to −28.5.

* * * * *

```
                        SEQUENCE LISTING

<160> NUMBER OF SEQ ID NOS: 123

<210> SEQ ID NO 1
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 1
atgtgtgcga cctcttctca atttactcag attaccgagc ataattcccg tcgttccgca       60
aactatcagc caaacctgtg gaatttcgaa ttcctgcaat ccctggagaa cgacctgaaa      120
gtggaaaagc tggaggagaa agcgaccaaa ctggaggaag aagttcgctg catgatcaac      180
cgtgtagaca cccagccgct gtccctgctg gagctgatcg acgatgtgca gcgcctgggt      240
ctgacctaca aatttgaaaa agacatcatt aaagccctgg aaaacatcgt actgctggac      300
gaaaacaaaa gaacaaatc tgacctgcac gcaaccgctc tgtctttccg tctgctgcgt      360
cagcacggtt tcgaggtttc tcaggatgtt tttgagcgtt tcaaggataa agaaggtggt      420
ttcagcggtg aactgaaagg tgacgtccaa ggcctgctga gcctgtatga agcgtcttac      480
ctgggtttcg agggtgagaa cctgctggag gaggcgcgta cctttttccat cacccacctg      540 aagaacaacc tgaaagaagg cattaatacc aaggttgcag aacaagtgag ccacgccctg      600
gaactgccat atcaccagcg tctgcaccgt ctggaggcac gttggttcct ggataaatac      660
gaaccgaaag aaccgcatca ccagctgctg ctggagctgg cgaagctgga ttttaacatg      720
gtacagaccc tgcaccagaa agagctgcaa gatctgtccc gctggtggac cgagatgggc      780
ctggctagca aactggattt tgtacgcgac cgcctgatgg aagtttattt ctgggcactg      840
ggtatggcgc cagacccgca gtttggtgaa tgtcgcaaag ctgttactaa aatgtttggt      900
ctggtgacga tcatcgatga cgtgtatgac gtttatggca ctctggacga actgcaactg      960
ttcaccgatg ctgtagagcg ctgggacgtt aacgctatta cacccctgcc ggactatatg     1020
aaactgtgtt tcctggcact gtacaacacc gttaacgaca cgtccattc tattctgaaa     1080 gagaaaggtc ataacaacct gtcctatctg acgaaaagct ggcgtgaact gtgcaaagcc     1140
```

```
tttctgcaag aggcgaaatg gtccaacaac aaaattatcc cggctttctc caagtacctg    1200
gaaaacgcca gcgtttcctc ctccggtgta gcgctgctgg cgccgtctta cttttccgta    1260
tgccagcagc aggaagacat ctccgaccac gcgctgcgtt ccctgaccga cttccatggt    1320
ctggtgcgtt ctagctgcgt tatcttccgc ctgtgcaacg atctggccac ctctgcggcg    1380
gagctggaac gtggcgagac taccaattct atcattagct acatgcacga aaacgatggt    1440
accagcgagg aacaggcccg cgaagaactg cgtaaactga tcgacgccga atggaaaaag    1500
atgaatcgtg aacgcgttag cgactccacc ctgctgccta aagcgttcat ggaaatcgca    1560
gttaacatgg cacgtgtttc ccactgcacc taccagtatg cgatggtct gggtcgccca    1620 gactacgcga ctgaaaaccg catcaaactg ctgctgattg acccttttccc gattaaccag    1680 ctgatgtatg tctaactgca g                                              1701

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgtgtgc    420
gacctcttct caatttactc agattaccga gcataattcc cgtcgttccg caaactatca    480
gccaaacctg tggaatttcg aattcctgca atccctggag aacgacctga agtggaaaa    540 gctggaggag aaagcgacca aactggagga agaagttcgc tgcatgatca accgtgtaga    600
cacccagccg ctgtccctgc tggagctgat cgacgatgtg cagcgcctgg gtctgaccta    660
caaatttgaa aaagacatca ttaaagccct ggaaaacatc gtactgctgg acgaaaacaa    720
aaagaacaaa tctgacctgc acgcaaccgc tctgtctttc cgtctgctgc gtcagcacgg    780
tttcgaggtt tctcaggatg ttttttgagcg tttcaaggat aaagaaggtg gtttcagcgg    840
tgaactgaaa ggtgacgtcc aaggcctgct gagcctgtat gaagcgtctt acctgggttt    900
cgagggtgag aacctgctgg aggaggcgcg tacctttttcc atcacccacc tgaagaacaa    960
cctgaaagaa ggcattaata ccaaggttgc agaacaagtg agccacgccc tggaactgcc    1020
atatcaccag cgtctgcacc gtcttggagc acgttggttc ctggataaat cgaaccgaa    1080 agaaccgcat caccagctgc tgctggagct ggcgaagctg gattttaaca tggtacagac    1140
cctgcaccag aaagagctgc aagatctgtc ccgctggtgg accagatgg gcctggctag    1200 caaactggat tttgtacgcg accgcctgat ggaagtttat ttctgggcac tgggtatggc    1260
gccagacccg cagtttggtg aatgtcgcaa agctgttact aaaatgtttg gtctggtgac    1320
gatcatcgat gacgtgtatg acgtttatgg cactctggac gaactgcaac tgttcaccga    1380
tgctgtagag cgctgggacg ttaacgctat taacaccctg ccggactata tgaaactgtg    1440
tttcctggca ctgtacaaca ccgttaacga cacgtcctat tctattctga agagaaagg    1500
```

```
tcataacaac ctgtcctatc tgacgaaaag ctggcgtgaa ctgtgcaaag cctttctgca    1560
agaggcgaaa tggtccaaca acaaaattat cccggctttc tccaagtacc tggaaaacgc    1620
cagcgtttcc tcctccggtg tagcgctgct ggcgccgtct tacttttccg tatgccagca    1680
gcaggaagac atctccgacc acgcgctgcg ttccctgacc gacttccatg gtctggtgcg    1740
ttctagctgc gttatcttcc gcctgtgcaa cgatctggcc acctctgcgg cggagctgga    1800
acgtggcgag actaccaatt ctatcattag ctacatgcac gaaaacgatg gtaccagcga    1860
ggaacaggcc cgcgaagaac tgcgtaaact gatcgacgcc gaatggaaaa agatgaatcg    1920
tgaacgcgtt agcgactcca ccctgctgcc taaagcgttc atggaaatcg cagttaacat    1980
ggcacgtgtt tcccactgca cctaccagta tggcgatggt ctgggtcgcc cagactacgc    2040
gactgaaaac cgcatcaaac tgctgctgat tgacccttc ccgattaacc agctgatgta    2100
tgtctaactg cagctggtac catatgggaa ttcgaagctt tctagaacaa aaactcatct    2160
cagaaggagg tctgaatagc gccgtcgacc atcatcatca tcatcattga gtttaaacgg    2220
tctccagctt ggctgttttg gcggatgaga agagtttct agcctgatac agattaaatc    2280
agaacgcaga gcggtctga taaaacagaa tttgcctggc ggcagtagcg cggtggtccc    2340
acctgacccc atgccgaact cagaagtgaa acgccgtagc gccgatggta gtgtggggtc    2400
tccccatgcg agagtaggga actgccaggc atcaaataaa acgaaaggct cagtcgaaag    2460
actgggcctt tcgttttatc tgttgtttgt cggtgaacgc tctcctgagt aggacaaatc    2520
cgccgggagc ggatttgaac gttgcgaagc aacggcccgg agggtggcgg caggacgcc    2580 cgccataaac tgccaggcat caaattaagc agaaggccat cctgacggat ggcctttttg    2640
cgtttctaca aactctttt gtttattttt ctaaatacat tcaaatatgt atccgctcat    2700
gagacaataa ccctgataaa tgcttcaata atattgaaaa aggaagagta tgagtattca    2760
acatttccgt gtcgcccta ttccctttt tgcggcattt gccttcctg ttttgctca      2820 cccagaaacg ctggtgaaag taaaagatgc tgaagatcag ttgggtgcac gagtgggtta    2880
catcgaactg gatctcaaca gcggtaagat ccttgagagt tttcgccccg aagaacgttt    2940
tccaatgatg agcacttta aagttctgct atgtggcgcg gtattatccc gtgttgacgc    3000
cgggcaagag caactcggtc gccgcataca ctattctcag aatgacttgg ttgagtactc    3060
accagtcaca gaaaagcatc ttacggatgg catgacagta agagaattat gcagtgctgc    3120
cataaccatg agtgataaca ctgcggccaa cttacttctg acaacgatcg gaggaccgaa    3180
ggagctaacc gcttttttgc acaacatggg ggatcatgta actcgccttg atcgttggga    3240
accggagctg aatgaagcca taccaaacga cgagcgtgac accacgatgc ctgtagcaat    3300
ggcaacaacg ttgcgcaaac tattaactgg cgaactactt actctagctt cccggcaaca    3360
attaatagac tggatggagg cggataaagt tgcaggacca cttctgcgct cggcccttcc    3420
ggctggctgg tttattgctg ataaatctgg agccggtgag cgtgggtctc gcggtatcat    3480
tgcagcactg gggccagatg gtaagccctc ccgtatcgta gttatctaca cgacggggag    3540
tcaggcaact atggatgaac gaaatagaca gatcgctgag ataggtgcct cactgattaa    3600
gcattggtaa ctgtcagacc aagtttactc atatatactt tagattgatt taaaacttca    3660
tttttaattt aaaaggatct aggtgaagat cctttttgat aatctcatga ccaaaatccc    3720
ttaacgtgag ttttcgttcc actgagcgtc agaccccgta gaaaagatca aaggatcttc    3780
ttgagatcct ttttttctgc gcgtaatctg ctgcttgcaa acaaaaaaac caccgctacc    3840
agcggtggtt tgtttgccgg atcaagagct accaactctt tttccgaagg taactggctt    3900
```

```
cagcagagcg cagataccaa atactgtcct tctagtgtag ccgtagttag gccaccactt    3960
caagaactct gtagcaccgc ctacatacct cgctctgcta atcctgttac cagtggctgc    4020
tgccagtggc gataagtcgt gtcttaccgg gttggactca agacgatagt taccggataa    4080
ggcgcagcgg tcgggctgaa cgggggggttc gtgcacacag cccagcttgg agcgaacgac    4140
ctacaccgaa ctgagatacc tacagcgtga gctatgagaa agcgccacgc ttcccgaagg    4200
gagaaaggcg gacaggtatc cggtaagcgg cagggtcgga acaggagagc gcacgaggga    4260
gcttccaggg ggaaacgcct ggtatcttta tagtcctgtc gggtttcgcc acctctgact    4320
tgagcgtcga tttttgtgat gctcgtcagg ggggcgagc ctatggaaaa acgccagcaa    4380
cgcggccttt ttacggttcc tggccttttg ctggcttttt gctcacatgt tctttcctgc    4440
gttatcccct gattctgtgg ataaccgtat taccgccttt gagtgagctg ataccgctcg    4500
ccgcagccga acgaccgagc gcagcgagtc agtgagcgag gaagcggaag agcgcctgat    4560
gcggtatttt ctccttacgc atctgtgcgg tatttcacac cgcatatggt gcactctcag    4620
tacaatctgc tctgatgccg catagttaag ccagtataca ctccgctatc gctacgtgac    4680
tgggtcatgg ctgcgccccg acacccgcca cacccgctg acgcgccctg acgggcttgt    4740
ctgctcccgg catccgctta cagacaagct gtgaccgtct ccgggagctg catgtgtcag    4800
aggttttcac cgtcatcacc gaaacgcgcg aggcagcaga tcaattcgcg cgcgaaggcg    4860
aagcggcatg catttacgtt gacaccatcg aatggtgcaa aacctttcgc ggtatggcat    4920
gatagcgccc ggaagagagt caattcaggg tggtgaatgt gaaaccagta acgttatacg    4980
atgtcgcaga gtatgccggt gtctcttatc agaccgtttc ccgcgtggtg aaccaggcca    5040
gccacgtttc tgcgaaaacg cgggaaaaag tggaagcggc gatggcggag ctgaattaca    5100
ttcccaaccg cgtggcacaa caactggcgg gcaaacagtc gttgctgatt ggcgttgcca    5160
cctccagtct ggccctgcac gcgccgtcgc aaattgtcgc ggcgattaaa tctcgcgccg    5220
atcaactggg tgccagcgtg gtggtgtcga tggtagaacg aagcggcgtc gaagcctgta    5280
aagcggcggt gcacaatctt ctcgcgcaac gcgtcagtgg gctgatcatt aactatccgc    5340
tggatgacca ggatgccatt gctgtggaag ctgcctgcac taatgttccg gcgttatttc    5400
ttgatgtctc tgaccagaca cccatcaaca gtattatttt ctcccatgaa gacggtacgc    5460
gactgggcgt ggagcatctg gtcgcattgg gtcaccagca aatcgcgctg ttagcgggcc    5520
cattaagttc tgtctcggcg cgtctgcgtc tggctggctg gcataaatat ctcactcgca    5580
atcaaattca gccgatagcg gaacgggaag gcgactggag tgccatgtcc ggttttcaac    5640
aaaccatgca aatgctgaat gagggcatcg ttcccactgc gatgctggtt gccaacgatc    5700
agatggcgct gggcgcaatg cgcgccatta ccgagtccgg gctgcgcgtt ggtgcggata    5760
tctcggtagt gggatacgac gataccgaag acagctcatg ttatatcccg ccgtcaacca    5820
ccatcaaaca ggattttcgc ctgctggggc aaaccagcgt ggaccgcttg ctgcaactct    5880
ctcagggcca ggcggtgaag ggcaatcagc tgttgcccgt ctcactggtg aaaagaaaaa    5940
ccaccctggc gcccaatacg caaaccgcct ctccccgcgc gttggccgat tcattaatgc    6000
agctggcacg acaggtttcc cgactggaaa gcgggcagtg agcgcaacgc aattaatgtg    6060
agttagcgcg aattgatctg                                                6080
```

<210> SEQ ID NO 3  
<211> LENGTH: 37  
<212> TYPE: DNA  
<213> ORGANISM: Artificial Sequence  
<220> FEATURE:

```
<223> OTHER INFORMATION: Synthetic Construct

<400> SEQUENCE: 3
cgtgagatca tatgtgtgcg acctcttctc aatttac                              37

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
cggtcgacgg atccctgcag ttagacatac atcagctg                             38

<210> SEQ ID NO 5
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 5
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc cggatatagt tcctcctttc agcaaaaaac ccctcaagac ccgtttagag    240
gccccaaggg gttatgctag ttattgctca gcggtggcag cagccaactc agcttccttt    300
cgggctttgt tagcagccgg atccctgcag ttagacatac atcagctggt taatcgggaa    360
agggtcaatc agcagcagtt tgatgcggtt ttcagtcgcg tagtctgggc gacccagacc    420
atcgccatac tggtaggtgc agtgggaaac acgtgccatg ttaactgcga tttccatgaa    480
cgctttaggc agcagggtgg agtcgctaac gcgttcacga ttcatctttt tccattcggc    540
gtcgatcagt ttacgcagtt cttcgcgggc ctgttcctcg ctggtaccat cgttttcgtg    600
catgtagcta atgatagaat tggtagtctc gccacgttcc agctccgccg cagaggtggc    660
cagatcgttg cacaggcgga agataacgca gctagaacgc accagaccat ggaagtcggt    720
cagggaacgc agcgcgtggt cggagatgtc ttcctgctgc tggcatacgg aaaagtaaga    780
cggcgccagc agcgctacac cggaggagga aacgctggcg ttttccaggt acttggagaa    840
agccgggata ttttgttgt tggaccattt cgcctcttgc agaaaggctt tgcacagttc     900
acgccagctt ttcgtcagat aggacaggtt gttatgacct ttctctttca gaatagaata    960
ggacgtgtcg ttaacggtgt tgtacagtgc caggaaacac agtttcatat agtccggcag   1020
ggtgttaata gcgttaacgt cccagcgctc tacagcatcg gtgaacagtt gcagttcgtc   1080
cagagtgcca taaacgtcat acacgtcatc gatgatcgtc accagaccaa acattttagt   1140
aacagctttg cgacattcac caaactgcgg gtctggcgcc atacccagtg cccagaaata   1200
aacttccatc aggcggtcgc gtacaaaatc cagtttgcta gccaggccca tctcggtcca   1260
ccagcgggac agatcttgca gctctttctg gtgcagggtc tgtaccatgt taaaatccag   1320
cttcgccagc tccagcagca gctggtgatg cggttctttc ggttcgtatt tatccaggaa   1380
ccaacgtgcc tccagacggt gcagacgctg gtgatatggc agttccaggg cgtggctcac   1440
ttgttctgca accttggtat taatgccttc tttcaggttg ttcttcaggt gggtgatgga   1500
aaaggtacgc gcctcctcca gcaggttctc accctcgaaa cccaggtaag acgcttcata   1560
```

```
caggctcagc aggccttgga cgtcaccttt cagttcaccg ctgaaaccac cttctttatc    1620
cttgaaacgc tcaaaaacat cctgagaaac ctcgaaaccg tgctgacgca gcagacggaa    1680
agacagagcg gttgcgtgca ggtcagattt gttcttttg ttttcgtcca gcagtacgat     1740
gttttccagg gctttaatga tgtcttttc aaatttgtag gtcagaccca ggcgctgcac     1800
atcgtcgatc agctccagca gggacagcgg ctgggtgtct acacggttga tcatgcagcg    1860
aacttcttcc tccagtttgg tcgctttctc ctccagcttt tccactttca ggtcgttctc    1920
cagggattgc aggaattcga aattccacag gtttggctga tagtttgcgg aacgacggga    1980
attatgctcg gtaatctgag taaattgaga agaggtcgca cacatatgac gaccttcgat    2040
atggccgctg ctgtgatgat gatgatgatg atgatgatga tggcccatgg tatatctcct    2100
tcttaaagtt aaacaaaatt atttctagag gggaattgtt atccgctcac aattccccta    2160
tagtgagtcg tattaatttc gcgggatcga gatctcgatc ctctacgccg gacgcatcgt    2220
ggccggcatc accggcgcca caggtgcggt tgctggcgcc tatatcgccg acatcaccga    2280
tggggaagat cgggctcgcc acttcgggct catgagcgct tgtttcggcg tgggtatggt    2340
ggcaggcccc gtggccgggg gactgttggg cgccatctcc ttgcatgcac cattccttgc    2400
ggcggcggtg ctcaacggcc tcaacctact actgggctgc ttcctaatgc aggagtcgca    2460
taagggagag cgtcgagatc ccggacacca tcgaatggcg caaaaccttt cgcggtatgg    2520
catgatagcg cccggaagag agtcaattca gggtggtgaa tgtgaaacca gtaacgttat    2580
acgatgtcgc agagtatgcc ggtgtctctt atcagaccgt ttcccgcgtg gtgaaccagg    2640
ccagccacgt ttctgcgaaa acgcgggaaa aagtggaagc ggcgatggcg gagctgaatt    2700
acattcccaa ccgcgtggca caacaactgg cgggcaaaca gtcgttgctg attggcgttg    2760
ccacctccag tctggccctg cacgcgccgt cgcaaattgt cgcggcgatt aaatctcgcg    2820
ccgatcaact gggtgccagc gtggtggtgt cgatggtaga acgaagcggc gtcgaagcct    2880
gtaaagcggc ggtgcacaat cttctcgcgc aacgcgtcag tgggctgatc attaactatc    2940
cgctggatga ccaggatgcc attgctgtgg aagctgcctg cactaatgtt ccggcgttat    3000
ttcttgatgt ctctgaccag acacccatca acagtattat tttctcccat gaagacggta    3060
cgcgactggg cgtggagcat ctggtcgcat tgggtcacca gcaaatcgcg ctgttagcgg    3120
gcccattaag ttctgtctcg gcgcgtctgc gtctggctgg ctggcataaa tatctcactc    3180
gcaatcaaat tcagccgata gcggaacggg aaggcgactg gagtgccatg tccggttttc    3240
aacaaaccat gcaaatgctg aatgagggca tcgttcccac tgcgatgctg gttgccaacg    3300
atcagatggc gctgggcgca atgcgcgcca ttaccgagtc cgggctgcgc gttggtgcgg    3360
atatctcggt agtgggatac gacgataccg aagacagctc atgttatatc ccgccgttaa    3420
ccaccatcaa acaggatttt cgcctgctgg ggcaaaccag cgtggaccgc ttgctgcaac    3480
tctctcaggg ccaggcggtg aagggcaatc agctgttgcc cgtctcactg gtgaaaagaa    3540
aaaccaccct ggcgcccaat acgcaaaccg cctctccccg cgcgttggcc gattcattaa    3600
tgcagctggc acgacaggtt tcccgactgg aaagcgggca gtgagcgcaa cgcaattaat    3660
gtaagttagc tcactcatta ggcaccggga tctcgaccga tgcccttgag agccttcaac    3720
ccagtcagct ccttccggtg ggcgcggggc atgactatcg tcgccgcact tatgactgtc    3780
ttctttatca tgcaactcgt aggacaggtg ccggcagcgc tctgggtcat tttcggcgag    3840
gaccgctttc gctggagcgc gacgatgatc ggcctgtcgc ttgcggtatt cggaatcttg    3900
cacgccctcg ctcaagcctt cgtcactggt cccgccacca aacgtttcgg cgagaagcag    3960
```

```
gccattatcg ccggcatggc ggccgacgcg ctgggctacg tcttgctggc gttcgcgacg    4020
cgaggctgga tggccttccc cattatgatt cttctcgctt ccggcggcat cgggatgccc    4080
gcgttgcagg ccatgctgtc caggcaggta gatgacgacc atcagggaca gcttcaagga    4140
tcgctcgcgg ctcttaccag cctaacttcg atcactggac cgctgatcgt cacggcgatt    4200
tatgccgcct cggcgagcac atggaacggg ttggcatgga ttgtaggcgc cgccctatac    4260
cttgtctgcc tccccgcgtt gcgtcgcggt gcatggagcc gggccacctc gacctgaatg    4320
gaagccggcg gcacctcgct aacggattca ccactccaag aattggagcc aatcaattct    4380
tgcggagaac tgtgaatgcg caaaccaacc cttggcagaa catatccatc gcgtccgcca    4440
tctccagcag ccgcacgcgg cgcatctcgg gcagcgttgg gtcctggcca cgggtgcgca    4500
tgatcgtgct cctgtcgttg aggacccggc taggctggcg gggttgcctt actggttagc    4560
agaatgaatc accgatacgc gagcgaacgt gaagcgactg ctgctgcaaa acgtctgcga    4620
cctgagcaac aacatgaatg gtcttcggtt ccgtgtttc gtaaagtctg gaaacgcgga    4680
agtcagcgcc ctgcaccatt atgttccgga tctgcatcgc aggatgctgc tggctaccct    4740
gtggaacacc tacatctgta ttaacgaagc gctggcattg accctgagtg attttctct    4800 ggtcccgccg catccatacc gccagttgtt taccctcaca acgttccagt aaccgggcat    4860
gttcatcatc agtaacccgt atcgtgagca tcctctctcg tttcatcggt atcattaccc    4920
ccatgaacag aaatccccct tacacggagg catcagtgac caaacaggaa aaaccgccc    4980 ttaacatggc ccgctttatc agaagccaga cattaacgct tctggagaaa ctcaacgagc    5040
tggacgcgga tgaacaggca gacatctgtg aatcgcttca cgaccacgct gatgagcttt    5100
accgcagctg cctcgcgcgt ttcggtgatg acggtgaaaa cctctgacac atgcagctcc    5160
cggagacggt cacagcttgt ctgtaagcgg atgccgggag cagacaagcc cgtcagggcg    5220
cgtcagcggg tgttggcggg tgtcggggcg cagccatgac ccagtcacgt agcgatagcg    5280
gagtgtatac tggcttaact atgcggcatc agagcagatt gtactgagag tgcaccatat    5340
atgcggtgtg aaataccgca cagatgcgta aggagaaaat accgcatcag gcgctcttcc    5400
gcttcctcgc tcactgactc gctgcgctcg tcgttcggc tgcggcgagc ggtatcagct    5460
cactcaaagg cggtaatacg gttatccaca gaatcagggg ataacgcagg aaagaacatg    5520
tgagcaaaag gccagcaaaa ggccaggaac cgtaaaaagg ccgcgttgct ggcgtttttc    5580
cataggctcc gcccccctga cgagcatcac aaaaatcgac gctcaagtca gaggtggcga    5640
aacccgacag gactataaag ataccaggcg tttccccctg gaagctccct cgtgcgctct    5700
cctgttccga ccctgccgct taccggatac ctgtccgcct ttctcccttc gggaagcgtg    5760
gcgctttctc atagctcacg ctgtaggtat ctcagttcgg tgtaggtcgt tcgctccaag    5820
ctgggctgtg tgcacgaacc ccccgttcag cccgaccgct gcgccttatc cggtaactat    5880
cgtcttgagt ccaacccggt aagacacgac ttatcgccac tggcagcagc cactggtaac    5940
aggattagca gagcgaggta tgtaggcggt gctacagagt tcttgaagtg gtggcctaac    6000
tacggctaca ctagaaggac agtatttggt atctgcgctc tgctgaagcc agttaccttc    6060
ggaaaaagag ttggtagctc ttgatccggc aaacaaacca ccgctggtag cggtggtttt    6120
tttgtttgca agcagcagat tacgcgcaga aaaaaaggat ctcaagaaga tcctttgatc    6180
ttttctacgg ggtctgacgc tcagtggaac gaaaactcac gttaagggat tttggtcatg    6240
agattatcaa aaaggatctt cacctagatc cttttaaatt aaaaatgaag ttttaaatca    6300
atctaaagta tatatgagta aacttggtct gacagttacc aatgcttaat cagtgaggca    6360
```

-continued

| | |
|---|---|
| cctatctcag cgatctgtct atttcgttca tccatagttg cctgactccc cgtcgtgtag | 6420 |
| ataactacga tacgggaggg cttaccatct ggccccagtg ctgcaatgat accgcgagac | 6480 |
| ccacgctcac cggctccaga tttatcagca ataaaccagc cagccggaag ggccgagcgc | 6540 |
| agaagtggtc ctgcaacttt atccgcctcc atccagtcta ttaattgttg ccgggaagct | 6600 |
| agagtaagta gttcgccagt taatagtttg cgcaacgttg ttgccattgc tgcaggcatc | 6660 |
| gtggtgtcac gctcgtcgtt tggtatggct tcattcagct ccggttccca acgatcaagg | 6720 |
| cgagttacat gatcccccat gttgtgcaaa aaagcggtta gctccttcgg tcctccgatc | 6780 |
| gttgtcagaa gtaagttggc cgcagtgtta tcactcatgg ttatggcagc actgcataat | 6840 |
| tctcttactg tcatgccatc cgtaagatgc ttttctgtga ctggtgagta ctcaaccaag | 6900 |
| tcattctgag aatagtgtat gcggcgaccg agttgctctt gcccggcgtc aacacgggat | 6960 |
| aataccgcgc cacatagcag aactttaaaa gtgctcatca ttggaaaacg ttcttcgggg | 7020 |
| cgaaaactct caaggatctt accgctgttg agatccagtt cgatgtaacc cactcgtgca | 7080 |
| cccaactgat cttcagcatc ttttactttc accagcgttt ctgggtgagc aaaaacagga | 7140 |
| aggcaaaatg ccgcaaaaaa gggaataagg gcgacacgga aatgttgaat actcatactc | 7200 |
| ttcctttttc aatattattg aagcatttat cagggttatt gtctcatgag cggatacata | 7260 |
| tttgaatgta tttagaaaaa taaacaaata ggggttccgc gcacatttcc ccgaaaagtg | 7320 |
| ccacctgacg tctaagaaac cattattatc atgacattaa cctataaaaa taggcgtatc | 7380 |
| acgaggccct ttcgtcttca agaa | 7404 |

<210> SEQ ID NO 6
<211> LENGTH: 41
<212> TYPE: DNA
<213> ORGANISM: Artificial Sequence
<220> FEATURE:
<223> OTHER INFORMATION: Synthetic Construct

<400> SEQUENCE: 6

| | |
|---|---|
| catatgaaag cttgtatcga ttaaataagg aggaataaac c | 41 |

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7

| | |
|---|---|
| cccgtcttac tgtcgggaat tcgcgttggc cgattcatta atgcagctgg cacgacaggt | 60 |
| ttcccgactg gaaagcgggc agtgagcgca acgcaattaa tgtgagttag ctcactcatt | 120 |
| aggcacccca ggctttacac tttatgcttc cggctcgtat gttgtgtgga attgtgagcg | 180 |
| gataacaatt tcacacagga aacagctatg accatgatta cgccaagctt gtatcgatta | 240 |
| aataaggagg aataaaccat gtgtgcgacc tcttctcaat ttactcagat taccgagcat | 300 |
| aattcccgtc gttccgcaaa ctatcagcca aacctgtgga atttcgaatt cctgcaatcc | 360 |
| ctggagaacg acctgaaagt ggaaaagctg gaggagaaag cgaccaaact ggaggaagaa | 420 |
| gttcgctgca tgatcaaccg tgtagacacc cagccgctgt ccctgctgga gctgatcgac | 480 |
| gatgtgcagc gcctgggtct gacctacaaa tttgaaaaag acatcattaa agccctggaa | 540 |
| aacatcgtac tgctggacga aaacaaaaag aacaaatctg acctgcacgc aaccgctctg | 600 |
| tctttccgtc tgctgcgtca gcacggtttc gaggtttctc aggatgtttt tgagcgtttc | 660 |

-continued

```
aaggataaag aaggtggttt cagcggtgaa ctgaaaggtg acgtccaagg cctgctgagc    720
ctgtatgaag cgtcttacct gggtttcgag ggtgagaacc tgctggagga ggcgcgtacc    780
ttttccatca cccacctgaa gaacaacctg aaagaaggca ttaataccaa ggttgcagaa    840
caagtgagcc acgccctgga actgccatat caccagcgtc tgcaccgtct ggaggcacgt    900
tggttcctgg ataaatacga accgaaagaa ccgcatcacc agctgctgct ggagctggcg    960
aagctggatt taacatggt acagaccctg caccagaaag agctgcaaga tctgtcccgc   1020
tggtggaccg agatgggcct ggctagcaaa ctggattttg tacgcgaccg cctgatggaa   1080
gtttatttct gggcactggg tatggcgcca gacccgcagt tggtgaatg tcgcaaagct   1140 gttactaaaa tgtttggtct ggtgacgatc atcgatgacg tgtatgacgt ttatggcact   1200
ctggacgaac tgcaactgtt caccgatgct gtagagcgct gggacgttaa cgctattaac   1260
accctgccgg actatatgaa actgtgtttc ctggcactgt acaacaccgt taacgacacg   1320
tcctattcta ttctgaaaga gaaggtcat aacaacctgt cctatctgac gaaaagctgg   1380
cgtgaactgt gcaaagcctt tctgcaagag gcgaaatggt ccaacaacaa aattatcccg   1440
gctttctcca gtacctgga aaacgccagc gtttcctcct ccggtgtagc gctgctggcg   1500
ccgtcttact tttccgtatg ccagcagcag gaagacatct ccgaccacgc gctgcgttcc   1560
ctgaccgact ccatggtct ggtgcgttct agctgcgtta tcttccgcct gtgcaacgat   1620
ctggccacct ctgcggcgga gctggaacgt ggcgagacta ccaattctat cattagctac   1680
atgcacgaaa acgatggtac cagcgaggaa caggcccgcg aagaactgcg taaactgatc   1740
gacgccgaat ggaaaaagat gaatcgtgaa cgcgttagcg actccaccct gctgcctaaa   1800
gcgttcatgg aaatcgcagt taacatggca cgtgtttccc actgcaccta ccagtatggc   1860
gatggtctgg tcgcccaga ctacgcgact gaaaaccgca tcaaactgct gctgattgac   1920
ccttccccga ttaaccagct gatgtatgtc taactgcagg tcgactctag aggatccccg   1980
ggtaccgagc tcgaattcac tggccgtcgt tttacaacgt cgtgactggg aaaaccctgg   2040
cgttacccaa cttaatcgcc ttgcagcaca tccccctttc gccagctggc gtaatagcga   2100
agaggcccgc accgatcgcc cttcccaaca gttgcgcagc ctgaatggcg aatggcgcct   2160
gatgcggtat tttctcctta cgcatctgtg cggtatttca caccgcatat ggtgcactct   2220
cagtacaatc tgctctgatg ccgcatagtt aagccagccc cgacacccgc caacacccgc   2280
tgacgagctt agtaaagccc tcgctagatt ttaatgcgga tgttgcgatt acttcgccaa   2340
ctattgcgat aacaagaaaa agccagcctt tcatgatata tctcccaatt tgtgtagggc   2400
ttattatgca cgcttaaaaa taataaaagc agacttgacc tgatagtttg gctgtgagca   2460
attatgtgct tagtgcatct aacgcttgag ttaagccgcg ccgcgaagcg gcgtcggctt   2520
gaacgaattg ttagacatta tttgccgact accttggtga tctcgccttt cacgtagtgg   2580
acaaattctt ccaactgatc tgcgcgcgag gccaagcgat cttcttcttg tccaagataa   2640
gcctgtctag cttcaagtat gacgggctga tactgggccg gcaggcgctc cattgcccag   2700
tcggcagcga catccttcgg cgcgattttg ccggttactg cgctgtacca aatgcgggac   2760
aacgtaagca ctacatttcg ctcatcgcca gcccagtcgg gcggcgagtt ccatagcgtt   2820
aaggtttcat ttagcgcctc aaatagatcc tgttcaggaa ccggatcaaa gagttcctcc   2880
gccgctggac ctaccaaggc aacgctatgt tctcttgctt ttgtcagcaa gatagccaga   2940
tcaatgtcga tcgtggctgg ctcgaagata cctgcaagaa tgtcattgcg ctgccattct   3000
ccaaattgca gttcgcgctt agctggataa cgccacggaa tgatgtcgtc gtgcacaaca   3060
```

```
atggtgactt ctacagcgcg gagaatctcg ctctctccag gggaagccga agtttccaaa    3120
aggtcgttga tcaaagctcg ccgcgttgtt catcaagcc ttacggtcac cgtaaccagc     3180
aaatcaatat cactgtgtgg cttcaggccg ccatccactg cggagccgta caaatgtacg    3240
gccagcaacg tcggttcgag atggcgctcg atgacgccaa ctacctctga tagttgagtc    3300
gatacttcgg cgatcaccgc ttccctcatg atgtttaact ttgttttagg gcgactgccc    3360
tgctgcgtaa catcgttgct gctccataac atcaaacatc gacccacggc gtaacgcgct    3420
tgctgcttgg atgcccgagg catagactgt accccaaaaa aacagtcata acaagccatg    3480
aaaaccgcca ctgcgccgtt accaccgctg cgttcggtca aggttctgga ccagttgcgt    3540
gagcgcatac gctacttgca ttacagctta cgaaccgaac aggcttatgt ccactgggtt    3600
cgtgccttca tccgtttcca cggtgtgcgt caccccggcaa ccttgggcag cagcgaagtc    3660
gaggcatttc tgtcctggct ggcgaacgag cgcaaggttt cggtctccac gcatcgtcag    3720
gcattggcgg ccttgctgtt cttctacggc aaggtgctgt gcacggatct gccctggctt    3780
caggagatcg gaagacctcg gccgtcgcgg cgcttgccgg tggtgctgac cccggatgaa    3840
gtggttcgca tcctcggttt tctggaaggc gagcatcgtt tgttcgccca gcttctgtat    3900
ggaacgggca tgcggatcag tgagggtttg caactgcggg tcaaggatct ggatttcgat    3960
cacggcacga tcatcgtgcg ggagggcaag ggctccaagg atcgggcctt gatgttaccc    4020
gagagcttgg cacccagcct gcgcgagcag gggaattaat tcccacgggt tttgctgccc    4080
gcaaacgggc tgttctggtg ttgctagttt gttatcagaa tcgcagatcc ggcttcagcc    4140
ggtttgccgg ctgaaagcgc tatttcttcc agaattgcca tgattttttc cccacgggag    4200
gcgtcactgg ctcccgtgtt gtcggcagct ttgattcgat aagcagcatc gcctgtttca    4260
ggctgtctat gtgtgactgt tgagctgtaa caagttgtct caggtgttca atttcatgtt    4320
ctagttgctt tgttttactg gtttcacctg ttctattagg tgttacatgc tgttcatctg    4380
ttacattgtc gatctgttca tggtgaacag cttttgaatgc accaaaaact cgtaaaagct    4440
ctgatgtatc tatctttttt acaccgtttt catctgtgca tatggacagt tttcccttttg    4500 atatgtaacg gtgaacagtt gttctacttt tgtttgttag tcttgatgct tcactgatag    4560
atacaagagc cataagaacc tcagatcctt ccgtatttag ccagtatgtt ctctagtgtg    4620
gttcgttgtt tttgcgtgag ccatgagaac gaaccattga gatcatactt actttgcatg    4680
tcactcaaaa attttgcctc aaaactggtg agctgaattt ttgcagttaa agcatcgtgt    4740 agtgttttc ttagtccgtt atgtaggtag gaatctgatg taatggttgt tggtattttg     4800
tcaccattca tttttatctg gttgttctca agttcggtta cgagatccat ttgtctatct    4860
agttcaactt ggaaaatcaa cgtatcagtc gggcggcctc gcttatcaac caccaatttc    4920
atattgctgt aagtgtttaa atctttactt attggtttca aaacccattg gttaagcctt    4980
ttaaactcat ggtagttatt ttcaagcatt aacatgaact taaattcatc aaggctaatc    5040
tctatatttg ccttgtgagt tttcttttgt gttagttctt ttaataacca ctcataaatc    5100
ctcatagagt atttgttttc aaaagactta acatgttcca gattatattt tatgaatttt    5160
tttaactgga aaagataagg caatatctct tcactaaaaa ctaattctaa tttttcgctt    5220
gagaacttgg catagtttgt ccactggaaa atctcaaagc ctttaaccaa aggattcctg    5280
atttccacag ttctcgtcat cagctctctg gttgctttag ctaatacacc ataagcattt    5340
tccctactga tgttcatcat ctgagcgtat tggtttataag tgaacgatac cgtccgttct    5400
ttccttgtag ggttttcaat cgtggggttg agtagtgcca cacagcataa aattagcttg    5460
```

-continued

| | |
|---|---|
| gtttcatgct ccgttaagtc atagcgacta atcgctagtt catttgcttt gaaacaact | 5520 |
| aattcagaca tacatctcaa ttggtctagg tgattttaat cactatacca attgagatgg | 5580 |
| gctagtcaat gataattact agtccttttc ctttgagttg tgggtatctg taaattctgc | 5640 |
| tagacctttg ctggaaaact tgtaaattct gctagaccct ctgtaaattc cgctagacct | 5700 |
| ttgtgtgttt tttttgttta tattcaagtg gttataattt atagaataaa gaaagaataa | 5760 |
| aaaaagataa aaagaataga tcccagccct gtgtataact cactacttta gtcagttccg | 5820 |
| cagtattaca aaaggatgtc gcaaacgctg tttgctcctc tacaaaacag accttaaaac | 5880 |
| cctaaaggct taagtagcac cctcgcaagc tcgggcaaat cgctgaatat tccttttgtc | 5940 |
| tccgaccatc aggcacctga gtcgctgtct ttttcgtgac attcagttcg ctgcgctcac | 6000 |
| ggctctggca gtgaatgggg gtaaatgcca ctacaggcgc ctttatgga ttcatgcaag | 6060 |
| gaaactaccc ataatacaag aaaagcccgt cacgggcttc tcagggcgtt ttatggcggg | 6120 |
| tctgctatgt ggtgctatct gacttttttgc tgttcagcag ttcctgccct ctgattttcc | 6180 |
| agtctgacca cttcggatta tcccgtgaca ggtcattcag actggctaat gcacccagta | 6240 |
| aggcagcggt atcatcaaca ggctta | 6266 |

<210> SEQ ID NO 8
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 8

| | |
|---|---|
| atgtgtgcaa cctcctccca gtttactcag attaccgagc ataattctcg acgatctgct | 60 |
| aactaccagc cgaacctttg gaactttgag tttctccagt ctctcgaaaa tgacctgaag | 120 |
| gtggaaaagc tcgaggagaa ggcgaccaaa ctcgaggagg aggtgcgatg tatgatcaac | 180 |
| agagttgaca cccaaccccct gtctttgctg gagctgatcg acgatgtgca gcggttgggt | 240 |
| ttgacttata aattcgagaa ggacattatc aaggcactgg agaacattgt gctcctcgac | 300 |
| gagaacaaga agaacaagtc tgatcttcac gctaccgctc tctctttccg acttcttcga | 360 |
| caacacggct tcgaggtgtc gcaggacgtc ttcgagagat ttaaggacaa ggagggagga | 420 |
| tttagcggcg agctgaaggg agacgttcag ggtcttctct ccttgtacga ggcgtcctac | 480 |
| ctgggattcg agggagagaa cctcctggag gaagctcgta cattttccat cactcacctt | 540 |
| aagaataacc ttaaggaggg aattaacacc aaggtggccg agcaggtttc tcacgccctg | 600 |
| gagctcccct accaccaacg gctccataga ctggaggctc gttggttcct ggacaaatat | 660 |
| gagccaaagg agcctcatca tcagttgctg ttggagttgg ccaagctgga cttcaatatg | 720 |
| gttcagacgc tgcaccaaaa ggagttgcag gacctgtctc gatggtggac cgagatggga | 780 |
| ttggcctcga gctggatttt tgtccgtgac cgacttatgg aggtctattt ttgggccctt | 840 |
| ggaatggcgc ctgaccccca gttcggagag tgccggaagg cggtgacgaa gatgttcggt | 900 |
| cttgtgacta tcatcgacga cgtctacgat gtctacggca cactcgacga gttgcagctg | 960 |
| ttcactgacg ccgtcgagcg atgggatgtg aacgccatta atactctccc tgactatatg | 1020 |
| aagctgtgct tcctggctct gtacaacact gtcaacgata cctcgtactc tatcctcaag | 1080 |
| gagaagggac acaacaatct ctcctacttg accaaatcct ggcgagaact gtgcaaggct | 1140 |
| tttctgcagg aggctaaatg gtccaataac aagatcattc ctgcttttc taaataccctg | 1200 |
| gaaaatgcct cggtgtcgag ctctggcgtc gcccttctgg cccttcccta cttctccgtc | 1260 |

| | |
|---|---|
| tgccagcagc aggaggatat tccgatcat gctcttagat cgctgaccga ttttcacggc | 1320 |
| ctcgtgcgat cttcctgcgt gatttttcgg ttgtgtaatg accttgcgac ctctgctgct | 1380 |
| gagctggaac gaggcgagac tacaaattcc attatttctt acatgcacga aaacgatgga | 1440 |
| acatctgaag aacaggctag agaggaactg cgaaagttga tcgacgccga gtggaagaag | 1500 |
| atgaacagag agcgggtgtc cgactctacc ctgcttccca aggccttcat ggagatcgcc | 1560 |
| gtgaacatgg ctcgagtttc ccattgtact taccagtacg gtgacggcct gggtcgtccg | 1620 |
| gactacgcta cagagaaccg aatcaagctg ctgctcatcg accccttccc tatcaaccaa | 1680 |
| ttgatgtacg tgtaa | 1695 |

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9

| | |
|---|---|
| gcttatggat cctctagact attacacgta catcaattgg | 40 |

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10

| | |
|---|---|
| caccatgtgt gcaacctcct cccagtttac | 30 |

<210> SEQ ID NO 11
<211> LENGTH: 8191
<212> TYPE: DNA
<213> ORGANISM: Artificial Sequence
<220> FEATURE:
<223> OTHER INFORMATION: Synthetic Construct

<400> SEQUENCE: 11

| | |
|---|---|
| tcgaccggtg agaagaacag catcgggaca agggaaggaa gaacaaagac aaagaaaaca | 60 |
| aaagaaagca attgaaaaca aaacaaaaca atttcattc cttctcttat cattcctttt | 120 |
| cttttctttt ctctcattca acgcactcca tcgtatccgt attcctctta ttttttctct | 180 |
| ttctctatat ccattcttt ctctctaggt gtgtcctctc tctctcttca atttctctac | 240 |
| tccgcattcc aacgcatcct tcccccaacc tcccatttcc tccttacggc ccgatagcga | 300 |
| tcgtcttttcc ctcgctatca ctcgctaccg gcccctcctc tgcaccgtaa cctcctacgt | 360 |
| atttaccata tcataaagtt ttttccgacg cttatcgctg accccctgtc gccctcctat | 420 |
| tggcttccgg attatcttct tgtccataag gtgatccatg cttcctgaag attcccgaaa | 480 |
| tgtgtccact ttggcgggga atcattccat ccacttcttt ctctctcgct ttcctcattc | 540 |
| ggcgctcccc ttccgcgtct cattggtctt ccgctccgtt tttgctttgc cgatgttact | 600 |
| tggggagagg tgcgataatc ctttcgcaaa aactcggttt gacgcctccc atggtataaa | 660 |
| tagtgggtgg tggacaggtg ccttcgcttt tctttaagca agagaatccc attgtcttga | 720 |
| ctatcacgaa ttcacataca ttatgaagat caccgctgtc attgcccttt tattctcact | 780 |
| tgctgctgcc tcacctattc cagttgccga tcctggtgtg gtttcagtta gcaagtcata | 840 |
| tgctgatttc cttcgtgttt accaaagttg gaacactttt gctaatcctg atagacccaa | 900 |

```
ccttaagaag agaaatgata cacctgcaag tggatatcaa gttgaaaaag tcgtaatttt    960
gtcacgtcac ggtgttaggg cccctacaaa aatgactcaa accatgcgtg atgtcactcc   1020
taatacatgg ccagaatggc ccgttaaatt aggatatatt acaccaagag gtgaacactt   1080
gatatcactt atgggcggtt tttaccgtca aaaattccag caacaaggaa tcctttctca   1140
gggctcctgt cctactccta actccatata tgtctgggct gacgtcgatc agcgtacttt   1200
aaaaactggt gaagcattcc ttgctggttt ggcaccacaa tgtggcttga caattcatca   1260
ccaacaaaat cttgagaaag ctgatcctct ttttcatccc gttaaagctg aacctgctc    1320
tatggataaa actcaagttc aacaagctgt tgagaaggag gcacaaactc ctatagataa   1380
tttgaatcaa cattacatcc ccttttttagc tttaatgaat acaacattaa attttagtac   1440
ttctgcctgg tgccaaaaac actctgctga taaatcctgt gacctaggtt tatccatgcc   1500
ttctaaattg tccataaaag ataatggtaa caaggtcgca ttggatggag ctattggtct   1560
atcctctact ttggccgaga ttttcttct tgaatatgct caaggcatgc ctcaagctgc    1620
ttggggtaac atccactcag agcaagagtg ggcttccttg ctaaagttgc ataatgttca   1680
attcgatttg atggcccgaa caccttatat tgctcgacat aacggtactc ctttattgca   1740
agctatatca aatgcccctta atcccaacgc cactgaatca aaacttccag atatttcacc   1800
tgataacaaa atattgttca ttgcaggtca tgacacaaat attgctaata tagccggcat   1860
gttaaatatg cgttggacat taccaggtca accagataat actcctccag gtggtgccct   1920
agtatttgaa cgtcttgctg ataaaagtgg aaaacaatat gtttctgtat ctatggttta   1980
tcaaacacta gaacaacttc gatcacagac tccccttttct ctaaatcagc ctgccggatc   2040
tgttcaactt aaaattccag gttgcaatga tcaaacagcc gagggttact gtcctctttc   2100
cactttttaca agagttgttt cccaatctgt tgaacctgga tgccaacttc aataatgagg   2160
atccaagtaa gggaatgaga atgtgatcca cttttaattc ctaatgaata catgcctata   2220
gttcttttct tttgttcttt atgtcgtttt tcgatggtac ggccgttgtc aatctcagtt   2280
tgtgtgcttg gttgcagctt ggtttcaaat ctgttcatct catgaatctt ttaccatttc   2340
accacacgtt tataccattc tctcatagaa tcttcatcaa accatctcgg ggttagagtg   2400
gaaagaaagt cttgttcttt tatttccttt tttccatctt caaggctttt ctttttcttcc   2460
tcctcctcgt tcatcttgag gtttgacgtg tctgtttaga attttgagct gttgcagcat   2520
cttattttt gttttgcgaa aacgaagcgc tttactctct tcatcagttg gacgattgta    2580
cctttgaaaa ccaactactt ttgcatgttt tgtatagaaa tcaatgatat tagaatccca   2640
tcctttaatt tctttcaaag tagttgagct atagttaagt gtaagggccc tactgcgaaa   2700
gcatttgcca aggatgtttt cattaatcaa gaacgaaagt tagggatcg aagacgatca    2760
gataccgtcg tagtcttaac cataaactat gccgactagg gatcgggcaa tgtttcattt   2820
atcgacttgc tcggcacctt acgagaaatc aaagtctttg ggttccgggg ggagtatggt   2880
cgcaaggctg aaacttaaag gaattgacgg aagggcacca caatggagtg gagcctgcgg   2940
cttaatttga ctcaacacgg ggaaactcac caggtccaga catagtaagg attgacagat   3000
tgagagctct ttcttgattc tatgggtggt ggtgcatggc cgttcttagt tggtggagtg   3060
atttgtctgc ttaattgcga taacgaacga gaccttaacc tgctaaatag ctggatcagc   3120
cattttggct gatcattagc ttcttagagg gactattggc ataaagccaa tggaagtttg   3180
aggcaataac aggtctgtga tgcccttaga tgttctgggc cgcacgcgcg ctacactgac   3240
ggagccaacg agttgaaaaa aatctttga ttttttatcc ttggccggaa ggtctgggta    3300
```

```
atcttgttaa actccgtcgt gctggggata gagcattgca attattgcgg ccgctcctca    3360
attcgatgtt gcagatttta caagttttta aaatgtattt cattattact ttttatatgc    3420
ctaataaaaa agccatagtt taatctatag ataactttt ttccagtgca ctaacggacg     3480
ttacattccc atacaaaact gcgtagttaa agctaaggaa aagttaatat catgttaatt    3540
aaatacgcta tttacaataa gacattgaac tcatttatat cgttgaatat gaataaccaa    3600
tttcagcgaa tttttaacaa acatcgttca cctcgtttaa ggatatcttg tgtatggggt    3660
gttgacttgc tttatcgaat aattaccgta cctgtaattg gcttgctgga tatagcggta    3720
gtctaatatc tagcaaaaat cttttgggtg aaaaggcttg caatttcacg acaccgaact    3780
atttgtcatt ttttaataag gaagttttcc ataaattcct gtaattctcg gttgatctaa    3840
ttgaaaagag tagttttgca tcacgatgag gagggctttt gtagaaagaa atacgaacga    3900
aacgaaaatc agcgttgcca tcgctttgga caaagctccc ttacctgaag agtcgaattt    3960
tattgatgaa cttataactt ccaagcatgc aaaccaaaag ggagaacaag taatccaagt    4020
agacacggga attggattct tggatcacat gtatcatgca ctggctaaac atgcaggctg    4080
gagcttacga ctttactcaa gaggtgattt aatcatcgat gatcatcaca ctgcagaaga    4140
tactgctatt gcacttggta ttgcattcaa gcaggctatg ggtaactttg ccggcgttaa    4200
aagatttgga catgcttatt gtccacttga cgaagctctt tctagaagcg tagttgactt    4260
gtcgggacgg ccctatgctg ttatcgattt gggattaaag cgtgaaaagg ttggggaatt    4320
gtcctgtgaa atgatccctc acttactata ttccttttcg gtagcagctg gaattacttt    4380
gcatgttacc tgcttatatg gtagtaatga ccatcatcgt gctgaaagcg cttttaaatc    4440
tctggctgtt gccatgcgcg cggctactag tcttactgga agttctgaag tcccaagcac    4500
gaagggagtg ttgtaaagat gaattggatt atgtcaggaa aagaacgaca attttgcatc    4560
caaattgtct aaattttaga gttgcttgaa aacaatagaa ccttacttgc tttataatta    4620
cgttaattag aagcgttatc tcgtgaagga atatagtacg tagccgtata aattgaattg    4680
aatgttcagc ttatagaata gagacacttt gctgttcaat gcgtcgtcac ttaccatact    4740
cactttatta tacgactta agtataaact ccgcggttat ggtaaaatta atgatgcaca     4800
aacgtccgat tccatatggg tacactacaa ttaaatactt ttaagctgat cccccacaca    4860
ccatagcttc aaaatgtttc tactcctttt ttactcttcc agattttctc ggactccgcg    4920
catcgccgta ccacttcaaa acacccaagc acagcatact aaattttccc tctttcttcc    4980
tctagggtgt cgttaattac ccgtactaaa ggtttggaaa agaaaaaga gaccgcctcg     5040
tttctttttc ttcgtcgaaa aaggcaataa aaattttat cacgtttctt tttcttgaaa     5100
ttttttttt tagttttttt ctctttcagt gacctccatt gatatttaag ttaataaacg    5160
gtcttcaatt tctcaagttt cagtttcatt tttcttgttc tattacaact tttttactt    5220
cttgttcatt agaagaaag catagcaatc taatctaagg gcggtgttga caattaatca    5280
tcggcatagt atatcggcat agtataatac gacaaggtga ggaactaaac catggccaag    5340
ttgaccagtg ccgttccggt gctcaccgcg cgcgacgtcg ccggagcggt cgagttctgg    5400
accgaccggc tcgggttctc ccgggacttc gtggaggacg acttcgccgg tgtggtccgg    5460
gacgacgtga ccctgttcat cagcgcggtc caggaccagg tggtgccgga caacaccctg    5520
gcctgggtgt gggtgcgcgg cctggacgag ctgtacgccg agtggtcgga ggtcgtgtcc    5580
acgaacttcc gggacgcctc cgggccggcc atgaccgaga tcggcgagca gccgtggggg    5640
cgggagttcg ccctgcgcga cccggccggc aactgcgtgc acttcgtggc cgaggagcag    5700
```

```
gactgacacg tccgacggcg gcccacgggt cccaggcctc ggagatccgt ccccctttc      5760
ctttgtcgat atcatgtaat tagttatgtc acgcttacat tcacgcctc cccccacatc      5820
cgctctaacc gaaaggaag gagttagaca acctgaagtc taggtccta tttattttt        5880
tatagttatg ttagtattaa gaacgttatt tatatttcaa attttctttt tttttctgta     5940
cagacgcgag cttcccagta aatgtgccat ctcgtaggca gaaaacggtt ccccgtagg     6000
gtctctctct tggcctcctt tctaggtcgg gctgattgct cttgaagctc tctagggggg    6060
ctcacaccat aggcagataa cgttccccac cggctcgcct cgtaagcgca caaggactgc    6120
tcccaaagat cctaggcggg attttgccga tttcggccta aaggaaccgg aacacgtaga    6180
aagccagtcc gcagaaacgg tgctgacccc ggatgaatgt cagctactgg gctatctgga    6240
caagggaaaa cgcaagcgca aagagaaagc aggtagcttg cagtgggctt acatggcgat    6300
agctagactg ggcggtttta tggacagcaa gcgaaccgga attgccagct ggggcgccct    6360
ctggtaaggt tgggaagccc tgcaaagtaa actggatggc tttcttgccg ccaaggatct    6420
gatggcgcag gggatcaaga tctgatcaag agacaggatg aggatcgttt cgcatgattg    6480
aacaagatgg attgcacgca ggttctccgg ccgcttgggt ggagaggcta ttcggctatg    6540
actgggcaca acagacaatc ggctgctctg atgccgccgt gttccggctg tcagcgcagg    6600
ggcgcccggt tctttttgtc aagaccgacc tgtccggtgc cctgaatgaa ctgcaggacg    6660
aggcagcgcg gctatcgtgg ctggccacga cgggcgttcc ttgcgcagct gtgctcgacg    6720
ttgtcactga agcgggaagg gactggctgc tattgggcga agtgccgggg caggatctcc    6780
tgtcatctcg ccttgctcct gccgagaaag tatccatcat ggctgatgca atgcggcggc    6840
tgcatacgct tgatccggct acctgcccat tcgaccacca agcgaaacat cgcatcgagc    6900
gagcacgtac tcggatggaa gccggtcttg tcgatcagga tgatctggac gaagagcatc    6960
aggggctcgc gccagccgaa ctgttcgcca ggctcaaggc gcgcatgccc gacggcgagg    7020
atctcgtcgt gatccatggc gatgcctgct tgccgaatat catggtggaa aatggccgct    7080
tttctggatt caacgactgt ggccggctgg gtgtggcgga ccgctatcag gacatagcgt    7140
tggatacccg tgatattgct gaagagcttg gcggcgaatg ggctgaccgc ttcctcgtgc    7200
tttacggtat cgccgctccc gattcgcagc gcatcgcctt ctatcgcctt cttgacgagt    7260
tcttctgaat tgaaaaaggt accaagttta ctcatatata ctttagattg atttaaaact    7320
tcattttta tttaaaagga tctaggtgaa gatccttttt gataatctca tgaccaaaat    7380
cccttaacgt gagttttcgt tccactgagc gtcagacccc gtagaaaaga tcaaaggatc    7440
ttcttgagat cctttttttc tgcgcgtaat ctgctgcttg caaacaaaaa aaccaccgct    7500
accagcggtg gtttgtttgc cggatcaaga gctaccaact cttttccga aggtaactgg    7560
cttcagcaga gcgcagatac caaatactgt ccttctagtg tagccgtagt taggccacca    7620
cttcaagaac tctgtagcac cgcctacata cctcgctctg ctaatcctgt taccagtggc    7680
tgctgccagt ggcgataagt cgtgtcttac cgggttggac tcaagacgat agttaccgga    7740
taaggcgcag cggtcgggct gaacgggggg ttcgtgcaca cagcccagct tggagcgaac    7800
gacctacacc gaactgagat acctacagcg tgagcattga gaaagcgcca cgcttcccga    7860
agggagaaag gcggacaggt atccggtaag cggcagggtc ggaacaggag agcgcacgag    7920
ggagcttcca gggggaaacg cctggtatct ttatagtcct gtcgggtttc gccacctctg    7980
acttgagcgt cgatttttgt gatgctcgtc aggggggcgg agcctatgga aaaacgccag    8040
caacgcggcc tttttacggt tcctggcctt ttgctggcct tttgctcaca tgttctttcc    8100
```

```
tgcgttatcc cctgattctg tggataaccg tattaccgcc tttgagtgag ctgataccgc    8160
tcgccgcagc cgaacgaccg agcgcagcga g                                   8191

<210> SEQ ID NO 12
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 12
gaattcaaaa caaaatgtgt gcaacctcct cccagtttac tcagattacc gagcataatt      60
ctcgacgatc tgctaactac cagccgaacc tttggaactt tgagtttctc cagtctctcg     120
aaaatgacct gaaggtggaa aagctcgagg agaaggcgac caaactcgag gaggaggtgc     180
gatgtatgat caacagagtt gacacccaac ccctgtcttt gctggagctg atcgacgatg     240
tgcagcggtt gggttttgact ataaattcg agaaggacat tatcaaggca ctggagaaca     300
ttgtgctcct cgacgagaac aagaagaaca agtctgatct tcacgctacc gctctctctt     360
tccgacttct tcgacaacac ggcttcgagg tgtcgcagga cgtcttcgag agatttaagg     420
acaaggaggg aggatttagc ggcgagctga agggagacgt tcagggtctt ctctccttgt     480
acgaggcgtc ctacctggga ttcgagggag agaacctcct ggaggaagct cgtacatttt     540
ccatcactca ccttaagaat aaccttaagg agggaattaa caccaaggtg gccgagcagg     600
tttctcacgc cctggagctc cctaccacc aacggctcca tagactggag gctcgttggt     660
tcctggacaa atatgagcca aaggagcctc atcatcagtt gctgttggag ttggccaagc     720
tggacttcaa tatggttcag acgctgcacc aaaaggagtt gcaggacctg tctcgatggt     780
ggaccgagat gggattggcc tcgaagctgg atttttgtccg tgaccgactt atggaggtct     840
attttttggc ccttggaatg gcgcctgacc cccagttcgg agagtgccgg aaggcggtga     900
cgaagatgtt cggtcttgtg actatcatcg acgacgtcta cgatgtctac ggcacactcg     960
acgagttgca gctgttcact gacgccgtcg agcgatggga tgtgaacgcc attaatactc    1020
tccctgacta tgaagctgtg tgcttcctgg ctctgtacaa cactgtcaac gatacctcgt    1080
actctatcct caaggagaag ggacacaaca atctctccta cttgaccaaa tcctggcgag    1140
aactgtgcaa ggcttttctg caggaggcta atggtccaa taacaagatc attcctgctt    1200
tttctaaata cctggaaaat gcctcggtgt cgagctctgg cgtcgccctt ctggccccttt    1260 cctacttctc cgtctgccag cagcaggagg atatttccga tcatgctctt agatcgctga    1320
ccgattttca cggcctcgtg cgatcttcct gcgtgatttt tcggttgtgt aatgaccttg    1380
cgacctctgc tgctgagctg gaacgaggcg agactacaaa ttccattatt tcttacatgc    1440
acgaaaacga tggaacatct gaagaacagg ctagagagga actgcgaaag ttgatcgacg    1500
ccgagtggaa gaagatgaac agagagcggg tgtccgactc taccctgctt cccaaggcct    1560
tcatggagat cgccgtgaac atggctcgag tttcccattg tacttaccag tacggtgacg    1620
gcctgggtcg tccggactac gctacagaga accgaatcaa gctgctgctc atcgacccct    1680
tccctatcaa ccaattgatg tacgtgtaat agtctagagg atcc                     1724

<210> SEQ ID NO 13
<211> LENGTH: 1701
<212> TYPE: DNA
<213> ORGANISM: Artificial Sequence
<220> FEATURE:
<223> OTHER INFORMATION: Synthetic Construct
```

<400> SEQUENCE: 13

```
gaattcaaca aaatgtgct ctgtttccac tgagaacgtg tcctttactg agactgagac      60
tgaagcacgt agaagcgcca actacgaacc caactcctgg gattatgact ttctgctgtc    120
ttctgacacc gacgagtcga tcgaggttta aaggataag gccaagaaac ttgaggccga     180
ggtcagacga gagattaaca acgagaaggc cgagttcctg acccttcttg agctgatcga   240
caacgttcaa cgacttggtc ttggttaccg tttcgaatcc gatatccgac gtgcattgga   300
tcgatttgtc tcgtccggag gtttcgatgg tgtgactaag acgtcgctgc acgccacagc   360
tctttccttc agactgttgc ggcagcatgg atttgaggtt tcccaggaag ccttttctgg   420
tttcaaggat cagaacggaa acttttttgga gaatctcaag gaggacacca aggccatcct   480
gtcgttgtat gaggcctcgt tcctggctct tgagggcgag aatattctgg atgaggctcg    540
ggttttcgct atttcgcacc tgaaggagtt gtcggaggaa aagatcggaa aggaactggc   600
cgagcaggtc aaccatgcac ttgaacttcc cctgcatcga cgtacccagc gactggaggc   660
cgtgtggagc atcgaggcgt acagaaaaaa ggaggatgct aatcaggttc tgctcgaact   720
cgctatcctc gactataaca tgattcgag cgtgtaccag cgtgacttgc gagagacaag    780
ccggtggtgg cgacgggtgg gactggccac gaagctccac tttgctaaag atcgattgat   840
tgagtcgttc tactgggcag tgggtgtggc ctttgagcct cagtactccg actgccgaaa    900
ctccgttgca aagatgtttt cttttgtcac tatcatcgac gacatctacg atgtttacgg   960
cactctcgat gaactcgaac tcttcacgga cgctgtcgag cgatgggatg tgaatgccat   1020
taatgatctg ccagattata tgaagttgtg tttcttggcg ctctacaaca caattaatga   1080
aattgcctac gacaacctca aggacaaggg agagaacatt ctgccctacc ttactaaagc   1140
ctgggccgac ctgtgtaacg cctttttgca ggaagccaag tggctctata acaaatctac   1200
tcctacattt gatgactact tcggcaacgc ttggaagtct tccagcggcc ctctccagtt   1260
gatcttcgct tactttgcag tggtccagaa catcaagaaa gaggagattg agaacctcca   1320
gaagtatcac gacatcatct cccgaccttc gcacatcttt cgactgtgca atgaccttgc   1380
ctccgcatcc gctgagattg cccgaggaga aacagcaat tctgtgtcgt gttacatgcg    1440
tacaaagggc atctccgagg agctggctac cgagtctgtg atgaacctga tcgatgaaac   1500
ctgtaagaag atgaacaaag agaaactggg cggttctctg ttcgccaaac catttgttga   1560
aaccgcgatc aatctggctc gtcagtctca ttgtacttac cataacggtg acgcgcacac   1620
ttcgccggac gaattgaccc gtaagcgtgt gctttcggtg attaccgagc cgatcctgcc   1680
gttcgaaaga taataggatc c                                             1701
```

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14

```
gatcaagctt aaccggaatt gccagctg                                         28
```

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

```
<400> SEQUENCE: 15
gatccgatcg tcagaagaac tcgtcaagaa ggc                                   33

<210> SEQ ID NO 16
<211> LENGTH: 38
<212> TYPE: DNA
<213> ORGANISM: Artificial Sequence
<220> FEATURE:
<223> OTHER INFORMATION: Synthetic Construct

<400> SEQUENCE: 16
catcaatgca tcgcccttag gaggtaaaaa aaaatgac                              38

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
ccttctgcag gacgcgttgt tatagc                                           26

<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
gatcatgcat tcgcccttag gaggtaaaaa aacatgagtt ttgatattgc caaatacccg      60

<210> SEQ ID NO 19
<211> LENGTH: 31
<212> TYPE: DNA
<213> ORGANISM: Artificial Sequence
<220> FEATURE:
<223> OTHER INFORMATION: Synthetic Construct

<400> SEQUENCE: 19
catgctgcag ttatgccagc caggccttga t                                     31

<210> SEQ ID NO 20
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 20
gctggtacca tatgggaatt cgaagctttc tagaacaaaa actcatctca gaagaggatc      60
tgaatagcgc cgtcgaccat catcatcatc atcattgagt ttaaacggtc tccagcttgg     120
ctgttttggc ggatgagaga agattttcag cctgatacag attaaatcag aacgcagaag     180
cggtctgata aaacagaatt tgcctggcgg cagtagcgcg gtggtcccac ctgaccccat     240
gccgaactca gaagtgaaac gccgtagcgc cgatggtagt gtggggtctc cccatgcgag     300
agtagggaac tgccaggcat caaataaaac gaaaggctca gtcgaaagac tgggcctttc     360
gttttatctg ttgtttgtcg gtgaacgctc tcctgagtag acaaatccg  ccgggagcgg     420 atttgaacgt tgcgaagcaa cggcccggag ggtggcgggc aggacgcccg ccataaactg     480
ccaggcatca aattaagcag aaggccatcc tgacggatgg cctttttgcg tttctacaaa     540
```

```
ctcttttgt ttatttttct aaatacattc aaatatgtat ccgcttaacc ggaattgcca    600
gctggggcgc cctctggtaa ggttgggaag ccctgcaaag taaactggat ggctttctcg    660
ccgccaagga tctgatggcg caggggatca agctctgatc aagagacagg atgaggatcg    720
tttcgcatga ttgaacaaga tggattgcac gcaggttctc cggccgcttg ggtggagagg    780
ctattcggct atgactgggc acaacagaca atcggctgct ctgatgccgc cgtgttccgg    840
ctgtcagcgc aggggcgccc ggttcttttt gtcaagaccg acctgtccgg tgccctgaat    900
gaactgcaag acgaggcagc gcggctatcg tggctggcca cgacgggcgt tccttgcgca    960
gctgtgctcg acgttgtcac tgaagcggga agggactggc tgctattggg cgaagtgccg   1020
gggcaggatc tcctgtcatc tcaccttgct cctgccgaga agtatccat catggctgat    1080 gcaatgcggc ggctgcatac gcttgatccg gctacctgcc cattcgacca ccaagcgaaa   1140
catcgcatcg agcgagcacg tactcggatg aagccggtc ttgtcgatca ggatgatctg    1200
gacgaagagc atcaggggct cgcgccagcc gaactgttcg ccaggctcaa ggcgagcatg   1260
cccgacggcg aggatctcgt cgtgacccat ggcgatgcct gcttgccgaa tatcatggtg   1320
gaaaatggcc gcttttctgg attcatcgac tgtggccggc tgggtgtggc ggaccgctat   1380
caggacatag cgttggctac ccgtgatatt gctgaagagc ttggcggcga atgggctgac   1440
cgcttcctcg tgctttacgg tatcgccgct cccgattcgc agcgcatcgc cttctatcgc   1500
cttcttgacg agttcttctg acatgaccaa aatcccttaa cgtgagtttt cgttccactg   1560
agcgtcagac cccgtagaaa agatcaaagg atcttcttga gatccttttt ttctgcgcgt   1620
aatctgctgc ttgcaaacaa aaaaaccacc gctaccagcg gtggtttgtt tgccggatca   1680
agagctacca actctttttc cgaaggtaac tggcttcagc agagcgcaga taccaaatac   1740
tgtccttcta gtgtagccgt agttaggcca ccacttcaag aactctgtag caccgcctac   1800
atacctcgct ctgctaatcc tgttaccagt ggctgctgcc agtggcgata agtcgtgtct   1860
taccgggttg gactcaagac gatagttacc ggataaggcg cagcggtcgg gctgaacggg   1920
gggttcgtgc acacagccca gcttggagcg aacgacctac accgaactga gatacctaca   1980
gcgtgagcta tgagaaagcg ccacgcttcc cgaagggaga aaggcggaca ggtatccggt   2040
aagcggcagg gtcggaacag gagagcgcac gagggagctt ccaggggga acgcctggta   2100 tctttatagt cctgtcgggt ttcgccacct ctgacttgag cgtcgatttt tgtgatgctc   2160
gtcagggggg cggagcctat ggaaaaacgc cagcaacgcg gcctttttac ggttcctggc   2220
cttttgctgg ccttttgctc acatgttctt cctgcgtta tccctgatt ctgtggataa    2280 ccgtattacc gcctttgagt gagctgatac cgctcgccgc agccgaacga ccgagcgcag   2340
cgagtcagtg agcgaggaag cggaagagcg cctgatgcgg tattttctcc ttacgcatct   2400
gtgcggtatt tcacaccgca tatggtgcac tctcagtaca atctgctctg atgccgcata   2460
gttaagccag tatacactcc gctatcgcta cgtgactggg tcatggctgc gccccgacac   2520
ccgccaacac ccgctgacgc gccctgacgg gcttgtctgc tcccggcatc cgcttacaga   2580
caagctgtga ccgtctccgg gagctgcatg tgtcagaggt tttcaccgtc atcaccgaaa   2640
cgcgcgaggc agcagatcaa ttcgcgcgcg aaggcgaagc ggcatgcatt tacgttgaca   2700
ccatcgaatg gtgcaaaacc tttcgcggta tggcatgata gcgcccggaa gagagtcaat   2760
tcagggtggt gaatgtgaaa ccagtaacgt tatacgatgt cgcagagtat gccggtgtct   2820
cttatcagac cgtttcccgc gtggtgaacc aggccagcca cgtttctgcg aaaacgcggg   2880
aaaaagtgga agcggcgatg gcggagctga attacattcc caaccgcgtg gcacaacaac   2940
```

```
tggcgggcaa acagtcgttg ctgattggcg ttgccacctc cagtctggcc ctgcacgcgc   3000
cgtcgcaaat tgtcgcggcg attaaatctc gcgccgatca actgggtgcc agcgtggtgg   3060
tgtcgatggt agaacgaagc ggcgtcgaag cctgtaaagc ggcggtgcac aatcttctcg   3120
cgcaacgcgt cagtgggctg atcattaact atccgctgga tgaccaggat gccattgctg   3180
tggaagctgc ctgcactaat gttccggcgt tatttcttga tgtctctgac cagacaccca   3240
tcaacagtat tattttctcc catgaagacg gtacgcgact gggcgtggag catctggtcg   3300
cattgggtca ccagcaaatc gcgctgttag cgggcccatt aagttctgtc tcggcgcgtc   3360
tgcgtctggc tggctggcat aaatatctca ctcgcaatca aattcagccg atagcggaac   3420
gggaaggcga ctggagtgcc atgtccggtt ttcaacaaac catgcaaatg ctgaatgagg   3480
gcatcgttcc cactgcgatg ctggttgcca acgatcagat ggcgctgggc gcaatgcgcg   3540
ccattaccga gtccgggctg cgcgttggtg cggatatctc ggtagtggga tacgacgata   3600
ccgaagacag ctcatgttat atcccgccgt caaccaccat caaacaggat tttcgcctgc   3660
tggggcaaac cagcgtggac cgcttgctgc aactctctca gggccaggcg gtgaagggca   3720
atcagctgtt gcccgtctca ctggtgaaaa gaaaaaccac cctggcgccc aatacgcaaa   3780
ccgcctctcc ccgcgcgttg gccgattcat taatgcagct ggcacgacag gtttcccgac   3840
tggaaagcgg gcagtgagcg caacgcaatt aatgtgagtt agcgcgaatt gatctggttt   3900
gacagcttat catcgactgc acggtgcacc aatgcttctg gcgtcaggca gccatcggaa   3960
gctgtggtat ggctgtgcag gtcgtaaatc actgcataat tcgtgtcgct caaggcgcac   4020
tcccgttctg gataatgttt tttgcgccga catcataacg gttctggcaa atattctgaa   4080
atgagctgtt gacaattaat catccggctc gtataatgtg tggaattgtg agcggataac   4140
aatttcacac aggaaacagc gccgctgaga aaaagcgaag cggcactgct ctttaacaat   4200
ttatcagaca atctgtgtgg gcactcgacc ggaattatcg attaacttta ttattaaaaa   4260
ttaaagaggt atatattaat gtatcgatta ataaggagg aataaaccat gtgtgcgacc   4320
tcttctcaat ttactcagat taccgagcat aattcccgtc gttccgcaaa ctatcagcca   4380
aacctgtgga atttcgaatt cctgcaatcc ctggagaacg acctgaaagt ggaaaagctg   4440
gaggagaaag cgaccaaact ggaggaagaa gttcgctgca tgatcaaccg tgtagacacc   4500
cagccgctgt ccctgctgga gctgatcgac gatgtgcagc gcctgggtct gacctacaaa   4560
tttgaaaaag acatcattaa agccctggaa aacatcgtac tgctggacga aaacaaaaag   4620
aacaaatctg acctgcacgc aaccgctctg tcttttccgtc tgctgcgtca gcacggtttc   4680
gaggtttctc aggatgtttt tgagcgtttc aaggataaag aaggtggttt cagcggtgaa   4740
ctgaaaggtg acgtccaagg cctgctgagc ctgtatgaag cgtcttacct gggtttcgag   4800
ggtgagaacc tgctggagga ggcgcgtacc ttttccatca cccacctgaa gaacaacctg   4860
aaagaaggca ttaataccaa ggttgcagaa caagtgagcc acgccctgga actgccatat   4920
caccagcgtc tgcaccgtct ggaggcacgt tggttcctgg ataaatacga accgaaagaa   4980
ccgcatcacc agctgctgct ggagctggcg aagctggatt ttaacatggt acagaccctg   5040
caccagaaag agctgcaaga tctgtcccgc tggtggaccg agatgggcct ggctagcaaa   5100
ctggattttg tacgcgaccg cctgatggaa gtttatttct gggcactggg tatgcgccaa   5160
gacccgcagt ttggtgaatg tcgcaaagct gttactaaaa tgtttggtct ggtgacgatc   5220
atcgatgacg tgtatgacgt ttatggcact ctggacgaac tgcaactgtt caccgatgct   5280
gtagagcgct gggacgttaa cgctattaac accctgccgg actatatgaa actgtgtttc   5340
```

```
ctggcactgt acaacaccgt taacgacacg tcctattcta ttctgaaaga gaaaggtcat    5400
aacaacctgt cctatctgac gaaaagctgg cgtgaactgt gcaaagcctt tctgcaagag    5460
gcgaaatggt ccaacaacaa aattatcccg gctttctcca agtacctgga aaacgccagc    5520
gtttcctcct ccggtgtagc gctgctggcg ccgtcttact tttccgtatg ccagcagcag    5580
gaagacatct ccgaccacgc gctgcgttcc ctgaccgact ccatggtct ggtgcgttct    5640 agctgcgtta tcttccgcct gtgcaacgat ctggccaccc tgcggcgga gctgaacgt     5700 ggcgagacta ccaattctat cattagctac atgcacgaaa acgatggtac cagcgaggaa    5760
caggcccgcg aagaactgcg taaactgatc gacgccgaat ggaaaaagat gaatcgtgaa    5820
cgcgttagcg actccaccct gctgcctaaa gcgttcatgg aaatcgcagt taacatggca    5880
cgtgtttccc actgcaccta ccagtatggc gatggtctgg gtcgcccaga ctacgcgact    5940
gaaaaccgca tcaaactgct gctgattgac cctttcccga ttaaccagct gatgtatgtc    6000
taactgcatc gcccttagga ggtaaaaaaa aatgactgcc gacaacaata gtatgcccca    6060
tggtgcagta tctagttacg ccaaattagt gcaaaaccaa acacctgaag acattttgga    6120
agagtttcct gaaattattc cattacaaca aagacctaat acccgatcta gtgagacgtc    6180
aaatgacgaa agcggagaaa catgttttc tggtcatgat gaggagcaaa ttaagttaat     6240
gaatgaaaat tgtattgttt tggattggga cgataatgct attggtgccg gtaccaagaa    6300
agtttgtcat ttaatggaaa atattgaaaa gggtttacta catcgtgcat tctccgtctt    6360
tattttcaat gaacaaggtg aattacttt acaacaaaga gccactgaaa aataactttt     6420
ccctgatctt tggactaaca catgctgctc tcatccacta tgtattgatg acgaattagg    6480
tttgaagggt aagctagacg ataagattaa gggcgctatt actgcggcgg tgagaaaact    6540
agatcatgaa ttaggtattc cagaagatga aactaagaca aggggtaagt ttcactttt     6600 aaacagaatc cattacatgg caccaagcaa tgaaccatgg ggtgaacatg aaattgatta    6660
catcctattt tataagatca acgctaaaga aaacttgact gtcaacccaa acgtcaatga    6720
agttagagac ttcaaatggg tttcaccaaa tgatttgaaa actatgtttg ctgacccaag    6780
ttacaagttt acgccttggt ttaagattat ttgcgagaat tacttattca actggtggga    6840
gcaattagat gacctttctg aagtggaaaa tgacaggcaa attcatgaaa tgctataaca    6900
acgcgtcctg cattcgccct taggaggtaa aaaacatga gttttgatat tgccaaatac    6960
ccgaccctgg cactggtcga ctccacccag gagttacgac tgttgccgaa agagagttta    7020
ccgaaactct gcgacgaact gcgccgctat ttactcgaca gcgtgagccg ttccagcggg    7080
cacttcgcct ccgggctggg cacggtcgaa ctgaccgtgg cgctgcacta tgtctacaac    7140
accccgtttg accaattgat ttgggatgtg gggcatcagg cttatccgca taaaattttg    7200
accggacgcc gcgacaaaat cggcaccatc cgtcagaaag gcggtctgca cccgttcccg    7260
tggcgcggca aaagcgaata tgacgtatta agcgtcgggc attcatcaac ctccatcagt    7320
gccggaattg gtattgcggt tgctgccgaa aaagaaggca aaatcgccg caccgtctgt    7380 gtcattggcg atggcgcgat taccgcaggc atggcgtttg aagcgatgaa tcacgcgggc    7440
gatatccgtc ctgatatgct ggtgattctc aacgacaatg aaatgtcgat ttccgaaaat    7500
gtcggcgcgc tcaacaacca tctggcacag ctgctttccg gtaagcttta ctcttcactg    7560
cgcgaaggcg ggaaaaaagt tttctctggc gtgccgccaa ttaaagagct gctcaaacgc    7620
accgaagaac atattaaagg catggtagtg cctggcacgt tgtttgaaga gctgggcttt    7680
aactacatcg gcccggtgga cggtcacgat gtgctggggc ttatcaccac gctaaagaac    7740
```

```
atgcgcgacc tgaaaggccc gcagttcctg catatcatga ccaaaaaagg tcgtggttat    7800
gaaccggcag aaaagaccc gatcactttc cacgccgtgc ctaaatttga tccctccagc    7860
ggttgtttgc cgaaaagtag cggcggtttg ccgagctatt caaaaatctt tggcgactgg    7920
ttgtgcgaaa cggcagcgaa agacaacaag ctgatggcga ttactccggc gatgcgtgaa    7980
ggttccggca tggtcgagtt ttcacgtaaa ttcccggatc gctacttcga cgtggcaatt    8040
gccgagcaac acgcggtgac cttttgctgcg ggtctggcga ttggtgggta caaacccatt    8100
gtcgcgattt actccacttt cctgcaacgc gcctatgatc aggtgctgca tgacgtggcg    8160
attcaaaagc ttccggtcct gttcgccatc gaccgcgcgg gcattgttgg tgctgacggt    8220
caaacccatc agggtgcttt tgatctctct tacctgcgct gcataccgga aatggtcatt    8280 atgacccga gcgatgaaaa cgaatgtcgc cagatgctct ataccggcta tcactataac    8340
gatggcccgt cagcggtgcg ctacccgcgt ggcaacgcgg tcggcgtgga actgacgccg    8400
ctggaaaaac taccaattgg caaaggcatt gtgaagcgtc gtggcgagaa actggcgatc    8460
cttaactttg gtacgctgat gccagaagcg gcgaaagtcg ccgaatcgct gaacgccacg    8520
ctggtcgata tgcgttttgt gaaaccgctt gatgaagcgt taattctgga atgggccgcc    8580
agccatgaag cgctggtcac cgtagaagaa acgccatta tgggcggcgc aggcagcggc    8640
gtgaacgaag tgctgatggc ccatcgtaaa ccagtacccg tgctgaacat ggcctgccg    8700 gacttcttta ttccgcaagg aactcaggaa gaaatgcgcg ccgaactcgg cctcgatgcc    8760
gctggtatgg aagccaaaat caaggcctgg ctggcataac tgca                   8804

<210> SEQ ID NO 21
<211> LENGTH: 41
<212> TYPE: DNA
<213> ORGANISM: Artificial Sequence
<220> FEATURE:
<223> OTHER INFORMATION: Synthetic Construct

<400> SEQUENCE: 21
aggaggtaaa aaaacatgtc attaccgttc ttaacttctg c                          41

<210> SEQ ID NO 22
<211> LENGTH: 52
<212> TYPE: DNA
<213> ORGANISM: Artificial Sequence
<220> FEATURE:
<223> OTHER INFORMATION: Synthetic Construct

<400> SEQUENCE: 22
atggctgcag gcctatcgca aattagctta tgaagtccat ggtaaattcg tg              52

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23
gaattcgccc ttctgcagct acc                                              23

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct
```

```
<400> SEQUENCE: 24
cgactggtgc acccttaagg aggaaaaaaa catgtcag                     38

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
gtgctggaat tcgcccttct gcagc                                   25

<210> SEQ ID NO 26
<211> LENGTH: 32
<212> TYPE: DNA
<213> ORGANISM: Artificial Sequence
<220> FEATURE:
<223> OTHER INFORMATION: Synthetic Construct

<400> SEQUENCE: 26
gtagatgcat gcagaattcg cccttaagga gg                           32

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
ccttctgcag gacgcgttgt tatagc                                  26

<210> SEQ ID NO 28
<211> LENGTH: 38
<212> TYPE: DNA
<213> ORGANISM: Artificial Sequence
<220> FEATURE:
<223> OTHER INFORMATION: Synthetic Construct

<400> SEQUENCE: 28
catcaatgca tcgcccttag gaggtaaaaa aaaatgac                     38

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
gtgtgatgga tatctgcaga attcg                                   25

<210> SEQ ID NO 30
<211> LENGTH: 36
<212> TYPE: DNA
<213> ORGANISM: Artificial Sequence
<220> FEATURE:
<223> OTHER INFORMATION: Synthetic Construct

<400> SEQUENCE: 30
catcaatgca tcgcccttag gaggtaaaaa aacatg                       36

<210> SEQ ID NO 31
<211> LENGTH: 60
<212> TYPE: DNA
```

```
<213> ORGANISM: Artificial Sequence
<220> FEATURE:
<223> OTHER INFORMATION: Synthetic Construct

<400> SEQUENCE: 31
gatcatgcat tcgcccttag gaggtaaaaa aacatgtgtg cgacctcttc tcaatttact        60

<210> SEQ ID NO 32
<211> LENGTH: 38
<212> TYPE: DNA
<213> ORGANISM: Artificial Sequence
<220> FEATURE:
<223> OTHER INFORMATION: Synthetic Construct

<400> SEQUENCE: 32
cggtcgacgg atccctgcag ttagacatac atcagctg                               38

<210> SEQ ID NO 33
<211> LENGTH: 10992
<212> TYPE: DNA
<213> ORGANISM: Artificial Sequence
<220> FEATURE:
<223> OTHER INFORMATION: Synthetic Construct

<400> SEQUENCE: 33
gtttgacagc ttatcatcga ctgcacggtg caccaatgct tctggcgtca ggcagccatc        60
ggaagctgtg gtatggctgt gcaggtcgta aatcactgca taattcgtgt cgctcaaggc       120
gcactcccgt tctggataat gttttttgcg ccgacatcat aacggttctg caaatattc        180 tgaaatgagc tgttgacaat taatcatccg gctcgtataa tgtgtggaat tgtgagcgga       240
taacaatttc acacaggaaa cagcgccgct gagaaaaagc gaagcggcac tgctctttaa       300
caatttatca gacaatctgt gtgggcactc gaccggaatt atcgattaac tttattatta       360
aaaattaaag aggtatatat taatgtatcg attaaataag gaggaataaa ccatggatcc       420
gagctcggat ccactagtaa cggccgccag tgtgctggaa ttcgcccta ggaggtaaaa       480 aaacatgtca ttaccgttct taacttctgc accgggaaag gttattattt tggtgaaca       540 ctctgctgtg tacaacaagc ctgccgtcgc tgctagtgtg tctgcgttga aacctacct       600 gctaataagc gagtcatctg caccagatac tattgaattg gacttcccgg acattagctt       660
taatcataag tggtccatca atgatttcaa tgccatcacc gaggatcaag taaactccca       720
aaaattggcc aaggctcaac aagccaccga tggcttgtct caggaactcg ttagtctttt       780
ggatccgttg ttagctcaac tatccgaatc cttccactac catgcagcgt tttgtttcct       840
gtatatgttt gtttgcctat gcccccatgc caagaatatt aagttttctt taaagtctac       900
tttacccatc ggtgctgggt tgggctcaag cgcctctatt tctgtatcac tggccttagc       960
tatggcctac ttgggggggt taataggatc taatgacttg gaaaagctgt cagaaaacga      1020
taagcatata gtgaatcaat gggccttcat aggtgaaaag tgtattcacg gtacccttc      1080 aggaatagat aacgctgtgg ccacttatgg taatgccctg ctatttgaaa aagactcaca      1140
taatggaaca ataaacacaa acaatttaa gttcttagat gatttcccag ccattccaat      1200
gatcctaacc tatactagaa ttccaaggtc tacaaaagat cttgttgctc gcgttcgtgt      1260
gttggtcacc gagaaatttc ctgaagttat gaagccaatt ctagatgcca tgggtgaatg      1320
tgccctacaa ggcttagaga tcatgactaa gttaagtaaa tgtaaaggca ccgatgacga      1380
ggctgtagaa actaataatg aactgtatga acaactattg gaattgataa gaataaatca      1440
tggactgctt gtctcaatcg gtgtttctca tcctggatta gaacttatta aaaatctgag      1500
```

```
cgatgatttg agaattggct ccacaaaact taccggtgct ggtggcggcg gttgctcttt    1560
gactttgtta cgaagagaca ttactcaaga gcaaattgac agcttcaaaa agaaattgca    1620
agatgatttt agttacgaga catttgaaac agacttgggt gggactggct gctgtttgtt    1680
aagcgcaaaa aatttgaata aagatcttaa aatcaaatcc ctagtattcc aattatttga    1740
aaataaaact accacaaagc aacaaattga cgatctatta ttgccaggaa acacgaattt    1800
accatggact tcataagcta atttgcgata ggcctgcacc cttaaggagg aaaaaaacat    1860
gtcagagttg agagccttca gtgccccagg gaaagcgtta ctagctggtg gatatttagt    1920
tttagataca aaatatgaag catttgtagt cggattatcg gcaagaatgc atgctgtagc    1980
ccatccttac ggttcattgc aagggtctga taagtttgaa gtgcgtgtga aaagtaaaca    2040
atttaaagat ggggagtggc tgtaccatat aagtcctaaa agtggcttca ttcctgtttc    2100
gataggcgga tctaagaacc cttttcattga aaaagttatc gctaacgtat ttagctactt    2160
taaacctaac atggacgact actgcaatag aaacttgttc gttattgata ttttctctga    2220
tgatgcctac cattctcagg aggatagcgt taccgaacat cgtggcaaca gaagattgag    2280
ttttcattcg cacagaattg aagaagttcc caaaacaggg ctgggctcct cggcaggttt    2340
agtcacagtt ttaactacag ctttggcctc cttttttgta tcggacctgg aaaataatgt    2400
agacaaatat agagaagtta ttcataattt agcacaagtt gctcattgtc aagctcaggg    2460
taaaattgga agcgggtttg atgtagcggc ggcagcatat ggatctatca gatatagaag    2520
attcccaccc gcattaatct ctaatttgcc agatattgga agtgctactt acggcagtaa    2580
actggcgcat ttggttgatg aagaagactg gaatattacg attaaaagta accatttacc    2640
ttcgggatta actttatgga tgggcgatat taagaatggt tcagaaacag taaaactggt    2700
ccagaaggta aaaaattggt atgattcgca tatgccagaa agcttgaaaa tatatacaga    2760
actcgatcat gcaaattcta gatttatgga tggactatct aaactagatc gcttacacga    2820
gactcatgac gattacagcg atcagatatt tgagtctctt gagaggaatg actgtacctg    2880
tcaaaagtat cctgaaatca cagaagttag agatgcagtt gccacaatta gacgttcctt    2940
tagaaaaata actaaagaat ctggtgccga tatcgaacct cccgtacaaa ctagcttatt    3000
ggatgattgc cagaccttaa aaggagttct tacttgctta atacctggtg ctggtggtta    3060
tgacgccatt gcagtgatta ctaagcaaga tgttgatctt agggctcaaa ccgctaatga    3120
caaaagattt tctaaggttc aatggctgga tgtaactcag gctgactggg gtgttaggaa    3180
agaaaaagat ccggaaactt atcttgataa ataacttaag gtagctgcat gcagaattcg    3240
cccttaagga ggaaaaaaaa atgaccgttt acacagcatc cgttaccgca cccgtcaaca    3300
tcgcaaccct taagtattgg gggaaaaggg acacgaagtt gaatctgccc accaattcgt    3360
ccatatcagt gactttatcg caagatgacc tcagaacgtt gacctctgcg gctactgcac    3420
ctgagtttga acgcgacact ttgtggttaa atggagaacc acacagcatc gacaatgaaa    3480
gaactcaaaa ttgtctgcgc gacctacgcc aattaagaaa ggaaatggaa tcgaaggacg    3540
cctcattgcc cacattatct caatggaaac tccacattgt ctccgaaaat aacttttccta    3600 cagcagctgg tttagcttcc tccgctgctg gctttgctgc attggtctct gcaattgcta    3660 agttataccca attaccacag tcaacttcag aaatatctag aatagcaaga aaggggtctg    3720
gttcagcttg tagatcgttg tttggcggat acgtggcctg ggaaatggga aaagctgaag    3780
atggtcatga ttccatggca gtacaaatcg cagacagctc tgactggcct cagatgaaag    3840
cttgtgtcct agttgtcagc gatattaaaa aggatgtgag ttccactcag ggtatgcaat    3900
```

```
tgaccgtggc aacctccgaa ctatttaaag aaagaattga acatgtcgta ccaaagagat   3960
ttgaagtcat gcgtaaagcc attgttgaaa aagatttcgc caccttttgca aaggaaacaa   4020 tgatggattc caactctttc catgccacat gtttggactc tttccctcca atattctaca   4080
tgaatgacac ttccaagcgt atcatcagtt ggtgccacac cattaatcag ttttacggag   4140
aaacaatcgt tgcatacacg tttgatgcag gtccaaatgc tgtgttgtac tacttagctg   4200
aaaatgagtc gaaactcttt gcatttatct ataaattgtt tggctctgtt cctggatggg   4260
acaagaaatt tactactgag cagcttgagg cttttcaacca tcaatttgaa tcatctaact   4320
ttactgcacg tgaattggat cttgagttgc aaaaggatgt tgccagagtg attttaactc   4380
aagtcggttc aggcccacaa gaaacaaacg aatctttgat tgacgcaaag actggtctac   4440
caaaggaata agatcaattc gctgcatcgc ccttaggagg taaaaaaaaa tgactgccga   4500
caacaatagt atgccccatg gtgcagtatc tagttacgcc aaattagtgc aaaaccaaac   4560
acctgaagac attttggaag agtttcctga aattattcca ttacaacaaa gacctaatac   4620
ccgatctagt gagacgtcaa atgacgaaag cggagaaaca tgttttttctg gtcatgatga   4680 ggagcaaatt aagttaatga atgaaaattg tattgttttg gattgggacg ataatgctat   4740
tggtgccggt accaagaaag tttgtcattt aatggaaaat attgaaaagg gtttactaca   4800
tcgtgcattc tccgtctta ttttcaatga acaaggtgaa ttacttttac aacaaagagc   4860
cactgaaaaa ataactttcc ctgatctttg gactaacaca tgctgctctc atccactatg   4920
tattgatgac gaattaggtt tgaagggtaa gctagcgat aagattaagg gcgctattac   4980
tgcggcggtg agaaaactag atcatgaatt aggtattcca gaagatgaaa ctaagacaag   5040
gggtaagttt cacttttttaa acagaatcca ttacatggca ccaagcaatg aaccatgggg   5100
tgaacatgaa attgattaca tcctattta taagatcaac gctaaagaaa acttgactgt   5160
caacccaaac gtcaatgaag ttagagactt caaatgggtt tcaccaaatg atttgaaaac   5220
tatgtttgct gacccaagtt acaagtttac gccttggttt aagattattt gcgagaatta   5280
cttattcaac tggtgggagc aattagatga ccttttctgaa gtggaaaatg acaggcaaat   5340
tcatagaatg ctataacaac gcgtcctgca ttcgcccttta ggaggtaaaa aaacatgtgt   5400
gcgacctctt ctcaatttac tcagattacc gagcataatt cccgtcgttc cgcaaactat   5460
cagccaaacc tgtggaattt cgaattcctg caatccctgg agaacgacct gaaagtggaa   5520
aagctggagg agaaagcgac caaactggag gaagaagttc gctgcatgat caaccgtgta   5580
gacacccagc cgctgtccct gctggagctg atcgacgatg tgcagcgcct gggtctgacc   5640
tacaaatttg aaaaagacat cattaaagcc ctggaaaaca tcgtactgct ggacgaaaac   5700
aaaaagaaca atctgacct gcacgcaacc gctctgtctt ccgtctgct gcgtcagcac   5760 ggtttcgagg tttctcagga tgttttttgag cgtttcaagg ataaagaagg tggtttcagc   5820
ggtgaactga aggtgacgt ccaaggcctg ctgagcctgt atgaagcgtc ttacctgggt   5880
ttcgagggtg agaacctgct ggaggaggcg cgtaccttt ccatcaccca cctgaagaac   5940
aacctgaaag aaggcattaa taccaaggtt gcagaacaag tgagccacgc cctgaactg   6000 ccatatcacc agcgtctgca ccgtctggag gcacgttggt tcctggataa atacgaaccg   6060
aaagaaccgc atcaccagct gctgctggag ctggcgaagc tggattttaa catggtacag   6120
accctgcacc agaaagagct gcaagatctg tcccgctggt ggaccgagat gggcctggct   6180
agcaaactgg attttgtacg cgaccgcctg atggaagttt atttctgggc actgggtatg   6240
gcgccagacc cgcagtttgg tgaatgtcgc aaagctgtta ctaaaatgtt tggtctggtg   6300
```

-continued

```
acgatcatcg atgacgtgta tgacgtttat ggcactctgg acgaactgca actgttcacc    6360
gatgctgtag agcgctggga cgttaacgct attaacaccc tgccggacta tatgaaactg    6420
tgtttcctgg cactgtacaa caccgttaac gacacgtcct attctattct gaaagagaaa    6480
ggtcataaca acctgtccta tctgacgaaa agctggcgtg aactgtgcaa agcctttctg    6540
caagaggcga atggtccaa caacaaaatt atcccggctt ctccaagta cctggaaaac     6600 gccagcgttt cctcctccgg tgtagcgctg ctggcgccgt cttactttc cgtatgccag     6660 cagcaggaag acatctccga ccacgcgctg cgttccctga ccgacttcca tggtctggtg    6720
cgttctagct gcgttatctt ccgcctgtgc aacgatctgg ccacctctgc ggcggagctg    6780
gaacgtggcg agactaccaa ttctatcatt agctacatgc acgaaaacga tggtaccagc    6840
gaggaacagg cccgcgaaga actgcgtaaa ctgatcgacg ccgaatggaa aaagatgaat    6900
cgtgaacgcg ttagcgactc caccctgctg cctaaagcgt tcatggaaat cgcagttaac    6960
atggcacgtg tttcccactg cacctaccag tatggcgatg gtctgggtcg cccagactac    7020
gcgactgaaa accgcatcaa actgctgctg attgacccct tcccgattaa ccagctgatg    7080
tatgtctaac tgcagctggt accatatggg aattcgaagc tttctagaac aaaaactcat    7140
ctcagaagag gatctgaata gcgccgtcga ccatcatcat catcatcatt gagtttaaac    7200
ggtctccagc ttggctgttt tggcggatga gagaagattt tcagcctgat acagattaaa    7260
tcagaacgca gaagcggtct gataaaacag aatttgcctg gcggcagtag cgcggtggtc    7320
ccacctgacc ccatgccgaa ctcagaagtg aaacgccgta cgccgatgg tagtgtgggg     7380 tctccccatg cgagagtagg gaactgccag gcatcaaata aaacgaaagg ctcagtcgaa    7440
agactgggcc tttcgtttta tctgttgttt gtcggtgaac gctctcctga gtaggacaaa    7500
tccgccggga gcggatttga acgttgcgaa gcaacggccc ggagggtggc gggcaggacg    7560
cccgccataa actgccaggc atcaaattaa gcagaaggcc atcctgacgg atggcctttt    7620
tgcgtttcta caaactcttt ttgtttattt ttctaaatac attcaaatat gtatccgctc    7680
aaccggaatt gccagctggg gcgccctctg gtaaggttgg aagccctgc aaagtaaact      7740 ggatggcttt ctcgccgcca aggatctgat ggcgcagggg atcaagctct gatcaagaga    7800
caggatgagg atcgtttcgc atgattgaac aagatggatt gcacgcaggt tctccggccg    7860
cttgggtgga gaggctattc ggctatgact gggcacaaca gacaatcggc tgctctgatg    7920
ccgccgtgtt ccggctgtca gcgcaggggc gcccggttct ttttgtcaag accgacctgt    7980
ccggtgccct gaatgaactg caagacgagg cagcgcggct atcgtggctg gccacgacgg    8040
gcgttccttg cgcagctgtg ctcgacgttg tcactgaagc gggaagggac tggctgctat    8100
tgggcgaagt gccggggcag gatctcctgt catctcacct tgctcctgcc gagaaagtat    8160
ccatcatggc tgatgcaatg cggcggctgc atacgcttga tccggctacc tgcccattcg    8220
accaccaagc gaaacatcgc atcgagcgag cacgtactcg gatggaagcc ggtcttgtcg    8280
atcaggatga tctggacgaa gagcatcagg ggctcgcgcc agccgaactg ttcgccaggc    8340
tcaaggcgag catgcccgac ggcgaggatc tcgtcgtgac ccatggcgat gcctgcttgc    8400
cgaatatcat ggtggaaaat ggccgctttt ctggattcat cgactgtggc cggctgggtg    8460
tggcggaccg ctatcaggac atagcgttgg ctacccgtga tattgctgaa gagcttggcg    8520
gcgaatgggc tgaccgcttc ctcgtgcttt acggtatcgc cgctcccgat tcgcagcgca    8580
tcgccttcta tcgccttctt gacgagttct tctgacgcat gaccaaaatc ccttaacgtg    8640
agttttcgtt ccactgagcg tcagaccccg tagaaaagat caaaggatct tcttgagatc    8700
```

```
cttttttttct gcgcgtaatc tgctgcttgc aaacaaaaaa accaccgcta ccagcggtgg    8760
tttgtttgcc ggatcaagag ctaccaactc tttttccgaa ggtaactggc ttcagcagag    8820
cgcagatacc aaatactgtc cttctagtgt agccgtagtt aggccaccac ttcaagaact    8880
ctgtagcacc gcctacatac ctcgctctgc taatcctgtt accagtggct gctgccagtg    8940
gcgataagtc gtgtcttacc gggttggact caagacgata gttaccggat aaggcgcagc    9000
ggtcgggctg aacgggggt tcgtgcacac agcccagctt ggagcgaacg acctacaccg    9060
aactgagata cctacagcgt gagctatgag aaagcgccac gcttcccgaa gggagaaagg    9120
cggacaggta tccggtaagc ggcagggtcg aacaggaga gcgcacgagg gagcttccag    9180
ggggaaacgc ctggtatctt tatagtcctg tcgggtttcg ccacctctga cttgagcgtc    9240 gattttgtg atgctcgtca gggggcgga gccatggaa aaacgccagc aacgcggcct    9300
ttttacggtt cctggccttt tgctggcctt ttgctcacat gttctttcct gcgttatccc    9360
ctgattctgt ggataaccgt attaccgcct ttgagtgagc tgataccgct cgccgcagcc    9420
gaacgaccga gcgcagcgag tcagtgagcg aggaagcgga agagcgcctg atgcggtatt    9480
ttctccttac gcatctgtgc ggtatttcac accgcatatg gtgcactctc agtacaatct    9540
gctctgatgc cgcatagtta agccagtata cactccgcta tcgctacgtg actgggtcat    9600
ggctgcgccc cgacacccgc caacaccgc tgacgcgccc tgacgggctt gtctgctccc    9660
ggcatccgct tacagacaag ctgtgaccgt ctccgggagc tgcatgtgtc agaggttttc    9720
accgtcatca ccgaaacgcg cgaggcagca gatcaattcg cgcgcgaagg cgaagcggca    9780
tgcatttacg ttgacaccat cgaatggtgc aaaacctttc gcggtatggc atgatagcgc    9840
ccggaagaga gtcaattcag ggtggtgaat gtgaaaccag taacgttata cgatgtcgca    9900
gagtatgccg gtgtctctta tcagaccgtt tcccgcgtgg tgaaccaggc cagccacgtt    9960
tctgcgaaaa cgcgggaaaa agtggaagcg gcgatggcgg agctgaatta cattcccaac    10020
cgcgtggcac aacaactggc gggcaaacag tcgttgctga ttggcgttgc cacctccagt    10080
ctggccctgc acgcgccgtc gcaaattgtc gcggcgatta atctcgcgc cgatcaactg    10140 ggtgccagcg tggtggtgtc gatggtagaa cgaagcggcg tcgaagcctg taaagcggcg    10200
gtgcacaatc ttctcgcgca acgcgtcagt gggctgatca ttaactatcc gctggatgac    10260
caggatgcca ttgctgtgga agctgcctgc actaatgttc cggcgttatt cttgatgtc     10320 tctgaccaga cacccatcaa cagtattatt ttctcccatg aagacggtac gcgactgggc    10380
gtggagcatc tggtcgcatt gggtcaccag caaatcgcgc tgttagcggg cccattaagt    10440
tctgtctcgg cgcgtctgcg tctggctggc tggcataaat atctcactcg caatcaaatt    10500
cagccgatag cggaacggga aggcgactgg agtgccatgt ccggttttca acaaaccatg    10560
caaatgctga atgagggcat cgttcccact gcgatgctgg ttgccaacga tcagatggcg    10620
ctgggcgcaa tgcgcgccat taccgagtcc ggctgcgcg ttggtgcgga tatctcggta    10680
gtgggatacg acgataccga agacagctca tgttatatcc cgccgtcaac caccatcaaa    10740
caggattttc gcctgctggg gcaaaccagc gtggaccgct tgctgcaact ctctcagggc    10800
caggcggtga agggcaatca gctgttgccc gtctcactgg tgaaaagaaa aaccaccctg    10860
gcgcccaata cgcaaaccgc ctctccccgc gcgttggccg attcattaat gcagctggca    10920
cgacaggttt cccgactgga aagcgggcag tgagcgcaac gcaattaatg tgagttagcg    10980
cgaattgatc tg                                                       10992
```

<210> SEQ ID NO 34

```
<211> LENGTH: 50
<212> TYPE: DNA
<213> ORGANISM: Artificial Sequence
<220> FEATURE:
<223> OTHER INFORMATION: Synthetic Construct

<400> SEQUENCE: 34
gagacatgag ctcaggaggt aaaaaaacat gaaaacagta gttattatt g            50

<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

<400> SEQUENCE: 35
tttatcaatc ccaattgtca tgttttttta cctcctttat tgttttctta aatc         54

<210> SEQ ID NO 36
<211> LENGTH: 54
<212> TYPE: DNA
<213> ORGANISM: Artificial Sequence
<220> FEATURE:
<223> OTHER INFORMATION: Synthetic Construct

<400> SEQUENCE: 36
gatttaagaa aacaataaag gaggtaaaaa aacatgacaa ttgggattga taaa         54

<210> SEQ ID NO 37
<211> LENGTH: 40
<212> TYPE: DNA
<213> ORGANISM: Artificial Sequence
<220> FEATURE:
<223> OTHER INFORMATION: Synthetic Construct

<400> SEQUENCE: 37
gacatgacat agatctttag tttcgataag aacgaacggt                         40

<210> SEQ ID NO 38
<211> LENGTH: 26
<212> TYPE: DNA
<213> ORGANISM: Artificial Sequence
<220> FEATURE:
<223> OTHER INFORMATION: Synthetic Construct

<400> SEQUENCE: 38
atgaaaacag tagttattat tgatgc                                        26

<210> SEQ ID NO 39
<211> LENGTH: 33
<212> TYPE: DNA
<213> ORGANISM: Artificial Sequence
<220> FEATURE:
<223> OTHER INFORMATION: Synthetic Construct

<400> SEQUENCE: 39
atgttattgt tttcttaaat catttaaaat agc                                33

<210> SEQ ID NO 40
<211> LENGTH: 26
<212> TYPE: DNA
<213> ORGANISM: Artificial Sequence
<220> FEATURE:
<223> OTHER INFORMATION: Synthetic Construct

<400> SEQUENCE: 40
```

```
atgacaattg ggattgataa aattag                                           26
```

<210> SEQ ID NO 41
<211> LENGTH: 24
<212> TYPE: DNA
<213> ORGANISM: Artificial Sequence
<220> FEATURE:
<223> OTHER INFORMATION: Synthetic Construct

<400> SEQUENCE: 41

```
ttagtttcga taagaacgaa cggt                                             24
```

<210> SEQ ID NO 42
<211> LENGTH: 23
<212> TYPE: DNA
<213> ORGANISM: Artificial Sequence
<220> FEATURE:
<223> OTHER INFORMATION: Synthetic Construct

<400> SEQUENCE: 42

```
gaaatagccc cattagaagt atc                                              23
```

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43

```
ttgccaatca tatgattgaa aatc                                             24
```

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44

```
gctatgcttc attagatcct tatcg                                            25
```

<210> SEQ ID NO 45
<211> LENGTH: 25
<212> TYPE: DNA
<213> ORGANISM: Artificial Sequence
<220> FEATURE:
<223> OTHER INFORMATION: Synthetic Construct

<400> SEQUENCE: 45

```
gaaacctaca tccaatcttt tgccc                                            25
```

<210> SEQ ID NO 46
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 46

```
cccgtcttac tgtcgggaat tcgcgttggc cgattcatta atgcagattc tgaaatgagc      60
tgttgacaat taatcatccg gctcgtataa tgtgtggaat tgtgagcgga taacaatttc     120
acacaggaaa cagcgccgct gagaaaaagc gaagcggcac tgctctttaa caatttatca     180
gacaatctgt gtgggcactc gaccggaatt atcgattaac tttattatta aaaattaaag     240
```

```
aggtatatat taatgtatcg attaaataag gaggaataaa ccatggatcc gagctcagga    300
ggtaaaaaaa catgaaaaca gtagttatta ttgatgcatt acgaacacca attggaaaat    360
ataaaggcag cttaagtcaa gtaagtgccg tagacttagg aacacatgtt acaacacaac    420
ttttaaaaag acattccact atttctgaag aaattgatca agtaatcttt ggaaatgttt    480
tacaagctgg aaatggccaa atcccgcac gacaaatagc aataaacagc ggtttgtctc    540
atgaaattcc cgcaatgacg gttaatgagg tctgcggatc aggaatgaag gccgttattt    600
tggcgaaaca attgattcaa ttaggagaag cggaagtttt aattgctggc gggattgaga    660
atatgtccca agcacctaaa ttacaacgtt ttaattacga aacagaaagc tacgatgcgc    720 cttttctag tatgatgtat gatggattaa cggatgcctt tagtggtcag gcaatgggct    780
taactgctga aaatgtggcc gaaaagtatc atgtaactag agaagagcaa gatcaatttt    840
ctgtacattc acaattaaaa gcagctcaag cacaagcaga agggatattc gctgacgaaa    900
tagccccatt agaagtatca ggaacgcttg tggagaaaga tgaagggatt cgccctaatt    960
cgagcgttga gaagctagga acgcttaaaa cagttttttaa agaagacggt actgtaacag   1020
cagggaatgc atcaaccatt aatgatgggg cttctgcttt gattattgct tcacaagaat   1080
atgccgaagc acacggtctt ccttatttag ctattattcg agacagtgtg gaagtcggta   1140
ttgatccagc ctatatggga atttcgccga ttaaagccat tcaaaaactg ttagcgcgca   1200
atcaacttac tacggaagaa attgatctgt atgaaatcaa cgaagcattt gcagcaactt   1260
caatcgtggt ccaaagagaa ctggctttac cagaggaaaa ggtcaacatt tatggtggcg   1320
gtatttcatt aggtcatgcg attggtgcca caggtgctcg tttattaacg agtttaagtt   1380
atcaattaaa tcaaaagaa aagaaatatg gagtggcttc tttatgtatc ggcggtggct   1440
taggactcgc tatgctacta gagagacctc agcaaaaaaa aaacagccga ttttatcaaa   1500
tgagtcctga ggaacgcctg gcttctcttc ttaatgaagg ccagatttct gctgatacaa   1560
aaaaagaatt tgaaaatacg gctttatctt cgcagattgc caatcatatg attgaaaatc   1620
aaatcagtga acagaagtg ccgatgggcg ttggcttaca tttaacagtg gacgaaactg   1680
attatttggt accaatggcg acagaagagc cctcagttat tgcggctttg agtaatggtg   1740
caaaaatagc acaaggattt aaaacagtga atcaacaacg cttaatgcgt ggacaaatcg   1800 tttttttacga tgttgcagat cccgagtcat tgattgataa actacaagta agagaagcgg   1860 aagttttttca acaagcagag ttaagttatc catctatcgt taaacggggc ggcggcttaa   1920
gagatttgca atatcgtact tttgatgaat catttgtatc tgtcgacttt ttagtagatg   1980
ttaaggatgc aatgggggca aatatcgtta acgctatgtt ggaaggtgtg gccgagttgt   2040
tccgtgaatg gtttgcggag caaagattt tattcagtat tttaagtaat tatgccacgg   2100
agtcggttgt tacgatgaaa acggctattc cagtttcacg tttaagtaag gggagcaatg   2160
gccgggaaat tgctgaaaaa attgttttag cttcacgcta tgcttcatta gatccttatc   2220
gggcagtcac gcataacaaa ggaatcatga atggcattga agctgtagtt ttagctacag   2280
gaaatgatac acgcgctgtt agcgcttctt gtcatgcttt tgcggtgaag gaaggtcgct   2340
accaaggctt gactagttgg acgctggatg gcgaacaact aattggtgaa atttcagttc   2400
cgcttgcttt agccacggtt ggcggtgcca caaagtctt acctaaatct caagcagctg   2460
ctgatttgtt agcagtgacg gatgcaaaag aactaagtcg agtagtagcg gctgttggtt   2520
tggcacaaaa tttagcggcg ttacgggcct tagtctctga aggaattcaa aaaggacaca   2580
tggctctaca agcacgttct ttagcgatga cggtcggagc tactggtaaa gaagttgagg   2640
```

```
cagtcgctca acaattaaaa cgtcaaaaaa cgatgaacca agaccgagcc atggctattt    2700
taaatgattt aagaaaacaa taaaggaggt aaaaaaacat gacaattggg attgataaaa    2760
ttagtttttt tgtgcccect tattatattg atatgacggc actggctgaa gccagaaatg    2820
tagaccctgg aaaatttcat attggtattg ggcaagacca aatggcggtg aacccaatca    2880
gccaagatat tgtgacattt gcagccaatg ccgcagaagc gatcttgacc aaagaagata    2940
aagaggccat tgatatggtg attgtcggga ctgagtccag tatcgatgag tcaaaagcgg    3000
ccgcagttgt cttacatcgt ttaatgggga ttcaaccttt cgctcgctct ttcgaaatca    3060
aggaagcttt ttacggagca acagcaggct tacagttagc taagaatcac gtagccttac    3120
atccagataa aaaagtcttg gtcgtagcgg cagatattgc aaaatatggc ttaaattctg    3180
gcggtgagcc tacacaagga gctggggcgg ttgcaatgtt agttgctagt gaaccgcgca    3240
ttttggcttt aaaagaggat aatgtgatgc tgacgcaaga tatctatgac ttttggcgtc    3300
caacaggcca cccgtatcct atggtcgatg gtcctttgtc aaacgaaacc tacatccaat    3360
cttttgccca agtctgggat gaacataaaa aacgaaccgg tcttgatttt gcagattatg    3420
atgctttagc gttccatatt ccttacacaa aaatgggcaa aaaagcctta ttagcaaaaa    3480
tctccgacca aactgaagca gaacaggaac gaattttagc ccgttatgaa gaaagtatcg    3540
tctatagtcg tcgcgtagga aacttgtata cgggttcact ttatctggga ctcatttccc    3600
ttttagaaaa tgcaacgact ttaaccgcag gcaatcaaat tggtttattc agttatggtt    3660
ctggtgctgt cgctgaattt ttcactggtg aattagtagc tggttatcaa atcatttac     3720
aaaaagaaac tcatttagca ctgctggata tcggacaga actttctatc gctgaatatg     3780
aagccatgtt tgcagaaact ttagacacag acattgatca aacgttagaa gatgaattaa    3840
aatatagtat ttctgctatt aataataccg ttcgttctta tcgaaactaa gagatctgca    3900
gctggtacca tatgggaatt cgaagcttgg gcccgaacaa aaactcatct cagaagagga    3960
tctgaatagc gccgtcgacc atcatcatca tcatcattga gtttaaacgg tctccagctt    4020
ggctgttttg gcggatgaga gaagattttc agcctgatac agattaaatc agaacgcaga    4080
agcggtctga taaaacagaa tttgcctggc ggcagtagcg cggtggtccc acctgacccc    4140
atgccgaact cagaagtgaa acgccgtagc gccgatggta gtgtggggtc tccccatgcg    4200
agagtaggga actgccaggc atcaaataaa acgaaaggct cagtcgaaag actgggcctt    4260
tcgttttatc tgttgtttgt cggtgaacgc tctcctgagt aggacaaatc cgccgggagc    4320
ggatttgaac gttgcgaagc aacggcccgg agggtggcgg gcaggacgcc cgccataaac    4380
tgccaggcat caaattaagc agaaggccat cctgacggat ggcctttttg cgtttctaca    4440
aactcttttt gttatttttt ctaaatacat tcaaatatgt atccgctcat gagacaataa    4500
ccctgataaa tgcttcaata atctggcgta atagcgaaga ggcccgcacc gatcgccctt    4560
cccaacagtt gcgcagcctg aatggcgaat ggcgcctgat gcggtatttt ctccttacgc    4620
atctgtgcgg tatttcacac cgcatatggt gcactctcag tacaatctgc tctgatgccg    4680
catagttaag ccagccccga cacccgccaa cacccgctga cgagcttagt aaagccctcg    4740
ctagatttta atgcggatgt tgcgattact tcgccaacta ttgcgataac aagaaaaagc    4800
cagcctttca tgatatatct cccaatttgt gtagggctta ttatgcacgc ttaaaaataa    4860
taaaagcaga cttgacctga tagtttggct gtgagcaatt atgtgcttag tgcatctaac    4920
gcttgagtta agccgcgccg cgaagcggcg tcggcttgaa cgaattgtta gacattattt    4980
gccgactacc ttggtgatct cgcctttcac gtagtggaca aattcttcca actgatctgc    5040
```

```
gcgcgaggcc aagcgatctt cttcttgtcc aagataagcc tgtctagctt caagtatgac    5100
gggctgatac tgggccggca ggcgctccat tgcccagtcg gcagcgacat ccttcggcgc    5160
gattttgccg gttactgcgc tgtaccaaat gcgggacaac gtaagcacta catttcgctc    5220
atcgccagcc cagtcgggcg gcgagttcca tagcgttaag gtttcattta gcgcctcaaa    5280
tagatcctgt tcaggaaccg gatcaaagag ttcctccgcc gctggaccta ccaaggcaac    5340
gctatgttct cttgcttttg tcagcaagat agccagatca atgtcgatcg tggctggctc    5400
gaagatacct gcaagaatgt cattgcgctg ccattctcca aattgcagtt cgcgcttagc    5460
tggataacgc cacggaatga tgtcgtcgtg cacaacaatg gtgacttcta cagcgcggag    5520
aatctcgctc tctccagggg aagccgaagt ttccaaaagg tcgttgatca aagctcgccg    5580
cgttgtttca tcaagcctta cggtcaccgt aaccagcaaa tcaatatcac tgtgtggctt    5640
caggccgcca tccactgcgg agccgtacaa atgtacggcc agcaacgtcg gttcgagatg    5700
gcgctcgatg acgccaacta cctctgatag ttgagtcgat acttcggcga tcaccgcttc    5760
cctcatgatg tttaactttg ttttagggcg actgccctgc tgcgtaacat cgttgctgct    5820
ccataacatc aaacatcgac ccacggcgta acgcgcttgc tgcttggatg cccgaggcat    5880
agactgtacc ccaaaaaaac agtcataaca agccatgaaa accgccactg cgccgttacc    5940
accgctgcgt tcggtcaagg ttctggacca gttgcgtgag cgcatacgct acttgcatta    6000
cagcttacga accgaacagg cttatgtcca ctgggttcgt gccttcatcc gtttccacgg    6060
tgtgcgtcac ccggcaacct tgggcagcag cgaagtcgag gcatttctgt cctggctggc    6120
gaacgagcgc aaggtttcgg tctccacgca tcgtcaggca ttggcggcct tgctgttctt    6180
ctacggcaag gtgctgtgca cggatctgcc ctggcttcag gagatcggaa gacctcggcc    6240
gtcgcggcgc ttgccggtgg tgctgacccc ggatgaagtg gttcgcatcc tcggttttct    6300
ggaaggcgag catcgtttgt tcgcccagct tctgtatgga acgggcatgc ggatcagtga    6360
gggtttgcaa ctgcgggtca aggatctgga tttcgatcac ggcacgatca tcgtgcggga    6420
gggcaagggc tccaaggatc gggccttgat gttacccgag agcttggcac ccagcctgcg    6480
cgagcagggg aattaattcc cacgggtttt gctgcccgca acgggctgt tctggtgttg    6540 ctagtttgtt atcagaatcg cagatccggc ttcagccggt ttgccggctg aaagcgctat    6600
ttcttccaga attgccatga ttttttcccc acgggaggcg tcactggctc ccgtgttgtc    6660
ggcagctttg attcgataag cagcatcgcc tgtttcaggc tgtctatgtg tgactgttga    6720
gctgtaacaa gttgtctcag gtgttcaatt tcatgttcta gttgctttgt tttactggtt    6780
tcacctgttc tattaggtgt tacatgctgt tcatctgtta cattgtcgat ctgttcatgg    6840
tgaacagctt tgaatgcacc aaaaactcgt aaaagctctg atgtatctat ctttttttaca    6900 ccgttttcat ctgtgcatat ggacagtttt ccctttgata tgtaacggtg aacagttgtt    6960 ctactttttgt ttgttagtct tgatgcttca ctgatagata caagagccat aagaacctca    7020
gatccttccg tatttagcca gtatgttctc tagtgtggtt cgttgttttt gcgtgagcca    7080
tgagaacgaa ccattgagat catacttact ttgcatgtca ctcaaaaatt ttgcctcaaa    7140
actggtgagc tgaattttg cagttaaagc atcgtgtagt gttttttctta gtccgttatg    7200 taggtaggaa tctgatgtaa tggttgttgg tattttgtca ccattcattt ttatctggtt    7260
gttctcaagt tcggttacga gatccatttg tctatctagt tcaacttgga aaatcaacgt    7320
atcagtcggg cggcctcgct tatcaaccac caatttcata ttgctgtaag tgtttaaatc    7380
tttacttatt ggtttcaaaa cccattggtt aagccttttta aactcatggt agttatttc    7440
```

| | |
|---|---|
| aagcattaac atgaacttaa attcatcaag gctaatctct atatttgcct tgtgagtttt | 7500 |
| cttttgtgtt agttctttta ataaccactc ataaatcctc atagagtatt tgttttcaaa | 7560 |
| agacttaaca tgttccagat tatattttat gaatttttt aactggaaaa gataaggcaa | 7620 |
| tatctcttca ctaaaaacta attctaattt ttcgcttgag aacttggcat agtttgtcca | 7680 |
| ctggaaaatc tcaaagcctt taaccaaagg attcctgatt tccacagttc tcgtcatcag | 7740 |
| ctctctggtt gctttagcta atacaccata agcattttcc ctactgatgt tcatcatctg | 7800 |
| agcgtattgg ttataagtga acgataccgt ccgttctttc cttgtagggt tttcaatcgt | 7860 |
| ggggttgagt agtgccacac agcataaaat tagcttggtt tcatgctccg ttaagtcata | 7920 |
| gcgactaatc gctagttcat ttgctttgaa acaactaat tcagacatac atctcaattg | 7980 |
| gtctaggtga ttttaatcac tataccaatt gagatgggct agtcaatgat aattactagt | 8040 |
| ccttttcctt tgagttgtgg gtatctgtaa attctgctag acctttgctg gaaaacttgt | 8100 |
| aaattctgct agaccctctg taaattccgc tagacctttg tgtgtttttt ttgtttatat | 8160 |
| tcaagtggtt ataatttata gaataaagaa agaataaaaa aagataaaaa gaatagatcc | 8220 |
| cagcccgtgt gtataactcac tactttagtc agttccgcag tattacaaaa ggatgtcgca | 8280 |
| aacgctgttt gctcctctac aaaacagacc ttaaaaccct aaaggcttaa gtagcaccct | 8340 |
| cgcaagctcg gcaaatcgc tgaatattcc ttttgtctcc gaccatcagg cacctgagtc | 8400 |
| gctgtctttt tcgtgacatt cagttcgctg cgctcacggc tctggcagtg aatgggggta | 8460 |
| aatggcacta caggcgcctt ttatggattc atgcaaggaa actacccata atacaagaaa | 8520 |
| agcccgtcac gggcttctca gggcgtttta tggcgggtct gctatgtggt gctatctgac | 8580 |
| ttttgctgt tcagcagttc ctgccctctg attttccagt ctgaccactt cggattatcc | 8640 |
| cgtgacaggt cattcagact ggctaatgca cccagtaagg cagcggtatc atcaacaggc | 8700 |
| tta | 8703 |

<210> SEQ ID NO 47
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 47

| | |
|---|---|
| tgtaaccttt gctttcaaat gagtagaaat aatgcacatc catgtttgta tcgtgcaaat | 60 |
| aaagtgtttc atccgtagga aaaatgact ttagtatctg ttccgctttt tctgatgaaa | 120 |
| tgtgctcccc gacaaaattg aatgaatcat ggacatttgc tggctttgat acagcgaaag | 180 |
| cagccgttcc tatgttatat atcggattta acagcaggac aaaaaacacc atgacagcca | 240 |
| tcgtcaccca cttattcaca cgcacataaa cctttcctga cttttggaac agatgatagc | 300 |
| tcatcaaaaa tcccgccatt gccaaataaa tcgtatatgg cattactgca ccataatctt | 360 |
| ttgagatttg attgggatat ggcgcaagca gcaagacaag cagtccgata atcagcgtat | 420 |
| aaaataagcc tagtaagatc ttatccgttc tccaatacag cttgaaaaac actacattca | 480 |
| acgcaatggg aagagtgatg atgaaaaaca gaaacacgaa tgcaatcggc tccatcccat | 540 |
| ccgggtattc cttccaatac gaaaagaaac taaaaatcat ttgtacgatc ggcaaactga | 600 |
| caacagcaag gtcgaacgta taaaacttac cctttccgcc atgatcacgc ggcatcagca | 660 |
| tatagtgaaa agccgtcagc agcacatatc cgtataacaa aaaatgcagc agcggcagca | 720 |
| gttcttttcc gtcctctctt aagtaagcgc tggtgaagtt tgttgattgc acctggtgaa | 780 |

```
taagttcaac agacactccc gccagcagca caatccgcaa tataacaccc gccaagaaca    840
ttgtgcgctg ccggtttatt ttgggatgat gcaccaaaag atataagccc gccagaacaa    900
caattgacca ttgaatcagc agggtgcttt gtctgcttaa tataaaataa cgttcgaaat    960
gcaatacata atgactgaat aactccaaca cgaacaacaa ctccatttc ttctgctatc    1020 aaaataacag actcgtgatt ttccaaacga gctttcaaaa aagcctctgc cccttgcaaa    1080
tcggatgcct gtctataaaa ttcccgatat tggttaaaca gcggcgcaat ggcggccgca    1140
tctgatgtct ttgcttggcg aatgttcatc ttatttcttc ctccctctca ataattttt    1200 cattctatcc cttttctgta aagtttattt ttcagaatac ttttatcatc atgctttgaa    1260
aaaatatcac gataatatcc attgttctca cggaagcaca cgcaggtcat ttgaacgaat    1320 ttttcgaca ggaatttgcc gggactcagg agcatttaac ctaaaaaagc atgacatttc    1380
agcataatga acatttactc atgtctattt tcgttctttt ctgtatgaaa atagttattt    1440
cgagtctcta cggaaatagc gagagatgat atacctaaat agagataaaa tcatctcaaa    1500
aaaatgggtc tactaaaata ttattccatc tattacaata aattcacaga atagtctttt    1560
aagtaagtct actctgaatt tttttaaaag gagagggtaa agagtgtcat taccgttctt    1620
aacttctgca ccgggaaagg ttattatttt tggtgaacac tctgctgtgt acaacaagcc    1680
tgccgtcgct gctagtgtgt ctgcgttgag aacctacctg ctaataagcg agtcatctgc    1740
accagatact attgaattgg acttcccgga cattagcttt aatcataagt ggtccatcaa    1800
tgatttcaat gccatcaccg aggatcaagt aaactcccaa aaattggcca aggctcaaca    1860
agccaccgat ggcttgtctc aggaactcgt tagtcttttg gatccgttgt tagctcaact    1920
atccgaatcc ttccactacc atgcagcgtt ttgtttcctg tatatgtttg tttgcctatg    1980
cccccatgcc aagaatatta agttttcttt aaagtctact ttacccatcg gtgctgggtt    2040
gggctcaagc gcctctattt ctgtatcact ggccttagct atggcctact tgggggggtt    2100
aataggatct aatgacttgg aaaagctgtc agaaaacgat aagcatatag tgaatcaatg    2160
ggccttcata ggtgaaaagt gtattcacgg tacccttca ggaatagata acgcgtgtggc    2220 cacttatggt aatgccctgc tatttgaaaa agactccacat aatggaacaa taaacacaaa    2280
caattttaag ttcttagatg atttcccagc cattccaatg atcctaacct atactagaat    2340
tccaaggtct acaaaagatc ttgttgctcg cgttcgtgtg ttggtcaccg agaaatttcc    2400
tgaagttatg aagccaattc tagatgccat gggtgaatgt gccctacaag gcttagagat    2460
catgactaag ttaagtaaat gtaaaggcac cgatgacgag gctgtagaaa ctaataatga    2520
actgtatgaa caactattgg aattgataag aataaatcat ggactgcttg tctcaatcgg    2580
tgtttctcat cctggattag aacttattaa aaatctgagc gatgatttga gaattggctc    2640
cacaaaactt accggtgctg gtggcggcgg ttgctctttg actttgttac gaagagacat    2700
tactcaagag caaattgaca gcttcaaaaa gaaattgcaa gatgattta gttacgagac    2760 atttgaaaca gacttgggtg ggactggctg ctgtttgtta agcgcaaaaa atttgaataa    2820
agatcttaaa atcaaatccc tagtattcca attatttgaa aataaaacta ccacaaagca    2880
acaaattgac gatctattat tgccaggaaa cacgaattta ccatggactt cataaaagga    2940
gagggtgtca gagttgagag ccttcagtgc cccagggaaa gcgttactag ctggtggata    3000
tttagtttta gatacaaaat atgaagcatt tgtagtcgga ttatcggcaa gaatgcatgc    3060
tgtagcccat ccttacggtt cattgcaagg gtctgataag tttgaagtgc gtgtgaaaag    3120
taaacaattt aaagatgggg agtggctgta ccatataagt cctaaaagtg gcttcattcc    3180
```

```
tgtttcgata ggcggatcta agaacccttt cattgaaaaa gttatcgcta acgtatttag    3240
ctactttaaa cctaacatgg acgactactg caatagaaac ttgttcgtta ttgatatttt    3300
ctctgatgat gcctaccatt ctcaggagga tagcgttacc gaacatcgtg gcaacagaag    3360
attgagtttt cattcgcaca gaattgaaga agttcccaaa acagggctgg gctcctcggc    3420
aggtttagtc acagttttaa ctacagcttt ggcctccttt tttgtatcgg acctggaaaa    3480
taatgtagac aaatatagag aagttattca taatttagca caagttgctc attgtcaagc    3540
tcagggtaaa attggaagcg ggtttgatgt agcggcggca gcatatggat ctatcagata    3600
tagaagattc ccacccgcat taatctctaa tttgccagat attggaagtg ctacttacgg    3660
cagtaaactg gcgcatttgg ttgatgaaga agactggaat attacgatta aaagtaacca    3720
tttaccttcg ggattaactt tatggatggg cgatattaag aatggttcag aaacagtaaa    3780
actggtccag aaggtaaaaa attggtatga ttcgcatatg ccagaaagct gaaaatata    3840 tacagaactc gatcatgcaa attctagatt tatggatgga ctatctaaac tagatcgctt    3900
acacgagact catgacgatt acagcgatca gatatttgag tctcttgaga ggaatgactg    3960
tacctgtcaa aagtatcctg aaatcacaga agttagagat gcagttgcca caattagacg    4020
ttcctttaga aaaataacta aagaatctgg tgccgatatc gaacctcccg tacaaactag    4080
cttattggat gattgccaga ccttaaaagg agttcttact tgcttaatac ctggtgctgg    4140
tggttatgac gccattgcag tgattactaa gcaagatgtt gatcttaggg ctcaaaccgc    4200
taatgacaaa agattttcta aggttcaatg gctggatgta actcaggctg actgggtgt    4260 taggaaagaa aaagatccgg aaacttatct tgataaataa aaggagaggg tgaccgttta    4320
cacagcatcc gttaccgcac ccgtcaacat cgcaaccctt aagtattggg ggaaagggga    4380
cacgaagttg aatctgccca ccaattcgtc catatcagtg actttatcgc aagatgacct    4440
cagaacgttg acctctgcgg ctactgcacc tgagtttgaa cgcgacactt tgtggttaaa    4500
tggagaacca cacagcatcg acaatgaaag aactcaaaat tgtctgcgcg acctacgcca    4560
attaagaaag gaaatggaat cgaaggacgc ctcattgccc acattatctc aatggaaact    4620
ccacattgtc tccgaaaata actttcctac agcagctggt ttagcttcct ccgctgctgg    4680
ctttgctgca ttggtctctg caattgctaa gttataccaa ttaccacagt caacttcaga    4740
aatatctaga atagcaagaa aggggtctgg ttcagcttgt agatcgttgt ttggcggata    4800
cgtggcctgg gaaatgggaa aagctgaaga tggtcatgat tccatggcag tacaaatcgc    4860
agacagctct gactggcctc agatgaaagc ttgtgtccta gttgtcagcg atattaaaaa    4920
ggatgtgagt tccactcagg gtatgcaatt gaccgtggca acctccgaac tatttaaaga    4980
aagaattgaa catgtcgtac caaagagatt tgaagtcatg cgtaaagcca ttgttgaaaa    5040
agatttcgcc accttttgcaa aggaaacaat gatggattcc aactcttttcc atgccacatg    5100 tttggactct ttccctccaa tattctacat gaatgacact tccaagcgta tcatcagttg    5160
gtgccacacc attaatcagt tttacggaga acaatcgtt gcatacacgt ttgatgcagg    5220
tccaaatgct gtgttgtact acttagctga aaatgagtcg aaactctttg catttatcta    5280
taaattgttt ggctctgttc ctggatggga caagaaattt actactgagc agcttgaggc    5340
tttcaaccat caatttgaat catctaactt tactgcacgt gaattggatc ttgagttgca    5400
aaaggatgtt gccagagtga tttaactca gtcggttca ggcccacaag aaacaaacga    5460
atctttgatt gacgcaaaga ctggtctacc aaaggaataa aaggagaggg tgactgccga    5520
caacaatagt atgcccatg gtgcagtatc tagttacgcc aaattagtgc aaaaccaaac    5580
```

-continued

```
acctgaagac attttggaag agtttcctga aattattcca ttacaacaaa gacctaatac    5640
ccgatctagt gagacgtcaa atgacgaaag cggagaaaca tgtttttctg gtcatgatga    5700
ggagcaaatt aagttaatga atgaaaattg tattgttttg gattgggacg ataatgctat    5760
tggtgccggt accaagaaag tttgtcattt aatggaaaat attgaaaagg gtttactaca    5820
tcgtgcattc tccgtcttta ttttcaatga acaaggtgaa ttacttttac aacaaagagc    5880
cactgaaaaa ataactttcc ctgatctttg gactaacaca tgctgctctc atccactatg    5940
tattgatgac gaattaggtt tgaagggtaa gctagacgat aagattaagg gcgctattac    6000
tgcggcggtg agaaaactag atcatgaatt aggtattcca gaagatgaaa ctaagacaag    6060
gggtaagttt cacttttttaa acagaatcca ttacatggca ccaagcaatg aaccatgggg    6120
tgaacatgaa attgattaca tcctatttta taagatcaac gctaaagaaa acttgactgt    6180
caacccaaac gtcaatgaag ttagagactt caaatgggtt tcaccaaatg atttgaaaac    6240
tatgtttgct gacccaagtt acaagtttac gccttggttt aagattattt gcgagaatta    6300
cttattcaac tggtgggagc aattagatga cctttctgaa gtggaaaatg acaggcaaat    6360
tcatagaatg ctataaaaaa aaccggcctt ggccccgccg gttttttatt attttctttc    6420
ctccgcatgt tcaatccgct ccataatcga cggatggctc cctctgaaaa ttttaacgag    6480
aaacggcggg ttgacccggc tcagtcccgt aacggccaag tcctgaaacg tctcaatcgc    6540
cgcttcccgg tttccggtca gctcaatgcc gtaacggtcg gcggcgtttt cctgataccg    6600
ggagacggca ttcgtaattt gaatacatac gaacaaatta ataaagtgaa aaaaatactt    6660
cggaaacatt taaaaaataa ccttattggt acttacatgt ttggatcagg agttgagagt    6720
ggactaaaac caaatagtga tcttgacttt ttagtcgtcg tatctgaacc attgacagat    6780
caaagtaaag aaatacttat acaaaaaatt agacctattt caaaaaaaat aggagataaa    6840
agcaacttac gatatattga attaacaatt attattcagc aagaaatggt accgtggaat    6900
catcctccca aacaagaatt tatttatgga gaatggttac aagagcttta tgaacaagga    6960
tacattcctc agaaggaatt aaattcagat ttaaccataa tgctttacca agcaaaacga    7020
aaaaataaaa gaatatacgg aaaattatgac ttagaggaat tactacctga tattccattt    7080
tctgatgtga gaagagccat tatggattcg tcagaggaat taatagataa ttatcaggat    7140
gatgaaacca actctatatt aactttatgc cgtatgattt taactatgga cacgggtaaa    7200
atcataccaa aagatattgc gggaaatgca gtggctgaat cttctccatt agaacatagg    7260
gagagaattt tgttagcagt tcgtagttat cttggagaga atattgaatg gactaatgaa    7320
aatgtaaatt taactataaa ctatttaaat aacagattaa aaaaattata atgtaacctt    7380
tgctttcaaa tgagtagaaa taatgcacat ccatgtttgt atcgtgcaaa taagtgtttt    7440
catccgtagg aaaaaatgac tttagtatct gttccgcttt ttctgatgaa atgtgctccc    7500
cgacaaaatt gaatgaatca tggacatttg ctggctttga tacagcgaaa gcagccgttc    7560
ctatgttata tatcggattt aacagcagga caaaaaacac catgacagcc atcgtcaccc    7620
acttattcac acgcacataa accttttcctg acttttggaa cagatgatag ctcatcaaaa    7680
atcccgccat tgccaaataa atcgtatatg gcattactgc accataatct tttgagattt    7740
gattgggata tggcgcaagc agcaagacaa gcagtccgat aatcagcgta taaataagc    7800 ctagtaagat cttatccgtt ctccaataca gcttgaaaaa cactacattc aacgcaatgg    7860
gaagagtgat gatgaaaaac agaaacacga atgcaatcgg ctccatccca tccgggtatt    7920
ccttccaata cgaaaagaaa ctaaaaatca tttgtacgat cggcaaactg acaacagcaa    7980
```

| | |
|---|---|
| ggtcgaacgt ataaaactta cccctttccgc catgatcacg cggcatcagc atatagtgaa | 8040 |
| aagccgtcag cagcacatat ccgtataaca aaaaatgcag cagcggcagc agttcttttc | 8100 |
| cgtcctctct taagtaagcg ctggtgaagt tgttgattg cacctggtga ataagttcaa | 8160 |
| cagacactcc cgccagcagc acaatccgca atataacacc cgccaagaac attgtgcgct | 8220 |
| gccggtttat tttgggatga tgcaccaaaa gatataagcc cgccagaaca caattgacc | 8280 |
| attgaatcag cagggtgctt tgtctgctta atataaaata cgttcgaaa tgcaatacat | 8340 |
| aatgactgaa taactccaac acgaacaaca aaagtgcgca ttttataaaa gctaatgatt | 8400 |
| cagtccacat aattgataga cgaattctgc tacaggtcac gtggctatgt gaaggatcgc | 8460 |
| gcgtccagtt aagagcaaaa acattgacaa aaaaatttat ttatgctaaa atttactatt | 8520 |
| aatatatttg tatgtataat aagattctcc tggccagggg aatcttattt tttgtggagg | 8580 |
| atcatttcat gaggaaaaat gagtccagct taacgtctct aatttcagct tttgcccgtg | 8640 |
| catatcacag ccgatatgac acacctctta tttttgatga ttttatcgca aaagatctca | 8700 |
| ttaacgaaaa agagtttatc gacatcagta aaaatatgat tcaagaaata tcgttttca | 8760 |
| acaaagagat cgccgaacgt cttcaaaatg atcctgaaaa atattaaaa tgggttgcac | 8820 |
| aaatccagct gtctccaacg cccctagcac gtgcttctta ttgtgaaaaa gtcttgcaca | 8880 |
| acgaattaat cctgggggca aaacagtatg tcattcttgg agcgggactg gatactttct | 8940 |
| gctttcggca tccagaatta gaaaacagct tacaggtttt cgaggttgat catccggcca | 9000 |
| cacagcaatt gaaaaaaaat aagctgaagg atgcaaatct gacaattccg ggtcatcttc | 9060 |
| attttgttcc tatggatttc accaaaacgt tttcgtatga tcctctctta gatgaaggat | 9120 |
| ttaaaaacac aaaaacattc ttcagccttc tcggagtgtc ttattatgta acacgggaag | 9180 |
| aaaatgcaag cttgatcagc aatttatttt ctcatgtccc gcctggaagc tctattgttt | 9240 |
| ttgattatgc ggacgaaaca cttttttacag caaaagggac gtcgaatcga gttgaacata | 9300 |
| tggtgaagat ggctgccgca agcggggaac cgatgaaatc atgtttcact tatcaagaga | 9360 |
| ttgaacatct g | 9371 |

<210> SEQ ID NO 48
<211> LENGTH: 4339
<212> TYPE: DNA
<213> ORGANISM: Artificial Sequence
<220> FEATURE:
<223> OTHER INFORMATION: Synthetic Construct

<400> SEQUENCE: 48

| | |
|---|---|
| tagaaaaact catcgagcat caaatgaaac tgcaatttat tcatatcagg attatcaata | 60 |
| ccatattttt gaaaaagccg tttctgtaat gaaggagaaa actcaccgag gcagttccat | 120 |
| aggatggcaa gatcctggta tcggtctgcg attccgactc gtccaacatc aatacaacct | 180 |
| attaatttcc cctcgtcaaa ataaggtta tcaagtgaga atcaccatg agtgacgact | 240 |
| gaatccggtg agaatggcaa aagtttatgc atttcttcc agacttgttc aacaggccag | 300 |
| ccattacgct cgtcatcaaa atcactcgca tcaaccaaac cgttattcat tcgtgattgc | 360 |
| gcctgagcga ggcgaaatac gcgatcgctg ttaaaaggac aattacaaac aggaatcgag | 420 |
| tgcaaccggc gcaggaacac tgccagcgca tcaacaatat tttcacctga atcaggatat | 480 |
| tcttctaata cctggaacgc tgttttccg gggatcgcag tggtgagtaa ccatgcatca | 540 |
| tcaggagtac ggataaaatg cttgatggtc ggaagtggca taaattccgt cagccagttt | 600 |
| agtctgacca tctcatctgt aacatcattg gcaacgctac ctttgccatg tttcagaaac | 660 |

```
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttaggggtg tcgcccttta gtcgctgaac atgtgctctg    1200
tttctaccga gaacgtttcc ttcactgaga cggaaaccga ggcacgtcgt agcgcgaact   1260
acgagccgaa tagctgggac tacgatttcc tgctgtcttc cgatactgac gaatctattg   1320
aggtgtacaa agacaaagca aagaaactgg aggctgaagt gcgccgcgaa attaacaacg   1380
agaaagctga attcctgact ctgctggagc tgatcgataa cgtacagcgc ctgggtctgg   1440
gttaccgctt cgaatctgat atccgtcgcg cactggatcg tttcgtaagc agcggcggtt   1500
tcgatggcgt gaccaaaacg agcctgcacg ctaccgcgct gtccttccgt ctgctgcgtc   1560
agcacgcgtt cgaagtttct caggaagcat tctccggttt caaagatcaa aacggtaact   1620
tcctggaaaa cctgaaagaa gacactaagg cgatcctgag cctgtatgag gcaagctttc   1680
tggccctgga gggtgagaac atcctggatg aggcgcgcgt attcgccatc tcccatctga   1740
aagagctgtc tgaagagaaa atcggtaagg aactggcaga gcaggttaat cacgcactgg   1800
aactgccgct gcatcgtcgt acccagcgtc tggaggcggt ttggtccatc gaagcgtacc   1860
gcaaaaagga ggatgctaac caggttctgc tggaactggc catcctggac tacaacatga   1920
tccagtccgt ttaccagcgt gatctgcgtg aaacctcccg ttggtggcgc cgtgtgggcc   1980
tggcgaccaa actgcacttc gctaaggacc gcctgattga gtctttttac tgggcagtcg   2040
gcgttgcgtt cgaacctcag tattctgact gccgtaacag cgttgcgaaa atgttcagct   2100
tcgttactat tatcgacgac atctacgacg tttacggtac tctggacgag ctggaactgt   2160
ttaccgacgc tgtcgaacgt tgggatgtta acgccatcaa cgatctgcct gactacatga   2220
aactgtgctt cctggcactg tataacacga tcaacgaaat tgcatacgac aacctgaaag   2280
acaaaggtga aaacatcctg ccgtacctga ctaaagcgtg gcggatctg tgtaacgctt    2340
ttctgcaaga agcgaaatgg ctgtataaca aatccactcc gaccttttgac gattatttcg   2400
gcaatgcctg gaaatccagc tctggcccgc tgcaactgat cttcgcttat tttgcggttg   2460
tccaaaacat caaaaggag gaaattgaaa acctgcaaaa ataccacgat atcattagcc    2520
gtccttctca tatctttcgc ctgtgcaacg acctggcaag cgcgtccgca gagatcgcac   2580
gtggcgaaac cgctaactct gtttcctgct acatgcgcac caagggcatt tccgaagagc   2640
tggcaaccga gagcgtaatg aatctgatcg acgaaacctg taagaaaatg aacaaagaaa   2700
aactgggtgg ctccctgttc gctaaaccgt tcgtagagac tgctattaac ctggcacgtc   2760
agagccactg cacctaccac aatggtgacg cacatactag cccggatgaa ctgactcgta   2820
aacgtgtact gtctgttatc accgaaccga ttctgccgtt cgaacgttaa ctgcagcgtc   2880
aatcgaaagg gcgacacaaa atttattcta aatgcataat aaatactgat aacatcttat   2940
agtttgtatt atattttgta ttatcgttga catgtataat tttgatatca aaaactgatt   3000
ttcccttat tattttcgag atttattttc ttaattctct ttaacaaact agaaatattg    3060
```

| | |
|---|---|
| tatatacaaa aaatcataaa taatagatga atagtttaat tataggtgtt catcaatcga | 3120 |
| aaaagcaacg tatcttattt aaagtgcgtt gctttttcct catttataag gttaaataat | 3180 |
| tctcatatat caagcaaagt gacaggcgcc cttaaatatt ctgacaaatg ctctttccct | 3240 |
| aaactccccc cataaaaaaa cccgccgaag cgggttttta cgttatttgc ggattaacga | 3300 |
| ttactcgtta tcagaaccgc ccaggggggcc cgagcttaag actggccgtc gttttacaac | 3360 |
| acagaaagag tttgtagaaa cgcaaaaagg ccatccgtca ggggccttct gcttagtttg | 3420 |
| atgcctggca gttccctact ctcgccttcc gcttcctcgc tcactgactc gctgcgctcg | 3480 |
| gtcgttcggc tgcggcgagc ggtatcagct cactcaaagg cggtaatacg gttatccaca | 3540 |
| gaatcagggg ataacgcagg aaagaacatg tgagcaaaag gccagcaaaa ggccaggaac | 3600 |
| cgtaaaaagg ccgcgttgct ggcgtttttc cataggctcc gccccctga cgagcatcac | 3660 |
| aaaaatcgac gctcaagtca gaggtggcga acccgacag gactataaag ataccaggcg | 3720 |
| tttccccctg gaagctccct cgtgcgctct cctgttccga ccctgccgct taccggatac | 3780 |
| ctgtccgcct ttctcccttc gggaagcgtg gcgctttctc atagctcacg ctgtaggtat | 3840 |
| ctcagttcgg tgtaggtcgt tcgctccaag ctgggctgtg tgcacgaacc ccccgttcag | 3900 |
| cccgaccgct gcgccttatc cggtaactat cgtcttgagt ccaacccggt aagacacgac | 3960 |
| ttatcgccac tggcagcagc cactggtaac aggattagca gagcgaggta tgtaggcgt | 4020 |
| gctacagagt tcttgaagtg gtgggctaac tacggctaca ctagaagaac agtatttggt | 4080 |
| atctgcgctc tgctgaagcc agttaccttc ggaaaaagag ttggtagctc ttgatccggc | 4140 |
| aaacaaacca ccgctggtag cggtggtttt tttgtttgca agcagcagat tacgcgcaga | 4200 |
| aaaaaggat ctcaagaaga tcctttgatc ttttctacgg ggtctgacgc tcagtggaac | 4260 |
| gacgcgcgcg taactcacgt taagggattt tggtcatgag cttcgccgt cccgtcaagt | 4320 |
| cagcgtaatg ctctgctttt | 4339 |

<210> SEQ ID NO 49
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 49

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatgtgctc | 420 |
| tgtttctacc gagaacgttt ccttcactga cacggaaacc gaggcacgtc gtagcgcgaa | 480 |
| ctacgagccg aatagctggg actacgattt cctgctgtct tccgatactg acgaatctat | 540 |
| tgaggtgtac aaagacaaag caaagaaact ggaggctgaa gtgcgccgcg aaattaacaa | 600 |
| cgagaaagct gaattcctga ctctgctgga gctgatcgat aacgtacagc gcctgggtct | 660 |
| gggttaccgc ttcgaatctg atatccgtcg cgcactggat cgtttcgtaa gcagcggcgg | 720 |
| tttcgatggc gtgaccaaaa cgagcctgca cgctaccgcg ctgtccttcc gtctgctgcg | 780 |

-continued

```
tcagcacggc ttcgaagttt ctcaggaagc attctccggt ttcaaagatc aaaacggtaa    840
cttcctggaa aacctgaaag aagacactaa ggcgatcctg agcctgtatg aggcaagctt    900
tctggccctg gagggtgaga acatcctgga tgaggcgcgc gtattcgcca tctcccatct    960
gaaagagctg tctgaagaga aaatcggtaa ggaactggca gagcaggtta atcacgcact   1020
ggaactgccg ctgcatcgtc gtacccagcg tctggaggcg gtttggtcca tcgaagcgta   1080
ccgcaaaaag gaggatgcta accaggttct gctggaactg gccatcctgg actacaacat   1140
gatccagtcc gtttaccagc gtgatctgcg tgaaacctcc cgttggtggc gccgtgtggg   1200
cctggcgacc aaactgcact tcgctaagga ccgcctgatt gagtcttttt actgggcagt   1260
cggcgttgcg ttcgaacctc agtattctga ctgccgtaac agcgttgcga aaatgttcag   1320
cttcgttact attatcgacg acatctacga cgtttacggt actctggacg agctggaact   1380
gtttaccgac gctgtcgaac gttgggatgt taacgccatc aacgatctgc tgactacat    1440
gaaactgtgc ttcctggcac tgtataacac gatcaacgaa attgcatacg acaacctgaa   1500
agacaaaggt gaaaacatcc tgccgtacct gactaaagcg tgggcggatc tgtgtaacgc   1560
ttttctgcaa gaagcgaaat ggctgtataa caaatccact ccgaccttg  acgattattt    1620
cggcaatgcc tggaaatcca gctctggccc gctgcaactg atcttcgctt attttgcggt   1680
tgtccaaaac atcaaaaagg aggaaattga aacctgcaa  aaataccacg atatcattag    1740
ccgtccttct catatctttc gcctgtgcaa cgacctggca agcgcgtccg cagagatcgc   1800
acgtggcgaa accgctaact ctgttttcct ctacatgcgc accaagggca tttccgaaga   1860
gctggcaacc gagagcgtaa tgaatctgat cgacgaaacc tgtaagaaaa tgaacaaaga   1920
aaaactgggt ggctccctgt cgctaaacc  gttcgtagag actgctatta acctggcacg    1980
tcagagccac tgcacctacc acaatggtga cgcacatact agcccggatg aactgactcg   2040
taaacgtgta ctgtctgtta tcaccgaacc gattctgccg ttcgaacgtt aactgcagct   2100
ggtaccatat gggaattcga agcttttag  aacaaaaact catctcagaa gaggatctga    2160
atagcgccgt cgaccatcat catcatcatc attgagttta acggtctcc  agcttggctg    2220
ttttggcgga tgagagaaga ttttcagcct gatacagatt aaatcagaac gcagaagcgg   2280
tctgataaaa cagaatttgc ctggcggcag tagcgcggtg gtcccacctg accccatgcc   2340
gaactcagaa gtgaaacgcc gtagcgccga tggtagtgtg gggtctcccc atgcgagagt   2400
agggaactgc caggcatcaa ataaaacgaa aggctcagtc gaaagactgg gcctttcgtt   2460
ttatctgttg tttgtcggtg aacgctctcc tgagtaggac aaatccgccg ggagcggatt   2520
tgaacgttgc gaagcaacgg cccggagggt ggcgggcagg acgcccgcca taaactgcca   2580
ggcatcaaat taagcagaag ccatcctga  cggatggcct ttttgcgttt ctacaaactc    2640
tttttgttta tttttctaaa tacattcaaa tatgtatccg ctcatgagac aataaccctg   2700
ataaatgctt caataatatt gaaaaaggaa gagtatgagt attcaacatt tccgtgtcgc   2760
ccttattccc ttttttgcgg catttt gcct tcctgttttt gctcacccag aaacgctggt   2820
gaaagtaaaa gatgctgaag atcagttggg tgcacgagtg ggttacatcg aactggatct   2880
caacagcggt aagatccttg agagttttcg ccccgaagaa cgttttccaa tgatgagcac   2940
ttttaaagtt ctgctatgtg gcgcggtatt atccgtgtt  gacgccgggc aagagcaact    3000
cggtcgccgc atacactatt ctcagaatga cttggttgag tactcaccag tcacagaaaa   3060
gcatcttacg gatggcatga cagtaagaga attatgcagt gctgccataa ccatgagtga   3120
taacactgcg gccaacttac ttctgacaac gatcggagga ccgaaggagc taaccgcttt   3180
```

```
tttgcacaac atgggggatc atgtaactcg ccttgatcgt tgggaaccgg agctgaatga    3240
agccatacca aacgacgagc gtgacaccac gatgcctgta gcaatggcaa caacgttgcg    3300
caaactatta actggcgaac tacttactct agcttcccgg caacaattaa tagactggat    3360
ggaggcggat aaagttgcag gaccacttct gcgctcggcc cttccggctg ctggtttat     3420 tgctgataaa tctggagccg gtgagcgtgg gtctcgcggt atcattgcag cactggggcc    3480
agatggtaag ccctcccgta tcgtagttat ctacacgacg gggagtcagg caactatgga    3540
tgaacgaaat agacagatcg ctgagatagg tgcctcactg attaagcatt ggtaactgtc    3600
agaccaagtt tactcatata tactttagat tgatttaaaa cttcattttt aatttaaaag    3660
gatctaggtg aagatccttt ttgataatct catgaccaaa atcccttaac gtgagttttc    3720
gttccactga gcgtcagacc ccgtagaaaa gatcaaagga tcttcttgag atcctttttt    3780
tctgcgcgta atctgctgct tgcaaacaaa aaaaccaccg ctaccagcgg tggtttgttt    3840
gccggatcaa gagctaccaa ctcttttccc gaaggtaact ggcttcagca gagcgcagat    3900
accaaatact gtccttctag tgtagccgta gttaggccac cacttcaaga actctgtagc    3960
accgcctaca tacctcgctc tgctaatcct gttaccagtg gctgctgcca gtggcgataa    4020
gtcgtgtctt accgggttgg actcaagacg atagttaccg gataaggcgc agcggtcggg    4080
ctgaacgggg ggttcgtgca cacagcccag cttggagcga acgacctaca ccgaactgag    4140
atacctacag cgtgagctat gagaaagcgc cacgcttccc gaagggagaa aggcggacag    4200
gtatccggta gcggcagggt cggaacagga gagcgcacg agggagcttc caggggggaaa   4260 cgcctggtat ctttatagtc ctgtcgggtt tcgccacctc tgacttgagc gtcgattttt    4320
gtgatgctcg tcaggggggc ggagcctatg gaaaaacgcc agcaacgcgg ccttttttacg   4380 gttcctggcc ttttgctggc cttttgctca catgttcttt cctgcgttat cccctgattc    4440
tgtggataac cgtattaccg cctttgagtg agctgatacc gctcgccgca gccgaacgac    4500
cgagcgcagc gagtcagtga gcgaggaagc ggaagagcgc ctgatgcggt attttctcct    4560
tacgcatctg tgcggtattt cacaccgcat atggtgcact ctcagtacaa tctgctctga   4620
tgccgcatag ttaagccagt atacactccg ctatcgctac gtgactgggt catggctgcg    4680
ccccgacacc cgccaacacc cgctgacgcg ccctgacggg cttgtctgct cccggcatcc    4740
gcttacagac aagctgtgac cgtctccggg agctgcatgt gtcagaggtt ttcaccgtca    4800
tcaccgaaac gcgcgaggca gcagatcaat tcgcgcgcga aggcgaagcg gcatgcattt    4860
acgttgacac catcgaatgg tgcaaaacct ttcgcggtat ggcatgatag cgcccggaag    4920
agagtcaatt cagggtggtg aatgtgaaac cagtaacgtt atacgatgtc gcagagtatg    4980
ccggtgtctc ttatcagacc gtttcccgcg tggtgaacca ggccagccac gtttctgcga    5040
aaacgcggga aaagtggaa gcggcgatgg cggagctgaa ttacattccc aaccgcgtgg     5100
cacaacaact ggcgggcaaa cagtcgttgc tgattggcgt tgccacctcc agtctggccc    5160
tgcacgcgcc gtcgcaaatt gtcgcggcga ttaaatctcg cgccgatcaa ctgggtgcca    5220
gcgtggtggt gtcgatggta gaacgaagcg gcgtcgaagc ctgtaaagcg gcggtgcaca    5280
atcttctcgc gcaacgcgtc agtgggctga tcattaacta tccgctggat gaccaggatg    5340
ccattgctgt ggaagctgcc tgcactaatg ttccggcgtt atttcttgat gtctctgacc    5400
agacacccat caacagtatt attttctccc atgaagacgg tacgcgactg ggcgtggagc    5460
atctggtcgc attgggtcac cagcaaatcg cgctgttagc gggcccatta agttctgtct    5520
cggcgcgtct gcgtctggct ggctggcata aatatctcac tcgcaatcaa attcagccga    5580
```

| | |
|---|---:|
| tagcggaacg ggaaggcgac tggagtgcca tgtccggttt tcaacaaacc atgcaaatgc | 5640 |
| tgaatgaggg catcgttccc actgcgatgc tggttgccaa cgatcagatg gcgctgggcg | 5700 |
| caatgcgcgc cattaccgag tccgggctgc gcgttggtgc ggatatctcg gtagtgggat | 5760 |
| acgacgatac cgaagacagc tcatgttata tcccgccgtc aaccaccatc aaacaggatt | 5820 |
| tcgcctgct ggggcaaacc agcgtggacc gcttgctgca actctctcag gccaggcgg | 5880 |
| tgaagggcaa tcagctgttg cccgtctcac tggtgaaaag aaaaaccacc ctggcgccca | 5940 |
| atacgcaaac cgcctctccc cgcgcgttgg ccgattcatt aatgcagctg gcacgacagg | 6000 |
| tttcccgact ggaaagcggg cagtgagcgc aacgcaatta atgtgagtta gcgcgaattg | 6060 |
| atctg | 6065 |

<210> SEQ ID NO 50
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 50

| | |
|---|---:|
| ttgtctgctc ccggcatccg cttacagaca agctgtgacc gtctccggga gctgcatgtg | 60 |
| tcagaggttt tcaccgtcat caccgaaacg cgcgaggcag cagatcaatt cgcgcgcgaa | 120 |
| ggcgaagcgg catgcattta cgttgacacc atcgaatggt gcaaaacctt tcgcggtatg | 180 |
| gcatgatagc gcccggaaga gagtcaattc agggtggtga atgtgaaacc agtaacgtta | 240 |
| tacgatgtcg cagagtatgc cggtgtctct tatcagaccg tttcccgcgt ggtgaaccag | 300 |
| gccagccacg tttctgcgaa aacgcgggaa aaagtggaag cggcgatggc ggagctgaat | 360 |
| tacattccca accgcgtggc acaacaactg gcgggcaaac agtcgttgct gattggcgtt | 420 |
| gccacctcca gtctggccct gcacgcgccg tcgcaaattg tcgcggcgat taaatctcgc | 480 |
| gccgatcaac tgggtgccag cgtggtggtg tcgatgctag aacgaagcgg cgtcgaagcc | 540 |
| tgtaaagcgg cggtgcacaa tcttctcgcg caacgcgtca gtgggctgat cattaactat | 600 |
| ccgctggatg accaggatgc cattgctgtg gaagctgcct gcactaatgt tccggcgtta | 660 |
| tttcttgatg tctctgacca gacacccatc aacagtatta ttttctccca tgaagacggt | 720 |
| acgcgactgg gcgtggagca tctggtcgca ttgggtcacc agcaaatcgc gctgttagcg | 780 |
| ggcccattaa gttctgtctc ggcgcgtctg cgtctggctg gctggcataa atatctcact | 840 |
| cgcaatcaaa ttcagccgat agcggaacgg gaaggcgact ggagtgccat gtccggtttt | 900 |
| caacaaacca tgcaaatgct gaatgagggc atcgttccca ctgcgatgct ggttgccaac | 960 |
| gatcagatgg cgctgggcgc aatgcgcgcc attaccgagt ccgggctgcg cgttggtgcg | 1020 |
| gatatctcgg tagtgggata cgacgatacc gaagacagct catgttatat cccgccgtca | 1080 |
| accaccatca acaggatttt cgcctgctg ggcaaaccag cgtggaccg cttgctgcaa | 1140 |
| ctctctcagg ccaggcggt gaagggcaat cagctgttgc ccgtctcact ggtgaaaaga | 1200 |
| aaaaccaccc tggcgcccaa tacgcaaacc gcctctcccc gcgcgttggc cgattcatta | 1260 |
| atgcagctgg cacgacaggt ttcccgactg gaaagcgggc agtgagcgca acgcaattaa | 1320 |
| tgtgagttag cgcgaattga tctggtttga cagcttatca tcgactgcac ggtgcaccaa | 1380 |
| tgcttctggc gtcaggcagc catcggaagc tgtggtatgg ctgtgcaggt cgtaaatcac | 1440 |
| tgcataattc gtgtcgctca aggcgcactc ccgttctgga taatgttttt tgcgccgaca | 1500 |
| tcataacggt tctggcaaat attctgaaat gagctgttga caattaatca tccggctcgt | 1560 |

```
ataatgtgtg gaattgtgag cggataacaa tttcacacag gaaacagcgc cgctgagaaa    1620
aagcgaagcg gcactgctct ttaacaattt atcagacaat ctgtgtgggc actcgaccgg    1680
aattatcgat taactttatt attaaaaatt aaagaggtat atattaatgt atcgattaaa    1740
taaggaggaa taaccatgt gtgcgacctc ttctcaattt actcagatta ccgagcataa    1800
ttcccgtcgt tccgcaaact atcagccaaa cctgtggaat ttcgaattcc tgcaatccct    1860
ggagaacgac ctgaaagtgg aaaagctgga ggagaaagcg accaaactgg aggaagaagt    1920
tcgctgcatg atcaaccgtg tagacaccca gccgctgtcc ctgctggagc tgatcgacga    1980
tgtgcagcgc ctgggtctga cctacaaatt tgaaaaagac atcattaaag ccctggaaaa    2040
catcgtactg ctggacgaaa acaaaaagaa caaatctgac ctgcacgcaa ccgctctgtc    2100
tttccgtctg ctgcgtcagc acggtttcga ggtttctcag gatgttttg agcgtttcaa     2160
ggataaagaa ggtggtttca gcggtgaact gaaaggtgac gtccaaggcc tgctgagcct    2220
gtatgaagcg tcttacctgg gtttcgaggg tgagaacctg ctggaggagg cgcgtacctt    2280
ttccatcacc cacctgaaga acaacctgaa agaaggcatt aataccaagg ttgcagaaca    2340
agtgagccac gccctggaac tgccatatca ccagcgtctg caccgtctgg aggcacgttg    2400
gttcctggat aaatacgaac cgaaagaacc gcatcaccag ctgctgctgg agctggcgaa    2460
gctggatttt aacatggtac agaccctgca ccagaaagag ctgcaagatc tgtcccgctg    2520
gtggaccgag atgggcctgg ctagcaaact ggattttgta cgcgaccgcc tgatggaagt    2580
ttatttctgg gcactgggta tggcgccaga cccgcagttt ggtgaatgtc gcaaagctgt    2640
tactaaaatg tttggtctgg tgacgatcat cgatgacgtg tatgacgttt atggcactct    2700
ggacgaactg caactgttca ccgatgctgt agagcgctgg gacgttaacg ctattaacac    2760
cctgccggac tatatgaaac tgtgtttcct ggcactgtac aacaccgtta acgacacgtc    2820
ctattctatt ctgaaagaga aaggtcataa caacctgtcc tatctgacga aaagctggcg    2880
tgaactgtgc aaagcctttc tgcaagaggc gaaatggtcc aacaacaaaa ttatcccggc    2940
tttctccaag tacctggaaa acgccagcgt ttcctcctcc ggtgtagcgc tgctggcgcc    3000
gtcttacttt tccgtatgcc agcagcagga agacatctcc gaccacgcgc tgcgttccct    3060
gaccgacttc catggtctgg tgcgttctag ctgcgttatc ttccgcctgt gcaacgatct    3120
ggccacctct gcggcggagc tggaacgtgg cgagactacc aattctatca ttagctacat    3180
gcacgaaaac gatggtacca gcgaggaaca ggcccgcgaa gaactgcgta aactgatcga    3240
cgccgaatgg aaaagatga atcgtgaacg cgttagcgac tccaccctgc tgcctaaagc    3300
gttcatggaa atcgcagtta acatggcacg tgtttcccac tgcacctacc agtatggcga    3360
tggtctgggt cgcccagact acgcgactga aaaccgcatc aaactgctgc tgattgaccc    3420
tttcccgatt aaccagctga tgtatgtcta actgcatcgc ccttaggagg taaaaaaaaa    3480
tgactgccga caacaatagt atgccccatg gtgcagtatc tagttacgcc aaattagtgc    3540
aaaaccaaac acctgaagac atttttggaag agtttcctga aattattcca ttacaacaaa    3600
gacctaatac ccgatctagt gagacgtcaa atgacgaaag cggagaaaca tgttttttctg   3660
gtcatgatga ggagcaaatt aagttaatga atgaaaattg tattgttttg gattgggacg    3720
ataatgctat tggtgccggt accaagaaag tttgtcattt aatggaaaat attgaaaagg    3780
gtttactaca tcgtgcattc tccgtcttta ttttcaatga acaaggtgaa ttacttttac    3840
aacaaagagc cactgaaaaa ataacttttcc ctgatctttg gactaacaca tgctgctctc    3900
atccactatg tattgatgac gaattaggtt tgaagggtaa gctagcgat aagattaagg     3960
```

```
gcgctattac tgcggcggtg agaaaactag atcatgaatt aggtattcca gaagatgaaa    4020
ctaagacaag gggtaagttt cacttttaa acagaatcca ttacatggca ccaagcaatg    4080
aaccatgggg tgaacatgaa attgattaca tcctatttta taagatcaac gctaaagaaa    4140
acttgactgt caacccaaac gtcaatgaag ttagagactt caaatgggtt tcaccaaatg    4200
atttgaaaac tatgtttgct gacccaagtt acaagtttac gccttggttt aagattattt    4260
gcgagaatta cttattcaac tggtgggagc aattagatga cctttctgaa gtggaaaatg    4320
acaggcaaat tcatagaatg ctataacaac gcgtcctgca gctggtacca tatgggaatt    4380
cgaagctttc tagaacaaaa actcatctca gaagaggatc tgaatagcgc cgtcgaccat    4440
catcatcatc atcattgagt ttaaacggtc tccagcttgg ctgttttggc ggatgagaga    4500
agattttcag cctgatacag attaaatcag aacgcagaag cggtctgata aacagaattt    4560
tgcctggcgg cagtagcgcg gtggtcccac ctgaccccat gccgaactca gaagtgaaac    4620
gccgtagcgc cgatggtagt gtgggtctc cccatgcgag agtagggaac tgccaggcat    4680
caaataaaac gaaaggctca gtcgaaagac tgggcctttc gttttatctg ttgtttgtcg    4740
gtgaacgctc tcctgagtag acaaatccg ccgggagcgg atttgaacgt tgcgaagcaa    4800
cggcccggag ggtggcgggc aggacgcccg ccataaactg ccaggcatca aattaagcag    4860
aaggccatcc tgacggatgg cctttttgcg tttctacaaa ctcttttgt ttatttttct    4920 aaatacattc aaatatgtat ccgcttaacc ggaattgcca gctggggcgc cctctggtaa    4980
ggttgggaag ccctgcaaag taaactggat ggctttctcg ccgccaagga tctgatggcg    5040
caggggatca agctctgatc aagagacagg atgaggatcg tttcgcatga ttgaacaaga    5100
tggattgcac gcaggttctc cggccgcttg ggtggagagg ctattcggct atgactgggc    5160
acaacagaca atcggctgct ctgatgccgc cgtgttccgg ctgtcagcgc aggggcgccc    5220
ggttcttttt gtcaagaccg acctgtccgg tgccctgaat gaactgcaag acgaggcagc    5280
gcggctatcg tggctggcca cgacgggcgt tccttgcgca gctgtgctcg acgttgtcac    5340
tgaagcggga agggactggc tgctattggg cgaagtgccg gggcaggatc tcctgtcatc    5400
tcaccttgct cctgccgaga aagtatccat catggctgat gcaatgcggc ggctgcatac    5460
gcttgatccg gctacctgcc cattcgacca ccaagcgaaa catcgcatcg agcgagcacg    5520
tactcggatg aagccggtc ttgtcgatca ggatgatctg gacgaagagc atcaggggct    5580
cgcgccagcc gaactgttcg ccaggctcaa ggcgagcatg cccgacggcg aggatctcgt    5640
cgtgacccat ggcgatgcct gcttgccgaa tatcatggtg aaaatggcc gcttttctgg    5700 attcatcgac tgtggccggc tgggtgtggc ggaccgctat caggacatag cgttggctac    5760
ccgtgatatt gctgaagagc ttggcggcga atgggctgac cgcttcctcg tgctttacgg    5820
tatcgccgct cccgattcgc agcgcatcgc cttctatcgc cttcttgacg agttcttctg    5880
acatgaccaa aatcccttaa cgtgagtttt cgttccactg agcgtcagac cccgtagaaa    5940
agatcaaagg atcttcttga gatccttttt ttctgcgcgt aatctgctgc ttgcaaacaa    6000
aaaaaccacc gctaccagcg gtggtttgtt tgccggatca agagctacca actctttttc    6060
cgaaggtaac tggcttcagc agagcgcaga taccaaatac tgtccttcta gtgtagccgt    6120
agttaggcca ccacttcaag aactctgtag caccgcctac atacctcgct ctgctaatcc    6180
tgttaccagt ggctgctgcc agtggcgata agtcgtgtct taccgggttg gactcaagac    6240
gatagttacc ggataaggcg cagcggtcgg gctgaacggg gggttcgtgc acacagccca    6300
gcttggagcg aacgacctac accgaactga gatacctaca gcgtgagcta tgagaaagcg    6360
```

```
ccacgcttcc cgaagggaga aaggcggaca ggtatccggt aagcggcagg gtcggaacag    6420
gagagcgcac gagggagctt ccaggggaa  acgcctggta tctttatagt cctgtcgggt    6480
ttcgccacct ctgacttgag cgtcgatttt tgtgatgctc gtcaggggg  cggagcctat    6540 ggaaaaacgc cagcaacgcg gccttttac  ggttcctggc cttttgctgg cttttgctc     6600 acatgttctt tcctgcgtta tcccctgatt ctgtggataa ccgtattacc gcctttgagt    6660
gagctgatac cgctcgccgc agccaacga  ccgagcgcag cgagtcagtg agcgaggaag    6720
cggaagagcg cctgatgcgg tattttctcc ttacgcatct gtgcggtatt tcacaccgca    6780
tatggtgcac tctcagtaca atctgctctg atgccgcata gttaagccag tatacactcc    6840
gctatcgcta cgtgactggg tcatggctgc gccccgacac ccgccaacac ccgctgacgc    6900
gccctgacgg gc                                                       6912

<210> SEQ ID NO 51
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 51
ttgtctgctc ccggcatccg cttacagaca agctgtgacc gtctccggga gctgcatgtg      60
tcagaggttt tcaccgtcat caccgaaacg cgcgaggcag cagatcaatt cgcgcgcgaa     120
ggcgaagcgg catgcattta cgttgacacc atcgaatggt gcaaaacctt cgcggtatg     180 gcatgatagc gcccggaaga gagtcaattc agggtggtga atgtgaaacc agtaacgtta    240
tacgatgtcg cagagtatgc cggtgtctct tatcagaccg tttcccgcgt ggtgaaccag    300
gccagccacg tttctgcgaa aacgcgggaa aaagtggaag cggcgatggc ggagctgaat    360
tacattccca accgcgtggc acaacaactg gcgggcaaac agtcgttgct gattggcgtt    420
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
tgtaaagcgg cggtgcacaa tcttctcgcg caacgcgtca gtgggctgat cattaactat    600
ccgctggatg accaggatgc cattgctgtg gaagctgcct gcactaatgt tccggcgtta    660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca acaggatttt cgcctgctg  gggcaaacca gcgtggaccg cttgctgcaa   1140
ctctctcagg ccaggcggt  gaagggcaat cagctgttgc ccgtctcact ggtgaaagaa   1200
aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggttga  cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
```

```
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aagaggtat atattaatgt atcgattaaa    1740
taaggaggaa taaaccatgt gtgcgacctc ttctcaattt actcagatta ccgagcataa   1800
ttcccgtcgt tccgcaaact atcagccaaa cctgtgaat ttcgaattcc tgcaatccct    1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgttttg agcgtttcaa    2160 ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga caacctgaa agaaggcatt aataccaagg ttgcagaaca    2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gacccacgcg tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaaagatga atcgtgaacg cgttagcgac tccaccctgc tgcctaaagc   3300
gttcatggaa atcgcagtta acatggcacg tgtttcccac tgcacctacc agtatggcga   3360
tggtctgggt cgcccagact acgcgactga aaaccgcatc aaactgctgc tgattgaccc   3420
tttcccgatt aaccagctga tgtatgtcta actgcattcg cccttaggag gtaaaaaaac   3480
atgagttttg atattgccaa atacccgacc ctggcactgg tcgactccac ccaggagtta   3540
cgactgttgc cgaaagagag tttaccgaaa ctctgcgacg aactgcgccg ctatttactc   3600
gacagcgtga gccgttccag cgggcacttc gcctccgggc tgggcacggt cgaactgacc   3660
gtggcgctgc actatgtcta caacaccccg tttgaccaat tgatttggga tgtgggcat    3720 caggcttatc cgcataaaat tttgaccgga cgccgcgaca aaatcggcac catccgtcag   3780
aaaggcggtc tgcacccgtt cccgtggcgc ggcgaaagcg aatatgacgt attaagcgtc   3840
gggcattcat caacctccat cagtgccgga attggtattg cggttgctgc cgaaaaagaa   3900
```

```
ggcaaaaatc gccgcaccgt ctgtgtcatt ggcgatggcg cgattaccgc aggcatggcg    3960
tttgaagcga tgaatcacgc gggcgatatc cgtcctgata tgctggtgat tctcaacgac    4020
aatgaaatgt cgatttccga aaatgtcggc gcgctcaaca accatctggc acagctgctt    4080
tccggtaagc tttactcttc actgcgcgaa ggcgggaaaa agttttctc tggcgtgccg     4140
ccaattaaag agctgctcaa acgcaccgaa gaacatatta aggcatggt agtgcctggc     4200
acgttgtttg aagagctggg ctttaactac atcggcccgg tggacggtca cgatgtgctg    4260
gggcttatca ccacgctaaa gaacatgcgc gacctgaaag gcccgcagtt cctgcatatc    4320
atgaccaaaa aaggtcgtgg ttatgaaccg gcagaaaaag acccgatcac tttccacgcc    4380
gtgcctaaat tgatccctc cagcggttgt tgccgaaaa gtagcggcgg tttgccgagc      4440
tattcaaaaa tctttggcga ctggttgtgc gaaacggcag cgaaagacaa caagctgatg    4500
gcgattactc cggcgatgcg tgaaggttcc ggcatggtcg agttttcacg taaattcccg    4560
gatcgctact tcgacgtggc aattgccgag caacacgcgg tgacctttgc tgcgggtctg    4620
gcgattggtg ggtacaaacc cattgtcgcg atttactcca cttcctgca acgcgcctat     4680
gatcaggtgc tgcatgacgt ggcgattcaa aagcttccgg tcctgttcgc catcgaccgc    4740
gcgggcattg ttggtgctga cggtcaaacc catcaggtg cttttgatct ctcttacctg     4800
cgctgcatac cggaaatggt cattatgacc ccgagcgatg aaaacgaatg tcgcagatg     4860
ctctataccg gctatcacta taacgatggc ccgtcagcgg tgcgctaccc gcgtggcaac    4920
gcggtcggcg tggaactgac gccgctggaa aaactaccaa ttggcaaagg cattgtgaag    4980
cgtcgtggcg agaaactggc gatccttaac tttggtacgc tgatgccaga agcggcgaaa    5040
gtcgccgaat cgctgaacgc cacgctggtc gatatgcgtt ttgtgaaacc gcttgatgaa    5100
gcgttaattc tggaaatggc cgccagccat gaagcgctgg tcaccgtaga agaaaacgcc    5160
attatgggcg gcgcaggcag cggcgtgaac gaagtgctga tggcccatcg taaaccagta    5220
cccgtgctga acattggcct gccggacttc tttattccgc aaggaactca ggaagaaatg    5280
cgcgccgaac tcggcctcga tgccgctggt atggaagcca aaatcaaggc ctggctggca    5340
taactgcagc tggtaccata tgggaattcg aagctttcta gaacaaaaac tcatctcaga    5400
agaggatctg aatagcgccg tcgaccatca tcatcatcat cattgagttt aaacggtctc    5460
cagcttggct gttttggcgg atgagagaag attttcagcc tgatacagat taaatcagaa    5520
cgcagaagcg gtctgataaa acagaatttg cctggcggca gtagcgcggt ggtcccacct    5580
gacccccatgc cgaactcaga agtgaaacgc cgtagcgccg atggtagtgt ggggtctccc   5640
catgcgagag tagggaactg ccaggcatca aataaaacga aggctcagt cgaaagactg     5700
ggcctttcgt tttatctgtt gtttgtcggt gaacgctctc ctgagtagga caaatccgcc    5760
gggagcggat ttgaacgttg cgaagcaacg gcccggaggg tggcgggcag gacgcccgcc    5820
ataaactgcc aggcatcaaa ttaagcagaa ggccatcctg acggatggcc ttttgcgtt    5880
tctacaaact cttttgtttt atttttctaa atacattcaa atatgtatcc gcttaaccgg    5940
aattgccagc tggggcgccc tctggtaagg ttgggaagcc ctgcaaagta aactggatgg    6000
ctttctcgcc gccaaggatc tgatggcgca ggggatcaag ctctgatcaa gagacaggat    6060
gaggatcgtt tcgcatgatt gaacaagatg gattgcacgc aggttctccg gccgcttggg    6120
tggagaggct attcggctat gactgggcac aacagacaat cggctgctct gatgccgccg    6180
tgttccggct gtcagcgcag gggcgcccgg ttctttttgt caagaccgac ctgtccggtg    6240
ccctgaatga actgcaagac gaggcagcgc ggctatcgtg gctggccacg acgggcgttc    6300
```

```
cttgcgcagc tgtgctcgac gttgtcactg aagcgggaag ggactggctg ctattgggcg   6360
aagtgccggg gcaggatctc ctgtcatctc accttgctcc tgccgagaaa gtatccatca   6420
tggctgatgc aatgcggcgg ctgcatacgc ttgatccggc tacctgccca ttcgaccacc   6480
aagcgaaaca tcgcatcgag cgagcacgta ctcggatgga agccggtctt gtcgatcagg   6540
atgatctgga cgaagagcat caggggctcg cgccagccga actgttcgcc aggctcaagg   6600
cgagcatgcc cgacgcgag gatctcgtcg tgacccatgg cgatgcctgc ttgccgaata   6660
tcatggtgga aaatggccgc ttttctggat tcatcgactg tggccggctg ggtgtggcgg   6720
accgctatca ggacatagcg ttggctaccc gtgatattgc tgaagagctt ggcggcgaat   6780
gggctgaccg cttcctcgtg ctttacggta tcgccgctcc cgattcgcag cgcatcgcct   6840
tctatcgcct tcttgacgag ttcttctgac gcatgaccaa aatcccttaa cgtgagtttt   6900
cgttccactg agcgtcagac cccgtagaaa agatcaaagg atcttcttga tccttttt    6960
ttctgcgcgt aatctgctgc ttgcaaacaa aaaaaccacc gctaccagcg gtggtttgtt   7020
tgccggatca agagctacca actcttttc cgaaggtaac tggcttcagc agagcgcaga   7080
taccaaatac tgtccttcta gtgtagccgt agttaggcca ccacttcaag aactctgtag   7140
caccgcctac atacctcgct ctgctaatcc tgttaccagt ggctgctgcc agtggcgata   7200
agtcgtgtct taccgggttg gactcaagac gatagttacc ggataaggcg cagcggtcgg   7260
gctgaacggg gggttcgtgc acacagccca gcttggagcg aacgacctac accgaactga   7320
gataccta cgcgtgagcta tgagaaagcg ccacgcttcc cgaagggaga aaggcggaca   7380
ggtatccggt aagcggcagg gtcggaacag gagagcgcac gagggagctt ccaggggga   7440
acgcctggta tctttatagt cctgtcgggt ttcgccacct ctgacttgag cgtcgatttt   7500
tgtgatgctc gtcaggggg cggagcctat ggaaaaacgc cagcaacgcg gcctttttac   7560
ggttcctggc cttttgctgg ccttttgctc acatgttctt tcctgcgtta tcccctgatt   7620
ctgtggataa ccgtattacc gcctttgagt gagctgatac cgctcgccgc agccgaacga   7680
ccgagcgcag cgagtcagtg agcgaggaag cggaagagcg cctgatgcgg tatttttctcc   7740
ttacgcatct gtgcggtatt tcacaccgca tatggtgcac tctcagtaca atctgctctg   7800
atgccgcata gttaagccag tatacactcc gctatcgcta cgtgactggg tcatggctgc   7860
gccccgacac ccgccaacac ccgctgacgc gccctgacgg gc                       7902

<210> SEQ ID NO 52
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 52
ctggcgtaat agcgaagagg cccgcaccga tcgcccttcc caacagttgc gcagcctgaa     60
tggcgaatgg cgcctgatgc ggtattttct ccttacgcat ctgtgcggta tttcacaccg    120
catatggtgc actctcagta caatctgctc tgatgccgca tagttaagcc agccccgaca    180
cccgccaaca cccgctgacg agcttagtaa agccctcgct atttttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
```

```
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt aactttgtt    1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
tttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct ttttacacc gttttcatct gtgcatatgg    2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgttttgc gtgagccatg agaacgaacc attgagatca    2580
tacttacttt gcatgtcact caaaaatttt gcctcaaaac tggtgagctg aattttttgca  2640
gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
```

```
cattggttaa gccttttaaa ctcatggtag ttattttcaa gcattaacat gaacttaaat   2940
tcatcaaggc taatctctat atttgccttg tgagttttct tttgtgttag ttcttttaat   3000
aaccactcat aaatcctcat agagtatttg ttttcaaaag acttaacatg ttccagatta   3060
tattttatga attttttttaa ctggaaaaga taaggcaata tctcttcact aaaaactaat   3120 tctaatttttt cgcttgagaa cttggcatag tttgtccact ggaaaatctc aaagccttta   3180
accaaaggat tcctgatttc cacagttctc gtcatcagct ctctggttgc tttagctaat   3240
acaccataag catttttccct actgatgttc atcatctgag cgtattggtt ataagtgaac   3300
gataccgtcc gttctttcct tgtagggttt caatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac ctttgctgga aaacttgtaa attctgctag accctctgta   3600
aattccgcta gacctttgtg tgttttttttt gtttatattc aagtggttat aatttataga   3660
ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtcttttc gtgacattca   3900 gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
gcgttttatg gcgggtctgc tatgtggtgc tatctgactt tttgctgttc agcagttcct   4080
gccctctgat tttccagtct gaccacttcg gattatcccg tgacaggtca ttcagactgg   4140
ctaatgcacc cagtaaggca gcggtatcat caacaggctt accgtcttta ctgtcgggaa   4200
ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta acaatttatc agacaatctg tgtgggcact   4380
cgaccggaat tatcgattaa ctttattatt aaaaattaaa gaggtatata ttaatgtatc   4440
gattaaataa ggaggaataa accatgtgtg cgacctcttc tcaatttact cagattaccg   4500
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
aagaagttcg ctgcatgatc aaccgtgtag acacccagcc gctgtccctg ctggagctga   4680
tcgacgatgt gcagcgcctg ggtctgacct acaaatttga aaaagacatc attaaagccc   4740
tggaaaacat cgtactgctg gacgaaaaca aaaagaacaa atctgacctg cacgcaaccg   4800
ctctgtcttt ccgtctgctg cgtcagcacg gtttcgaggt ttctcaggat gttttttgagc   4860 gtttcaagga taagaaggt ggtttcagcg gtgaactgaa aggtgacgtc caaggcctgc   4920
tgagcctgta tgaagcgtct tacctgggtt tcgagggtga aacctgctg gaggaggcgc   4980 gtaccttttc catcacccac ctgaagaaca acctgaaaga aggcattaat accaaggttg   5040
cagaacaagt gagccacgcc ctggaactgc catatcacca gcgtctgcac cgtctggagg   5100
cacgttggtt cctggataaa tacgaaccga aagaaccgca tcaccagctg ctgctggagc   5160
tggcgaagct ggatttttaac atggtacaga ccctgcacca gaaagagctg caagatctgt   5220
cccgctggtg gaccgagatg ggcctggcta gcaaactgga ttttgtacgc gaccgcctga   5280
```

| | |
|---|---:|
| tggaagttta tttctgggca ctgggtatgg cgccagaccc gcagtttggt gaatgtcgca | 5340 |
| aagctgttac taaaatgttt ggtctggtga cgatcatcga tgacgtgtat gacgtttatg | 5400 |
| gcactctgga cgaactgcaa ctgttcaccg atgctgtaga gcgctgggac gttaacgcta | 5460 |
| ttaacaccct gccggactat atgaaactgt gtttcctggc actgtacaac accgttaacg | 5520 |
| acacgtccta ttctattctg aaagagaaag gtcataacaa cctgtcctat ctgacgaaaa | 5580 |
| gctggcgtga actgtgcaaa gcctttctgc aagaggcgaa atggtccaac aacaaaatta | 5640 |
| tcccggcttt ctccaagtac ctggaaaacg ccagcgtttc ctcctccggt gtagcgctgc | 5700 |
| tggcgccgtc ttacttttcc gtatgccagc agcaggaaga catctccgac cacgcgctgc | 5760 |
| gttccctgac cgacttccat ggtctggtgc gttctagctg cgttatcttc cgcctgtgca | 5820 |
| acgatctggc cacctctgcg gcggagctgg aacgtggcga gactaccaat tctatcatta | 5880 |
| gctacatgca cgaaaacgat ggtaccagcg aggaacaggc ccgcgaagaa ctgcgtaaac | 5940 |
| tgatcgacgc cgaatggaaa aagatgaatc gtgaacgcgt tagcgactcc accctgctgc | 6000 |
| ctaaagcgtt catggaaatc gcagttaaca tggcacgtgt tcccactgca acctaccagt | 6060 |
| atggcgatgg tctgggtcgc ccagactacg cgactgaaaa ccgcatcaaa ctgctgctga | 6120 |
| ttgacccttt cccgattaac cagctgatgt atgtctaact gcagctggta ccatatggga | 6180 |
| attcgaagct ttctagaaca aaaactcatc tcagaagagg atctgaatag cgccgtcgac | 6240 |
| catcatcatc atcatcattg agtttaaacg gtctccagct tggctgtttt ggcggatgag | 6300 |
| agaagatttt cagcctgata cagattaaat cagaacgcag aagcggtctg ataaaacaga | 6360 |
| atttgcctgg cggcagtagc gcggtggtcc cacctgaccc catgccgaac tcagaagtga | 6420 |
| aacgccgtag cgccgatggt agtgtggggt ctccccatgc gagagtaggg aactgccagg | 6480 |
| catcaaataa aacgaaaggc tcagtcgaaa gactgggcct ttcgttttat ctgttgtttg | 6540 |
| tcggtgaacg ctctcctgag taggacaaat ccgccgggag cggatttgaa cgttgcgaag | 6600 |
| caacggcccg gagggtggcg gcaggacgc ccgccataaa ctgccaggca tcaaattaag | 6660 |
| cagaaggcca tcctgacgga tggcctttttt gcgtttctac aaactctttt tgtttatttt | 6720 |
| tctaaataca ttcaaatatg tatccgctca tgagacaata accctgataa atgcttcaat | 6780 |
| aat | 6783 |

<210> SEQ ID NO 53
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 53

| | |
|---|---:|
| cccgtcttac tgtcgggaat tcgcgttggc cgattcatta atgcagatta ttgaagcatt | 60 |
| tatcagggtt attgtctcat gagcggatac atatttgaat gtatttagaa aaataaacaa | 120 |
| aaagagtttg tagaaacgca aaaaggccat ccgtcaggat ggccttctgc ttaatttgat | 180 |
| gcctggcagt ttatggcggg cgtcctgccc gccaccctcc gggccgttgc ttcgcaacgt | 240 |
| tcaaatccgc tcccggcgga tttgtcctac tcaggagagc gttcaccgac aaacaacaga | 300 |
| taaaacgaaa ggcccagtct ttcgactgag cctttcgttt tatttgatgc ctggcagttc | 360 |
| cctactctcg catggggaga ccccacacta ccatcggcgc tacggcgttt cacttctgag | 420 |
| ttcggcatgg ggtcaggtgg gaccaccgcg ctactgccgc caggcaaatt ctgttttatc | 480 |
| agaccgcttc tgcgttctga tttaatctgt atcaggctga aaatcttctc tcatccgcca | 540 |

-continued

```
aaacagccaa gctggagacc gtttaaactc aatgatgatg atgatgatgg tcgacggcgc    600
tattcagatc ctcttctgag atgagttttt gttctagaaa gcttcgaatt cccatatggt    660
accagctgca gttagacata catcagctgg ttaatcggga aagggtcaat cagcagcagt    720
ttgatgcggt tttcagtcgc gtagtctggg cgacccagac catcgccata ctggtaggtg    780
cagtgggaaa cacgtgccat gttaactgcg atttccatga acgctttagg cagcagggtg    840
gagtcgctaa cgcgttcacg attcatcttt ttccattcgg cgtcgatcag tttacgcagt    900
tcttcgcggg cctgttcctc gctggtacca tcgttttcgt gcatgtagct aatgatagaa    960
ttggtagtct cgccacgttc cagctccgcc gcagaggtgg ccagatcgtt gcacaggcgg   1020
aagataacgc agctagaacg caccagacca tggaagtcgg tcagggaacg cagcgcgtgg   1080
tcggagatgt cttcctgctg ctggcatacg gaaaagtaag acggcgccag cagcgctaca   1140
ccggaggagg aaacgctggc gttttccagg tacttggaga agccgggat aatttgttg    1200 ttggaccatt tcgcctcttg cagaaaggct ttgcacagtt cacgccagct tttcgtcaga   1260
taggacaggt tgttatgacc tttctctttc agaatagaat aggacgtgtc gttaacggtg   1320
ttgtacagtg ccaggaaaca cagtttcata tagtccggca gggtgttaat agcgttaacg   1380
tcccagcgct ctacagcatc ggtgaacagt tgcagttcgt ccagagtgcc ataaacgtca   1440
tacacgtcat cgatgatcgt caccagacca aacattttag taacagcttt gcgacattca   1500
ccaaactgcg ggtctggcgc catacccagt gcccagaaat aaacttccat caggcggtcg   1560
cgtacaaaat ccagtttgct agccaggccc atctcggtcc accagcggga cagatcttgc   1620
agctcttctc ggtgcagggt ctgtaccatg ttaaaatcca gcttcgccag ctccagcagc   1680
agctggtgat gcggttcttt cggttcgtat ttatccagga accaacgtgc ctccagacgg   1740
tgcagacgct ggtgatatgg cagttccagg gcgtggctca cttgttctgc aaccttggta   1800
ttaatgcctt ctttcaggtt gttcttcagg tgggtgatgg aaaaggtacg cgcctcctcc   1860
agcaggttct caccctcgaa acccaggtaa gacgcttcat acaggctcag caggccttgg   1920
acgtcacctt tcagttcacc gctgaaacca ccttctttat ccttgaaacg ctcaaaaaca   1980
tcctgagaaa cctcgaaacc gtgctgacgc agcagacgga aagacagagc ggttgcgtgc   2040
aggtcagatt tgttcttttt gttttcgtcc agcagtacga tgttttccag ggctttaatg   2100
atgtcttttt caaatttgta ggtcagaccc aggcgctgca catcgtcgat cagctccagc   2160
agggacagcg gctgggtgtc tacacggttg atcatgcagc gaacttcttc ctccagtttg   2220 gtcgcttttct cctccagctt ttccacttc aggtcgttct ccaggattg caggaattcg   2280 aaattccaca ggtttggctg atagtttgcg gaacgacggg aattatgctc ggtaatctga   2340
gtaaattgag aagaggtcgc acacatggtt tattcctcct tatttaatcg atacattaat   2400
atatacctct ttaatttta ataataaagt taatcgataa ttccggtcga gtgcccacac   2460
agattgtctg ataaattgtt aaagagcagt gccgcttcgc ttttcctcag cggcgctgtt   2520
tcctgtgtga aattgttatc cgctcacaat tccacacatt atacgagccg gatgattaat   2580
tgtcaacagc tcatttcaga atctggcgta atagcgaaga ggcccgcacc gatcgccctt   2640
cccaacagtt gcgcagcctg aatggcgaat ggcgcctgat gcggtatttt ctccttacgc   2700
atctgtgcgg tatttcacac cgcatatggt gcactctcag tacaatctgc tctgatgccg   2760
catagttaag ccagccccga cacccgccaa cacccgctga cgagcttagt aaagccctcg   2820
ctagatttta atgcggatgt tgcgattact tcgccaacta ttgcgataac aagaaaaagc   2880
cagcctttca tgatatatct cccaatttgt gtagggctta ttatgcacgc ttaaaaataa   2940
```

-continued

```
taaaagcaga cttgacctga tagtttggct gtgagcaatt atgtgcttag tgcatctaac    3000
gcttgagtta agccgcgccg cgaagcggcg tcggcttgaa cgaattgtta gacattattt    3060
gccgactacc ttggtgatct cgcctttcac gtagtggaca aattcttcca actgatctgc    3120
gcgcgaggcc aagcgatctt cttcttgtcc aagataagcc tgtctagctt caagtatgac    3180
gggctgatac tgggccggca ggcgctccat tgcccagtcg gcagcgacat ccttcggcgc    3240
gattttgccg gttactgcgc tgtaccaaat gcgggacaac gtaagcacta catttcgctc    3300
atcgccagcc cagtcgggcg gcgagttcca tagcgttaag gtttcattta gcgcctcaaa    3360
tagatcctgt tcaggaaccg gatcaaagag ttcctccgcc gctggaccta ccaaggcaac    3420
gctatgttct cttgcttttg tcagcaagat agccagatca atgtcgatcg tggctggctc    3480
gaagatacct gcaagaatgt cattgcgctg ccattctcca aattgcagtt cgcgcttagc    3540
tggataacgc cacggaatga tgtcgtcgtg cacaacaatg gtgacttcta cagcgcggag    3600
aatctcgctc tctccagggg aagccgaagt ttccaaaagg tcgttgatca aagctcgccg    3660
cgttgtttca tcaagcctta cggtcaccgt aaccagcaaa tcaatatcac tgtgtggctt    3720
caggccgcca tccactgcgg agccgtacaa atgtacggcc agcaacgtcg gttcgagatg    3780
gcgctcgatg acgccaacta cctctgatag ttgagtcgat acttcggcga tcaccgcttc    3840
cctcatgatg tttaactttg ttttagggcg actgccctgc tgcgtaacat cgttgctgct    3900
ccataacatc aaacatcgac ccacggcgta acgcgcttgc tgcttggatg cccgaggcat    3960
agactgtacc ccaaaaaaac agtcataaca agccatgaaa accgccactg cgccgttacc    4020
accgctgcgt tcggtcaagg ttctggacca gttgcgtgag cgcatacgct acttgcatta    4080
cagcttacga accgaacagg cttatgtcca ctgggttcgt gccttcatcc gtttccacgg    4140
tgtgcgtcac ccggcaacct tgggcagcag cgaagtcgag gcatttctgt cctggctggc    4200
gaacgagcgc aaggtttcgg tctccacgca tcgtcaggca ttggcggcct tgctgttctt    4260
ctacggcaag gtgctgtgca cggatctgcc ctggcttcag gagatcggaa gacctcggcc    4320
gtcgcggcgc ttgccggtgg tgctgacccc ggatgaagtg gttcgcatcc tcggtttttct   4380
ggaaggcgag catcgtttgt tcgcccagct tctgtatgga acgggcatgc ggatcagtga    4440
gggtttgcaa ctgcgggtca aggatctgga tttcgatcac ggcacgatca tcgtgcggga    4500
gggcaagggc tccaaggatc gggccttgat gttaccgag agcttggcac ccagcctgcg     4560
cgagcagggg aattaattcc cacgggtttt gctgcccgca aacgggctgt tctggtgttg    4620
ctagtttgtt atcagaatcg cagatccggc ttcagccggt ttgccggctg aaagcgctat    4680
ttcttccaga attgccatga tttttttcccc acgggaggcg tcactggctc ccgtgttgtc    4740
ggcagctttg attcgataag cagcatcgcc tgtttcaggc tgtctatgtg tgactgttga    4800
gctgtaacaa gttgtctcag gtgttcaatt tcatgttcta gttgctttgt tttactggtt    4860
tcacctgttc tattaggtgt tacatgctgt tcatctgtta cattgtcgat ctgttcatgg    4920
tgaacagctt tgaatgcacc aaaaactcgt aaaagctctg atgtatctat ctttttttaca   4980
ccgttttcat ctgtgcatat ggacagtttt ccctttgata tgtaacggtg aacagttgtt    5040
ctacttttgt ttgttagtct tgatgcttca ctgatagata caagagccat aagaacctca    5100
gatccttccg tatttagcca gtatgttctc tagtgtggtt cgttgttttt gcgtgagcca    5160
tgagaacgaa ccattgagat catacttact ttgcatgtca ctcaaaaatt ttgcctcaaa    5220
actggtgagc tgaattttttg cagttaaagc atcgtgtagt gttttctta gtccgttatg     5280
taggtaggaa tctgatgtaa tggttgttgg tattttgtca ccattcattt ttatctggtt    5340
```

-continued

```
gttctcaagt tcggttacga gatccatttg tctatctagt tcaacttgga aaatcaacgt    5400
atcagtcggg cggcctcgct tatcaaccac caatttcata ttgctgtaag tgtttaaatc    5460
tttacttatt ggtttcaaaa cccattggtt aagccttta aactcatggt agttattttc     5520
aagcattaac atgaacttaa attcatcaag gctaatctct atatttgcct tgtgagtttt    5580
cttttgtgtt agttctttta ataaccactc ataaatcctc atagagtatt tgttttcaaa    5640
agacttaaca tgttccagat tatattttat gaattttttt aactggaaaa gataaggcaa    5700
tatctcttca ctaaaaacta attctaattt ttcgcttgag aacttggcat agtttgtcca    5760
ctggaaaatc tcaaagcctt taaccaaagg attcctgatt tccacagttc tcgtcatcag    5820
ctctctggtt gctttagcta atacaccata agcattttcc ctactgatgt tcatcatctg    5880
agcgtattgg ttataagtga acgataccgt ccgttctttc cttgtagggt tttcaatcgt    5940
ggggttgagt agtgccacac agcataaaat tagcttggtt tcatgctccg ttaagtcata    6000
gcgactaatc gctagttcat ttgctttgaa acaactaat tcagacatac atctcaattg      6060
gtctaggtga ttttaatcac tataccaatt gagatgggct agtcaatgat aattactagt    6120
ccttttcctt tgagttgtgg gtatctgtaa attctgctag acctttgctg gaaaacttgt    6180
aaattctgct agaccctctg taaattccgc tagacctttg tgtgtttttt ttgtttatat    6240
tcaagtggtt ataatttata gaataaagaa agaataaaaa aagataaaaa gaatagatcc    6300
cagccctgtg tataactcac tactttagtc agttccgcag tattacaaaa ggatgtcgca    6360
aacgctgttt gctcctctac aaaacagacc ttaaaaccct aaaggcttaa gtagcaccct    6420
cgcaagctcg ggcaaatcgc tgaatattcc ttttgtctcc gaccatcagg cacctgagtc    6480
gctgtctttt tcgtgacatt cagttcgctg cgctcacggc tctggcagtg aatggggta    6540 aatggcacta caggcgcctt ttatggattc atgcaaggaa actacccata atacaagaaa    6600
agcccgtcac gggcttctca gggcgtttta tggcgggtct gctatgtggt gctatctgac    6660
tttttgctgt tcagcagttc ctgccctctg attttccagt ctgaccactt cggattatcc    6720
cgtgacaggt cattcagact ggctaatgca cccagtaagg cagcggtatc atcaacaggc    6780
tta                                                                  6783
```

<210> SEQ ID NO 54
<211> LENGTH: 7687
<212> TYPE: DNA
<213> ORGANISM: Artificial Sequence
<220> FEATURE:
<223> OTHER INFORMATION: Synthetic Construct

<400> SEQUENCE: 54

```
ctggcgtaat agcgaagagg cccgcaccga tcgcccttcc caacagttgc gcagcctgaa     60
tggcgaatgg cgcctgatgc ggtatttct ccttacgcat ctgtgcggta tttcacaccg    120
catatggtgc actctcagta caatctgctc tgatgccgca tagttaagcc agccccgaca    180
cccgccaaca cccgctgacg agcttagtaa agccctcgct agattttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
```

-continued

```
cgctccattg cccagtcggc agcgacatcc ttcggcgcga ttttgccggt tactgcgctg      660
taccaaatgc gggacaacgt aagcactaca tttcgctcat cgccagccca gtcgggcggc      720
gagttccata gcgttaaggt ttcatttagc gcctcaaata gatcctgttc aggaaccgga      780
tcaaagagtt cctccgccgc tggacctacc aaggcaacgc tatgttctct tgcttttgtc      840
agcaagatag ccagatcaat gtcgatcgtg gctggctcga agataccgtgc aagaatgtca     900 ttgcgctgcc attctccaaa ttgcagttcg cgcttagctg gataacgcca cggaatgatg      960
tcgtcgtgca caacaatggt gacttctaca gcgcggagaa tctcgctctc tccaggggaa     1020
gccgaagttt ccaaaaggtc gttgatcaaa gctcgccgcg ttgtttcatc aagccttacg     1080
gtcaccgtaa ccagcaaatc aatatcactg tgtggcttca ggccgccatc cactgcggag     1140
ccgtacaaat gtacggccag caacgtcggt tcgagatggc gctcgatgac gccaactacc     1200
tctgatagtt gagtcgatac ttcggcgatc accgcttccc tcatgatgtt aactttgtt     1260 ttagggcgac tgccctgctg cgtaacatcg ttgctgctcc ataacatcaa acatcgaccc     1320
acggcgtaac gcgcttgctg cttggatgcc cgaggcatag actgtacccc aaaaaaacag     1380
tcataacaag ccatgaaaac cgccactgcg ccgttaccac cgctgcgttc ggtcaaggtt     1440
ctggaccagt tgcgtgagcg catacgctac ttgcattaca gcttacgaac cgaacaggct     1500
tatgtccact gggttcgtgc cttcatccgt ttccacggtg tgcgtcaccc ggcaaccttg     1560
ggcagcagcg aagtcgaggc atttctgtcc tggctggcga acgagcgcaa ggtttcggtc     1620
tccacgcatc gtcaggcatt ggcggccttg ctgttcttct acggcaaggt gctgtgcacg     1680
gatctgccct ggcttcagga gatcggaaga cctcggccgt cgcggcgctt gccggtggtg     1740
ctgaccccgg atgaagtggt tcgcatcctc ggttttctgg aaggcgagca tcgtttgttc     1800
gcccagcttc tgtatggaac gggcatgcgg atcagtgagg gtttgcaact gcgggtcaag     1860
gatctggatt tcgatcacgg cacgatcatc gtgcggagg gcaagggctc caaggatcgg     1920
gccttgatgt tacccgagag cttggcaccc agcctgcgcg agcaggggaa ttaattccca     1980
cgggttttgc tgcccgcaaa cgggctgttc tggtgttgct agtttgttat cagaatcgca     2040
gatccggctt cagccggttt gccggctgaa agcgctattt cttccagaat tgccatgatt     2100
tttcccccac gggaggcgtc actggctccc gtgttgtcgg cagctttgat tcgataagca     2160
gcatcgcctg tttcaggctg tctatgtgtg actgttgagc tgtaacaagt tgtctcaggt     2220
gttcaatttc atgttctagt tgctttgttt tactggtttc acctgttcta ttaggtgtta     2280
catgctgttc atctgttaca ttgtcgatct gttcatggtg aacagctttg aatgcaccaa     2340
aaactcgtaa aagctctgat gtatctatct tttttacacc gttttcatct gtgcatatgg     2400
acagttttcc ctttgatatg taacggtgaa cagttgttct acttttgttt gttagtcttg     2460
atgcttcact gatagataca agagccataa gaacctcaga tccttccgta tttagccagt     2520
atgttctcta gtgtggttcg ttgttttttgc gtgagccatg agaacgaacc attgagatca     2580
tacttacttt gcatgtcact caaaaatttt gcctcaaaac tggtgagctg aattttttgca    2640 gttaaagcat cgtgtagtgt ttttcttagt ccgttatgta ggtaggaatc tgatgtaatg     2700
gttgttggta ttttgtcacc attcattttt atctggttgt tctcaagttc ggttacgaga     2760
tccatttgtc tatctagttc aacttggaaa atcaacgtat cagtcgggcg gcctcgctta     2820
tcaaccacca atttcatatt gctgtaagtg tttaaatctt tacttattgg tttcaaaacc     2880
cattggttaa gccttttaaa ctcatggtag ttattttcaa gcattaacat gaacttaaat     2940
tcatcaaggc taatctctat atttgccttg tgagtttttct tttgtgttag ttcttttaat     3000
```

```
aaccactcat aaatcctcat agagtatttg ttttcaaaag acttaacatg ttccagatta   3060
tattttatga atttttttaa ctggaaaaga taaggcaata tctcttcact aaaaactaat   3120
tctaattttt cgcttgagaa cttggcatag tttgtccact ggaaaatctc aaagccttta   3180
accaaaggat tcctgatttc cacagttctc gtcatcagct ctctggttgc tttagctaat   3240
acaccataag cattttccct actgatgttc atcatctgag cgtattggtt ataagtgaac   3300
gataccgtcc gttcttcct tgtagggttt tcaatcgtgg ggttgagtag tgccacacag    3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac ctttgctgga aaacttgtaa attctgctag accctctgta   3600
aattccgcta gaccttgtg tgtttttttt gtttatattc aagtggttat aatttataga    3660
ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtcttttc gtgacattca    3900 gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020 gcgtttatg gcgggtctgc tatgtggtgc tatctgactt tttgctgttc agcagttcct     4080
gccctctgat tttccagtct gaccacttcg gattatcccg tgacaggtca ttcagactgg   4140
ctaatgcacc cagtaaggca gcggtatcat caacaggctt acccgtctta ctgtcgggaa   4200
ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta caatttatc agacaatctg tgtgggcact    4380
cgaccggaat tatcgattaa ctttattatt aaaaattaaa gaggtatata ttaatgtatc   4440
gattaaataa ggaggaataa accatgtgtg cgacctcttc tcaatttact cagattaccg   4500
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
aagaagttcg ctgcatgatc aaccgtgtag acacccagcc gctgtccctg ctggagctga   4680
tcgacgatgt gcagcgcctg ggtctgacct acaaatttga aaaagacatc attaaagccc   4740
tggaaaacat cgtactgctg gacgaaaaca aaagaacaa atctgacctg cacgcaaccg    4800
ctctgtcttt ccgtctgctg cgtcagcacg gtttcgaggt ttctcaggat gttttgagc    4860 gtttcaagga taagaaggt ggtttcagcg gtgaactgaa aggtgacgtc caaggcctgc    4920
tgagcctgta tgaagcgtct tacctgggtt tcgagggtga aacctgctg gaggaggcgc    4980 gtacctttc catcacccac ctgaagaaca acctgaaaga aggcattaat accaaggttg    5040
cagaacaagt gagccacgcc ctggaactgc catatcacca gcgtctgcac cgtctggagg   5100
cacgttggtt cctggataaa tacgaaccga aagaaccgca tcaccagctg ctgctggagc   5160
tggcgaagct ggattttaac atggtacaga ccctgcacca gaaagagctg caagatctgt   5220
cccgctggtg gaccgagatg ggcctggcta gcaaactgga ttttgtacgc gaccgcctga   5280
tggaagttta tttctgggca ctgggtatgg cgccagaccc gcagtttggt gaatgtcgca   5340
aagctgttac taaaatgttt ggtctggtga cgatcatcga tgacgtgtat gacgtttatg   5400
```

```
gcactctgga cgaactgcaa ctgttcaccg atgctgtaga gcgctgggac gttaacgcta    5460
ttaacaccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaaacg ccagcgtttc ctcctccggt gtagcgctgc    5700
tggcgccgtc ttacttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
tgatcgacgc cgaatggaaa aagatgaatc gtgaacgcgt tagcgactcc accctgctgc    6000
ctaaagcgtt catggaaatc gcagttaaca tggcacgtgt tcccactgc  acctaccagt    6060 atggcgatgg tctgggtcgc ccagactacg cgactgaaaa ccgcatcaaa ctgctgctga    6120 ttgaccettt cccgattaac cagctgatgt atgtctaact gcatcgccct taggaggtaa    6180
aaaaaaatga ctgccgacaa caatagtatg ccccatggtg cagtatctag ttacgccaaa    6240
ttagtgcaaa accaaacacc tgaagacatt ttggaagagt ttcctgaaat tattccatta    6300
caacaaagac ctaatacccg atcagtgag  acgtcaaatg acgaaagcgg agaaacatgt    6360
ttttctggtc atgatgagga gcaaattaag ttaatgaatg aaaattgtat tgttttggat    6420
tgggacgata atgctattgg tgccggtacc aagaaagttt gtcatttaat ggaaaatatt    6480
gaaaagggtt tactacatcg tgcattctcc gtctttattt tcaatgaaca aggtgaatta    6540
cttttacaac aaagagccac tgaaaaaata actttccctg atctttggac taacacatgc    6600
tgctctcatc cactatgtat tgatgacgaa ttaggtttga agggtaagct agacgataag    6660
attaagggcg ctattactgc ggcggtgaga aaactagatc atgaattagg tattccagaa    6720
gatgaaacta agacaagggg taagtttcac ttttttaaaca gaatccatta catggcacca    6780
agcaatgaac catggggtga acatgaaatt gattacatcc tattttataa gatcaacgct    6840
aaagaaaact tgactgtcaa cccaaacgtc aatgaagtta gagacttcaa atgggtttca    6900
ccaaatgatt tgaaaactat gtttgctgac ccaagttaca agtttacgcc ttggtttaag    6960
attatttgcg agaattactt attcaactgg tgggagcaat tagatgacct ttctgaagtg    7020
gaaaatgaca ggcaaattca tagaatgcta taacgacgcg tcctgcagct ggtaccatat    7080
gggaattcga agctttctag aacgaaaact catctcagaa gaggatctga atagcgccgt    7140
cgaccatcat catcatcatc attgagtta  aacggtctcc agcttggctg ttttggcgga    7200
tgagagaaga ttttcagcct gatacagatt aaatcagaac gcagaagcgg tctgataaaa    7260
cagaatttgc ctggcggcag tagcgcggtg gtcccacctg accccatgcc gaactcagaa    7320
gtgaaacgcc gtagcgccga tggtagtgtg ggtctcccc  atgcgagagt agggaactgc    7380
caggcatcaa ataaaacgaa aggctcagtc gaaagactgg gcctttcgtt ttatctgttg    7440
tttgtcggtg aacgctctcc tgagtaggac aaatccgccg ggagcggatt tgaacgttgc    7500
gaagcaacgg cccggagggt ggcgggcagg acgcccgcca taaactgcca ggcatcaaat    7560
taagcagaag gccatcctga cggatggcct tttgcgtttc tacaaactc  ttttgtttta    7620 tttttctaaa tacattcaaa tatgtatccg ctcatgagac aataaccctg ataaatgctt    7680
caataat                                                              7687
```

<210> SEQ ID NO 55

<211> LENGTH: 8675
<212> TYPE: DNA
<213> ORGANISM: Artificial Sequence
<220> FEATURE:
<223> OTHER INFORMATION: Synthetic Construct

<400> SEQUENCE: 55

| | | | | | |
|---|---|---|---|---|---|
| cccgtcttac | tgtcgggaat | tcgcgttggc | cgattcatta | atgcagatta | ttgaagcatt | 60 |
| tatcagggtt | attgtctcat | gagcggatac | atatttgaat | gtatttagaa | aaataaacaa | 120 |
| aaagagtttg | tagaaacgca | aaaaggccat | ccgtcaggat | ggccttctgc | ttaatttgat | 180 |
| gcctggcagt | ttatggcggg | cgtcctgccc | gccaccctcc | gggccgttgc | ttcgcaacgt | 240 |
| tcaaatccgc | tcccggcgga | tttgtcctac | tcaggagagc | gttcaccgac | aaacaacaga | 300 |
| taaaacgaaa | ggcccagtct | ttcgactgag | cctttcgttt | tatttgatgc | ctggcagttc | 360 |
| cctactctcg | catggggaga | ccccacacta | ccatcggcgc | tacggcgttt | cacttctgag | 420 |
| ttcggcatgg | ggtcaggtgg | gaccaccgcg | ctactgccgc | caggcaaatt | ctgttttatc | 480 |
| agaccgcttc | tgcgttctga | tttaatctgt | atcaggctga | aaatcttctc | tcatccgcca | 540 |
| aaacagccaa | gctggagacc | gtttaaactc | aatgatgatg | atgatgatgg | tcgacggcgc | 600 |
| tattcagatc | ctcttctgag | atgagttttt | gttctagaaa | gcttcgaatt | cccatatggt | 660 |
| accagctgca | gttatgccag | ccaggccttg | attttggctt | ccataccagc | ggcatcgagg | 720 |
| ccgagttcgg | cgcgcatttc | ttcctgagtt | ccttgcggaa | taagaagtc | cggcaggcca | 780 |
| atgttcagca | cgggtactgg | tttacgatgg | ccatcagca | cttcgttcac | gccgctgcct | 840 |
| gcgccgccca | taatggcgtt | tcttctacg | gtgaccagcg | cttcatggct | ggcggccatt | 900 |
| tccagaatta | acgcttcatc | aagcggtttc | acaaaacgca | tatcgaccag | cgtggcgttc | 960 |
| agcgattcgg | cgactttcgc | cgcttctggc | atcagcgtac | caaagttaag | gatcgccagt | 1020 |
| ttctcgccac | gacgcttcac | aatgcctttg | ccaattggta | gttttccag | cggcgtcagt | 1080 |
| tccacgccga | ccgcgttgcc | acgcgggtag | cgcaccgctg | acgggccatc | gttatagtga | 1140 |
| tagccggtat | agagcatctg | gcgacattcg | ttttcatcgc | tcggggtcat | aatgaccatt | 1200 |
| tccggtatgc | agcgcaggta | agagagatca | aaagcaccct | gatgggtttg | accgtcagca | 1260 |
| ccaacaatgc | ccgcgcggtc | gatggcgaac | aggaccggaa | gcttttgaat | cgccacgtca | 1320 |
| tgcagcacct | gatcataggc | gcgttgcagg | aaagtggagt | aaatcgcgac | aatgggtttg | 1380 |
| tacccaccaa | tcgccagacc | cgcagcaaag | gtcaccgcgt | gttgctcggc | aattgccacg | 1440 |
| tcgaagtagc | gatccgggaa | tttacgtgaa | aactcgacca | tgccggaacc | ttcacgcatc | 1500 |
| gccggagtaa | tcgccatcag | cttgttgtct | ttcgctgccg | tttcgcacaa | ccagtcgcca | 1560 |
| aagattttg | aatagctcgg | caaaccgccg | ctacttttcg | gcaaacaacc | gctggaggga | 1620 |
| tcaaatttag | gcacggcgtg | gaaagtgatc | gggtcttttt | ctgccggttc | ataaccacga | 1680 |
| ccttttttgg | tcatgatatg | caggaactgc | gggcctttca | ggtcgcgcat | gttctttagc | 1740 |
| gtggtgataa | gccccagcac | atcgtgaccg | tccaccgggc | cgatgtagtt | aaagcccagc | 1800 |
| tcttcaaaca | acgtgccagg | cactaccatg | cctttaatat | gttcttcggt | gcgtttgagc | 1860 |
| agctctttaa | ttggcggcac | gccagagaaa | acttttttcc | cgccttcgcg | cagtgaagag | 1920 |
| taaagcttac | cggaaagcag | ctgtgccaga | tggttgttga | gcgcgccgac | attttcggaa | 1980 |
| atcgacattt | cattgtcgtt | gagaatcacc | agcatatcag | gacggatatc | gcccgcgtga | 2040 |
| ttcatcgctt | caaacgccat | gcctgcggta | atcgcgccat | cgccaatgac | acagacggtg | 2100 |
| cggcgatttt | tgccttcttt | ttcggcagca | accgcaatac | caattccggc | actgatggag | 2160 |

```
gttgatgaat gcccgacgct taatacgtca tattcgcttt cgccgcgcca cgggaacggg    2220
tgcagaccgc ctttctgacg gatggtgccg attttgtcgc ggcgtccggt caaaattta    2280 tgcggataag cctgatgccc cacatcccaa atcaattggt caaacggggt gttgtagaca    2340
tagtgcagcg ccacggtcag ttcgaccgtg cccagcccgg aggcgaagtg cccgctggaa    2400
cggctcacgc tgtcgagtaa atagcggcgc agttcgtcgc agagtttcgg taaactctct    2460
ttcggcaaca gtcgtaactc ctgggtggag tcgaccagtg ccagggtcgg gtatttggca    2520
atatcaaaac tcatgttttt ttacctccta agggcgaatg cagttagaca tacatcagct    2580
ggttaatcgg gaaagggtca atcagcagca gtttgatgcg gttttcagtc gcgtagtctg    2640
ggcgacccag accatcgcca tactggtagg tgcagtggga aacacgtgcc atgttaactg    2700
cgatttccat gaacgcttta ggcagcaggg tggagtcgct aacgcgttca cgattcatct    2760
ttttccattc ggcgtcgatc agtttacgca gttcttcgcg ggcctgttcc tcgctggtac    2820
catcgttttc gtgcatgtag ctaatgatag aattggtagt ctcgccacgt tccagctccg    2880
ccgcagaggt ggccagatcg ttgcacaggc ggaagataac gcagctagaa cgcaccagac    2940
catggaagtc ggtcagggaa cgcagcgcgt ggtcggagat gtcttcctgc tgctggcata    3000
cggaaaagta agacggcgcc agcagcgcta caccggagga ggaaacgctg gcgttttcca    3060
ggtacttgga gaaagccggg ataattttgt tgttggacca tttcgcctct tgcagaaagg    3120 cttttgcacag ttcacgccag ctttttcgtca gataggacag gttgttatga cctttctctt    3180
tcagaataga ataggacgtg tcgttaacgg tgttgtacag tgccaggaaa cacagtttca    3240
tatagtccgg cagggtgtta atagcgttaa cgtcccagcg ctctacagca tcggtgaaca    3300
gttgcagttc gtccagagtg ccataaacgt catacacgtc atcgatgatc gtcaccagac    3360
caaacatttt agtaacagct ttgcgacatt caccaaactg cgggtctggc gccatacca    3420 gtgcccagaa ataaacttcc atcaggcggt cgcgtacaaa atccagtttg ctagccaggc    3480
ccatctcggt ccaccagcgg gacagatctt gcagctcttt ctggtgcagg gtctgtacca    3540
tgttaaaatc cagcttcgcc agctccagca gcagctggtg atgcggttct ttcggttcgt    3600
atttatccag gaaccaacgt gcctccagac ggtgcagacg ctggtgatat ggcagttcca    3660
gggcgtggct cacttgttct gcaaccttgg tattaatgcc ttctttcagg ttgttcttca    3720
ggtgggtgat ggaaaaggta cgcgcctcct ccagcaggtt ctcaccctcg aaacccaggt    3780
aagacgcttc atacaggctc agcaggcctt ggacgtcacc tttcagttca ccgctgaaac    3840
caccttcttt atccttgaaa cgctcaaaaa catcctgaga aacctcgaaa ccgtgctgac    3900
gcagcagacg gaaagacaga gcggttgcgt gcaggtcaga tttgttcttt ttgttttcgt    3960
ccagcagtac gatgttttcc agggctttaa tgatgtcttt ttcaaatttg taggtcagac    4020
ccaggcgctg cacatcgtcg atcagctcca gcagggacag cggctgggtg tctacacggt    4080
tgatcatgca gcgaacttct tcctccagtt tggtcgcttt ctcctccagc ttttccactt    4140
tcaggtcgtt ctccagggat tgcaggaatt cgaaattcca caggtttggc tgatagtttg    4200
cggaacgacg ggaattatgc tcggtaatct gagtaaattg agaagaggtc gcacacatgg    4260
tttattcctc cttatttaat cgatacatta atatataccct ctttaatttt taataataaa    4320
gttaatcgat aattccggtc gagtgcccac acagattgtc tgataaattg ttaaagagca    4380
gtgccgcttc gcttttctc agcggcgctg tttcctgtgt gaaattgtta ccgctcaca    4440 attccacaca ttatacgagc cggatgatta attgtcaaca gctcatttca gaatctggcg    4500
taatagcgaa gaggcccgca ccgatcgccc ttcccaacag ttgcgcagcc tgaatggcga    4560
```

```
atggcgcctg atgcggtatt ttctccttac gcatctgtgc ggtatttcac accgcatatg    4620
gtgcactctc agtacaatct gctctgatgc cgcatagtta agccagcccc gacacccgcc    4680
aacacccgct gacgagctta gtaaagcccc cgctagattt taatgcggat gttgcgatta    4740
cttcgccaac tattgcgata caagaaaaa gccagccttt catgatatat ctcccaattt    4800
gtgtagggct tattatgcac gcttaaaaat aataaaagca gacttgacct gatagtttgg    4860
ctgtgagcaa ttatgtgctt agtgcatcta acgcttgagt taagccgcgc cgcgaagcgg    4920
cgtcggcttg aacgaattgt tagacattat ttgccgacta ccttggtgat ctcgcctttc    4980
acgtagtgga caaattcttc caactgatct gcgcgcgagg ccaagcgatc ttcttcttgt    5040
ccaagataag cctgtctagc ttcaagtatg acgggctgat actgggccgg caggcgctcc    5100
attgcccagt cggcagcgac atccttcggc gcgattttgc cggttactgc gctgtaccaa    5160
atgcgggaca acgtaagcac tacatttcgc tcatcgccag cccagtcggg cggcgagttc    5220
catagcgtta aggtttcatt tagcgcctca aatagatcct gttcaggaac cggatcaaag    5280
agttcctccg ccgctggacc taccaaggca acgctatgtt ctcttgcttt tgtcagcaag    5340
atagccagat caatgtcgat cgtggctggc tcgaagatac ctgcaagaat gtcattgcgc    5400
tgccattctc caaattgcag ttcgcgctta gctggataac gccacggaat gatgtcgtcg    5460
tgcacaacaa tggtgacttc tacagcgcgg agaatctcgc tctctccagg ggaagccgaa    5520
gtttccaaaa ggtcgttgat caaagctcgc cgcgttgttt catcaagcct tacggtcacc    5580
gtaaccagca atcaatatc actgtgtggc ttcaggccgc catccactgc ggagccgtac    5640
aaatgtacgg ccagcaacgt cggttcgaga tggcgctcga tgacgccaac tacctctgat    5700
agttgagtcg atacttcggc gatcaccgct tccctcatga tgtttaactt tgttttaggg    5760
cgactgccct gctgcgtaac atcgttgctg ctccataaca tcaaacatcg acccacggcg    5820
taacgcgctt gctgcttgga tgcccgaggc atagactgta ccccaaaaaa acagtcataa    5880
caagccatga aaaccgccac tgcgccgtta ccaccgctgc gttcggtcaa ggttctggac    5940
cagttgcgtg agcgcatacg ctacttgcat tacagcttac gaaccgaaca ggcttatgtc    6000
cactgggttc gtgccttcat ccgtttccac ggtgtgcgtc acccggcaac cttgggcagc    6060
agcgaagtcg aggcatttct gtcctggctg gcgaacgagc gcaaggtttc ggtctccacg    6120
catcgtcagg cattggcggc cttgctgttc ttctacggca aggtgctgtg cacggatctg    6180
ccctggcttc aggagatcgg aagacctcgg ccgtcgcggc gcttgccggt ggtgctgacc    6240
ccggatgaag tggttcgcat cctcggtttt ctggaaggcg agcatcgttt gttcgcccag    6300
cttctgtatg aacgggcat gcggatcagt gagggtttgc aactgcgggt caaggatctg    6360
gatttcgatc acggcacgat catcgtgcgg gagggcaagg gctccaagga tcgggccttg    6420
atgttacccg agagcttggc acccagcctg cgcgagcagg ggaattaatt cccacgggtt    6480
ttgctgcccg caaacgggct gttctggtgt gctagtttg ttatcagaat cgcagatccg    6540
gcttcagccg gtttgccggc tgaaagcgct atttcttcca gaattgccat gatttttcc    6600
ccacgggagg cgtcactggc tcccgtgttg tcggcagctt tgattcgata agcagcatcg    6660
cctgtttcag gctgtctatg tgtgactgtt gagctgtaac aagttgtctc aggtgttcaa    6720
tttcatgttc tagttgcttt gttttactgg tttcacctgt tctattaggt gttacatgct    6780
gttcatctgt tacattgtcg atctgttcat ggtgaacagc tttgaatgca ccaaaaactc    6840
gtaaaagctc tgatgtatct atcttttta caccgttttc atctgtgcat atggacagtt    6900
ttcccttga tatgtaacgg tgaacagttg ttctactttt gtttgttagt cttgatgctt    6960
```

```
cactgataga tacaagagcc ataagaacct cagatccttc cgtatttagc cagtatgttc    7020
tctagtgtgg ttcgttgttt ttgcgtgagc catgagaacg aaccattgag atcatactta    7080
ctttgcatgt cactcaaaaa ttttgcctca aaactggtga gctgaatttt tgcagttaaa    7140
gcatcgtgta gtgttttctc tagtccgtta tgtaggtagg aatctgatgt aatggttgtt    7200
ggtattttgt caccattcat ttttatctgg ttgttctcaa gttcggttac gagatccatt    7260
tgtctatcta gttcaacttg gaaaatcaac gtatcagtcg ggcggcctcg cttatcaacc    7320
accaatttca tattgctgta agtgtttaaa tctttactta ttggtttcaa acccattgg     7380 ttaagccttt taaactcatg gtagttattt tcaagcatta acatgaactt aaattcatca    7440
aggctaatct ctatatttgc cttgtgagtt ttcttttgtg ttagttcttt taataaccac    7500
tcataaatcc tcatagagta tttgttttca aaagacttaa catgttccag attatatttt    7560
atgaattttt ttaactggaa aagataaggc aatatctctt cactaaaaac taattctaat    7620 tttcgcttg agaacttggc atagtttgtc cactggaaaa tctcaaagcc tttaaccaaa     7680
ggattcctga tttccacagt tctcgtcatc agctctctgg ttgctttagc taatacacca    7740
taagcatttt ccctactgat gttcatcatc tgagcgtatt ggttataagt gaacgatacc    7800
gtccgttctt tccttgtagg gttttcaatc gtggggttga gtagtgccac acagcataaa    7860
attagcttgg tttcatgctc cgttaagtca tagcgactaa tcgctagttc atttgctttg    7920
aaaacaacta attcagacat acatctcaat tggtctaggt gattttaatc actataccaa    7980
ttgagatggg ctagtcaatg ataattacta gtccttttcc tttgagttgt gggtatctgt    8040
aaattctgct agacctttgc tggaaaactt gtaaattctg ctagaccctc tgtaaattcc    8100
gctagacctt tgtgtgtttt ttttgtttat attcaagtgg ttataattta tagaataaag    8160
aaagaataaa aaaagataaa aagaatagat cccagccctg tgtataactc actactttag    8220
tcagttccgc agtattacaa aaggatgtcg caaacgctgt ttgctcctct acaaaacaga    8280
ccttaaaacc ctaaaggctt aagtagcacc ctcgcaagct cgggcaaatc gctgaatatt    8340
ccttttgtct ccgaccatca ggcacctgag tcgctgtctt tttcgtgaca ttcagttcgc    8400
tgcgctcacg gctctggcag tgaatggggg taaatgcac tacaggcgcc tttttatggat    8460 tcatgcaagg aaactaccca taatacaaga aaagcccgtc acgggcttct cagggcgttt    8520
tatggcgggt ctgctatgtg gtgctatctg acttttgct gttcagcagt tcctgccctc     8580 tgatttttcca gtctgaccac ttcggattat cccgtgacag gtcattcaga ctggctaatg   8640
cacccagtaa ggcagcggta tcatcaacag gctta                               8675
```

<210> SEQ ID NO 56
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 56

```
tcgctgcgct cggtcgttcg gctgcggcga gcggtatcag ctcactcaaa ggcggtaata     60
cggttatcca cagaatcagg ggataacgca ggaaagaaca tgtgagcaaa aggccagcaa    120
aaggccagga accgtaaaaa ggccgcgttg ctggcgtttt tccataggct ccgcccccct    180
gacgagcatc acaaaaatcg acgctcaagt cagaggtggc gaaacccgac aggactataa    240
agataccagg cgtttccccc tggaagctcc ctcgtgcgct ctcctgttcc gaccctgccg    300
cttaccggat acctgtccgc ctttctccct tcgggaagcg tggcgctttc tcatagctca    360
```

```
cgctgtaggt atctcagttc ggtgtaggtc gttcgctcca agctgggctg tgtgcacgaa    420
ccccccgttc agcccgaccg ctgcgcctta tccggtaact atcgtcttga gtccaacccg    480
gtaagacacg acttatcgcc actggcagca gccactggta acaggattag cagagcgagg    540
tatgtaggcg gtgctacaga gttcttgaag tggtggccta actacggcta cactagaaga    600
acagtatttg gtatctgcgc tctgctgaag ccagttacct tcggaaaaag agttggtagc    660
tcttgatccg gcaaacaaac caccgctggt agcggtggtt ttttgtttg caagcagcag    720
attacgcgca gaaaaaaagg atctcaagaa gatcctttga tcttttctac ggggtctgac    780
gctcagtgga acgaaaactc acgttaaggg attttggtca tgagattatc aaaaaggatc    840
ttcacctaga tcctttaaa ttaaaaatga gttttaaat caatctaaag tatatatgag    900
taaacttggt ctgacagtta ccaatgctta atcagtgagg cacctatctc agcgatctgt    960
ctatttcgtt catccatagt tgcctgactc cccgtcgtgt agataactac gatacgggag   1020
ggcttaccat ctggccccag tgctgcaatg ataccgcgag acccacgctc accggctcca   1080
gatttatcag caataaacca gccagccgga agggccgagc gcagaagtgg tcctgcaact   1140
ttatccgcct ccatccagtc tattaattgt tgccgggaag ctagagtaag tagttcgcca   1200
gttaatagtt tgcgcaacgt tgttgccatt gctacaggca tcgtggtgtc acgctcgtcg   1260
tttggtatgg cttcattcag ctccggttcc caacgatcaa ggcgagttac atgatccccc   1320
atgttgtgca aaaaagcggt tagctccttc ggtcctccga tcgttgtcag aagtaagttg   1380
gccgcagtgt tatcactcat ggttatggca gcactgcata attctcttac tgtcatgcca   1440
tccgtaagat gcttttctgt gactggtgag tactcaacca agtcattctg agaatagtgt   1500
atgcggcgac cgagttgctc ttgcccggcg tcaatacggg ataataccgc gccacatagc   1560
agaactttaa aagtgctcat cattggaaaa cgttcttcgg ggcgaaaact ctcaaggatc   1620
ttaccgctgt tgagatccag ttcgatgtaa cccactcgtg cacccaactg atcttcagca   1680
tcttttactt tcaccagcgt ttctgggtga gcaaaaacag gaaggcaaaa tgccgcaaaa   1740
aagggaataa gggcgacacg gaaatgttga atactcatac tcttcctttt tcaatattat   1800
tgaagcattt atcagggtta ttgtctcatg agcggataca tatttgaatg tatttagaaa   1860
aataaacaaa taggggttcc gcgcacattt ccccgaaaag tgccacctga cgtctaagaa   1920
accattatta tcatgacatt aacctataaa aataggcgta tcacgaggcc ctttcgtctc   1980
gcgcgtttcg gtgatgacgg tgaaaacctc tgacacatgc agctcccgga cggtcaca    2040
gcttgtctgt aagcggatgc cgggagcaga caagcccgtc agggcgcgtc agcgggtgtt   2100
ggcgggtgtc ggggctggct taactatgcg gcatcagagc agattgtact gagagtgcac   2160
catagatctg gagctgtaat ataaaaacct tcttcaacta acggggcagg ttagtgacat   2220
tagaaaaccg actgtaaaaa gtacagtcgg cattatctca tattataaaa gccagtcatt   2280
aggcctatct gacaattcct gaatagagtt cataaacaat cctgcatgat aaccatcaca   2340
aacagaatga tgtacctgta agatagcgg taaatatatt gaattacctt tattaatgaa   2400
ttttcctgct gtaataatgg gtagaaggta attactatta ttattgatat ttaagttaaa   2460
cccagtaaat gaagtccatg gaataataga aagagaaaaa gcattttcag gtataggtgt   2520
tttgggaaac aatttccccg aaccattata tttctctaca tcagaaaggt ataaatcata   2580
aaactctttg aagtcattct ttacaggagt ccaaatacca gagaatgttt tagatacacc   2640
atcaaaaatt gtataagtg gctctaactt atcccaataa cctaactctc cgtcgctatt   2700
gtaaccagtt ctaaaagctg tatttgagtt tatcaccctt gtcactaaga aaataaatgc   2760
```

```
agggtaaaat ttatatcctt cttgttttat gtttcggtat aaaacactaa tatcaatttc    2820
tgtggttata ctaaaagtcg tttgttggtt caaataatga ttaaatatct cttttctctt    2880
ccaattgtct aaatcaattt tattaaagtt catttgatat gcctcctaaa ttttttatcta   2940
aagtgaattt aggaggctta cttgtctgct ttcttcatta gaatcaatcc tttttttaaaa   3000
gtcaatatta ctgtaacata aatatatatt ttaaaaatat cccactttat ccaattttcg    3060
tttgttgaac taatgggtgc tttagttgaa gaataaaaga cctatgcggt gtgaaatacc    3120
gcacagatgc gtaaggagaa ataccgcat caggcgccat tcgccattca ggctgcgcaa     3180
ctgttgggaa gggcgatcgg tgcgggcctc ttcgctatta cgccagctgg cgaaagggg     3240
atgtgctgca aggcgattaa gttgggtaac gccagggttt tcccagtcac gacgttgtaa    3300
aacgacggcc agtgccaagc ttgcatgcct gcactccatt ttcttctgct atcaaaataa    3360
cagactcgtg attttccaaa cgagctttca aaaaagcctc tgccccttgc aaatcggatg    3420
cctgtctata aaattcccga tattggtaa acagcggcgc aatggcggcc gcatctgatg     3480
tctttgcttg gcgaatgttc atcttatttc ttcctccctc tcaataattt tttcattcta    3540
tcccttttct gtaaagttta ttttcagaa tactttatc atcatgcttt gaaaaaatat      3600
cacgataata tccattgttc tcacggaagc acacgcaggt catttgaacg aattttttcg    3660
acaggaattt gccgggactc aggagcattt aacctaaaaa agcatgacat ttcagcataa    3720
tgaacattta ctcatgtcta ttttcgttct tttctgtatg aaaatagtta tttcgagtct    3780
ctacggaaat agcagagat gatataccta aatagagata aaatcatctc aaaaaaatgg     3840
gtctactaaa atattattcc atctattaca ataaattcac agaatagtct tttaagtaag    3900
tctactctga atttttttaa aaggagaggg taaagagtga aaacagtagt tattattgat    3960
gcattacgaa caccaattgg aaaatataaa ggcagcttaa gtcaagtaag tgccgtagac    4020
ttaggaacac atgttacaac acaactttta aaaagacatt ccactatttc tgaagaaatt    4080
gatcaagtaa tctttggaaa tgttttacaa gctggaaatg ccaaaatcc cgcacgacaa     4140
atagcaataa acagcggttt gtctcatgaa attcccgcaa tgacggttaa tgaggtctgc    4200
ggatcaggaa tgaaggccgt tattttggcg aaacaattga ttcaattagg agaagcggaa    4260
gttttaattg ctggcgggat tgagaatatg tcccaagcac ctaaaattaca acgttttaat   4320
tacgaaacag aaagctacga tgcgcctttt tctagtatga tgtatgatgg attaacggat    4380
gcctttagtg gtcaggcaat gggcttaact gctgaaaatg tggccgaaaa gtatcatgta    4440
actagagaag agcaagatca attttctgta cattcacaat aaaagcagc tcaagcacaa     4500
gcagaaggga tattcgctga cgaaatagcc ccattagaag tatcaggaac gcttgtggag    4560
aaagatgaag ggattcgccc taattcgagc gttgagaagc taggaacgct taaaacagtt    4620
tttaaagaag acggtactgt aacagcaggg aatgcatcaa ccattaatga tgggcttct    4680
gctttgatta ttgcttcaca agaatatgcc gaagcacacg tcttcctta tttagctatt    4740
attcgagaca gtgtggaagt cggtattgat ccagcctata tgggaatttc gccgattaaa   4800
gccattcaaa aactgttagc gcgcaatcaa cttactacgg aagaaattga tctgtatgaa    4860
atcaacgaag catttgcagc aacttcaatc gtggtccaaa gagaactggc tttaccagag    4920
gaaaaggtca acatttatgg tggcggtatt tcattaggtc atgcgattgg tgccacaggt    4980
gctcgtttat taacgagttt aagttatcaa ttaaatcaaa agaaaagaa atatggagtg    5040
gcttctttat gtatcggcgg tggcttagga ctcgctatgc tactagagag acctcagcaa   5100
aaaaaaaaca gccgatttta tcaaatgagt cctgaggaac gcctggcttc tcttcttaat   5160
```

```
gaaggccaga tttctgctga tacaaaaaaa gaatttgaaa atacggcttt atcttcgcag    5220
attgccaatc atatgattga aaatcaaatc agtgaaacag aagtgccgat gggcgttggc    5280
ttacatttaa cagtggacga aactgattat ttggtaccaa tggcgacaga agagccctca    5340
gttattgcgg ctttgagtaa tggtgcaaaa atagcacaag gatttaaaac agtgaatcaa    5400
caacgcttaa tgcgtggaca aatcgttttt tacgatgttg cagatcccga gtcattgatt    5460
gataaactac aagtaagaga agcggaagtt tttcaacaag cagagttaag ttatccatct    5520
atcgttaaac ggggcggcgg cttaagagat ttgcaatatc gtacttttga tgaatcattt    5580
gtatctgtcg acttttagt agatgttaag gatgcaatgg gggcaaatat cgttaacgct    5640
atgttggaag gtgtggccga gttgttccgt gaatggtttg cggagcaaaa gattttattc    5700
agtattttaa gtaattatgc cacggagtcg gttgttacga tgaaaacggc tattccagtt    5760
tcacgtttaa gtaaggggag caatggccgg gaaattgctg aaaaaattgt tttagcttca    5820
cgctatgctt cattagatcc ttatcgggca gtcacgcata caaaggaat catgaatggc    5880 attgaagctg tagttttagc tacaggaaat gatacacgcg ctgttagcgc ttcttgtcat    5940
gcttttgcgg tgaaggaagg tcgctaccaa ggcttgacta gttggacgct ggatggcgaa    6000
caactaattg gtgaaatttc agttccgctt gctttagcca cggttggcgg tgccacaaaa    6060
gtcttaccta aatctcaagc agctgctgat ttgttagcag tgacggatgc aaaagaacta    6120
agtcgagtag tagcggctgt tggtttggca caaaatttag cggcgttacg ggccttagtc    6180
tctgaaggaa ttcaaaaagg acacatggct ctacaagcac gttctttagc gatgacggtc    6240
ggagctactg gtaaagaagt tgaggcagtc gctcaacaat taaaacgtca aaaaacgatg    6300
aaccaagacc gagccatggc tattttaaat gatttaagaa acaataaaa ggagagggtg    6360 acaattggga ttgataaaat tagttttttt gtgccccctt attatattga tatgacggca    6420
ctggctgaag ccagaaatgt agaccctgga aaatttcata ttggtattgg gcaagaccaa    6480
atggcggtga acccaatcag ccaagatatt gtgacatttg cagccaatgc cgcagaagcg    6540
atcttgacca agaagataa agaggccatt gatatggtga ttgtcgggac tgagtccagt    6600
atcgatgagt caaaagcggc cgcagttgtc ttacatcgtt taatgggat tcaacctttc    6660 gctcgctctt tcgaaatcaa ggaagcttgt tacggagcaa cagcaggctt acagttagct    6720
aagaatcacg tagccttaca tccagataaa aaagtcttgg tcgtagcggc agatattgca    6780
aaatatggct taaattctgg cggtgagcct acacaaggag ctggggcggt tgcaatgtta    6840
gttgctagtg aaccgcgcat tttggcttta aagaggata atgtgatgct gacgcaagat    6900
atctatgact tttggcgtcc aacaggccac ccgtatccta tggtcgatgg tcctttgtca    6960
aacgaaacct acatccaatc ttttgcccaa gtctgggatg aacataaaaa acgaaccggt    7020
cttgattttg cagattatga tgctttagcg ttccatattc cttacacaaa aatgggcaaa    7080
aaagccttat tagcaaaaat ctccgaccaa actgaagcag aacaggaacg aattttagcc    7140
cgttatgaag aaagtatcgt ctatagtcgt cgcgtaggaa acttgtatac gggttcactt    7200
tatctgggac tcatttccct tttagaaaat gcaacgactt taaccgcagg caatcaaatt    7260
ggtttattca gttatggttc tggtgctgtc gctgaatttt tcactggtga attagtagct    7320
ggttatcaaa atcatttaca aaagaaaact catttagcac tgctggataa tcggacagaa    7380 cttctatcg ctgaatatga agccatgttt gcagaaactt tagacacaga cattgatcaa    7440
acgttagaag atgaattaaa atatagtatt tctgctatta ataataccgt tcgttcttat    7500
cgaaactaaa aaaaccggc cttggccccg ccggtttttt attatttttc ttcctccgca    7560
```

-continued

```
tgttcaatcc gctccataat cgacggatgg ctccctctga aaattttaac gagaaacggc    7620
gggttgaccc ggctcagtcc cgtaacggcc aagtcctgaa acgtctcaat cgccgcttcc    7680
cggtttccgg tcagctcaat gccgtaacgg tcggcggcgt tttcctgata ccgggagacg    7740
gcattcgtaa tcgggatccc cgggtaccga gctcgaattc gtaatcatgt catagctgtt    7800
tcctgtgtga aattgttatc cgctcacaat tccacacaac atacgagccg gaagcataaa    7860
gtgtaaagcc tggggtgcct aatgagtgag ctaactcaca ttaattgcgt tgcgctcact    7920
gcccgctttc cagtcgggaa acctgtcgtg ccagctgcat taatgaatcg gccaacgcgc    7980
ggggagaggc ggtttgcgta ttgggcgctc ttccgcttcc tcgctcactg ac            8032
```

<210> SEQ ID NO 57
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 57

```
gaattgctcc attttcttct gctatcaaaa taacagactc gtgattttcc aaacgagctt      60
tcaaaaaagc ctctgcccct tgcaaatcgg atgcctgtct ataaaattcc cgatattggt     120
taaacagcgg cgcaatggcg gccgcatctg atgtctttgc ttggcgaatg ttcatcttat     180
ttcttcctcc ctctcaataa ttttttcatt ctatcccttt tctgtaaagt ttattttca     240
gaatactttt atcatcatgc tttgaaaaaa tatcacgata atatccattg ttctcacgga     300
agcacacgca ggtcatttga acgaattttt tcgacaggaa tttgccggga ctcaggagca     360
tttaacctaa aaaagcatga catttcagca taatgaacat ttactcatgt ctattttcgt     420
tcttttctgt atgaaaatag ttatttcgag tctctacgga aatagcgaga gatgatatac     480
ctaaatagag ataaaatcat ctcaaaaaaa tgggtctact aaaatattat tccatctatt     540
acaataaatt cacagaatag tcttttaagt aagtctactc tgaattttt taaaaggaga     600
gggtaaagag tgtgtgcgac ctcttctcaa tttactcaga ttaccgagca taattcccgt     660
cgttccgcaa actatcagcc aaacctgtgg aatttcgaat tcctgcaatc cctggagaac     720
gacctgaaag tggaaaagct ggaggagaaa gcgaccaaac tggaggaaga agttcgctgc     780
atgatcaacc gtgtagacac ccagccgctg tccctgctgg agctgatcga cgatgtgcag     840
cgcctgggtc tgacctacaa atttgaaaaa gacatcatta agccctgga aacatcgta     900
ctgctggacg aaaacaaaaa gaacaaatct gacctgcacg caaccgctct gtctttccgt     960
ctgctgcgtc agcacggttt cgaggttct caggatgttt ttgagcgttt caaggataaa    1020
gaaggtggtt tcagcggtga actgaaaggt gacgtccaag gcctgctgag cctgtatgaa    1080
gcgtcttacc tgggttcga gggtgagaac ctgctggagg aggcgcgtac cttttccatc    1140
acccacctga gaacaaccct gaagaaggc attaatacca aggttgcaga acaagtgagc    1200
cacgccctgg aactgccata tcaccagcgt ctgcaccgtc tggaggcacg ttggttcctg    1260
gataaatacg aaccgaaaga accgcatcac cagctgctgc tggagctggc gaagctggat    1320
tttaacatgg tacagaccct gcaccagaaa gagctgcaag atcgtcccg ctggtggacc    1380
gagatgggcc tggctagcaa actggatttt gtacgcgacc gcctgatgga agtttatttc    1440
tgggcactgg gtatggcgcc agacccgcag tttggtgaat gtcgcaaagc tgttactaaa    1500
atgtttggtc tggtgacgat catcgatgac gtgtatgacg tttatggcac tctggacgaa    1560
ctgcaactgt tcaccgatgc tgtagagcgc tgggacgtta acgctattaa cacccctgccg    1620
```

```
gactatatga aactgtgttt cctggcactg tacaacaccg ttaacgacac gtcctattct    1680
attctgaaag agaaaggtca taacaacctg tcctatctga cgaaaagctg gcgtgaactg    1740
tgcaaagcct ttctgcaaga ggcgaaatgg tccaacaaca aaattatccc ggctttctcc    1800
aagtacctgg aaaacgccag cgtttcctcc tccggtgtag cgctgctggc gccgtcttac    1860 tttccgtat gccagcagca ggaagacatc tccgaccacg cgctgcgttc cctgaccgac     1920
ttccatggtc tggtgcgttc tagctgcgtt atcttccgcc tgtgcaacga tctgccacc     1980 tctgcggcgg agctggaacg tggcgagact accaattcta tcattagcta catgcacgaa    2040
aacgatggta ccagcgagga acaggcccgc gaagaactgc gtaaactgat cgacgccgaa    2100
tggaaaaaga tgaatcgtga acgcgttagc gactccaccc tgctgcctaa agcgttcatg    2160
gaaatcgcag ttaacatggc acgtgtttcc cactgcacct accagtatgg cgatggtctg    2220
ggtcgcccag actacgcgac tgaaaaccgc atcaaactgc tgctgattga ccctttcccg    2280
attaaccagc tgatgtatgt ctaaaaaaaa ccggccttgg ccccgccggt tttttattat    2340
ttttcttcct ccgcatgttc aatccgctcc ataatcgacg gatggctccc tctgaaaatt    2400
ttaacgagaa acgcgggtt gacccggctc agtcccgtaa cggccaagtc ctgaaacgtc      2460
tcaatcgccg cttcccggtt tccggtcagc tcaatgccgt aacggtcggc ggcgttttcc    2520
tgataccggg agacggcatt cgtaatcgga tcctctagag tcgacctgca ggcatgcaag    2580
ctttgcctcg cgcgtttcgg tgatgacggt gaaaacctct gacacatgca gctcccggag    2640
acggtcacag cttgtctgta agcggatgcc gggagcagac aagcccgtca gggcgcgtca    2700
gcgggtgttg gcgggtgtcg gggcgcagcc atgacccagt cacgtagcga tagcggagtg    2760
tatactggct taactatgcg gcatcagagc agattgtact gagagtgcac catatgcggt    2820
gtgaaatacc gcacagatgc gtaaggagaa ataccgcat caggcgctct tccgcttcct     2880
cgctcactga ctcgctgcgc tcggtcgttc ggctgcggcg agcggtatca gctcactcaa    2940
aggcggtaat acggttatcc acagaatcag gggataacgc aggaaagaac atgtgagcaa    3000
aaggccagca aaaggccagg aaccgtaaaa aggccgcgtt gctggcgttt ttccataggc    3060
tccgcccccc tgacgagcat cacaaaaatc gacgctcaag tcagaggtgg cgaaacccga    3120
caggactata aagataccag gcgtttcccc ctggaagctc cctcgtgcgc tctcctgttc    3180
cgaccctgcc gcttaccgga tacctgtccg cctttctccc ttcgggaagc gtggcgcttt    3240
ctcaatgctc acgctgtagg tatctcagtt cggtgtaggt cgttcgctcc aagctgggct    3300
gtgtgcacga accccccgtt cagcccgacc gctgcgcctt atccggtaac tatcgtcttg    3360
agtccaaccc ggtaagacac gacttatcgc cactggcagc agccactggt aacaggatta    3420
gcagagcgag gtatgtaggc ggtgctacag agttcttgaa gtggtggcct aactacggct    3480
acactagaag gacagtattt ggtatctgcg ctctgctgaa gccagttacc ttcggaaaaa    3540
gagttggtag ctcttgatcc ggcaaacaaa ccaccgctgg tagcggtggt ttttttgttt    3600
gcaagcagca gattacgcgc agaaaaaaag gatctcaaga agatcctttg atcttttcta    3660
cggggtctga cgctcagtgg aacgaaaact cacgttaagg gattttggtc atgagattat    3720
caaaaaggat cgaagtcggt tcagaaaaag aaggatatgg atctggagct gtaatataaa    3780
aaccttcttc aactaacggg gcaggttagt gacattagaa aaccgactgt aaaaagtaca    3840
gtcggcatta tctcatatta taaaagccag tcattaggcc tatctgacaa ttcctgaata    3900
gagttcataa acaatcctgc atgataacca tcacaaacag aatgatgtac ctgtaaagat    3960
agcggtaaat atattgaatt accttttatta atgaattttc ctgctgtaat aatgggtaga    4020
```

```
aggtaattac tattattatt gatatttaag ttaaacccag taaatgaagt ccatggaata    4080
atagaaagag aaaaagcatt ttcaggtata ggtgttttgg gaaacaattt aaaagaacca    4140
ttatatttct ctacatcaga aaggtataaa tcataaaact ctttgaagtc attctttaca    4200
ggagtccaaa taccagagaa tgttttagat acaccatcaa aaattgtata aagtggctct    4260
aacttatccc aataacctaa ctctccgtcg ctattgtaac cagttctaaa agctgtattt    4320
gagtttatca cccttgtcac taagaaaata aatgcagggt aaaatttata tccttcttgt    4380
tttatgtttc ggtataaaac actaatatca atttctgtgg ttatactaaa agtcgtttgt    4440
tggttcaaat aatgattaaa tatctctttt ctcttccaat tgtctaaatc aattttatta    4500
aagttcattt gatatgcctc ctaaattttt atctaaagtg aatttaggag cttacttgt     4560 ctgctttctt cattagaatc aatccttttt taaagtcaat attactgtaa cataaatata    4620
tattttaaaa atatcccact ttatccaatt ttcgtttgtt gaactaatgg gtgctttagt    4680
tgaagaataa agaccacatt aaaaaatgtg gtcttttgtg ttttttttaaa ggatttgagc    4740 gtacgcgaaa aatccttttc tttctttctt atcttgataa taagggtaac tattgccggt    4800
tgtccattca tggctgaact ctgcttcctc tgttgacatg acacacatca tctcaatatc    4860
cgaatagggc ccatcagtct gacgaccaag agagccataa acaccaatag ccttaacatc    4920
atccccatat ttatccaata ttcgttcctt aatttcatga acaatcttca ttctttcttc    4980
tctagtcatt attattggtc cattcactat tctcattccc ttttcagata attttagatt    5040
tgcttttcta aataagaata tttggagagc accgttctta ttcagctatt aataactcgt    5100
cttcctaagc atccttcaat cctttttaata acaattatag catctaatct tcaacaaact    5160
ggcccgtttg ttgaactact cttttaataaa ataattttc cgttcccaat tccacattgc     5220
aataatagaa aatccatctt catcggcttt ttcgtcatca tctgtatgaa tcaaatcgcc    5280
ttcttctgtg tcatcaaggt ttaattttt atgtatttct tttaacaaac caccatagga    5340
gattaacctt ttacggtgta aaccttcctc caaatcagac aaacgtttca aattcttttc    5400
ttcatcatcg gtcataaaat ccgtatcctt tacaggatat tttgcagttt cgtcaattgc    5460
cgattgtata tccgatttat atttattttt cggtcgaatc atttgaactt ttacatttgg    5520
atcatagtct aatttcattg cctttttcca aaattgaatc cattgttttt gattcacgta    5580
gttttctgtt attctaaaat aagttggttc cacacatacc attacatgca tgtgctgatt    5640
ataagaatta tctttattat ttattgtcac atccgttgca cgcataaaac caacaagatt    5700
tttattaatt ttttatatt gcatcattcg gcgaaatcct tgagccatat ctgtcaaact    5760
cttatttaat tcttcgccat cataaacatt tttaactgtt aatgtgagaa acaaccaacg    5820
aactgttggc ttttgtttaa taacttcagc aacaaccttt tgtgactgaa tgccatgttt    5880
cattgctctc ctccagttgc acattggaca aagcctggat ttgcaaaacc acactcgata    5940
ccactttctt tcgcctgttt cacgattttg tttatactct aatatttcag cacaatcttt    6000
tactctttca gccttttttaa attcaagaat atgcagaagt tcaaagtaat caacattagc    6060 gatttcttt tctctccatg gtctcacttt tccactttt gtcttgtcca ctaaaaccct    6120
tgatttttca tctgaataaa tgctactatt aggacacata atattaaaag aaaccccat    6180 ctatttagtt atttgtttag tcacttataa ctttaacaga tggggttttt ctgtgcaacc    6240
aattttaagg gttttcaata ctttaaaaca catacatacc aacacttcaa cgcacctttc    6300
agcaactaaa ataaaaatga cgttattct atatgtatca agataagaaa gaacaagttc    6360
aaaaccatca aaaaaagaca ccttttcagg tgcttttttt attttataaa ctcattccct    6420
```

-continued

```
gatctcgact tcgttctttt tttacctctc ggttatgagt tagttcaaat tcgttctttt    6480
taggttctaa atcgtgtttt tcttggaatt gtgctgtttt atcctttacc ttgtctacaa    6540 acccccttaaa aacgttttta aaggctttta agccgtctgt acgttcctta ag          6592
```

<210> SEQ ID NO 58
<211> LENGTH: 31
<212> TYPE: DNA
<213> ORGANISM: Artificial Sequence
<220> FEATURE:
<223> OTHER INFORMATION: Synthetic Construct

<400> SEQUENCE: 58

```
gacatcaatt gctccatttt cttctgctat c                                   31
```

<210> SEQ ID NO 59
<211> LENGTH: 40
<212> TYPE: DNA
<213> ORGANISM: Artificial Sequence
<220> FEATURE:
<223> OTHER INFORMATION: Synthetic Construct

<400> SEQUENCE: 59

```
attgagaaga ggtcgcacac actctttacc ctctcctttg                          40
```

<210> SEQ ID NO 60
<211> LENGTH: 41
<212> TYPE: DNA
<213> ORGANISM: Artificial Sequence
<220> FEATURE:
<223> OTHER INFORMATION: Synthetic Construct

<400> SEQUENCE: 60

```
taaaaggaga gggtaaagag tgtgtgcgac ctcttctcaa t                        41
```

<210> SEQ ID NO 61
<211> LENGTH: 41
<212> TYPE: DNA
<213> ORGANISM: Artificial Sequence
<220> FEATURE:
<223> OTHER INFORMATION: Synthetic Construct

<400> SEQUENCE: 61

```
ccaaggccgg ttttttttag acatacatca gctggttaat c                        41
```

<210> SEQ ID NO 62
<211> LENGTH: 41
<212> TYPE: DNA
<213> ORGANISM: Artificial Sequence
<220> FEATURE:
<223> OTHER INFORMATION: Synthetic Construct

<400> SEQUENCE: 62

```
gattaaccag ctgatgtatg tctaaaaaaa accggccttg g                        41
```

<210> SEQ ID NO 63
<211> LENGTH: 32
<212> TYPE: DNA
<213> ORGANISM: Artificial Sequence
<220> FEATURE:
<223> OTHER INFORMATION: Synthetic Construct

<400> SEQUENCE: 63

```
gacatgacgg atccgattac gaatgccgtc tc                                  32
```

<210> SEQ ID NO 64

```
<211> LENGTH: 31
<212> TYPE: DNA
<213> ORGANISM: Artificial Sequence
<220> FEATURE:
<223> OTHER INFORMATION: Synthetic Construct

<400> SEQUENCE: 64
gacatcaatt gctccatttt cttctgctat c                                          31

<210> SEQ ID NO 65
<211> LENGTH: 27
<212> TYPE: DNA
<213> ORGANISM: Artificial Sequence
<220> FEATURE:
<223> OTHER INFORMATION: Synthetic Construct

<400> SEQUENCE: 65
gacatgaatt cctccatttt cttctgc                                               27

<210> SEQ ID NO 66
<211> LENGTH: 20
<212> TYPE: DNA
<213> ORGANISM: Artificial Sequence
<220> FEATURE:
<223> OTHER INFORMATION: Synthetic Construct

<400> SEQUENCE: 66
aggagagggt aaagagtgag                                                       20

<210> SEQ ID NO 67
<211> LENGTH: 22
<212> TYPE: DNA
<213> ORGANISM: Artificial Sequence
<220> FEATURE:
<223> OTHER INFORMATION: Synthetic Construct

<400> SEQUENCE: 67
cttttccatc acccacctga ag                                                    22

<210> SEQ ID NO 68
<211> LENGTH: 28
<212> TYPE: DNA
<213> ORGANISM: Artificial Sequence
<220> FEATURE:
<223> OTHER INFORMATION: Synthetic Construct

<400> SEQUENCE: 68
ggcgaaatgg tccaacaaca aaattatc                                              28

<210> SEQ ID NO 69
<211> LENGTH: 51
<212> TYPE: DNA
<213> ORGANISM: Artificial Sequence
<220> FEATURE:
<223> OTHER INFORMATION: Synthetic Construct

<400> SEQUENCE: 69
ggtgaattca gtctactggg gattcccaaa tctatatata ctgcaggtga c                    51

<210> SEQ ID NO 70
<211> LENGTH: 23
<212> TYPE: DNA
<213> ORGANISM: Artificial Sequence
<220> FEATURE:
<223> OTHER INFORMATION: Synthetic Construct

<400> SEQUENCE: 70
```

```
gcaggtggga aactatgcac tcc                                            23

<210> SEQ ID NO 71
<211> LENGTH: 36
<212> TYPE: DNA
<213> ORGANISM: Artificial Sequence
<220> FEATURE:
<223> OTHER INFORMATION: Synthetic Construct

<400> SEQUENCE: 71
cctgaattct gttggattgg aggattggat agtggg                              36

<210> SEQ ID NO 72
<211> LENGTH: 30
<212> TYPE: DNA
<213> ORGANISM: Artificial Sequence
<220> FEATURE:
<223> OTHER INFORMATION: Synthetic Construct

<400> SEQUENCE: 72
ggtgtcgacg tacggtcgag cttattgacc                                     30

<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
ggtgggcccg cattttgcca cctacaagcc ag                                  32

<210> SEQ ID NO 74
<211> LENGTH: 40
<212> TYPE: DNA
<213> ORGANISM: Artificial Sequence
<220> FEATURE:
<223> OTHER INFORMATION: Synthetic Construct

<400> SEQUENCE: 74
ggtgaattct agaggatccc aacgctgttg cctacaacgg                          40

<210> SEQ ID NO 75
<211> LENGTH: 36
<212> TYPE: DNA
<213> ORGANISM: Artificial Sequence
<220> FEATURE:
<223> OTHER INFORMATION: Synthetic Construct

<400> SEQUENCE: 75
ggtgcggccg ctgtctggac ctggtgagtt tccccg                              36

<210> SEQ ID NO 76
<211> LENGTH: 37
<212> TYPE: DNA
<213> ORGANISM: Artificial Sequence
<220> FEATURE:
<223> OTHER INFORMATION: Synthetic Construct

<400> SEQUENCE: 76
ggtgggccca ttaaatcagt tatcgtttat ttgatag                             37

<210> SEQ ID NO 77
<211> LENGTH: 35
<212> TYPE: DNA
<213> ORGANISM: Artificial Sequence
<220> FEATURE:
```

-continued

<223> OTHER INFORMATION: Synthetic Construct

<400> SEQUENCE: 77
ggtgaccagc aagtccatgg gtggtttgat catgg                      35

<210> SEQ ID NO 78
<211> LENGTH: 35
<212> TYPE: DNA
<213> ORGANISM: Artificial Sequence
<220> FEATURE:
<223> OTHER INFORMATION: Synthetic Construct

<400> SEQUENCE: 78
ggtgcggccg cctttggagt acgactccaa ctatg                      35

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
gcggccgcag actaaattta tttcagtctc c                          31

<210> SEQ ID NO 80
<211> LENGTH: 7
<212> TYPE: DNA
<213> ORGANISM: Artificial Sequence
<220> FEATURE:
<223> OTHER INFORMATION: Synthetic Construct

<400> SEQUENCE: 80 aggaggt                                                     7

<210> SEQ ID NO 81
<211> LENGTH: 7
<212> TYPE: DNA
<213> ORGANISM: Artificial Sequence
<220> FEATURE:
<223> OTHER INFORMATION: Synthetic Construct

<400> SEQUENCE: 81 aaggagg                                                     7

<210> SEQ ID NO 82
<211> LENGTH: 27
<212> TYPE: DNA
<213> ORGANISM: Artificial Sequence
<220> FEATURE:
<223> OTHER INFORMATION: Synthetic Construct

<400> SEQUENCE: 82
gacatctgca gctccatttt cttctgc                               27

<210> SEQ ID NO 83
<211> LENGTH: 42
<212> TYPE: DNA
<213> ORGANISM: Artificial Sequence
<220> FEATURE:
<223> OTHER INFORMATION: Synthetic Construct

<400> SEQUENCE: 83
caataataac tactgttttc actctttacc ctctcctttt aa              42

<210> SEQ ID NO 84

```
<211> LENGTH: 42
<212> TYPE: DNA
<213> ORGANISM: Artificial Sequence
<220> FEATURE:
<223> OTHER INFORMATION: Synthetic Construct

<400> SEQUENCE: 84
ttaaaaggag agggtaaaga gtgaaaacag tagttattat tg                          42

<210> SEQ ID NO 85
<211> LENGTH: 45
<212> TYPE: DNA
<213> ORGANISM: Artificial Sequence
<220> FEATURE:
<223> OTHER INFORMATION: Synthetic Construct

<400> SEQUENCE: 85
cggggccaag gccggttttt tttagtttcg ataagaacga acggt                       45

<210> SEQ ID NO 86
<211> LENGTH: 45
<212> TYPE: DNA
<213> ORGANISM: Artificial Sequence
<220> FEATURE:
<223> OTHER INFORMATION: Synthetic Construct

<400> SEQUENCE: 86
accgttcgtt cttatcgaaa ctaaaaaaaa ccggccttgg ccccg                       45

<210> SEQ ID NO 87
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 87
tggcgaatgg gacgcgccct gtagcggcgc attaagcgcg gcgggtgtgg tggttacgcg       60
cagcgtgacc gctacacttg ccagcgccct agcgcccgct cctttcgctt tcttcccttc      120 cttttctcgcc acgttcgccg ctttccccg tcaagctcta atcgggggc tccctttagg       180 gttccgattt agtgctttac ggcacctcga ccccaaaaaa cttgattagg gtgatggttc      240
acgtagtggg ccatcgccct gatagacggt ttttcgccct tgacgttgg agtccacgtt       300 ctttaatagt ggactcttgt tccaaactgg aacaacactc aaccctatct cggtctattc      360
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttatttttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa aagtttatgc atttctttcc      840
agacttgttc aacaggccag ccattacgct cgtcatcaaa atcactcgca tcaaccaaac      900
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
```

```
tggtgagtaa ccatgcatca tcaggagtac ggataaaatg cttgatggtc ggaagaggca   1140
taaattccgt cagccagttt agtctgacca tctcatctgt aacatcattg caacgctac    1200 ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gtttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggggtg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagactttac   3000 cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
```

```
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg cgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg cgatataggcgcc agcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttcacc gaaactgaaa ccgaagctcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280
gaccctgctg gaactgattg acaacgtcca gcgcctgggc ctgggttacc gtttcgagtc    5340
tgatatccgt ggtgcgctgg atcgcttcgt ttcctccggc ggcttcgatg cggtaaccaa    5400
gacttccctg cacggtacgg cactgtcttt ccgtctgctg cgtcaacacg gttttgaggt    5460
ttctcaggaa gcgttcagcg gcttcaaaga ccaaaacggc aacttcctgg agaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagagctgg cagaacaggt gaaccatgca ctggaactgc cactgcatcg    5700
ccgtactcag cgtctggaag cagtatggtc tatcgaggcc taccgtaaaa aggaggacgc    5760
gaatcaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880
```

```
ctttgctcgt gaccgcctga ttgagagctt ctactgggcc gtgggtgtag cattcgaacc   5940
gcaatactcc gactgccgta actccgtcgc aaaaatgttt tctttcgtaa ccattatcga   6000
cgatatctac gatgtatacg gcaccctgga cgaactggag ctgtttactg atgcagttga   6060
gcgttgggac gtaaacgcca tcaacgacct gccggattac atgaaactgt gctttctggc   6120
tctgtataac actattaacg aaatcgccta cgacaacctg aaagataaag gtgagaacat   6180
cctgccgtat ctgaccaaag cctgggctga cctgtgcaac gctttcctgc aagaagccaa   6240
gtggctgtac aacaaatcta ctccgacctt tgacgactac ttcggcaacg catggaaatc   6300
ctcttctggc ccgctgcaac tggtgttcgc ttacttcgct gtcgtgcaga acattaaaaa   6360
ggaagagatc gaaaacctgc aaaaatacca tgacaccatc tctcgtcctt cccatatctt   6420
ccgtctgtgc aatgacctgg ctagcgcgtc tgcggaaatt gcgcgtggtg aaaccgcaaa   6480
tagcgttttt tgttacatgc gcactaaagg tatctccgaa gaactggcta ccgaaagcgt   6540
gatgaatctg atcgatgaaa cctggaaaaa gatgaacaag gaaaaactgg gtggtagcct   6600
gttcgcgaaa ccgttcgtgg aaaccgcgat caacctggca cgtcaatctc actgcactta   6660
tcataacggc gacgcgcata cctctccgga tgagctgacc cgcaaacgcg ttctgtctgt   6720
aatcactgaa ccgattctgc cgtttgaacg ctaaggatcc gaattcgagc tccgtcgaca   6780
agcttgcggc cgcactcgag caccaccacc accaccactg agatccggct gctaacaaag   6840
cccgaaagga agctgagttg gctgctgcca ccgctgagca ataactagca taacccctttg   6900 gggcctctaa acgggtcttg agggttttt tgctgaaagg aggaactata tccggat      6957

<210> SEQ ID NO 88
<211> LENGTH: 6068
<212> TYPE: DNA
<213> ORGANISM: Artificial Sequence
<220> FEATURE:
<223> OTHER INFORMATION: Synthetic Construct

<400> SEQUENCE: 88
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gtttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgagatg    420
tagcgtgtcc accgaaaatg tgtctttcac cgaaactgaa accgaagctc gtcgttctgc    480
gaactacgaa cctaacagct gggactatga ttacctgctg tcctccgaca cggacgagtc    540
catcgaagta tacaaagaca aagcgaaaaa gctggaagcc gaagttcgtc gcagagattaa    600 taacgaaaaa gcagaatttc tgaccctgct ggaactgatt gacaacgtcc agcgcctggg    660
cctgggttac cgtttcgagt ctgatatccg tggtgcgctg gatcgcttcg tttcctccgg    720
cggcttcgat gcggtaacca agacttccct gcacggtacg gcactgtctt ccgtctgct    780 gcgtcaacac ggttttgagg tttctcagga agcgttcagc ggcttcaaag accaaaacgg    840
caacttcctg gagaacctga aggaagatat caaagctatc ctgagcctgt acgaggccag    900
cttcctggct ctggaaggcg aaaacatcct ggacgaggcg aaggttttcg caatctctca    960
tctgaaagaa ctgtctgaag aaaagatcgg taaagagctg gcagaacagg tgaaccatgc   1020
```

```
actggaactg ccactgcatc gccgtactca gcgtctggaa gcagtatggt ctatcgaggc    1080
ctaccgtaaa aaggaggacg cgaatcaggt tctgctggaa ctggcaattc tggattacaa    1140
catgatccag tctgtatacc agcgtgatct gcgtgaaacg tcccgttggt ggcgtcgtgt    1200
gggtctggcg accaaactgc actttgctcg tgaccgcctg attgagagct ctactgggc    1260 cgtgggtgta gcattcgaac cgcaatactc cgactgccgt aactccgtcg caaaaatgtt    1320
ttctttcgta accattatcg acgatatcta cgatgtatac ggcaccctgg acgaactgga    1380
gctgtttact gatgcagttg agcgttggga cgtaaacgcc atcaacgacc tgccggatta    1440
catgaaactg tgctttctgg ctctgtataa cactattaac gaaatcgcct acgacaacct    1500
gaaagataaa ggtgagaaca tcctgccgta tctgaccaaa gcctgggctg acctgtgcaa    1560
cgctttcctg caagaagcca gtggctgta caacaaatct actccgacct ttgacgacta    1620
cttcggcaac gcatggaaat cctcttctgg cccgctgcaa ctggtgttcg cttacttcgc    1680
tgtcgtgcag aacattaaaa aggaagagat cgaaaacctg caaaaatacc atgacaccat    1740
ctctcgtcct tcccatatct tccgtctgtg caatgacctg gctagcgcgt ctgcggaaat    1800
tgcgcgtggt gaaaccgcaa atagcgtttc ttgttacatg cgcactaaag gtatctccga    1860
agaactggct accgaaagcg tgatgaatct gatcgatgaa acctggaaaa agatgaacaa    1920
ggaaaaactg ggtggtagcc tgttcgcgaa accgttcgtg gaaaccgcga tcaacctggc    1980
acgtcaatct cactgcactt atcataacgg cgacgcgcat acctctccgg atgagctgac    2040
ccgcaaacgc gttctgtctg taatcactga accgattctg ccgtttgaac gctaactgca    2100
gctggtacca tatgggaatt cgaagctttc tagaacaaaa actcatctca gaagaggatc    2160
tgaatagcgc cgtcgaccat catcatcatc atcattgagt ttaaacggtc tccagcttgg    2220
ctgttttggc ggatgagaga agattttcag cctgatacag attaaatcag aacgcagaag    2280
cggtctgata aaacagaatt tgcctggcgg cagtagcgcg gtggtcccac ctgaccccat    2340
gccgaactca gaagtgaaac gccgtagcgc cgatggtagt gtgggtctc cccatgcgag    2400 agtagggaac tgccaggcat caaataaaac gaaaggctca gtcgaaagac tgggcctttc    2460
gttttatctg ttgtttgtcg gtgaacgctc tcctgagtag acaaatccg ccgggagcgg    2520 atttgaacgt tgcgaagcaa cggcccggag ggtggcgggc aggacgcccg ccataaactg    2580
ccaggcatca aattaagcag aaggccatcc tgacggatgg ccttttttgcg tttctacaaa    2640 ctcttttttgt ttatttttct aaatacattc aaatatgtat ccgctcatga gacaataacc    2700
ctgataaatg cttcaataat attgaaaaag gaagagtatg agtattcaac atttccgtgt    2760
cgcccttatt cccttttttg cggcattttg ccttcctgtt tttgctcacc cagaaacgct    2820
ggtgaaagta aaagatgctg aagatcagtt gggtgcacga gtgggttaca tcgaactgga    2880
tctcaacagc ggtaagatcc ttgagagttt tcgccccgaa gaacgttttc caatgatgag    2940
cacttttaaa gttctgctat gtggcgcggt attatcccgt gttgacgccg ggcaagagca    3000
actcggtcgc cgcatacact attctcagaa tgacttggtt gagtactcac cagtcacaga    3060
aaagcatctt acggatggca tgacagtaag agaattatgc agtgctgcca taaccatgag    3120
tgataacact gcggccaact tacttctgac aacgatcgga ggaccgaagg agctaaccgc    3180
ttttttgcac aacatggggg atcatgtaac tcgccttgat cgttgggaac cggagctgaa    3240
tgaagccata ccaaacgacg agcgtgacac cacgatgcct gtagcaatgg caacaacgtt    3300
gcgcaaacta ttaactggcg aactacttac tctagcttcc cggcaacaat taatagactg    3360
gatggaggcg gataaagttg caggaccact tctgcgctcg gcccttccgg ctggctggtt    3420
```

```
tattgctgat aaatctggag ccggtgagcg tgggtctcgc ggtatcattg cagcactggg   3480
gccagatggt aagccctccc gtatcgtagt tatctacacg acggggagtc aggcaactat   3540
ggatgaacga aatagacaga tcgctgagat aggtgcctca ctgattaagc attggtaact   3600
gtcagaccaa gtttactcat atatacttta gattgattta aaacttcatt tttaatttaa   3660
aaggatctag gtgaagatcc ttttttgataa tctcatgacc aaaatccctt aacgtgagtt   3720
ttcgttccac tgagcgtcag accccgtaga aaagatcaaa ggatcttctt gagatccttt   3780
ttttctgcgc gtaatctgct gcttgcaaac aaaaaaacca ccgctaccag cggtggtttg   3840
tttgccggat caagagctac caactctttt tccgaaggta actggcttca gcagagcgca   3900
gataccaaat actgtccttc tagtgtagcc gtagttaggc caccacttca agaactctgt   3960
agcaccgcct acatacctcg ctctgctaat cctgttacca gtggctgctg ccagtggcga   4020
taagtcgtgt cttaccgggt tggactcaag acgatagtta ccggataagg cgcagcggtc   4080
gggctgaacg gggggttcgt gcacacagcc cagcttggag cgaacgacct acaccgaact   4140
gagataccta cagcgtgagc tatgagaaag cgccacgctt cccgaaggga gaaaggcgga   4200
caggtatccg gtaagcggca gggtcggaac aggagagcgc acgagggagc ttccaggggg   4260
aaacgcctgg tatctttata gtcctgtcgg gtttcgccac ctctgacttg agcgtcgatt   4320
tttgtgatgc tcgtcagggg gcggagcct atggaaaaac gccagcaacg cggccttttt   4380
acggttcctg gccttttgct ggccttttgc tcacatgttc tttcctgcgt tatcccctga   4440
ttctgtggat aaccgtatta ccgcctttga gtgagctgat accgctcgcc gcagccgaac   4500
gaccgagcgc agcgagtcag tgagcgagga agcggaagag cgcctgatgc ggtatttttct   4560
ccttacgcat ctgtgcggta tttcacaccg catatggtgc actctcagta caatctgctc   4620
tgatgccgca tagttaagcc agtatacact ccgctatcgc tacgtgactg ggtcatggct   4680
gcgccccgac acccgccaac acccgctgac gcgccctgac gggcttgtct gctcccggca   4740
tccgcttaca caagctgt gaccgtctcc gggagctgca tgtgtcagag gttttcaccg   4800
tcatcaccga aacgcgcgag gcagcagatc aattcgcgcg cgaaggcgaa gcggcatgca   4860
tttacgttga caccatcgaa tggtgcaaaa cctttcgcgg tatggcatga tagcgcccgg   4920
aagagagtca attcagggtg gtgaatgtga accagtaac gttatacgat gtcgcagagt   4980
atgccggtgt ctcttatcag accgtttccc gcgtggtgaa ccaggccagc cacgtttctg   5040
cgaaaacgcg ggaaaaagtg gaagcggcga tggcggagct gaattacatt cccaaccgcg   5100
tggcacaaca actggcgggc aaacagtcgt tgctgattgg cgttgccacc tccagtctgg   5160
ccctgcacgc gccgtcgcaa attgtcgcgg cgattaaatc tcgcgccgat caactgggtg   5220
ccagcgtggt ggtgtcgatg gtagaacgaa gcggcgtcga agcctgtaaa gcggcggtgc   5280
acaatcttct cgcgcaacgc gtcagtgggc tgatcattaa ctatccgctg gatgaccagg   5340
atgccattgc tgtggaagct gcctgcacta atgttccggc gttatttctt gatgtctctg   5400
accagacacc catcaacagt attatttttct cccatgaaga cggtacgcga ctgggcgtgg   5460
agcatctggt cgcattgggt caccagcaaa tcgcgctgtt agcgggccca ttaagttctg   5520
tctcggcgcg tctgcgtctg gctggctggc ataaatatct cactcgcaat caaattcagc   5580
cgatagcgga acgggaaggc gactggagtg ccatgtccgg ttttcaacaa accatgcaaa   5640
tgctgaatga gggcatcgtt cccactgcga tgctggttgc caacgatcag atggcgctgg   5700
gcgcaatgcg cgccattacc gagtccgggc tgcgcgttgg tgcggatatc tcggtagtgg   5760
gatacgacga taccgaagac agctcatgtt atatcccgcc gtcaaccacc atcaaacagg   5820
```

```
attttcgcct gctggggcaa accagcgtgg accgcttgct gcaactctct cagggccagg    5880
cggtgaaggg caatcagctg ttgcccgtct cactggtgaa agaaaaacc accctggcgc     5940 ccaatacgca aaccgcctct ccccgcgcgt tggccgattc attaatgcag ctggcacgac    6000
aggtttcccg actggaaagc gggcagtgag cgcaacgcaa ttaatgtgag ttagcgcgaa    6060
ttgatctg                                                            6068
```

<210> SEQ ID NO 89
<211> LENGTH: 6906
<212> TYPE: DNA
<213> ORGANISM: Artificial Sequence
<220> FEATURE:
<223> OTHER INFORMATION: Synthetic Construct

<400> SEQUENCE: 89

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgagatg     420
tagcgtgtcc accgaaaatg tgtctttcac cgaaactgaa accgaagctc gtcgttctgc     480
gaactacgaa cctaacagct gggactatga ttacctgctg cctccgaca cggacgagtc      540 catcgaagta tacaaagaca aagcgaaaaa gctggaagcc gaagttcgtc gcagagattaa    600 taacgaaaaa gcagaatttc tgaccctgct ggaactgatt gacaacgtcc agcgcctggg     660
cctgggttac cgtttcgagt ctgatatccg tggtgcgctg gatcgcttcg tttcctccgg     720
cggcttcgat gcggtaacca agacttccct gcacggtacg gcactgtctt ccgtctgct      780 gcgtcaacac ggttttgagg tttctcagga agcgttcagc ggcttcaaag accaaaacgg    840
caacttcctg gagaacctga aggaagatat caaagctatc ctgagcctgt acgaggccag    900
cttcctggct ctggaaggcg aaaacatcct ggacgaggcg aaggttttcg caatctctca    960
tctgaaagaa ctgtctgaag aaagatcgg taaagagctg cagaacagg tgaaccatgc     1020 actggaactg ccactgcatc gccgtactca gcgtctggaa gcagtatggt ctatcgaggc    1080
ctaccgtaaa aagaggacg cgaatcaggt tctgctggaa ctggcaattc tggattacaa    1140
catgatccag tctgtatacc agcgtgatct gcgtgaaacg tcccgttggt ggcgtcgtgt    1200
gggtctggcg accaaactgc actttgctcg tgaccgcctg attgagagct tctactgggc    1260
cgtgggtgta gcattcgaac cgcaatactc cgactgccgt aactccgtcg caaaaatgtt    1320
ttctttcgta accattatcg acgatatcta cgatgtatac ggcacccctg gacgaactgga    1380 gctgtttact gatgcagttg agcgttggga cgtaaacgcc atcaacgacc tgccggatta    1440
catgaaactg tgctttctgg ctctgtataa cactattaac gaaatcgcct acgacaacct    1500
gaaagataaa ggtgagaaca tcctgccgta tctgaccaaa gcctgggctg acctgtgcaa    1560
cgctttcctg caagaagcca agtggctgta caacaaatct actccgacct tgacgacta    1620 cttcggcaac gcatggaaat cctcttctgg cccgctgcaa ctggtgttcg cttacttcgc    1680
tgtcgtgcag aacattaaaa aggaagagat cgaaaacctg caaaaatacc atgacaccat    1740
ctctcgtcct tcccatatct tccgtctgtg caatgacctg gctagcgcgt ctgcggaaat    1800
```

```
tgcgcgtggt gaaaccgcaa atagcgtttc ttgttacatg cgcactaaag gtatctccga   1860
agaactggct accgaaagcg tgatgaatct gatcgatgaa acctggaaaa agatgaacaa   1920
ggaaaaactg ggtggtagcc tgttcgcgaa accgttcgtg gaaaccgcga tcaacctggc   1980
acgtcaatct cactgcactt atcataacgg cgacgcgcat acctctccgg atgagctgac   2040
ccgcaaacgc gttctgtctg taatcactga accgattctg ccgtttgaac gctaactgca   2100
taaaggaggt aaaaaaacat ggtatcctgt tctgcgccgg gtaagattta cctgttcggt   2160
gaacacgccg tagtttatgg cgaaactgca attgcgtgtg cggtggaact gcgtacccgt   2220
gttcgcgcgg aactcaatga ctctatcact attcagagcc agatcggccg caccggtctg   2280
gatttcgaaa agcacccttg tgtgtctgcg gtaattgaga aaatgcgcaa atctattcct   2340
attaacggtg ttttcttgac cgtcgattcc gacatcccgg tgggctccgg tctgggtagc   2400
agcgcagccg ttactatcgc gtctattggt gcgctgaacg agctgttcgg cttttggcctc  2460
agcctgcaag aaatcgctaa actgggccac gaaatcgaaa ttaaagtaca gggtgccgcg   2520
tccccaaccg atacgtatgt ttctaccttc ggcggcgtgg ttaccatccc ggaacgtcgc   2580
aaactgaaaa ctccggactg cggcattgtg attggcgata ccggcgtttt ctcctccacc   2640
aaagagttag tagctaacgt acgtcagctg cgcgaaagct acccggattt gatcgaaccg   2700
ctgatgacct ctattggcaa aatctctcgt atcggcgaac aactggttct gtctggcgac   2760
tacgcatcca tcggccgcct gatgaacgtc aaccagggtc tcctggacgc cctgggcgtt   2820
aacatcttag aactgagcca gctgatctat tccgctcgtg cggcaggtgc gtttggcgct   2880
aaaatcacgg gcgctggcgg cggtggctgt atggttgcgc tgaccgctcc ggaaaaatgc   2940
aaccaagtgg cagaagcggt agcaggcgct ggcggtaaag tgactatcac taaaccgacc   3000
gagcaaggtc tgaaagtaga ttaaagtcta gttaaagttt aaacggtctc cagcttggct   3060
gttttggcgg atgagagaag attttcagcc tgatacagat taaatcagaa cgcagaagcg   3120
gtctgataaa acagaatttg cctggcggca gtagcgcggt ggtcccacct gacccccatgc  3180
cgaactcaga agtgaaacgc cgtagcgccg atggtagtgt ggggtctccc catgcgagag   3240
tagggaactg ccaggcatca aataaaacga aaggctcagt cgaaagactg gccctttcgt   3300
tttatctgtt gtttgtcggt gaacgctctc ctgagtagga caaatccgcc gggagcggat   3360
ttgaacgttg cgaagcaacg gcccggaggg tggcgggcag gacgcccgcc ataaactgcc   3420
aggcatcaaa ttaagcagaa ggccatcctg acggatggcc ttttttgcgtt tctacaaact   3480
cttttttgttt atttttctaa atacattcaa atatgtatcc gctcatgaga caataaccct   3540
gataaatgct tcaataatat tgaaaaagga agagtatgag tattcaacat ttccgtgtcg   3600
cccttattcc cttttttgcg gcattttgcc ttcctgtttt tgctcaccca gaaacgctgg   3660
tgaaagtaaa agatgctgaa gatcagttgg gtgcacgagt gggttacatc gaactggatc   3720
tcaacagcgg taagatcctt gagagttttc gccccgaaga acgttttcca atgatgagca   3780
cttttaaagt tctgctatgt ggcgcggtat tatcccgtgt tgacgccggg caagagcaac   3840
tcggtcgccg catacactat tctcagaatg acttggttga gtactcacca gtcacagaaa   3900
agcatcttac ggatggcatg acagtaagag aattatgcag tgctgccata accatgagtg   3960
ataacactgc ggccaactta cttctgacaa cgatcgagg accgaaggag ctaaccgctt   4020
ttttgcacaa catgggggat catgtaactc gccttgatcg ttgggaaccg gagctgaatg   4080
aagccatacc aaacgacgag cgtgacacca cgatgcctgt agcaatggca acaacgttgc   4140
gcaaactatt aactggcgaa ctacttactc tagcttcccg gcaacaatta atagactgga   4200
```

```
tggaggcgga taaagttgca ggaccacttc tgcgctcggc ccttccggct ggctggttta   4260
ttgctgataa atctggagcc ggtgagcgtg ggtctcgcgg tatcattgca gcactggggc   4320
cagatggtaa gccctcccgt atcgtagtta tctacacgac ggggagtcag gcaactatgg   4380
atgaacgaaa tagacagatc gctgagatag gtgcctcact gattaagcat tggtaactgt   4440
cagaccaagt ttactcatat atactttaga ttgatttaaa acttcatttt taatttaaaa   4500
ggatctaggt gaagatcctt tttgataatc tcatgaccaa atcccttaa cgtgagtttt   4560 cgttccactg agcgtcagac cccgtagaaa agatcaaagg atcttcttga tccttttttt   4620
ttctgcgcgt aatctgctgc ttgcaaacaa aaaaaccacc gctaccagcg gtggtttgtt   4680
tgccggatca gagctacca actcttttc cgaaggtaac tggcttcagc agagcgcaga   4740
taccaaatac tgtccttcta gtgtagccgt agttaggcca ccacttcaag aactctgtag   4800
caccgcctac atacctcgct ctgctaatcc tgttaccagt ggctgctgcc agtggcgata   4860
agtcgtgtct taccgggttg gactcaagac gatagttacc ggataaggcg cagcggtcgg   4920
gctgaacggg gggttcgtgc acacagccca gcttggagcg aacgacctac accgaactga   4980 gataccctaca gcgtgagcta tgagaaagcg ccacgcttcc cgaagggaga aaggcggaca   5040
ggtatccggt aagcggcagg gtcggaacag gagagcgcac gagggagctt ccaggggggaa   5100 acgcctggta tctttatagt cctgtcgggt ttcgccacct ctgacttgag cgtcgatttt   5160
tgtgatgctc gtcagggggg cggagcctat ggaaaaacgc cagcaacgcg gcctttttac   5220
ggttcctggc cttttgctgg cctttgctc acatgttctt tcctgcgtta tcccctgatt   5280
ctgtggataa ccgtattacc gcctttgagt gagctgatac cgctcgccgc agccgaacga   5340
ccgagcgcag cgagtcagtg agcgaggaag cggaagagcg cctgatgcgg tattttctcc   5400
ttacgcatct gtgcggtatt tcacaccgca tatggtgcac tctcagtaca atctgctctg   5460
atgccgcata gttaagccag tatacactcc gctatcgcta cgtgactggg tcatggctgc   5520
gccccgacac ccgccaacac ccgctgacgc gccctgacgg gcttgtctgc tcccggcatc   5580
cgcttacaga caagctgtga ccgtctccgg gagctgcatg tgtcagaggt tttcaccgtc   5640
atcaccgaaa cgcgcgaggc agcagatcaa ttcgcgcgcg aaggcgaagc ggcatgcatt   5700
tacgttgaca ccatcgaatg gtgcaaaacc tttcgcggta tggcatgata gcgcccggaa   5760
gagagtcaat tcagggtggt gaatgtgaaa ccagtaacgt tatacgatgt cgcagagtat   5820
gccggtgtct cttatcagac cgtttcccgc gtggtgaacc aggccagcca cgtttctgcg   5880
aaaacgcggg aaaagtggaa gcggcgatg gcggagctga attacattcc caaccgcgtg   5940
gcacaacaac tggcgggcaa acagtcgttg ctgattggcg ttgccacctc cagtctggcc   6000
ctgcacgcgc cgtcgcaaat tgtcgcggcg attaaatctc gcgccgatca actgggtgcc   6060
agcgtggtgg tgtcgatggt agaacgaagc ggcgtcgaag cctgtaaagc ggcggtgcac   6120
aatcttctcg cgcaacgcgt cagtgggctg atcattaact atccgctgga tgaccaggat   6180
gccattgctg tggaagctgc ctgcactaat gttccggcgt tatttcttga tgtctctgac   6240
cagacaccca tcaacagtat tattttctcc catgaagacg gtacgcgact gggcgtggag   6300
catctggtcg cattgggtca ccagcaaatc gcgctgttag cgggcccatt aagttctgtc   6360
tcggcgcgtc tgcgtctggc tggctggcat aaatatctca ctcgcaatca aattcagccg   6420
atagcggaac gggaaggcga ctggagtgcc atgtccggtt ttcaacaaac catgcaaatg   6480
ctgaatgagg gcatcgttcc cactgcgatg ctggttgcca acgatcagat ggcgctgggc   6540
gcaatgcgcg ccattaccga gtccgggctg cgcgttggtg cggatatctc ggtagtggga   6600
```

```
tacgacgata ccgaagacag ctcatgttat atcccgccgt caaccaccat caaacaggat    6660
tttcgcctgc tggggcaaac cagcgtggac cgcttgctgc aactctctca gggccaggcg    6720
gtgaagggca atcagctgtt gcccgtctca ctggtgaaaa gaaaaaccac cctggcgccc    6780
aatacgcaaa ccgcctctcc ccgcgcgttg gccgattcat taatgcagct ggcacgacag    6840
gtttcccgac tggaaagcgg gcagtgagcg caacgcaatt aatgtgagtt agcgcgaatt    6900
gatctg                                                               6906

<210> SEQ ID NO 90
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 90
aagggcgagc tcaacgatcc ggctgctaac aaagcccgaa aggaagctga gttggctgct      60
gccaccgctg agcataaact agcataaccc cttggggcct ctaaacgggt cttgaggagt     120
tttttgctga aggaggaac tatatccgga tatcccgcaa gaggcccggc agtaccggca     180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata ataatggttt cttagacgtc     420
aggtggcact tttcggggaa atgtgcgcgg aacccctatt tgtttatttt tctaaataca     480
ttcaaatatg tatccgctca tgagacaata accctgataa atgcttcaat aatattgaaa     540
aaggaagagt atgattgaac aagatggatt gcacgcaggt tctccggccg cttgggtgga     600
gaggctattc ggctatgact gggcacaact gacaatcggc tgctctgatg ccgccgtgtt     660
ccggctgtca gcgcagggggc gcccggttct ttttgtcaag accgacctgt ccggtgccct     720
gaatgaactg caggacgagg cagcgcggct atcgtggctg gccacgacgg gcgttccttg     780
cgcagctgtg ctcgacgttg tcactgaagc gggaagggac tggctgctat tgggcgaagt     840
gccggggcag gatctcctgt catctcacct tgctcctgcc gagaaagtat ccatcatggc     900
tgatgcaatg cggcggctgc atacgcttga tccggctacc tgcccattcg accaccaagc     960
gaaacatcgc atcgagcggg cacgtactcg gatggaagcc ggtcttgtcg atcaggatga    1020
tctggacgaa gagcatcagg ggctcgcgcc agccgaactg ttcgccaggc tcaaggcgcg    1080
catgcccgac ggcgaggatc tcgtcgtgac acatggcgat gcctgcttgc cgaatatcat    1140
ggtggaaaat ggccgctttt ctggattcat cgactgtggc cggctgggtg tggcggaccg    1200
ctatcaggac atagcgttgg ctacccgtga tattgctgaa gagcttggcg gcgaatgggc    1260
tgaccgcttc ctcgtgcttt acggtatcgc cgctcccgat tcgcagcgca tcgccttcta    1320
tcgccttctt gacgagttct tctgagcggg actctggggt tcgaaatgac cgaccaagcg    1380
acgcctaact gtcagaccaa gtttactcat atatacttta gattgattta aaacttcatt    1440
tttaatttaa aaggatctag gtgaagatcc ttttttgataa tctcatgacc aaaatccctt    1500
aacgtgagtt tcgttccac tgagcgtcag accccgtaga aaagatcaaa ggatcttctt    1560
gagatccttt ttttctgcgc gtaatctgct gcttgcaaac aaaaaaacca ccgctaccag    1620
cggtggtttg tttgccggat caagagctac caactctttt tccgaaggta actggcttca    1680
gcagagcgca gataccaaat actgtccttc tagtgtagcc gtagttaggc caccacttca    1740
```

```
agaactctgt agcaccgcct acatacctcg ctctgctaat cctgttacca gtggctgctg    1800
ccagtggcga taagtcgtgt cttaccgggt tggactcaag acgatagtta ccggataagg    1860
cgcagcggtc gggctgaacg gggggttcgt gcacacagcc cagcttggag cgaacgacct    1920
acaccgaact gagataccta cagcgtgagc tatgagaaag cgccacgctt cccgaaggga    1980
gaaaggcgga caggtatccg gtaagcggca gggtcggaac aggagagcgc acgagggagc    2040
ttccagggga aaacgcctgg tatctttata gtcctgtcgg gtttcgccac ctctgacttg    2100
agcgtcgatt tttgtgatgc tcgtcagggg ggcggagcct atggaaaaac gccagcaacg    2160
cggccttttt acgttcctg gccttttgct ggcctttgc tcacatgttc tttcctgcgt    2220
tatcccctga ttctgtggat aaccgtatta ccgcctttga gtgagctgat accgctcgcc    2280
gcagccgaac gaccgagcgc agcgagtcag tgagcgagga gcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctccaga    2700
agcgttaatg tctggcttct gataaagcgg gccatgttaa gggcggtttt ttcctgtttg    2760
gtcactgatg cctccgtgta agggggattt ctgttcatgg gggtaatgat accgatgaaa    2820
cgagagagga tgctcacgat acgggttact gatgatgaac atgcccggtt actggaacgt    2880
tgtgagggta acaactggc ggtatggatg cggcggacc agagaaaaat cactcagggt    2940
caatgccagc gcttcgttaa tacagatgta ggtgttccac agggtagcca gcagcatcct    3000
gcgatgcaga tccggaacat aatggtgcag ggcgctgact ccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480
tccatgccaa cccgttccat gtgctcgccg aggcggcata aatcgccgtg acgatcagcg    3540
gtccaatgat cgaagttagg ctggtaagag ccgcgagcga tccttgaagc tgtccctgat    3600
ggtcgtcatc tacctgcctg gacagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tccggtgcc taatgagtga gctaacttac attaattgcg ttgcgctcac    4080
tgcccgcttt ccagtcggga aacctgtcgt gccagctgca ttaatgaatc ggccaacgcg    4140
```

```
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatacccca cgccgaaaca    5400 agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580 aacaattccc ctctagaaat aattttgttt aactttaaga aggagatata catatgaatt    5640
aaccctcact aaagggcggc cgcgaagttc ctattctcta aaagtatag gaacttcatt    5700 ctaccgggta ggggaggcgc ttttcccaag gcagtctgga gcatgcgctt tagcagcccc    5760
gctgggcact tggcgctaca caagtggcct ctggcctcgc acacattcca catccaccgg    5820
taggcgccaa ccgctccgt tctttggtgg ccccttcgcg ccaccttcca ctcctcccct    5880
agtcaggaag ttcccccccg ccccgcagct cgcgtcgtgc aggacgtgac aaatggaagt    5940
agcacgtctc actagtctcg tgcagatgga cagcaccgct gagcaatgga agcgggtagg    6000
cctttggggc agcggccaat agcagctttg ctccttcgct ttctgggctc agaggctggg    6060
aaggggtggg tccgggggcg ggctcagggg cgggctcagg ggcggggcgg gcgcccgaag    6120
gtcctccgga ggcccggcat tctgcacgct tcaaagcgc acgtctgccg cgctgttctc    6180
ctcttcctca tctccgggcc tttcgacctg cagcagcacg tgttgacaat taatcatcgg    6240
catagtatat cggcatagta taatacgaca aggtgaggaa ctaaaccatg gagaaaaaaa    6300
tcactggata taccaccgtt gatatatccc aatggcatcg taaagaacat tttgaggcat    6360
ttcagtcagt tgctcaatgt acctataacc agaccgttca gctggatatt acggcctttt    6420
taaagaccgt aaagaaaaat aagcacaagt tttatccggc ctttattcac attcttgccc    6480
gcctgatgaa tgctcatccg gaattccgta tggcaatgaa agacggtgag ctggtgatat    6540
```

| | |
|---|---|
| gggatagtgt tcacccttgt tacaccgttt ccatgagca aactgaaacg ttttcatcgc | 6600 |
| tctggagtga ataccacgac gatttccggc agtttctaca catatattcg caagatgtgg | 6660 |
| cgtgttacgg tgaaaacctg gcctatttcc ctaaagggtt tattgagaat atgttttcg | 6720 |
| tctcagccaa tccctgggtg agtttcacca gttttgattt aaacgtggcc aatatggaca | 6780 |
| acttcttcgc cccgtttc accatgggca aatattatac gcaaggcgac aaggtgctga | 6840 |
| tgccgctggc gattcaggtt catcatgccg tttgtgatgg cttccatgtc ggcagaatgc | 6900 |
| ttaatgaatt acaacagtac tgcgatgagt ggcagggcgg ggcgtaagcg ggactctggg | 6960 |
| gttcgaataa agaccgacca agcgacgtct gagagctccc tggcgaattc ggtaccaata | 7020 |
| aaagagcttt attttcatga tctgtgtgtt ggttttgtg tgcggcgcgg aagttcctat | 7080 |
| tctctagaaa gtataggaac ttcctcgagc cctatagtga gtcgtattag atcgcggccg | 7140 |
| cgcccttgac aatgccacat cctgagcaaa taattcaacc actaattgtg agcggataac | 7200 |
| aaaggaggta aaaaaacatg gtatcctgtt ctgcgccggg taagatttac ctgttcggtg | 7260 |
| aacacgccgt agtttatggc gaaactgcaa ttgcgtgtgc ggtggaactg cgtacccgtg | 7320 |
| ttcgcgcgga actcaatgac tctatcacta ttcagagcca gatcggccgc accggtctgg | 7380 |
| atttcgaaaa gcacccttat gtgtctgcgg taattgagaa aatgcgcaaa tctattccta | 7440 |
| ttaacggtgt tttcttgacc gtcgattccg acatcccggt gggctccggt ctgggtagca | 7500 |
| gcgcagccgt tactatcgcg tctattggtg cgctgaacga gctgttcggc tttggcctca | 7560 |
| gcctgcaaga aatcgctaaa ctgggccacg aaatcgaaat taagtacag ggtgccgcgt | 7620 |
| ccccaaccga tacgtatgtt tctaccttcg gcggcgtggt taccatcccg gaacgtcgca | 7680 |
| aactgaaaac tccggactgc ggcattgtga ttggcgatac cggcgttttc tcctccacca | 7740 |
| aagagttagt agctaacgta cgtcagctgc gcgaaagcta cccggatttg atcgaaccgc | 7800 |
| tgatgacctc tattggcaaa atctctcgta tcggcgaaca actggttctg tctggcgact | 7860 |
| acgcatccat cggccgcctg atgaacgtca accagggtct cctggacgcc ctgggcgtta | 7920 |
| acatcttaga actgagccag ctgatctatt ccgctcgtgc ggcaggtgcg tttggcgcta | 7980 |
| aaatcacggg cgctggcggc ggtggctgta tggttgcgct gaccgctccg gaaaaatgca | 8040 |
| accaagtggc agaagcggta gcaggcgctg gcggtaaagt gactatcact aaaccgaccg | 8100 |
| agcaaggtct gaaagtagat taa | 8123 |

<210> SEQ ID NO 91
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 91

| | |
|---|---|
| aagggcgagc tcaacgatcc ggctgctaac aaagcccgaa aggaagctga gttggctgct | 60 |
| gccaccgctg agcaataact agcataaccc cttggggcct ctaaacgggt cttgaggagt | 120 |
| tttttgctga aggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catacacggt gcctgactgc gttagcaatt taactgtgat aaactaccgc | 300 |
| attaaagctt atcgatgata agctgtcaaa catgagaatt aattcttgaa gacgaaaggg | 360 |
| cctcgtgata cgcctatttt tataggttaa tgtcatgata ataatggttt cttagacgtc | 420 |
| aggtggcact tttcggggaa atgtgcgcgg aaccccctatt tgtttatttt tctaaataca | 480 |

-continued

```
ttcaaatatg tatccgctca tgagacaata accctgataa atgcttcaat aatattgaaa      540
aaggaagagt atgattgaac aagatggatt gcacgcaggt tctccggccg cttgggtgga      600
gaggctattc ggctatgact gggcacaact gacaatcggc tgctctgatg ccgccgtgtt      660
ccggctgtca gcgcagggc gcccggttct ttttgtcaag accgacctgt ccggtgccct       720
gaatgaactg caggacgagg cagcgcggct atcgtggctg gccacgacgg gcgttccttg      780
cgcagctgtg ctcgacgttg tcactgaagc gggaagggac tggctgctat tgggcgaagt      840
gccggggcag gatctcctgt catctcacct tgctcctgcc gagaaagtat ccatcatggc      900
tgatgcaatg cggcggctgc atacgcttga tccggctacc tgcccattcg accaccaagc      960
gaaacatcgc atcgagcggg cacgtactcg gatggaagcc ggtcttgtcg atcaggatga     1020
tctggacgaa gagcatcagg ggctcgcgcc agccgaactg ttcgccaggc tcaaggcgcg     1080
catgcccgac ggcgaggatc tcgtcgtgac acatggcgat gcctgcttgc cgaatatcat     1140
ggtggaaaat ggccgctttt ctggattcat cgactgtggc cggctgggtg tggcggaccg     1200
ctatcaggac atagcgttgg ctacccgtga tattgctgaa gagcttggcg gcgaatgggc     1260
tgaccgcttc ctcgtgcttt acggtatcgc cgctcccgat tcgcagcgca tcgccttcta     1320
tcgccttctt gacgagttct tctgagcggg actctggggt tcgaaatgac cgaccaagcg     1380
acgcctaact gtcagaccaa gtttactcat atatacttta gattgattta aaacttcatt     1440
tttaatttaa aaggatctag gtgaagatcc ttttttgataa tctcatgacc aaaatccctt     1500
aacgtgagtt ttcgttccac tgagcgtcag accccgtaga aaagatcaaa ggatcttctt     1560
gagatccttt ttttctgcgc gtaatctgct gcttgcaaac aaaaaaacca ccgctaccag     1620
cggtggtttg tttgccggat caagagctac caactctttt tccgaaggta actggcttca     1680
gcagagcgca gataccaaat actgtccttc tagtgtagcc gtagttaggc caccacttca     1740
agaactctgt agcaccgcct acatacctcg ctctgctaat cctgttacca gtggctgctg     1800
ccagtggcga taagtcgtgt cttaccgggt tggactcaag acgatagtta ccggataagg     1860
cgcagcggtc gggctgaacg gggggttcgt gcacacagcc cagcttggag cgaacgacct     1920
acaccgaact gagatacccta cagcgtgagc tatgagaaag cgccacgctt cccgaaggga     1980
gaaaggcgga caggtatccg gtaagcggca gggtcggaac aggagagcgc acagggagc     2040 ttccagggg aaacgcctgg tatctttata gtcctgtcgg gtttcgccac ctctgacttg      2100
agcgtcgatt tttgtgatgc tcgtcagggg gcggagcct atggaaaaac gccagcaacg      2160 cggcctttt acgttcctg gccttttgct ggccttttgc tcacatgttc tttcctgcgt       2220
tatcccctga ttctgtggat aaccgtatta ccgcctttga gtgagctgat accgctcgcc     2280
gcagccgaac gaccgagcgc agcgagtcag tgagcgagga agcggaagag cgcctgatgc     2340
ggtattttct ccttacgcat ctgtgcggta tttcacaccg caatggtgca ctctcagtac     2400
aatctgctct gatgccgcat agttaagcca gtatacactc cgctatcgct acgtgactgg     2460
gtcatggctg cgccccgaca cccgccaaca cccgctgacg cgccctgacg ggcttgtctg     2520
ctcccggcat ccgcttacag acaagctgtg accgtctccg ggagctgcat gtgtcagagg     2580
ttttcaccgt catcaccgaa acgcgcgagg cagctgcggt aaagctcatc agcgtggtcg     2640
tgaagcgatt cacagatgtc tgcctgttca tccgcgtcca gctcgttgag tttctccaga     2700
agcgttaatg tctggcttct gataaagcgg gccatgttaa gggcggtttt ttcctgtttg     2760
gtcactgatg cctccgtgta agggggattt ctgttcatgg gggtaatgat accgatgaaa     2820
cgagagagga tgctcacgat acgggttact gatgatgaac atgcccggtt actggaacgt     2880
```

```
tgtgagggta acaactggc ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag ggcgctgact tccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480 tccatgccaa cccgttccat gtgctcgccg aggcggcata aatcgccgtg acgatcagcg    3540
gtccaatgat cgaagttagg ctggtaagag ccgcgagcga tccttgaagc tgtccctgat    3600
ggtcgtcatc tacctgcctg acagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctcccttat gcgactcct gcattaggaa    5280
```

```
gcagcccagt agtaggttga ggccgttgag caccgccgcc gcaaggaatg gtgcatgcaa    5340
ggagatggcg cccaacagtc ccccggccac ggggcctgcc accatacccc cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580 aacaattccc ctctagaaat aattttgttt aactttaaga aggagatata catatgaatt    5640
aaccctcact aaagggcggc cgcgaagttc ctattctcta gaaagtatag gaacttcatt    5700
ctaccgggta ggggaggcgc ttttcccaag gcagtctgga gcatgcgctt tagcagcccc    5760
gctgggcact tggcgctaca caagtggcct ctggcctcgc acacattcca catccaccgg    5820
taggcgccaa ccggctccgt tctttggtgg ccccttcgcg ccaccttcca ctcctcccct    5880
agtcaggaag ttccccccg ccccgcagct cgcgtcgtgc aggacgtgac aaatggaagt    5940
agcacgtctc actagtctcg tgcagatgga cagcaccgct gagcaatgga agcgggtagg    6000
cctttggggc agcggccaat agcagctttg ctccttcgct ttctgggctc agaggctggg    6060
aaggggtggg tccgggggcg ggctcagggg cgggctcagg ggcggggcgg gcgcccgaag    6120
gtcctccgga ggcccggcat tctgcacgct tcaaaagcgc acgtctgccg cgctgttctc    6180
ctcttcctca tctccgggcc tttcgacctg cagcagcacg tgttgacaat taatcatcgg    6240
catagtatat cggcatagta taatacgaca aggtgaggaa ctaaaccatg gagaaaaaaa    6300
tcactggata taccaccgtt gatatatccc aatggcatcg taaagaacat tttgaggcat    6360
ttcagtcagt tgctcaatgt acctataacc agaccgttca gctggatatt acggcctttt    6420
taaagaccgt aaagaaaaat aagcacaagt tttatccggc ctttattcac attcttgccc    6480
gcctgatgaa tgctcatccg gaattccgta tggcaatgaa agacggtgag ctggtgatat    6540
gggatagtgt tcacccttgt tacaccgttt tccatgagca aactgaaacg ttttcatcgc    6600
tctggagtga ataccacgac gatttccggc agtttctaca catatattcg caagatgtgg    6660
cgtgttacgg tgaaaacctg gcctatttcc ctaaagggtt tattgagaat atgtttttcg    6720
tctcagccaa tccctgggtg agtttcacca gttttgattt aaacgtggcc aatatggaca    6780
acttcttcgc cccgttttc accatgggca aatattatac gcaaggcgac aaggtgctga    6840
tgccgctggc gattcaggtt catcatgccg tttgtgatgg cttccatgtc ggcagaatgc    6900
ttaatgaatt acaacagtac tgcgatgagt ggcagggcgg ggcgtaagcg gactctggg    6960 gttcgaataa agaccgacca agcgacgtct gagagctccc tggcgaattc ggtaccaata    7020
aaagagcttt attttcatga tctgtgtgtt ggttttgtg tgcggcgcgg aagttcctat    7080
tctctagaaa gtataggaac ttcctcgagc cctatagtga gtcgtattag atcgcggccg    7140
cgcccttgac catgccacat cctgagcaaa taattcaacc actaattgtg agcggataac    7200
aaaggaggta aaaaacatg gtatcctgtt ctgcgccggg taagatttac ctgttcggtg    7260
aacacgccgt agtttatggc gaaactgcaa ttgcgtgtgc ggtggaactg cgtacccgtg    7320
ttcgcgcgga actcaatgac tctatcacta ttcagagcca gatcggccgc accggtctgg    7380
atttcgaaaa gcacccttat gtgtctgcgg taattgagaa aatgcgcaaa tctattccta    7440 ttaacgtgt tttcttgacc gtcgattccg acatcccggt gggctccggt ctgggtagca    7500
gcgcagccgt tactatcgcg tctattggtg cgctgaacga gctgttcggc tttggcctca    7560
gcctgcaaga aatcgctaaa ctgggccacg aaatcgaaat taagtacag ggtgccgcgt    7620 ccccaaccga tacgtatgtt tctaccttcg gcggcgtggt taccatcccg gaacgtcgca    7680
```

| | | | | |
|---|---|---|---|---|
| aactgaaaac | tccggactgc | ggcattgtga | ttggcgatac | cggcgttttc tcctccacca | 7740 |
| aagagttagt | agctaacgta | cgtcagctgc | gcgaaagcta | cccggatttg atcgaaccgc | 7800 |
| tgatgacctc | tattggcaaa | atctctcgta | tcggcgaaca | actggttctg tctggcgact | 7860 |
| acgcatccat | cggccgcctg | atgaacgtca | accaggtct | cctggacgcc ctgggcgtta | 7920 |
| acatcttaga | actgagccag | ctgatctatt | ccgctcgtgc | ggcaggtgcg tttggcgcta | 7980 |
| aaatcacggg | cgctggcggc | ggtggctgta | tggttgcgct | gaccgctccg gaaaaatgca | 8040 |
| accaagtggc | agaagcggta | gcaggcgctg | gcggtaaagt | gactatcact aaaccgaccg | 8100 |
| agcaaggtct | gaaagtagat | taa | | | 8123 |

<210> SEQ ID NO 92
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 92

| | | | | | |
|---|---|---|---|---|---|
| aagggcgagc | tcaacgatcc | ggctgctaac | aaagcccgaa | aggaagctga gttggctgct | 60 |
| gccaccgctg | agcaataact | agcataaccc | cttggggcct | ctaaacgggt cttgaggagt | 120 |
| tttttgctga | aaggaggaac | tatatccgga | tatcccgcaa | gaggcccggc agtaccggca | 180 |
| taaccaagcc | tatgcctaca | gcatccaggg | tgacggtgcc | gaggatgacg atgagcgcat | 240 |
| tgttagattt | catacacggt | gcctgactgc | gttagcaatt | taactgtgat aaactaccgc | 300 |
| attaaagctt | atcgatgata | agctgtcaaa | catgagaatt | aattcttgaa gacgaaaggg | 360 |
| cctcgtgata | cgcctatttt | tataggttaa | tgtcatgata | ataatggttt cttagacgtc | 420 |
| aggtggcact | tttcggggaa | atgtgcgcgg | aacccctatt | tgtttatttt tctaaataca | 480 |
| ttcaaatatg | tatccgctca | tgagacaata | accctgataa | atgcttcaat aatattgaaa | 540 |
| aaggaagagt | atgattgaac | aagatggatt | gcacgcaggt | tctccggccg cttgggtgga | 600 |
| gaggctattc | ggctatgact | gggcacaact | gacaatcggc | tgctctgatg ccgccgtgtt | 660 |
| ccggctgtca | gcgcaggggc | gcccggttct | ttttgtcaag | accgacctgt ccggtgccct | 720 |
| gaatgaactg | caggacgagg | cagcgcggct | atcgtggctg | gccacgacgg gcgttccttg | 780 |
| cgcagctgtg | ctcgacgttg | tcactgaagc | gggaagggac | tggctgctat gggcgaagt | 840 |
| gccgggggcag | gatctcctgt | catctcacct | tgctcctgcc | gagaaagtat ccatcatggc | 900 |
| tgatgcaatg | cggcggctgc | atacgcttga | tccggctacc | tgcccattcg accaccaagc | 960 |
| gaaacatcgc | atcgagcggg | cacgtactcg | gatggaagcc | ggtcttgtcg atcaggatga | 1020 |
| tctggacgaa | gagcatcagg | ggctcgcgcc | agccgaactg | ttcgccaggc tcaaggcgcg | 1080 |
| catgcccgac | ggcgaggatc | tcgtcgtgac | acatggcgat | gcctgcttgc cgaatatcat | 1140 |
| ggtggaaaat | ggccgctttt | ctggattcat | cgactgtggc | cggctgggtg tggcggaccg | 1200 |
| ctatcaggac | atagcgttgg | ctacccgtga | tattgctgaa | gagcttggcg gcgaatgggc | 1260 |
| tgaccgcttc | ctcgtgcttt | acggtatcgc | cgctcccgat | tcgcagcgca tcgccttcta | 1320 |
| tcgccttctt | gacgagttct | tctgagcggg | actctggggt | tcgaaatgac cgaccaagcg | 1380 |
| acgcctaact | gtcagaccaa | gtttactcat | atatacttta | gattgattta aaacttcatt | 1440 |
| tttaatttaa | aaggatctag | gtgaagatcc | tttttgataa | tctcatgacc aaaatccctt | 1500 |
| aacgtgagtt | ttcgttccac | tgagcgtcag | accccgtaga | aaagatcaaa ggatcttctt | 1560 |
| gagatccttt | ttttctgcgc | gtaatctgct | gcttgcaaac | aaaaaaacca ccgctaccag | 1620 |

```
cggtggtttg tttgccggat caagagctac caactcttt tccgaaggta actggcttca    1680
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttaccgggt tggactcaag acgatagtta ccggataagg    1860
cgcagcggtc gggctgaacg gggggttcgt gcacacagcc cagcttggag cgaacgacct    1920
acaccgaact gagataccta cagcgtgagc tatgagaaag cgccacgctt cccgaaggga    1980
gaaaggcgga caggtatccg gtaagcggca gggtcggaac aggagagcgc acgagggagc    2040
ttccagggg aaacgcctgg tatctttata gtcctgtcgg gtttcgccac ctctgacttg     2100
agcgtcgatt tttgtgatgc tcgtcagggg ggcggagcct atggaaaaac gccagcaacg    2160
cggccttttt acgttcctg gccttttgct ggccttttgc tcacatgttc tttcctgcgt     2220
tatcccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctcccaga    2700
agcgttaatg tctggcttct gataaagcgg gccatgttaa gggcggtttt tcctgtttg     2760
gtcactgatg cctccgtgta agggggattt ctgttcatgg gggtaatgat accgatgaaa    2820
cgagagagga tgctcacgat acgggttact gatgatgaac atgcccggtt actggaacgt    2880
tgtgagggta acaactggc ggtatggatg cggcggacc agagaaaaat cactcagggt      2940
caatgccagc gcttcgttaa tacagatgta ggtgttccac agggtagcca gcagcatcct    3000
gcgatgcaga tccggaacat aatggtgcag ggcgctgact ccgcgtttc cagactttac     3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtataggggcg gcgcctacaa    3480
tccatgccaa cccgttccat gtgctcgccg aggcggcata aatcgccgtg acgatcagcg    3540
gtccaatgat cgaagttagg ctggtaagag ccgcgagcga tccttgaagc tgtccctgat    3600
ggtcgtcatc tacctgcctg gacagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
```

```
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgccaccaa cgcgcagcccg   4380 gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatacccca cgccgaaaca    5400 agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580 aacaattccc ctctagaaat aattttgttt aactttaaga aggagatata catatgaatt    5640
aaccctcact aaagggcggc cgcgaagttc ctattctcta gaaagtatag gaacttcatt    5700
ctaccgggta ggggaggcgc ttttcccaag gcagtctgga gcatgcgctt tagcagcccc    5760
gctgggcact tggcgctaca caagtggcct ctggcctcgc acacattcca catccaccgg    5820
taggcgccaa ccgctccgt tctttggtgg ccccttcgcg ccaccttcca ctcctcccct    5880
agtcaggaag ttcccccccg ccccgcagct cgcgtcgtgc aggacgtgac aaatggaagt    5940
agcacgtctc actagtctcg tgcagatgga cagcaccgct gagcaatgga agcgggtagg    6000 cctttgggc agcggccaat agcagctttg ctccttcgct ttctgggctc agaggctggg    6060
aaggggtggg tccgggggcg ggctcagggg cgggctcagg ggcggggcgg gcgcccgaag    6120
gtcctccgga ggcccggcat tctgcacgct tcaaaagcgc acgtctgccg cgctgttctc    6180
ctcttcctca tctccgggcc tttcgacctg cagcagcacg tgttgacaat taatcatcgg    6240
catagtatat cggcatagta taatacgaca aggtgaggaa ctaaaccatg agaaaaaaa    6300 tcactggata taccaccgtt gatatatccc aatggcatcg taaagaacat tttgaggcat    6360
ttcagtcagt tgctcaatgt acctataacc agaccgttca gctggatatt acggcctttt    6420
```

-continued

| | |
|---|---|
| taaagaccgt aaagaaaaat aagcacaagt tttatccggc ctttattcac attcttgccc | 6480 |
| gcctgatgaa tgctcatccg gaattccgta tggcaatgaa agacggtgag ctggtgatat | 6540 |
| gggatagtgt tcacccttgt tacaccgttt tccatgagca aactgaaacg ttttcatcgc | 6600 |
| tctgagtga ataccacgac gatttccggc agtttctaca catatattcg caagatgtgg | 6660 |
| cgtgttacgg tgaaaacctg gcctatttcc ctaaagggtt tattgagaat atgtttttcg | 6720 |
| tctcagccaa tccctgggtg agtttcacca gttttgattt aaacgtggcc aatatggaca | 6780 |
| acttcttcgc ccccgttttc accatgggca aatattatac gcaaggcgac aaggtgctga | 6840 |
| tgccgctggc gattcaggtt catcatgccg tttgtgatgg cttccatgtc ggcagaatgc | 6900 |
| ttaatgaatt acaacagtac tgcgatgagt ggcagggcgg ggcgtaagcg ggactctggg | 6960 |
| gttcgaataa agaccgacca agcgacgtct gagagctccc tggcgaattc ggtaccaata | 7020 |
| aaagagcttt attttcatga tctgtgtgtt ggttttttgt gtgcggcgcgg aagttcctat | 7080 |
| tctctagaaa gtataggaac ttcctcgagc cctatagtga gtcgtattag atcgcggccg | 7140 |
| cgcccttgac gatgccacat cctgagcaaa taattcaacc actaattgtg agcggataac | 7200 |
| aaaggaggta aaaaaacatg gtatcctgtt ctgcgccggg taagatttac ctgttcggtg | 7260 |
| aacacgccgt agtttatggc gaaactgcaa ttgcgtgtgc ggtggaactg cgtacccgtg | 7320 |
| ttcgcgcgga actcaatgac tctatcacta ttcagagcca gatcggccgc accggtctgg | 7380 |
| atttcgaaaa gcacccttat gtgtctgcgg taattgagaa aatgcgcaaa tctattccta | 7440 |
| ttaacggtgt tttcttgacc gtcgattccg acatcccggt gggctccggt ctgggtagca | 7500 |
| gcgcagccgt tactatcgcg tctattggtg cgctgaacga gctgttcggc tttggcctca | 7560 |
| gcctgcaaga aatcgctaaa ctgggccacg aaatcgaaat taagtacag ggtgccgcgt | 7620 |
| ccccaaccga tacgtatgtt tctaccttcg gcggcgtggt taccatcccg gaacgtcgca | 7680 |
| aactgaaaac tccggactgc ggcattgtga ttggcgatac cggcgttttc cctccacca | 7740 |
| aagagttagt agctaacgta cgtcagctgc gcgaaagcta cccggatttg atcgaaccgc | 7800 |
| tgatgacctc tattggcaaa atctctcgta tcggcgaaca actggttctg tctggcgact | 7860 |
| acgcatccat cggccgcctg atgaacgtca accagggtct cctggacgcc ctgggcgtta | 7920 |
| acatcttaga actgagccag ctgatctatt ccgctcgtgc ggcaggtgcg tttggcgcta | 7980 |
| aaatcacggg cgctggcggc ggtggctgta tggttgcgct gaccgctccg gaaaaatgca | 8040 |
| accaagtggc agaagcggta gcaggcgctg gcggtaaagt gactatcact aaaccgaccg | 8100 |
| agcaaggtct gaaagtagat taa | 8123 |

<210> SEQ ID NO 93
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 93

| | |
|---|---|
| aagggcgagc tcaacgatcc ggctgctaac aaagcccgaa aggaagctga gttggctgct | 60 |
| gccaccgctg agcaataact agcataaccc cttggggcct ctaaacgggt cttgaggagt | 120 |
| tttttgctga aaggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catacacggt gcctgactgc gttagcaatt taactgtgat aaactaccgc | 300 |
| attaaagctt atcgatgata agctgtcaaa catgagaatt aattcttgaa gacgaaaggg | 360 |

```
cctcgtgata cgcctatttt tataggttaa tgtcatgata ataatggttt cttagacgtc    420
aggtggcact tttcggggaa atgtgcgcgg aaccccctatt tgtttatttt tctaaataca    480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcagggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatcctctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc ttttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg gcggagcct atggaaaaac gccagcaacg   2160
cggcctttttt acgttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
```

```
gtcactgatg cctccgtgta agggggattt ctgttcatgg gggtaatgat accgatgaaa    2820
cgagagagga tgctcacgat acgggttact gatgatgaac atgcccggtt actggaacgt    2880
tgtgagggta acaactggc ggtatggatg cggcgggacc agagaaaaat cactcagggt     2940
caatgccagc gcttcgttaa tacagatgta ggtgttccac agggtagcca gcagcatcct    3000
gcgatgcaga tccggaacat aatggtgcag ggcgctgact tccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa     3480 tccatgccaa cccgttccat gtgctcgccg aggcggcata atcgccgtg acgatcagcg     3540 gtccaatgat cgaagttagg ctggtaagag ccgcgagcga tccttgaagc tgtccctgat    3600
ggtcgtcatc tacctgcctg acagcatgg cctgcaacgc gggcatcccg atgccgccgg     3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccgtgcc taatgagtga gctaacttac attaattgcg ttgcgctcac     4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg atagttaat gatcagccca     4800 ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac      4980
tgtttgcccg ccagttgttg tgccacgcgg ttgggaatgt aattcagctc cgccatcgcc    5040
gcttccactt ttcccgcgt tttcgcagaa acgtggctgg cctggttcac cacgcgggaa      5100
acggtctgat aagagacacc ggcatactct gcgacatcgt ataacgttac tggtttcaca    5160
```

```
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatcccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580
aacaattccc ctctagaaat aattttgttt aactttaaga aggagatata catatgaatt    5640
aaccctcact aaagggcggc cgcgaagttc ctattctcta gaaagtatag gaacttcatt    5700
ctaccgggta ggggaggcgc ttttcccaag gcagtctgga gcatgcgctt tagcagcccc    5760
gctgggcact tggcgctaca caagtggcct ctggcctcgc acacattcca catccaccgg    5820
taggcgccaa ccggctccgt tctttggtgg cccccttcgcg ccaccttcca ctcctcccct    5880
agtcaggaag ttcccccccg ccccgcagct cgcgtcgtgc aggacgtgac aaatggaagt    5940
agcacgtctc actagtctcg tgcagatgga cagcaccgct gagcaatgga agcgggtagg    6000
cctttggggc agcggccaat agcagctttg ctccttcgct ttctgggctc agaggctggg    6060
aaggggtggg tccggggggcg ggctcagggg cgggctcagg ggcggggcgg gcgcccgaag    6120
gtcctccgga ggcccggcat tctgcacgct tcaaaagcgc acgtctgccg cgctgttctc    6180
ctcttcctca tctccgggcc tttcgacctg cagcagcacg tgttgacaat taatcatcgg    6240
catagtatat cggcatagta ataatacgaca aggtgaggaa ctaaaccatg gagaaaaaaa    6300
tcactggata taccaccgtt gatatatccc aatggcatcg taaagaacat tttgaggcat    6360
ttcagtcagt tgctcaatgt acctataacc agaccgttca gctggatatt acggcctttt    6420
taaagaccgt aaagaaaaat aagcacaagt tttatccggc ctttattcac attcttgccc    6480
gcctgatgaa tgctcatccg gaattccgta tggcaatgaa agacggtgag ctggtgatat    6540
gggatagtgt tcacccttgt tacaccgttt ccatgagca aactgaaacg ttttcatcgc    6600
tctggagtga ataccacgac gatttccggc agtttctaca catatattcg caagatgtgg    6660
cgtgttacgg tgaaaacctg gcctatttcc ctaaagggtt tattgagaat atgttttcg    6720
tctcagccaa tccctgggtg agtttcacca gttttgattt aaacgtggcc aatatggaca    6780
acttcttcgc ccccgttttc accatgggca atatattac gcaaggcgac aaggtgctga    6840
tgccgctggc gattcaggtt catcatgccg tttgtgatgg cttccatgtc ggcagaatgc    6900
ttaatgaatt acaacagtac tgcgatgagt ggcagggcgg ggcgtaagcg gactctggg    6960
gttcgaataa agaccgacca agcgacgtct gagagctccc tggcgaattc ggtaccaata    7020
aaagagcttt attttcatga tctgtgtgtt ggttttgtg tgcggcgcgg aagttcctat    7080
tctctagaaa gtataggaac ttcctcgagc cctatagtga gtcgtattag atcgcggccg    7140
cgcccttgac tatgccacat cctgagcaaa taattcaacc actaattgtg agcggataac    7200
aaaggaggta aaaaacatg gtatcctgtt ctgcgccggg taagatttac ctgttcggtg    7260
aacacgccgt agtttatggc gaaactgcaa ttgcgtgtgc ggtggaactg cgtacccgtg    7320
ttcgcgcgga actcaatgac tctatcacta ttcagagcca gatcggccgc accggtctgg    7380
atttcgaaaa gcacccttat gtgtctgcgg taattgagaa aatgcgcaaa tctattccta    7440
ttaacggtgt tttcttgacc gtcgattccg acatcccggt gggctccggt ctgggtagca    7500
gcgcagccgt tactatcgcg tctattggtg cgctgaacga gctgttcggc tttggcctca    7560
```

-continued

```
gcctgcaaga aatcgctaaa ctgggccacg aaatcgaaat taaagtacag ggtgccgcgt    7620
ccccaaccga tacgtatgtt tctaccttcg gcggcgtggt taccatcccg gaacgtcgca    7680
aactgaaaac tccggactgc ggcattgtga ttggcgatac cggcgttttc tcctccacca    7740
aagagttagt agctaacgta cgtcagctgc gcgaaagcta cccggatttg atcgaaccgc    7800
tgatgacctc tattggcaaa atctctcgta tcggcgaaca actggttctg tctggcgact    7860
acgcatccat cggccgcctg atgaacgtca accaggtct cctggacgcc ctgggcgtta    7920
acatcttaga actgagccag ctgatctatt ccgctcgtgc ggcaggtgcg tttggcgcta    7980
aaatcacggg cgctggcggc ggtggctgta tggttgcgct gaccgctccg gaaaaatgca    8040
accaagtggc agaagcggta gcaggcgctg gcggtaaagt gactatcact aaaccgaccg    8100
agcaaggtct gaaagtagat taa                                           8123
```

```
<210> SEQ ID NO 94
<211> LENGTH: 19
<212> TYPE: DNA
<213> ORGANISM: Artificial Sequence
<220> FEATURE:
<223> OTHER INFORMATION: Synthetic Construct

<400> SEQUENCE: 94
accaattgca cccggcaga                                                  19

<210> SEQ ID NO 95
<211> LENGTH: 21
<212> TYPE: DNA
<213> ORGANISM: Artificial Sequence
<220> FEATURE:
<223> OTHER INFORMATION: Synthetic Construct

<400> SEQUENCE: 95
gctaaagcgc atgctccaga c                                               21

<210> SEQ ID NO 96
<211> LENGTH: 20
<212> TYPE: DNA
<213> ORGANISM: Artificial Sequence
<220> FEATURE:
<223> OTHER INFORMATION: Synthetic Construct

<400> SEQUENCE: 96
gactggcctc agatgaaagc                                                 20

<210> SEQ ID NO 97
<211> LENGTH: 20
<212> TYPE: DNA
<213> ORGANISM: Artificial Sequence
<220> FEATURE:
<223> OTHER INFORMATION: Synthetic Construct

<400> SEQUENCE: 97
caaacatgtg gcatggaaag                                                 20

<210> SEQ ID NO 98
<211> LENGTH: 52
<212> TYPE: DNA
<213> ORGANISM: Artificial Sequence
<220> FEATURE:
<223> OTHER INFORMATION: Synthetic Construct

<400> SEQUENCE: 98
gggcccgttt aaactttaac tagactctgc agttagcgtt caaacggcag aa             52
```

<210> SEQ ID NO 99
<211> LENGTH: 38
<212> TYPE: DNA
<213> ORGANISM: Artificial Sequence
<220> FEATURE:
<223> OTHER INFORMATION: Synthetic Construct

<400> SEQUENCE: 99
cgcatgcatg tcatgagatg tagcgtgtcc accgaaaa                                38

<210> SEQ ID NO 100
<211> LENGTH: 22
<212> TYPE: DNA
<213> ORGANISM: Artificial Sequence
<220> FEATURE:
<223> OTHER INFORMATION: Synthetic Construct

<400> SEQUENCE: 100
acaatttcac acaggaaaca gc                                                 22

<210> SEQ ID NO 101
<211> LENGTH: 23
<212> TYPE: DNA
<213> ORGANISM: Artificial Sequence
<220> FEATURE:
<223> OTHER INFORMATION: Synthetic Construct

<400> SEQUENCE: 101
ccaggcaaat tctgttttat cag                                                23

<210> SEQ ID NO 102
<211> LENGTH: 22
<212> TYPE: DNA
<213> ORGANISM: Artificial Sequence
<220> FEATURE:
<223> OTHER INFORMATION: Synthetic Construct

<400> SEQUENCE: 102
gcactgtctt tccgtctgct gc                                                 22

<210> SEQ ID NO 103
<211> LENGTH: 66
<212> TYPE: DNA
<213> ORGANISM: Artificial Sequence
<220> FEATURE:
<223> OTHER INFORMATION: Synthetic Construct

<400> SEQUENCE: 103
gcgaacgatg cataaaggag gtaaaaaaac atggtatcct gttctgcgcc gggtaagatt        60
tacctg                                                                   66

<210> SEQ ID NO 104
<211> LENGTH: 48
<212> TYPE: DNA
<213> ORGANISM: Artificial Sequence
<220> FEATURE:
<223> OTHER INFORMATION: Synthetic Construct

<400> SEQUENCE: 104
gggcccgttt aaactttaac tagactttaa tctactttca gaccttgc                     48

<210> SEQ ID NO 105
<211> LENGTH: 24
<212> TYPE: DNA
<213> ORGANISM: Artificial Sequence
<220> FEATURE:

<223> OTHER INFORMATION: Synthetic Construct

<400> SEQUENCE: 105
gatagtaacg gctgcgctgc tacc                                              24

<210> SEQ ID NO 106
<211> LENGTH: 23
<212> TYPE: DNA
<213> ORGANISM: Artificial Sequence
<220> FEATURE:
<223> OTHER INFORMATION: Synthetic Construct

<400> SEQUENCE: 106
gacagcttat catcgactgc acg                                               23

<210> SEQ ID NO 107
<211> LENGTH: 22
<212> TYPE: DNA
<213> ORGANISM: Artificial Sequence
<220> FEATURE:
<223> OTHER INFORMATION: Synthetic Construct

<400> SEQUENCE: 107
caccatggta tcctgttctg cg                                                22

<210> SEQ ID NO 108
<211> LENGTH: 22
<212> TYPE: DNA
<213> ORGANISM: Artificial Sequence
<220> FEATURE:
<223> OTHER INFORMATION: Synthetic Construct

<400> SEQUENCE: 108
ttaatctact ttcagacctt gc                                                22

<210> SEQ ID NO 109
<211> LENGTH: 81
<212> TYPE: DNA
<213> ORGANISM: Artificial Sequence
<220> FEATURE:
<223> OTHER INFORMATION: Synthetic Construct

<400> SEQUENCE: 109
aaagtagccg aagatgacgg tttgtcacat ggagttggca ggatgtttga ttaaaagcaa       60
ttaaccctca ctaaagggcg g                                                 81

<210> SEQ ID NO 110
<211> LENGTH: 31
<212> TYPE: DNA
<213> ORGANISM: Artificial Sequence
<220> FEATURE:
<223> OTHER INFORMATION: Synthetic Construct

<400> SEQUENCE: 110
gatatacata tgaattaacc ctcactaaag g                                      31

<210> SEQ ID NO 111
<211> LENGTH: 125
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 80
<223> OTHER INFORMATION: n = A,T,C or G -continued

```
<400> SEQUENCE: 111
gcatgcatga catgttttt tacctccttt gttatccgct cacaattagt ggttgaatta    60
tttgctcagg atgtggcatn gtcaagggcg cggccgcgat ctaatacgac tcactatagg   120
gctcg                                                              125

<210> SEQ ID NO 112
<211> LENGTH: 87
<212> TYPE: DNA
<213> ORGANISM: Artificial Sequence
<220> FEATURE:
<223> OTHER INFORMATION: Synthetic Construct

<400> SEQUENCE: 112
aggctctcaa ctctgacatg ttttttcct ccttaagggt gcaggcctat cgcaaattag    60
cttaatctac tttcagacct tgctcgg                                       87

<210> SEQ ID NO 113
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 113
gcggccgcgc ccttgacgat gccacatcct gagcaaataa ttcaaccact aattgtgagc    60
ggataacaca aggaggaaac agccatggta tcctgttctg cgccgggtaa gatttacctg   120
ttcggtgaac acgccgtagt ttatggcgaa actgcaattg cgtgtgcggt ggaactgcgt   180
acccgtgttc gcgcggaact caatgactct atcactattc agagccagat cggccgcacc   240
ggtctggatt tcgaaaagca cccttatgtg tctgcggtaa ttgagaaaat gcgcaaatct   300
attcctatta acggtgtttt cttgaccgtc gattccgaca tcccggtggg ctccggtctg   360
ggtagcagcg cagccgttac tatcgcgtct attggtgcgc tgaacgagct gttcggcttt   420
ggcctcagcc tgcaagaaat cgctaaactg ggccacgaaa tcgaaattaa agtacagggt   480
gccgcgtccc aaccgatac gtatgtttct accttcggcg gcgtggttac catcccggaa   540
cgtcgcaaac tgaaaactcc ggactgcggc attgtgattg cgataccgg cgttttctcc   600 tccaccaaag agttagtagc taacgtacgt cagctgcgcg aaagctaccc ggatttgatc   660
gaaccgctga tgacctctat tggcaaaatc tctcgtatcg gcgaacaact ggttctgtct   720
ggcgactacg catccatcgg ccgcctgatg aacgtcaacc agggtctcct ggacgccctg   780
ggcgttaaca tcttagaact gagccagctg atctattccg ctcgtgcggc aggtgcgttt   840
ggcgctaaaa tcacgggcgc tggcggcggt ggctgtatgg ttgcgctgac cgctccggaa   900
aaatgcaacc aagtggcaga gcggtagca ggcgctggcg gtaaagtgac tatcactaaa   960
ccgaccgagc aaggtctgaa agtagattaa gccttgactt aatagctgct tatttcgccc  1020
ttatggtacc tagtaggagg aaaaaaacat ggaaatgcgt caaccggctg tcgcaggtca  1080 attctacca ctgcgttgcg agaacctgga aaacgaactg aaacgctgct cgaaggcct   1140 ggagatccgc gaacaagaag tgctgggcgc agtctgtccg cacgccggtt atatgtactc  1200
tggcaaagtt gcgcgcacg tctatgccac tctgccggaa gctgataccc acgtaatctt  1260
cggcccgaac cacaccggct acggtagccc tgtctctgtg agccgtgaaa cttgaagac   1320 cccgttgggc aatatcgatg ttgacctgga actggcggac ggcttcctgg ttccatcgt   1380 agatgcggat gaactcggtc acaaatacga acactctatc gaagttcagc tgccgtttct  1440
```

-continued

```
gcaataccgt tttgaacgcg atttcaaaat tctgccaatc tgcatgggta tgcaagacga       1500
agaaaccgcg gtcgaagtag gtaacctgct ggcggatctg atcagcgagt ccggtaaacg       1560
tgctgtgatc atcgcaagct ctgatttcac ccactatgag acggctgaac gtgccaaaga      1620
aatcgattcc gaagttattg attctatcct gaactttgac atctctggca tgtacgatcg       1680
cctgtatcgc cgtaacgcct ctgtttgcgg ttacggcccg atcaccgcta tgctgacggc       1740
aagcaaaaag ctgggcggct ctcgtgcgac tttgctgaaa tacgcaaaca gcggtgacgt       1800
gtccggtgat aaagacgctg tggtgggcta cgccgccatc atcgttgagt aagctgatta      1860
aaggttgaac agataggatt tcgtcatgga tcctacaagg aggaaaaaaa catgaatgct       1920
tctaatgaac cggtgattct gaaactgggt ggctctgcta ttaccgacaa aggtgcctac       1980
gaaggcgtag ttaaggaagc tgatttgctg cgcatcgcac aggaagttag cggtttccgt      2040
ggcaagatga tcgtggttca tggtgctggt agcttcggcc atacgtacgc gaagaaatac      2100
ggcctggacc gtaccttcga cccagagggc gcaattgtta ctcatgaatc tgttaaaaag      2160
ctcgcctcca aagttgtagg tgctctgaat agcttcggcg tgcgtgctat cgcggtgcat      2220
cctatggact gcgcagtatg ccgtaacggt cgtatcgaaa cgatgtatct ggactccatc      2280
aagttaatgc tggaaaaagg tctggtgccg gttctgcacg gcgacgtcgc aatggatatt      2340
gaactgggca cttgtatcct gtccggtgat caaatcgttc cttacctggc caaagaactg      2400
ggtatctccc gcctcggcct gggcagcgca gaggatggtg tgctggatat ggagggcaaa      2460
cctgtaccgg aaatcacccc agaaactttc gaagagttcc gccactgcat cggtggttct      2520
ggttctactg atgtaaccgg tggcatgctg gcaaagtgc tggaacttct ggaattgagc       2580
aaaaattctt ccattactag ctacattttc aacgctggta agcagacaa catctaccgc       2640 tttctgaatg gtgagtccat cggcactcgc atcagcccgg acaagcgtgt ttaagctagt      2700
tattaaccta aatgctctaa accagttatg agctctacaa ggaggaaaaa aacatgatta      2760
acactaccag ccgccgcaaa attgaacacc tgaaactctg cgcagaatcc ccggttgaag      2820
cgcgtcaggt atctgccggc tttgaagacg ttactctgat ccaccgcgct ttaccggagc      2880
tgaacatgga tgaactggac ctcagcgttg atttcctggg taaacgcatc aaagcgccgt      2940
tcctgattgc gtctatcacg ggtggtcacc cagataccat cccggttaac gctgcgctgg      3000
cagctgctgc tgaggagctg ggtgttggca tcggcgttgg ctctcagcgc gcggccattg      3060
atgatccgag ccaggaagac agcttccgtg tagtgcgtga tgaagcccca gatgcgtttg      3120
tttatggcaa cgtcggcgca gcacagatcc gtcagtatgt tgttgaaggt gttgaaaaac      3180
tgatcgaaat gattgacgca gatgccttgg caatccacct gaactttctg caagaagcgg      3240
tccaaccgga aggtgaccgc gacgcgaccg gttgctggga catgattacc gaaatttgct      3300
ctcagattaa aactccggta atcgtgaaag aaaccggtgc aggcattagc cgtgaagatg      3360
cgattctgtt ccagaaagct ggcgtgagcg caatcgacgt tggcggcgcg gcggcacct       3420 cctgggctgg cgtcgaggtc taccgtgcta agaaagccg tgactctgtt agcgagcgtt       3480
taggtgagct gttttgggat ttcggcattc cgacggtagc ttctctgatt gaatcccgcg      3540
tttccttgcc gctgatcgca accggcggta tccgtaacgg tctggacatt gctaaaagca      3600
ttgctctcgg cgcaagcgct gccagcgccg ctctgccgtt cgttggtccg tccctggagg      3660
gcaaagaatc cgttgtacgt gtgctgagct gcatgctgga agaatttaaa gcagcaatgt      3720
ttttgtgcgg ttgcggcaac atcaaagacc tgcacaactc tccagtagtg gtaactggtt      3780
ggacccgcga ataccttggag cagcgcggtt ttaacgttaa ggacctctcc ctgccgggca      3840
```

-continued

| | |
|---|---|
| acgctctgta agcttcaacg cgtctacaaa taaaaaaggc acgtcagatg acgtgccttt | 3900 |
| tttcttgtct aga | 3913 |

<210> SEQ ID NO 114
<211> LENGTH: 6648
<212> TYPE: DNA
<213> ORGANISM: Artificial Sequence
<220> FEATURE:
<223> OTHER INFORMATION: Synthetic Construct

<400> SEQUENCE: 114

| | |
|---|---|
| aagggcgagc tcaacgatcc ggctgctaac aaagcccgaa aggaagctga gttggctgct | 60 |
| gccaccgctg agcaataact agcataaccc cttggggcct ctaaacgggt cttgaggagt | 120 |
| tttttgctga aggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catacacggt gcctgactgc gttagcaatt taactgtgat aaactaccgc | 300 |
| attaaagctt atcgatgata agctgtcaaa catgagaatt aattcttgaa gacgaaaggg | 360 |
| cctcgtgata cgcctatttt tataggttaa tgtcatgata ataatggttt cttagacgtc | 420 |
| aggtggcact tttcggggaa atgtgcgcgg aacccctatt tgtttatttt tctaaataca | 480 |
| ttcaaatatg tatccgctca tgagacaata accctgataa atgcttcaat aatattgaaa | 540 |
| aaggaagagt atgattgaac aagatggatt gcacgcaggt tctccggccg cttgggtgga | 600 |
| gaggctattc ggctatgact gggcacaact gacaatcggc tgctctgatg ccgccgtgtt | 660 |
| ccggctgtca gcgcaggggc gcccggttct ttttgtcaag accgacctgt ccggtgccct | 720 |
| gaatgaactg caggacgagg cagcgcggct atcgtggctg gccacgacgg gcgttccttg | 780 |
| cgcagctgtg ctcgacgttg tcactgaagc gggaagggac tggctgctat gggcgaagt | 840 |
| gccggggcag gatctcctgt catctcacct tgctcctgcc gagaaagtat ccatcatggc | 900 |
| tgatgcaatg cggcggctgc atacgcttga tccggctacc tgcccattcg accaccaagc | 960 |
| gaaacatcgc atcgagcggg cacgtactcg gatggaagcc ggtcttgtcg atcaggatga | 1020 |
| tctggacgaa gagcatcagg ggctcgcgcc agccgaactt ttcgccaggc tcaaggcgcg | 1080 |
| catgcccgac ggcgaggatc tcgtcgtgac acatggcgat gcctgcttgc cgaatatcat | 1140 |
| ggtggaaaat ggccgctttt ctggattcat cgactgtggc cggctgggtg tggcggaccg | 1200 |
| ctatcaggac atagcgttgg ctacccgtga tattgctgaa gagcttggcg gcgaatgggc | 1260 |
| tgaccgcttc ctcgtgcttt acggtatcgc cgctcccgat tcgcagcgca tcgccttcta | 1320 |
| tcgccttctt gacgagttct tctgagcggg actctggggt tcgaaatgac cgaccaagcg | 1380 |
| acgcctaact gtcagaccaa gtttactcat atatacttta gattgattta aaacttcatt | 1440 |
| tttaatttaa aaggatctag gtgaagatcc tttttgataa tctcatgacc aaaatccctt | 1500 |
| aacgtgagtt ttcgttccac tgagcgtcag accccgtaga aagatcaaa ggatcttctt | 1560 |
| gagatccttt ttttctgcgc gtaatctgct gcttgcaaac aaaaaaacca ccgctaccag | 1620 |
| cggtggtttg tttgccggat caagagctac caactctttt tccgaaggta actggcttca | 1680 |
| gcagagcgca gataccaaat actgtccttc tagtgtagcc gtagttaggc caccacttca | 1740 |
| agaactctgt agcaccgcct acatacctcg ctctgctaat cctgttacca gtggctgctg | 1800 |
| ccagtggcga taagtcgtgt cttaccgggt tggactcaag acgatagtta ccggataagg | 1860 |
| cgcagcggtc gggctgaacg gggggttcgt gcacacagcc cagcttggag cgaacgacct | 1920 |
| acaccgaact gagataccta cagcgtgagc tatgagaaag cgccacgctt cccgaaggga | 1980 |

```
gaaaggcgga caggtatccg gtaagcggca gggtcggaac aggagagcgc acgagggagc    2040 ttccagggg  aaacgcctgg tatctttata gtcctgtcgg gtttcgccac ctctgacttg    2100
agcgtcgatt tttgtgatgc tcgtcagggg ggcggagcct atggaaaaac gccagcaacg    2160
cggccttttt acgttcctg  gccttttgct ggccttttgc tcacatgttc tttcctgcgt    2220
tatcccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctccaga    2700
agcgttaatg tctggcttct gataaagcgg gccatgttaa gggcggtttt tcctgtttg    2760 gtcactgatg cctccgtgta agggggattt ctgttcatgg gggtaatgat accgatgaaa    2820
cgagagagga tgctcacgat acgggttact gatgatgaac atgcccggtt actggaacgt    2880
tgtgagggta aacaactggc ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag ggcgctgact ccgcgtttc  cagactttac    3060 gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480 tccatgccaa cccgttccat gtgctcgccg aggcggcata atcgccgtg  acgatcagcg    3540 gtccaatgat cgaagttagg ctggtaagag ccgcgagcga tccttgaagc tgtccctgat    3600
ggtcgtcatc tacctgcctg acagcatgg  cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tccggtgcc  taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
```

```
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc cgctaacag cgcgatttgc     4620 tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg atagttaat gatcagccca     4800 ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac      4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc cccggccac ggggcctgcc accataccca cgccgaaaca     5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat     5580 aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catggtatcc tgttctgcgc    5760
cgggtaagat ttacctgttc ggtgaacacg ccgtagttta tggcgaaact gcaattgcgt    5820
gtgcggtgga actgcgtacc cgtgttcgcg cggaactcaa tgactctatc actattcaga    5880
gccagatcgg ccgcaccggt ctggatttcg aaaagcaccc ttatgtgtct gcggtaattg    5940
agaaaatgcg caaatctatt cctattaacg gtgttttctt gaccgtcgat tccgacatcc    6000
cggtgggctc cggtctgggt agcagcgcag ccgttactat cgcgtctatt ggtgcgctga    6060
acgagctgtt cggctttggc ctcagcctgc aagaaatcgc taaactgggc cacgaaatcg    6120
aaattaaagt acagggtgcc gcgtccccaa ccgatacgta tgtttctacc ttcggcggcg    6180
tggttaccat cccggaacgt cgcaaactga aaactccgga ctgcggcatt gtgattggcg    6240
ataccggcgt tttctcctcc accaaagagt tagtagctaa cgtacgtcag ctgcgcgaaa    6300
gctacccgga tttgatcgaa ccgctgatga cctctattgg caaaatctct cgtatcggcg    6360
aacaactggt tctgttctgg cgactacgca tccatcggcc gcctgatgaa cgtcaaccag    6420
ggtctcctgg acgccctggg cgttaacatc ttagaactga gccagctgat ctattccgct    6480
cgtgcggcag gtgcgtttgg cgctaaaatc acgggcgctg gcggcggtgg ctgtatggtt    6540
gcgctgaccg ctccggaaaa atgcaaccaa gtggcagaag cggtagcagg cgctggcggt    6600
aaagtgacta tcactaaacc gaccgagcaa ggtctgaaag tagattaa                 6648
```

<210> SEQ ID NO 115
<211> LENGTH: 67
<212> TYPE: DNA

```
<213> ORGANISM: Artificial Sequence
<220> FEATURE:
<223> OTHER INFORMATION: Synthetic Construct

<400> SEQUENCE: 115
accgccaaaa gcgactaatt ttagctgtta cagtcagttg aattaaccct cactaaaggg    60
cggccgc                                                              67

<210> SEQ ID NO 116
<211> LENGTH: 152
<212> TYPE: DNA
<213> ORGANISM: Artificial Sequence
<220> FEATURE:
<223> OTHER INFORMATION: Synthetic Construct

<400> SEQUENCE: 116
gctggcgata taaactgttt gcttcatgaa tgctcctttg ggttacctcc gggaaacgcg    60
gttgatttgt ttagtggttg aattatttgc tcaggatgtg gcatagtcaa gggcgtgacg   120
gctcgctaat acgactcact atagggctcg ag                                 152

<210> SEQ ID NO 117
<211> LENGTH: 30
<212> TYPE: DNA
<213> ORGANISM: Artificial Sequence
<220> FEATURE:
<223> OTHER INFORMATION: Synthetic Construct

<400> SEQUENCE: 117
cttgatatct tagtgtgcgt taaccaccac                                     30

<210> SEQ ID NO 118
<211> LENGTH: 21
<212> TYPE: DNA
<213> ORGANISM: Artificial Sequence
<220> FEATURE:
<223> OTHER INFORMATION: Synthetic Construct

<400> SEQUENCE: 118
cgtgaatttg ctggctctca g                                              21

<210> SEQ ID NO 119
<211> LENGTH: 21
<212> TYPE: DNA
<213> ORGANISM: Artificial Sequence
<220> FEATURE:
<223> OTHER INFORMATION: Synthetic Construct

<400> SEQUENCE: 119
ggtttagttc ctcaccttgt c                                              21

<210> SEQ ID NO 120
<211> LENGTH: 21
<212> TYPE: DNA
<213> ORGANISM: Artificial Sequence
<220> FEATURE:
<223> OTHER INFORMATION: Synthetic Construct

<400> SEQUENCE: 120
actgaaacgt tttcatcgct c                                              21

<210> SEQ ID NO 121
<211> LENGTH: 26
<212> TYPE: DNA
<213> ORGANISM: Artificial Sequence
<220> FEATURE:
```

<223> OTHER INFORMATION: Synthetic Construct

<400> SEQUENCE: 121
accgccaaaa gcgactaatt ttagct    26

<210> SEQ ID NO 122
<211> LENGTH: 7519
<212> TYPE: DNA
<213> ORGANISM: Artificial Sequence
<220> FEATURE:
<223> OTHER INFORMATION: Synthetic Construct

<400> SEQUENCE: 122

| | | | | | | |
|---|---|---|---|---|---|---|
| ctcgggccgt | ctcttgggct | tgatcggcct | tcttgcgcat | ctcacgcgct | cctgcggcgg | 60 |
| cctgtagggc | aggctcatac | ccctgccgaa | ccgcttttgt | cagccggtcg | gccacggctt | 120 |
| ccggcgtctc | aacgcgcttt | gagattccca | gcttttcggc | caatccctgc | ggtgcatagg | 180 |
| cgcgtggctc | gaccgcttgc | gggctgatgg | tgacgtggcc | cactggtggc | cgctccaggg | 240 |
| cctcgtagaa | cgcctgaatg | cgcgtgtgac | gtgccttgct | gccctcgatg | cccgttgca | 300 |
| gccctagatc | ggccacagcg | gccgcaaacg | tggtctggtc | gcgggtcatc | tgcgcttttgt | 360 |
| tgccgatgaa | ctccttggcc | gacagcctgc | cgtcctgcgt | cagcggcacc | acgaacgcgg | 420 |
| tcatgtgcgg | gctggtttcg | tcacggtgga | tgctggccgt | cacgatgcga | tccgccccgt | 480 |
| acttgtccgc | cagccacttg | tgcgccttct | cgaagaacgc | cgcctgctgt | tcttggctgg | 540 |
| ccgacttcca | ccattccggg | ctggccgtca | tgacgtactc | gaccgccaac | acagcgtcct | 600 |
| tgcgccgctt | ctctggcagc | aactcgcgca | gtcggcccat | cgcttcatcg | gtgctgctgg | 660 |
| ccgcccagtg | ctcgttctct | ggcgtcctgc | tggcgtcagc | gttgggcgtc | tcgcgctcgc | 720 |
| ggtaggcgtg | cttgagactg | gccgccacgt | tgcccatttt | cgccagcttc | ttgcatcgca | 780 |
| tgatcgcgta | tgccgccatg | cctgcccctc | cctttggtg | tccaaccggc | tcgacggggg | 840 |
| cagcgcaagg | cggtgcctcc | ggcgggccac | tcaatgcttg | agtatactca | ctagactttg | 900 |
| cttcgcaaag | tcgtgaccgc | ctacggcggc | tgcggcgccc | tacggcttg | ctctccgggc | 960 |
| ttcgccctgc | gcggtcgctg | cgctcccttg | ccagcccgtg | gatatgtgga | cgatggccgc | 1020 |
| gagcggccac | cggctggctc | gcttcgctcg | gcccgtggac | aaccctgctg | acaagctga | 1080 |
| tggacaggct | gcgcctgccc | acgagcttga | ccacagggat | tgcccaccgg | ctacccagcc | 1140 |
| ttcgaccaca | tacccaccgg | ctccaactgc | gcggcctgcg | gccttgcccc | atcaattttt | 1200 |
| ttaattttct | ctggggaaaa | gcctccggcc | tgcggcctgc | gcgcttcgct | tgccggttgg | 1260 |
| acaccaagtg | gaaggcgggt | caaggctcgc | gcagcgaccg | cgcagcggct | tggccttgac | 1320 |
| gcgcctggaa | cgacccaagc | ctatgcgagt | ggggggcagtc | gaaggcgaag | cccgcccgcc | 1380 |
| tgcccccga | gcctcacggc | ggcgagtgcg | ggggttccaa | gggggcagcg | ccaccttggg | 1440 |
| caaggccgaa | ggccgcgcag | tcgatcaaca | agccccggag | gggccacttt | ttgccggagg | 1500 |
| gggagccgcg | ccgaaggcgt | gggggaaccc | cgcagggggtg | cccttctttg | ggcaccaaag | 1560 |
| aactagatat | agggcgaaat | gcgaaagact | taaaaatcaa | caacttaaaa | aaggggggta | 1620 |
| cgcaacagct | cattgcggca | cccccgcaa | tagctcattg | cgtaggttaa | agaaaatctg | 1680 |
| taattgactg | ccacttttac | gcaacgcata | attgttgtcg | cgctgccgaa | aagttgcagc | 1740 |
| tgattgcgca | tggtgccgca | accgtgcggc | accctaccgc | atggagataa | gcatggccac | 1800 |
| gcagtccaga | gaaatcggca | ttcaagccaa | gaacaagccc | ggtcactggg | tgcaaacgga | 1860 |
| acgcaaagcg | catgaggcgt | gggccgggct | tattgcgagg | aaacccacgg | cggcaatgct | 1920 |

-continued

```
gctgcatcac ctcgtggcgc agatgggcca ccagaacgcc gtggtggtca gccagaagac      1980
actttccaag ctcatcggac gttctttgcg gacggtccaa tacgcagtca aggacttggt      2040
ggccgagcgc tggatctccg tcgtgaagct caacggcccc ggcaccgtgt cggcctacgt      2100
ggtcaatgac cgcgtggcgt ggggccagcc ccgcgaccag ttgcgcctgt cggtgttcag      2160
tgccgccgtg gtggttgatc acgacgacca ggacgaatcg ctgttggggc atggcgacct      2220
gcgccgcatc ccgaccctgt atccgggcga gcagcaacta ccgaccggcc ccggcgagga      2280
gccgcccagc cagcccggca ttccgggcat ggaaccagac ctgccagcct tgaccgaaac      2340
ggaggaatgg gaacgcgcg gcagcagcg cctgccgatg cccgatgagc cgtgttttct      2400
ggacgatggc gagccgttgg agccgccgac acgggtcacg ctgccgcgcc ggtagcactt      2460
gggttgcgca gcaacccgta agtgcgctgt tccagactat cggctgtagc cgcctcgccg      2520
ccctatacct tgtctgcctc cccgcgttgc gtcgcggtgc atggagccgg ccacctcga      2580 cctgaatgga agccggcggc acctcgctaa cggattcacc gttttatca ggctctggga      2640 ggcagaataa atgatcatat cgtcaattat tacctccacg gggagagcct gagcaaactg      2700
gcctcaggca tttgagaagc acacggtcac actgcttccg gtagtcaata aaccggtaaa      2760
ccagcaatag acataagcgg ctatttaacg accctgccct gaaccgacga ccgggtcgaa      2820 tttgcttcg aatttctgcc attcatccgc ttattatcac ttattcaggc gtagcaccag      2880
gcgtttaagg gcaccaataa ctgccttaaa aaaattacgc cccgccctgc cactcatcgc      2940
agtcggccta ttggttaaaa aatgagctga tttaacaaaa attaacgcg aattttaaca      3000 aaatattaac gcttacaatt tccattcgcc attcaggctg cgcaactgtt gggaagggcg      3060
atcggtgcgg gcctcttcgc tattacgcca gctggcgaaa ggggggatgtg ctgcaaggcg      3120 attaagttgg gtaacgccag ggttttccca gtcacgacgt tgtaaaacga cggccagtga      3180
gcgcgcgtaa tacgactcac tatagggcga attggagctc caccgcggtg gcggccgctc      3240
tagaactagt ggatccccg gctgcatgc tcgagcggcc gccagtgtga tggatatctg      3300
cagaattcgc ccttcttgat atcttagtgt gcgttaacca ccacccacat tggtccctgc      3360
ccgaccgcat agcggccttt ttcatgcagt agccctgct cgccaacaat ttcgtatacc      3420
gagatgtggt gagattttg cccggcggca atcagatact tgccgctgtg atcaacattg      3480
aagccgcgcg gctgggtttc cgttggctgg aagccttctt tactcaacac gctgccatct      3540
tccgaaacgc tgaaaacggt aatcaggctg gcggtacggt cgcaggcgta taaatggcga      3600
ccatccgggg tgatatgaat atcagccgcc caacgggtgt cggagaagtt ttccggcatc      3660
atatccagcg tctggacaca ttcgatatta ccgtgcggat ctttcagttc ccagacatcc      3720
actgagctgt taactcatt gacgcaatac gcatattgtt cgtttggatg gaataccata      3780
tgacgcgggc cggccccttc aacggtggtc acttccgcag ggtcctgcgc cacgagatga      3840
ccatcatcgc tgaccgtaaa caggcaaatg cgatcctgct ttaatgccgg aacccacagc      3900
gtacggttgt ccggtgagat attggcggaa tgcaaccgt ccagcccctc gaccacatcg      3960
acgacgccca ctggcaggcc atcttccaga gcgttacgc tcacgttacc cgcattgtaa      4020
gaacctacaa agacaaactg cccctggtga tcggtggaaa tatgcgtcgg actacccggc      4080
agcgcagact ctgcggcaaa ggtcagtgcg ccatcgtccg gggcgatacg atacgccagg      4140
acgcgaaact cagggcgaac accaacatag agataacgtt tgtccgggct gaccaccatc      4200
ggctgcacct gccccggcac atcgacaacc tgtgtcagcg tcagtgcgcc ttcatgattc      4260
agattccaga cgtgaatttg ctggctctca gggctggcga tataaactgt ttgcttcatg      4320
```

-continued

```
aatgctcctt tgggttacct ccgggaaacg cggttgattt gtttagtggt tgaattattt    4380
gctcaggatg tggcatagtc aagggcgtga cggctcgcta atacaactca ctatagggct    4440
cgaggaagtt cctatacttt ctagagaata ggaacttccg cgccgcacac aaaaaccaac    4500
acacagatca tgaaaataaa gctcttttat tggtaccgaa ttcgccaggg agctctcaga    4560
cgtcgcttgg tcggtcttta ttcgaacccc agagtcccgc ttacgccccg ccctgccact    4620
catcgcagta ctgttgtaat tcattaagca ttctgccgac atggaagcca tcacaaacgg    4680
catgatgaac ctgaatcgcc agcggcatca gcaccttgtc gccttgcgta taatatttgc    4740
ccatggtgaa aacgggggcg aagaagttgt ccatattggc cacgtttaaa tcaaaactgg    4800
tgaaactcac ccagggattg gctgagacga aaacatatt ctcaataaac cctttaggga    4860
aataggccag ttttcaccg taacacgcca catcttgcga atatatgtgt agaaactgcc    4920
ggaaatcgtc gtggtattca ctccagagcg atgaaaacgt tcagtttgc tcatggaaaa    4980 cggtgtaaca agggtgaaca ctatcccata tcaccagctc accgtctttc attgccatac    5040
ggaattccgg atgagcattc atcaggcggg caagaatgtg aataaaggcc ggataaaact    5100
tgtgcttatt tttctttacg gtcttaaaa aggccgtaat atccagctga acggtctggt    5160
tataggtaca ttgagcaact gactgaaatg cctcaaaatg ttctttacga tgccattggg    5220
atatatcaac ggtggtatat ccagtgattt ttttctccat ggttagttc ctcaccttgt    5280 cgtattatac tatgccgata tactatgccg atgattaatt gtcaacacgt gctgctgcag    5340
gtcgaaaggc ccggagatga ggaagaggag aacagcgcgg cagacgtgcg cttttgaagc    5400
gtgcagaatg ccgggcctcc ggaggacctt cgggcgcccg ccccgcccct gagcccgccc    5460
ctgagcccgc ccccggaccc accccttccc agcctctgag cccagaaagc gaaggagcaa    5520
agctgctatt ggccgctgcc ccaaaggcct acccgcttcc attgctcagc ggtgctgtcc    5580
atctgcacga gactagtgag acgtgctact tccatttgtc acgtcctgca cgacgcgagc    5640
tgcggggcgg gggggaactt cctgactagg ggaggagtgg aaggtggcgc gaaggggcca    5700
ccaaagaacg gagccggttg gcgcctaccg gtggatgtgg aatgtgtgcg aggccagagg    5760
ccacttgtgt agcgccaagt gcccagcggg gctgctaaag cgcatgctcc agactgcctt    5820
gggaaaagcg cctcccctac ccggtagaat gaagttccta tactttctag agaataggaa    5880
cttcgcggcc gcccttagt gagggttaat tcaactgact gtaacagcta aaattagtcg    5940
cttttggcgg taagggcgaa ttccagcaca ctggcggccg ttactagtgg atccgagctc    6000
ggtaccaagc ttgatgcagg aattcgatat caagcttatc gataccgtcg acctcgaggg    6060
ggggcccggt acccagcttt tgttcccttt agtgagggtt aattgcgcgc ttggcgtaat    6120
catggtcata gctgtttcct gtgtgaaatt gttatccgct cacaattcca cacaacatac    6180
gagccggaag cataaagtgt aaagcctggg gtgcctaatg agtgagctaa ctcacattaa    6240
ttgcgttgcg ctcactgccc gctttccagt cgggaaacct gtcgtgccag ctgcattaat    6300
gaatcggcca acgcgcgggg agaggcggtt tgcgtattgg gcgcatgcat aaaaactgtt    6360
gtaattcatt aagcattctg ccgacatgga agccatcaca aacggcatga tgaacctgaa    6420
tcgccagcgg catcagcacc ttgtcgcctt gcgtataata tttgcccatg gacgcacacc    6480
gtggaaacgg atgaaggcac gaacccagtt gacataagcc tgttcggttc gtaaactgta    6540
atgcaagtag cgtatgcgct cacgcaactg gtccagaacc ttgaccgaac gcagcggtgg    6600
taacggcgca gtggcggttt tcatggcttg ttatgactgt ttttttgtac agtctatgcc    6660
tcgggcatcc aagcagcaag gcgttacgc cgtgggtcga tgtttgatgt tatggagcag    6720
```

-continued

| | |
|---|---|
| caacgatgtt acgcagcagc aacgatgtta cgcagcaggg cagtcgccct aaaacaaagt | 6780 |
| taggtggctc aagtatgggc atcattcgca catgtaggct cggccctgac caagtcaaat | 6840 |
| ccatgcgggc tgctcttgat cttttcggtc gtgagttcgg agacgtagcc acctactccc | 6900 |
| aacatcagcc ggactccgat tacctcggga acttgctccg tagtaagaca ttcatcgcgc | 6960 |
| ttgctgcctt cgaccaagaa gcggttgttg gcgctctcgc ggcttacgtt ctgcccaggt | 7020 |
| ttgagcagcc gcgtagtgag atctatatct atgatctcgc agtctccggc gagcaccgga | 7080 |
| ggcagggcat tgccaccgcg ctcatcaatc tcctcaagca tgaggccaac gcgcttggtg | 7140 |
| cttatgtgat ctacgtgcaa gcagattacg gtgacgatcc cgcagtggct ctctatacaa | 7200 |
| agttgggcat acgggaagaa gtgatgcact tgatatcga cccaagtacc gccacctaac | 7260 |
| aattcgttca agccgagatc ggcttcccgg ccgcggagtt gttcggtaaa ttgtcacaac | 7320 |
| gccgccaggt ggcactttc ggggaaatgt gcgcgcccgc gttcctgctg gcgctgggcc | 7380 |
| tgtttctggc gctggacttc ccgctgttcc gtcagcagct tttcgcccac ggccttgatg | 7440 |
| atcgcggcgg ccttggcctg catatcccga ttcaacggcc caggggcgtc cagaacgggc | 7500 |
| ttcaggcgct cccgaaggt | 7519 |

<210> SEQ ID NO 123
<211> LENGTH: 4395
<212> TYPE: DNA
<213> ORGANISM: Artificial Sequence
<220> FEATURE:
<223> OTHER INFORMATION: Synthetic Construct

<400> SEQUENCE: 123

| | |
|---|---|
| tagaaaaact catcgagcat caaatgaaac tgcaatttat tcatatcagg attatcaata | 60 |
| ccatattttt gaaaaagccg tttctgtaat gaaggagaaa actcaccgag gcagttccat | 120 |
| aggatggcaa gatcctggta tcggtctgcg attccgactc gtccaacatc aatacaacct | 180 |
| attaatttcc cctcgtcaaa aataaggtta tcaagtgaga atcaccatg agtgacgact | 240 |
| gaatccggtg agaatggcaa aagtttatgc atttctttcc agacttgttc aacaggccag | 300 |
| ccattacgct cgtcatcaaa atcactcgca tcaaccaaac cgttattcat tcgtgattgc | 360 |
| gcctgagcga ggcgaaatac gcgatcgctg ttaaaaggac aattacaaac aggaatcgag | 420 |
| tgcaaccggc gcaggaacac tgccagcgca tcaacaatat tttcacctga atcaggatat | 480 |
| tcttctaata cctggaacgc tgttttccg gggatcgcag tggtgagtaa ccatgcatca | 540 |
| tcaggagtac ggataaaatg cttgatggtc ggaagtggca taaattccgt cagccagttt | 600 |
| agtctgacca tctcatctgt aacatcattg gcaacgctac ctttgccatg tttcagaaac | 660 |
| aactctggcg catcgggctt cccatacaag cgatagattg tcgcacctga ttgcccgaca | 720 |
| ttatcgcgag cccatttata cccatataaa tcagcatcca tgttggaatt taatcgcggc | 780 |
| ctcgacgttt cccgttgaat atggctcata ttcttccttt tcaatatta ttgaagcatt | 840 |
| tatcagggtt attgtctcat gagcggatac atatttgaat gtatttagaa aaataaacaa | 900 |
| ataggggtca gtgttacaac caattaacca attctgaaca ttatcgcgag cccatttata | 960 |
| cctgaatatg gctcataaca ccccttgttt gcctggcggc agtagcgcgg tggtcccacc | 1020 |
| tgaccccatg ccgaactcag aagtgaaacg ccgtagcgcc gatggtagtg tggggactcc | 1080 |
| ccatgcgaga gtagggaact gccaggcatc aaataaaacg aaaggctcag tcgaaagact | 1140 |
| gggcctttcg cccgggctaa ttaggggggtg tcgcccttcg attgacggtt acgggatcct | 1200 |
| cacacgtaca tcagctggtt gatggggaac gggtcgatga gcagcagctt gatgcggttc | 1260 |

```
tcggtggcgt aatccgggcg gcccagcccg tccccatatt ggtaggtgca gtggctcacg    1320
cgggccatgt tcacggcgat ctccatgaac gccttcggca gcagggtgct gtccgacacg    1380
cgctcgcggt tcattttctt ccactcggcg tcgatcagct tgcgcagctc ttcgcgggcc    1440
tgttcctcgc tcgtgccgtc gttctcgtgc atgtagctga tgatgctgtt ggtggtttcg    1500
ccgcgttcga gttccgccgc cgaggtcgcc agatcgttgc acagccgaaa gatcacgcag    1560
gacgagcgca ccaggccgtg gaagtcggtc agggagcgga gggcgtggtc cgagatatct    1620
tcctgctgct ggcagaccga gaagtagctc ggcgccagca gcgcgacccc gctggaggac    1680 acgctgcgt tctccaggta cttgctgaag gcggggatga tcttgttatt gctccacttg    1740
gcttcttgca ggaaggcctt gcacagttcg cgccagcttt tggtcagata gctcaggtta    1800
ttgtggccct tctccttcag gatggagtag gacgtgtcgt tcacggtgtt gtacagggcc    1860
aggaagcaca gcttcatata gtcgggcagc gtgttgatgg cgttcacgtc ccagcgttcc    1920
accgcgtcgg tgaagagctg cagttcgtcc agggtaccgt acacgtcata gacgtcatcg    1980
ataatggtga ccagaccgaa catcttggtg acggccttgc ggcattcgcc gaactgcggg    2040 tccgcgcca tgcccagcgc ccagaagtac acttccatca gcggtcccg cacgaaatcc    2100 agcttgctgg cgaggcccat ctcggtccac caccggctca ggtcctgcag ctcttttttgg    2160 tgcagggtct ggaccatgtt gaaatcgagt ttggccagtt ccagcagcag ctggtgatgc    2220
ggctccttgg gttcgtactt gtccagaaac caccgcgcct ccaggcggtg caggcgttga    2280
tgatacggca gctccagcgc gtgggacacc tgctcggcca ccttcgtgtt gatcccctcc    2340
ttgaggttgt tcttcagatg ggtgatgctg aaggtacggg cctcctccag cagattttcg    2400
ccttcgaaac cgagatagct ggcctcgtac aggctcagca ggccctgcac gtcacccttc    2460
agttccccgg agaagccccc ttctttgtcc ttgaagcgct cgaacacgtc ctggctcacc    2520
tcaaagccat gctgccgcag caggcggaag ctcaggcgg tcgcgtgcag atcgcttttg    2580
ttcttcttat tctcgtccag caggacgatg ttctccagcg ccttgatgat atctttctca    2640
aacttgtagg tcaggcccag gcgctgcacg tcgtcgatga gctccagcag gctcaggggc    2700
tgggtgtcca cccggttgat catgcaacgc acctcctcct ccagcttggt ggccttctct    2760
tcgagcttct ccaccttcag gtcgtttttcc aggctctgca ggaactcgaa gttccacagg    2820
ttgggctggt agttcgcgga ccgacggcta ttatgctcgg tgatctgggt gaactggctg    2880
ctggtggcgc acatatgtat atctccttct taaagttaaa caagcttaag atgttcagcg    2940
acaagggcga cacaaaattt attctaaatg cataataaat actgataaca tcttatagtt    3000
tgtattatat tttgtattat cgttgacatg tataattttg atatcaaaaa ctgattttcc    3060
ctttattatt ttcgagattt attttcttaa ttctctttaa caaactagaa atattgtata    3120
tacaaaaaat cataataat agatgaatag tttaattata ggtgttcatc aatcgaaaaa    3180
gcaacgtatc ttatttaaag tgcgttgctt ttttctcatt tataaggtta aataattctc    3240
atatatcaag caaagtgaca ggcgccctta atattctga caaatgctct ttccctaaac    3300
tccccccata aaaaaacccg ccgaagcggg ttttttacgtt atttgcggat taacgattac    3360
tcgttatcag aaccgcccag ggggcccgag cttaagactg gccgtcgttt tacaacacag    3420
aaagagtttg tagaaacgca aaaggccat ccgtcagggg ccttctgctt agtttgatgc    3480
ctggcagttc cctactctcg ccttccgctt cctcgctcac tgactcgctg cgctcggtcg    3540
ttcggctgcg gcgagcggta tcagctcact caaaggcggt aatacggtta tccacagaat    3600
caggggataa cgcaggaaag aacatgtgag caaaaggcca gcaaaaggcc aggaaccgta    3660
```

```
aaaaggccgc gttgctggcg tttttccata ggctccgccc ccctgacgag catcacaaaa  3720
atcgacgctc aagtcagagg tggcgaaacc cgacaggact ataaagatac caggcgtttc  3780
cccctggaag ctccctcgtg cgctctcctg ttccgaccct gccgcttacc ggatacctgt  3840
ccgcctttct cccttcggga agcgtggcgc tttctcatag ctcacgctgt aggtatctca  3900
gttcggtgta ggtcgttcgc tccaagctgg gctgtgtgca cgaaccccce gttcagcccg  3960 accgctgcgc cttatccggt aactatcgtc ttgagtccaa cccggtaaga cacgacttat  4020
cgccactggc agcagccact ggtaacagga ttagcagagc gaggtatgta ggcggtgcta  4080
cagagttctt gaagtggtgg gctaactacg gctacactag aagaacagta tttggtatct  4140
gcgctctgct gaagccagtt accttcggaa aaagagttgg tagctcttga tccggcaaac  4200
aaaccaccgc tggtagcggt ggttttttg tttgcaagca gcagattacg cgcagaaaaa  4260
aaggatctca agaagatcct ttgatctttt ctacgggtc tgacgctcag tggaacgacg  4320
cgcgcgtaac tcacgttaag ggattttggt catgagcttg cgccgtcccg tcaagtcagc  4380
gtaatgctct gcttt                                                   4395
```